US012729201B2

(12) United States Patent
Ray et al.

(10) Patent No.: US 12,729,201 B2
(45) Date of Patent: Sep. 8, 2026

(54) MALT-1 MODULATORS

(71) Applicant: RECURSION PHARMACEUTICALS, INC., Salt Lake City, UT (US)

(72) Inventors: Peter Ray, Oxford (GB); David Evans, Oxford (GB); Anthony Bradley, Oxford (GB); Chris Radoux, Oxford (GB); Simon Richards, Oxford (GB); Catarina Santos, Oxford (GB); Jérémy Besnard, Oxford (GB); Andrew John Cooke, Oxford (GB); Sylvie Félicité Gomez, Oxford (GB); Lorène Nathalie Sabine Cazaux-Lerou, Toulouse (FR); Marta Pinto, Toulouse (FR); Sabrina Pucci, Toulouse (FR); Claire Christiane Ginette Blanger, Toulouse (FR)

(73) Assignee: RECURSION PHARMACEUTICALS, INC., Salt Lake City, UT (US)

(*) Notice: Subject to any disclaimer, the term of this patent is extended or adjusted under 35 U.S.C. 154(b) by 320 days.

(21) Appl. No.: 18/253,572

(22) PCT Filed: Nov. 23, 2021

(86) PCT No.: PCT/GB2021/053031

§ 371 (c)(1),
(2) Date: May 18, 2023

(87) PCT Pub. No.: WO2022/106857

PCT Pub. Date: May 27, 2022

(65) Prior Publication Data

US 2025/0051327 A1 Feb. 13, 2025

(30) Foreign Application Priority Data

Nov. 23, 2020 (GB) ..................................... 2018412

(51) Int. Cl.

| | |
|---|---|
| *C07D 471/14* | (2006.01) |
| *A61K 31/4375* | (2006.01) |
| *A61K 31/5025* | (2006.01) |
| *A61K 31/519* | (2006.01) |
| *A61K 31/5377* | (2006.01) |
| *A61K 31/541* | (2006.01) |
| *C07D 471/04* | (2006.01) |
| *C07D 471/22* | (2006.01) |
| *C07D 487/04* | (2006.01) |
| *C07D 519/00* | (2006.01) |

(52) U.S. Cl.

CPC ........ *C07D 471/14* (2013.01); *A61K 31/4375* (2013.01); *A61K 31/5025* (2013.01); *A61K 31/519* (2013.01); *A61K 31/5377* (2013.01); *A61K 31/541* (2013.01); *C07D 471/04* (2013.01); *C07D 471/22* (2013.01); *C07D 487/04* (2013.01); *C07D 519/00* (2013.01)

(58) Field of Classification Search

CPC . C07D 471/14; C07D 519/00; A61K 31/4375
See application file for complete search history.

(56) References Cited

FOREIGN PATENT DOCUMENTS

| | | | |
|---|---|---|---|
| CN | 116916924 | A | 10/2023 |
| EP | 2125755 | A2 | 12/2009 |
| EP | 2803662 | A1 | 11/2014 |
| EP | 3149001 | A1 | 4/2017 |
| EP | 3305785 | A1 | 4/2018 |
| EP | 3374361 | A1 | 9/2018 |
| JP | 2018135274 | A | 8/2018 |
| JP | 2018203647 | A | 12/2018 |

(Continued)

OTHER PUBLICATIONS

Chikkulapalli, Anil, et al. "Convenient N-acetylation of amines in N, N-dimethylacetamide with N, N-carbonyldiimidazole." Tetrahedron Letters 56.24 (2015): 3799-3803.

(Continued)

*Primary Examiner* — Andrew D Kosar
*Assistant Examiner* — John D Mcanany
(74) *Attorney, Agent, or Firm* — MARSHALL, GERSTEIN & BORUN LLP

(57) ABSTRACT

Disclosed are compounds, compositions and methods for treating disease, syndromes, conditions and disorders that are affected by the modulation of MALT-1. Such compounds are represented by Formula (I) and Formula (II), wherein the variables are defined herein.

(I)

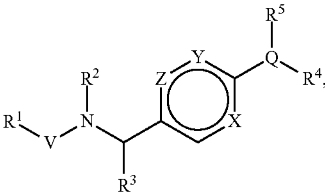

or (II)

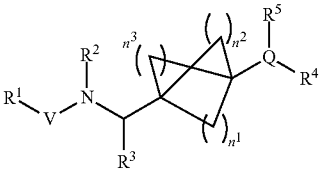

10 Claims, No Drawings

(56) References Cited

FOREIGN PATENT DOCUMENTS

| | | | | |
|---|---|---|---|---|
| WO | WO-03/004020 | A1 | 1/2003 | |
| WO | WO 2004/087652 | A2 | 10/2004 | |
| WO | WO 2010/097372 | A1 | 9/2010 | |
| WO | WO 2011/061548 | A2 | 5/2011 | |
| WO | WO 2012/143796 | A2 | 10/2012 | |
| WO | WO 2013/117645 | A1 | 8/2013 | |
| WO | WO 2013/126856 | A1 | 8/2013 | |
| WO | WO 2015/098991 | A1 | 7/2015 | |
| WO | WO 2015/181747 | A1 | 12/2015 | |
| WO | WO 2017/027717 | A1 | 2/2017 | |
| WO | WO 2017/081641 | A1 | 5/2017 | |
| WO | WO 2017/129769 | A1 | 8/2017 | |
| WO | WO 2018/078042 | A1 | 5/2018 | |
| WO | WO 2018/119036 | A1 | 6/2018 | |
| WO | WO 2018/226150 | A1 | 12/2018 | |
| WO | WO 2020/111087 | A1 | 6/2020 | |
| WO | WO-2022081967 | A1 | 4/2022 | |
| WO | WO-2022081995 | A1 * | 4/2022 | ............. A61K 45/06 |

OTHER PUBLICATIONS

Caiazzo A, Garcia PM, Wever R, van Hest JC, Rowan AE, Reek JN. Synergy between chemo- and bio-catalysts in multi-step transformations. Org Biomol Chem. Jul. 21, 2009;7(14):2926-32. doi: 10.1039/b901592b. Epub May 29, 2009. PMID: 19582303.

Le TG, Kundu A, Ghoshal A, Nguyen NH, Preston S, Jiao Y, Ruan B, Xue L, Huang F, Keiser J, Hofmann A, Chang BCH, Garcia-Bustos J, Wells TNC, Palmer MJ, Jabbar A, Gasser RB, Baell JB. Structure-Activity Relationship Studies of Tolfenpyrad Reveal Subnanomolar Inhibitors of Haemonchus contortus Development. J Med Chem. Jan. 24, 2019;62(2):1036-1053. doi: 10.1021/acs.jmedchem.8b01789. Epub Jan. 7, 2019. PMID: 30571110. Azimioara. Cheung M, Kuntz KW, Pobanz M, Salovich JM, Wilson BJ, Andrews CW 3rd, Shewchuk LM, Epperly AH, Hassler DF, Leesnitzer MA, Smith JL, Smith GK, Lansing TJ, Mook RA Jr. Imidazo[5,1-f][1,2,4]triazin-2-amines as novel inhibitors of polo-like kinase 1. Bioorg Med Chem Lett. Dec. 1, 2008;18(23):6214-7. doi: 10.1016/j.bmcl.2008.09.100. Epub Oct. 2, 2008. PMID: 18929484.

Bardet M, Unterreiner A, Malinverni C, Lafossas F, Vedrine C, Boesch D, Kolb Y, Kaiser D, Glück A, Schneider MA, Katopodis A, Renatus M, Simic O, Schlapbach A, Quancard J, Régnier CH, Bold G, Pissot-Soldermann C, Carballido JM, Kovarik J, Calzascia T, Bornancin F. The T-cell fingerprint of MALT1 paracaspase revealed by selective inhibition. Immunol Cell Biol. Jan. 2018;96(1):81-99. doi: 10.1111/imcb.1018. Epub Dec. 21, 2017. PMID: 29359407.

Basarab GS, Hill PJ, Rastagar A, Webborn PJ. Design of Helicobacter pylori glutamate racemase inhibitors as selective antibacterial agents: a novel pro-drug approach to increase exposure. Bioorg Med Chem Lett. Aug. 15, 2008;18(16):4716-4722. doi: 10.1016/j.bmcl.2008.06.092. Epub Jul. 2, 2008. PMID: 18640833.Gib.

Biswas S, Chalishazar A, Helou Y, DiSpirito J, DeChristopher B, Chatterjee D, Merselis L, Vincent B, Monroe JG, Rabah D, Long AJ. Pharmacological Inhibition of MALT1 Ameliorates Autoimmune Pathogenesis and Can Be Uncoupled From Effects on Regulatory T-Cells. Front Immunol. May 9, 2022;13:875320. doi: 10.3389/fimmu.2022.875320. PMID: 35615349; PMCID: PMC9125252.

Bornancin F, Renner F, Touil R, Sic H, Kolb Y, Touil-Allaoui I, Rush JS, Smith PA, Bigaud M, Junker-Walker U, Burkhart C, Dawson J, Niwa S, Katopodis A, Nuesslein-Hildesheim B, Weckbecker G, Zenke G, Kinzel B, Traggiai E, Brenner D, Brüstle A, St Paul M, Zamurovic N, McCoy KD, Rolink A, Régnier CH, Mak TW, Ohashi PS, Patel DD, Calzascia T. Deficiency of MALT1 paracaspase activity results in unbalanced regulatory and effector T and B cell responses leading to multiorgan inflammation. J Immunol. Apr. 15, 2015;194(8):3723-34. doi: 10.4049/jimmunol.1402254. Epub Mar. 11, 2015. PMID: 25762782.

Cheng L, Deng N, Yang N, Zhao X, Lin X. Malt1 Protease Is Critical in Maintaining Function of Regulatory T Cells and May Be a Therapeutic Target for Antitumor Immunity. J Immunol. May 15, 2019;202(10):3008-3019. doi: 10.4049/jimmunol.1801614. Epub Apr. 12, 2019. PMID: 30979818.

Demeyer A, Staal J, Beyaert R. Targeting MALT1 Proteolytic Activity in Immunity, Inflammation and Disease: Good or Bad? Trends Mol Med. Feb. 2016;22(2):135-150. doi: 10.1016/j.molmed.2015.12.004. Epub Jan. 17, 2016. PMID: 26787500.

Demeyer A, Skordos I, Driege Y, Kreike M, Hochepied T, Baens M, Staal J, Beyaert R. MALT1 Proteolytic Activity Suppresses Autoimmunity in a T Cell Intrinsic Manner. Front Immunol. Aug. 14, 2019;10:1898. doi: 10.3389/fimmu.2019.01898. PMID: 31474984; PMCID: PMC6702287.

Demeyer A, Driege Y, Skordos I, Coudenys J, Lemeire K, Elewaut D, Staal J, Beyaert R. Long-Term MALT1 Inhibition in Adult Mice Without Severe Systemic Autoimmunity. Science. Sep. 12, 2020;23(10):101557. doi: 10.1016/j.isci.2020.101557. PMID: 33083726; PMCID: PMC7522757.

Di Pilato M, Kim EY, Cadilha BL, Prüßmann JN, Nasrallah MN, Seruggia D, Usmani SM, Misale S, Zappulli V, Carrizosa E, Mani V, Ligorio M, Warner RD, Medoff BD, Marangoni F, Villani AC, Mempel TR. Targeting the CBM complex causes Treg cells to prime tumours for immune checkpoint therapy. Nature. Jun. 2019;570(7759):112-116. doi: 10.1038/s41586-019-1215-2. Epub May 15, 2019. PMID: 31092922; PMCID: PMC6656391.

Farinha P, Gascoyne RD. Molecular pathogenesis of mucosa-associated lymphoid tissue lymphoma. J Clin Oncol. Sep. 10, 2005;23(26):6370-8. doi: 10.1200/JCO.2005.05.011. PMID: 16155022.

Fontán L, Qiao Q, Hatcher JM, Casalena G, Us I, Teater M, Durant M, Du G, Xia M, Bilchuk N, Chennamadhavuni S, Palladino G, Inghirami G, Philippar U, Wu H, Scott DA, Gray NS, Melnick A. Specific covalent inhibition of MALT1 paracaspase suppresses B cell lymphoma growth. J Clin Invest. Oct. 1, 2018;128(10):4397-4412. doi: 10.1172/JCI99436. Epub Jul. 19, 2018. PMID: 30024860; PMCID: PMC6159983.

Gewies A, Gorka O, Bergmann H, Pechloff K, Petermann F, Jeltsch KM, Rudelius M, Kriegsmann M, Weichert W, Horsch M, Beckers J, Wurst W, Heikenwalder M, Korn T, Heissmeyer V, Ruland J. Uncoupling Malt1 threshold function from paracaspase activity results in destructive autoimmune inflammation. Cell Rep. Nov. 20, 2014;9(4):1292-1305. doi: 10.1016/j.celrep.2014.10.044. Epub Nov. 13, 2014. PMID: 25456129.

Gibhard L, Njoroge M, Paquet T, Brunschwig C, Taylor D, Lawrence N, Abay E, Wittlin S, Wiesner L, Street LJ, Chibale K, Basarab GS. Investigating Sulfoxide-to-Sulfone Conversion as a Prodrug Strategy for a Phosphatidylinositol 4-Kinase Inhibitor in a Humanized Mouse Model of Malaria. Antimicrob Agents Chemother. Nov. 26, 2018;62(12):e00261-18. doi: 10.1128/AAC.00261-18. PMID: 30249687; PMCID: PMC6256810.

Hamp I, O'Neill TJ, Plettenburg O, Krappmann D. A patent review of MALT1 inhibitors (2013-present). Expert Opin Ther Pat. Dec. 2021;31(12):1079-1096. doi: 10.1080/13543776.2021.1951703. Epub Jul. 15, 2021. PMID: 34214002.

O'Neill TJ, Tofaute MJ, Krappmann D. Function and targeting of MALT1 paracaspase in cancer. Cancer Treat Rev. Jun. 2023;117:102568. doi: 10.1016/j.ctrv.2023.102568. Epub Apr. 26, 2023. PMID: 37126937.

Rosebeck S, Lucas PC, McAllister-Lucas LM. Protease activity of the API2-MALT1 fusion oncoprotein in MALT lymphoma development and treatment. Future Oncol. May 2011;7(5):613-7. doi: 10.2217/fon. 11.35. PMID: 21568677; PMCID: PMC3124218.

Rosenbaum M, Gewies A, Pechloff K, Heuser C, Engleitner T, Gehring T, Hartjes L, Krebs S, Krappmann D, Kriegsmann M, Weichert W, Rad R, Kurts C, Ruland J. Bcl10-controlled Malt1 paracaspase activity is key for the immune suppressive function of regulatory T cells. Nat Commun. May 28, 2019;10(1):2352. doi: 10.1038/s41467-019-10203-2. PMID: 31138793; PMCID: PMC6538646.

Ruland J, Hartjes L. CARD-BCL-10-MALT1 signalling in protective and pathological immunity. Nat Rev Immunol. Feb. 2019;19(2):118-134. doi: 10.1038/s41577-018-0087-2. PMID: 30467369.

Saba NS, Wong DH, Tanios G, Iyer JR, Lobelle-Rich P, Dadashian EL, Liu D, Fontan L, Flemington EK, Nichols CM, Underbayev C, Safah H, Melnick A, Wiestner A, Herman Sem. MALT1 Inhibition Is Efficacious in Both Naïve and Ibrutinib-Resistant Chronic Lymphocytic Leukemia. Cancer Res. Dec. 15, 2017;77(24):7038-

(56) References Cited

OTHER PUBLICATIONS 7048. doi: 10.1158/0008-5472.CAN-17-2485. Epub Oct. 9, 2017. PMID: 28993409; PMCID: PMC5732856.

Tan H, Xie Y, Zhang X, Wu S, Zhao H, Wu J, Wang W, Lin C. Integrative Analysis of MALT1 as a Potential Therapeutic Target for Prostate Cancer and its Immunological Role in Pan-Cancer. Front Mol Biosci. Dec. 2, 2021;8:714906. doi: 10.3389/fmolb.2021.714906. PMID: 34926571; PMCID: PMC8674617.

Yu JW, Hoffman S, Beal AM, Dykon A, Ringenberg MA, Hughes AC, Dare L, Anderson AD, Finger J, Kasparcova V, Rickard D, Berger SB, Ramanjulu J, Emery JG, Gough PJ, Bertin J, Foley KP. MALT1 Protease Activity Is Required for Innate and Adaptive Immune Responses. PLoS One. May 12, 2015;10(5):e0127083. doi: 10.1371/journal.pone.0127083. PMID: 25965667; PMCID: PMC4428694.

Azimioara M, Alper P, Cow C, Mutnick D, Nikulin V, Lelais G, Mecom J, McNeill M, Michellys PY, Wang Z, Reding E, Paliotti M, Li J, Bao D, Zoll J, Kim Y, Zimmerman M, Groessl T, Tuntland T, Joseph SB, McNamara P, Seidel HM, Epple R. Novel tricyclic pyrazolopyrimidines as potent and selective GPR119 agonists. Bioorg Med Chem Lett. Dec. 1, 2014;24(23):5478-83. doi: 10.1016/j.bmcl.2014.10.010. Epub Oct. 13, 2014. PMID: 25455488.

Vasbinder MM, Aquila B, Augustin M, Chen H, Cheung T, Cook D, Drew L, Fauber BP, Glossop S, Grondine M, Hennessy E, Johannes J, Lee S, Lyne P, Mortl M, Omer C, Palakurthi S, Pontz T, Read J, Sha L, Shen M, Steinbacher S, Wang H, Wu A, Ye M. Discovery and optimization of a novel series of potent mutant B-Raf(V600E) selective kinase inhibitors. J Med Chem. Mar. 14, 2013;56(5):1996-2015. doi: 10.1021/jm301658d. Epub Feb. 27, 2013. PMID: 23398453.

Jaworski M, Thome M. The paracaspase MALT1: biological function and potential for therapeutic inhibition. Cell Mol Life Sci. Feb. 2016;73(3):459-73. doi: 10.1007/s00018-015-2059-z. Epub Oct. 27, 2015. PMID: 26507244; PMCID: PMC4713714.

Meininger I, Krappmann D. Lymphocyte signaling and activation by the CARMA1-BCL10-MALT1 signalosome. Biol Chem. Dec. 1, 2016;397(12):1315-1333. doi: 10.1515/hsz-2016-0216. PMID: 27420898.

Juilland M, Thome M. Role of the CARMA1/BCL10/MALT1 complex in lymphoid malignancies. Curr Opin Hematol. Jul. 2016;23(4):402-9. doi: 10.1097/MOH.0000000000000257. PMID: 27135977; PMCID: PMC4900422.

Juilland M, Thome M. Holding All the CARDs: How MALT1 Controls CARMA/CARD-Dependent Signaling. Front Immunol. Aug. 30, 2018;9:1927. doi: 10.3389/fimmu.2018.01927. PMID: 30214442; PMCID: PMC6125328.

Liang X, Cao Y, Li C, Yu H, Yang C, Liu H. MALT1 as a promising target to treat lymphoma and other diseases related to MALT1 anomalies. Med Res Rev. Jul. 2021;41(4):2388-2422. doi: 10.1002/med.21799. Epub Mar. 25, 2021. PMID: 33763890.

Minderman M, Lantermans HC, Grüneberg LJ, Cillessen SAGM, Bende RJ, van Noesel CJM, Kersten MJ, Pals ST, Spaargaren M. MALT1-dependent cleavage of CYLD promotes NF-κB signaling and growth of aggressive B-cell receptor-dependent lymphomas. Blood Cancer J. Mar. 15, 2023;13(1):37. doi: 10.1038/s41408-023-00809-7. PMID: 36922488; PMCID: PMC10017792.

Gomez Solsona B, Schmitt A, Schulze-Osthoff K, Hailfinger S. The Paracaspase MALT1 in Cancer. Biomedicines. Feb. 1, 2022;10(2):344. doi: 10.3390/biomedicines10020344. PMID: 35203553; PMCID: PMC8961791.

International Search Report and Written Opinion in Application No. PCT/GB2021/053031; International Filing Date Nov. 23, 2021; 22 pages.

Eurasian Office Action for Application No. 202390902 dated Mar. 28, 2024; 14 pages.

Search Report under Section 17(5) for Application No. GB2018412.3 dated Mar. 19, 2021; 5 pages.

Search Report under Section 17(5) for Application No. GB2018411.5 dated Mar. 18, 2021; 5 pages.

* cited by examiner

MALT-1 MODULATORS

TECHNICAL FIELD

The present disclosure relates to novel compounds capable of modulating MALT-1 proteolytic and/or autoproteolytic activity. Such proteolytic and/or autoproteolytic activity may be inhibited by the compounds described herein. The present invention further describes the synthesis of the compounds and their uses as medicaments in diseases or disorders where MALT-1 modulation may be beneficial.

BACKGROUND

The involvement of the paracaspase, MALT-1 (also referred to as Mucosa-Associated Lymphoid Tissue Lymphoma Translocation Protein-1), in influencing immune responses is described for example in Jaworski et al., (2016), Cell Mol Life Science, 73, 459-473 and Demeyer et al., (2016), Trends Mol. Med., 22:135-150.

MALT-1 is the active subunit of the CBM protein complex which is formed upon activation of cell surface receptors with immune receptor tyrosine-based activation motifs (ITAMs), including the B-cell and T-cell receptors. The CBM complex consists of three proteins or subunits: CARD 11 (Caspase Recruitment Domain Family Member 11; membrane-associated guanylate kinase-like domain-containing protein 1), BCL10 (B-cell CLL/Lymphoma 10) and MALT-1. MALT-1 has an essential role in NF-kB signalling through both scaffolding and protease functions. Following activation, Malt1 acts as a scaffold in the CBM complex to recruit TRAF6 which in turn leads to the recruitment and activation of IkK (I-kappaB kinase) and the degradation of IkB NF-kB inhibitor, IkB. Further, MALT-1 affects NFκB signalling by its function as a cysteine protease which cleaves and thereby deactivates negative regulators of NFκB signalling, such as RelB, A20 or CYLD (Jaworski et al., (2016), Cell Mol Life Science, 73, 459-473). In addition to its role in NF-kB signalling, MALT1 protease cleaves the endoribonucleases Regnase-1 and Roquin, and increases the stability of mRNAs in activated T-cells (Meininger and Krappmann Biol. Chem. 2016; 397(12): 1315-1333).

As MALT-1 is a key mediator of the NFκB signalling pathway, the inventors consider that it may be a useful drug target for many diseases or disorders. Diseases or disorders which may benefit from MALT-1 modulation are, for example, autoimmune disorders and inflammatory diseases, such as rheumatoid arthritis, multiple sclerosis, psoriasis, Sjogren's syndrome and systemic lupus erythematosus or vasculitic conditions, cancers of hematopoietic origin or solid tumors, including chronic myelogenous leukemia, myeloid leukemia, non-Hodgkin lymphoma and other B cell lymphomas.

To date, only a few compounds have been proposed to modulate MALT-1: for example, WO2017/081641, WO2015/181747 and WO2018/119036 describe pyrazolo pyrimidine and pyrazolo derivatives that may be capable of modulating MALT-1. WO2020/111087 describes MALT-1 inhibitors that include a urea core scaffold. A summary is provided in the following review: Isabel Hamp, Thomas J. O'Neill, Oliver Plettenburg & Daniel Krappmann (2021) A patent review of MALT1 inhibitors (2013-present), *Expert Opinion on Therapeutic Patents.*

To date there is no effective and approved medical treatment available which is based on the inhibition of MALT-1.

The present invention has been devised with the above observations in mind.

SUMMARY OF THE INVENTION

In one aspect of the invention there is provided a compound of formula (I):

(I)

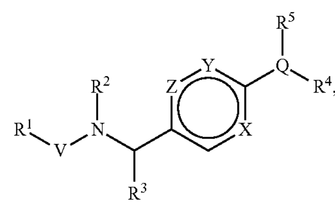

or a pharmaceutically acceptable salt, solvate, prodrug, or pharmaceutically active metabolite thereof, or combinations thereof, wherein:

Q is N or $CR^a$, where $R^a$ is selected from hydrogen, OH, alkyl, alkoxy;

X, Y and Z are each selected independently from N or $CR^b$, where $R^b$ is selected from hydrogen, alkoxy, alkyl, halo alkyl, halogen;

V is selected from the group consisting of: CO, SO and $SO_2$;

$R^1$ is selected from the group consisting of: alkyl, alkenyl, alkynyl, hydroxyalkyl, alkoxy, cycloalkyl, a 4-7 membered saturated or unsaturated heterocyclic ring having heteroatoms selected from N, S and O optionally substituted with hydroxyl, nitrile, oxo, amino, aminoalkyl and/or dioxo, sulfonyl, sulfoxide, sulfoximine, alkyl sulfonyl, alkyl sulfoxide, cycloalkyl sulfonyl, cycloalkyl sulfoxide, sulfamoyl, alkyl sulfamoyl, cycloalkyl sulfamoyl; or one of the following structures:

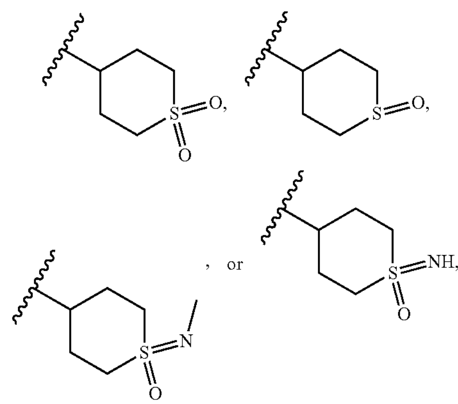

, or or any one of the following structures: structures:

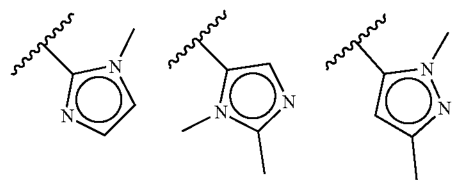

-continued
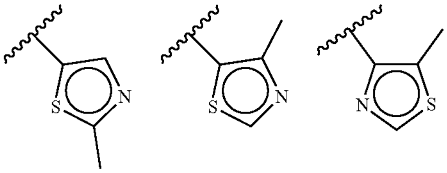
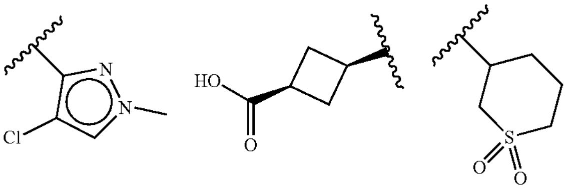
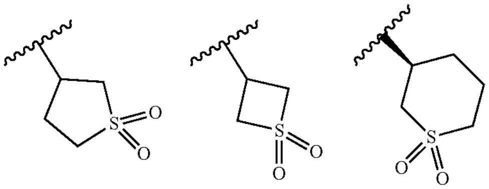
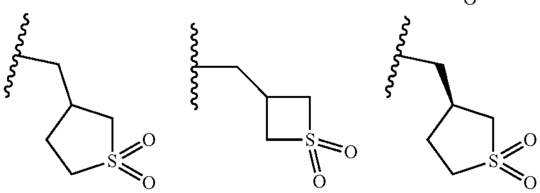
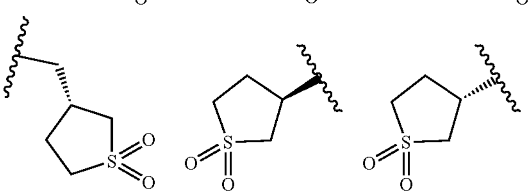
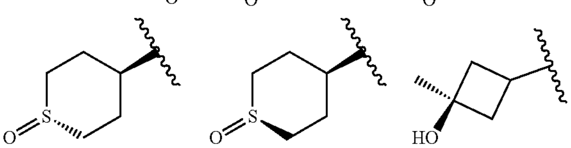
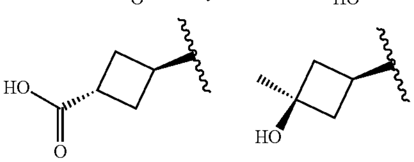
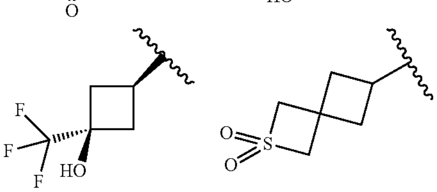
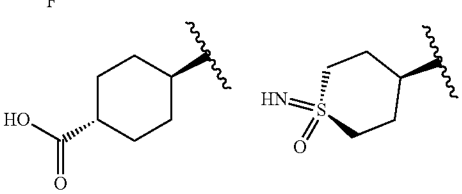
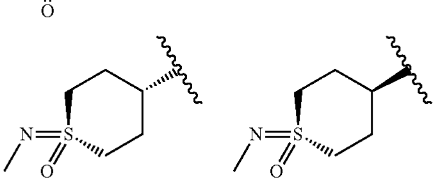
-continued
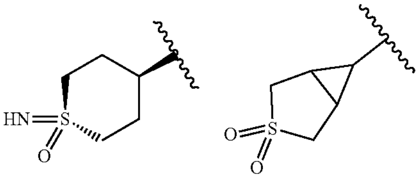
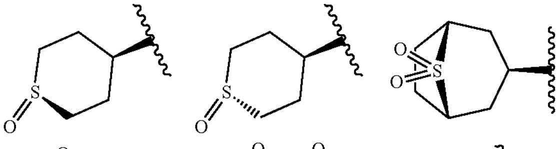
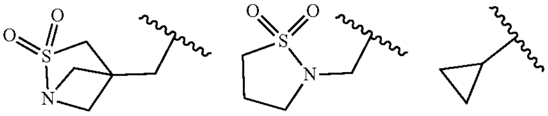
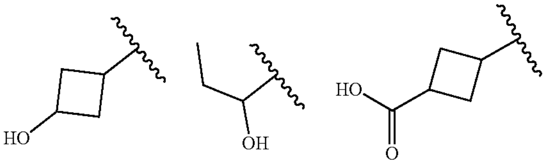
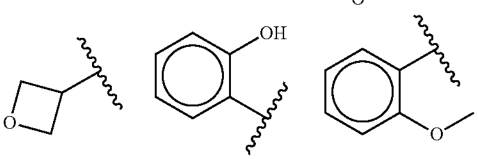
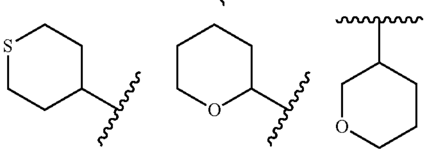
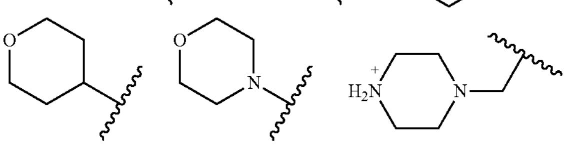
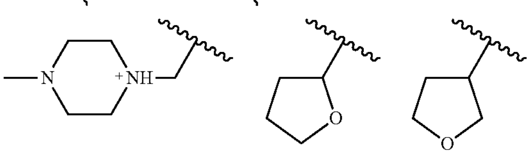
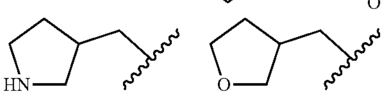
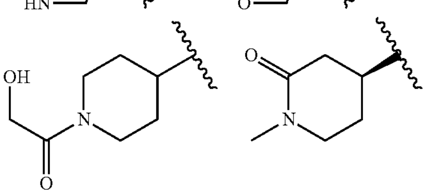
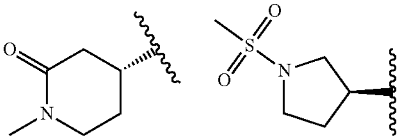
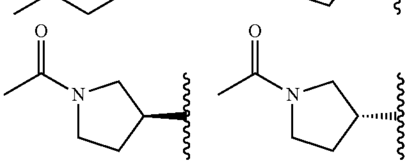

-continued
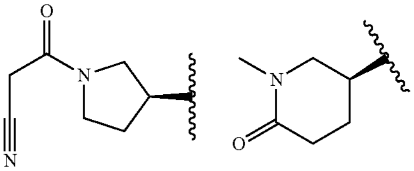
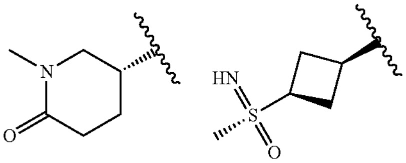
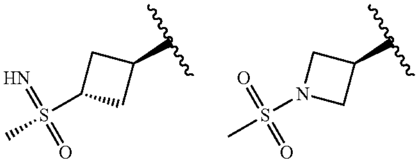
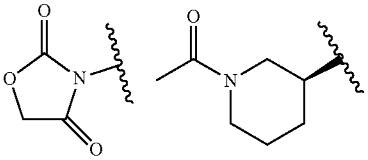
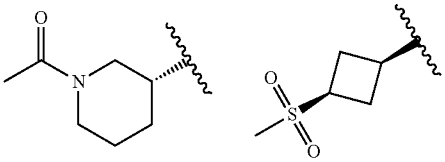
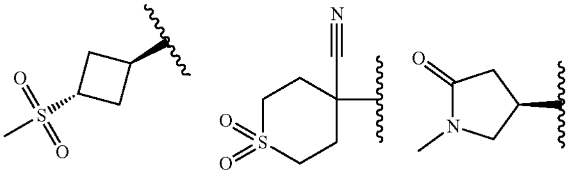
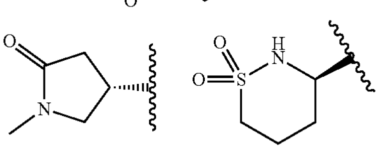
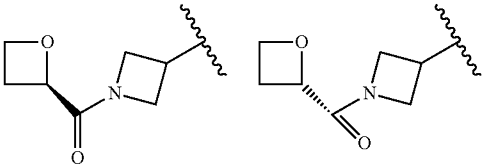
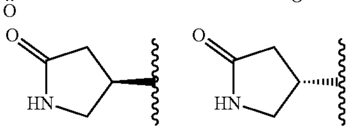
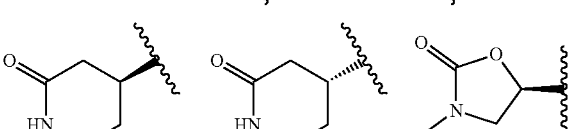
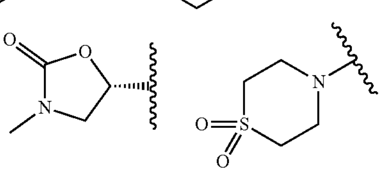
-continued
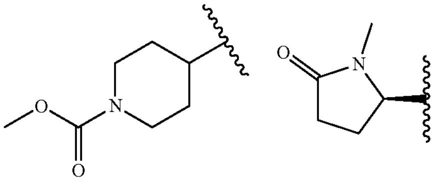
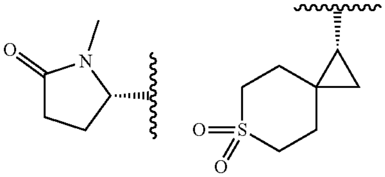
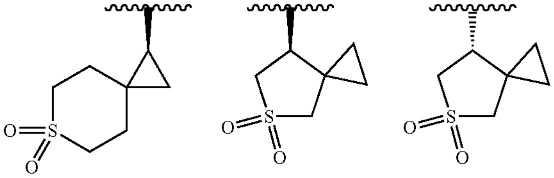
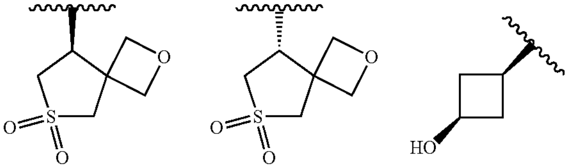
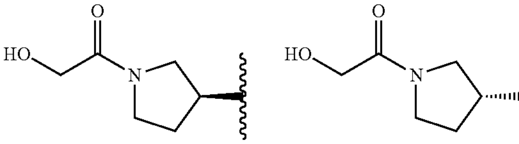
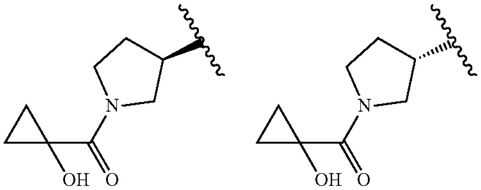
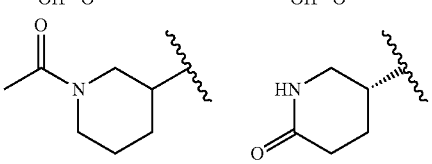
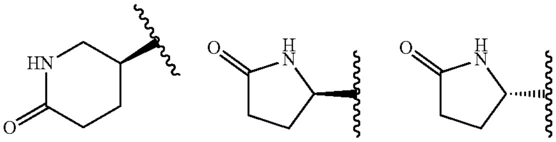
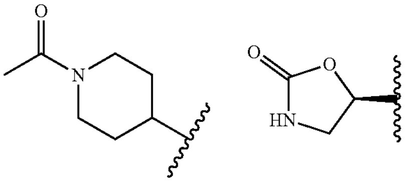
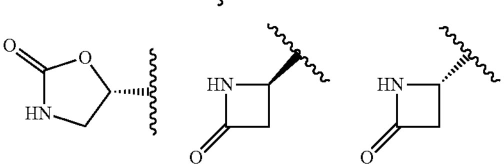

-continued

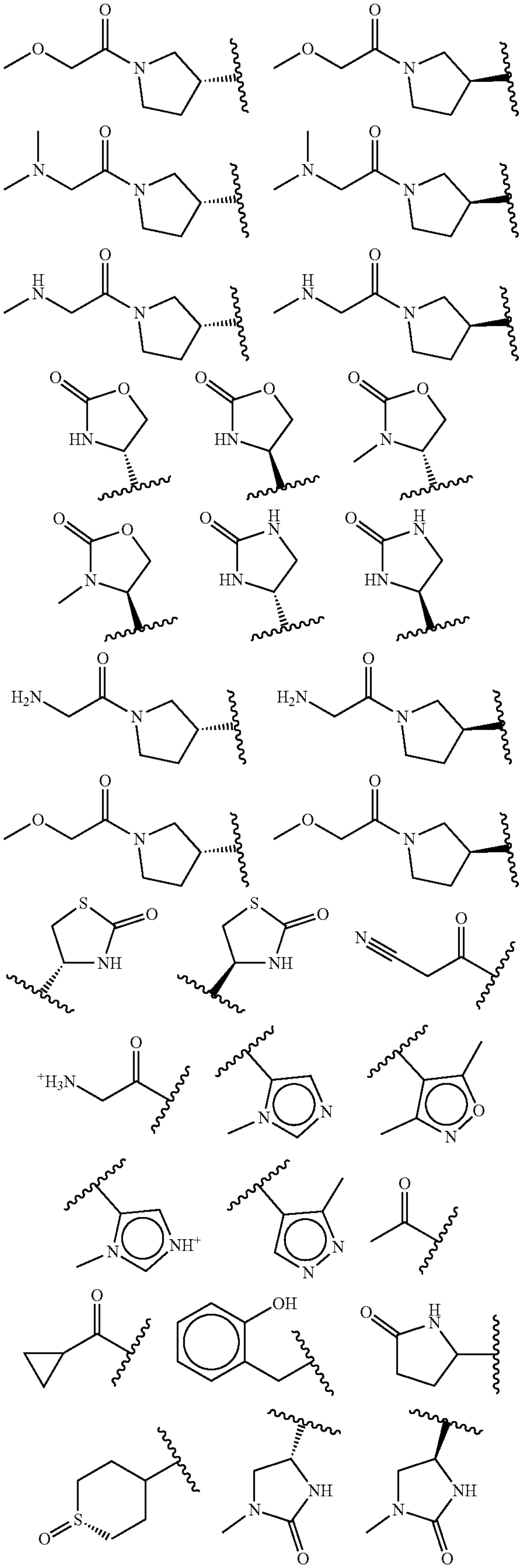

-continued

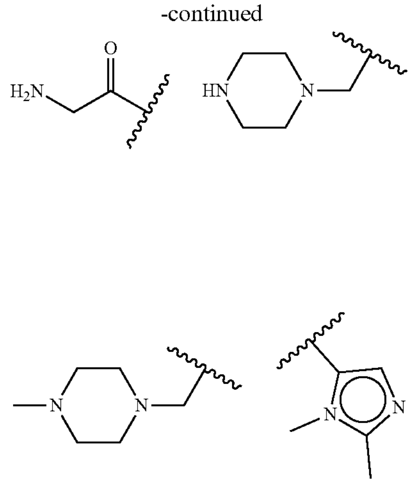

where each of the afore-mentioned hydrocarbon groups may be further substituted by one or more residues independently selected from halogen, hydroxyl, nitrile or C1-4-alkoxy groups;

$R^2$ is selected from the group consisting of: hydrogen, C1-3 alkyl, C1-3 alkoxyl, or C1-3 haloalkyl; or $R^1$ and $R^2$ together form a 4-7 membered ring; particularly a 5-6 membered heterocyclic ring having a further heteroatom selected from N, or O, which is optionally substituted with oxo, amino, aminoalkyl, sulfoxide, sulfoxide imine, sulfonyl, alkyl sulfoxide, sulfoximine, alkyl sulfonyl, cycloalkyl sulfoxide, cycloalkyl sulfonyl, sulfamoyl, alkyl sulfamoyl, cycloalkyl sulfamoyl;

$R^3$ is selected from the group consisting of: hydrogen, C1-3 alkyl, C1-3 alkoxyl, or C1-3 haloalkyl; or $R^4$ and $R^5$ are each independently selected from the group consisting of: hydrogen, C1-3 alkyl, pyridinyl, phenyl, pyrazidinyl or pyrimidinyl, optionally wherein the pyridinyl, phenyl, pyrazidinyl or pyrimidinyl is fused with a pyrrolyl, phenyl, pyrimidinyl, pyrazidinyl, imidazolyl, triazolyl, pyrazolyl, pyridinyl, quinolinyl, isoquinolinyl, quinazolinyl, which may be optionally substituted with C1-3 alkyl, C1-3 alkoxy, cyano, amine, difluoromethyl or halogen; or $R^4$ and $R^5$ together with the Q to which they attach form a non-aromatic heterocyclic 4-8 membered ring containing at least one heteroatom, particularly nitrogen, and optionally an additional heteroatom such as nitrogen or oxygen; and wherein the ring is fused with phenyl, pyridinyl, pyrazidinyl, pyrimidinyl which may be optionally substituted with halogen, nitrile, methyl, methoxy, difluoromethyl, aminyl, or trifluoromethyl, pyrazidinyl or pyrimidinyl, wherein the phenyl, pyridinyl, pyrazidinyl or pyrimidinyl is optionally fused with a further heterocyclic 5- or 6-membered, which is optionally substituted with 1 to 3 groups selected from the group consisting of: C1-3 alkyl, C1-3 alkoxyl, C1-3 haloalkyl, pyrrolyl, imidazolyl, triazolyl, nitro, cyano, hydroxyl or halogen; or $R^4$ and $R^5$ together with the Q to which they attach form one of the following structures:

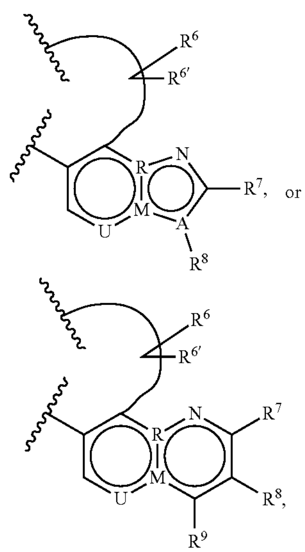

or

M, R and A are selected independently from the group consisting of: N, S or C, preferably M and R are selected independently from the group consisting of: N, S or C and A is C;

U is selected from the group consisting of: N, or $CR^c$, wherein $R^c$ is selected from hydrogen, halogen or alkyl;

$R^6$ and $R^{6'}$ are independently selected from the group consisting of: hydrogen, halogen C1-3 alkyl, C1-3 alkoxyl, C1-3 alkyl alkoxy, hydroxyl, alkyl hydroxyl, amino alkyl, C1-3 alkyl amino alkyl, tertiary aminyl, cyclic aminyl, spirocyclic aminyl, C1-2 alkyl-4-6 saturated heterocyclic aminyl, C0-2 alkyl oxetane, C0-2 alkyl oxolane, C0-2 alkyl azetidinyl or C0-2 alkyl pyrrolidinyl, C1-3 carboxyl, C1-3 haloalkyl, methylacetyl (OAc) or ethanoate;

alternatively, $R^{6'}$ and $R^6$ together form a C3-5 membered saturated ring or C4-5 membered saturated heterocycle ring containing oxygen;

$R^7$ is selected from the group consisting of: C1-3 alkyl, C1-3 alkoxyl, C1-3 haloalkyl, nitro, cyano, SMe, SOMe, $SO_2Me$, pyrrolyl, imidazolyl, triazolyl, or halogen; and $R^8$ and $R^9$ are each independently selected from the group consisting of: hydrogen, C1-3 alkyl, C1-3 alkoxyl, hydroxyl, C1-3 hydroxyalkyl or halogen.

In embodiments, where $R^5$ is hydrogen or methyl, $R^4$ may be selected from one of the following structures:

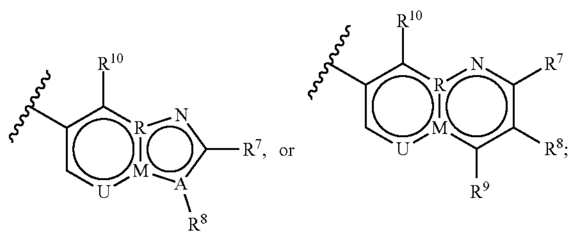

wherein

M, R and A are selected independently from the group consisting of: N, S or C;

U is selected from the group consisting of: N, S or $CR^c$, wherein $R^c$ is selected from hydrogen, halogen or alkyl; suitably at least two of X, Y and Z are C;

$R^7$ is selected from the group consisting of: C1-3 alkyl, C1-3 alkoxyl, C1-3 haloalkyl, nitro, cyano, SMe, SOMe, $SO_2Me$, pyrrolyl, imidazolyl, triazolyl, or halogen;

$R^8$ and $R^9$ are each independently selected from the group consisting of: hydrogen, C1-3 alkyl, C1-3 alkoxyl, hydroxyl, C1-3 hydroxyalkyl or halogen; and $R^{10}$ is selected from the group consisting of: hydrogen, C1-3 alkyl, C1-3 alkoxyl, C1-3 hydroxy alkyl, halogen, amide, C3-5 membered saturated ring or C4-5 membered saturated heterocycle ring.

In another aspect there is provided a compound selected from the group of compounds shown in Table 1. In embodiments, the compound may be selected from the group of compounds of Table 1 having an IC50 against Malt-1≤250 nM, ≤200 nM, ≤150 nM, ≤100 nM, ≤50 nM, or ≤25 nM. In other aspects and embodiments, the compound may be selected from any one of the compounds of Examples 1 to 295.

In another aspect the invention provides a pharmaceutical composition comprising a compound according to this disclosure.

In yet another aspect there is provided a method of treating or preventing autoimmune disorder, inflammatory disease, cancer and/or oncologic disease (particularly autoimmune disorders and inflammatory diseases) in a subject in need thereof, the method comprising administering to the subject an effective amount of the compound or pharmaceutical composition according to this disclosure.

In another aspect there is provided a compound according to this disclosure, or the pharmaceutical composition according to this disclosure for use in the treatment of autoimmune disorders and/or inflammatory diseases and/or oncologic disease and/or cancers. For example, for use in treating a disorder or disease selected from the group consisting of: rheumatoid arthritis, multiple sclerosis, psoriasis, Sjogren's syndrome and systemic lupus erythematosus or vasculitic conditions, cancers of hematopoietic origin or solid tumors, including chronic myelogenous leukemia, myeloid leukemia, non-Hodgkin lymphoma and other B cell lymphomas.

Within the scope of this disclosure it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible. More particularly, it is specifically intended that any embodiment of any aspect may form an embodiment of any other aspect, and all such combinations are encompassed within the scope of the invention. The applicant reserves the right to change any originally filed claim or file any new claim accordingly, including the right to amend any originally filed claim to depend from and/or incorporate any feature of any other claim although not originally claimed in that manner.

DETAILED DESCRIPTION

Described herein are compounds and compositions (e.g. organic molecules, research tools, pharmaceutical formulations and therapeutics); uses for the compounds and compositions of the disclosure (in vitro and in vivo); as well as corresponding methods, whether diagnostic, therapeutic or for research applications. The chemical synthesis and biological testing of the compounds of the disclosure are also described. Beneficially, the compounds, compositions, uses and methods have utility in research towards and/or the treatment of diseases or disorders in animals, such as humans. Diseases or disorders which may benefit from MALT-1 modulation include, for example, autoimmune disorder, inflammatory disease, cancer and/or oncologic disease, such as rheumatoid arthritis, multiple sclerosis, psoriasis, Sjogren's syndrome and systemic lupus erythematosus or vasculitic conditions, cancers of hematopoietic origin or solid tumors, including chronic myelogenous leukemia, myeloid leukemia, non-Hodgkin lymphoma and other B cell lymphomas.

However, the compounds may also or alternatively be useful as lead molecules for the selection, screening and development of further derivatives that may have one or more improved beneficial drug property, as desired. Such further selection and screening may be carried out using the proprietary computational evolutionary algorithm described e.g. in the Applicant's earlier published patent application WO 2011/061548, which is hereby incorporated by reference in its entirety.

The disclosure also encompasses salts, solvates and functional derivatives of the compounds described herein. These compounds may be useful in the treatment of diseases or disorders which may benefit from MALT-1 modulation, such as the autoimmune disorders, inflammatory diseases, cancers and/or oncologic diseases identified herein.

Unless defined otherwise, all technical and scientific terms used herein have the same meaning as commonly understood by one of ordinary skill in the art (e.g. in organic, physical or theoretical chemistry; biochemistry and molecular biology).

Unless otherwise indicated, the practice of the present invention employs conventional techniques in chemistry and chemical methods, biochemistry, molecular biology, pharmaceutical formulation, and delivery and treatment regimens for patients, which are within the capabilities of a person of ordinary skill in the art. Such techniques are also described in the literature cited herein. All documents cited in this disclosure are herein incorporated by reference in their entirety.

Prior to setting forth the detailed description of the invention, a number of definitions are provided that will assist in the understanding of the disclosure.

In accordance with this disclosure, the terms 'molecule' or 'molecules' are used interchangeably with the terms 'compound' or 'compounds', and sometimes the term ('chemical structure'. The term 'drug' is typically used in the context of a pharmaceutical, pharmaceutical composition, medicament or the like, which has a known or predicted physiological or in vitro activity of medical significance; but such characteristics and qualities are not excluded in a molecule or compound of the disclosure. The term 'drug' is therefore used interchangeably with the alternative terms and phrases 'therapeutic (agent)', 'pharmaceutical (agent)', and 'active (agent)'. Therapeutics according to the disclosure also encompass compositions and pharmaceutical formulations comprising the compounds of the disclosure.

The term "compound," as used herein is meant to include all stereoisomers, geometric isomers, tautomers, and isotopically enriched variants of the structures depicted. Compounds herein identified by name or structure as one particular tautomeric form are intended to include other tautomeric forms unless otherwise specified. The term "tautomer," as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the disclosure, and the naming of the compounds does not exclude any tautomer.

It will be appreciated that certain compounds provided herein may contain one or more centers of asymmetry and may therefore be prepared and isolated in a mixture of isomers such as a racemic mixture, or in an enantiomerically pure form.

Compounds provided herein may also contain unnatural proportions of atomic isotopes at one or more of the atoms that constitute such compounds. That is, an atom, in particular when mentioned in relation to a compound according to Formula (I) or (II), comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof; unless expressly noted otherwise. For example, in deuteroalkyl and deuteroalkoxy groups, where one or more hydrogen atoms are specifically replaced with deuterium ($^{2}H$). As some of the aforementioned isotopes are radioactive, the compounds provided herein therefore also comprise compounds with one or more isotopes of one or more atoms, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present disclosure.

Prodrugs and solvates of the compounds of the disclosure are also encompassed within the scope of the disclosure. The term 'prodrug' means a compound (e.g. a drug precursor) that is transformed in vivo to yield a compound of the disclosure or a pharmaceutically acceptable salt, solvate or ester of the compound. The transformation may occur by various mechanisms (e.g. by metabolic or chemical processes), such as by hydrolysis of a hydrolysable bond, e.g. in blood (see Higuchi & Stella (1987), "Pro-drugs as Novel Delivery Systems", *vol.* 14 *of the A.C.S. Symposium Series*; (1987), "*Bioreversible Carriers in Drug Design*", Roche, ed., American Pharmaceutical Association and Pergamon Press). The compositions and medicaments of the disclosure therefore may comprise prodrugs of the compounds of the disclosure. In some aspects and embodiments, the compounds of the disclosure are themselves prodrugs which may be metabolised in vivo to give the therapeutically effective compound. For example, a sulfoxide prodrug may be metabolized in vivo to the therapeutically active sulfone (see Basarab G. S. et al., (2008), *Bioorg Med Chem Lett,* 18(16), 4716-4722; Gibhard L. et al., (2008), *Antimicrobial Agents and Chemotherapy,* 62(12),00261-18).

In the context of the present disclosure, the terms 'individual', 'subject', or 'patient' are used interchangeably to indicate an animal that may be suffering from a medical (pathological) condition and may be responsive to a molecule, pharmaceutical drug, medical treatment or therapeutic treatment regimen of the disclosure. The animal is suitably a mammal, such as a human, cow, sheep, pig, dog, cat, bat, mouse or rat. In particular, the subject may be a human.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment The term "preventing" as used herein means the prevention of the onset, recurrence or spread, in whole or in part, of the disease or condition as described herein, or a symptom thereof.

The term "halo" refers to one of the halogens, group 17 of the periodic table. In particular, the term refers to fluorine, chlorine, bromine and iodine. Preferably, the term refers to fluorine or chlorine.

The term 'alkyl' refers to a monovalent, optionally substituted, saturated aliphatic hydrocarbon radical. Any number of carbon atoms may be present, but typically the number of carbon atoms in the alkyl group may be from 1 to about 20, from 1 to about 12, from 1 to about 6 or from 1 to about 4. Usefully, the number of carbon atoms is indicated, for example, a C1-12 alkyl (or C1-12 alkyl) refers to any alkyl group containing 1 to 12 carbon atoms in the chain. An alkyl group may be a straight chain (i.e. linear), branched chain, or cyclic. 'Lower alkyl' refers to an alkyl of 1 to 6 carbon atoms in the chain, and may have from 1 to 4 carbon atoms, or 1 to 2 carbon atoms. Thus, representative examples of lower alkyl radicals include methyl, ethyl, n-propyl, n-butyl, n-pentyl, n-hexyl, isopropyl, isobutyl, isopentyl, amyl ($C_5H_{11}$), sec-butyl, tert-butyl, sec-amyl, tert-pentyl, 2-ethylbutyl, 2,3-dimethylbutyl, and the like. 'Higher alkyl' refers to alkyls of 7 carbons and above, including n-heptyl, n-octyl, n-nonyl, n-decyl, n-dodecyl, n-tetradecyl, n-hexadecyl, n-octadecyl, n-eicosyl, and the like, along with branched variations thereof. A linear carbon chain of say 4 to 6 carbons would refer to the chain length not including any carbons residing on a branch, whereas in a branched chain it would refer to the total number. Optional substituents for alkyl and other groups are described below.

The term 'substituted' means that one or more hydrogen atoms (attached to a carbon or heteroatom) is replaced with a selection from the indicated group of substituents, provided that the designated atom's normal valency under the existing circumstances is not exceeded. The group may be optionally substituted with particular substituents at positions that do not significantly interfere with the preparation of compounds falling within the scope of this invention and on the understanding that the substitution(s) does not significantly adversely affect the biological activity or structural stability of the compound. Combinations of substituents are permissible only if such combinations result in stable compounds. By 'stable compound' or 'stable structure', it is meant a compound that is sufficiently robust to survive isolation to a useful degree of purity from a reaction mixture and/or formulation into an efficacious therapeutic agent. By 'optionally substituted' it is meant that the group concerned is either unsubstituted, or at least one hydrogen atom is replaced with one of the specified substituent groups, radicals or moieties.

Any radical/group/moiety described herein that may be substituted (or optionally substituted) may be substituted with one or more (e.g. one, two, three, four or five) substituents, which are independently selected from the designated group of substituents. Thus, substituents may be selected from the group: halogen (or 'halo', e.g. F, Cl and Br), hydroxyl (—OH), amino or aminyl (—$NH_2$), thiol (—SH), cyano (—CN), (lower) alkyl, (lower) alkoxy, (lower) alkenyl, (lower) alkynyl, aryl, heteroaryl, (lower) alkylthio, oxo, haloalkyl, hydroxyalkyl, nitro (—$NO_2$), phosphate, azido (—$N_3$), alkoxycarbonyl, carboxy, alkylcarboxy, alkylamino, dialkylamino, aminoalkyl, alkylaminoalkyl, dialkylaminoalkyl, thioalkyl, alkylsulfonyl, arylsulfinyl, alkylaminosulfonyl, arylaminosulfonyl, alkylsulfonylamino, arylsulfonylamino, carbamoyl, alkylcarbamoyl, dialkylcarbamoyl, arylcarbamoyl, alkylcarbonylamino, arylcarbonylamino, cycloalkyl, heterocycloalkyl, unless otherwise indicated. Alternatively, where the substituents are on an aryl or other cyclic ring system, two adjacent atoms may be substituted with a methylenedioxy or ethylenedioxy group. More suitably, the substituents are selected from: halogen, hydroxy, amino, thiol, cyano, ($C_1$-$C_6$)alkyl, ($C_1$-$C_6$)alkoxy, ($C_1$-$C_6$)alkenyl, ($C_1$-$C_6$)alkynyl, aryl, aryl ($C_1$-$C_6$)alkyl, aryl ($C_1$-$C_6$)alkoxy, heteroaryl, ($C_1$-$C_6$)alkylthio, oxo, halo($C_1$-$C_6$)alkyl, hydroxy($C_1$-$C_6$)alkyl, nitro, phosphate, azido, ($C_1$-$C_6$)alkoxycarbonyl, carboxy, ($C_1$-$C_6$) alkylcarboxy, ($C_1$-$C_6$)alkylamino, di($C_1$-$C_6$)alkylamino, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, thio($C_1$-$C_6$)alkyl, ($C_1$-$C_6$)alkylsulfonyl, arylsulfinyl, ($C_1$-$C_6$)alkylaminosulfonyl, arylaminosulfonyl, ($C_1$-$C_6$)alkylsulfonylamino, arylsulfonylamino, carbamoyl, ($C_1$-$C_6$)alkylcarbamoyl, di($C_1$-$C_6$)alkylcarbamoyl, arylcarbamoyl, ($C_1$-$C_6$)alkylcarbonylamino, arylcarbonylamino, ($C_1$-$C_6$)cycloalkyl, and heterocycloalkyl. Still more suitably, the substituents are selected from one or more of: fluoro, chloro, bromo, hydroxy, ($C_1$-$C_6$)alkyl, ($C_1$-$C_6$)haloalkyl, ($C_1$-$C_6$)alkoxy, ($C_5$-$C_6$)aryl, a 5- or 6-membered heteroaryl, ($C_4$-$C_6$)cycloalkyl, a 4- to 6-membered heterocycloalkyl, cyano, ($C_1$-$C_6$) alkylthio, amino, —NH(alkyl), —NH(($C_1$-$C_6$)cycloalkyl), —N(($C_1$-$C_6$)alkyl)$_2$, —OC(O)—($C_1$-$C_6$)alkyl, —OC(O)—($C_5$-$C_6$)aryl, —OC(O)—($C_1$-$C_6$)cycloalkyl, carboxy and —C(O)O—($C_1$-$C_6$)alkyl. Most suitably, the substituents are selected from one or more of: fluoro, chloro, bromo, hydroxy, amino, ($C_1$-$C_6$)alkyl and ($C_1$-$C_6$)alkoxy, wherein alkyl and alkoxy are optionally substituted by one or more chloro. Particularly preferred substituents are: chloro, methyl, ethyl, methoxy and ethoxy.

The term 'halo' refers to a monovalent halogen radical chosen from chloro, bromo, iodo, and fluoro. A 'halogenated' compound is one substituted with one or more halo substituent. Preferred halo groups are F, Cl and Br, and most preferred is Cl.

As used herein, the term "cyano" refers to a —CN radical. As used herein, the term "hydroxyl" refers to an —OH radical. As used herein, the term "amino" refers to an —$NH_2$ group. As used herein, the term "oxo" refers to an "═O" group attached to a carbon atom.

The term "$C_1$-$C_6$ haloalkyl" refers to a hydrocarbon chain substituted with at least one halogen atom independently chosen at each occurrence, for example fluorine, chlorine, bromine and iodine. The halogen atom may be present at any position on the hydrocarbon chain. Similarly, a C1-C3 haloalkyl group is linear or branched hydrocarbon chain containing 1, 2, or 3 carbon atoms substituted with at least one halogen atom. For example, $C_1$-$C_3$ haloalkyl may refer to chloromethyl, fluoromethyl, trifluoromethyl, chloroethyl e.g. 1-chloroethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

As used herein, the term "geminal" refers to substituent atoms or groups attached to the same atom in a molecule. As used herein, the term "vicinal" refers to substituent atoms or groups attached to adjacent atoms in a molecule. The stereochemical relationship between the substituent atoms or groups can be cis, trans, undefined, or unresolved.

When used herein, the term 'independently', in reference to the substitution of a parent moiety with one or more substituents, means that the parent moiety may be substituted with any of the listed substituents, either individually or in combination, and any number of chemically possible substituents may be used. In any of the embodiments, where a group is substituted, it may contain up to 5, up to 4, up to 3, or 1 and 2 substituents. As a non-limiting example, useful substituents include: phenyl or pyridine, independently substituted with one or more lower alkyl, lower alkoxy or halo substituents, such as: chlorophenyl, dichlorophenyl, trichlorophenyl, tolyl, xylyl, 2-chloro-3-methylphenyl, 2,3-dichloro-4-methylphenyl, etc.

"Alkylene" or "alkylenyl" means a difunctional group obtained by removal of a hydrogen atom from an alkyl group as defined above. Non-limiting examples of alkylene include methylene, ethylene and propylene. 'Lower alkylene' means an alkylene having from 1 to 6 carbon atoms in the chain, and may be straight or branched. Alkylene groups are optionally substituted.

The term 'alkenyl' refers to a monovalent, optionally substituted, unsaturated aliphatic hydrocarbon radical. Therefore, an alkenyl has at least one carbon-carbon double bond (C═C). The number of carbon atoms in the alkenyl group may be indicated, such as from 2 to about 20. For example, a C2-12 alkenyl (or $C_{2-12}$ alkenyl) refers to an alkenyl group containing 2 to 12 carbon atoms in the structure. Alkenyl groups may be straight (i.e. linear), branched chain, or cyclic. 'Lower alkenyl' refers to an alkenyl of 1 to 6 carbon atoms, and may have from 1 to 4 carbon atoms, or 1 to 2 carbon atoms. Representative examples of lower alkenyl radicals include ethenyl, 1-propenyl, 1-butenyl, 1-pentenyl, 1-hexenyl, isopropenyl, isobutenyl, and the like. Higher alkenyl refers to alkenyls of seven carbons and above, such as 1-heptenyl, 1-octenyl, 1-nonenyl, 1-decenyl, 1-dodecenyl, 1-tetradecenyl, 1-hexadecenyl, 1-octadecenyl, 1-eicosenyl, and the like, along with branched variations thereof. Optional substituents include are described elsewhere.

'Alkenylene' means a difunctional group obtained by removal of a hydrogen from an alkenyl group that is defined above. Non-limiting examples of alkenylene include —CH═CH—, $—C(CH_3)═CH—$, and $—CH═CHCH_2—$.

'Alkynyl' and 'lower alkynyl' is defined similarly to the term 'alkenyl', except that it includes at least one carbon-carbon triple bond.

The term 'alkoxy' refers to a monovalent radical of the formula RO—, where R is any alkyl, alkenyl or alkynyl as defined herein. Alkoxy groups may be optionally substituted by any of the optional substituents described herein. 'Lower alkoxy' has the formula RO—, where the R group is a lower alkyl, alkenyl or alkynyl. Representative alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Preferred alkoxy groups are methoxy and ethoxy.

The term 'aryl' as used herein refers to a substituted or unsubstituted aromatic carbocyclic radical containing from 5 to about 15 carbon atoms; and preferably 5 or 6 carbon atoms. An aryl group may have only one individual carbon ring, or may comprise one or more fused rings in which at least one ring is aromatic in nature. A 'phenyl' is a radical formed by removal of a hydrogen atom from a benzene ring, and may be substituted or unsubstituted. A 'phenoxy' group, therefore, is a radical of the formula RO—, wherein R is a phenyl radical. 'Benzyl' is a radical of the formula $R—CH_2—$, wherein R is phenyl, and 'benzyloxy' is a radical of the formula RO—, wherein R is benzyl. Non-limiting examples of aryl radicals include, phenyl, naphthyl, benzyl, biphenyl, furanyl, pyridinyl, indanyl, anthraquinolyl, tetrahydronaphthyl, a benzoic acid radical, a furan-2-carboxylic acid radical, and the like.

A 'heteroaryl' group is herein defined as a substituted or unsubstituted 'aryl' group in which one or more carbon atoms in the ring structure has been replaced with a heteroatom, such as nitrogen, oxygen or sulphur. Generally, the heteroaryl group contains one or two heteroatoms. A preferred heteroatom is N. Exemplary heteroaryl groups include: furan, benzofuran, isobenzofuran, pyrrole, indole, isoindole, thiophene, benzothiophene, benzo[c]thiophene, imidazole, benzimidazole, purine, pyrazole, indazole, oxazole, benzoxazole, isoxazole, benzisoxazole, thiazole, benzothiazole, pyridine, quinoline, isoquinoline, pyrazine, quinoxaline, acridine, pyrimidine, quinazoline, pyridazine and cinnoline.

The terms 'heterocycle' or 'heterocyclic' group as used herein refer to a monovalent radical of from about 4- to about 15-ring atoms, and preferably 4-, 5- or 6,7-ring members. Generally, the heterocyclic group contains one, two or three heteroatoms, selected independently from nitrogen, oxygen and sulphur. A preferred heteroatom is N. A heterocyclic group may have only one individual ring, or may comprise one or more fused rings in which at least one ring contains a heteroatom. It may be fully saturated or partially saturated, and may be substituted or unsubstituted as in the case or aryl and heteroaryl groups. Representative examples of unsaturated 5-membered heterocycles with only one heteroatom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolindinyl, 2- or 3-tetrahydrofuranyl, and 2- or 3-tetrahydrothiophenyl. Representative unsaturated 5-membered heterocyclic radicals having two heteroatoms include imidazolyl, oxazolyl, thiazolyl, pyrazolyl, and the like. The corresponding fully saturated and partially saturated radicals are also included. Representative examples of unsaturated 6-membered heterocycles with only one heteroatom include 2-, 3-, or 4-pyridinyl, 2H-pyranyl, and 4H-pryanyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two heteroatoms include 3- or 4-pyridazinyl, 2-, 4-, or 5-pyrimidinyl, 2-pyrazinyl, morpholino, and the like. The corresponding fully saturated and partially saturated radicals are also included, e.g. 2-piperazine. The heterocyclic radical is bonded through an available carbon atom or heteroatom in the heterocyclic ring directly to the entity or through a linker such as an alkylene such as methylene or ethylene.

The term “pharmaceutically acceptable” indicates that the compound, or salt or composition thereof is compatible chemically and/or toxicologically with the other ingredients comprising a formulation and/or the subject being treated therewith.

Unless defined otherwise, ‘room temperature’ is intended to mean a temperature of from about 18 to 28° C., typically between about 18 and 25° C., and more typically between about 18 and 22° C. As used herein, the phrase ‘room temperature’ may be shortened to ‘rt’ or ‘RT’.

Molecules and Compounds

In some embodiments, the compounds of the disclosure may be amide compounds.

Disclosed herein is a compound having the structural formula (I) or (II), or a pharmaceutically acceptable salt, solvate, prodrug, or pharmaceutically active metabolite thereof:

(I)

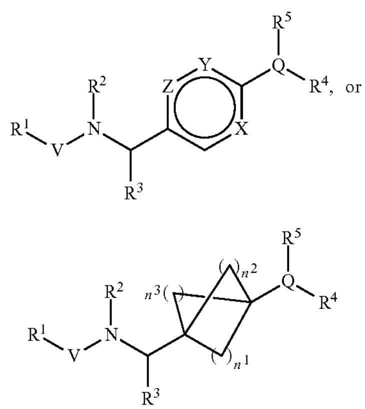

(II)

wherein

- Q is N or $CR^a$, where $R^a$ is selected from hydrogen, OH, alkyl, alkoxy (e.g. OMe), preferably where Q is N;
- X, Y and Z are each selected independently from N or $CR^b$, where $R^b$ is selected from hydrogen, halo alkyl (e.g. $CF_3$), halogen (e.g. F), in some embodiments one of X, Y and Z is CF and the rest are CH; preferably where X is CF. In some embodiments one of X, Y and Z is N, preferably one of X or Y is N and the rest are CH. In some embodiments X, Y and Z are CH, in some embodiments X or Y is CF and Z is CH;
- V is selected from the group consisting of: CO, SO, SONH, SONMe, and $SO_2$, preferably CO;
- $n^1$, $n^2$ and $n^3$ are independently selected from 1 to 3 (e.g. 1 and 2); particularly, $n^1$ may be 1 and $n^2$ may be 2. In some beneficial embodiments $n^1$=$n^2$=$n^3$ and is 1 or 2;
- $R^1$ is selected from the group consisting of: hydroxyl, cyano, alkyl (e.g. ethyl), alkenyl, alkynyl, hydroxyalkyl, alkoxy, cycloalkyl, a 4-7 membered saturated or unsaturated heterocyclic ring having heteroatoms selected from N, S and O optionally substituted with hydroxyl, nitrile, oxo, amino, aminoalkyl and/or dioxo, sulfonyl, sulfoxide, sulfoximine, alkyl sulfonyl, alkyl sulfoxide, cycloalkyl sulfonyl, cycloalkyl sulfoxide, sulfamoyl, alkyl sulfamoyl, cycloalkyl sulfamoyl or the following structures:

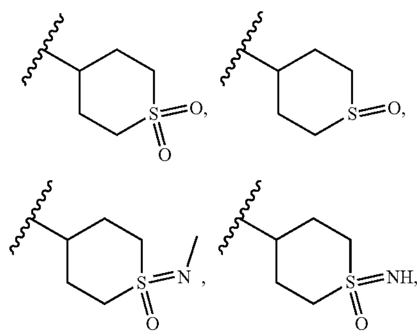

or any one of the following structures:

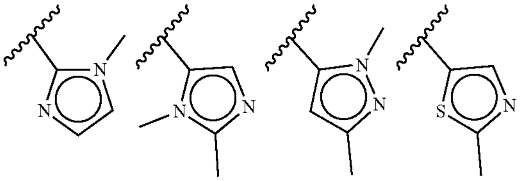

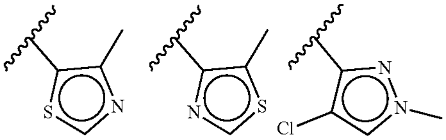

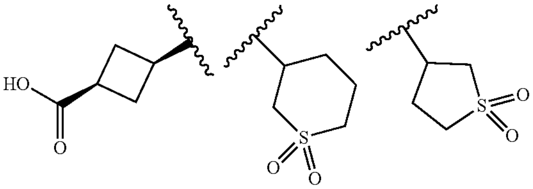

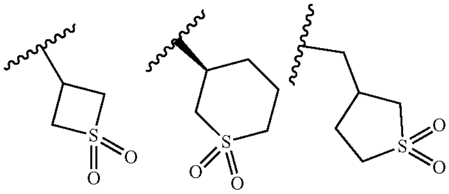

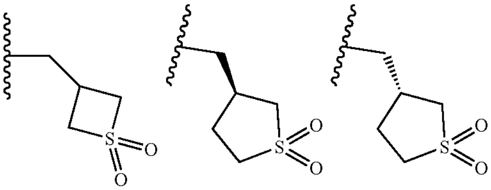

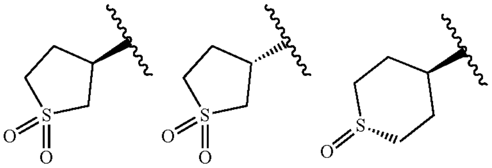

-continued
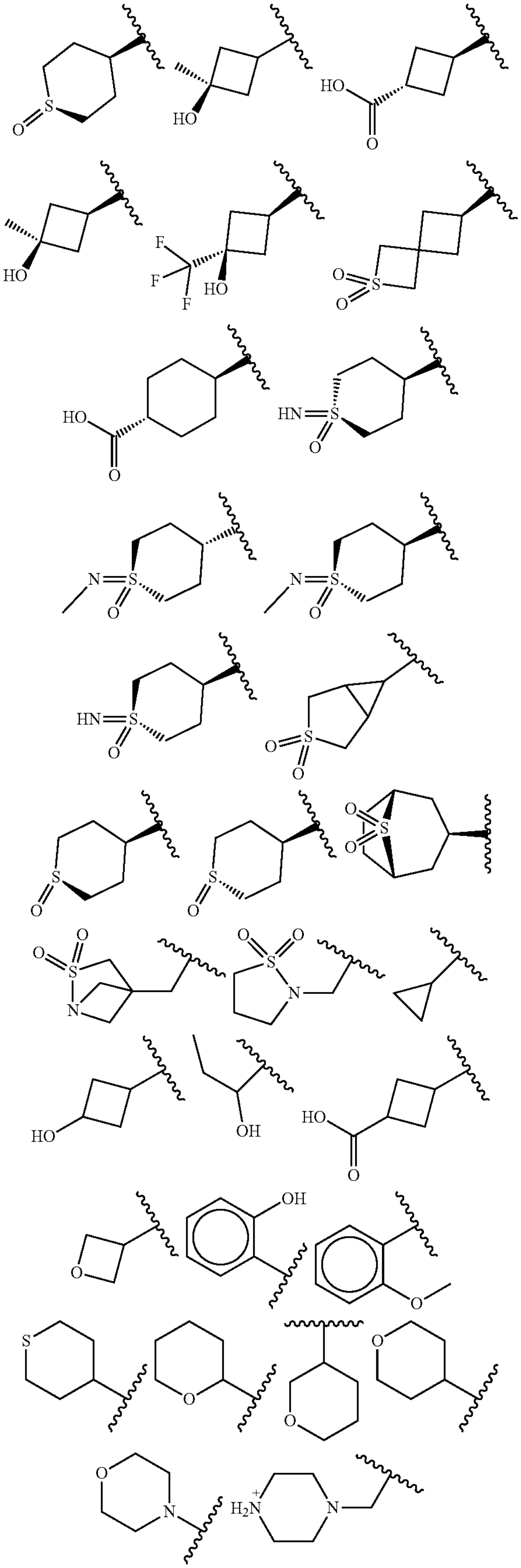
-continued
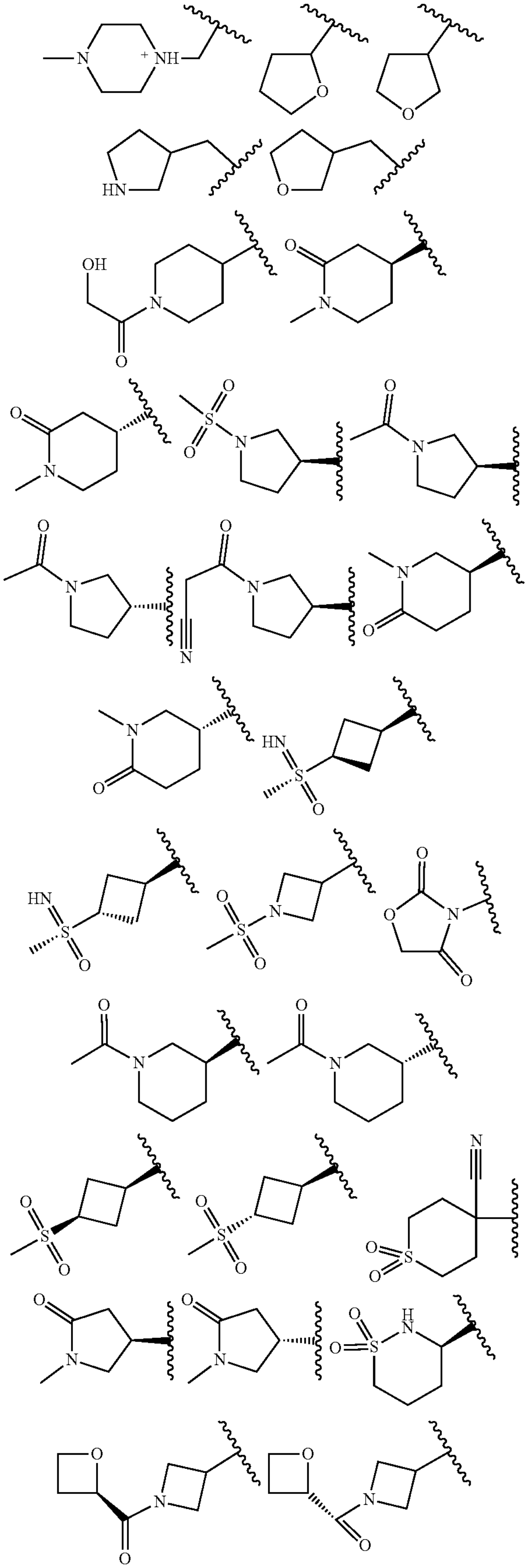

-continued
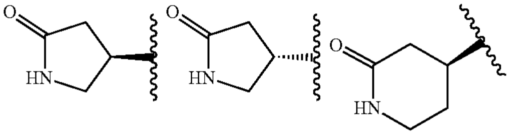
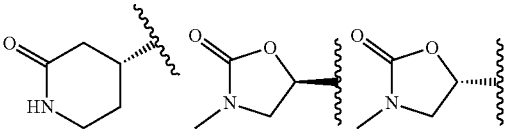
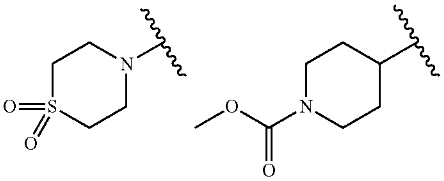
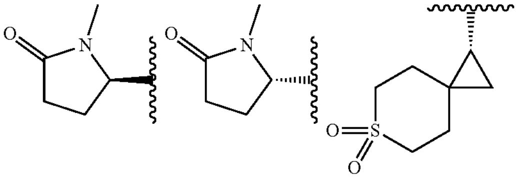
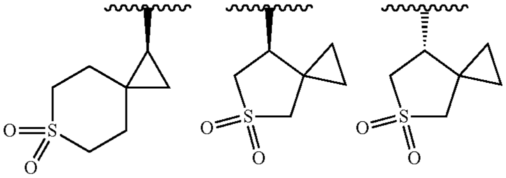
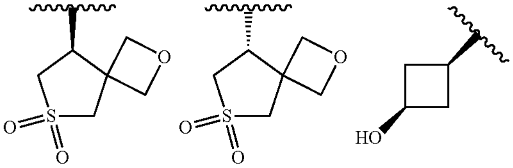
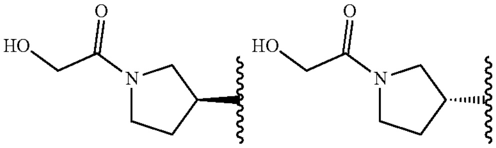
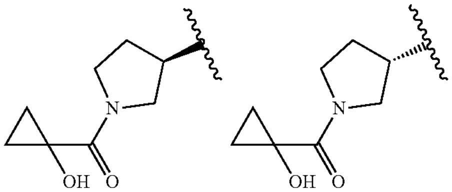
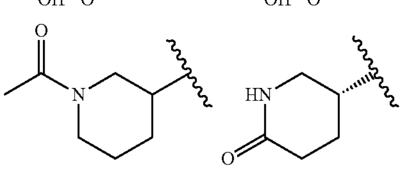
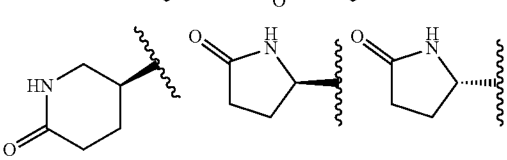
-continued
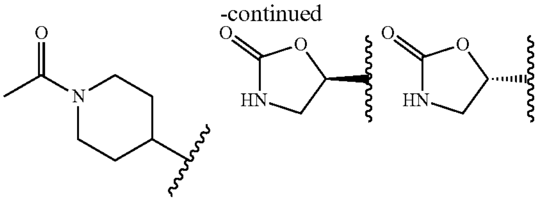
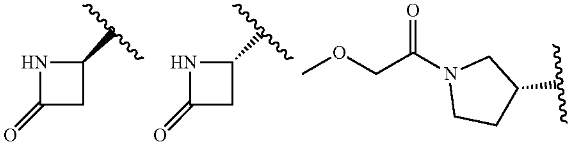
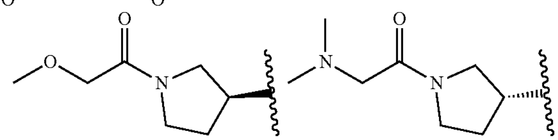
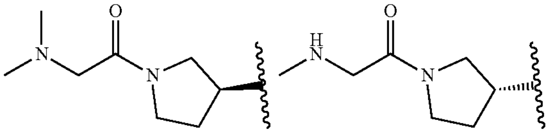
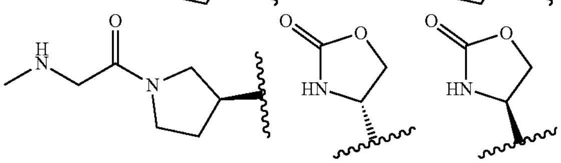
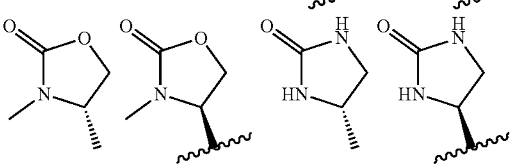
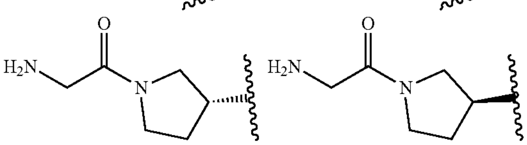
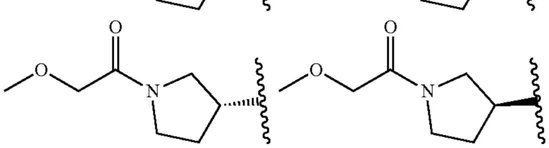
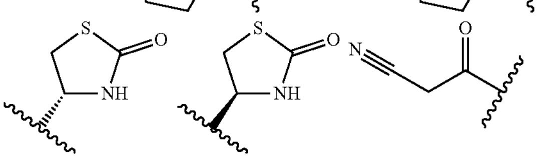
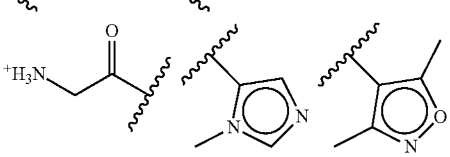
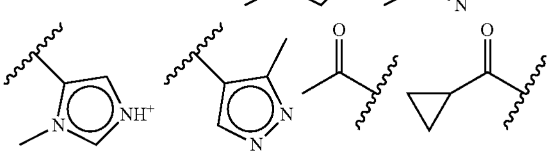
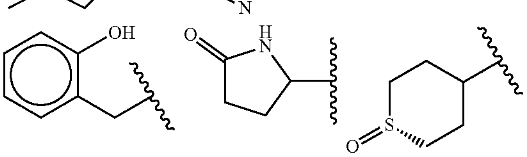

-continued

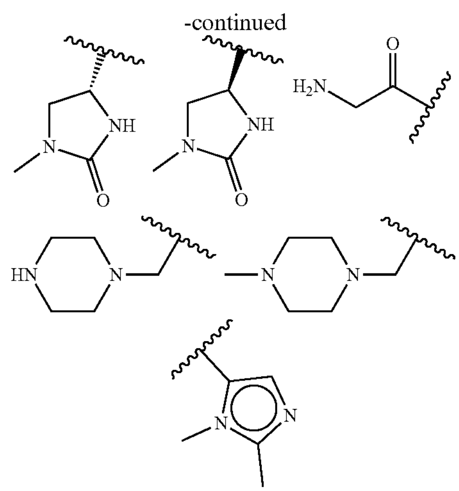

where each of the afore-mentioned hydrocarbon groups (e.g., alkyl, alkenyl, alkynyl, alkoxy residues) may be further substituted by one or more residues independently selected from halogen, hydroxyl, nitrile or C1-4-alkoxy groups;

$R^2$ is selected from the group consisting of: hydrogen, C1-3 alkyl, C1-3 alkoxyl, or C1-3 haloalkyl, preferably $R^2$ is methyl; or $R^1$ and $R^2$ together form a 4-7 membered ring; particularly a 5-6 membered heterocyclic ring having a further heteroatom selected from N, or O, which is optionally substituted with oxo, amino, aminoalkyl, sulfoxide, sulfoxide imine, sulfonyl, alkyl sulfoxide, sulfoximine, alkyl sulfonyl, cycloalkyl sulfoxide, cycloalkyl sulfonyl, sulfamoyl, alkyl sulfamoyl, cycloalkyl sulfamoyl;

$R^3$ is selected from the group consisting of: hydrogen, C1-3 alkyl (particularly $CH_2CH_3$ or $CH_3$, preferably $CH_3$), C1-3 alkoxyl, or C1-3 haloalkyl (particularly $CF_3$); or $R^4$ and $R^5$ are each independently selected from the group consisting of: hydrogen, C1-3 alkyl (e.g. methyl), pyridinyl, phenyl, pyrazidinyl or pyrimidinyl, optionally wherein the pyridinyl, phenyl, pyrazidinyl or pyrimidinyl is fused with a pyrrolyl, phenyl, pyrimidinyl, pyrazidinyl, imidazolyl, triazolyl, pyrazolyl, pyridinyl, quinolinyl, isoquinolinyl, quinazolinyl, which may be optionally substituted with C1-3 alkyl, C1-3 alkoxy, cyano, amine, difluoromethyl or halogen; or $R^4$ and $R^5$ together with the Q to which they attach form a non-aromatic heterocyclic 4-8 membered ring containing at least one heteroatom, particularly nitrogen, and optionally an additional heteroatom such as nitrogen or oxygen; and wherein the ring is fused with phenyl, pyridinyl, pyrazidinyl, pyrimidinyl which may be optionally substituted with halogen (e.g. bromine or chlorine), nitrile, methyl, methoxy, difluoromethyl, aminyl, or trifluoromethyl, pyrazidinyl or pyrimidinyl, wherein the phenyl, pyridinyl, pyrazidinyl or pyrimidinyl is optionally fused with a further heterocyclic 5- or 6-membered ring (e.g. pyrrolyl, imidazolyl, triazolyl, pyrazolyl or pyridinyl), which is optionally substituted with 1 to 3 groups selected from the group consisting of: C1-3 alkyl, C1-3 alkoxyl, C1-3 haloalkyl, pyrrolyl, imidazolyl, triazolyl, nitro, cyano, hydroxyl or halogen; or $R^4$ and $R^5$ together with the Q to which they attach form one of the following tricyclic ring structures:

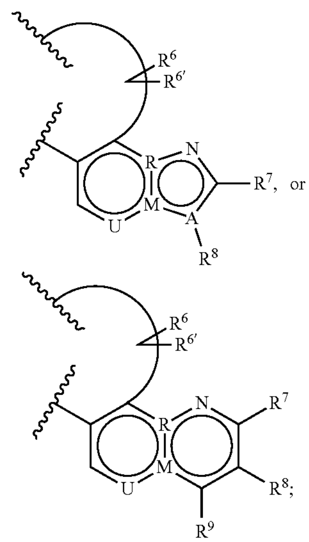

or

M, R and A are selected independently from the group consisting of: N, S or C, preferably M and R are selected independently from the group consisting of: N or C and A is selected independently from the group consisting of: N, S or C, preferably A is C;

U is selected from the group consisting of: N, or $CR^c$, wherein $R^c$ is selected from hydrogen, halogen, C1-3 alkyl, or C1-3 haloalkyl; suitably $R^c$ is selected from hydrogen, halogen or alkyl (particularly C1-3 alkyl);

$R^6$ and $R^{6'}$ are independently selected from the group consisting of: hydrogen, halogen (e.g. F), C1-3 alkyl (e.g. Me), C1-3 alkoxyl (e.g. OMe), C1-3 alkyl alkoxy (e.g. $CH_2OMe$), hydroxyl, alkyl hydroxyl (e.g. $CH_2OH$), amino alkyl (e.g. NHMe or $N(Me)_2$), C1-3 alkyl amino alkyl (e.g. $CH_2NHMe$ or $CH_2NH(Me)_2$), tertiary aminyl, cyclic aminyl (e.g. azetidinyl, morpholinyl), spirocyclic aminyl, C1-2 alkyl-4-6 saturated heterocyclic aminyl (e.g. $CH_2$-azetidinyl, $CH_2$-pyrrolidinyl or $CH_2$-morpholinyl), C0-2 alkyl oxetane, C0-2 alkyl oxolane, C0-2 alkyl azetidinyl or C0-2 alkyl pyrrolidinyl, C1-3 carboxyl, C1-3 haloalkyl (e.g. $CF_3$), methylacetyl (OAc) or ethanoate; preferably $R^6$ and $R^{6'}$ are both methyl (particularly gem dimethyl) or hydrogen, methyl or $CH_2OMe$; or $R^{6'}$ and $R^6$ together form a C3-5 membered saturated ring (e.g. cyclopropyl or thetrahydrofuran) or C4-5 membered saturated heterocycle ring containing oxygen (e.g. oxetane or furan such as tetrahydrofuran);

$R^7$ is selected from the group consisting of: C1-3 alkyl, C1-3 alkoxyl, C1-3 haloalkyl, nitro, cyano, SMe, SOMe, $SO_2Me$, pyrrolyl, imidazolyl, triazolyl, or halogen (particularly fluorine, methoxy or chlorine); and $R^8$ and $R^9$ are each independently selected from the group consisting of: hydrogen, C1-3 alkyl, C1-3 alkoxyl, hydroxyl, C1-3 hydroxyalkyl or halogen, and are suitably each independently selected from hydrogen, hydroxyl, or halogen (particularly F or Cl).

Suitably, in various aspects and embodiments, $R^1$ may be selected from the group consisting of the following structures:

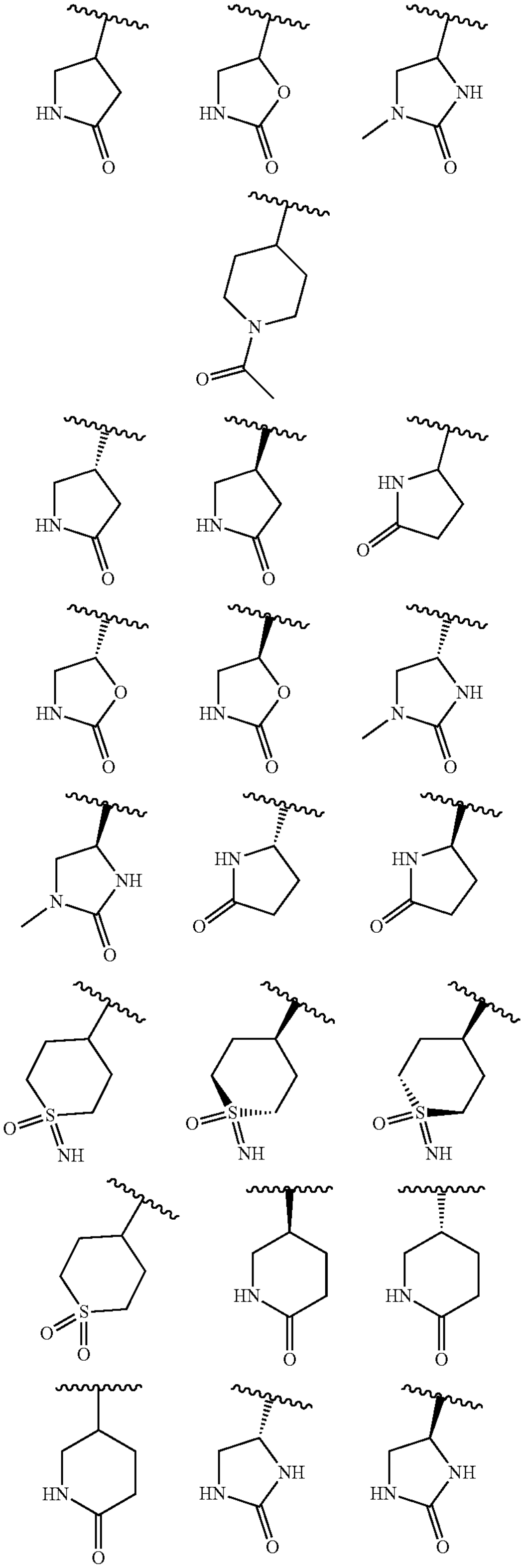

-continued

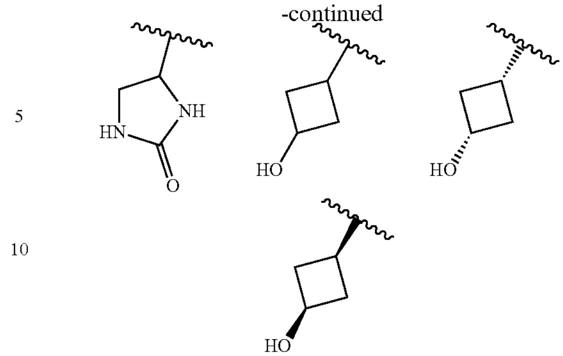

In various aspects and embodiments, $R^1$ may be selected from the group consisting of the following structures:

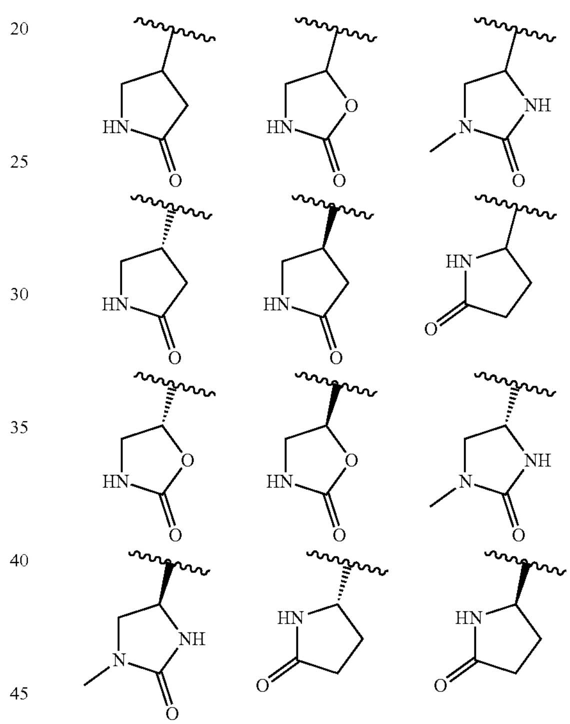

Suitably, $R^6$ and/or $R^{6'}$ may be independently selected from the group consisting of hydrogen, fluorine, methyl, ethyl, methoxy, ethoxy, haloalkyl, hydroxyl, $CH_2OH$, $CF_3$, $CH_2NHMe$ and $CH_2N(Me)_2$, preferably $R^6$ and $R^{6'}$ together are gem dimethyl, cyclopropyl, oxetane or furane such as tetrahydrofuran. More preferably, $R^6$ and/or $R^{6'}$ is installed in the benzylic position.

Suitably, U is selected from N or $CR^c$, particularly U is N. Suitably, R and M are each independently selected from N or C; in embodiments one of R and M is N and the other is C. In other embodiments, both of R and M are C. Suitably, A is selected from S or C. More suitably and particularly for 6,5 fused rings systems, A is S and M and R are C.

Typically, in embodiments as described above where A is S, $R^7$ is suitably methyl, and in embodiments where R, M are C or N, $R^7$ may be halogen, suitably chlorine or fluorine. In these embodiments, $R^8$ and $R^9$ may particularly be hydrogen. In these embodiments U is typically N. Suitably, where $R^7$ is attached to a fused pyridinyl, $R^7$ is typically methoxy or chlorine.

Suitably, in compounds of this disclosure, $R^3$ is selected from the group consisting of: C1-3 haloalkyl, particularly C1-3 trihaloalkyl or more particularly trifluoromethyl.

In embodiments of the disclosure as described herein $R^4$ and $R^5$ may together form one or the following structures:

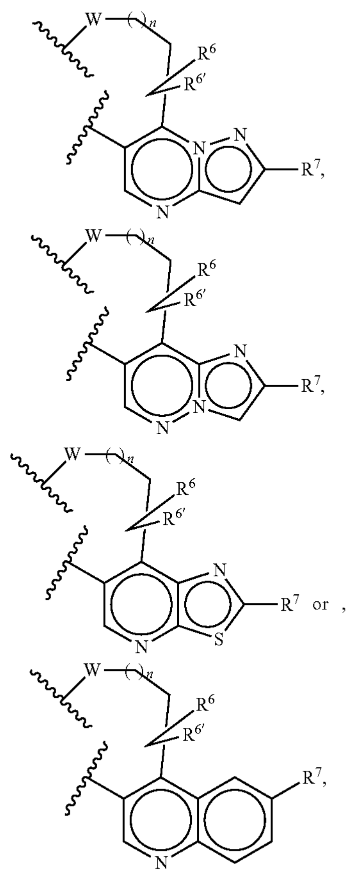

or , wherein W is selected from the group consisting of $CR^dR^e$, $NR^f$ or O, wherein $R^d$, $R^e$ and $R^f$ are each independently selected from hydrogen, C1-3 alkyl (e.g. Me), C1-3 alkyl alkoxy (e.g. $CH_2OMe$), alkyl hydroxyl (e.g. $CH_2OH$), C1-3 alkyl amino alkyl (e.g. $CH_2NHMe$ or $CH_2NH(Me)_2$), tertiary aminyl, cyclic aminyl (e.g. azetidinyl, morpholinyl), spirocyclic aminyl, C1-2 alkyl-4-6 saturated heterocyclic aminyl (e.g. $CH_2$-azetidinyl, $CH_2$-pyrrolidinyl or $CH_2$-morpholinyl), C0-2 alkyl oxetane, C0-2 alkyl oxolane, C0-2 alkyl azetidinyl or C0-2 alkyl pyrrolidinyl, preferably $R^d$ and $R^e$ are both hydrogen or methyl (gem dimethyl), n is from 0-3, particularly 1 or 2 and is suitably 2;

$R^6$ and/or $R^{6'}$ are located at any position on the cyclic/heterocyclic ring system; suitably $R^6$ and/or $R^{6'}$ are located at the benzylic position and are each independently selected from hydrogen, hydroxyl, fluorine, methyl or methoxy. In embodiments, at least one of $R^6$ and $R^{6'}$ is methyl. haloalkyl or methoxyl (e.g. $CH_2OMe$, OMe, $CF_3$); in embodiments at least one of $R^6$ and $R^{6'}$ is hydrogen. Alternatively, $R^{6'}$ and $R^6$ together form a C3-5 membered saturated ring (e.g. cyclopropyl) or C4-5 membered saturated heterocycle ring containing oxygen (e.g. oxetane or furan such as tetrahydrofuran).

In some embodiments both $R^6$ and $R^{6'}$ are methyl; in other embodiments both of $R^6$ and $R^{6'}$ are hydrogen; and $R^7$ may be particularly hydroxyl, chlorine, fluorine, methoxy or methyl.

Beneficially, W is $CR^dR^e$, wherein $R^d$ and $R^e$ are each independently selected from hydrogen, or methyl; particularly, wherein $R^d$ and $R^e$ are hydrogen.

Typically, in embodiments, where $R^d$ and $R^e$ are not hydrogen, $R^6$ and/or $R^{6'}$ may particularly be hydrogen.

More suitably, in various embodiments of the disclosure $R^4$ and $R^5$ together with the Q to which they attach, form one of the following tricyclic structures:

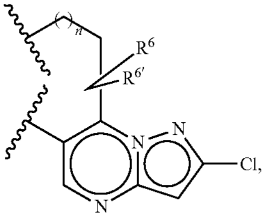

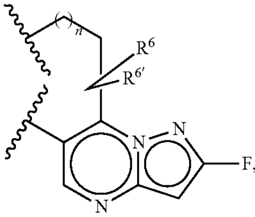

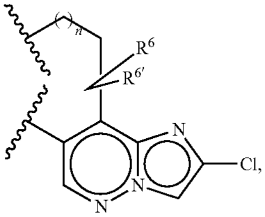

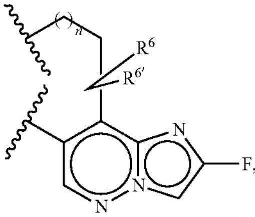

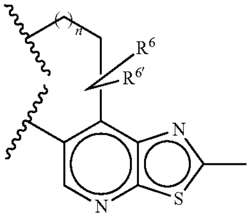

,

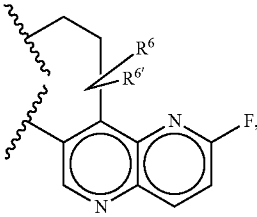

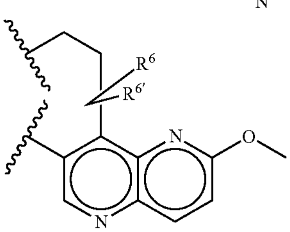

or

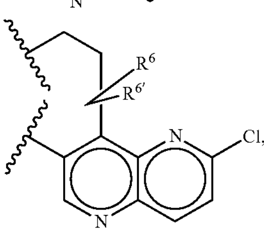

wherein $R^6$, $R^{6'}$ and n are as disclosed above or elsewhere herein.

Even more suitably, in various embodiments of the disclosure, typically n=1 and $W{=}CR^dR^e$, and $R^4$ and $R^5$ together with the Q to which they attach form one of the following tricyclic structures:

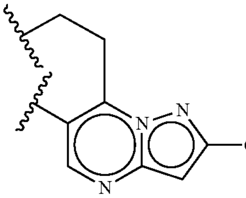,
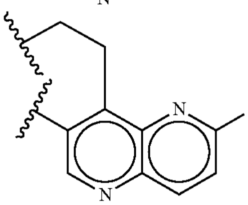,
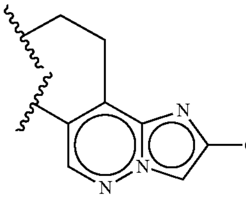,
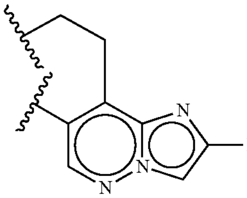,
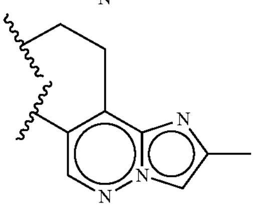,
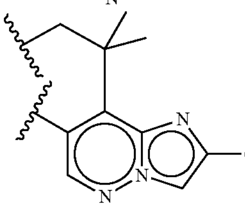,
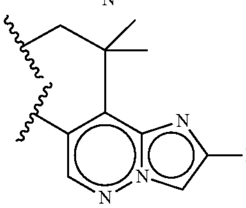,
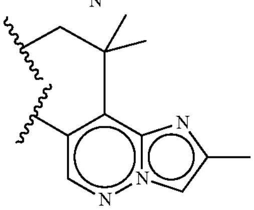,
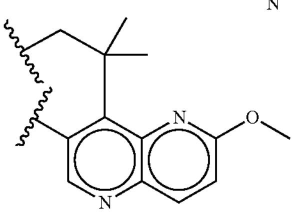,
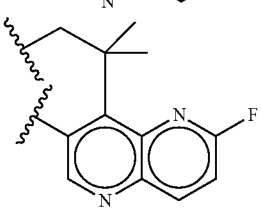 or
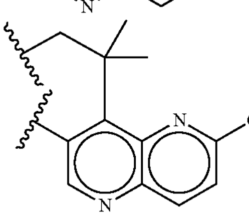.
Typically, in various embodiments of the disclosure, where n=2 and W═$CR^dR^e$, $R^4$ and $R^5$ together form one of the following 6-membered tricyclic structures, wherein $R^6$ is suitably selected from Me, OMe, $CH_2OMe$ and OH and $R^{6'}$ is H:
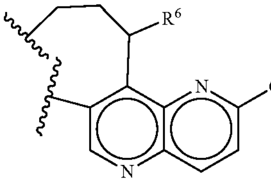,
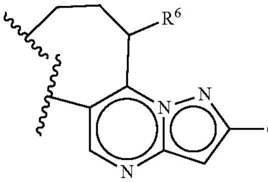,
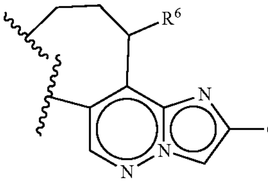,
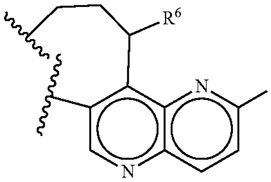,
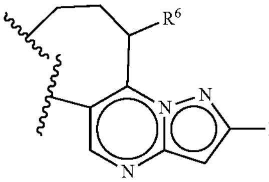,
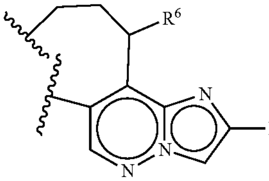,
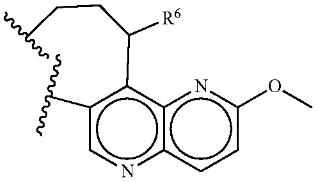
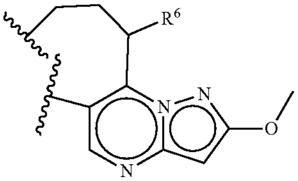,
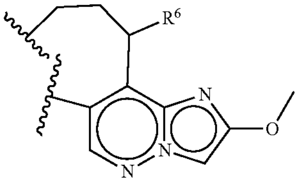, or -continued

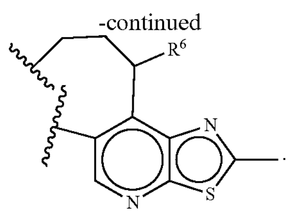

Suitably, in various embodiments of the disclosure, n=2 and W═$CH_2$, and $R^4$ and $R^5$ together form a tricyclic structure wherein $R^6$ and $R^{6'}$ are H, such as the compound is selected from compounds of the following structure:

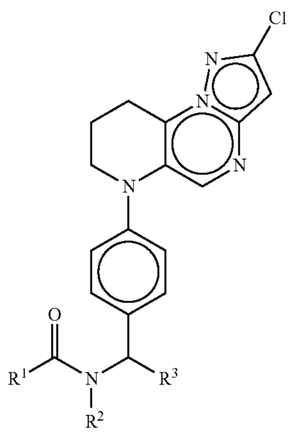

wherein $R^1$ is a lactone or lactam and may suitably be selected from the group consisting of:

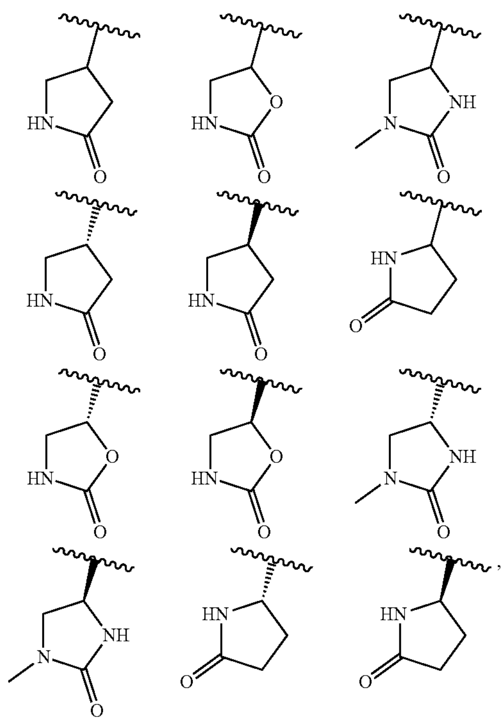

and optionally wherein $R^2$ may be methyl or hydrogen, and $R^3$ may be haloalkl, particularly trifluoromethyl.

In various embodiments of the disclosure, where n=2 and where W is selected from $CR^dR^e$ or O, $R^4$ and $R^5$ together form one of the following 6-membered tricyclic structures, wherein $R^6$ and $R^{6'}$ are suitably selected from H or Me:

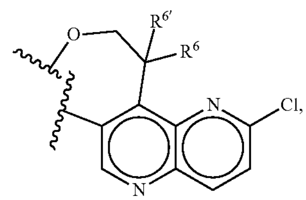

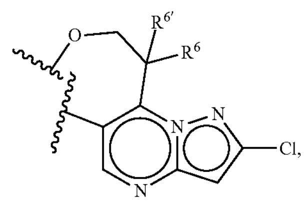

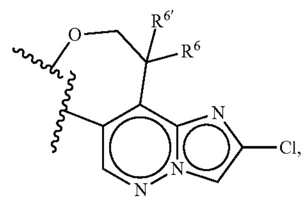

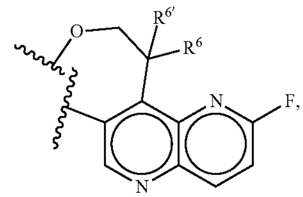

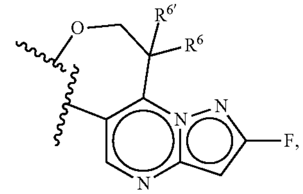

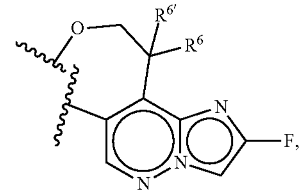

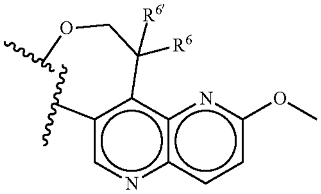

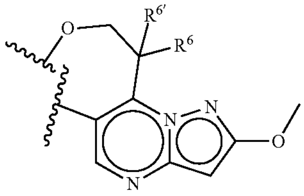

-continued
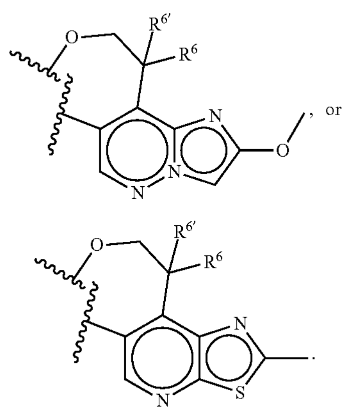
In various alternative embodiments of the disclosure, $R^4$ and $R^5$ together with the Q to which they attach form one of the following bicyclic structures, wherein n=1-3:
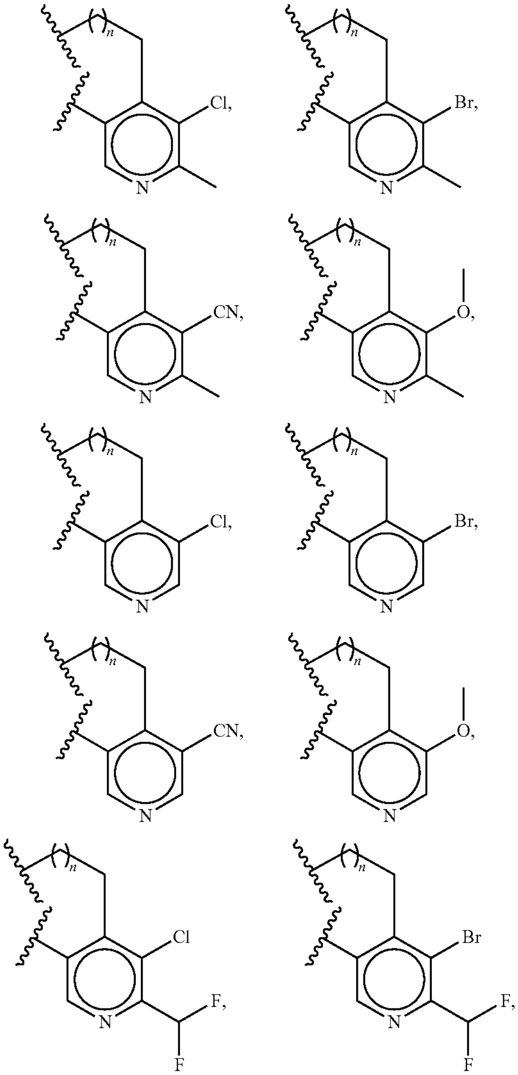
-continued
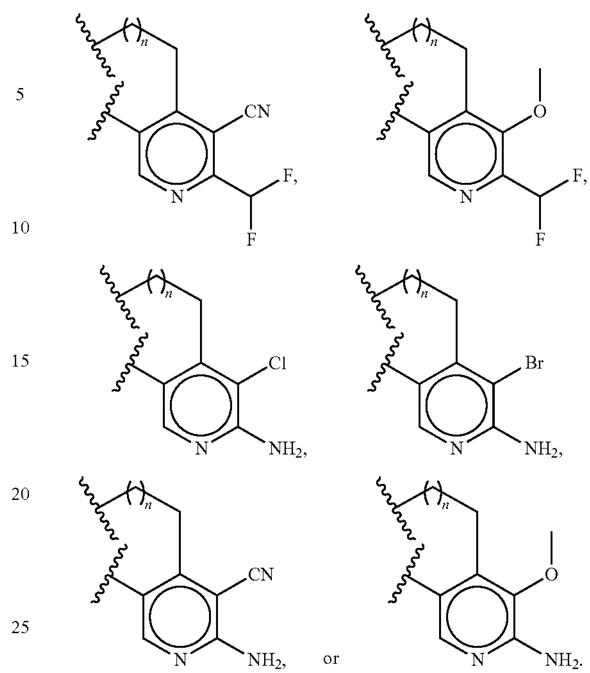
Suitably, $R^4$ and $R^5$ together with the Q to which they attach form one of the following bicyclic structures, wherein n=1-3:
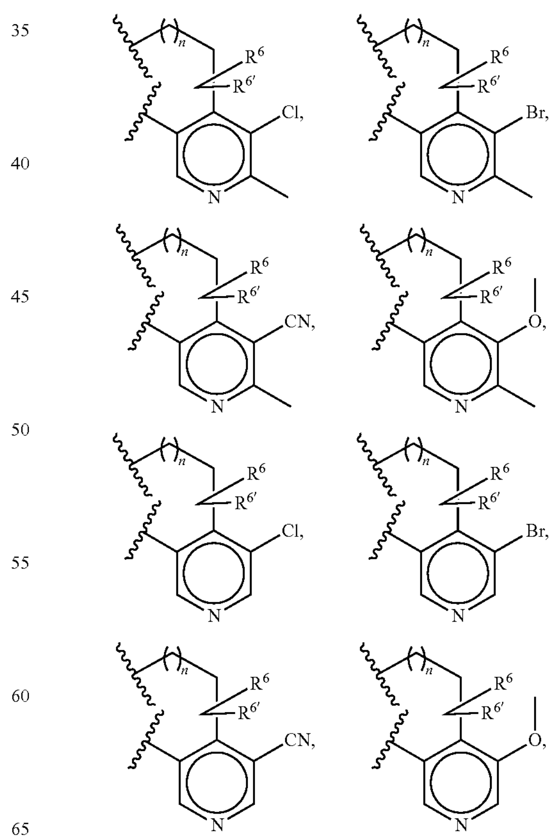

-continued

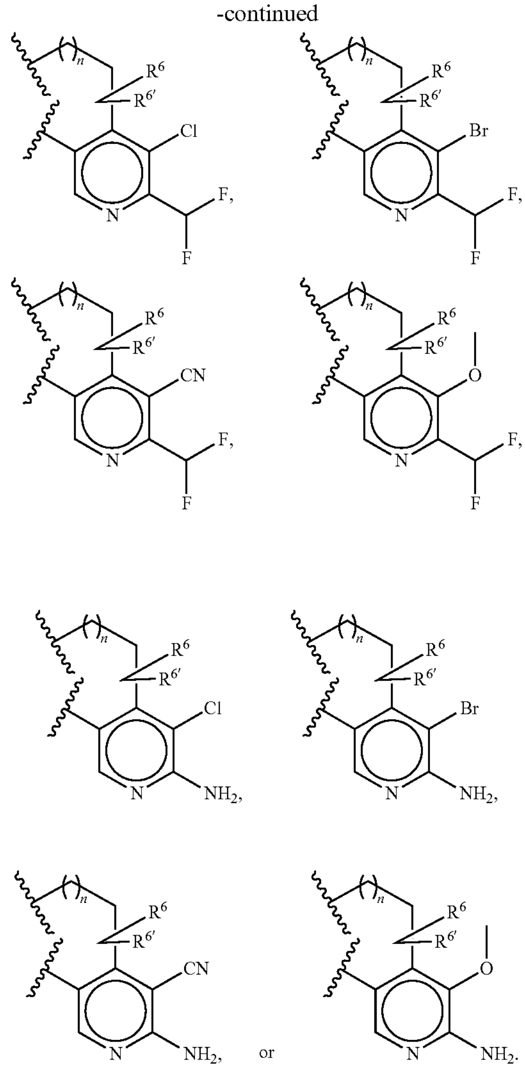

Suitably, $R^6$ and/or $R^{6'}$ may be independently selected from the group consisting of hydrogen, fluorine, methyl, ethyl, methoxy, ethoxy, hydroxyl, $CH_2OH$, $CH_2NHMe$ and $CH_2N(Me)_2$, preferably $R^6$ and $R^{6'}$ together are gem dimethyl or cyclopropyl. More preferably, $R^6$ and/or $R^{6'}$ is installed in the benzylic position.

More suitably, $R^4$ and $R^5$ together with the Q (where Q is N) to which they attach form the following bicyclic structure, wherein n=1:

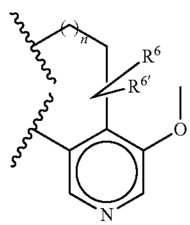

In particular, $R^4$ and $R^5$ together with the Q (where Q is N) to which they attach may form the following bicyclic structure, wherein n=1, X, Y, and Z are C and V is CO:

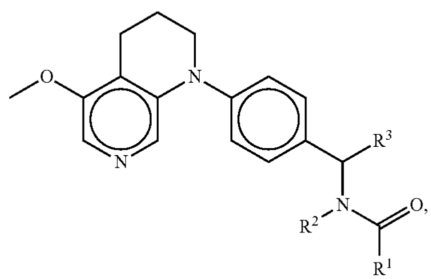

where $R^1$ is selected from the group consisting of: sulfonyl, sulfoxide, sulfoximine, alkyl sulfonyl, alkyl sulfoxide, cycloalkyl sulfonyl, cycloalkyl sulfoxide, sulfamoyl, alkyl sulfamoyl, cycloalkyl sulfamoyl or the following structures:

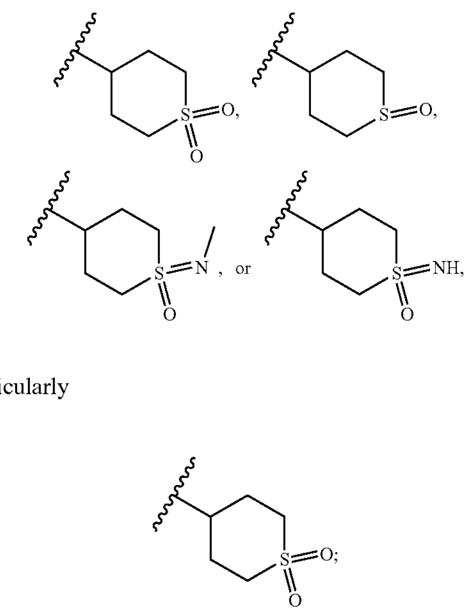

particularly

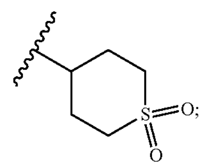 [SMILES: *C1CCS(=O)(=O)CC1]

and optionally further wherein $R^2$ is selected from the group consisting of: hydrogen, methyl or ethyl (particularly methyl); and $R^3$ is selected from the group consisting of: alkyl or haloalkyl (particularly trifluoromethyl).

Linear Non-Cyclised Series

Also disclosed herein is a compound having the structural formula (I) or (II), or a pharmaceutically acceptable salt, solvate, prodrug, or pharmaceutically active metabolite thereof:

(I)

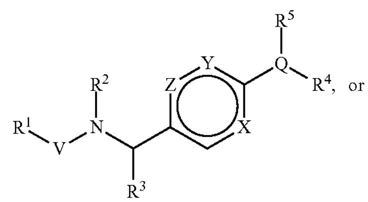

-continued (II)

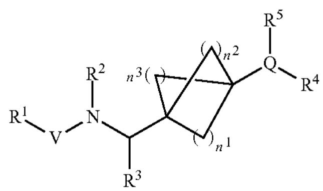

wherein

Q is N or $CR^a$, where $R^a$ is selected from hydrogen, OH, carbonyl, alkyl, alkoxy (e.g. OMe), preferably where Q is N;

X, Y and Z are each selected independently from N or $CR^b$, where $R^b$ is selected from hydrogen, halo alkyl (e.g. $CF_3$), halogen (e.g. F); in some embodiments one of X, Y and Z is CF and the rest are CH; preferably where X is CF. In some embodiments one of X, Y and Z is N, preferably one of X or Y is N and the rest are CH. In some embodiments X or Y is CF and Z is CH. In some preferred embodiments X, Y and Z are CH;

V is selected from the group consisting of: CO, SO, SONH, SOMe and $SO_2$;

$n^1$, $n^2$ and $n^3$ are independently selected from 1 to 3 (e.g. 1 and 2); particularly, $n^1$ may be 1 and $n^2$ may be 2. In some beneficial embodiments $n^1=n^2=n^3$ and is 1 or 2;

$R^1$ is selected from the group consisting of: alkyl, alkenyl, alkynyl, hydroxyalkyl, alkoxy, cycloalkyl, a 4-7 membered saturated or unsaturated heterocyclic ring having heteroatoms selected from N, S and O optionally substituted with hydroxyl (e.g. $CH_2OH$), nitrile (e.g. $CH_2CN$), oxo, amino, aminoalkyl and/or dioxo, sulfonyl, sulfoxide, sulfoximine, alkyl sulfonyl, alkyl sulfoxide, cycloalkyl sulfonyl, cycloalkyl sulfoxide, sulfamoyl, alkyl sulfamoyl, cycloalkyl sulfamoyl or the following structures:

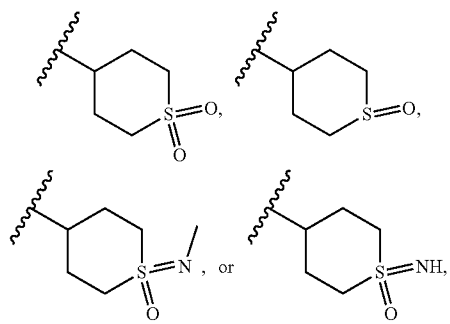

or any one of the following structures:

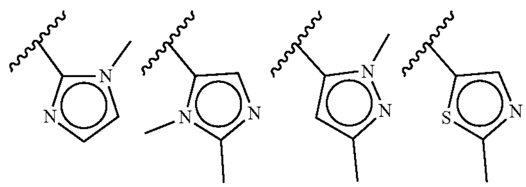

-continued

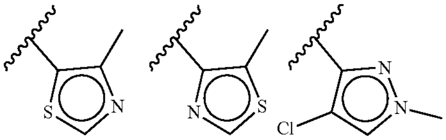

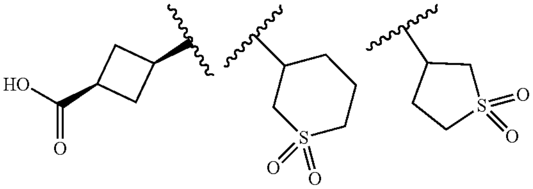

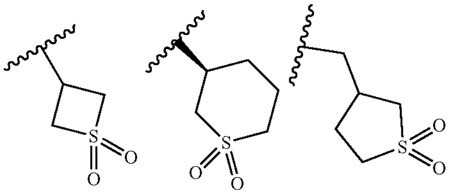

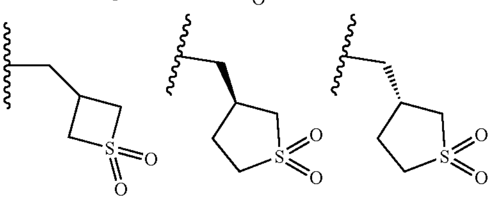

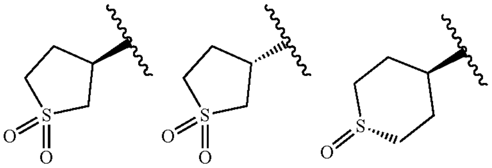

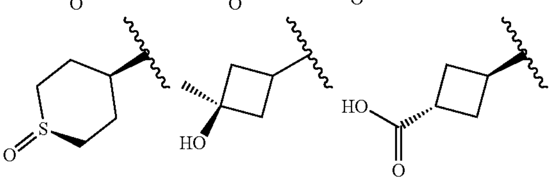

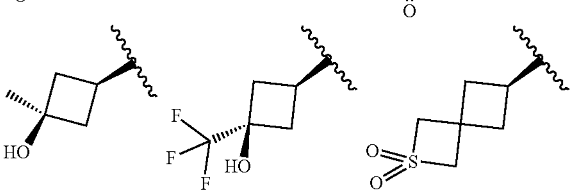

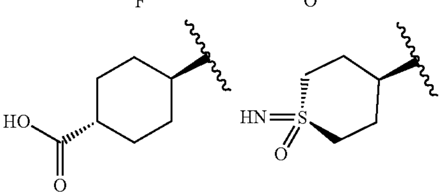

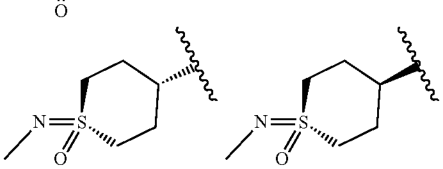

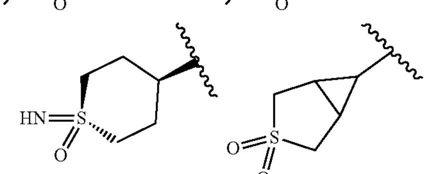

-continued
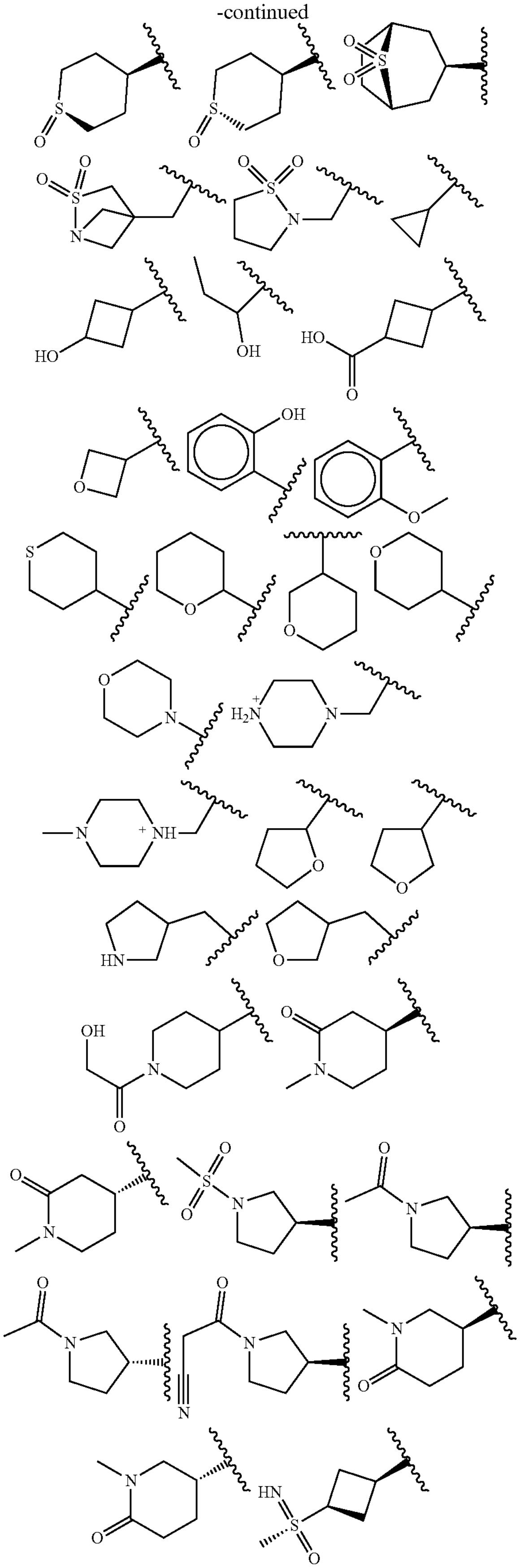
-continued
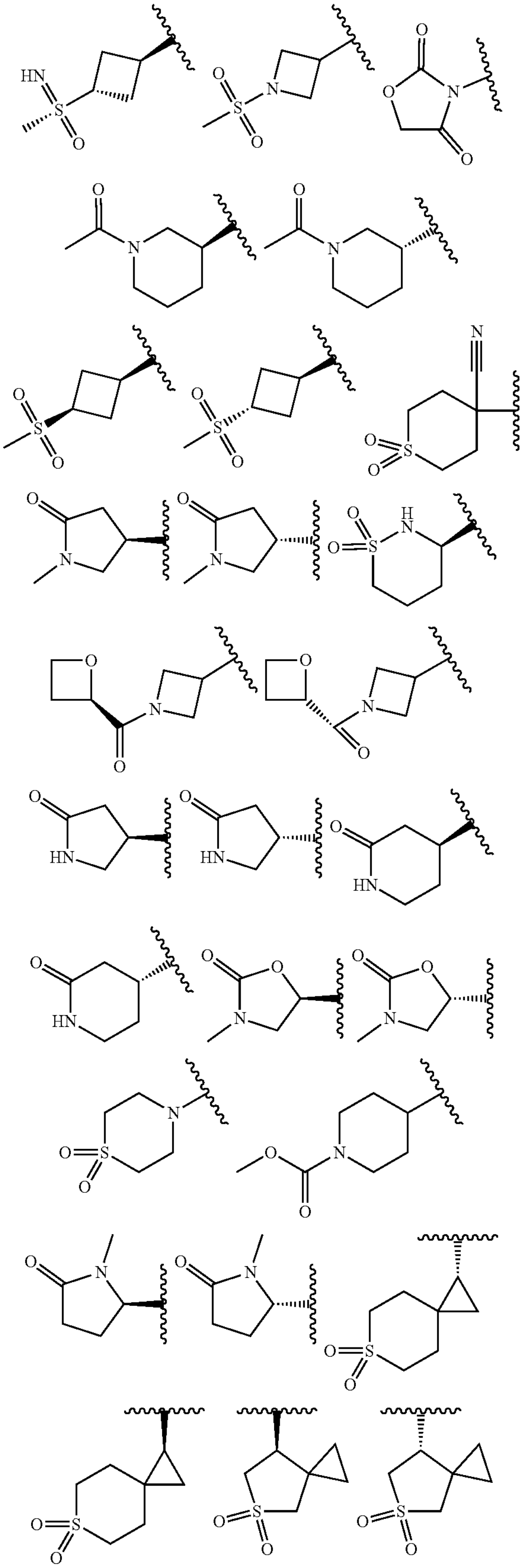

-continued

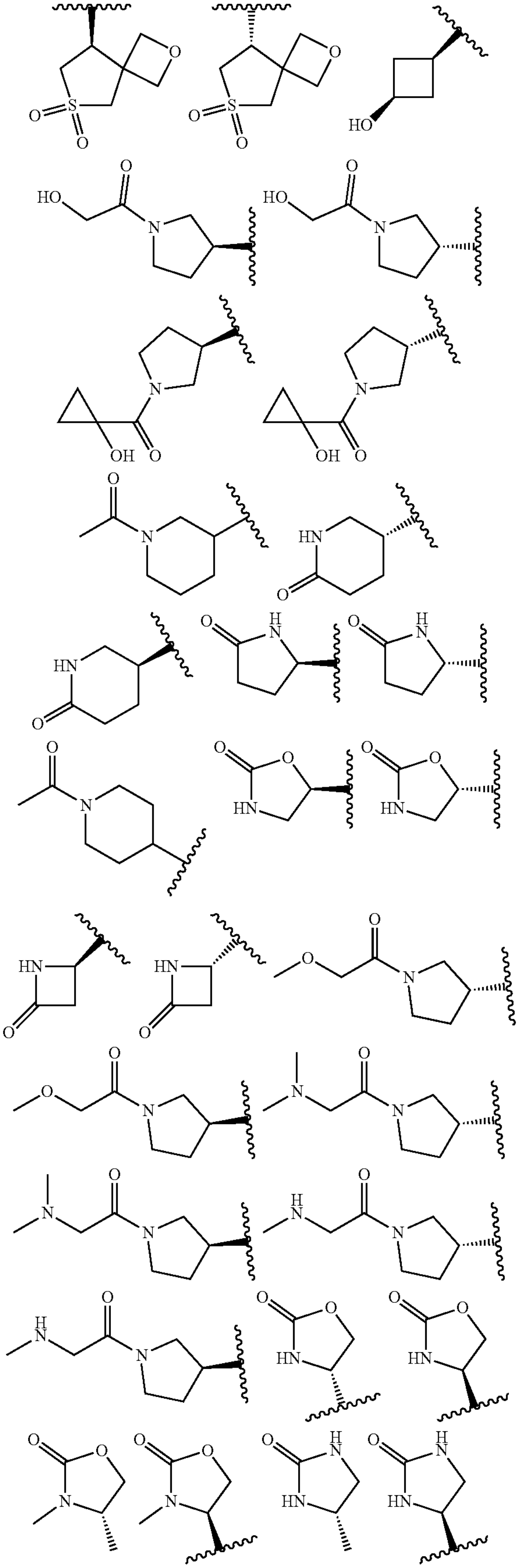

-continued

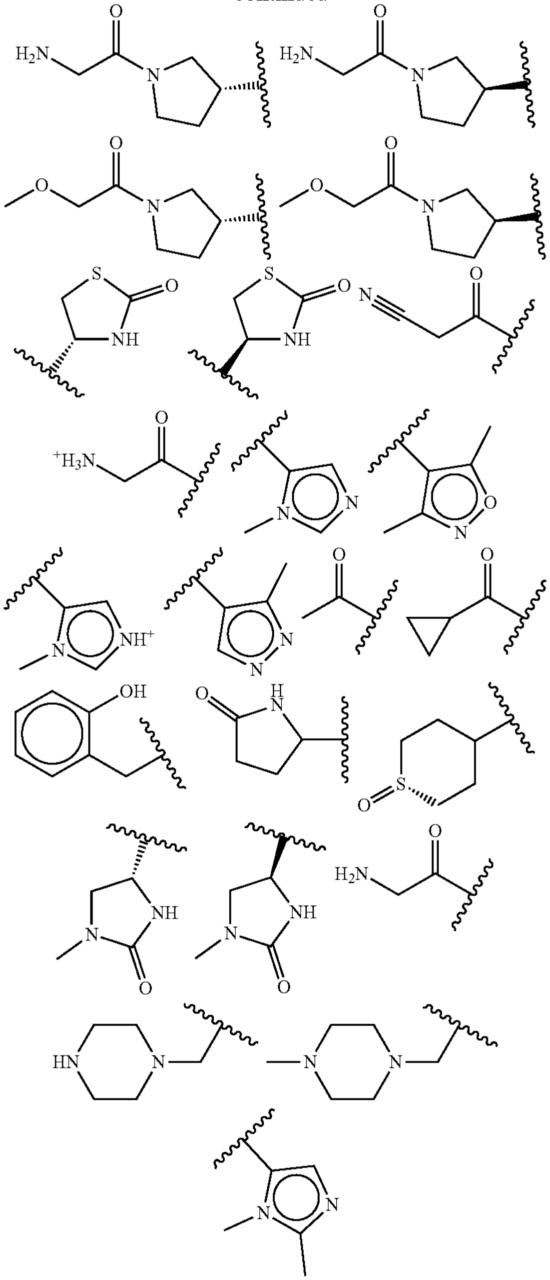

where each of the afore-mentioned hydrocarbon groups (e.g., alkyl, alkenyl, alkynyl, alkoxy residues) may be further substituted by one or more residues independently selected from halogen, hydroxyl, nitrile or C1-4-alkoxy groups;

$R^2$ is selected from the group consisting of: hydrogen, C1-3 alkyl, C1-3 alkoxyl, C1-3 haloalkyl, preferably $R^2$ is methyl, or $R^1$ and $R^2$ together form a 4-7 membered ring; particularly a 5-6 membered heterocyclic ring having a further heteroatom selected from N or O, which is optionally substituted with oxo, amino, aminoalkyl, sulfoxide, sulfoximine, sulfonyl, alkyl sulfoxide, alkyl sulfonyl, cycloalkyl sulfoxide, cycloalkyl sulfonyl, sulfamoyl, alkyl sulfamoyl, cycloalkyl sulfamoyl;

- $R^3$ is selected from the group consisting of: hydrogen, C1-3 alkyl (particularly or $CH_2CH_3$ or $CH_3$, preferably $CH_3$), C1-3 alkoxyl, C1-3 haloalkyl (particularly $CF_3$);
- $R^4$ is phenyl, pyridinyl, pyrazidinyl, pyrimidinyl which may be optionally substituted with halogen (e.g. bromine or chlorine), nitrile, methyl, methoxy, difluoromethyl, aminyl, or trifluoromethyl, pyrazidinyl or pyrimidinyl, wherein the phenyl, pyridinyl, pyrazidinyl or pyrimidinyl is optionally fused with a further heterocyclic 5- or 6-membered ring (e.g. pyrrolyl, imidazolyl, triazolyl, pyrazolyl or pyridinyl), which is optionally substituted with 1 to 3 groups selected from the group consisting of: C1-3 alkyl, C1-3 alkoxyl, C1-3 haloalkyl, pyrrolyl, imidazolyl, triazolyl, nitro, cyano, hydroxyl or halogen;
- or is one of the following bicyclic structures and $R^5$ is hydrogen or methyl:

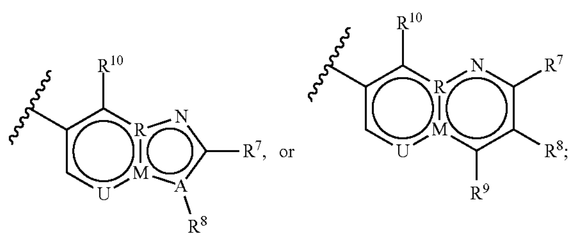

or wherein

- M, R and A are selected independently from the group consisting of: N, S or C, preferably M and R are selected independently from the group consisting of: N or C and A is selected independently from the group consisting of: N, S or C, preferably A is C;
- U is selected from the group consisting of: N, S or $CR^c$, wherein $R^c$ is selected from hydrogen, halogen or alkyl; suitably at least two of X, Y and Z are C;
- $R^7$ is selected from the group consisting of: C1-3 alkyl, C1-3 alkoxyl, C1-3 haloalkyl, nitro, cyano, SMe, SOMe, $SO_2Me$, pyrrolyl, imidazolyl, triazolyl, or halogen (particularly chlorine, methoxy or fluorine);
- $R^8$ and $R^9$ are each independently selected from the group consisting of: hydrogen, C1-3 alkyl, C1-3 alkoxyl, hydroxyl, C1-3 hydroxyalkyl or halogen; suitably $R^8$ and $R^9$ are each independently selected from hydrogen, methyl, hydroxyl, methoxy or chlorine, preferably hydrogen; and
- $R^{10}$ is selected from the group consisting of: hydrogen, C1-3 alkyl, C1-3 alkoxyl, C1-3 hydroxy alkyl, halogen, amide, C3-5 membered saturated ring (e.g. cyclopropyl) or C4-5 membered saturated heterocycle ring. Optionally substituted with OMe or halogen (e.g. F), particularly $R^{10}$ is selected from the group consisting of: $CHOMeCH_3$, $CHOHCH_3$, $COCH_3$, $CH_2OCH_3$, $CH_2O$cyclopropyl, $CHNH_2CH_3$, $CHNHMeCH_3$, $CHNMe_2CH_3$, CO-aziridine amide, tetrahydrofuran or oxetane.

Suitably, $R^1$ is selected from the group consisting of the following structures:

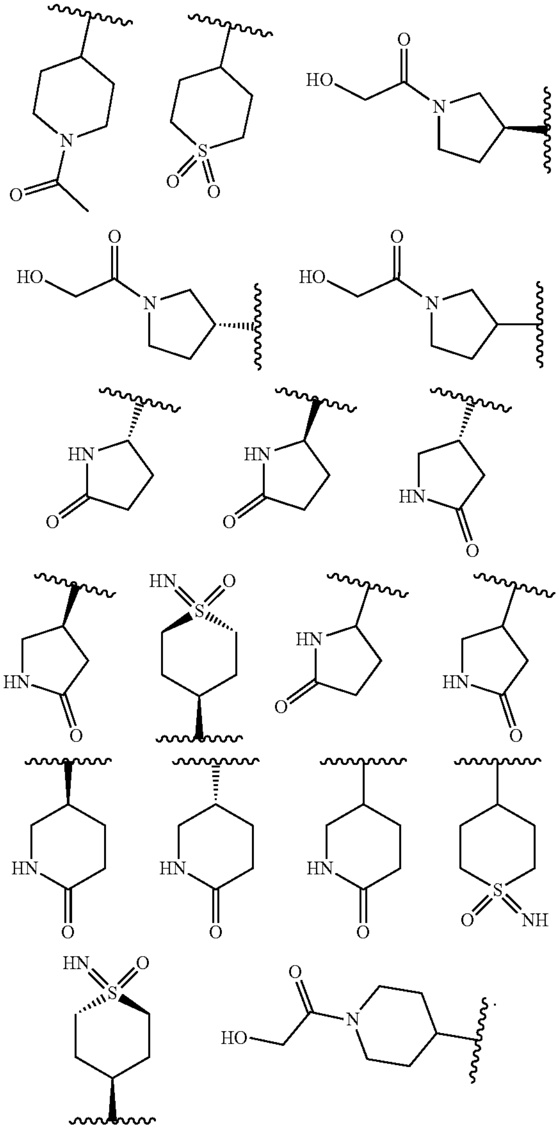

Preferably, $R^1$ is selected from the group consisting of the following structures:

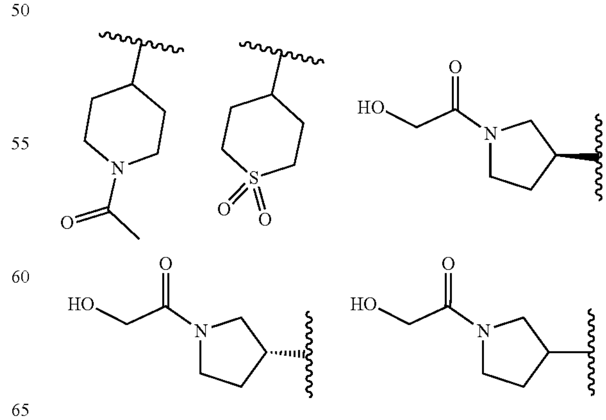

-continued
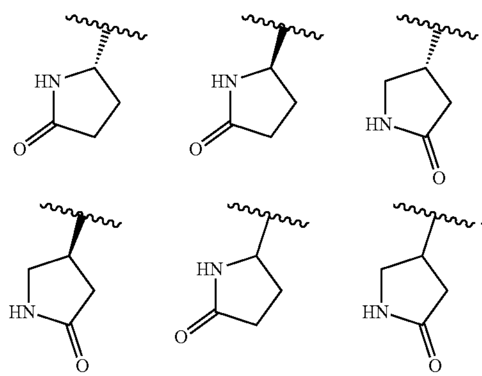
In embodiments, in any of the above compounds $R^4$ may particularly be selected from the group consisting of:
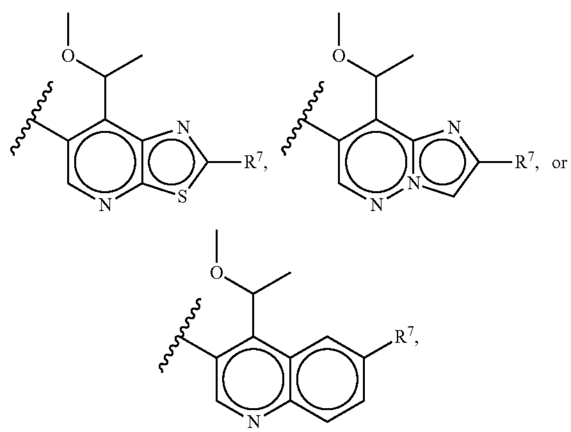
wherein
$R^7$ is as defined above or elsewhere herein, and may particularly be methoxy.
In embodiments, in any of the above compounds $R^4$ may be selected from the group consisting of:
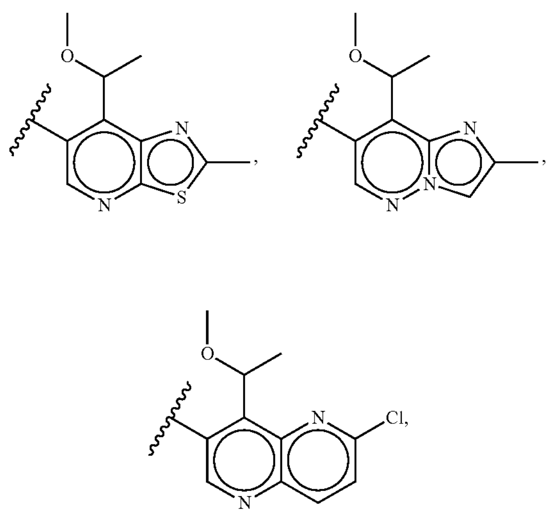
-continued
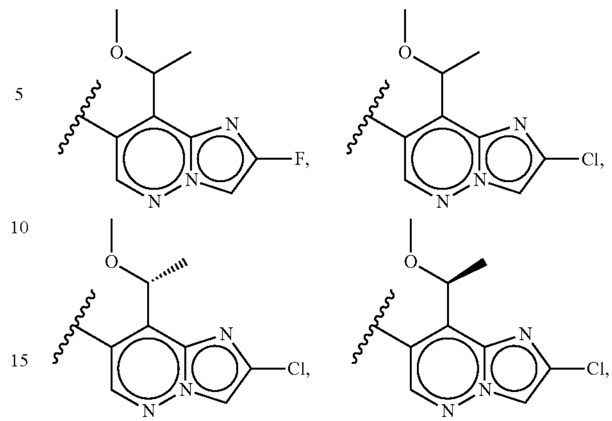
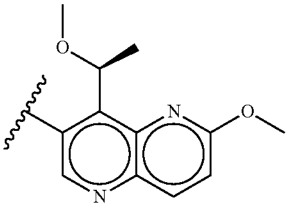
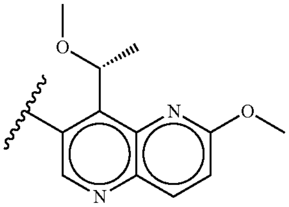
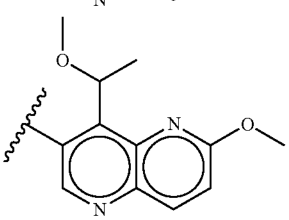
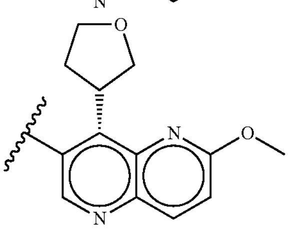
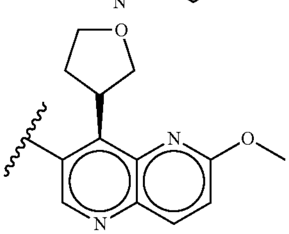
or
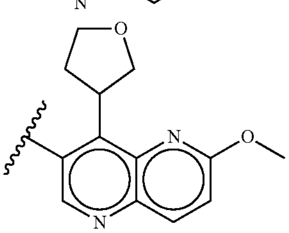

In various aspects and embodiments, compounds of the following structures are provided:

(Ia)

(Ib)

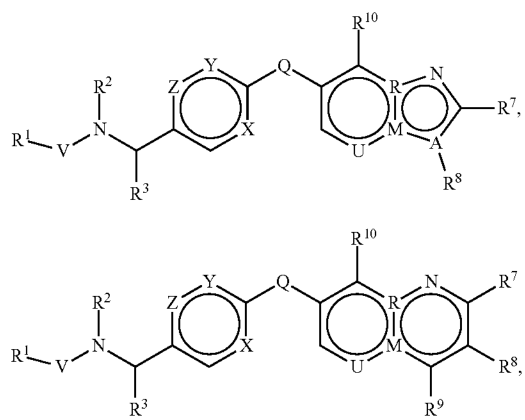

wherein

M and R are selected independently from the group consisting of: N, S or C, preferably M and R are selected independently from the group consisting of: N or C, preferably A is C;

U is selected from the group consisting of: N, S or $CR^c$, wherein $R^c$ is selected from hydrogen, halogen or alkyl (particularly C1-3 alkyl);

Q is N or $CR^a$, where $R^a$ is selected from hydrogen, OH, carbonyl, alkyl, alkoxy (e.g. OMe), preferably where Q is N;

X, Y and Z are each selected independently from N or $CR^b$, where $R^b$ is selected from hydrogen, halo alkyl (e.g. $CF_3$), halogen (e.g. F); in some embodiments one of X, Y and Z is CF and the rest are CH; preferably where X is CF. In some embodiments one of X, Y and Z is N, preferably one of X or Y is N and the rest are CH. In some embodiments X or Y is CF and Z is CH. In some preferred embodiments X, Y and Z are CH;

V is selected from the group consisting of: CO, SO, SONH, SONMe, and $SO_2$, preferably CO;

$R^1$ is selected from the group consisting of: alkyl, alkenyl, alkynyl, hydroxalkyl (e.g. $CH_2OH$), alkoxy, cycloalkyl, a 4-7 membered saturated or unsaturated heterocyclic ring having heteroatoms selected from N, S and O optionally substituted with hydroxyl, nitrile (e.g. $CH_2CN$), oxo, amino, aminoalkyl and/or dioxo, sulfonyl, sulfoxide, sulfoximine, alkyl sulfonyl, alkyl sulfoxide, cycloalkyl sulfonyl, cycloalkyl sulfoxide, sulfamoyl, alkyl sulfamoyl, cycloalkyl sulfamoyl or the following structures:

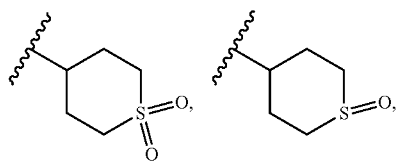

-continued

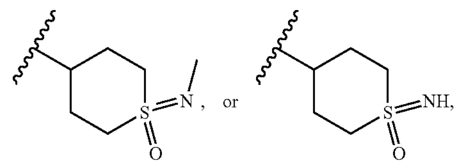

or any one of the following structures:

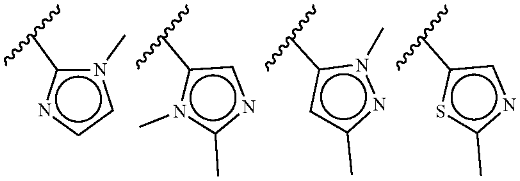

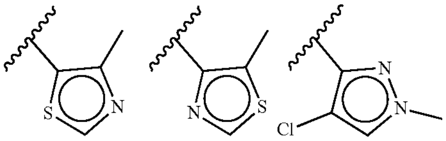

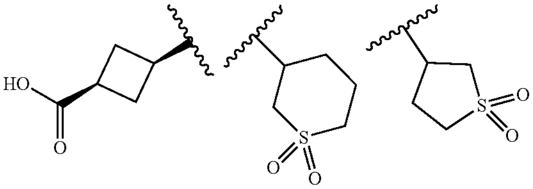

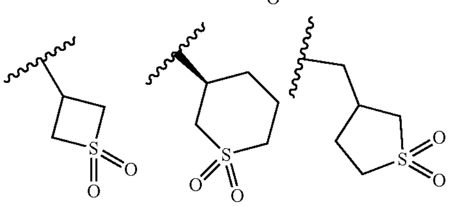

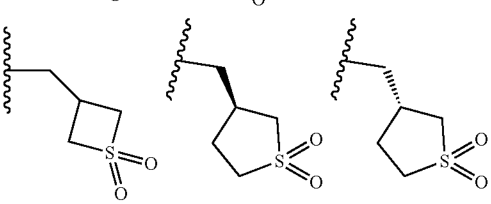

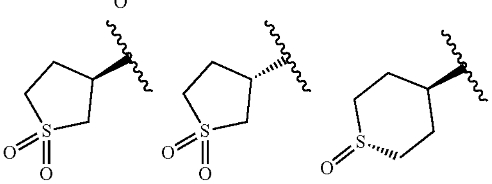

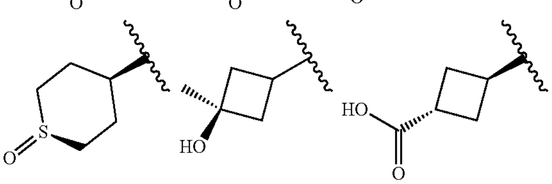

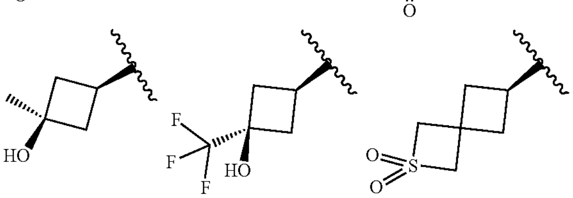

-continued
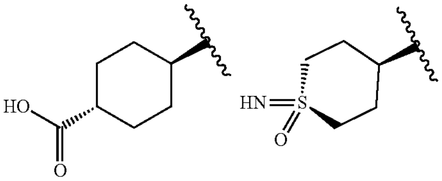
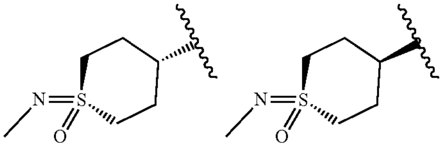
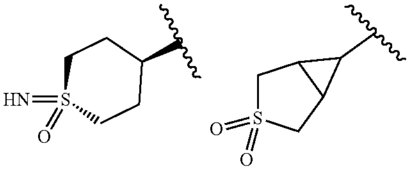
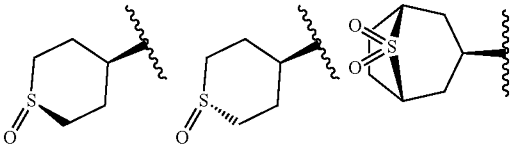
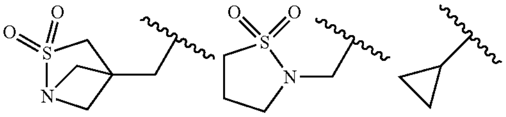
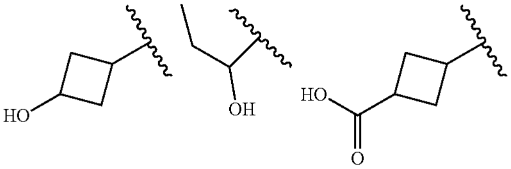
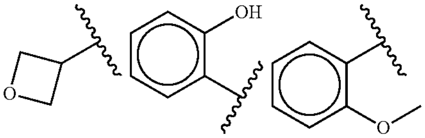
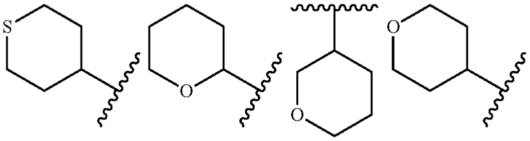
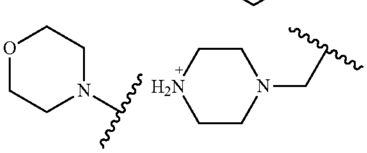
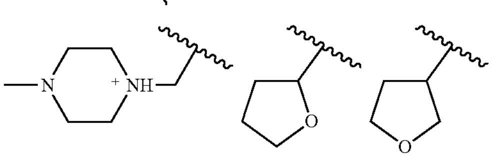
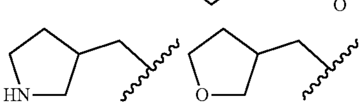
-continued
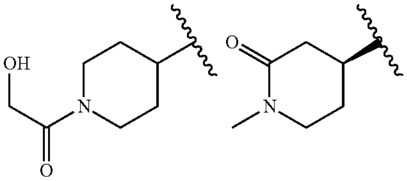
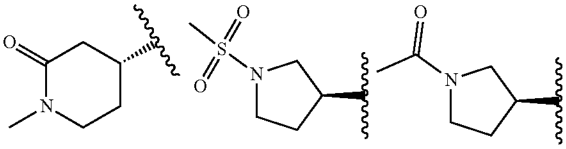
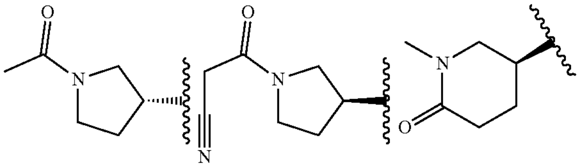
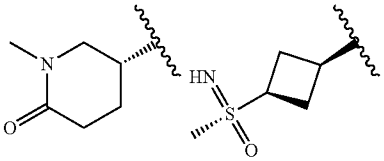
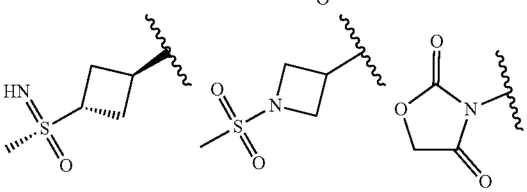
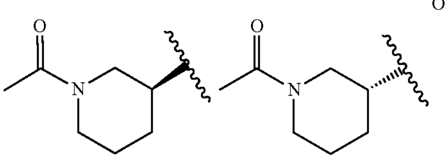
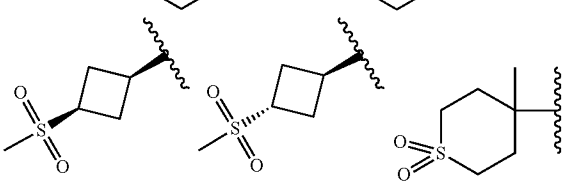
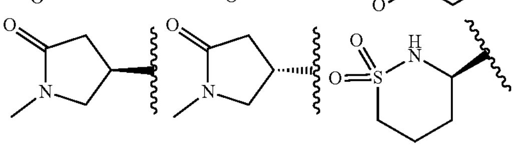
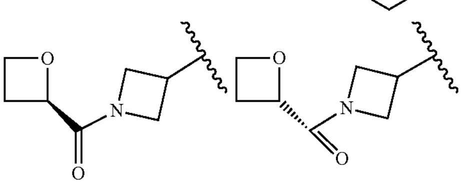
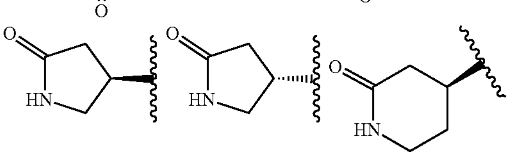
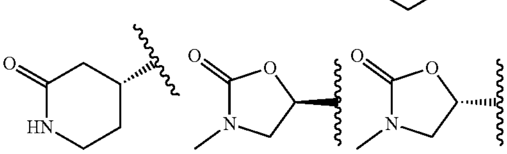

-continued
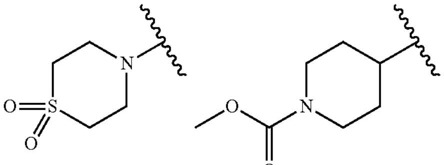
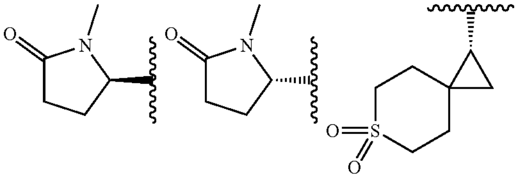
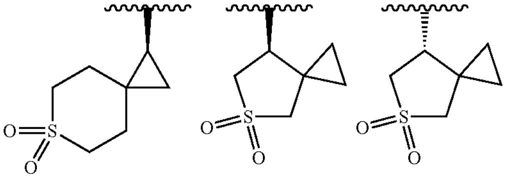
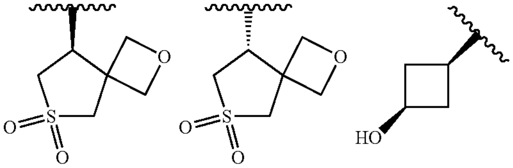
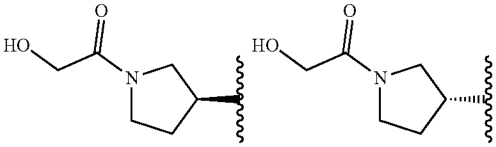
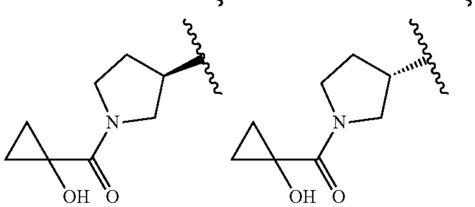
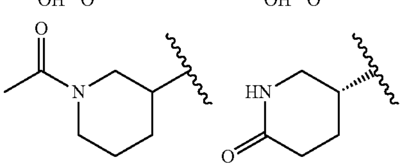
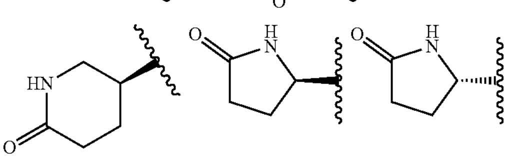
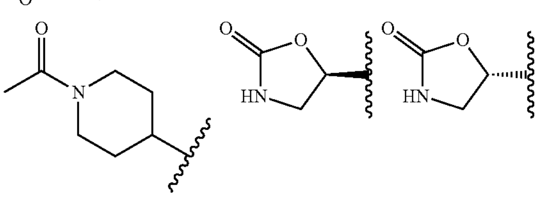
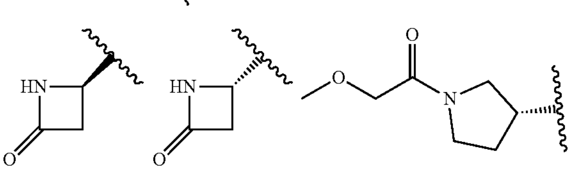
-continued
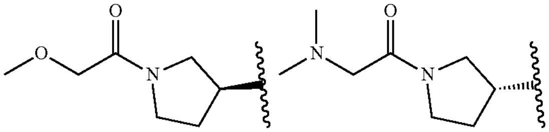
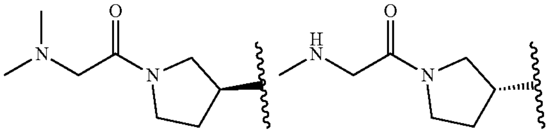
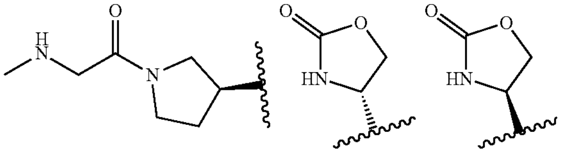
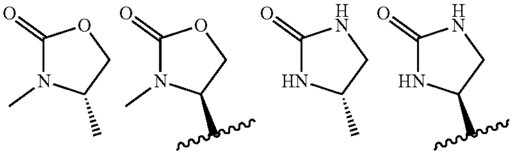
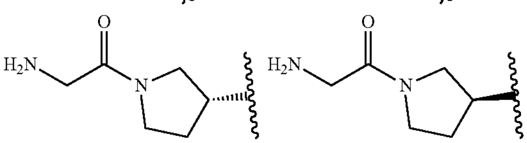
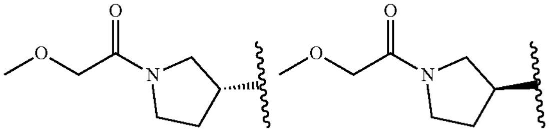
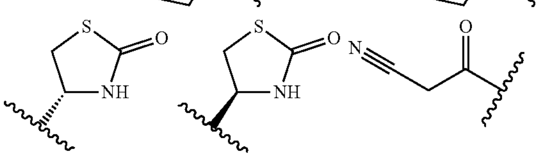
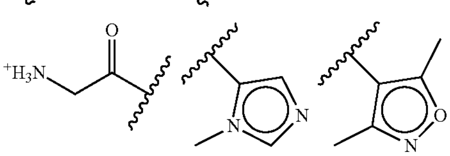
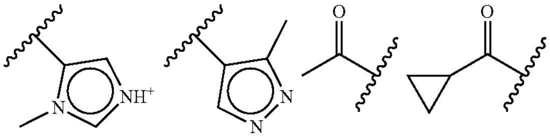
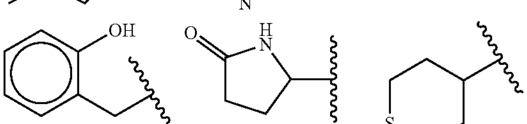
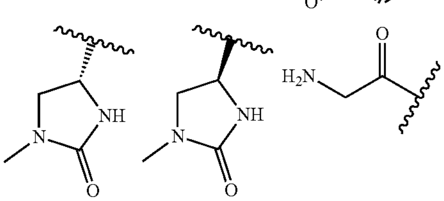
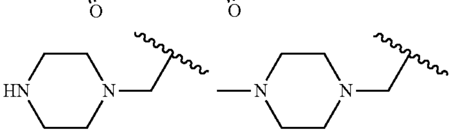

-continued

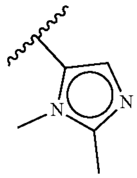

where each of the aforementioned hydrocarbon groups (e.g., alkyl, akenyl, alkynyl, alkoxy residues) may be further substituted by one or more residues independently selected from halogen, hydroxyl or C1-4-alkoxy groups;

$R^2$ is selected from the group consisting of: hydrogen, C1-3 alkyl, C1-3 alkoxyl, or C1-3 haloalkyl, preferably $R^2$ is methyl; or $R^1$ and $R^2$ together form a 4-7 membered ring; particularly a 5-6 membered heterocyclic ring having a further heteroatom selected from N, or O, which is optionally substituted with oxo, amino, aminoalkyl, sulfoxide, sulfoxide imine, sulfonyl, alkyl sulfoxide, sulfoximine, alkyl sulfonyl, cycloalkyl sulfoxide, cycloalkyl sulfonyl, sulfamoyl, alkyl sulfamoyl, cycloalkyl sulfamoyl;

$R^3$ is selected from the group consisting of: hydrogen, C1-3 alkyl (particularly or $CH_2CH_3$, or $CH_3$, preferably $CH_3$), C1-3 alkoxyl, C1-3 haloalkyl (particularly $CF_3$), nitro, cyano, hydroxyl or halogen (particularly chlorine);

$R^7$ is selected from the group consisting of: C1-3 alkyl, C1-3 alkoxyl, C1-3 haloalkyl, nitro, cyano, SMe, SOMe, $SO_2Me$, pyrrolyl, imidazolyl, triazolyl, or halogen (particularly fluorine or chlorine); $R^8$ and $R^9$ are each independently selected from the group consisting of: hydrogen, C1-3 alkyl, C1-3 alkoxyl, hydroxyl, hydroxyl C1-3 alkyl or halogen, and are suitably each is independently selected from hydrogen, hydroxyl, or halogen (particularly F or Cl);

$R^8$ and $R^9$ are each independently selected from the group consisting of: hydrogen, C1-3 alkyl, C1-3 alkoxyl, hydroxyl, C1-3 hydroxyalkyl or halogen, and are suitably each independently selected from hydrogen, hydroxyl, or halogen (particularly F or Cl); and $R^{10}$ is selected from the group consisting of: hydrogen, C1-3 alkyl, C1-3 alkoxyl, C1-3 hydroxy alkyl, halogen, amide, C3-5 membered saturated ring (e.g. cyclopropyl) or C4-5 membered saturated heterocycle ring. Optionally substituted with OMe or halogen (e.g. F), particularly $R^{10}$ is selected from the group consisting of: $CHOMeCH_3$ (e.g. R or S enantiomers of mixtures thereof), $CHOHCH_3$, $COCH_3$, $CH_2OCH_3$, $CH_2O$cyclopropyl, $CHNH_2CH_3$, $CHNHMeCH_3$, $CHNMe_2CH_3$, CO-aziridine amide, tetrahydrofuran or oxetane.

In particular embodiments of compounds Ia and Ib, Q is selected from the group consisting of: NH, N—C1-3 alkyl, N—C1-3 alkoxyl, N—C1-3 haloalkyl, CH-nitro, CH-cyano, CH-hydroxyl or CH-halogen (particularly CHCl). In some embodiments, Q is $NR^g$ wherein $R^g$ is hydrogen.

In particular embodiments of compound Ib, R7 is selected from OMe or Cl, preferably OMe.

In embodiments, compounds of the disclosure may be selected from the group consisting of:

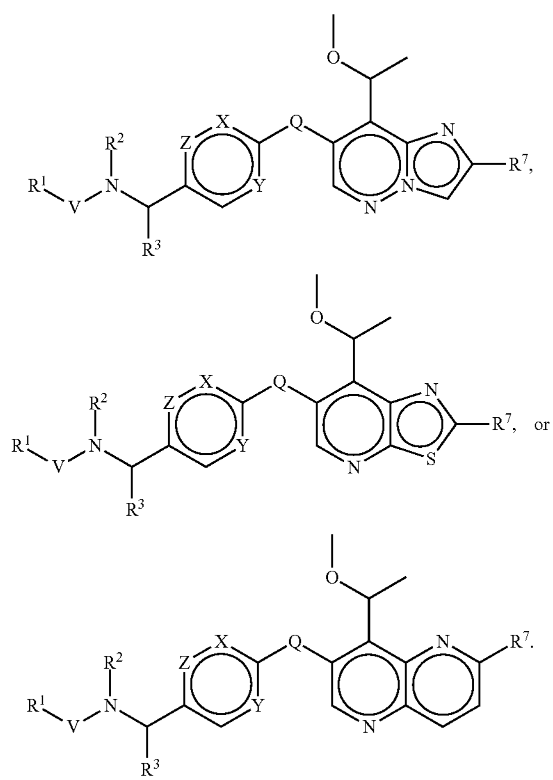

In embodiments, the compounds of the disclosure may be selected from the group consisting of:

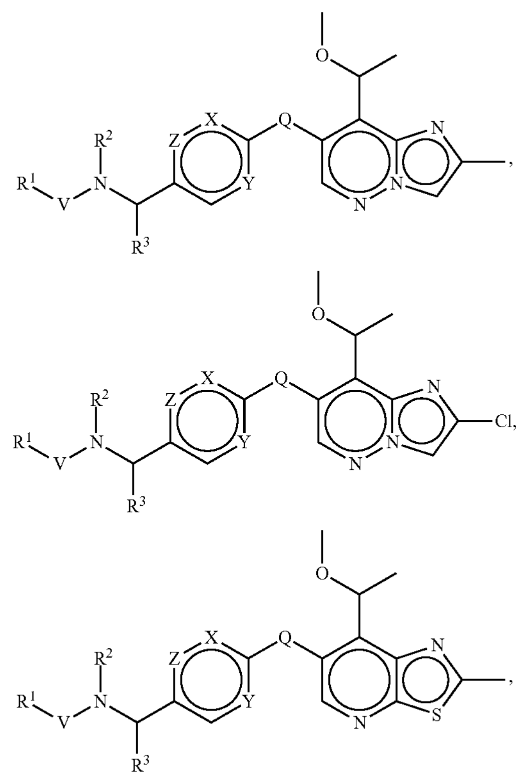

-continued

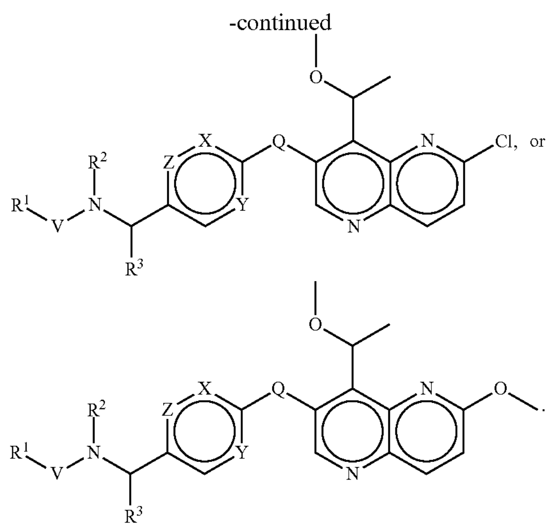

or

In embodiments, the compounds of the disclosure may be selected from the group consisting of, where X, Y and Z are C and V is CO; and where $R^1$, $R^2$, $R^3$, $R^7$, $R^8$, $R^9$, $R^{10}$ are as described above:

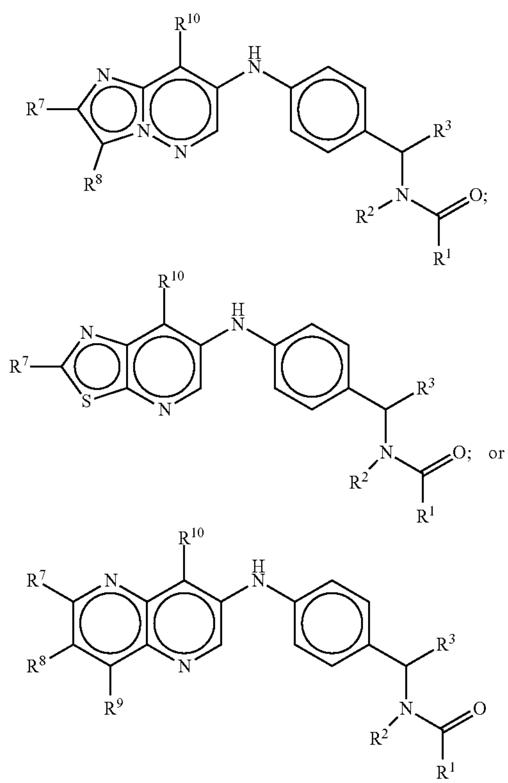

or

In any of the below definitions of embodiments and compounds of the invention or disclosure, it is expressly intended that any broad, optional, preferred, suitable, beneficial or particular definition of any group, moiety or portion of a compound may be combined with any definition of any other group, moiety or portion of a compound, whether that other definition is broad, optional, preferred, suitable, beneficial or particular for that other group, moiety or portion of a compound.

Suitable compounds according to various aspects and embodiments may have the structures as described in Table 1.

MALT-1 Activity, Prodrugs and Metabolites of Compounds

MALT-1 is a key component of innate and adaptive immune signalling (Ruland and Hartjes, 2019); and in particular, is known for its role in T cell receptor signalling leading to NFκB dependent gene expression, which mediates the activation and proliferation of T cells and the development of regulatory T cells. T cell receptor engagement activates MALT1 proteolytic activity, leading to the cleavage of substrates that are critical negative regulators of pro-inflammatory gene expression, and studies have shown that MALT-1 protease activity can regulate signaling pathways well beyond NFκB (Bardet et al., (2018), *Immunol Cell Biol,* 96, 81-99). Indeed, MALT-1 proteolytic activity is essential to drive T cell survival and expansion, and is also essential for the survival and proliferation of certain cancer cells (Juilland and Thome, (2016), *Curr. Opin. Hematol.,* 23, 402-9). MALT1 inhibition may also indirectly decrease tumor growth by interfering with the immune suppressive function of Tregs (Di Pilato et al., (2019), *Nature,* 570, 112-116; Rosenbaum et al., (2019), *Nat. Commun.,* 10, 2352). Thus, MALT-1 has become an interesting target for potential cancer and autoimmune therapies.

Several independent studies have shown that knock-in mice constitutively expressing a catalytically inactive MALT-1 mutant rapidly develop lethal autoimmune inflammation in multiple organs (e.g. Gewies et al., (2014), *Cell Rep.,* 9, 1292-305; Yu et al., (2015), *PLoS One,* 10, e0127083; Demeyer et al., (2019), *Front Immunol.,* 10, 1898). MALT-1 protease activity is also critical for maintaining regulatory T-cell function (Cheng et al., (2019), *J Immunol,* 202, 3008-3019), implicating a risk for autoimmunity when MALT-1 protease activity is lost in adulthood. This is a particular concern in the lungs and stomach upon MALT-1 inhibition, which may reflect a specific role for MALT-1 in immune tolerance toward locally displayed antigens. Indeed, long-term inducible inhibition of MALT-1 protease activity in adult mice has been demonstrated to be associated with local immune cell infiltration in stomach and lungs (Demeyer et al., (2020), *Science*, doi.org/10.1016/j.isci.2020.101557).

In order to address such concerns, in aspects and embodiments, compounds (or 'active agents') of the disclosure may beneficially be provided as prodrugs of compounds of the disclosure.

The term 'active agent' is typically used to refer to a compound according to the disclosure which has inhibition activity against MALT-1; especially under physiological conditions. However, it is often the case that the active agent may be difficult to administer or deliver to the physiological site of relevance, e.g. due to solubility, half-life or many other chemical or biological reasons. Therefore, it is known to use 'prodrugs' of the active agent in order to overcome physiochemical, biological or other barriers in drug efficiency and/or toxicity. Moreover, prodrug strategy may be used to increase the selectivity of drugs for their intended target. In accordance with the disclosure, therefore, prodrugs may be beneficial in targeting the active agent to the biological sites of interest while advantageously bypassing e.g. the stomach (or lungs), where problematic of inconvenient side-effects may be manifested due to localised inhibition of MALT-1 activity.

An active agent may be formed from a compound or prodrug of the disclosure by metabolism of the drug in vivo, and/or by chemical or enzymatic cleavage of the prodrug in vivo. Typically, a prodrug may be a pharmacologically inactive compound that requires chemical or enzymatic transformation to become an effective, active agent inside the body in which it is intended to have its therapeutic effect. On the other hand, since a prodrug may, in some embodiments, have very close structural similarity to the active agent, in some such embodiments, the prodrug may also have activity against the MALT-1 target. This may be particularly the case where the active agent is formed from a compound of prodrug of the disclosure by metabolism or a minor chemical transformation, such that the metabolite is closely related to the parent compound/prodrug. Accordingly, prodrugs of the disclosure may be active inhibitors of MALT-1. Suitably, however, such prodrugs may be characterised by having lower inhibition activity against MALT-1 than the drug/active agent that is derived from the prodrug of the disclosure.

On the other hand, where the therapeutic effect is derived from the release of the active agent from a larger chemical entity, then the eventual active agent/compound/drug may have significant structural differences compared to the prodrug from which is was derived. In such cases, the prodrug can effectively 'mask' the form(s) of the active agent, and in such cases the prodrug may be completely (or essentially) completely inactive under physiological conditions.

Dosage Forms, Medicaments and Pharmaceuticals

The compounds, molecules or agents of the disclosure may be used to treat (e.g. cure, alleviate or prevent) one or more diseases, infections or disorders. Thus, in accordance with the disclosure, the compounds and molecules may be manufactured into medicaments or may be incorporated or formulated into pharmaceutical compositions.

The molecules, compounds and compositions of the disclosure may be administered by any convenient route, for example, methods of administration include intradermal, intramuscular, intraperitoneal, intravenous, subcutaneous, intranasal, epidural, oral, sublingual, intranasal, intravaginal, transdermal, rectally, by inhalation, or topically to the skin. Delivery systems are also known to include, for example, encapsulation in liposomes, microgels, microparticles, microcapsules, capsules, etc. Any other suitable delivery system known in the art is also envisioned in use. Administration can be systemic or local. The mode of administration may be left to the discretion of the practitioner.

The dosage administered will, of course, vary depending upon known factors, such as the pharmacodynamic properties of the particular active agent; the chosen mode and route of administration; the age, health and weight of the recipient; the nature of the disease or disorder to be treated; the extent of the symptoms; any simultaneous or concurrent treatments; the frequency of treatment; and the effect desired. In general, a daily dosage of active agent of between about 0.001 and about 1,000 mg/kg of body weight can be expected. For some applications, the dosage may suitably be within the range of about 0.01 to about 100 mg/kg; between about 0.1 to about 25 mg/kg, or between about 0.5 and 10 mg/kg.

Depending on known factors, such as those noted above, the required dosage of the active agent may be administered in a single daily dose, or the total daily dosage may be administered in divided doses of e.g. two, three, or four times daily. Suitably, the therapeutic treatment regime according to the disclosure is devised for a single daily dose or for a divided daily dose of two doses.

Dosage forms of the pharmaceutical compositions of the disclosure suitable for administration may contain from about 1 mg to about 2,000 mg of the active ingredient per unit. Typically, the daily dosage of compounds may be at least about 10 mg and at most about 1,500 mg per human dose; such as between about 25 and 1,250 mg or suitably between about 50 and 1,000 mg. Typically, the daily dosage of compounds may be at most about 1000 mg. In such compositions the compound of the invention will ordinarily be present in an amount of about 0.5-95% by weight based on the total weight of the composition.

The 'effective amount' or 'therapeutically effective amount' is meant to describe an amount of compound or a composition of the disclosure that is effective in curing, inhibiting, alleviating, reducing or preventing the adverse effects of the diseases or disorders to be treated, or the amount necessary to achieve a physiological or biochemically-detectable effect. Thus, at the effective amount, the compound or agent is able to produce the desired therapeutic, ameliorative, inhibitory or preventative effect in relation to disease or disorder. Beneficially, an effective amount of the compound or composition of the disclosure may have the effect of inhibiting MALT-1. Diseases or disorders which may benefit from MALT-1 inhibition include, for example, autoimmune disorders, inflammatory diseases, cancers and/or oncologic diseases, such as rheumatoid arthritis, multiple sclerosis, psoriasis, Sjogren's syndrome and systemic lupus erythematosus or vasculitic conditions, cancers of hematopoietic origin or solid tumors, including chronic myelogenous leukemia, myeloid leukemia, non-Hodgkin lymphoma and other B cell lymphomas.

For therapeutic applications, the effective amount or therapeutically effective amount of a compound/active agent of the disclosure may be at least about 50 nM or at least about 100 nM; typically at least about 200 nM or at least about 300 nM in the blood of the subject. The effective amount or therapeutically effective amount may be at most about 5 μM, at most about 3 μM, suitably at most about 2 μM and typically at most about 1 μM in the blood of the subject. For example, the therapeutically effective amount may be at most about 500 nM, such as between about 100 nM and 500 nM. In some embodiments the amount of therapeutic compound is measured in serum of the subject and the above concentrations may then apply to serum concentration of the compounds of the disclosure.

When administered to a subject, a compound of the disclosure is suitably administered as a component of a composition that comprises a pharmaceutically acceptable carrier or vehicle. One or more additional pharmaceutical acceptable carrier (such as diluents, adjuvants, excipients or vehicles) may be combined with the compound of the disclosure in a pharmaceutical composition. Suitable pharmaceutical carriers are described in "*Remington's Pharmaceutical Sciences*" by E. W. Martin. Pharmaceutical formulations and compositions of the disclosure are formulated to conform to regulatory standards and according to the chosen route of administration.

Acceptable pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilising, thickening, lubricating and colouring agents may be used. When administered to a subject, the pharmaceutically acceptable vehicles are generally sterile. Water is a suitable vehicle when the compound is to be administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or buffering agents.

The medicaments and pharmaceutical compositions of the disclosure can take the form of solutions, suspensions, emulsion, tablets, pills, pellets, powders, gels, capsules (for example, capsules containing liquids or powders), modified-release formulations (such as slow or sustained-release formulations), suppositories, emulsions, aerosols, sprays, suspensions, or any other form suitable for use. Other examples of suitable pharmaceutical vehicles are described in Remington's Pharmaceutical Sciences, Alfonso R. Gennaro ed., Mack Publishing Co. Easton, Pa., 19th ed., 1995, see for example pages 1447-1676.

Suitably, the therapeutic compositions or medicaments of the disclosure are formulated in accordance with routine procedures as a pharmaceutical composition adapted for oral administration (more suitably for humans). Compositions for oral delivery may be in the form of tablets, lozenges, aqueous or oily suspensions, granules, powders, emulsions, capsules, syrups, or elixirs, for example. Thus, in one embodiment, the pharmaceutically acceptable vehicle is a capsule, tablet or pill.

Orally administered compositions may contain one or more agents, for example, sweetening agents such as fructose, aspartame or saccharin; flavouring agents such as peppermint, oil of wintergreen, or cherry; colouring agents; and preserving agents, to provide a pharmaceutically palatable preparation. When the composition is in the form of a tablet or pill, the compositions may be coated to delay disintegration and absorption in the gastrointestinal tract, so as to provide a sustained release of active agent over an extended period of time. Selectively permeable membranes surrounding an osmotically active driving compound are also suitable for orally administered compositions. In these dosage forms, fluid from the environment surrounding the capsule is imbibed by the driving compound, which swells to displace the agent or agent composition through an aperture. These dosage forms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. For oral formulations, the location of release may be the stomach, the small intestine (the duodenum, the jejunem, or the ileum), or the large intestine. One skilled in the art is able to prepare formulations that will not dissolve in the stomach yet will release the material in the duodenum or elsewhere in the intestine. Suitably, the release will avoid the deleterious effects of the stomach environment, either by protection of the compound (or composition) or by release of the compound (or composition) beyond the stomach environment, such as in the intestine. To ensure full gastric resistance a coating impermeable to at least pH 5.0 would be essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac, which may be used as mixed films.

While it can be beneficial to provide therapeutic compositions and/or compounds of the disclosure in a form suitable for oral administration, for example, to improve patient compliance and for ease of administration, in some embodiments compounds or compositions of the disclosure may cause undesirable side-effects, such as intestinal inflammation which may lead to premature termination of a therapeutic treatment regime. Thus, in some embodiments, the therapeutic treatment regime is adapted to accommodate 'treatment holidays', e.g. one or more days of non-administration. For example, treatment regimens and therapeutic methods of the disclosure may comprise a repetitive process comprising administration of the therapeutic composition or compound for a number of consecutive days, followed by a treatment holiday of one or more consecutive days. For example, a treatment regime of the disclosure may comprise a repetitive cycle of administration of the therapeutic composition or compound for between 1 and 49 consecutive days, between 2 and 42 days, between 3 and 35 days, between 4 and 28 days, between 5 and 21 days, between 6 and 14 days, or between 7 and 10 days; followed by a treatment holiday of between 1 and 14 consecutive days, between 1 and 12 days, between 1 and 10 days, or between 1 and 7 days (e.g. 1, 2, 3, 4, 5, 6 or 7 days).

To aid dissolution of the therapeutic agent into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. Potential nonionic detergents that could be included in the formulation as surfactants include: lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants, when used, could be present in the formulation of the compound or derivative either alone or as a mixture in different ratios.

Typically, compositions for intravenous administration comprise sterile isotonic aqueous buffer. Where necessary, the compositions may also include a solubilising agent.

Another suitable route of administration for the therapeutic compositions of the disclosure is via pulmonary or nasal delivery.

Additives may be included to enhance cellular uptake of the therapeutic agent of the disclosure, such as the fatty acids oleic acid, linoleic acid and linolenic acid.

The therapeutic agents of the disclosure may also be formulated into compositions for topical application to the skin of a subject.

Where the invention provides more than one active compound/agent for use in combination, generally, the agents may be formulated separately or in a single dosage form, depending on the prescribed most suitable administration regime for each of the agents concerned. When the therapeutic agents are formulated separately, the pharmaceutical compositions of the invention may be used in a treatment regime involving simultaneous, separate or sequential administration with the other one or more therapeutic agent. The other therapeutic agent(s) may comprise a compound of the disclosure or a therapeutic agent known in the art).

The compounds and/or pharmaceutical compositions of the disclosure may be formulated and suitable for administration to the central nervous system (CNS) and/or for crossing the blood-brain barrier (BBB).

The invention will now be described by way of the following non-limiting examples.

EXAMPLES

Materials and Methods

Sample preparation: Powders were solubilized in DMSO-$d_6$, vortexed vigorously until the solution was clear and transferred to an NMR tube for data acquisition.

NMR Spectroscopy:

Liquid-state NMR experiments were recorded on a 600 MHz (14.1 Tesla) Bruker Avance III NMR spectrometer (600 MHz for $^{1}$H, 151 MHz for $^{13}$C) using a triple-resonance $^{1}$H, $^{15}$N, $^{13}$C CP-TCI 5 mm cryoprobe (Bruker Biospin, Germany).

Liquid-state NMR experiments were recorded on a 500 MHz (11.75 Tesla) Bruker Avance I NMR spectrometer (500 MHz for $^{1}$H, 125 MHz for $^{13}$C) using a Dual Resonance BBI 5 mm probe (Bruker Biospin, Germany).

Liquid-state NMR experiments were recorded on a 400 MHz (9.4 Tesla) Bruker Avance NEO NMR spectrometer (400 MHz for $^{1}$H, 100 MHz for $^{13}$C) using a SEI 5 mm probe (Bruker Biospin, Germany).

All the experiments used for the resonance assignment procedure and the elucidation of the products structure (1D $^{1}$H, 2D $^{1}$H-$^{1}$H-COSY, 2D $^{1}$H-$^{1}$H-ROESY, 2D $^{1}$H-$^{13}$C-HSQC, 2D $^{1}$H-$^{13}$C-HMBC) were recorded at 300 K. $^{1}$H chemical shifts are reported in δ ppm as s (singlet), d (doublet), t (triplet), q (quartet), dd (double doublet), m (multiplet) or br s (broad singlet).

LCMS Chromatography:

LCMS chromatography analysis were recorded using the following apparatus using:

- Waters HPLC: Alliance 2695, UV: PDA 996, MS: ZQ (simple Quad) ZQ2
- Waters UPLC: Acquity, UV: Acquity PDA, MS: Qda
- Waters UPLC: Acquity, UV: Acquity TUV, MS: Qda
- Waters UPLC: Acquity, UV: Acquity PDA, MS: QDa, ELSD The apparatus was tested using a column Gemini NX—C18 Phenomenex (30×2 mm) 3 μm for the Waters HPLC or a CSH C18 Waters (50×2.1 mm), 1.7 μm for the UPLC Waters. All of them used a combination of the following eluents: $H_2O$+0.05% TFA (v/v) and MeCN+0.035% TFA (v/v) and a positive electrospray ES+ as ionization mode. The UV detection was set up at 220 and 254 nm.

Temperatures are given in degrees Celsius (° C.). The reactants used in the examples below may be obtained from commercial sources or they may be prepared from commercially available starting materials as described herein or by methods known in the art. All of the compounds of the invention are synthesized according to the Examples described herein. The progress of the reactions described herein were followed as appropriate by e.g. LC, GC or TLC, and as the skilled person will readily realise, reaction times and temperatures may be adjusted accordingly.

Abbreviations

In addition to the definitions above, the following abbreviations are used in the synthetic schemes below. If an abbreviation used herein is not defined, it has its generally accepted meaning:

ABC Ammonium bicarbonate
Ac Acetyl
AcOH Acetic acid
Rac-BINAP (±)-2,2'-Bis(diphenylphosphino)-1,1'-binaphthalene
Bn Benzyl
Boc tert-butyloxycarbonyl
CDI 1,1'-Carbonyldiimidazole
$CHCl_3$ Chloroform
DCM Dichloromethane
DIPEA Diisopropylethylamine
DMAP 4-Dimethylaminopyridine
DME 1,2-Dimethoxyethane
DMSO Dimethylsulfoxide
Et Ethyl
EtOAc Ethyl acetate
$Et_3N$ Triethylamine
EtOH Ethanol
$Et_2O$ Diethyl ether
h hour
$H_2O$ water
IPAm Isopropyl amine
iPr2O Isopropyl ether
IPOH Isopropanol
LiOH Lithium hydroxide
LiHMDS Lithium bis(trimethylsilyl)amide
L-selectride Lithium tri-sec-butylborohydride
m-CPBA 3-chlorobenzenecarboperoxoic acid
min Minutes
Me Methyl
MeCN Acetonitrile
MeO Methoxy
MeOH Methanol
$MgSO_4$ Magnesium sulfate
MS Mass spectrometry
$Na_2SO_4$ Sodium sulfate
$NaHCO_3$Sodium bicarbonate
$NH_4Cl$ Ammonium chloride
$N_2$ Nitrogen
Pd Xphos G2 Chloro(2-dicyclohexylphosphino-2',4',6'-triisopropyl-1,1'-biphenyl) [2-(2'-amino-1,1'-biphenyl)]palladium(II)
Ph Phenyl
rt room temperature (18 to 22° C.)
TBAF Tetrabutylammonium fluoride
$Ti(OiPr)_4$ Tetraisopropoxytitanium
TFA Trifluoroacetic acid
THF Tetrahydrofuran
T3P 2,4,6-Tripropyl-1,3,5,2,4,6-trioxatriphosphorinane-2,4,6-trioxide solution Intermediates 41-60 and 60-b were synthesised following Scheme 1 or Scheme 2

Scheme 1

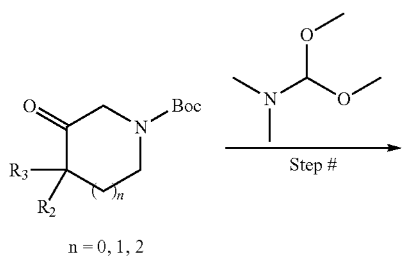

-continued

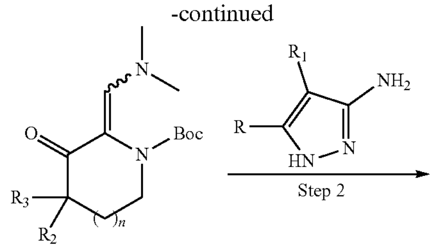

n = 0, 1, 2

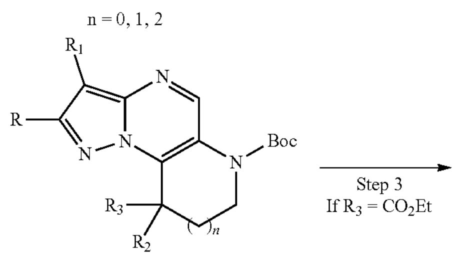

n = 0, 1, 2

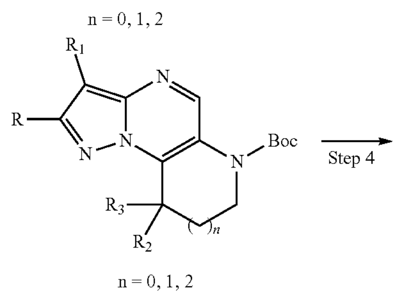

n = 0, 1, 2

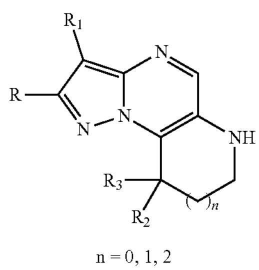

n = 0, 1, 2

Scheme 2

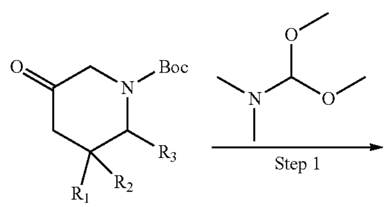

-continued

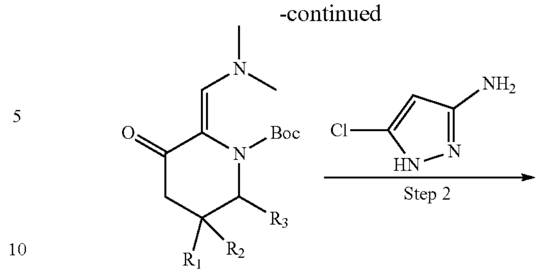

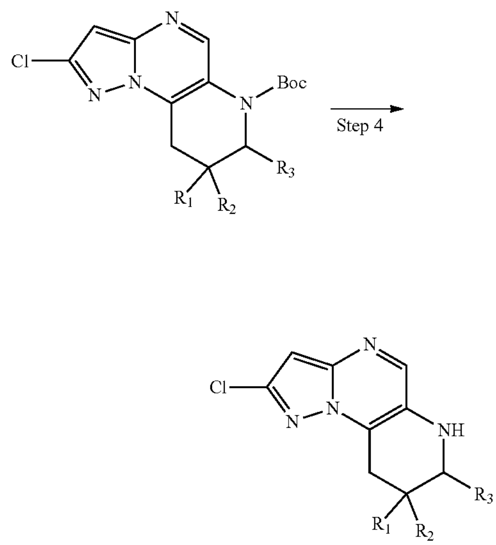

Step 1-Scheme 1 and Scheme 2

Procedure

A solution of the ketone (ketone which led to intermediate 11 was prepared according to the procedure described in WO2001087838 A1) (1 mol) in dry DMF (4 M) was treated with 1,1-dimethoxy-N,N-dimethyl-methanamine (1.8 mol) and stirred at 90° C. in a sealed tube for 2 h. The reaction mixture was cooled and concentrated in vacuo. The crude was:

a) purified by flash column chromatography (heptane/EtOAc; from 0% to 100% of EtOAc)

b) used as such without further purification

| Name | Structure | Analysis | Procedure | Yield % |
|---|---|---|---|---|
| 1-tert-butyl 4-ethyl (2Z or 2E)-2-[(dimethylamino)-methylidene]-3-oxopiperidine-1,4-dicarboxylate Intermediate 1 | 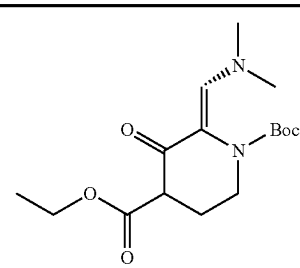 | m/z: 327 [M + H]$^+$ | b | 97 |

-continued

| Name | Structure | Analysis | Procedure | Yield % |
|---|---|---|---|---|
| tert-butyl (2Z or 2E)-2-[(dimethylamino)methyl-idene]-4,4-dimethyl-3-oxopiperidine-1-carbox-ylate Intermediate 2 | 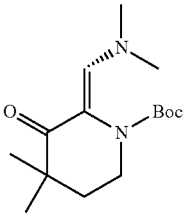 | m/z: 283 [M + H]$^+$ | a | 62 |
| tert-butyl (5Z or 5E)-5-[(dimethylamino)methyl-idene]-4-oxo-6-azaspiro-[2.5]octane-6-carbox-ylate Intermediate 3 | 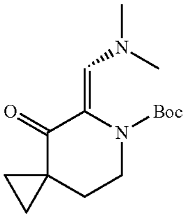 | $^1$H NMR (400 MHz, DMSO-$d_6$) δ ppm 7.15 (s, 1H), 4.21-3.96 (m, 1H), 2.96 (s, 7H), 2.00 (d, J = 14.1 Hz, 1H), 1.53 (dt, J = 13.6, 3.6 Hz, 1H), 1.40 (s, 9H), 1.03 (s, 2H), 0.63-0.48 (m, 2H). m/z: 281 [M + H]$^+$ | a | 79 |
| tert-butyl (2Z or 2E)-2-(dimethylaminomethyl-ene)-4-methyl-3-oxo-piperidine-1-carboxylate Intermediate 4 | 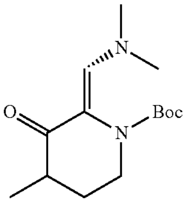 | m/z: 269 [M + H]$^+$ | b | 87 |
| 1-tert-butyl 3-ethyl (5Z or 5E)-5-(dimethyl-amino)-methylidene]-4-oxopyrrolidine-1,3-di-carboxylate Intermediate 5 | 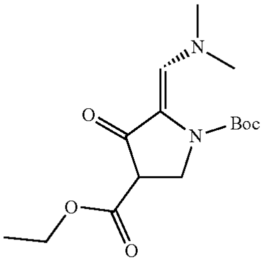 | m/z: 312 [M + H]$^+$ | b | 100 |
| tert-butyl (2Z or 2E)-2-[(dimethylamino)meth-ylidene]-4,4-dimethyl-3-oxopyrrolidine-1-carboxylate Intermediate 6 | 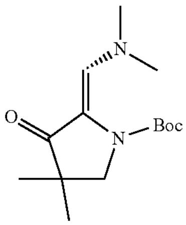 | m/z: 269 [M + H]$^+$ | b | 100 |
| tert-butyl (6Z or 6E)-6-[(dimethylamino)meth-ylidene]-7-oxo-5-aza-spiro[2.4]heptane-5-carboxylate Intermediate 7 | 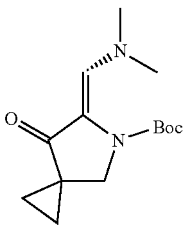 | m/z: mass not found | b | 98 |

-continued

| Name | Structure | Analysis | Procedure | Yield % |
|---|---|---|---|---|
| tert-butyl (2Z or 2E)-2-(dimethylaminomethylene)-5,5-dimethyl-3-oxo-piperidine-1-carboxylate Intermediate 8 | 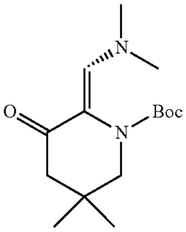 | m/z: 283 $[M + H]^+$ | b | 100 |
| tert-butyl (6Z or 6E)-6-(dimethylaminomethylene)-7-oxo-5-azaspiro-[2.5]octane-5-carboxylate Intermediate 9 | 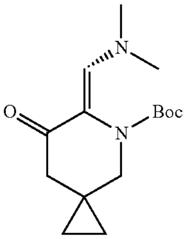 | m/z: 281 $[M + H]^+$ | b | 100 |
| tert-butyl (2Z or 2E)-2-(dimethylaminomethylene)-6-methyl-3-oxo-piperidine-1-carboxylate Intermediate 10 | 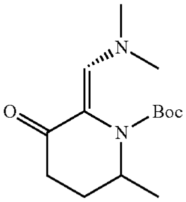 | m/z: 269 $[M + H]^+$ | b | 38 |
| tert-butyl (7E or 7Z)-7-(dimethylaminomethylene)-6-oxo-2-oxa-8-azaspiro [4.5]decane-8-carboxylate Intermediate 11 | 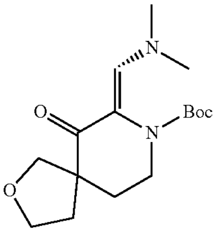 | m/z: 310 $[M + H]^+$ | b | 99 |
| tert-butyl (2E or 2Z)-2-(dimethylaminomethylene)-4-(methoxymethyl)-3-oxo-piperidine-1-carboxylate Intermediate 12 | 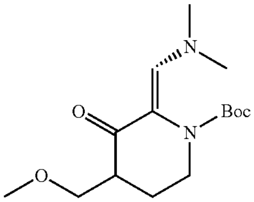 | m/z: 299 $[M + H]^+$ | b | 48 |
| tert-butyl (2E or 2Z)-2-(dimethylaminomethylene)-4-(methoxymethyl)-4-methyl-3-oxo-piperidine-1-carboxylate Intermediate 13 | 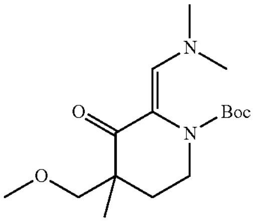 [SMILES: COCC1(C)CCN(C(=O)OC(C)(C)C)/C(=C\N(C)C)C1=O] | m/z: 313 $[M + H]^+$ | b | 97 |

Step 2—Scheme 1 and Scheme 2

General Procedure

A solution of Intermediates 1-13 (1 mol) and 1H-pyrazol-3-amine derivatives (1 mol) in dry ethanol (0.2 M) was treated with AcOH (10 mol) and stirred at 80° C. for 18 h. The reaction mixture was concentrated in vacuo then partitioned between water (10 mL) and DCM (10 mL). The aqueous layer was extracted with DCM (3×10 mL). The organic layers were combined, washed with brine, dried over anhydrous $MgSO_4$, filtered, evaporated and concentrated under reduced pressure. The crude was purified by flash column chromatography (heptane/EtOAc, from 0% to 100% of EtOAc) to afford the desired intermediates.

| Name | Structure | Analysis | Yield % |
|---|---|---|---|
| 10-tert-butyl 13-ethyl 4-chloro-2,3,7,10-tetra-azatricyclo[7.4.0.0$^{2,6}$]trideca-1(9),3,5,7-tetraene-10,13-dicarboxylate Intermediate 14 | 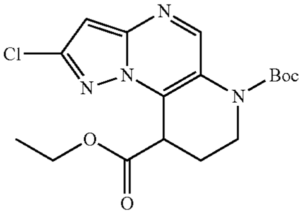 [SMILES: CCOC(=O)C1CCN(C(=O)OC(C)(C)C)c2cnc3cc(Cl)nn3c21] | $^{1}$H NMR (400 MHz, DMSO-$d_6$) δ ppm 8.95 (s, 1H), 6.91 (s, 1H), 4.37 (dd, J = 7.8, 5.2 Hz, 1H), 4.14 (q, J = 7.1 Hz, 2H), 3.89 (ddd, J = 13.4, 6.8, 3.0 Hz, 1H), 3.70-3.57 (m, 1H), 2.37 (dtd, J = 13.9, 8.8, 3.0 Hz, 1H), 2.14 (ddd, J = 14.0, 8.6, 4.0 Hz, 1H), 1.50 (s, 9H), 1.15 (t, J = 7.1 Hz, 3H) m/z: 381[M + H]$^+$ | 61 |
| 10-tert-butyl 13-ethyl 4-methoxy-2,3,7,10-tetra-azatricyclo[7.4.0.0$^{2,6}$]trideca-1(9),3,5,7-tetraene-10,13-dicarboxylate Intermediate 15 | 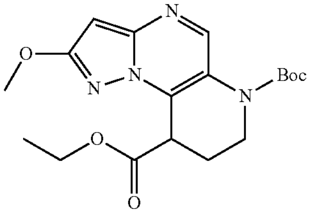 [SMILES: CCOC(=O)C1CCN(C(=O)OC(C)(C)C)c2cnc3cc(OC)nn3c21] | $^{1}$H NMR (400 MHz, DMSO-$d_6$) δ ppm 8.75 (s, 1H), 6.16 (s, 1H), 4.28 (dd, J = 7.9, 5.4 Hz, 1H), 4.12 (qt, J = 7.3, 3.7 Hz, 2H), 3.90 (s, 3H), 3.85 (ddd, J = 13.3, 7.0, 2.9 Hz, 1H), 3.68-3.62 (m, 2H), 2.43-2.30 (m, 1H), 2.15-2.02 (m, 1H), 1.49 (s, 9H), 1.17 (t, J = 7.1 Hz, 3H). m/z: 376 [M + H]$^+$ | 11 |
| 10-tert-butyl 13-ethyl 4-hydroxy-2,3,7,10-tetra-azatricyclo[7.4.0.0$^{2,6}$]trideca-1(9),3,5,7-tetraene-10,13-dicarboxylate Intermediate 16 | 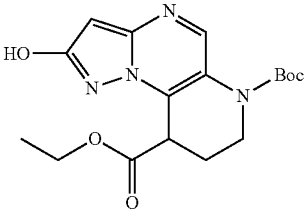 [SMILES: CCOC(=O)C1CCN(C(=O)OC(C)(C)C)c2cnc3cc(O)nn3c21] | $^{1}$H NMR (400 MHz, DMSO-$d_6$) δ ppm 10.86 (s, 1H), 8.67 (s, 1H), 5.86 (s, 1H), 4.25 (dd, J = 7.8, 4.9 Hz, 1H), 4.19-4.05 (m, 2H), 3.87 (ddd, J =13.3, 6.7, 3.0 Hz, 1H), 3.57 (ddd, J = 13.1, 9.1, 2.8 Hz, 1H), 2.34 (dtd, J = 13.9, 8.9, 3.0 Hz, 1H), 2.13-2.03 (m, 1H), 1.48 (s, 9H), 1.21-1.15 (m, 3H) m/z: 363 [M + H]$^+$ | 16 |
| 10-tert-butyl 13-ethyl 4-(methylsulfanyl)-2,3,7,10-tetraazatricyclo[7.4.0.0$^{2,6}$]trideca-1(9),3,5,7-tetraene-10,13-dicarboxylate Intermediate 17 | 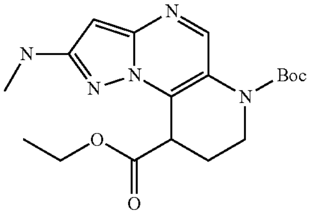 [SMILES: CCOC(=O)C1CCN(C(=O)OC(C)(C)C)c2cnc3cc(NC)nn3c21] | $^{1}$H NMR (400 MHz, DMSO-$d_6$) δ ppm 8.81 (s, 1H), 6.70 (s, 1H), 4.34 (dd, J = 7.8, 5.6 Hz, 1H), 4.21-4.04 (m, 2H), 3.84 (ddd, J = 13.3, 7.1, 2.8 Hz, 1H), 3.65 (ddd, J = 13.1, 8.9, 2.7 Hz, 1H), 2.55 (s, 3H), 2.43-2.27 (m, 1H), 2.16-2.03 (m, 1H), 1.49 (s, 9H), 1.15 (t, J = 7.1 Hz, 3H). m/z: 393 [M + H]$^+$ | 98 |
| 10-tert-butyl 13-ethyl 4-fluoro-2,3,7,10-tetra-azatricyclo[7.4.0.0$^{2,6}$]trideca-1(9),3,5,7-tetraene-10,13-dicarboxylate Intermediate 18 | 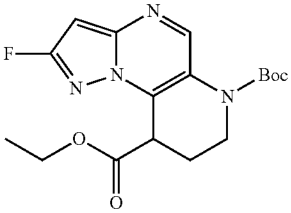 | $^{1}$H NMR (400 MHz, DMSO-$d_6$) δ ppm 8.93 (s, 1H), 6.53 (d, J = 5.1 Hz, 1H), 4.31 (dd, J = 7.8, 5.1 Hz, 1H), 4.13 (q, J = 7.1 Hz, 2H), 3.90 (ddd, J = 13.4, 6.8, 3.0 Hz, 1H), 3.62 (ddd, J = 16.2, 8.9, 4.4 Hz, 1H), 2.37 (dtd, J = 17.0, 8.8, 3.1 Hz, 1H), 2.21-2.05 (m, 1H), 1.49 (s, 9H), 1.15 (t,J = 7.1 Hz, 3H) m/z: 365 [M + H]$^+$ | 90 |
| 10-tert-butyl 13-ethyl 4-methyl-2,3,7,10-tetra-azatricyclo[7.4.0.0$^{2,6}$]trideca-1(9),3,5,7-tetraene-10,13-dicarboxylate Intermediate 19 | 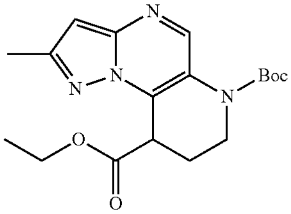 [SMILES: CCOC(=O)C1CCN(C(=O)OC(C)(C)C)c2cnc3cc(C)nn3c21] | $^{1}$H NMR (400 MHz, DMSO-$d_6$) δ ppm 8.78 (d, J = 3.1 Hz, 1H), 6.53 (s, 1H), 4.36 (ddd, J = 10.9, 7.8, 5.3 Hz, 1H), 4.12 (qt, J = 7.2, 3.6 Hz, 2H), 3.86 (ddt, J = 13.8, 7.0, 3.4 Hz, 1H), 3.69-3.60 (m, 3H), 2.42-2.31 (m, 5H, under the solvent peak), 2.11 (ddd, J = 13.8, 6.0, 2.6 Hz, 1H), 1.49 (s, 9H), 1.15 (t, J = 7.1 Hz, 3H). m/z: 361 [M + H]$^+$ | 64 |

-continued

| Name | Structure | Analysis | Yield % |
|---|---|---|---|
| 10-tert-butyl 13-ethyl 5-chloro-2,3,7,10-tetra-azatricyclo[7.4.0.0$^{2,6}$]-trideca-1(9),3,5,7-tetraene-10,13-dicarbox-ylate Intermediate 20 | 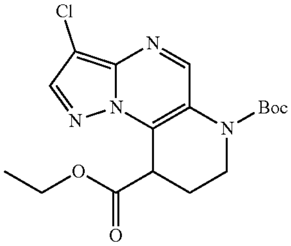 [SMILES: CCOC(=O)C1CCN(C(=O)OC(C)(C)C)c2cnc3c(Cl)cnn3c21] | $^1$H NMR (400 MHz, DMSO-$d_6$) δ ppm 8.97 (s, 1H), 8.33 (s, 1H), 4.38 (dd, J = 7.8, 5.1 Hz, 1H), 4.10 (q, J = 7.0 Hz, 2H), 3.92 (ddd, J = 13.4, 6.8, 2.9 Hz, 1H), 3.63 (ddd, J = 12.6, 9.0, 2.7 Hz, 1H), 2.46-2.31 (m, 1H), 2.15 (dd, J = 12.7, 6.1 Hz, 1H), 1.50 (s, 9H), 1.14 (t, J = 7.1 Hz, 3H). m/z: 381 [M + H]$^+$ | 51 |
| 5-tert-butyl 3-ethyl 11-chloro-1,5,8,12-tetra-azatricyclo[7.3.0.0$^{2,6}$] dodeca-2(6),7,9,11-tetraene-3,5-dicarbox-ylate Intermediate 21 | 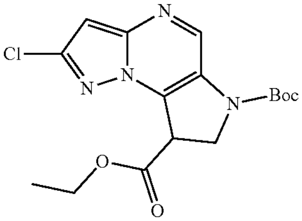 [SMILES: CCOC(=O)C1CN(C(=O)OC(C)(C)C)c2cnc3cc(Cl)nn3c21] | $^1$H NMR (400 MHz, DMSO-$d_6$) δ ppm 8.93 (d, J =108.3 Hz, 1H), 6.97 (s, 1H), 4.88 (dd, J = 11.2, 5.3 Hz, 1H), 4.40 (t, J = 11.3 Hz, 1H), 4.25-4.10 (m, 4H), 1.55 (d, J = 6.9 Hz, 9H), 1.19 (td, J = 7.1, 4.7 Hz, 3H) m/z: 367 [M + H]$^+$ | 59 |
| tert-butyl 4-chloro-13,13-dimethyl-2,3,7,10-tetrazatricyclo[7.4.0.0$^{2,6}$] trideca-1(9),3,5,7-tetraene-10-carboxylate Intermediate 22 | 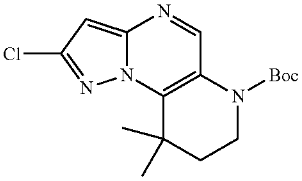 [SMILES: CC(C)(C)OC(=O)N1CCC(C)(C)c2c1cnc1cc(Cl)nn21] | $^1$H NMR (400 MHz, DMSO-$d_6$) δ ppm 8.77 (s, 1H), 6.85 (s, 1H), 3.77-3.69 (m, 2H), 1.94-1.86 (m, 2H), 1.61 (s, 6H), 1.48 (s, 9H). m/z: 337 [M + H]$^+$ | 62 |
| tert-butyl 4'-chloro-2',3',7',10'-tetraazaspiro [cyclopropane-1,13'-tricyclo[7.4.0.0$^{2,6}$] tridecane]-1'(9'),3',5',7'-tetraene-10'-carboxylate Intermediate 23 | 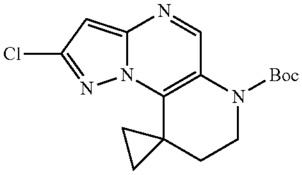 [SMILES: CC(C)(C)OC(=O)N1CCC2(CC2)c2c1cnc1cc(Cl)nn21] | $^1$H NMR (400 MHz, DMSO-$d_6$) δ ppm 8.65 (s, 1H), 6.77 (s, 1H), 3.81-3.66 (m, 2H), 2.57 (q, J = 3.3 Hz, 2H), 1.92-1.81 (m, 3H), 1.47 (s, 9H), 0.95 (q, J = 3.7 Hz, 2H). m/z: 335 [M + H]$^+$ | 100 |
| tert-butyl 4-chloro-13-methyl-2,3,7,10-tetra-zatricyclo[7.4.0.0$^{2,6}$] trideca-1(9),3,5,7-tetraene-10-carboxylate Intermediate 24 | 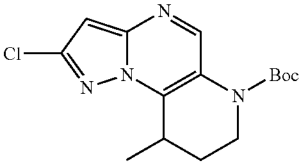 [SMILES: CC1CCN(C(=O)OC(C)(C)C)c2cnc3cc(Cl)nn3c21] | $^1$H NMR (400 MHz, DMSO-$d_6$) δ ppm 8.87 (s, 1H), 6.85 (s, 1H), 3.96 (ddd, J = 13.3, 5.6, 3.4 Hz, 1H), 3.61-3.48 (m, 2H), 2.11 (dddd, J = 13.8, 10.1, 6.5, 3.4 Hz, 1H), 1.82 (ddt, J = 13.8, 6.0, 3.0 Hz, 1H), 1.49 (s, 9H). m/z: 323 [M + H]$^+$ | 62 |
| tert-butyl 11-chloro-3,3-dimethyl-1,5,8,12-tetraazatricyclo[7.3.0.0$^{2,6}$] dodeca-2(6),7,9,11-tetraene-5-carboxylate Intermediate 25 | 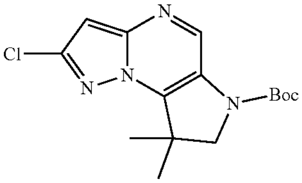 [SMILES: CC(C)(C)OC(=O)N1CC(C)(C)c2c1cnc1cc(Cl)nn21] | $^1$H NMR (400 MHz, DMSO-$d_6$) δ ppm 9.09 (d, J = 20.8 Hz, 1H), 6.89 (s, 1H), 3.85 (s, 2H), 1.59 (s, 6H), 1.53 (s, 9H). m/z: 323 [M + H]$^+$ | 32 |
| tert-butyl 11'-chloro-1',5',8',12'-tetraazaspiro [cyclopropane-1,3'-tricyclo[7.3.0.0$^{2,6}$] dodecane]-2'(6'),7',9',11'-tetraene-5'-carboxylate Intermediate 26 | 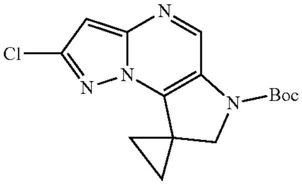 [SMILES: CC(C)(C)OC(=O)N1CC2(CC2)c2c1cnc1cc(Cl)nn21] | $^1$H NMR (400 MHz, DMSO-$d_6$) δ ppm 8.61 (s, 1H), 6.61 (s, 1H), 4.09 (s, 2H), 1.41 (s, 9H), 1.38 (d, J = 2.9 Hz, 2H), 1.36 (d, J = 3.1 Hz, 2H). m/z: 321 [M + H]$^+$ | 6 |

-continued

| Name | Structure | Analysis | Yield % |
|---|---|---|---|
| tert-butyl 4-chloro-12,12-dimethyl-2,3,7,10-tetrazatricyclo[7.4.0.0$^{2,6}$]trideca-1(9),3,5,7-tetraene-10-carboxylate Intermediate 27 | 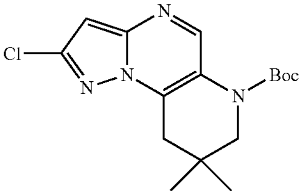 [SMILES: CC1(C)Cc2c(cnc3cc(Cl)nn23)N(C(=O)OC(C)(C)C)C1] | $^1$H NMR (500 MHz, DMSO-d$_6$) δ ppm 8.85 (s, 1H), 6.86 (s, 1H), 3.51 (s, 3H), 2.91 (s, 3H), 1.48 (s, 9H), 1.05 (s, 6H). m/z: 337 [M + H]$^+$ | 22 |
| tert-butyl 4-chlorospiro[2,3,7,10-tetrazatricyclo[7.4.0.0$^{2,6}$]trideca-1(9),3,5,7-tetraene-12,1'-cyclopropane]-10-carboxylate Intermediate 28 | 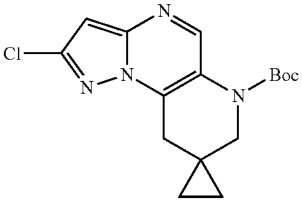 [SMILES: CC(C)(C)OC(=O)N1CC2(CC2)Cc2c1cnc1cc(Cl)nn21] | $^1$H NMR (400 MHz, DMSO-d$_6$) δ ppm 8.82 (s, 1H), 6.87 (s, 1H), 3.58 (s, 3H), 3.08 (s, 2H), 1.47 (s, 11H), 0.68 (s, 5H). m/z: 335 [M + H]$^+$ | 27 |
| tert-butyl 4-chloro-11-methyl-2,3,7,10-tetrazatricyclo[7.4.0.0$^{2,6}$]trideca-1(9),3,5,7-tetraene-10-carboxylate Intermediate 29 | 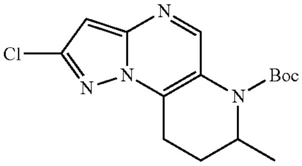 | $^1$H NMR (500 MHz, DMSO-d$_6$) δ ppm 8.82 (s, 1H), 6.85 (s, 1H), 4.71-4.77 (m, 1H), 3.11-3.21 (m, 1H), 2.97-3.07 (m, 1H), 1.96-2.06 (m, 2H), 1.47-1.49 (m, 9H), 1.08 (d, = 7.1 Hz, 3H). m/z: 333 [M + H]$^+$ | 25 |
| tert-butyl 4-chlorospiro[2,3,7,10-tetrazatricyclo[7.4.0.0$^{2,6}$]trideca-1(9),3,5,7-tetraene-13,3'-tetrahydrofuran]-10-carboxylate Intermediate 30 | 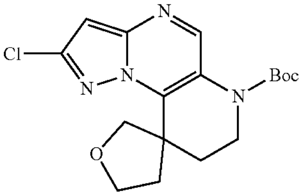 [SMILES: CC(C)(C)OC(=O)N1CCC2(CCOC2)c2c1cnc1cc(Cl)nn21] | $^1$H NMR (400 MHz, DMSO-d$_6$) δ ppm 8.81 (s, 1H), 6.90 (s, 1H), 4.30 (d, J = 8.0 Hz, 1H), 4.19 (q, J = 8.2 Hz, 1H), 4.13-4.05 (m, 1H), 4.02-3.96 (m, 1H), 3.53-3.44 (m, 1H), 3.28 (d, J = 10.2 Hz, 1H), 3.04 (ddd, J = 12.9, 8.4, 5.0 Hz, 1H), 2.12 (dd, J = 14.0, 3.8 Hz, 1H), 1.99-1.89 (m, 1H), 1.80-1.72 (m, 1H), 1.49 (s, 9H). m/z: 365 [M + H]$^+$ | 32 |
| tert-butyl 4-chloro-13-(methoxymethyl)-2,3,7,10-tetrazatricyclo[7.4.0.0$^{2,6}$]trideca-1(9),3,5,7-tetraene-10-carboxylate Intermediate 31 | 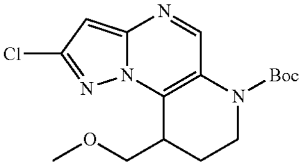 [SMILES: COCC1CCN(C(=O)OC(C)(C)C)c2cnc3cc(Cl)nn3c21] | $^1$H NMR (400 MHz, DMSO-d$_6$) δ ppm 8.83 (s, 1H), 6.86 (s, 1H), 3.89-3.77 (m, 3H), 3.69 (ddd, J = 13.2, 8.8, 3.6 Hz, 2H), 3.20 (s, 3H), 2.15 (ddt, J = 10.4, 6.5, 3.8 Hz, 1H), 2.10-1.99 (m, 1H), 1.47 (s, 10H). m/z: 353 [M + H]$^+$ | 46 |
| tert-butyl 4-chloro-13-(methoxymethyl)-13-methyl-2,3,7,10-tetrazatricyclo[7.4.0.0$^{2,6}$]trideca-1(9),3,5,7-tetraene-10-carboxylate Intermediate 32 | 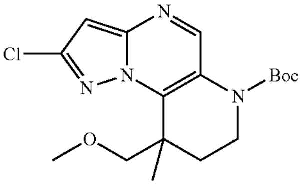 [SMILES: COCC1(C)CCN(C(=O)OC(C)(C)C)c2cnc3cc(Cl)nn3c21] | $^1$H NMR (400 MHz, DMSO-d$_6$) δ ppm 8.74 (s, 1H), 6.85 (s, 1H), 4.54 (d, J = 8.8 Hz, 1H), 4.02 (ddd, J = 13.3, 5.7, 3.2 Hz, 1H), 3.53-3.47 (m, 1H), 3.46 (d, J = 8.8 Hz, 1H), 3.10 (s, 3H), 2.24 (ddd, J = 13.6, 10.5, 3.1 Hz, 1H), 1.77 (ddd, J = 13.7, 5.7, 2.2 Hz, 1H), 1.47 (s, 3H), 1.47 (s, 9H). m/z: 367 [M + H]$^+$ | 68 |
| tert-butyl 4-fluoro-13-methyl-2,3,7,10-tetrazatricyclo[7.4.0.0$^{2,6}$]trideca-1(9),3,5,7-tetraene-10-carboxylate Intermediate 32-b | 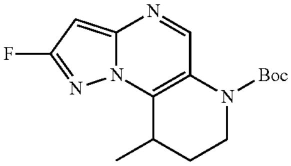 [SMILES: CC1CCN(C(=O)OC(C)(C)C)c2cnc3cc(F)nn3c21] | $^1$H NMR (400 MHz, DMSO-d$_6$) δ 8.84 (s, 1H), 6.45 (d, J = 5.2 Hz, 1H), 3.95 (ddd, J = 13.3, 5.6, 3.4 Hz, 1H), 3.54 (ddd, J = 13.3, 10.4, 2.8 Hz, 1H), 3.46 (pd, J = 7.6, 6.9, 4.2 Hz, 1H), 2.10 (dddd, J = 13.8, 10.1, 6.5, 3.4 Hz, 1H), 1.80 (ddt, J = 13.8, 5.9, 3.0 Hz, 1H), 1.48 (s, 9H), 1.39 (d, J = 7.0 Hz, 3H). m/z: 307 [M + H]$^+$ | 67 |

Step 3 Scheme 1 (if $R_3$ is $CO_2Et$)

Procedure: Intermediates 14-21 (1 mol) were partitioned between THF and water (0.2 M 1:1 ratio) prior addition of LiOH (5 mol), the reaction mixture was left at rt or 40° C. upon completion (4 h).

After that, the reaction mixture was diluted in EtOAc, the organic layer was acidified up to pH 4, washed with water then brine, dried over anhydrous $Na_2SO_4$, filtered and concentrated under reduced pressure. The crude was:

a) purified by flash chromatography using heptane or cyclohexane/EtOAc or DCM/MeOH b) used as such without further purification

| Name | Structure | Analysis | Procedure | Yield % |
|---|---|---|---|---|
| tert-butyl 4-chloro-2,3,7,10-tetrazatricyclo [7.4.0.0$^{2,6}$]trideca-1(9),3,5,7-tetraene-10-carboxylate Intermediate 33 | 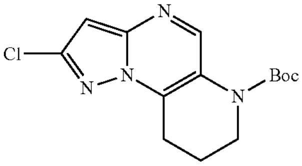 [SMILES: CC(C)(C)OC(=O)N1CCCc2c1cnc1cc(Cl)nn21] | $^1$H NMR (400 MHz, DMSO-$d_6$) δ ppm 8.83 (s, 1H), 6.86 (s, 1H), 3.78-3.67 (m, 2H), 3.11 (t, J = 6.8 Hz, 2H), 2.03 (dt, J = 12.3, 6.8 Hz, 2H), 1.49 (s, 9H). m/z: 309 $[M + H]^+$ | b | 68 |
| tert-butyl 4-methoxy-2,3,7,10-tetrazatricyclo [7.4.0.0$^{2,6}$]trideca-1(9),3,5,7-tetraene-10-carboxylate Intermediate 34 | 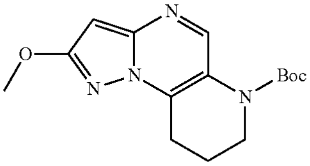 [SMILES: COc1cc2ncc3c(n2n1)CCCN3C(=O)OC(C)(C)C] | $^1$H NMR (400 MHz, DMSO-$d_6$) δ ppm 8.65 (s, 1H), 6.13 (s, 1H), 3.94 (s, 3H), 3.74-3.66 (m, 2H), 3.06 (t, J = 6.9 Hz, 2H), 2.01 (dt, J = 12.2, 6.8 Hz, 2H), 1.48 (s, 9H). m/z: 305 $[M + H]^+$ | a | 47 |
| tert-butyl 4-hydroxy-2,3,7,10-tetrazatricyclo [7.4.0.0$^{2,6}$]trideca-1(9),3,5,7-tetraene-10-carboxylate Intermediate 35 | 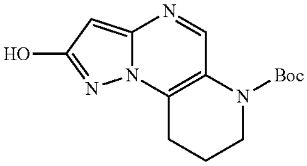 [SMILES: CC(C)(C)OC(=O)N1CCCc2c1cnc1cc(O)nn21] | $^1$H NMR (400 MHz, DMSO-$d_6$) δ ppm 8.21 (s, 1H), 5.19 (s, 1H), 3.84 (s, 1H), 3.61 (d, J = 6.1 Hz, 1H), 3.17 (s, 2H), 2.22-2.11 (m, 1H), 1.94 (s, 1H), 1.46 (s, 9H). m/z: 291 $[M + H]^+$ | b | 100 |
| tert-butyl 4-methylsulfanyl-2,3,7,10-tetrazatricyclo[7.4.0.0$^{2,6}$] trideca-1(9),3,5,7-tetraene-10-carboxylate Intermediate 36 | 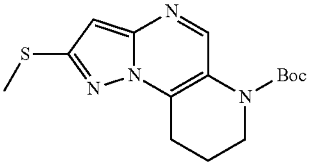 | $^1$H NMR (400 MHz, DMSO-$d_6$) δ ppm 8.71 (s, 1H), 6.68 (s, 1H), 3.77-3.64 (m, 2H), 3.11 (t, J = 6.8 Hz, 2H), 2.59 (s, 3H), 2.08-1.95 (m, 2H), 1.48 (s, 9H) m/z: 321 $[M + H]^+$ | b | 100 |
| tert-butyl 4-fluoro-2,3,7,10-tetrazatricyclo [7.4.0.0$^{2,6}$]trideca-1(9),3,5,7-tetraene-10-carboxylate Intermediate 37 | 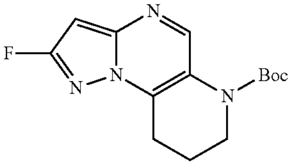 [SMILES: CC(C)(C)OC(=O)N1CCCc2c1cnc1cc(F)nn21] | $^1$H NMR (400 MHz, DMSO-$d_6$) δ ppm 8.81 (s, 1H), 6.47 (d, J = 5.1 Hz, 1H), 3.78-3.67 (m, 2H), 3.07 (t, J = 6.8 Hz, 2H), 2.07-1.93 (m, 2H), 1.49 (s, 9H) m/z: 293 $[M + H]^+$ | a | 85 |
| tert-butyl 4-methyl-2,3,7,10-tetrazatri-cyclo[7.4.0.0$^{2,6}$]trideca-1(9),3,5,7-tetraene-10-carboxylate Intermediate 38 | 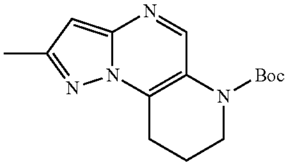 [SMILES: Cc1cc2ncc3c(n2n1)CCCN3C(=O)OC(C)(C)C] | $^1$H NMR (400 MHz, DMSO-$d_6$) δ ppm 8.67 (s, 1H), 6.49 (s, 1H), 3.77-3.66 (m, 2H), 3.11 (t, J = 6.9 Hz, 3H), 2.43 (s, 2H), 2.02 (tdd, J = 6.9, 5.0, 2.4 Hz, 2H), 1.48 (s, 9H). m/z: 289 $[M + H]^+$ | a | 100 |
| tert-butyl 5-chloro-2,3,7,10-tetrazatri-cyclo[7.4.0.0$^{2,6}$]trideca-1(9),3,5,7-tetraene-10-carboxylate Intermediate 39 | 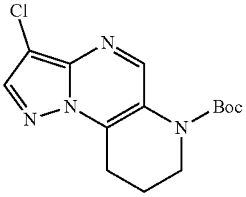 [SMILES: CC(C)(C)OC(=O)N1CCCc2c1cnc1c(Cl)cnn21] | $^1$H NMR (400 MHz, DMSO-$d_6$) δ ppm 8.85 (s, 1H), 8.33 (s, 1H), 3.78-3.66 (m, 2H), 3.14 (t, J = 6.8 Hz, 2H), 2.04 (dt, J = 12.2, 6.8 Hz, 2H), 1.49 (s, 9H) m/z: 309 $[M + H]^+$ | a | 97 |

-continued

| Name | Structure | Analysis | Procedure | Yield % |
|---|---|---|---|---|
| tert-butyl 11-chloro-1,5,8,12-tetrazatricyclo[7.3.0.0$^{2,6}$]dodeca-2(6),7,9,11-tetraene-5-carboxylate Intermediate 40 | 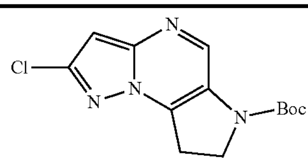 | $^1$H NMR (400 MHz, DMSO-$d_6$) δ ppm 9.00 (s, 1H), 6.88 (s, 1H), 4.09 (t, J = 8.9 Hz, 2H), 3.55 (t, J = 8.8 Hz, 2H), 1.52 (d, J = 12.5 Hz, 9H). m/z: 295 [M + H]$^+$ | a | 20 |

Step 4 Schema 1 or Schema 2:

Procedure Intermediates 22-32 or 32-b and 33-40 (1 mol) were dissolved in DCM (0.2 M) prior addition of either TFA or HCl 4N in 1,4-dioxane (15 mol). The reaction was stirred until completion (2-24 h). Volatiles were concentrated under reduced pressure and the residue was taken in DCM and basified with a sat. aq. $NaHCO_3$. The aqueous layer was extracted 3 times with DCM. The organic layer was dried over $MgSO_4$ anhydrous, filtered and concentrated in vacuo. The crude was:

a) Purified by flash chromatography using heptane/EtOAc or DCM/MeOH/$NH_3$ or DCM/MeOH as eluent b) Purified by reverse phase chromatography using $H_2O$/MeCN (neutral) as eluent c) Used as such without further purification d) Purified by preparative SFC (Chiralpak AD-H 5 μm, 250×20 mm, $CO_2$/MeOH 80/20) in order to separate the 2 enantiomers if necessary

| Name | Structure | Analysis | Procedure | Yield % |
|---|---|---|---|---|
| 4-chloro-2,3,7,10-tetrazatricyclo[7.4.0.0$^{2,6}$]trideca-1(9),3,5,7-tetraene Intermediate 41 | 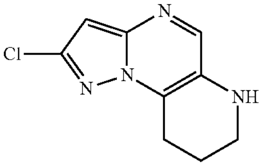 [SMILES: Clc1cc2ncc3c(n2n1)CCCN3] | $^1$H NMR (400 MHz, DMSO-$d_6$) δ ppm 8.16 (s, 1H), 6.64 (s, 1H), 5.85 (s, 1H), 3.18 (dq, J = 5.9, 2.7 Hz, 2H), 2.97 (t, J = 6.5 Hz, 2H), 1.96 (dt, J = 12.0, 6.5 Hz, 2H) m/z: 209 [M + H]$^+$ | a | 93 |
| 4-methoxy-2,3,7,10-tetraazatricyclo[7.4.0.0$^{2,6}$]trideca-1(9),3,5,7-tetraene Intermediate 42 | 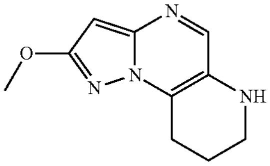 | $^1$H NMR (400 MHz, DMSO-$d_6$) δ ppm 8.02 (s, 1H), 5.92 (s, 1H), 3.88 (s, 3H), 3.20-3.10 (m, 2H), 2.93 (t, J = 6.6 Hz, 2H), 2.02-1.86 (m, 2H). m/z: 205 [M + H]$^+$ | a | 75 |
| 2,3,7,10-tetrazatricyclo[7.4.0.0$^{2,6}$]trideca-1(9),3,5,7-tetraen-4-ol Intermediate 43 | 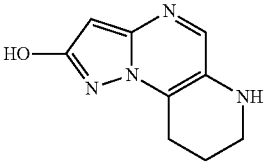 [SMILES: Oc1cc2ncc3c(n2n1)CCCN3] | $^1$H NMR (400 MHz, DMSO-$d_6$) δ ppm 10.42 (s, 1H), 7.94 (s, 1H), 5.63 (s, 1H), 5.40 (s, 1H), 3.13 (dt, J = 6.5, 2.9 Hz, 2H), 2.90 (t, J = 6.6 Hz, 2H), 1.94 (dt, J = 12.0, 6.6 Hz, 2H). m/z: 191 [M + H]$^+$ | b | 32 |
| 4-methylsulfanyl-2,3,7,10-tetrazatricyclo[7.4.0.0$^{2,6}$]trideca-1(9),3,5,7-tetraene Intermediate 44 | 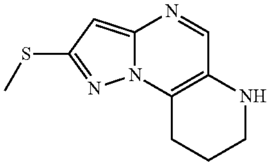 | $^1$H NMR (400 MHz, DMSO-$d_6$) δ ppm 8.07 (s, 1H), 6.50 (s, 1H), 5.73-5.63 (m, 1H), 3.22-3.11 (m, 2H), 2.98 (t, J = 6.6 Hz, 2H), 2.52-2.49 (m, 13H), 1.99-1.92 (m, 2H). m/z: 221 [M + H]$^+$ | c | 45 |
| 4-fluoro-2,3,7,10-Tetrazatricyclo[7.4.0.0$^{2,6}$]trideca-1(9),3,5,7-tetraene Intermediate 45 | 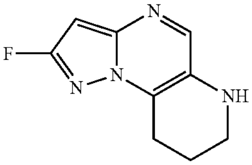 [SMILES: Fc1cc2ncc3c(n2n1)CCCN3] | $^1$H NMR (400 MHz, DMSO-$d_6$) δ ppm 8.15 (s, 1H), 6.22 (d, J = 5.2 Hz, 1H), 5.75 (s, 1H), 3.21-3.13 (m, 2H), 2.93 (t, J = 6.6 Hz, 2H), 1.96 (dq, J = 12.0, 6.6, 5.4 Hz, 2H). m/z: 193 [M + H]$^+$ | c | 93 |

-continued

| Name | Structure | Analysis | Procedure | Yield % |
|---|---|---|---|---|
| 4-methyl-2,3,7,10-Tetrazatricyclo[7.4.0.0$^{2,6}$]trideca-1(9),3,5,7-tetraene Intermediate 46 | 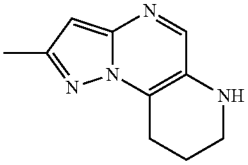 | $^1$H NMR (400 MHz, DMSO-$d_6$) δ ppm 8.04 (s, 1H), 6.31 (s, 1H), 5.58 (s, 1H), 3.16 (s, 2H), 2.98 (t, J = 6.5 Hz, 2H), 2.36 (s, 3H), 1.96 (p, J = 5.9 Hz, 2H). m/z: 189 [M + H]$^+$ | a | 69 |
| 5-chloro-2,3,7,10-Tetrazatricyclo[7.4.0.0$^{2,6}$]trideca-1(9),3,5,7-tetraene Intermediate 47 | 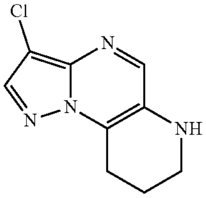 [SMILES: Clc1cnn2c3c(cnc12)NCCC3] | $^1$H NMR (400 MHz, DMSO-$d_6$) δ ppm 8.21 (s, 1H), 8.06 (s, 1H), 5.89 (s, 1H), 3.25-3.11 (m, 2H), 3.00 (t, J = 6.5 Hz, 2H), 2.04-1.90 (m, 2H) m/z: 209 [M + H]$^+$ | c | 60 |
| 4-chloro-13,13-dimethyl-2,3,7,10-tetraazatricyclo[7.4.0.0$^{2,6}$]trideca-1(9),3,5,7-tetraene Intermediate 48 | 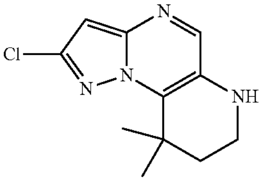 [SMILES: CC1(C)CCNc2cnc3cc(Cl)nn3c21] | $^1$H NMR (400 MHz, DMSO-$d_6$) δ ppm 8.17 (s, 1H), 6.63 (s, 1H), 5.96 (s, 1H), 3.20-3.10 (m, 2H), 1.89-1.77 (m, 2H), 1.56 (s, 6H) m/z: 237 [M + H]$^+$ | c | 97 |
| 4'-chloro-2',3',7',10'-tetraazaspiro[cyclopropane-1,13'-tricyclo[7.4.0.0$^{2,6}$]tridecane]-1'(9'),3',5',7'-tetraene Intermediate 49 | 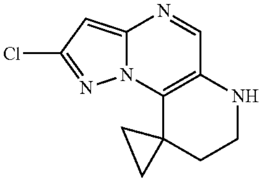 [SMILES: Clc1cc2ncc3c(n2n1)C1(CCN3)CC1] | $^1$H NMR (400 MHz, DMSO-$d_6$) δ ppm 8.11 (s, 1H), 6.56 (s, 1H), 5.98 (s, 1H), 3.23 (dt, J = 6.5, 2.7 Hz, 2H), 2.40 (q, J = 3.6 Hz, 2H), 1.86-1.72 (m, 2H), 0.76 (q, J = 3.7 Hz, 2H). m/z: 235 [M + H]$^+$ | c | 83 |
| 4-chloro-13-methyl-2,3,7,10-tetrazatricyclo[7.4.0.0$^{2,6}$]trideca-1(9),3,5,7-tetraene Intermediate 50 | 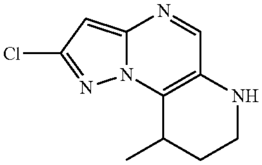 | $^1$H NMR (400 MHz, DMSO-$d_6$) δ ppm 8.18 (s, 1H), 6.62 (s, 1H), 3.42 (p, J = 6.8 Hz, 2H), 3.26 (dt, J = 12.4, 3.4 Hz, 1H), 3.17 (td, J = 12.2, 3.1 Hz, 1H), 1.88 (tt, J = 12.1, 4.8 Hz, 1H), 1.78 (dq, J = 13.4, 3.0 Hz, 1H), 1.36 (s, 3H). m/z: 223 [M + H]$^+$ | a | 100 |
| 11-chloro-1,5,8,12-tetrazatricyclo[7.3.0.0$^{2,6}$]dodeca-2(6),7,9,11-tetraene Intermediate 51 | 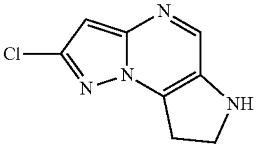 [SMILES: Clc1cc2ncc3c(n2n1)CCN3] | $^1$H NMR (400 MHz, DMSO-$d_6$) δ ppm o 8.23 (s, 1H), 6.71 (s, 1H), 5.58 (s, 1H), 3.68-3.60 (m, 2H), 3.47-3.39 (m, 2H). m/z: 195 [M + H]$^+$ | c | 65 |
| 11-chloro-3,3-dimethyl-1,5,8,12-tetrazatricyclo[7.3.0.0$^{2,6}$]dodeca-2(6),7,9,11-tetraene Intermediate 52 | 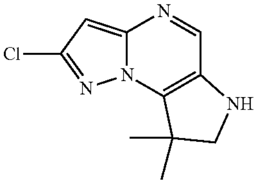 | $^1$H NMR (400 MHz, DMSO-$d_6$) δ ppm 8.24 (s, 1H), 6.71 (s, 1H), 5.65 (s, 1H), 3.36 (d, J = 2.8 Hz, 2H), 1.51 (s, 6H). m/z: 223 [M + H]$^+$ | c | 99 |
| 11'-chloro-1',5',8',12'-tetraazaspiro[cyclopropane-1,3'-tricyclo[7.3.0.0$^{2,6}$]dodecane]-2'(6'),7',9',11'-tetraene Intermediate 53 | 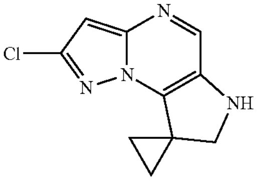 [SMILES: Clc1cc2ncc3c(n2n1)C1(CC1)CN3] | $^1$H NMR (400 MHz, DMSO-$d_6$) δ ppm 7.82 (d, J = 0.7 Hz, 1H), 6.41 (d, J = 0.7 Hz, 1H), 6.11 (s, 1H), 3.66 (d, J = 1.9 Hz, 2H), 1.28 (t, J = 2.9 Hz, 2H), 1.24-1.21 (m, 2H) m/z: 221 [M + H]$^+$ | c | 49 |

-continued

| Name | Structure | Analysis | Procedure | Yield % |
|---|---|---|---|---|
| 4-chloro-12,12-dimethyl-2,3,7,10-tetrazatricyclo [7.4.0.0$^{2,6}$]trideca-1(9),3,5,7-tetraene Intermediate 54 | 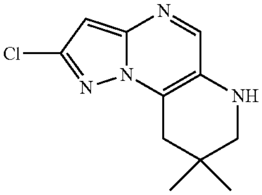 [SMILES: CC1(C)CNc2cnc3cc(Cl)nn3c2C1] | $^1$H NMR (400 MHz, DMSO-$d_6$) δ ppm 8.20 (s, 1H), 6.65 (s, 1H), 6.08 (s, 1H), 2.84 (d, J = 2.8 Hz, 2H), 2.75 (s, 2H), 1.02 (s, 6H). m/z: 237 [M + H]$^+$ | b | 99 |
| 4-chlorospiro[2,3,7,10-tetrazatricyclo[7.4.0.0$^{2,6}$] trideca-1(9),3,5,7-tetraene-12,1'-cyclopropane] Intermediate 55 | 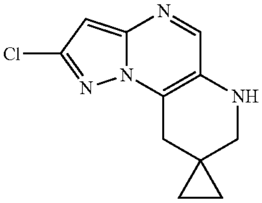 [SMILES: Clc1cc2ncc3c(n2n1)CC1(CC1)CN3] | $^1$H NMR (400 MHz, DMSO-$d_6$) δ ppm 8.21 (s, 1H), 6.65 (s, 1H), 5.94 (s, 1H), 2.92 (d, J = 2.6 Hz, 3H), 2.89 (s, 3H), 0.65-0.48 (m, 7H). m/z: 235 [M + H]$^+$ | c | 81 |
| (11rel-S)-4-chloro-11-methyl-2,3,7,10-tetrazatricyclo[7.4.0.0$^{2,6}$] trideca-1(9),3,5,7-tetraene Intermediate 56 | 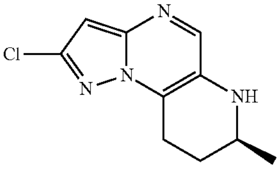 | $^1$H NMR (400 MHz, DMSO-$d_6$) δ ppm .16 (s, 1H), 6.64 (s, 1H), 5.84 (s, 1H), 3.11-2.87 (m, 2H), 2.09-1.99 (m, 1H), 1.58 (dtd, J = 13.2, 10.0, 6.4 Hz, 1H), 1.20 (d, J = 6.3 Hz, 3H). m/z: 223 [M + H]$^+$ | c | 31 |
| (11rel-R)-4-chloro-11-methyl-2,3,7,10-tetrazatricyclo[7.4.0.0$^{2,6}$] trideca-1(9),3,5,7-tetraene Intermediate 57 | 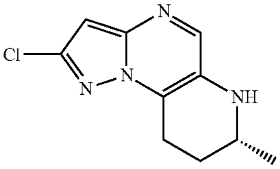 | $^1$H NMR (400 MHz, DMSO-$d_6$) δ ppm .16 (s, 1H), 6.64 (s, 1H), 5.84 (s, 1H), 3.11-2.87 (m, 2H), 2.09-1.99 (m, 1H), 1.58 (dtd, J = 13.2, 10.0, 6.4 Hz, 1H), 1.20 (d, J = 6.3 Hz, 3H). m/z: 223 [M + H]$^+$ | c | 34 |
| 4-chlorospiro[2,3,7,10-tetrazatricyclo[7.4.0.0$^{2,6}$] trideca-1(9),3,5,7-tetraene-13,3'-tetrahydrofuran] Intermediate 58 | 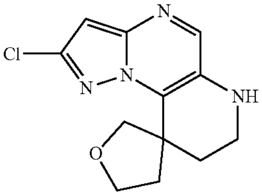 [SMILES: Clc1cc2ncc3c(n2n1)C1(CCN3)CCOC1] | $^1$H NMR (400 MHz, DMSO-$d_6$) δ ppm 8.20 (s, 1H), 6.69 (s, 1H), 6.10 (s, 1H), 4.24-4.04 (m, 3H), 3.51 (d, J = 8.1 Hz, 1H), 3.27-3.18 (m, 1H), 3.07 (ddt, J = 10.8, 7.7, 3.8 Hz, 2H), 2.06-1.98 (m, 1H), 1.89-1.80 (m, 1H), 1.64 (dt, J = 12.1, 7.3 Hz, 1H). m/z: 265 [M + H]$^+$ | c | 88 |
| 4-chloro-13-(methoxymethyl)-2,3,7,10-tetrazatricyclo[7.4.0.0$^{2,6}$] trideca-1(9),3,5,7-tetraene Intermediate 59 | 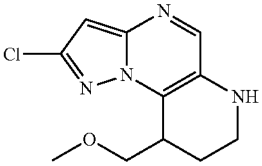 [SMILES: COCC1CCNc2cnc3cc(Cl)nn3c21] | $^1$H NMR (400 MHz, DMSO-$d_6$) δ ppm 8.17 (s, 1H), 6.64 (s, 1H), 6.06 (s, 1H), 3.76 (dd, J = 8.7, 2.2 Hz, 1H), 3.64-3.54 (m, 2H), 3.28 (s, 3H), 3.26-3.14 (m, 2H), 2.11 (d, J = 13.5 Hz, 1H), 1.74 (ddd, J = 18.4, 12.7, 4.9 Hz, 1H). m/z: 253 [M + H]$^+$ | b | 32 |
| 4-chloro-13-(methoxymethyl)-13-methyl-2,3,7,10-tetrazatricyclo [7.4.0.0$^{2,6}$]trideca-1(9),3,5,7-tetraene Intermediate 60 | 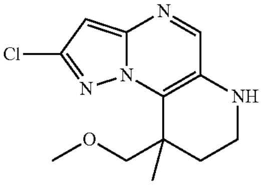 [SMILES: COCC1(C)CCNc2cnc3cc(Cl)nn3c21] | $^1$H NMR (400 MHz, DMSO-$d_6$) δ ppm 8.15 (s, 1H), 6.62 (s, 1H), 5.95 (s, 1H), 4.42 (d, J = 8.6 Hz, 1H), 3.48 (d, J = 8.7 Hz, 1H), 3.22 (dq, J = 9.7, 3.7, 3.0 Hz, 1H), 3.11 (s, 4H, CH3 + CH), 2.18 (ddd, J = 13.5, 9.9, 3.7 Hz, 1H), 1.65 (ddd, J = 13.4, 6.0, 3.0 Hz, 1H), 1.43 (s, 3H). m/z: 267 [M + H]$^+$ | c | 96 |

-continued

| Name | Structure | Analysis | Procedure | Yield % |
| --- | --- | --- | --- | --- |
| 4-fluoro-13-methyl-2,3,7,10-tetrazatricyclo [7.4.0.0$^{2,6}$]trideca-1(9),3,5,7-tetraene Intermediate 60-b | 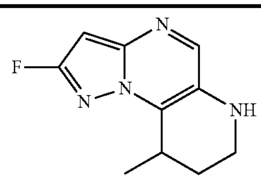 | $^1$H NMR (400 MHz, DMSO-$d_6$) δ ppm 8.16 (s, 1H), 6.20 (d, J = 5.2 Hz, 1H), 5.97-5.84 (m, 1H), 3.41-3.32 (m, 1H), 3.27-3.20 (m, 1H), 3.15 (tdd, J = 12.2, 3.0, 1.9 Hz, 1H), 1.93-1.82 (m, 1H), 1.82-1.72 (m, 1H), 1.34 (d, J = 6.9 Hz, 3H). | f | 96 |

Scheme 3

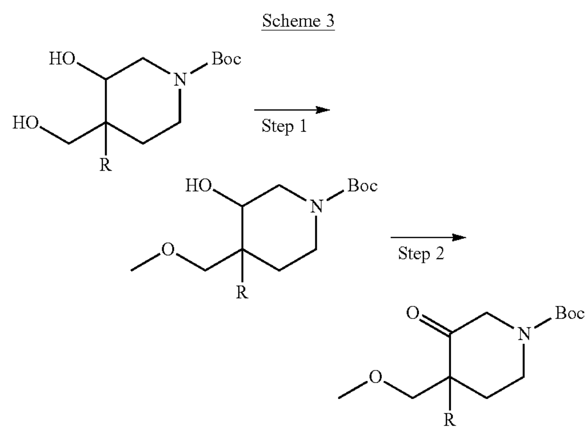

Step 1: Intermediates: 61-62

Tert-butyl piperidine-1-carboxylate derivative (1.74 g, 7.52 mmol) was dissolved in dry DCM-(1M) 2,6-di-tert-butylpyridine (97%, 3 mmol) was added followed by trimethyloxonium tetrafluoroborate (95%, 2 mmol) at 0° C. The reaction mixture was warmed to rt and stirred overnight. The reaction mixture was partitioned between DCM and sat. aq. $NaHCO_3$, phases were separated and the aqueous phase was extracted with DCM. The organic layers were combined, dried over anhydrous $Na_2SO_4$, filtered and concentrated under reduced pressure. The crude was purified by flash column chromatography (Heptane/EtOAc from 100/0 to 1/1) to afford the title compound.

| Name | Structure | Analysis | Yield % |
| --- | --- | --- | --- |
| tert-butyl 3-hydroxy-4-(methoxymethyl)piperidine-1-carboxylate Intermediate 61 | 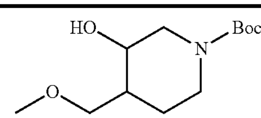 | $^1$H NMR (400 MHz, DMSO-$d_6$) δ ppm 4.89 (d, J = 5.2 Hz, 1H), 4.50 (s, 1H), 3.90 (d, J = 30.5 Hz, 4H), 3.67 (s, 1H), 3.48 (dd, J = 9.1, 3.4 Hz, 1H), 3.34 (dd, J = 9.2, 7.2 Hz, 1H), 3.29-3.25 (m, 1H), 3.22 (d, J = 1.9 Hz, 5H), 3.19-3.05 (m, 2H) 2.62 (s, 3H), 2.49 (s, 1H), 1.76-1.65 (m, 2H), 1.56-1.43 (m, 2H), 1.38 (s, 18H), 1.29 (dq, J = 9.5, 3.3 Hz, 2H). | 43 |
| tert-butyl 3-hydroxy-4-(methoxymethyl)-4-methyl-piperidine-1-carboxylate Intermediate 62 | 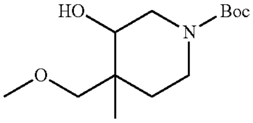 [SMILES: COCC1(C)CCN(C(=O)OC(C)(C)C)CC1O] | $^1$H NMR (DMSO-$d_6$, 500 MHz): δ ppm 4.68-4.79 (m, 1H), 3.59-3.79 (m, 1H), 3.32-3.38 (m, 1H), 3.26-3.30 (m, 1H), 3.23 (s, 3H), 3.22-3.25 (m, 1H), 3.19-3.23 (m, 1H), 3.03 (d, J = 8.8 Hz, 1H), 2.55-2.96 (m, 1H), 1.40-1.48 (m, 1H), 1.38 (s, 9H), 1.25-1.33 (m, 1H), 0.77-0.96 (m, 3H) | 49 |

Step 2: Intermediate 63-64

To a solution of intermediates 61 or 62 (1 mmol) in dry DCM (0.8 M) was added portion-wise Dess-Martin periodinane (2 mmol) at 0° C. The reaction mixture was warmed to rt and left stirring for 4 h, under nitrogen. The reaction mixture was quenched with 10% aqueous $Na_2S_2O_3$ Phases were separated and the aqueous phase was extracted with DCM. The organic layers were combined, dried over anhydrous $Na_2SO_4$, filtered and concentrated under reduced pressure. The crude was purified by flash column chromatography (Heptane/EtOAc from 100/0 to 50/50) to afford title compound -continued

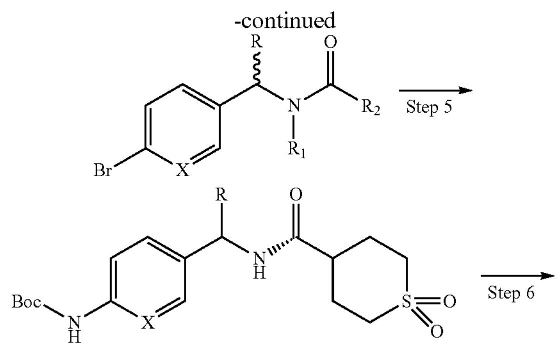

| Name | Structure | Analysis | Yield % |
|---|---|---|---|
| tert-butyl 4-(methoxymethyl)-3-oxo-piperidine-1-carboxylate Intermediate 63 | 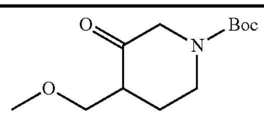 | $^1H$ NMR (400 MHz, DMSO-$d_6$) δ ppm 4.00-3.85 (m, 2H), 3.77 (dt, J = 13.0, 4.2 Hz, 1H), 3.56-3.43 (m, 2H), 3.21 (s, 3H), 2.70 (dq, J = 10.9, 5.9 Hz, 1H), 2.06 (ddt, J = 13.6, 5.8, 3.9 Hz, 1H), 1.76-1.64 (m, 1H), 1.40 (s, 9H). | 76 |
| tert-butyl 4-(methoxymethyl)-4-methyl-3-oxo-piperidine-1-carboxylate Intermediate 64 | 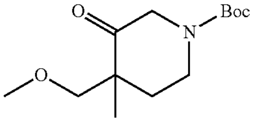 [SMILES: COCC1(C)CCN(C(=O)OC(C)(C)C)CC1=O] | $^1H$ NMR (400 MHz, DMSO-$d_6$) δ ppm 4.01-3.85 (m, 2H), 3.61 (dt, J = 13.1, 5.5 Hz, 1H), 3.46 (d, J = 9.0 Hz, 2H), 3.23 (d, J = 9.0 Hz, 1H), 3.20 (s, 3H), 2.05 (ddd, J = 14.2, 9.2, 5.0 Hz, 1H), 1.67 (ddd, J = 14.0, 6.1, 4.6 Hz, 1H), 1.40 (s, 9H), 1.01 (s, 3H). | 82 |

Scheme 4

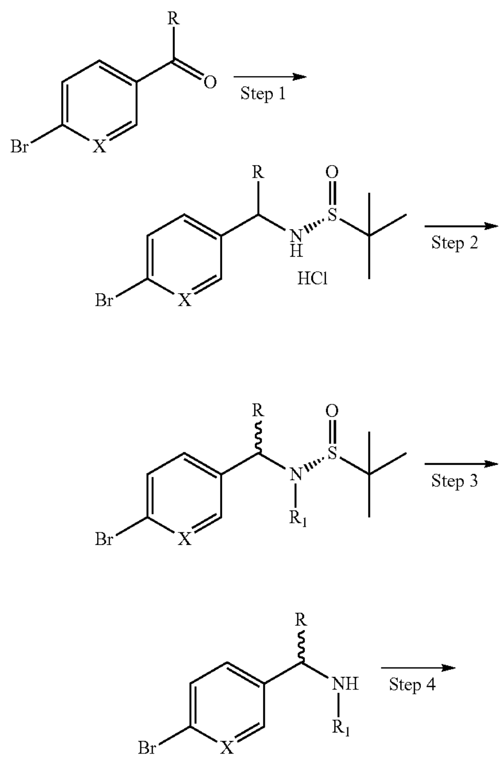

-continued

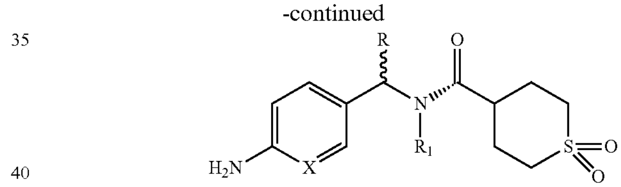

Step 1 (X=C, N)

General Procedure

To a solution of commercially available ketone (1 mol) and ({R})-2-methylpropane-2-sulfinamide (1.25 mol) in dry THF (0.25 M) was added $Ti(OiPr)_4$ (2.5 mol) at rt. After that, the reaction mixture was stirred at reflux for 24 h then cooled to rt and then to −78° C. prior addition of 1 M L-selectride in THF (3 mol), the reaction mixture was left at this temperature for 2 h. After quenching the reaction with brine at −78° C., the reaction was allowed to reach rt and was left stirring at rt for 1 h. The slurry mixture was filtered over a pad of isolute and the pad was washed 3 times with EtOAc. The organic phase was separated and the aqueous layer was extracted with EtOAc. The organic layers were combined, dried over anhydrous $Na_2SO_4$, filtered and concentrated under reduced pressure. The crude was purified by flash chromatography on silica (heptane/EtOAc) to afford the expected compound (Rs, S).

Using the same conditions with ({S})-2-methylpropane-2-sulfinamide, the expected compound (Ss, R) was obtained.

Intermediate 65-71

| Name | Structure | Analysis | Yield % |
|---|---|---|---|
| (R)-N-[(1S)-1-(4-bromophenyl)-2,2,2-trifluoro-ethyl]-2-methyl-propane-2-sulfinamide Intermediate 65 | 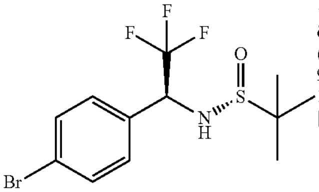 | $^1$H NMR (400 MHz, DMSO-$d_6$) δ ppm 7.70-7.60 (m, 2H), 7.58 (d, J = 8.5 Hz, 2H), 6.45 (d, J = 9.6 Hz, 1H), 5.27 (p, J = 8.5 Hz, 1H), 1.13 (s, 9H). m/z: 358 $[M + H]^+$ | 64 |
| (R)-N-[(1S)-1-(6-bromo-3-pyridyl)-2,2,2-trifluoro-ethyl]-2-methyl-propane-2-sulfinamide Intermediate 66 | 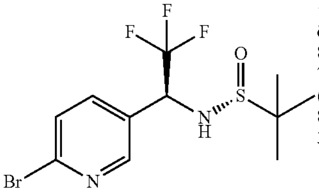 | $^1$H NMR (400 MHz, DMSO-$d_6$) δ ppm 8.63 (d, J = 2.4 Hz, 1H), 8.03 (dd, J = 8.4, 2.5 Hz, 1H), 7.80 (d, J = 8.4 Hz, 1H), 6.57 (d, J = 9.7 Hz, 1H), 5.48 (p, J = 8.3 Hz, 1H), 1.15 (s, 9H) m/z: 359 $[M + H]^+$ | 56 |
| (R)-N-[(1S)-1-(4-bromo-phenyl)-2,2-difluoro-ethyl]-2-methyl-propane-2-sulfinamide Intermediate 67 | 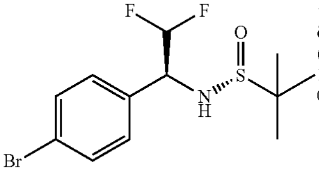 | $^1$H NMR (400 MHz, DMSO-$d_6$) δ ppm 7.62-7.54 (m, 2H), 7.42 (d, J = 8.5 Hz, 2H), 1.61 (s, 1H), 1.08 (d, J = 2.2 Hz, 9H), 0.86-0.82 (m, 1H). m/z: 340 $[M + H]^+$ | 98 |
| (R)-N-[(1R)-1-(4-bromo-phenyl)ethyl]-2-methyl-propane-2-sulfinamide Intermediate 68 | 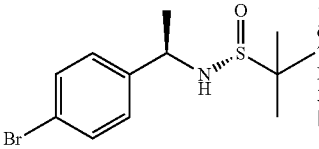 | $^1$H NMR (400 MHz, DMSO-$d_6$) δ ppm 7.62-7.42 (m, 2H), 7.42-7.16 (m, 2H), 5.39 (d, J = 5.2 Hz, 1H), 1.43 (d, J = 6.7 Hz, 3H), 1.10 (s, 9H). m/z: 304 $[M + H]^+$ | 38 |
| (R)-N-[(1S)-1-(4-bromo-phenyl)-2,2-difluoro-propyl]-2-methyl-propane-2-sulfinamide Intermediate 69 | 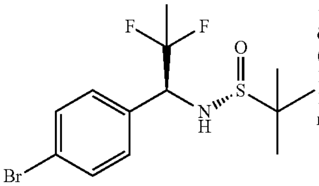 | $^1$H NMR (400 MHz, DMSO-$d_6$) δ ppm 7.65-7.39 (m, 4H), 6.10 (d, J = 9.8 Hz, 1H), 4.69 (q, J = 10.9 Hz, 1H), 1.61 (q, J = 21.0, 19.3 Hz, 3H), 1.14-1.00 (m, 9H). m/z: 354 $[M + H]^+$ | 35 |
| (S)-N-[(1R)-1-(4-bromo-phenyl)-2,2,2-trifluoro-ethyl]-2-methyl-propane-2-sulfinamide Intermediate 70 | 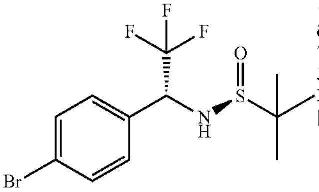 | $^1$H NMR (400 MHz, DMSO-$d_6$) δ ppm 7.64 (d, J = 8.6 Hz, 2H), 7.58 (d, J = 8.5 Hz, 2H), 6.46 (d, J = 9.6 Hz, 1H), 5.27 (p, J = 8.5 Hz, 1H), 1.13 (s, 9H) m/z: 359 $[M + H]^+$ | 61 |
| (S)-N-[(1R)-1-(6-bromo-3-pyridyl)-2,2,2-tri-fluoro-ethyl]-2-methyl-propane-2-sulfinamide Intermediate 71 | 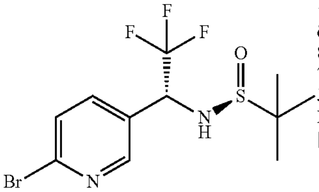 | $^1$H NMR (400 MHz, DMSO-$d_6$) δ ppm 8.62 (d, J = 2.5 Hz, 1H), 8.02 (dd, J = 8.3, 2.5 Hz, 1H), 7.79 (d, J = 8.3 Hz, 1H), 6.56 (d, J = 9.7 Hz, 1H), 5.47 (p, J = 8.5 Hz, 1H), 1.15 (s, 9H). m/z: 359 $[M + H]^+$ | 67 |

Step 2

General Procedure

A solution of intermediates 65-71 (1 mol) were dissolved in dry THF (0.3 M). The reaction mixture was degassed with $N_2$ for 5 min and stirred at 0° C. prior addition of 1 M LiHMDS in THF (1.5 mol). The reaction mixture was stirred at 0° C. for 20 min, and iodoalkane (5 mol) was then added dropwise. The reaction mixture was stirred at 0° C. for further 30 min. The reaction mixture was partitioned between EtOAc and sat. aq. $NH_4Cl$. The organic layers were washed with water, brine, dried over anhydrous $Na_2SO_4$, filtered and concentrated under reduced pressure. The crude was purified by flash column chromatography (Heptane/EtOAc) to afford intermediates 72-79.

| Name | Structure | Analysis | Yield % |
|---|---|---|---|
| (R)-N-[(1S)-1-(4-bromophenyl)-2,2,2-trifluoro-ethyl]-N,2-dimethyl-propane-2-sulfinamide Intermediate 72 | 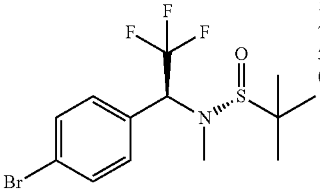 | $^1$H NMR (400 MHz, DMSO-$d_6$) δ ppm 7.74-7.58 (m, 2H), 7.41 (d, J = 8.4 Hz, 2H), 5.60 (q, J = 9.1 Hz, 1H), 2.41 (s, 3H), 1.13 (s, 9H) m/z: 372 [M + H]$^+$ | 77 |
| (R)-N-[(1S)-1-(6-bromo-3-pyridyl)-2,2,2-trifluoro-ethyl]-N,2-dimethyl-propane-2-sulfinamide Intermediate 73 | 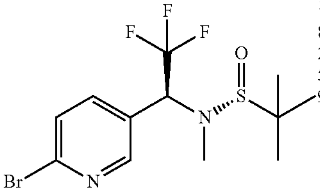 | $^1$H NMR (400 MHz, DMSO-$d_6$) δ ppm 8.49 (d, J = 2.4 Hz, 1H), 7.85 (dd, J = 8.4, 2.5 Hz, 1H), 7.80 (d, J = 8.3 Hz, 1H), 5.83-5.74 (m, 1H), 2.46 (s, 3H), 1.13 (s, 9H). m/z: 373 [M + H]$^+$ | 50 |
| (R)-N-[(1R)-1-(4-bromophenyl)ethyl]-N,2-dimethyl-propane-2-sulfinamide Intermediate 74 | 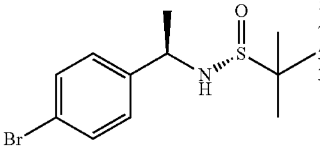 | $^1$H NMR (400 MHz, DMSO-$d_6$) δ ppm 7.62-7.42 (m, 2H), 7.42-7.16 (m, 2H), 5.39 (d, J = 5.2 Hz, 1H), 1.43 (d, J = 6.7 Hz, 3H), 1.10 (s, 9H). m/z: 304 [M + H]$^+$ | 38 |
| (R)-N-[(1S)-1-(4-bromophenyl)-2,2-difluoro-ethyl]-N,2-dimethyl-propane-2-sulfinamide Intermediate 75 | 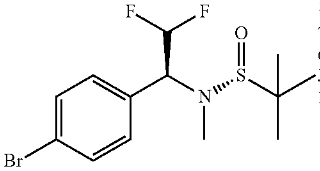 | $^1$H NMR (400 MHz, DMSO-$d_6$) δ ppm 7.67-7.61 (m, 2H), 7.51-7.43 (m, 2H), 6.75 (td, J = 54.6, 6.0 Hz, 1H), 4.74 (ddd, J = 13.3, 10.8, 6.0 Hz, 1H), 2.53 (s, 3H), 1.09 (s, 9H). m/z: 354 [M + H]$^+$ | 72 |
| (R)-N-[(1SR)-1-(4-bromophenyl)-2,2-difluoro-propyl]-N,2-dimethyl-propane-2-sulfinamide Intermediate 76 | 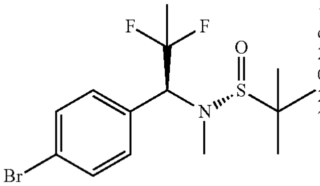 | $^1$H NMR (400 MHz, DMSO-$d_6$) (major diastereoisomere) δ ppm 7.66-7.59 (m, 2H), 7.44-7.37 (m, 2H), 4.96 (t, J = 15.2 Hz, 0.8 H),2.47 (s, 2.45 H), 1.68 (dt, J = 23.4, 19.3 Hz, 2.45 H), 1.13 (d, J = 35.6 Hz, 7.49 H). | 53 |
| (S)-N-[(1R)-1-(4-bromophenyl)-2,2,2-trifluoro-ethyl]-N,2-dimethyl-propane-2-sulfinamide Intermediate 77 | 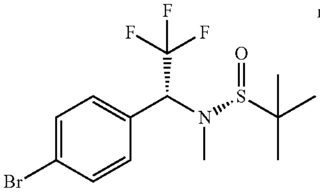 | m/z: 372 [M + H]$^+$ | 79 |
| (S)-N-[(1R)-1-(6-bromo-3-pyridyl)-2,2,2-trifluoro-ethyl]-N,2-dimethyl-propane-2-sulfinamide Intermediate 78 | 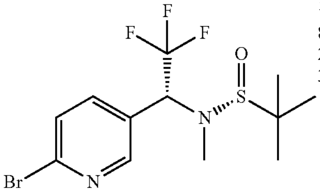 | $^1$H NMR (400 MHz, DMSO-$d_6$) δ ppm 8.49 (d, J = 2.5 Hz, 1H), 7.90-7.71 (m, 2H), 5.77 (q, J = 9.0 Hz, 1H), 2.45 (s, 3H), 1.13 (s, 9H). m/z: 373 [M + H]$^+$ | 83 |
| (R)-N-[(1S)-1-(4-bromophenyl)-2,2,2-trifluoro-ethyl]-N-ethyl-2-methyl-propane-2-sulfinamide Intermediate 79 | 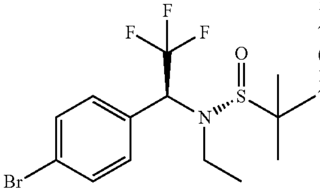 | $^1$H NMR (400 MHz, DMSO-$d_6$) δ ppm 7.69-7.65 (m, 2H), 7.45-7.40 (m, 2H), 5.46 (q, J = 9.2 Hz, 1H), 3.33 (dq, J = 14.5, 7.2 Hz, 1H), 2.81-2.65 (m, 1H), 1.19 (t, J = 7.1 Hz, 3H), 0.97 (s, 9H). m/z: 387 [M + H]$^+$. | 39 |

Step 3

General Procedure

To a solution of Intermediates 72-79 (1 mol) in EtOAc (0.1 M) was added 4 M hydrogen chloride in 1,4-dioxane (4 mol). The reaction mixture was left stirring for 2 h.

a) The mixture was concentrated under vacuum to obtain the title compounds as HCl salt.

b) The reaction mixture was slowly poured onto a sat. aq. $NaHCO_3$ solution, the phases were separated, and the aqueous solution extracted with EtOAc (3 times). The organic layers were combined, washed with brine, dried over anhydrous $Na_2SO_4$, filtered and concentrated under reduced pressure. The crude was purified by flash chromatography on silica (DCM/EtOAc) to afford Intermediates 80-85 as free bases.

| Name | Structure | Analysis | Procedure | Yield % |
|---|---|---|---|---|
| [(1S)-1-(4-bromophenyl)-2,2,2-trifluoroethyl](methyl) amine hydrochloride Intermediate 80 | 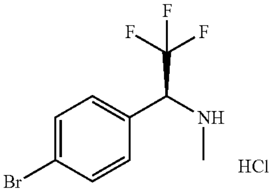 | $^1$H NMR (400 MHz, DMSO-$d_6$) δ ppm 10.56 (s, 1H), 7.77 (d, J = 8.5 Hz, 2H), 7.62 (d, J = 8.4 Hz, 2H), 5.48 (s, 1H). m/z: 268 [M + H]$^+$ | a | 97 |
| (1S)-1-(6-bromopyridin-3-yl)-2,2,2-trifluoroethyl](methyl) amine Intermediate 81 | 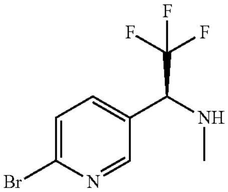 | $^1$H NMR (400 MHz, DMSO-$d_6$) δ ppm 7.90 (d, J = 8.5 Hz, 1H), 7.78 (d, J = 8.4 Hz, 1H), 4.65 (s, 1H), 2.29 (s, 3H). m/z: 269 [M + H]$^+$ | b | 65 |
| (1S)-1-(4-bromophenyl)-2,2-difluoro-N-methyl-ethanamine Intermediate 82 | 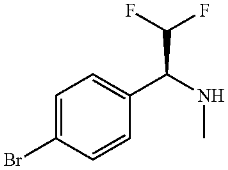 | $^1$H NMR (400 MHz, DMSO-$d_6$) δ ppm 10.12 (s, 1H), 7.88-7.68 (m, 2H), 7.57 (d, J = 8.4 Hz, 2H), 6.65 (td, J = 54.0, 3.5 Hz, 1H), 4.95 (t, J = 11.4 Hz, 1H), 2.48 (s, 3H). m/z: 250 [M + H]$^+$ | b | 86 |
| (1R)-1-(4-bromophenyl)-N-methylethanamine hydrochloride Intermediate 83 | 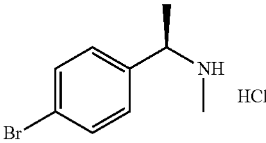 | $^1$H NMR (400 MHz, DMSO-$d_6$) δ ppm 9.15 (s, 1H), 7.79-7.61 (m, 2H), 7.52 (s, 2H), 4.31 (d, J = 6.3 Hz, 1H), 2.39 (s, 3H), 1.54 (d, J = 6.8 Hz, 3H) m/z: 214 [M + H]$^+$ | a | 93 |
| (1R)-1-(4-bromophenyl)-2,2,2-trifluoro-N-methyl-ethanamine hydrochloride Intermediate 84 | 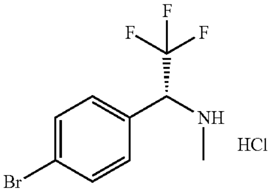 | $^1$H NMR (400 MHz, DMSO) δ ppm 7.88-7.74 (m, 2H), 7.63 (d, J = 8.2 Hz, 2H), 5.57 (s, 1H), 2.47 (s, 3H), 1.68 (t, J = 1.1 Hz, 1H). m/z: 268 [M + H]$^+$ | a | 100 |
| (1R)-1-(6-bromo-3-pyridyl)-2,2,2-trifluoro-N-methyl-ethanamine Intermediate 85 | 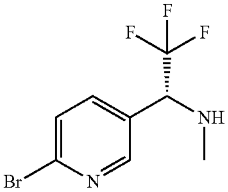 | $^1$H NMR (400 MHz, DMSO-$d_6$) δ ppm 8.48 (d, J = 2.4 Hz, 1H), 7.87 (dd, J = 8.3, 2.5 Hz, 1H), 7.74 (d, J = 8.2 Hz, 1H), 4.46 (p, J = 8.1 Hz, 1H), 3.09-2.90 (m, 1H), 2.22 (d, J = 5.5 Hz, 3H). m/z: 269 [M + H]$^+$ | b | 62 |

Schema 4-Step 4

Procedure

To a solution of 1,1-dioxo-16-thiane-4-carboxylic acid or tetrahydro-2H-thiopyran-4-carboxylic acid (1.5 mol), Intermediate 80-85 (1 mol) in dry DCM (0.2 M) was added TEA (8 mol). Then, a solution of T3P 50% in EtOAc (4 mol) was added at 0° C. and the reaction mixture was warmed to rt and stirred for 18 h. The reaction mixture was diluted with DCM, washed with a sat. aq. $NaHCO_3$ solution, brine, dried over anhydrous $Na_2SO_4$, filtered and concentrated under reduced pressure. The crude was purified by flash column chromatography (Heptane/EtOAc) as eluent to afford Intermediates 86-91.

| Name | Structure | Analysis | Yield % |
| --- | --- | --- | --- |
| N-[(1S)-1-(4-bromophenyl)-2,2,2-trifluoroethyl]-N-methyl-1,1-dioxo-1$\lambda^6$-thiane-4-carboxamide Intermediate 86 | 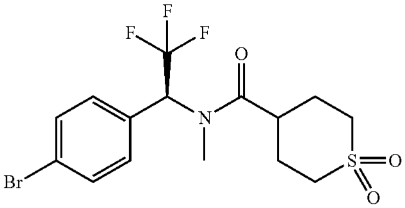 [SMILES: CN(C(=O)C1CCS(=O)(=O)CC1)[C@@H](c1ccc(Br)cc1)C(F)(F)F] | $^1H$ NMR (400 MHz, DMSO-$d_6$) δ ppm 7.68 (d, J = 8.5 Hz, 2H), 7.32 (d, J = 8.4 Hz, 2H), 6.54 (q, J = 9.2 Hz, 1H), 3.17 (ddt, J = 22.5, 18.4, 12.0 Hz, 5H), 2.89 (s, 3H), 2.17-1.88 (m, 4H). m/z: 428 $[M + H]^+$ | 88 |
| N-[(1S)-1-(6-bromopyridin-3-yl)-2,2,2-trifluoroethyl]-N-methyl-1,1-dioxo-1$\lambda^6$-thiane-4-carboxamide Intermediate 87 | 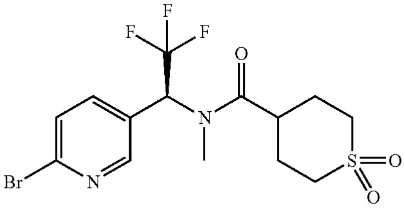 [SMILES: CN(C(=O)C1CCS(=O)(=O)CC1)[C@@H](c1ccc(Br)nc1)C(F)(F)F] | $^1H$ NMR (400 MHz, DMSO-$d_6$) δ ppm 8.40 (s, 1H), 7.78 (s, 2H), 6.71-6.56 (m, 1H), 3.28-3.03 (m, 5H), 2.94 (s, 3H), 2.18-1.90 (m, 5H), 1.17 (d, J = 7.0 Hz, 1H). m/z: 429 $[M + H]^+$ | 56 |
| N-[(1S)-1-(4-bromophenyl)-2,2-difluoro-ethyl]-N-methyl-1,1-dioxo-thiane-4-carboxamide Intermediate 87-b | 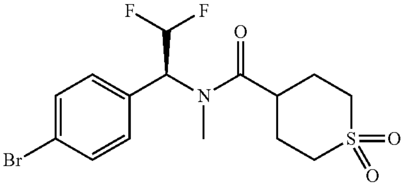 [SMILES: CN(C(=O)C1CCS(=O)(=O)CC1)[C@@H](c1ccc(Br)cc1)C(F)F] | $^1H$ NMR (400 MHz, DMSO-$d_6$) δ ppm 7.65 (dd, J = 21.6, 8.6 Hz, 2H), 7.40-7.30 (m, 2H), 3.21 (d, J = 12.7 Hz, 2H), 3.12 (s, 2H), 2.94 (s, 3H), 2.01 (s, 2H), 1.99 (s, 1H), 1.18 (t, J = 7.1 Hz, 1H), 1.11 (s, 2H). m/z: 410. $[M + H]^+$ | 96 |
| N-[(1R)-1-(4-bromophenyl)ethyl]-N-methyl-1,1-dioxo-1$\lambda^6$-thiane-4-carboxamide Intermediate 88 | 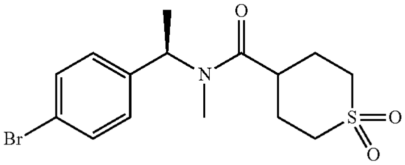 [SMILES: C[C@H](c1ccc(Br)cc1)N(C)C(=O)C1CCS(=O)(=O)CC1] | $^1H$ NMR (400 MHz, DMSO-$d_6$) δ ppm 7.66-7.44 (m, 2H), 7.22 (dd, J = 25.7, 8.3 Hz, 2H), 5.76 (q, J = 7.2 Hz, 1H), 3.34 (d, J = 6.9 Hz, 2H), 3.22 (dd, J = 10.9, 8.1 Hz, 2H), 3.13-3.01 (m, 3H), 2.71 (s, 2H), 2.07-2.01 (m, 3H), 1.56 (d, J = 6.8 Hz, 1H), 1.41 (d, J = 7.1 Hz, 2H). m/z: 374 $[M + H]^+$. | 99 |
| N-[(1R)-1-(6-bromopyridin-3-yl)-2,2,2-trifluoroethyl]-N-methyl-1,1-dioxo-1$\lambda^6$-thiane-4-carboxamide Intermediate 89 | 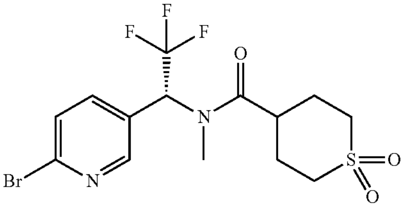 | $^1H$ NMR (400 MHz, DMSO-$d_6$) δ ppm 8.40 (s, 1H), 7.77 (s, 2H), 6.71-6.56 (m, 1H), 3.28-3.03 (m, 5H), 2.94 (s, 3H), 2.18-1.90 (m, 5H), 1.17 (d, J = 7.0 Hz, 1H). m/z: 429 $[M + H]_+$ | 54 |
| N-[(1S)-1-(4-bromophenyl)-2,2,2-trifluoro-ethyl]-N-methyl-tetrahydrothiopyran-4-carboxamide Intermediate 90 | 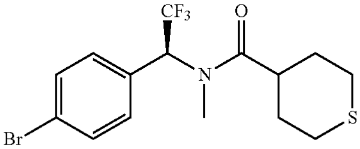 [SMILES: CN(C(=O)C1CCSCC1)[C@@H](c1ccc(Br)cc1)C(F)(F)F] | $^1H$ NMR (400 MHz, DMSO-$d_6$) δ ppm 7.77-7.59 (m, 2H), 7.39-7.22 (m, 2H), 6.65-6.27 (m, 1H), 2.91-2.81 (m, 4H), 2.80-2.65 (m, 2H), 2.63-2.55 (m, 2H), 2.05-1.92 (m, 2H), 1.74-1.58 (m, 2H). m/z: 396 $[M + H]^+$ | 42 |
| N-[(1R)-1-(4-bromophenyl)-2,2,2-trifluoro-ethyl]-N-methyl-tetrahydrothiopyran-4-carboxamide Intermediate 91 | 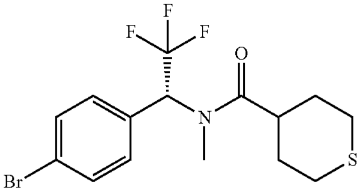 [SMILES: CN(C(=O)C1CCSCC1)[C@H](c1ccc(Br)cc1)C(F)(F)F] | $^1H$ NMR (400 MHz, DMSO) δ ppm 7.74-7.63 (m, 2H), 7.38-7.26 (m, 2H), 6.54 (q, J = 9.3 Hz, 1H), 2.85 (s, 3H), 2.81-2.66 (m, 2H), 2.65-2.54 (m, 3H), 2.04-1.90 (m, 2H), 1.74-1.58 (m, 2H). m/z: 396 $[M + H]^+$ | 52 |

N-[(1R)-1-(4-bromophenyl)-2,2,2-trifluoroethyl]-N-methyl-1,1-dioxo-1λ$^6$-thiane-4-carboxamide Intermediate 92

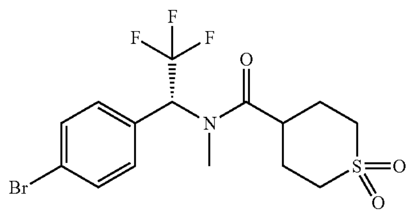 [SMILES: CN(C(=O)C1CCS(=O)(=O)CC1)[C@H](c1ccc(Br)cc1)C(F)(F)F]

Intermediate 91 (285 mg, 0.62 mmol) was dissolved in DCM (3 mL), then m-CPBA (285 mg, 1.24 mmol) was added and the reaction stirred at rt for 3 h. The reaction was quenched with a sat. aq. $Na_2SO_3$ solution. Layers were separated and the organic phase washed with sat $NaHCO_3$, dried over $MgSO_4$ and concentrated under reduce pressure to give Intermediate 92 (204 mg, 75.5% Yield). m/z: 428 $[M+H]^+$. $^1$H NMR (400 MHz, DMSO) δ ppm 7.75-7.64 (m, 2H), 7.32 (d, J=8.3 Hz, 2H), 6.54 (q, J=9.2 Hz, 1H), 3.25-3.06 (m, 5H), 2.88 (s, 3H), 2.10-1.95 (m, 4H).

Step 5 (Only if X═C and R2=1,1-dioxo-1-Δ$^6$-thiane-4-carboxylic acid):

Intermediate 86 (1 mol), tert-butyl carbamate (1.5 mol) and cesium carbonate (2 mol) were dissolved in dry 1,4-dioxane (0.2 M). The reaction mixture was degassed with $N_2$ for 5 min prior addition of Pd XPhos G2 (0.1 mol) at rt. The reaction mixture was then heated at 100° C. for 5 h. EtOAc and $H_2O$ were added to the reaction mixture, phases were separated, the aqueous phase was extracted twice with EtOAc. The organic layers were combined, washed with brine, dried over anhydrous $Na_2SO_4$, filtered and concentrated under reduced pressure. The crude was purified by flash column chromatography (Heptane/EtOAc) as eluent to obtain Intermediate 93

| Name | Structure | Analysis | Yield % |
|---|---|---|---|
| tert-butyl N-{4-[(1S)-1-[1-(1,1-dioxo-1λ$^6$-thian-4-yl)-N-methylformamido]-2,2,2-trifluoroethyl]phenyl}carbamate Intermediate 93 | 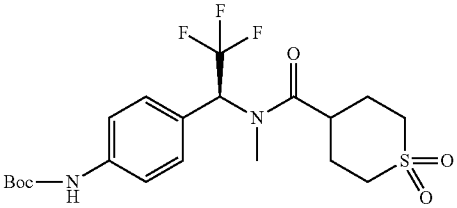 [SMILES: CN(C(=O)C1CCS(=O)(=O)CC1)[C@@H](c1ccc(NC(=O)OC(C)(C)C)cc1)C(F)(F)F] | $^1$H NMR (400 MHz, DMSO-$d_6$) δ ppm 9.51 (s, 1H), 7.52 (d, J = 8.7 Hz, 2H), 7.24 (d, J = 8.7 Hz, 2H), 6.44 (t, J = 9.4 Hz, 1H), 3.27-3.03 (m, 5H), 2.87 (s, 3H), 2.02 (d, J = 25.2 Hz, 4H), 1.47 (s, 9H). m/z: 487 $[M + Na]^+$ | 56 |

Step 6 (Only if X═C):

Under nitrogen, to a solution of Intermediate 93 (1 mol) in 1,4-dioxane/ethanol 1/1 (0.25 M) was added 4 M hydrogen chloride in 1,4-dioxane (5 mol) at rt. The reaction mixture was left stirring at rt for 2 h and then concentrated under reduced pressure to obtain the intermediate 94 as HCl salt.

| Name | Structure | Analysis | Yield % |
|---|---|---|---|
| N-[(1S)-1-(4-aminophenyl)-2,2,2-trifluoroethyl]-N-methyl-1,1-dioxo-1λ$^6$-thiane-4-carboxamide hydrochloride Intermediate 94 | 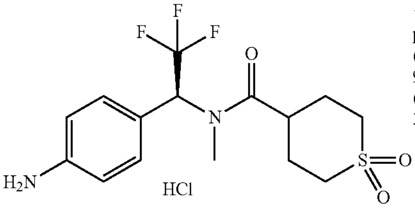 | $^1$H NMR (400 MHz, DMSO-$d_6$) δ ppm 7.23 (d, J = 8.0 Hz, 1H), 7.00 (d, J = 7.6 Hz, 1H), 6.44 (q, J = 9.2 Hz, 0H), 3.32-3.03 (m, 3H), 2.88 (s, 1H), 2.16-1.89 (m, 2H). m/z: 365 $[M + H]^+$ | 84 |

Scheme 5

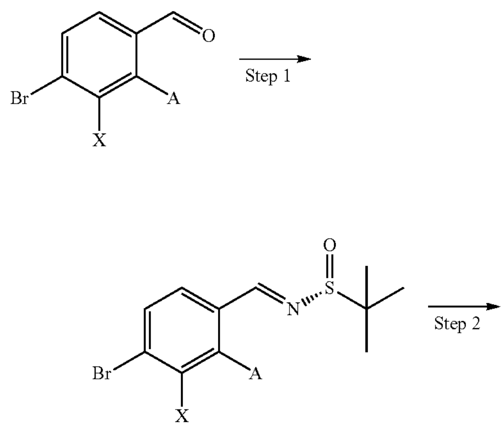

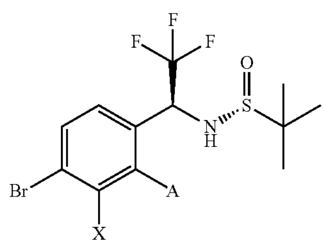

-continued

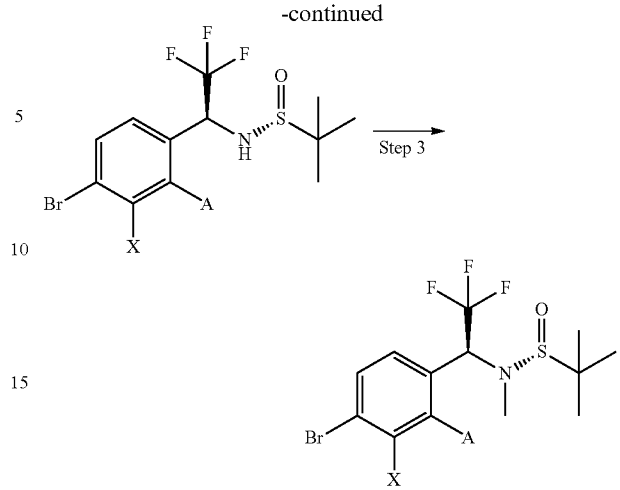

Step 1

To a solution of commercially available benzaldehyde (1 mmol) and (R)-2-methylpropane-2-sulfinamide (4 mmol) in dry DCM (1 M) was added cesium carbonate (1.2 mmol). The reaction mixture was stirred at rt upon completion. The reaction mixture was partitioned between DCM and $H_2O$. The phases were separated and the aqueous layer was extracted twice with DCM. The organic layers were combined, dried over anhydrous $MgSO_4$, filtered and concentrated in vacuo. The crude was purified by flash column chromatography (heptane/EtOAc, from 0% to 25% of EtOAc) intermediates 95-97.

| Name | Structure | Analysis | Yield % |
|---|---|---|---|
| (R)-N-[(4-bromo-3-fluorophenyl)methylene]-2-methyl-propane-2-sulfinamide Intermediate 95 | 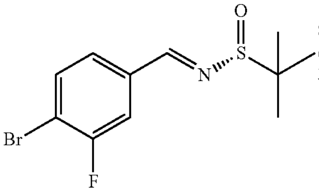 | $^1H$ NMR (400 MHz, DMSO-$d_6$) δ ppm 8.57 (s, 1H), 7.95-7.88 (m, 2H), 7.76 (dd, J = 8.3, 1.8 Hz, 1H), 1.20 (s, 9H). m/z: 306 [M + H].$^+$ | 96 |
| (R)-N-[(4-bromo-2-methylphenyl)methylene]-2-methyl-propane-2-sulfinamide Intermediate 96 | 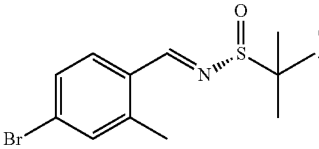 | $^1H$ NMR (400 MHz, DMSO-$d_6$) δ ppm 8.68 (s, 1H), 7.83 (d, J = 8.4 Hz, 1H), 7.62 (d, J = 1.7 Hz, 1H), 7.56 (dd, J = 8.3, 2.0 Hz, 1H), 2.55 (s, 3H), 1.18 (s, 9H). m/z: 302 [M + H].$^+$ | 79 |
| (R)-N-[(4-bromo-3-methoxyphenyl)methylene]-2-methyl-propane-2-sulfinamide Intermediate 97 | 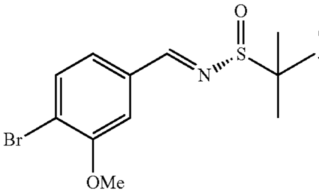 | $^1H$ NMR (400 MHz, DMSO-$d_6$) δ ppm 8.56 (s, 1H), 7.76 (d, J = 8.1 Hz, 1H), 7.66 (d, J = 1.8 Hz, 1H), 7.48 (dd, J = 8.1, 1.8 Hz, 1H), 3.93 (s, 3H), 1.20 (s, 9H). m/z: 318 [M + H].$^+$ | 89 |

Schema 5 Step 2—

A solution of intermediates 95-97 (1 mmol) and N,N,N-trimethylmethanaminium fluoride (1.2 mmol) in dry THF (0.3 M) at rt was cooled to −78° C. A solution of trimethyl (trifluoromethyl) silane (2 mmol) in dry THF (2M) at −78° C. was added and then stirred at same temperature upon completion. The reaction was quenched by addition of sat. aq. $NH_4Cl$ solution at 0° C. The organic layer was separated, the water phase was extracted with EtOAc. The organic layers were combined, dried over anhydrous $Na_2SO_4$ and concentrated under reduced pressure. The crude was purified by flash column chromatography (heptane/EtOAc, from 0% to 100% of EtOAc) to afford Intermediates 98-100.

| Name | Structure | Analysis | Yield % |
| --- | --- | --- | --- |
| (R)-N-[(1S)-1-(4-bromo-3-fluoro-phenyl)-2,2,2-trifluoro-ethyl]-2-methyl-propane-2-sulfinamide Intermediate 98 | 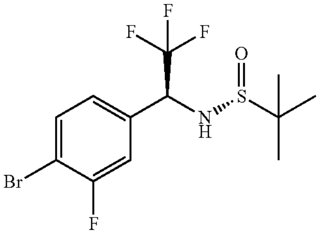 [SMILES: CC(C)(C)[S@@](=O)N[C@@H](c1ccc(Br)c(F)c1)C(F)(F)F] | $^1H$ NMR (400 MHz, DMSO-$d_6$) δ ppm 7.81 (dd, J = 8.2, 7.5 Hz, 1H), 7.72 (dd, J = 10.1, 1.8 Hz, 1H), 7.45 (dd, J = 8.3, 1.7 Hz, 1H), 6.49 (d, J = 9.9 Hz, 1H), 5.37 (p, J = 8.4 Hz, 1H), 1.15 (s, 9H). m/z: 376 $[M + H]^+$ | 75 |
| (R)-N-[(1S)-1-(4-bromo-2-methyl-phenyl)-2,2,2-trifluoro-ethyl]-2-methyl-propane-2-sulfinamide Intermediate 99 | 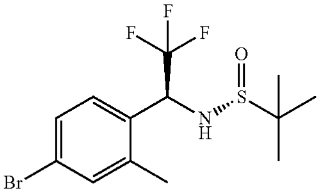 [SMILES: Cc1cc(Br)ccc1[C@H](N[S@](=O)C(C)(C)C)C(F)(F)F] | $^1H$ NMR (400 MHz, DMSO-$d_6$) δ ppm 7.56 (d, J = 8.8 Hz, 1H), 7.52 (s, 1H), 7.49 (s, 1H), 6.49 (d, J = 8.8 Hz, 1H), 5.16 (s, 1H), 2.40 (s, 3H), 1.10 (s, 9H). m/z: 372 $[M + H].^+$ | 88 |
| (R)-N-[(1S)-1-(4-bromo-3-methoxy-phenyl)-2,2,2-trifluoro-ethyl]-2-methyl-propane-2-sulfinamide Intermediate 100 | 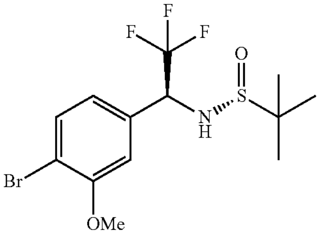 [SMILES: COc1cc([C@H](N[S@](=O)C(C)(C)C)C(F)(F)F)ccc1Br] | $^1H$ NMR (400 MHz, DMSO-$d_6$) δ ppm 7.63 (d, J = 8.2 Hz, 1H), 7.40 (d, J = 1.6 Hz, 1H), 7.15 (dd, J = 8.2, 1.6 Hz, 1H), 6.42 (d, J = 9.6 Hz, 1H), 5.24 (p, J = 8.4 Hz, 1H), 3.87 (s, 3H), 1.15 (s, 9H). m/z: 388 $[M + H].^+$ | 52 |

Intermediates 98-100 (1 mmol) were dissolved in dry THF (0.3 M). The reaction mixture was degassed with $N_2$ for 5 min and stirred at 0° C. prior addition of 1 M LiHMDS in THF (2 mmol). The reaction mixture was stirred at 0° C. for 20 min, then iodomethane (5 mmol) was added dropwise. The reaction mixture was allowed to reach rt and stirred for 2 h. The mixture was partitioned between EtOAc and a sat. aq. $NH_4Cl$. The organic layers were washed with water, brine, dried over anhydrous $Na_2SO_4$, filtered and concentrated under reduced pressure. The crude was purified by flash column chromatography (heptane/EtOAc, from 0% to 100% of EtOAc) to afford Intermediates 101-103.

| Name | Structure | Analysis | Yield % |
| --- | --- | --- | --- |
| (R)-N-[(1S)-1-(4-bromo-3-fluoro-phenyl)-2,2,2-trifluoro-ethyl]-N,2-dimethyl-propane-2-sulfinamide Intermediate 101 | 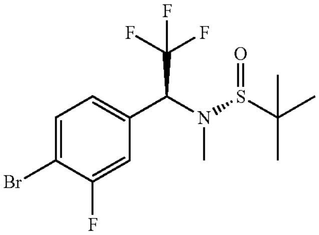 [SMILES: CN([C@@H](c1ccc(Br)c(F)c1)C(F)(F)F)[S@](=O)C(C)(C)C] | $^1H$ NMR (400 MHz, DMSO-$d_6$) δ ppm 7.85 (dd, J = 8.2, 7.6 Hz, 1H), 7.44 (dd, J = 9.9, 2.0 Hz, 1H), 7.27 (dd, J = 8.3, 1.5 Hz, 1H), 5.69 (q, J = 8.9 Hz, 1H), 2.45 (s, 3H), 1.14 (s, 9H). m/z: 390 $[M + H].^+$ | 61 |

-continued

| Name | Structure | Analysis | Yield % |
|---|---|---|---|
| (R)-N-[(1S)-1-(4-bromo-2-methyl-phenyl)-2,2,2-trifluoro-ethyl]-N,2-dimethyl-propane-2-sulfinamide Intermediate 102 | 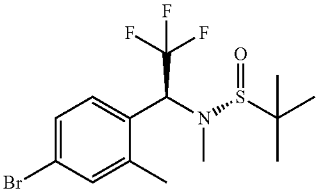 [SMILES: Cc1cc(Br)ccc1[C@H](N(C)[S@](=O)C(C)(C)C)C(F)(F)F] | m/z: 386 [M + H].+. | 69 |
| (R)-N-[(1S)-1-(4-bromo-3-methoxy-phenyl)-2,2,2-trifluoro-ethyl]-N,2-dimethyl-propane-2-sulfinamide Intermediate 103 | 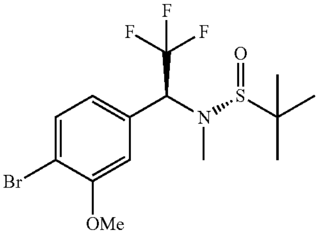 [SMILES: COc1cc([C@H](N(C)[S@](=O)C(C)(C)C)C(F)(F)F)ccc1Br] | $^1$H NMR (400 MHz, DMSO-$d_6$) δ ppm 8.29 (s, 1H), 7.68 (d, J = 8.2 Hz, 1H), 7.15 (d, J = 1.9 Hz, 1H), 6.98 (d, J = 8.3 Hz, 1H), 5.60 (q, J = 9.0 Hz, 1H), 3.86 (s, 3H), 2.44 (s, 3H), 1.15 (s, 9H). m/z: 402 [M + H].+ | 83 |

Intermediates 104-115

General Procedure 1

To a stirred heterogeneous solution of intermediates 72-79 (1 mmol), Intermediates 41-60 or 60-b (1 mmol) and caesium carbonate (6 mmol) in dry toluene (0.2 M) was degassed under argon for 20 min. Then, diacetoxypalladium (0.05 mmol) and Rac-BINAP (0.06 mmol) were added. The heterogeneous reaction mixture was heated at 100° C. for 2 h. The reaction mixture was partitioned between EtOAc and sat. aq. $NH_4Cl$. Phases were separated and the aqueous layer was extracted twice with EtOAc. Organic layers were combined, washed with brine, dried over anhydrous $MgSO_4$, filtered and concentrated under reduced pressure. The crude was purified by flash column chromatography (Heptane/EtOAc, from 0% to 100% of EtOAc) to afford relative Intermediates.

General Procedure 2

Intermediates 101-103 (1 mmol) and Intermediates 41-60 or 60-b (1 mmol) were dissolved in Toluene (0.2 M) and cesium carbonate (3 mmol) was added. The suspension was degassed with argon for 5 min. Pd XPhos G2 (0.01 mmol) was added and the reaction mixture was stirred at 60° C. upon completion. The reaction mixture was partitioned between EtOAc and sat. aq. $NH_4Cl$. Phases were separated and the aqueous layer was extracted twice with EtOAc. Organic layers were dried with anhydrous $MgSO_4$, filtered and concentrated under reduced pressure. The crude was purified by flash column chromatography (heptane/EtOAc, from 0% to 50% of EtOAc) to afford relative Intermediates.

| Name | Structure | Analysis | Procedure | Yield % |
|---|---|---|---|---|
| (R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N,2-dimethyl-propane-2-sulfinamide Intermediate 104 | 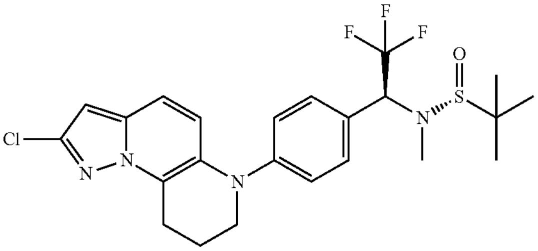 [SMILES: CN([C@@H](c1ccc(N2CCCc3c2ccc2cc(Cl)nn32)cc1)C(F)(F)F)[S@](=O)C(C)(C)C] | $^1$H NMR (DMSO-$d_6$, 400 MHz): δ ppm 8.29 (s, 1H), 7.39 (d, J = 8.5 Hz, 2H), 7.25 (d, J = 8.6 Hz, 2H), 6.82 (s, 1H), 5.50 (q, J = 9.1 Hz, 1H), 3.76-3.65 (m, 2H), 3.10 (t, J = 6.7 Hz, 2H), 2.42 (s, 3H), 2.03-1.88 (m, 2H), 1.14 (s, 9H). m/z 500 [M + H]+ | 1 | 80 |
| (R)-N,2-dimethyl-N-[(1S)-2,2,2-trifluoro-1-[4-(4-fluoro-2,3,7,10-tetrazatricyclo[7.4.0.0$^{2,6}$]trideca-1(9),3,5,7-tetraen-10-yl)phenyl]ethyl]propane-2-sulfinamide Intermediate 105 | 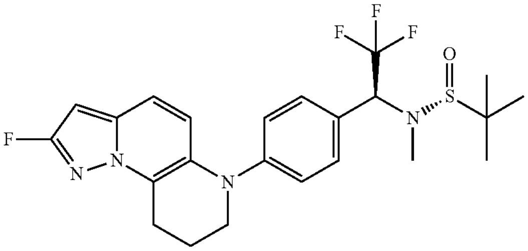 [SMILES: CN([C@@H](c1ccc(N2CCCc3c2ccc2cc(F)nn32)cc1)C(F)(F)F)[S@](=O)C(C)(C)C] | $^1$ (DMSO-$d_6$, 400 MHz): δ ppm 8.30 (s, 1H), 7.39 (d, J = 8.6 Hz, 2H), 7.29-7.22 (m, 2H), 6.44 (d, J = 5.1 Hz, 1H), 5.50 (q, J = 9.2 Hz, 1H), 3.75-3.70 (m, 2H), 3.06 (t, J = 6.7 Hz, 2H), 2.42 (s, 3H), 1.98-1.90 (m, 2H), 1.15 (s, 9H). m/z 484 [M + H]+ | 1 | 48 |

-continued

| Name | Structure | Analysis | Procedure | Yield % |
|---|---|---|---|---|
| (R)-N-[(1S)-1-[4-(4-chlorospiro[2,3,7,10-tetrazatricyclo[7.4.0.0$^{2,6}$]trideca-1(9),3,5,7-tetraene-13,1'-cyclopropane]-10-yl)phenyl]-2,2,2-trifluoro-ethyl]-N,2-dimethyl-propane-2-sulfinamide Intermediate 106 | 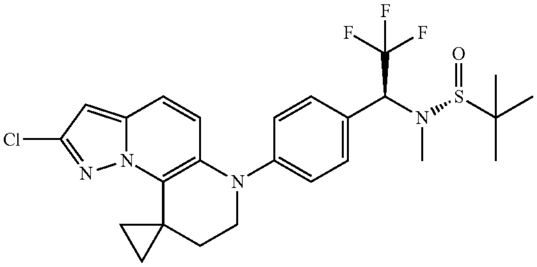 [SMILES: CN([C@@H](c1ccc(N2CCC3(CC3)c3c2ccc2cc(Cl)nn32)cc1)C(F)(F)F)[S@](=O)C(C)(C)C] | $^1$H NMR (DMSO-$d_6$, 400 MHz): δ ppm 8.20 (s, 1H), 7.40 (d, J = 8.5 Hz, 2H), 7.25 (d, J = 8.7 Hz, 2H), 6.75 (s, 1H), 5.51 (q, J = 9.1 Hz, 1H), 3.78 (dd, J = 7.4, 3.0 Hz, 2H), 2.56 (q, J = 3.2 Hz, 2H), 2.42 (s, 3H), 1.80 (dd, J = 6.3, 3.8 Hz, 2H), 1.15 (s, 9H), 0.94 (q, J = 2.9 Hz, 2H). m/z 526 [M + H]+ | 1 | 68 |
| (R)-N,2-dimethyl-N-[(1S)-2,2,2-trifluoro-1-[4-(4-fluorospiro[2,3,7,10-tetrazatricyclo[7.4.0.0$^{2,6}$]trideca-1(9),3,5,7-tetraene-13,1'-cyclopropane]-10-yl)phenyl]ethyl]propane-2-sulfinamide Intermediate 107 | 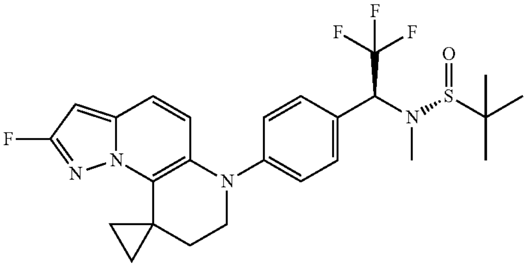 [SMILES: CN([C@@H](c1ccc(N2CCC3(CC3)c3c2ccc2cc(F)nn32)cc1)C(F)(F)F)[S@](=O)C(C)(C)C] | $^1$H NMR (DMSO-$d_6$, 400 MHz): δ ppm 8.20 (s, 1H), 7.39 (d, J = 8.5 Hz, 2H), 7.23 (d, J = 8.7 Hz, 2H), 6.38 (d, J = 5.2 Hz, 1H), 5.50 (d, J = 9.0 Hz, 1H), 3.78 (s, 2H), 2.53 (d, J = 2.8 Hz, 2H), 2.42 (s, 3H), 1.80 (s, 2H), 1.15 (s, 9H), 0.93 (d, J = 2.7 Hz, 2H). m/z: 510 [M + H]+ | 1 | 18 |
| N-[(1S)-1-[4-(4-chloro-13,13-dimethyl-2,3,7,10-tetrazatricyclo[7.4.0.0$^{2,6}$]trideca-1(9),3,5,7-tetraen-10-yl)phenyl]-2,2,2-trifluoro-ethyl]-N,2-dimethyl-propane-2-sulfinamide Intermediate 108 | 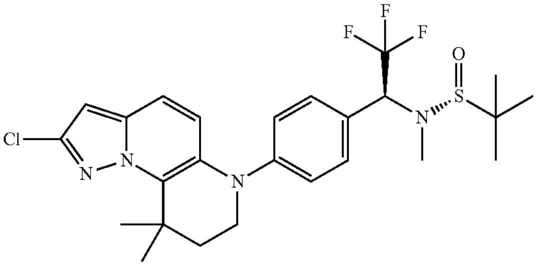 [SMILES: CN([C@@H](c1ccc(N2CCC(C)(C)c3c2ccc2cc(Cl)nn32)cc1)C(F)(F)F)[S@](=O)C(C)(C)C] | $^1$H NMR (DMSO-$d_6$, 400 MHz): δ ppm 8.25 (s, 1H), 7.40 (d, J = 8.5 Hz, 2H), 7.25 (d, J = 8.7 Hz, 2H), 6.82 (s, 1H), 5.50 (t, J = 9.2 Hz, 1H), 4.04 (q, J = 7.1 Hz, 2H), 3.77-3.64 (m, 2H), 2.42 (s, 3H), 1.99 (s, 3H), 1.88-1.76 (m, 2H), 1.64 (s, 6H), 1.18 (t, J = 7.1 Hz, 3H), 1.15 (s, 9H). m/z: 528 [M + H]+ | 1 | 56 |
| (R)-N,2-dimethyl-N-[(1S)-2,2,2-trifluoro-1-[4-(4-fluoro-13,13-dimethyl-2,3,7,10-tetrazatricyclo[7.4.0.0$^{2,6}$]trideca-1(9),3,5,7-tetraen-10-yl)phenyl]ethyl]propane-2-sulfinamide Intermediate 109 | 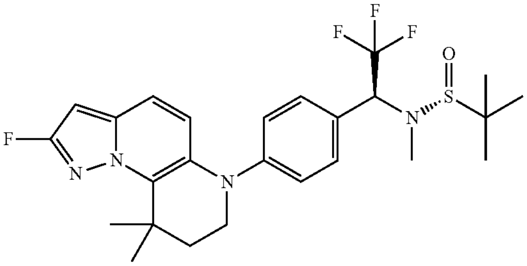 [SMILES: CN([C@@H](c1ccc(N2CCC(C)(C)c3c2ccc2cc(F)nn32)cc1)C(F)(F)F)[S@](=O)C(C)(C)C] | $^1$H NMR (DMSO-$d_6$, 400 MHz): δ ppm 8.25 (s, 1H), 7.39 (d, J = 8.5 Hz, 2H), 7.26-7.21 (m, 2H), 6.43 (d, J = 5.2 Hz, 1H), 5.51 (q, J = 9.2 Hz, 1H), 3.75-3.62 (m, 2H), 2.42 (s, 3H), 1.84-1.76 (m, 2H), 1.62 (s, 6H), 1.15 (s, 9H). m/z: 512 [M + H]+ | 1 | 83 |
| (R)-N-[(1S)-1-[4-(4-chloro-13-methyl-2,3,7,10-tetrazatricyclo[7.4.0.0$^{2,6}$]trideca-1(9),3,5,7-tetraen-10-yl)phenyl]-2,2,2-trifluoro-ethyl]-N,2-dimethyl-propane-2-sulfinamide Intermediate 110 | 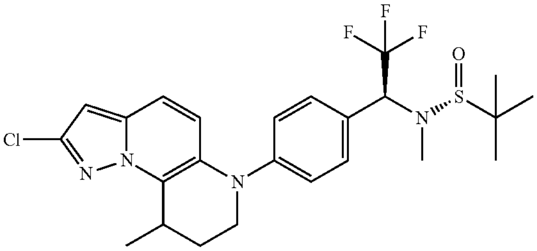 [SMILES: CC1CCN(c2ccc([C@H](N(C)[S@](=O)C(C)(C)C)C(F)(F)F)cc2)c2ccc3cc(Cl)nn3c21] | $^1$H NMR (DMSO-$d_6$, 400 MHz): δ ppm 8.26 (d, J = 3.7 Hz, 1H), 7.41 (d, J = 8.5 Hz, 2H), 7.29 (d, J = 8.7 Hz, 2H), 6.80 (d, J = 1.3 Hz, 1H), 5.52 (q, J = 9.1 Hz, 1H), 3.79-3.63 (m, 2H), 3.52 (ddd, J = 9.1, 6.7, 3.5 Hz, 1H), 2.42 (d, J = 2.5 Hz, 3H), 2.05 (ddt, J = 16.5, 10.6, 4.6 Hz, 1H), 1.84-1.69 (m, 1H), 1.44 (d, J = 6.9 Hz, 3H), 1.14 (s, 9H). m/z: 514 [M + H]+ Mixture of 2 diastereoisomers in proprotion 1/1 | 1 | 64 |

-continued

| Name | Structure | Analysis | Procedure | Yield % |
|---|---|---|---|---|
| (R)-N-[(1S)-1-[4-(4-chloro-2,3,7,10-tetrazatricyclo[7.4.0.0$^{2,6}$]trideca-1(9),3,5,7-tetraen-10-yl)-3-fluoro-phenyl]-2,2,2-trifluoro-ethyl]-N,2-dimethyl-propane-2-sulfinamide Intermediate 111 | 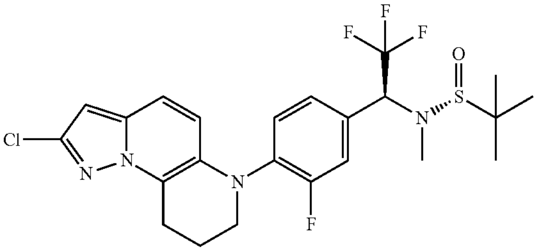 [SMILES: CN([C@@H](c1ccc(N2CCCc3c2ccc2cc(Cl)nn32)c(F)c1)C(F)(F)F)[S@](=O)C(C)(C)C] | m/z: 518 [M + H]. + | 2 | 8 |
| (R)-N-[(1S)-1-[4-(4-chloro-2,3,7,10-tetrazatricyclo[7.4.0.0$^{2,6}$]trideca-1(9),3,5,7-tetraen-10-yl)-2-methyl-phenyl]-2,2,2-trifluoro-ethyl]-N,2-dimethyl-propane-2-sulfinamide Intermediate 112 | 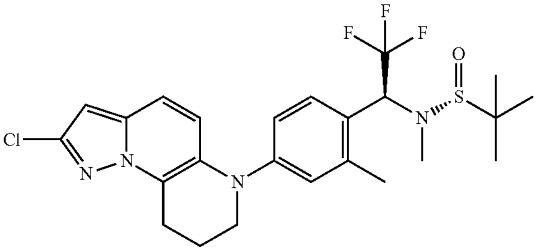 [SMILES: Cc1cc(N2CCCc3c2ccc2cc(Cl)nn32)ccc1[C@H](N(C)[S@](=O)C(C)(C)C)C(F)(F)F] | $^1$H NMR (400 MHz, DMSO-$d_6$) δ ppm 8.29 (s, 1H), 7.33 (d, J = 8.4 Hz, 1H), 7.14 (d, J = 2.5 Hz, 1H), 7.08 (dd, J = 8.5, 2.5 Hz, 1H), 6.82 (s, 1H), 5.43 (q, J = 9.1 Hz, 1H), 3.74-3.67 (m, 2H), 3.09 (t, J = 6.7 Hz, 2H), 2.42 (d, J = 9.7 Hz, 6H), 2.01-1.88 (m, 2H), 1.12 (s, 9H). m/z: 514 [M + H]+. | 2 | 59% |
| (R)-N-[(1S)-1-[4-(4-chloro-2,3,7,10-tetrazatricyclo[7.4.0.0$^{2,6}$]trideca-1(9),3,5,7-tetraen-10-yl)-3-methoxy-phenyl]-2,2,2-trifluoro-ethyl]-N,2-dimethyl-propane-2-sulfinamide Intermediate 113 | 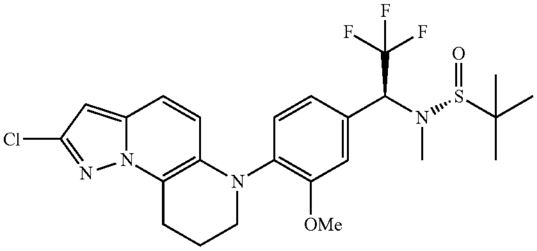 [SMILES: COc1cc([C@H](N(C)[S@](=O)C(C)(C)C)C(F)(F)F)ccc1N1CCCc2c1ccc1cc(Cl)nn21] | $^1$H NMR (400 MHz, DMSO-$d_6$) δ ppm 7.82 (s, 1H), 7.25 (d, J = 8.2 Hz, 1H), 7.17 (d, J = 1.8 Hz, 1H), 7.04 (d, J = 8.3 Hz, 1H), 6.74 (s, 1H), 5.58 (q, J = 8.8 Hz, 1H), 3.79 (s, 3H), 3.57-3.50 (m, 2H), 3.11 (t, J = 6.6 Hz, 2H), 2.45 (s, 3H), 2.10-2.00 (m, 2H), 1.16 (s, 9H). m/z: 530 [M + H]+. | 2 | 71% |
| (R)-N-[(1SR)-1-[4-(4-chloro-2,3,7,10-tetrazatricyclo[7.4.0.0$^{2,6}$]trideca-1(9),3,5,7-tetraen-10-yl)phenyl]-2,2-difluoro-propyl]-N,2-dimethyl-propane-2-sulfinamide Intermediate 114 | 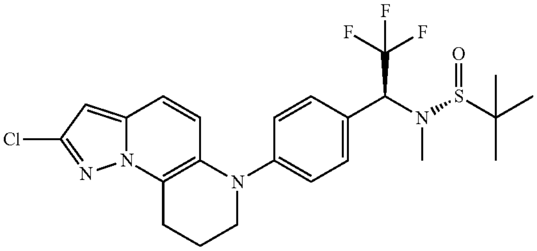 | $^1$H NMR (400 MHz, DMSO-$d_6$) δ ppm 8.28 (d, J = 2.3 Hz, 1H), 7.49-7.33 (m, 2H), 7.23-7.11 (m, 2H), 6.82 (d, J = 1.7 Hz, 1H), 4.09 (q, J = 5.3 Hz, 1H), 3.83-3.61 (m, 2H), 3.17 (d, J = 5.1 Hz, 4H), 3.10 (t, J = 6.7 Hz, 2H), 2.48 (s, 2H), 2.04-1.92 (m, 2H), 1.68 (t, J = 19.2 Hz, 3H), 1.14 (s, 9H). m/z: 496 [M + H]+. | 1 | 45 |
| (R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-ethyl-2-methyl-propane-2-sulfinamide Intermediate 115 | 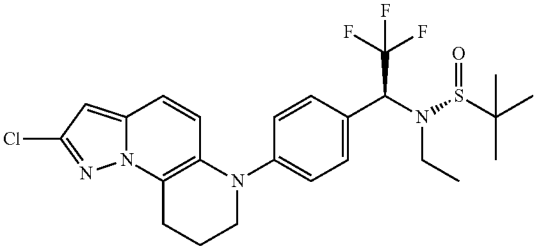 [SMILES: CCN([C@@H](c1ccc(N2CCCc3c2ccc2cc(Cl)nn32)cc1)C(F)(F)F)[S@](=O)C(C)(C)C] | $^1$H NMR (400 MHz, DMSO-$d_6$) δ ppm 8.24 (s, 1H), 7.41 (d, J = 8.6 Hz, 2H), 7.25 (d, J = 8.7 Hz, 2H), 6.82 (s, 1H), 5.39 (q, J = 9.3 Hz, 1H), 3.71 (dd, J = 6.4, 4.1 Hz, 2H), 3.31 (dq, J = 14.7, 7.3 Hz, 1H), 3.10 (t, J = 6.7 Hz, 2H), 2.68 (dd, J = 13.7, 7.5 Hz, 1H), 1.96 (dt, J = 12.2, 6.8 Hz, 2H), 1.18 (t, J = 7.1 Hz, 3H), 1.00 (s, 9H). m/z: 514 [M + H]+. | 1 | 39 |

-continued

| Name | Structure | Analysis | Procedure | Yield % |
|---|---|---|---|---|
| (R)-N-[(1S)-1-(6-{4-chloro-2,3,7,10-tetraazatricyclo[7.4.0.0$^{2,6}$]trideca-1(9),3,5,7-tetraen-10-yl}pyridin-3-yl)-2,2,2-trifluoroethyl]-N,2-dimethylpropane-2-sulfinamide Intermediate 116 | 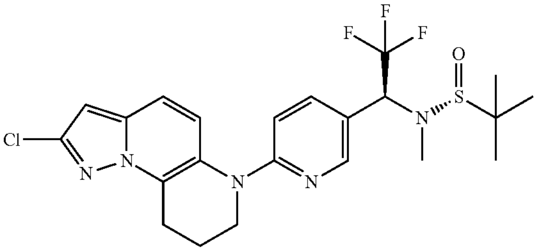 [SMILES: CN([C@@H](c1ccc(N2CCCc3c2ccc2cc(Cl)nn32)nc1)C(F)(F)F)[S@](=O)C(C)(C)C] | $^1$H NMR (400 MHz, DMSO-$d_6$) δ ppm 8.71 (s, 1H), 8.26 (d, J = 2.5 Hz, 1H), 7.76 (dd, J = 8.8, 2.6 Hz, 1H), 7.26 (d, J = 8.8 Hz, 1H), 6.86 (s, 1H), 5.58 (q, J = 9.1 Hz, 1H), 4.02-3.93 (m, 2H), 3.13 (t, J = 6.8 Hz, 2H), 2.46 (s, 3H), 2.05-1.97 (m, 2H), 1.15 (s, 9H). m/z: 501 [M + H]+ | 1 | 42 |

Intermediates 117-128

Procedure

To a stirred solution of intermediates 104-116 (1 mmol) in EtOAc (0.1 M) was added 4 M hydrogen chloride in 1,4-dioxane (1 to 5 mmol). The reaction mixture was stirred for 30 min to 18 h at rt then a) The mixture was concentrated in vacuum to obtain title compound as HCl salt.

b) The reaction mixture was slowly poured onto a sat. aq. $NaHCO_3$ solution, the phases were separated, and the aqueous solution extracted with EtOAc (3 times). The organic layers were combined, washed with brine, dried over $Na_2SO_4$ anhydrous, filtered and concentrated under reduced pressure to afford title compound as free base.

c) The mixture was concentrated in vacuum to obtain title compound as HCl salt which was triturated in $Et_2O$

| Name | Structure | Analysis | Procedure | Yield % |
|---|---|---|---|---|
| (1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-Nmethyl-ethanamine hydrochloride Intermediate 117 | 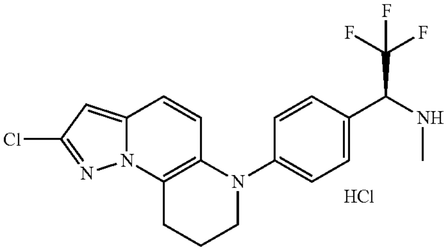 [SMILES: CN[C@@H](c1ccc(N2CCCc3c2ccc2cc(Cl)nn32)cc1)C(F)(F)F ; Cl] | $^1$H NMR (DMSO-$d_6$, 400 MHz): δ ppm 8.34 (s, 1H), 7.54 (s, 2H), 7.33 (d, J = 8.6 Hz, 2H), 6.84 (s, 1H), 3.75 (dd, J = 6.4, 4.0 Hz, 2H), 3.57 (s, 3H), 3.11 (t, J = 6.7 Hz, 2H), 2.00-1.92 (m, 2H). m/z: 395 $[M + H]^+$ | a | 100 |
| (1S)-1-[4-(4-chlorospiro[2,3,7,10-tetrazatricyclo[7.4.0.0$^{2,6}$]trideca-1(9),3,5,7-tetraene-13,1'-cyclopropane]-10-yl)phenyl]-2,2,2-trifluoro-N-methyl-ethanamine Intermediate 118 | 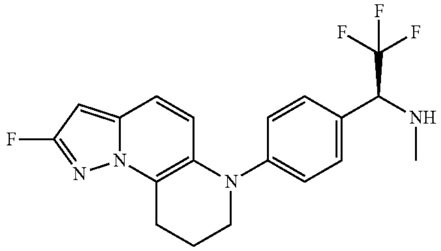 [SMILES: CN[C@@H](c1ccc(N2CCCc3c2ccc2cc(F)nn32)cc1)C(F)(F)F] | $^1$H NMR (DMSO-$d_6$, 400 MHz): δ ppm 8.26 (s, 1H), 7.42 (d, J = 8.4 Hz, 3H), 7.22 (d, J = 8.1 Hz, 2H), 6.42 (d, J = 5.1 Hz, 1H), 3.75-3.65 (m, 2H), 3.57 (s, 3H), 3.05 (t, J = 6.7 Hz, 2H), 2.27 (s, 3H), 1.97-1.89 (m, 2H). m/z: 380 $[M + H]^+$ | a | 100 |
| (1S)-2,2,2-trifluoro-1-[4-(4-fluorospiro[2,3,7,10-tetrazatricyclo[7.4.0.0$^{2,6}$]trideca-1(9),3,5,7-tetraene-13,1'-cyclopropane]-10-yl)phenyl]-N-methyl-ethanamine Intermediate 119 | 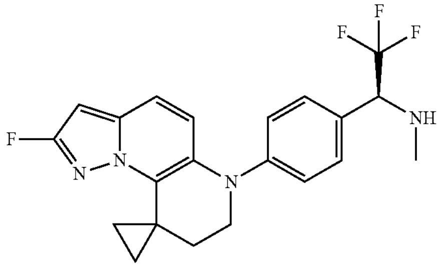 [SMILES: CN[C@@H](c1ccc(N2CCC3(CC3)c3c2ccc2cc(F)nn32)cc1)C(F)(F)F] | $^1$H NMR (400 MHz, DMSO-$d_6$) δ ppm 8.33 (s, 1H), 8.24 (s, 1H), 7.57 (t, J = 9.1 Hz, 3H), 7.37 (d, J = 8.7 Hz, 2H), 7.32 (d, J = 8.7 Hz, 1H), 6.45 (d, J = 5.1 Hz, 1H), 6.39 (d, J = 5.1 Hz, 1H), 3.59 (s, 2H), 2.58-2.52 (m, 2H), 2.02 (d, J = 4.5 Hz, 3H), 1.80 (s, 1H). m/z: 406 $[M + H]^+$ | b | 93 |

-continued

| Name | Structure | Analysis | Procedure | Yield % |
|---|---|---|---|---|
| (1S)-1-[4-(4-chloro-13,13-dimethyl-2,3,7,10-tetrazatricyclo[7.4.0.0$^{2,6}$]trideca-1(9),3,5,7-tetraen-10-yl)phenyl]-2,2,2-trifluoro-N-methyl-ethanamine hydrochloride Intermediate 120 | 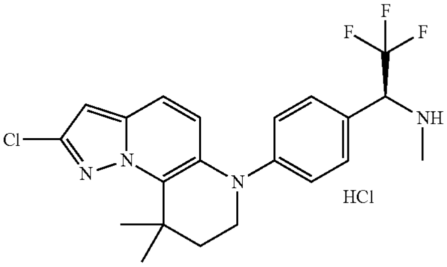 [SMILES: CN[C@@H](c1ccc(N2CCC(C)(C)c3c2ccc2cc(Cl)nn32)cc1)C(F)(F)F ; Cl] | m/z: 423 $[M + H]^+$ | a | 92 |
| (1S)-2,2,2-trifluoro-1-[4-(4-fluoro-13,13-dimethyl-2,3,7,10-tetrazatricyclo[7.4.0.0$^{2,6}$]trideca-1(9),3,5,7-tetraen-10-yl)phenyl]-N-methyl-ethanamine Intermediate 121 | 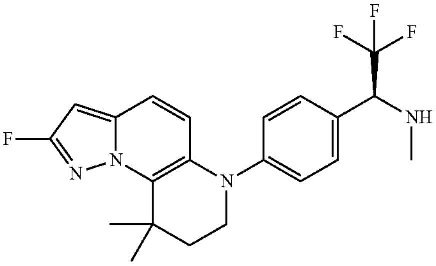 [SMILES: CN[C@@H](c1ccc(N2CCC(C)(C)c3c2ccc2cc(F)nn32)cc1)C(F)(F)F] | $^1$H NMR (DMSO-$d_6$, 400 MHz): δ ppm 8.25 (s, 1H), 7.51 (d, J = 8.5 Hz, 2H), 7.27 (d, J = 8.6 Hz, 2H), 6.44 (d, J = 5.2 Hz, 1H), 3.75-3.68 (m, 2H), 2.39 (s, 3H), 1.84-1.74 (m, 2H), 1.62 (s, 6H). m/z: 407 $[M + H]^+$ | b | 100 |
| (1S)-1-[4-(4-chloro-13-methyl-2,3,7,10-tetrazatricyclo[7.4.0.0$^{2,6}$]trideca-1(9),3,5,7-tetraen-10-yl)phenyl]-2,2,2-trifluoro-N-methyl-ethanamine Intermediate 122 | 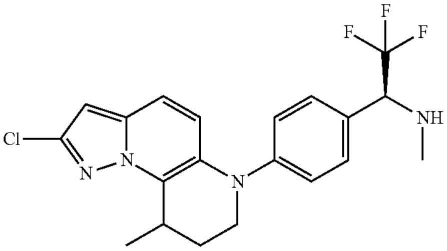 [SMILES: CN[C@@H](c1ccc(N2CCC(C)c3c2ccc2cc(Cl)nn32)cc1)C(F)(F)F] | $^1$H NMR (DMSO-$d_6$, 400 MHz): δ ppm 8.21 (s, 1H), 7.44 (d, J = 8.4 Hz, 2H), 7.25 (d, J = 8.5 Hz, 2H), 6.78 (s, 1H), 4.23 (p, J = 7.8 Hz, 1H), 3.76-3.61 (m, 2H), 3.52 (pd, J = 6.6, 2.3 Hz, 1H), 2.77 (p, J = 5.8 Hz, 1H), 2.24 (d, J = 5.5 Hz, 3H), 2.05 (dp, J = 15.4, 5.3 Hz, 1H), 1.75 (dq, J = 13.3, 2.7 Hz, 1H), 1.45 (d, J = 6.9 Hz, 3H). m/z: 409 $[M + H]^+$ Mixture of 2 diastereomers 1/1 | b | 83 |
| (1S)-1-[4-(4-chloro-2,3,7,10-tetrazatricyclo[7.4.0.0$^{2,6}$]trideca-1(9),3,5,7-tetraen-10-yl)-3-fluoro-phenyl]-2,2,2-trifluoro-N-methyl-ethanamine; hydrochloride Intermediate 123 | 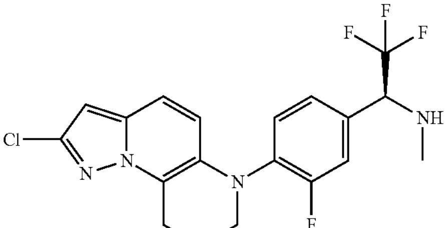 | m/z: 414 $[M + H]^+$ | c | 100 |
| (1S)-1-[4-(4-chloro-2,3,7,10-tetrazatricyclo[7.4.0.0$^{2,6}$]trideca-1(9),3,5,7-tetraen-10-yl)-2-methyl-phenyl]-2,2,2-trifluoro-N-methyl-ethanamine Intermediate 124 | 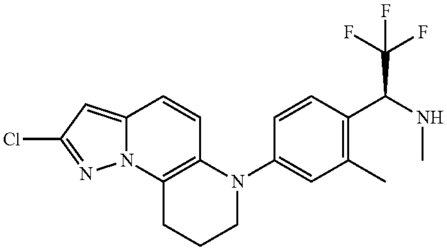 [SMILES: CN[C@@H](c1ccc(N2CCCc3c2ccc2cc(Cl)nn32)cc1C)C(F)(F)F] | $^1$H NMR (400 MHz, DMSO-$d_6$) δ ppm 8.25 (s, 1H), 7.47 (d, J = 8.1 Hz, 1H), 7.07 (d, J = 8.1 Hz, 2H), 6.81 (s, 1H), 4.40 (p, J = 7.9 Hz, 1H), 3.73-3.63 (m, 2H), 3.09 (t, J = 6.7 Hz, 2H), 2.75 (p, J = 6.0 Hz, 1H), 2.31 (s, 3H), 2.24 (d, J = 5.7 Hz, 3H), 1.98-1.91 (m, 2H). | c | 74 |

-continued

| Name | Structure | Analysis | Procedure | Yield % |
|---|---|---|---|---|
| (1S)-1-[4-(4-chloro-2,3,7,10-tetrazatricyclo[7.4.0.0$^{2,6}$]trideca-1(9),3,5,7-tetraen-10-yl)-3-methoxy-phenyl]-2,2,2-trifluoro-N-methyl-ethanamine Intermediate 125 | 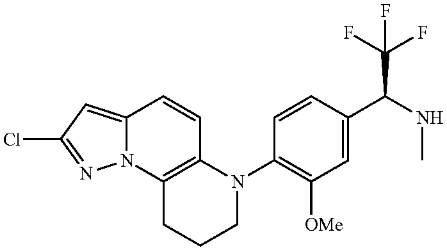 [SMILES: CN[C@@H](c1ccc(N2CCCc3c2ccc2cc(Cl)nn32)c(OC)c1)C(F)(F)F] | $^1$H NMR (400 MHz, DMSO-$d_6$) δ ppm 7.80 (s, 1H), 7.27 (s, 1H), 7.23 (d, J = 8.0 Hz, 1H), 7.09 (d, J = 7.7 Hz, 1H), 6.73 (s, 1H), 4.45 (s, 1H), 3.80 (s, 3H), 3.52 (d, J = 4.9 Hz, 2H), 3.11 (t, J = 6.5 Hz, 2H), 2.32 (s, 3H), 2.04 (s, 2H). m/z: 425 $[M + H]^+$ | C | 97 |
| (1S)-1-[4-(4-chloro-2,3,7,10-tetrazatricyclo[7.4.0.0$^{2,6}$]trideca-1(9),3,5,7-tetraen-10-yl)phenyl]-2,2-difluoro-N-methyl-propan-1-amine Intermediate 126 | 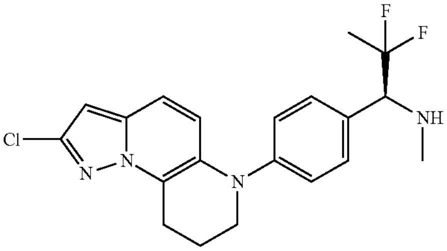 [SMILES: CN[C@@H](c1ccc(N2CCCc3c2ccc2cc(Cl)nn32)cc1)C(C)(F)F] | $^1$H NMR (400 MHz, DMSO-$d_6$) δ ppm 8.23 (s, 1H), 7.36 (d, J = 8.5 Hz, 2H), 7.22-7.13 (m, 2H), 6.80 (s, 1H), 3.80 (dd, J = 13.8, 9.6 Hz, 1H), 3.73-3.61 (m, 2H), 3.10 (t, J = 6.7 Hz, 2H), 2.18 (s, 3H), 1.98 (d, J = 9.0 Hz, 2H), 1.57 (t, J = 19.2 Hz, 3H). m/z: 391 [M + H]+. | C | 70 |
| (1S)-1-[4-(4-chloro-2,3,7,10-tetrazatricyclo[7.4.0.0$^{2,6}$]trideca-1(9),3,5,7-tetraen-10-yl)phenyl]-N-ethyl-2,2,2-trifluoroethanamine Intermediate 127 | 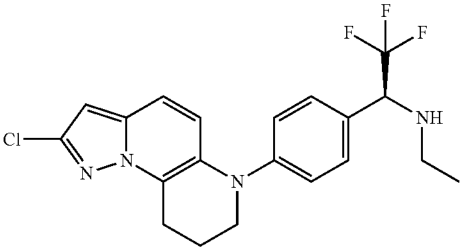 [SMILES: CCN[C@@H](c1ccc(N2CCCc3c2ccc2cc(Cl)nn32)cc1)C(F)(F)F] | $^1$H NMR (400 MHz, DMSO-$d_6$) δ ppm 8.25 (s, 1H), 7.44 (d, J = 8.4 Hz, 2H), 7.21 (d, J = 8.5 Hz, 2H), 6.81 (s, 1H), 4.49-4.21 (m, 1H), 3.74-3.65 (m, 2H), 3.09 (t, J = 6.7 Hz, 2H), 1.99-1.91 (m, 2H), 1.01 (t, J = 7.0 Hz, 3H). m/z: 409 $[M + H]^+$. | b | 96 |
| (1S)-1-(6-{4-chloro-2,3,7,10-tetraazatricyclo[7.4.0.0$^{2,6}$]trideca-1(9),3,5,7-tetraen-10-yl}pyridin-3-yl)-2,2,2-trifluoroethyl](methyl)amine Intermediate 128 | 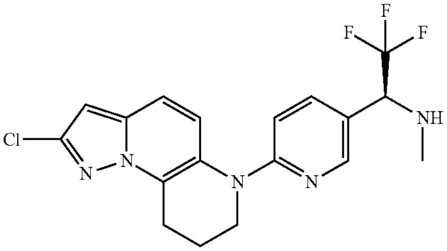 [SMILES: CN[C@@H](c1ccc(N2CCCc3c2ccc2cc(Cl)nn32)nc1)C(F)(F)F] | $^1$H NMR (400 MHz, DMSO-d6) δ ppm 8.68 (s, 1H), 8.24 (d, J = 2.4 Hz, 1H), 7.79 (dd, J = 8.7, 2.4 Hz, 1H), 7.23 (d, J = 8.7 Hz, 1H), 6.85 (s, 1H), 4.32-4.24 (m, 1H), 4.04-3.88 (m, 2H), 3.12 (t, J = 6.8 Hz, 2H), 2.90-2.78 (m, 1H), 2.24 (d, J = 5.8 Hz, 3H), 2.05-1.94 (m, 2H). m/z: 397 $[M + H]^+$. | b | 80 |

Intermediates 129-134

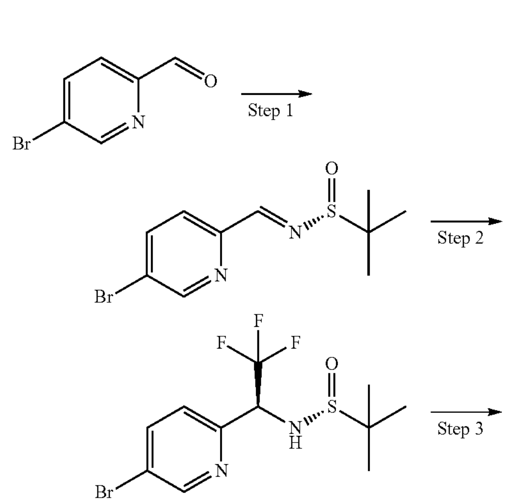

-continued

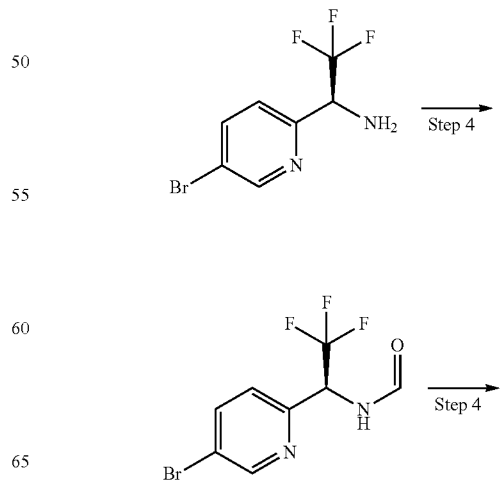

-continued

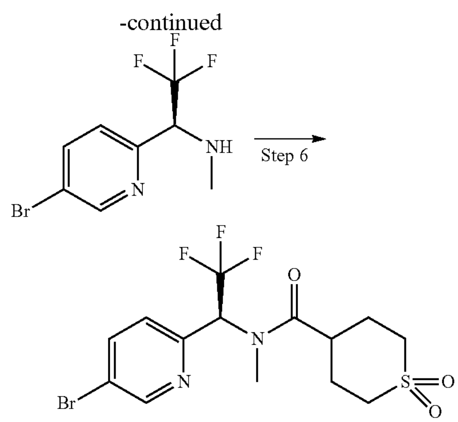

Step 1. (R)—N-[(5-bromo-2-pyridyl)methylene]-2-methyl-propane-2-sulfinamide (Intermediate 129)

Cesium carbonate (2.10 g, 6.45 mmol) was added to a mixture of 5-bromopyridine-2-carbaldehyde (3.00 g, 16.1 mmol) and ({R})-2-methylpropane-2-sulfinamide (6.65 g, 53.2 mmol) in DCM (15.4 mL). The mixture was stirred at rt for 20 h, then diluted with DCM, washed with $H_2O$, dried over anhydrous $Na_2SO_4$ and concentrated under reduced pressure. The crude was purified by flash column chromatography (heptane/EtOAC, from 0% to 20% of EtOAc) to afford intermediate 129 (4.46 g, 95%). m/z: 289 $[M+H]^+$. $^1H$ NMR (400 MHz, DMSO-$d_6$) δ ppm 8.91 (dd, J=2.3, 0.5 Hz, 1H), 8.46 (s, 1H), 8.30-8.21 (m, 1H), 8.04 (dd, J=8.4, 0.5 Hz, 1H), 1.21 (s, 9H).

Step 2. (R)—N-[(1S)-1-(5-bromo-2-pyridyl)-2,2,2-trifluoro-ethyl]-2-methyl-propane-2-sulfinamide (Intermediate 130)

A solution of Intermediate 129 (4.48 g, 15.5 mmol) and N,N,N-trimethylmethanaminium fluoride (1.73 g, 18.6 mmol) in dry THF (47 mL) at rt was purged with Argon for 15 min. To this was added trimethyl(trifluoromethyl) silane (5.7 mL, 38.7 mmol) at −78° C. The reaction mixture was stirred at same temperature for 1 h. The reaction was quenched by addition of sat. aq. $NH_4Cl$ solution at 0° C. The organic layer was separated, the water phase was extracted with EtOAc and the organic layers were combined, dried over anhydrous $Na_2SO_4$ and concentrated at reduced pressure. The crude was purified by flash column chromatography (heptane/EtOAc, from 0% to 100% of EtOAc) to afford intermediate 130 (1.85 g, 33%). m/z: 359 $[M+H]^+$. $^1H$ NMR (400 MHz, DMSO-$d_6$) δ ppm 8.79 (d, J=2.3 Hz, 1H), 8.23 (dd, J=8.4, 2.4 Hz, 1H), 7.70 (d, J=8.4 Hz, 1H), 6.08 (d, J=8.6 Hz, 1H), 5.50 (p, J=8.0 Hz, 1H), 1.17 (s, 9H).

Step 3. (1S)-1-(5-bromo-2-pyridyl)-2,2,2-trifluoro-ethanamine (Intermediate 131)

The intermediate 131 was prepared following the procedure used to prepare Intermediates 117-128 (467 mg, Quantitative). m/z: 255 $[M+H]^+$. $^1H$ NMR (400 MHz, DMSO-$d_6$) δ ppm 9.70 (s, 2H), 8.90 (d, J=2.3 Hz, 1H), 8.31 (dd, J=8.3, 2.4 Hz, 1H), 7.71 (d, J=8.4 Hz, 1H), 5.80 (q, J=7.5 Hz, 1H).

Step 4. N-[(1S)-1-(5-bromo-2-pyridyl)-2,2,2-trifluoroethyl]formamide (Intermediate 132)

To a solution of Intermediates 131 (1.90 g, 7.45 mmol) in Toluene (54 mL) was added formic acid (1.1 mL, 28.3 mmol). The resulting suspension was stirred at reflux for 6 h. The reaction mixture was cooled to rt and a sat. aq. $NaHCO_3$ was added (50 mL). The aqueous phase was separated and extracted with DCM (50 mL). The combined organic phases were dried over anhydrous $MgSO_4$, filtered and concentrated in vacuo. The residue was purified by flash column chromatography (heptane/EtOAC, from 0% to 100% of EtOAc) to afford Intermediates 132 (1.24 g, 58%). m/z: 283 $[M+H]^+$. $^1H$ NMR (400 MHz, DMSO-$d_6$) δ ppm 9.41 (d, J=9.4 Hz, 1H), 8.80 (d, J=2.4 Hz, 1H), 8.29-8.06 (m, 2H), 7.69 (d, J=8.4 Hz, 1H), 6.02 (p, J=8.2 Hz, 1H).

Step 5 (1S)-1-(5-bromo-2-pyridyl)-2,2,2-trifluoro-N-methyl-ethanamine (Intermediate 133)

To a solution of Intermediates 132 (1.24 g, 4.34 mmol) in THF (24.6 mL), was added borane methylsulfanylmethane (1.7 mL, 19.5 mmol) and the solution stirred at rt for 2 h. The reaction mixture was quenched with a sat. aq. $Na_2CO_3$ then extracted with DCM. The combined extracts were washed with brine, dried over anhydrous $Na_2SO_4$, filtered and concentrated under reduced pressure. The crude was purified by reverse-phase column chromatography (water/acetonitrile from water 100% to acetonitrile 100%) to afford Intermediates 133 (518 mg, 40%). m/z: 269 $[M+H]^+$. $^1H$ NMR (400 MHz, DMSO-$d_6$) δ ppm 8.76 (d, J=2.2 Hz, 1H), 8.16 (dd, J=8.3, 2.4 Hz, 1H), 7.58 (d, J=8.3 Hz, 1H), 4.43 (s, 1H), 2.85 (s, 1H), 2.25 (s, 3H).

Step 6: N-[(1S)-1-(5-bromo-2-pyridyl)-2,2,2-trifluoro-ethyl]-N-methyl-1,1-dioxo-thiane-4-carboxamide (Intermediate 134)

This intermediate was prepared as described for the preparation of Intermediates 86-91 (210 mg, 28.2%). m/z: 430 $[M+H]^+$. $^1H$ NMR (400 MHz, DMSO-$d_6$) δ ppm 8.80 (d, J=2.3 Hz, 1H), 8.17 (dd, J=8.4, 2.4 Hz, 1H), 7.48 (dd, J=42.7, 8.5 Hz, 1H), 6.70-6.24 (m, 1H), 3.17 (dd, J=23.5, 12.7 Hz, 4H), 3.00 (s, 3H), 2.67 (s, 1H), 2.13-1.98 (m, 4H).
Intermediate 135-136

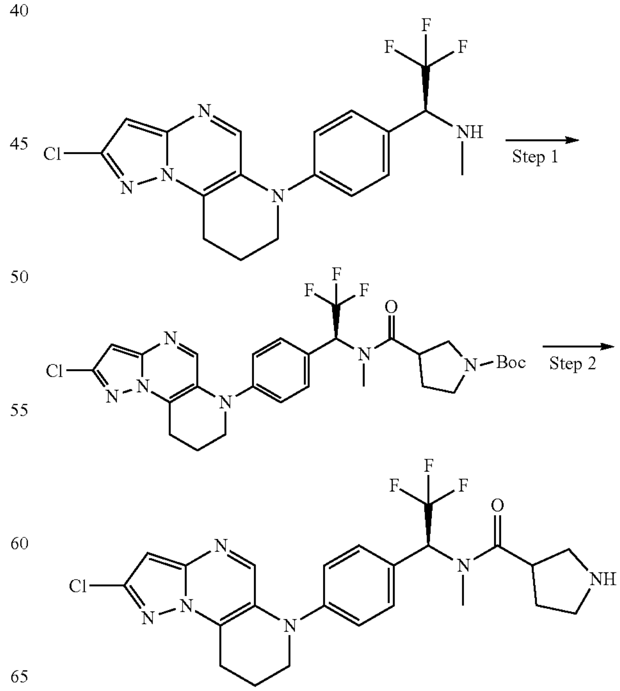

Step 1. tert-butyl 3-[[(1S)-1-[4-(4-chloro-2,3,7,10-tetrazatricyclo[7.4.0.02,6]trideca-1(9),3,5,7-tetraen-10-yl)phenyl]-2,2,2-trifluoro-ethyl]-methyl-carbamoyl]pyrrolidine-1-carboxylate (Intermediate 135)

To a solution of intermediate 117 (500 mg, 1.26 mmol) and (3S)-1-(tert-butoxycarbonyl) pyrrolidine-3-carboxylic acid (336 mg, 1.52 mmol) in dry DCM (6.3 mL), TEA (3.5 mL, 25.3 mmol) was added, followed by $T_3P$ in EtOAc (50%, 8.9 mL, 12.6 mmol). The reaction mixture was stirred at rt overnight. The reaction mixture was partitioned between water and EtOAc. Layers were separated and the aqueous phase was extracted twice with EtOAc. Organic layers were combined, washed with aqueous sat. aq. $NaHCO_3$, dried over anhydrous $Na_2SO_4$, filtered and concentrated in vacuo. The crude was purified by flash column chromatography eluting with EtOAc in Heptane (0 to 100%) to obtain Intermediate 136 (623 mg, 80% Yield). m/z 593 $[M+H]^+$. $^1H$ NMR (400 MHz, DMSO-$d_6$) δ ppm 8.32 (s, 1H), 7.37-7.22 (m, 4H), 6.83 (s, 1H), 6.51 (d, J=9.0 Hz, 1H), 3.72 (s, 2H), 3.53 (s, 1H), 3.47-3.33 (m, 2H), 3.10 (t, J=6.7 Hz, 2H), 2.92 (d, J=3.8 Hz, 3H), 2.69 (d, J=8.1 Hz, 1H), 1.96 (s, 2H), 1.41 (d, J=2.3 Hz, 9H).

Step 2. N-[(1S)-1-[4-(4-chloro-2,3,7,10-tetrazatricyclo[7.4.0.$0^{2,6}$]trideca-1(9),3,5,7-tetraen-10-yl)phenyl]-2,2,2-trifluoro-ethyl]-N-methyl-pyrrolidine-3-carboxamide (Intermediate 136)

To a solution of Intermediate 135 (623 mg, 1.01 mmol) in DCM (5. mL), TFA (0.77 mL, 10.1 mmol) was added. The reaction mixture was stirred at rt overnight. The reaction was quenched with a sat. aq. $NaHCO_3$ and DCM was added. The layers were separated and the organic layer was washed three times with a sat. aq. $NaHCO_3$, then dried over $MgSO_4$ and concentrated under vacuum to obtain Intermediate 136 (505 mg, 97% Yield). m/z: 493 $[M+H]^+$. $^1H$ NMR (400 MHz, DMSO-$d_6$) δ ppm 8.31 (s, 1H), 7.34-7.24 (m, 4H), 6.82 (s, 1H), 6.52 (q, J=9.1 Hz, 1H), 3.77-3.67 (m, 2H), 3.25-3.16 (m, 1H), 3.09 (q, J=6.1, 5.6 Hz, 3H), 2.89 (s, 3H), 2.79 (ddt, J=21.8, 10.8, 5.1 Hz, 3H), 2.02-1.92 (m, 3H), 1.90-1.71 (m, 2H).

Scheme 6

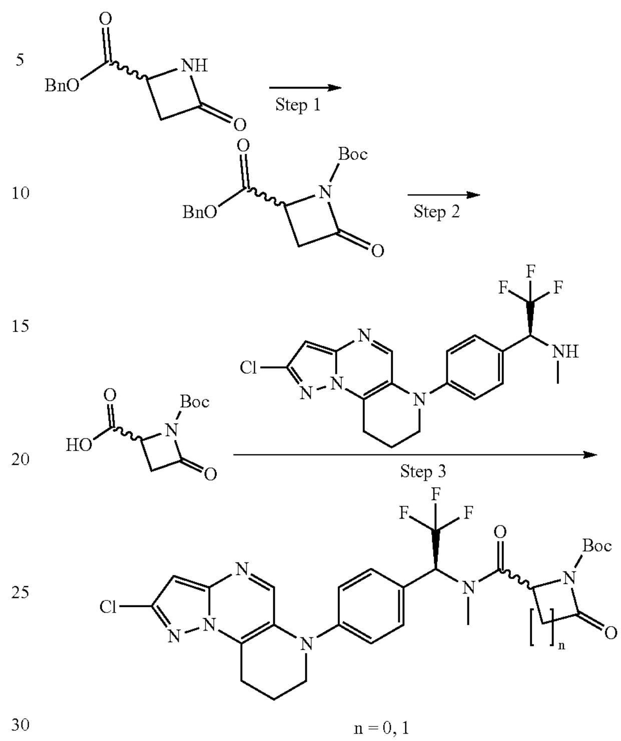

Step 1

Benzyl-4-oxoazetidine-2-carboxylate (1 mmol), N,N-dimethylpyridin-4-amine (2 mmol) and tert-butoxycarbonyl tert-butyl carbonate (1.5 mmol) were dissolved in dry acetonitrile (0.3 M). The reaction mixture was stirred for 3 h at rt. The solvent was removed and the crude was dissolved in EtOAC (10 ml). The organic phase was washed with sat. aq. $NH_4Cl$, brine, $NaHCO_3$ and then dried over anhydrous $MgSO_4$. The solvent was removed under reduce pressure to afford Intermediate 137-138, which were used as such without further purification.

| Name | Structure | Analysis | Yield % |
|---|---|---|---|
| Benzyl (2R) 4-oxoazetidine-2-carboxylate Intermediate 137 | 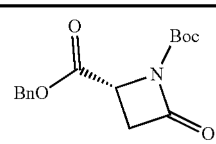 | $^1H$ NMR (400 MHz, DMSO) δ ppm 7.44-7.30 (m, 5H), 5.22 (d, J = 2.6 Hz, 2H), 4.51 (dd, J = 6.7, 3.2 Hz, 1H), 3.39 (dd, J = 15.8, 6.7 Hz, 1H), 3.09 (dd, J = 15.8, 3.2 Hz, 1H), 1.36 (s, 9H). m/z 328 $[M + Na]^+$. | 92 |
| Benzyl (2S) 4-oxoazetidine-2-carboxylate Intermediate 138 | 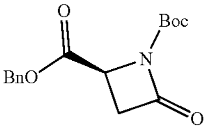 [SMILES: CC(C)(C)OC(=O)N1C(=O)C[C@H]1C(=O)OCc1ccccc1] | $^1H$ NMR (400 MHz, DMSO) δ ppm 7.49-7.24 (m, 5H), 5.22 (d, J = 2.5 Hz, 2H), 4.51 (dd, J = 6.7, 3.1 Hz, 1H), 3.39 (dd, J = 15.8, 6.6 Hz, 1H), 3.09 (dd, J = 15.8, 3.2 Hz, 1H), 1.36 (s, 9H). m/z 328 $[M + Na]^+$. | 89 |

Step 2

Intermediates 137-138 (1 mmol) were dissolved in methanol (0.1 M) at rt under argon. Palladium on charcoal (0.1 mmol) was added, the inert atmosphere was replaced with hydrogen and the reaction mixture was stirred at rt for 18 hours. The catalyst was removed by filtration over a pad of Celite, washed with MeOH and the filtrate was concentrated under reduced pressure to give Intermediates 139-140, which was used as such without further purification.

| Name | Structure | Analysis | Yield % |
|---|---|---|---|
| (2R)-1-tert-butoxycarbonyl-4-oxo-azetidine-2-carboxylic acid Intermediate 139 | 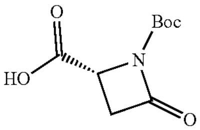 [SMILES: CC(C)(C)OC(=O)N1C(=O)C[C@@H]1C(=O)O] | $^1$H NMR (400 MHz, DMSO) δ ppm 4.29 (dd, J = 6.7, 3.1 Hz, 1H), 3.31 (dd, J = 15.8, 6.7 Hz, 2H), 2.94 (dd, J = 15.8, 3.2 Hz, 1H), 1.42 (s, 9H). | 100 |
| (2S)-1-tert-butoxycarbonyl-4-oxo-azetidine-2-carboxylic acid Intermediate 140 | 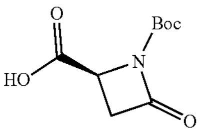 [SMILES: CC(C)(C)OC(=O)N1C(=O)C[C@H]1C(=O)O] | $^1$H NMR (400 MHz, DMSO) δ ppm 4.29 (dd, J = 6.7, 3.1 Hz, 1H), 3.31 (dd, J = 15.8, 6.6 Hz, 1H), 2.94 (dd, J = 15.8, 3.2 Hz, 1H), 1.42 (s, 9H) | 99 |

Step 3

The following intermediates were prepared according to the general procedure 3 described below for examples 37-127 starting from intermediate 117 and either intermediates 139-140 or commercially available carboxylic acid. Intermediates 141-143

| Name | Structure | Analysis | Yield % |
|---|---|---|---|
| tert-butyl (2R)-2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-4-oxo-azetidine-1-carboxylate Intermediate 141 | 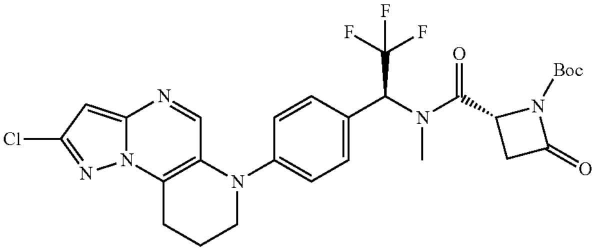 [SMILES: CN(C(=O)[C@H]1CC(=O)N1C(=O)OC(C)(C)C)[C@@H](c1ccc(N2CCCc3c2cnc2cc(Cl)nn32)cc1)C(F)(F)F] | $^1$H NMR (400 MHz, DMSO) δ ppm 8.31 (s, 1H), 7.38-7.22 (m, 4H), 6.82 (d, J = 2.2 Hz, 1H), 6.47 (q, J = 9.1 Hz, 1H), 4.99 (dd, J = 6.5, 3.2 Hz, 1H), 3.72 (t, J = 5.2 Hz, 2H), 3.38 (dd, J = 15.7, 6.5 Hz, 1H), 3.10 (t, J = 6.7 Hz, 2H), 2.94 (dd, J = 15.5, 3.2 Hz, 1H), 2.86 (s, 3H), 1.95 (d, J = 6.3 Hz, 2H), 1.42 (s, 9H). m/z 593 [M + H]$^+$ | 11 |
| tert-butyl (2S)-2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-4-oxo-azetidine-1-carboxylate Intermediate 142 | 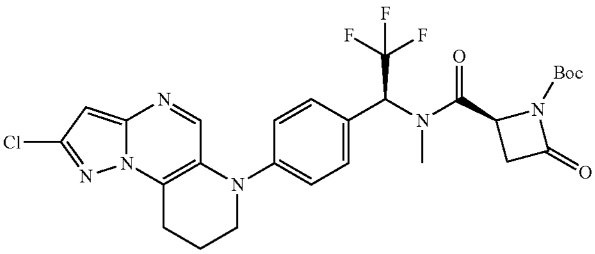 [SMILES: CN(C(=O)[C@@H]1CC(=O)N1C(=O)OC(C)(C)C)[C@@H](c1ccc(N2CCCc3c2cnc2cc(Cl)nn32)cc1)C(F)(F)F] | 1H NMR (400 MHz, DMSO) δ ppm 8.31 (d, J = 8.8 Hz, 1H), 7.37 (d, J = 8.4 Hz, 2H), 7.29 (d, J = 8.8 Hz, 2H), 6.83 (s, 1H), 6.49 (t, J = 9.2 Hz, 1H), 5.03 (dd, J = 6.5, 3.1 Hz, 1H), 4.09 (q, J = 5.3 Hz, 1H), 3.72 (t, J = 5.3 Hz, 2H), 3.44 (dd, J = 15.6, 6.4 Hz, 1H), 3.11 (t, J = 6.7 Hz, 2H), 2.95 (s, 3H), 1.97 (d, J = 6.2 Hz, 2H), 1.38 (d, J = 15.7 Hz, 9H). m/z 593 [M + H]+ | 55 |
| tert-butyl 2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-5-oxo-pyrrolidine-1-carboxylate Intermediate 143 | 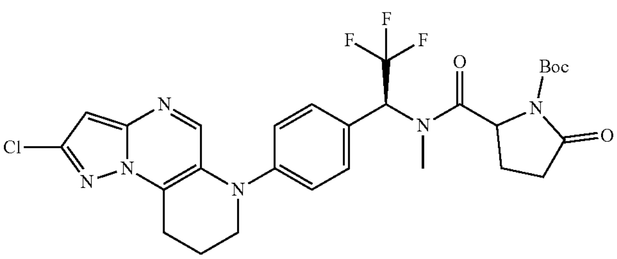 [SMILES: CN(C(=O)C1CCC(=O)N1C(=O)OC(C)(C)C)[C@@H](c1ccc(N2CCCc3c2cnc2cc(Cl)nn32)cc1)C(F)(F)F] | m/z 607 $[M + H]^+$ | 97 |

Scheme 7

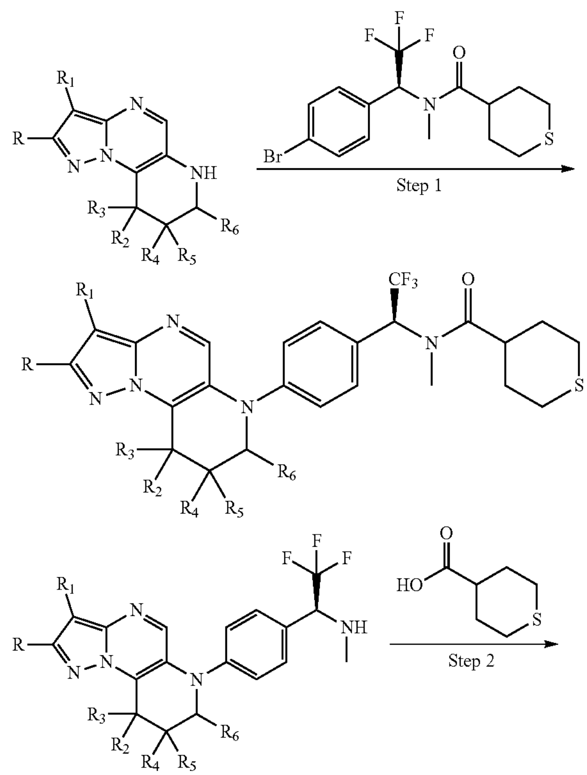

-continued

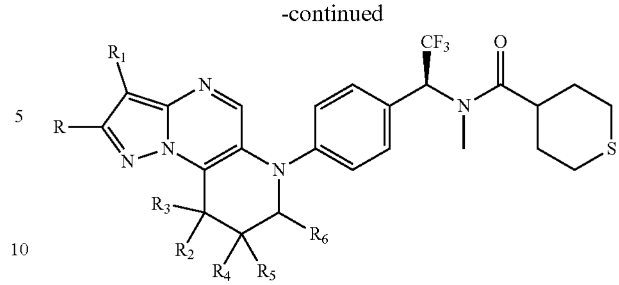

Step 1

Procedure 1

Intermediates 144-152 were prepared following the general procedure 3 described for examples 1-37

Step 2

Procedure 2

To a solution of intermediates 117-128 (1 mmol) in dry DCM (0.2 M) at rt under $N_2$ were added TEA (20 mmol) and $T_3P$-50% in EtOAc (10 mmol) followed by thiane-4-carboxylic acid (1.5 mmol). The reaction mixture was stirred at rt upon completion. The reaction mixture was quenched with a sat. aq. $NaHCO_3$, then diluted in DCM, the phases were separated and the aqueous phase extracted twice with DCM, dried over anhydrous $Na_2SO_4$ and concentrated under reduced pressure. The crude was purified by flash column chromatography (Hetpane/EtOAc or DCM/MeOH).

| Intermediate 144 | Procedure 2 | Intermediate 119 | Yield 89% |
|---|---|---|---|
| 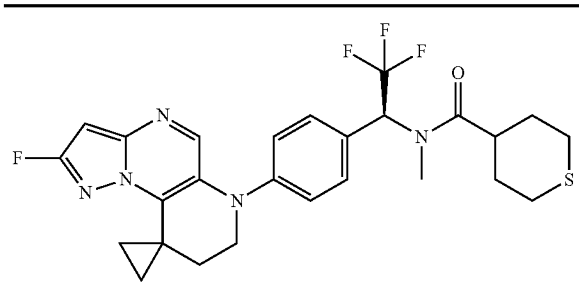 | $^1$H NMR (400 MHz, DMSO-d$_6$) δ ppm 8.21 (s, 1H), 7.42-7.02 (m, 4H), 6.64-6.25 (m, 2H), 3.77 (s, 2H), 2.89 (s, 3H), 2.72 (s, 1H), 2.68-2.55 (m, 3H), 2.07-1.90 (m, 2H), 1.79 (d, J = 4.2 Hz, 2H), 1.75-1.61 (m, 2H), 0.93 (d, J = 2.4 Hz, 2H). m/z: 534 [M + H]$^+$ | | |
| N-methyl-N-[(1S)-2,2,2-trifluoro-1-[4-(4-fluorospiro[2,3,7,10-tetrazatricyclo[7.4.0.0$^{2,6}$]trideca-1(9),3,5,7-tetraene-13,1'-cyclopropane]-10-yl)phenyl]ethyl]tetrahydrothiopyran-4-carboxamide | | | |

| Intermediate 144-b | Procedure 1 | Intermediate 90 and 60-b | Yield 53% |
|---|---|---|---|
| 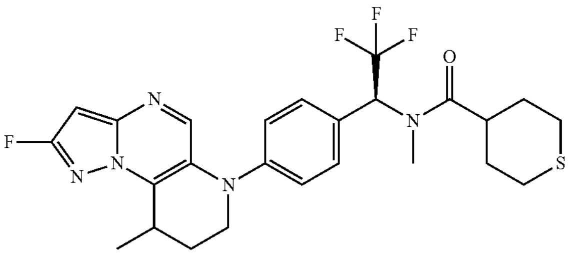 [SMILES: CC1CCN(c2ccc([C@H](N(C)C(=O)C3CCSCC3)C(F)(F)F)cc2)c2cnc3cc(F)nn3c21] | $^1$H NMR (400 MHz, DMSO) δ ppm 8.27 (d, J = 1.0 Hz, 1H), 7.39-7.24 (m, 4H), 6.52 (q, J = 9.4 Hz, 1H), 6.40 (d, J = 5.2 Hz, 1H), 3.77-3.63 (m, 2H), 3.50-3.42 (m, 1H), 2.89 (d, J = 2.8 Hz, 4H), 2.80-2.67 (m, 2H), 2.67-2.55 (m, 2H), 2.10-1.92 (m, 3H), 1.83-1.60 (m, 3H), 1.43 (d, J = 6.9 Hz, 3H). m/z: 522 [M + H]$^+$ | | |
| N-methyl-N-[(1S)-2,2,2-trifluoro-1-(4-{4-fluoro-13-methyl-2,3,7,10-tetraazatricyclo[7.4.0.0$^{2,6}$]trideca-1(9),3,5,7-tetraen-10-yl}phenyl)ethyl]thiane-4-carboxamide | | | |

-continued

| Intermediate 145 | Procedure 1 | Intermediate 90 and 48 | Yield 60% |
|---|---|---|---|

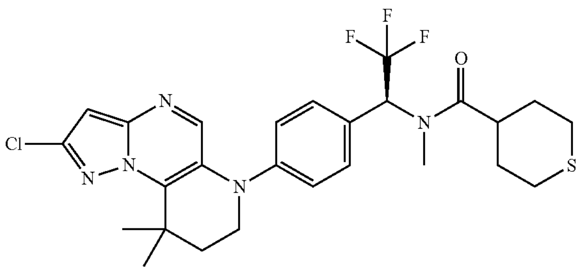 [SMILES: CN(C(=O)C1CCSCC1)[C@@H](c1ccc(N2CCC(C)(C)c3c2cnc2cc(Cl)nn32)cc1)C(F)(F)F]

$^1$H NMR (400 MHz, DMSO-$d_6$) δ ppm 8.26 (s, 1H), 7.42-7.23 (m, 4H), 6.82 (s, 1H), 6.52 (d, J = 9.5 Hz, 1H), 3.70 (s, 2H), 2.90 (s, 2H), 2.78-2.59 (m, 5H), 2.06-1.92 (m, 2H), 1.81 (s, 2H), 1.70 (d, J = 11.4 Hz, 1H), 1.64 (s, 6H), 1.26 (s, 3H). m/z: 552 $[M + H]^+$ N-[(1S)-1-[4-(4-chloro-13,13-dimethyl-2,3,7,10-tetrazatricyclo[7.4.0.0$^{2,6}$]trideca-1(9),3,5,7-tetraen-10-yl)phenyl]-2,2,2-trifluoro-ethyl]-N-methyl-tetrahydrothiopyran-4-carboxamide

| Intermediate 146 | Procedure 1 | Intermediate 121 | Yield 42% |
|---|---|---|---|

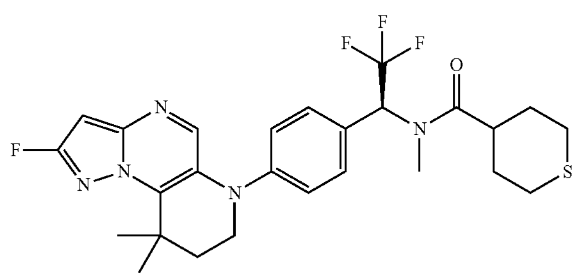 [SMILES: CN(C(=O)C1CCSCC1)[C@@H](c1ccc(N2CCC(C)(C)c3c2cnc2cc(F)nn32)cc1)C(F)(F)F]

$^1$H NMR (400 MHz, DMSO-$d_6$) δ ppm 8.25 (s, 1H), 7.32-7.21 (m, 4H), 6.50 (t, J = 9.4 Hz, 1H), 6.43 (d, J = 5.2 Hz, 1H), 3.75-3.64 (m, 2H), 2.89 (s, 4H), 2.80-2.68 (m, 2H), 2.67-2.57 (m, 2H), 1.97 (d, J = 12.9 Hz, 2H), 1.82-1.76 (m, 2H), 1.72-1.64 (m, 2H), 1.62 (s, 6H). m/z: 536 $[M + H]^+$ N-methyl-N-[(1S)-2,2,2-trifluoro-1-[4-(4-fluoro-13,13-dimethyl-2,3,7,10-tetrazatricyclo[7.4.0.0$^{2,6}$]trideca-1(9),3,5,7-tetraen-10-yl)phenyl]ethyl]tetrahydrothiopyran-4-carboxamide

| Intermediate 147 | Procedure 1 | Intermediate 50 and 90 | Yield 76% |
|---|---|---|---|

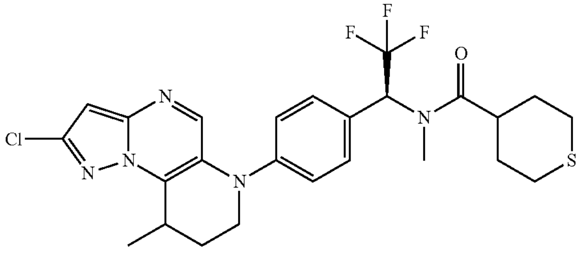 [SMILES: CC1CCN(c2ccc([C@H](N(C)C(=O)C3CCSCC3)C(F)(F)F)cc2)c2cnc3cc(Cl)nn3c21]

$^1$H NMR (400 MHz, DMSO-$d_6$) δ ppm 8.33-8.18 (m, 1H), 7.43-7.23 (m, 4H), 6.79 (s, 1H), 6.60-6.11 (m, 1H), 3.79-3.62 (m, 2H), 3.51 (tt, J = 6.9, 3.4 Hz, 1H), 2.92-2.80 (m, 4H), 2.79-2.66 (m, 2H), 2.66-2.54 (m, 2H), 2.14-1.92 (m, 3H), 1.79-1.55 (m, 3H), 1.44 (d, J = 6.9 Hz, 3H). m/z: 538 $[M + H]^+$ Mixture of 2 diastereomers 1/1

N-[(1S)-1-[4-(4-chloro-13-methyl-2,3,7,10-tetrazatricyclo[7.4.0.0$^{2,6}$]trideca-1(9),3,5,7-tetraen-10-yl)phenyl]-2,2,2-trifluoro-ethyl]-N-methyl-tetrahydrothiopyran-4-carboxamide

| Intermediate 148 | Procedure 1 | Intermediates 49 and 90 | Yield 53% |
|---|---|---|---|

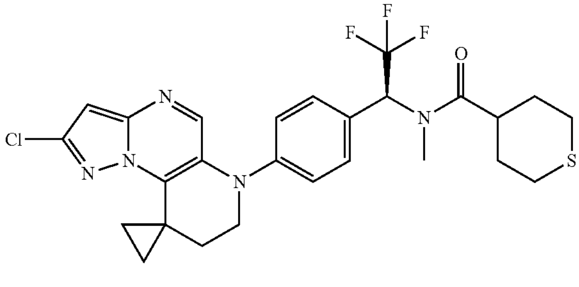 [SMILES: CN(C(=O)C1CCSCC1)[C@@H](c1ccc(N2CCC3(CC3)c3c2cnc2cc(Cl)nn32)cc1)C(F)(F)F]

$^1$H NMR (400 MHz, DMSO-$d_6$) δ ppm 8.21 (s, 1H), 7.32-7.20 (m, 4H), 6.75 (s, 1H), 6.50 (t, J = 9.3 Hz, 1H), 3.77 (d, J = 2.4 Hz, 2H), 2.89 (s, 3H), 2.80-2.68 (m, 2H), 2.61 (dd, J = 9.5, 3.6 Hz, 3H), 2.56 (d, J = 2.5 Hz, 2H), 2.00 (s, 2H), 1.80 (d, J = 4.1 Hz, 2H), 1.74-1.63 (m, 2H), 0.94 (d, J = 2.5 Hz, 2H). m/z: 550 $[M + H]^+$ N-[(1S)-1-[4-(4-chlorospiro[2,3,7,10-tetrazatricyclo[7.4.0.0$^{2,6}$]trideca-1(9),3,5,7-tetraene-13,1'-cyclopropane]-10-yl)phenyl]-2,2,2-trifluoro-ethyl]-N-methyl-tetrahydrothiopyran-4-carboxamide -continued

| Intermediate 148-b | Procedure 1 Intermediates 55 and 90 Yield 37% |
|---|---|
| 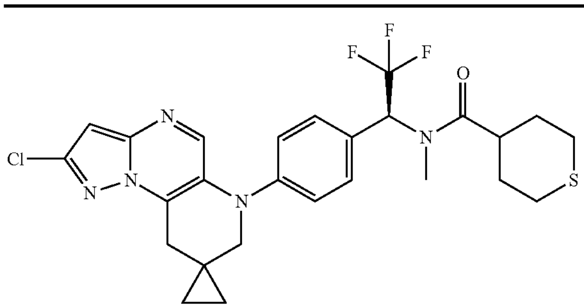 | $^1H$ NMR (400 MHz, DMSO-$d_6$) δ ppm 8.35 (s, 1H), 7.26 (s, 5H), 6.83 (s, 1H), 3.56 (s, 4H), 3.23 (d, J = 7.0 Hz, 3H), 3.06 (s, 3H), 2.87 (s, 5H), 1.10 (t, J = 7.1 Hz, 6H), 0.98 (t, J = 7.0 Hz, 5H), 0.59 (s, 3H), 0.42 (s, 2H). m/z: 550 [M + H]$^+$ |
| N-[(1S)-1-[4-(4-chlorospiro[2,3,7,10-tetrazatricyclo[7.4.0.0$^{2,6}$]trideca-1(9),3,5,7-tetraene-12,1'-cyclopropane]-10-yl)phenyl]-2,2,2-trifluoro-ethyl]-N-methyl-tetrahydrothiopyran-4-carboxamide | |
| Intermediate 149 | Procedure 1 Intermediate 60 and 90 Yield 46% |
| 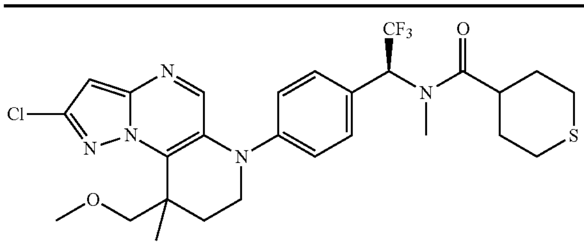 | $^1H$ NMR (400 MHz, DMSO-$d_6$) δ ppm 8.24 (s, 1H), 7.30 (d, J = 8.3 Hz, 2H), 7.20 (d, J = 8.6 Hz, 2H), 6.82 (s, 1H), 6.51 (q, J = 9.3 Hz, 1H), 4.49 (dd, J = 8.7, 2.6 Hz, 1H), 3.81 (d, J = 16.6 Hz, 1H), 3.64 (t, J = 11.2 Hz, 1H), 3.54 (dd, J = 8.7, 2.0 Hz, 1H), 3.12 (s, 3H), 2.89 (s, 3H), 2.85 (d, J = 11.3 Hz, 1H), 2.81-2.67 (m, 2H), 2.66-2.55 (m, 2H), 2.19 (t, J = 10.7 Hz, 1H), 1.99 (t, J = 16.1 Hz, 2H), 1.67 (t, J = 12.7 Hz, 3H), 1.52 (s, 3H). m/z: 582 [M + H]+. |
| N-[(1S)-1-[4-[4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-tetrahydrothiopyran-4-carboxamide | |
| Intermediate 150 | Procedure 1 Intermediate 54 and 90 Yield 36% |
| 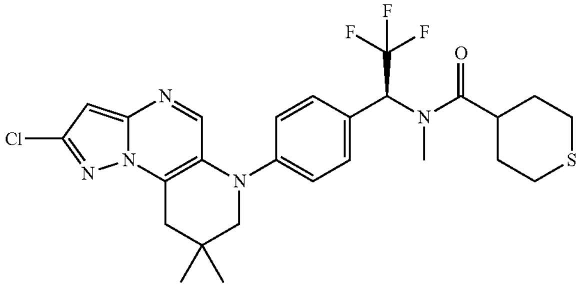 [SMILES: CN(C(=O)C1CCSCC1)[C@@H](c1ccc(N2CC(C)(C)Cc3c2cnc2cc(Cl)nn32)cc1)C(F)(F)F] | $^1H$ NMR (400 MHz, DMSO-$d_6$) δ ppm 8.41 (s, 1H), 7.48-7.22 (m, 5H), 6.81 (s, 1H), 6.51 (s, 1H), 3.47 (s, 2H), 2.93 (s, 2H), 2.90 (s, 2H), 2.68 (s, 8H), 1.03 (s, 6H).m/z: 552 [M + H]$^+$ |
| N-[(1S)-1-[4-(4-chloro-12,12-dimethyl-2,3,7,10-tetrazatricyclo[7.4.0.0$^{2,6}$]trideca-1(9),3,5,7-tetraen-10-yl)phenyl]-2,2,2-trifluoro-ethyl]-N-methyl-tetrahydrothiopyran-4 carboxamide | |
| Intermediate 151 | Procedure 1 Intermediates 56 and 90 Yield 60% |
| 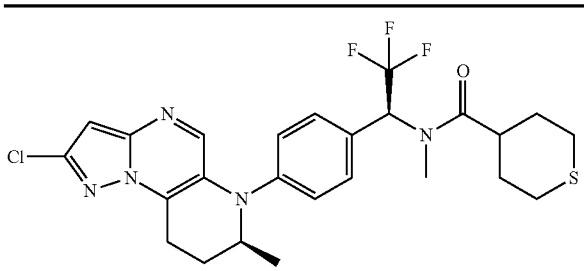 | $^1H$ NMR (400 MHz, DMSO-$d_6$) δ ppm 8.22 (s, 1H), 7.27 (dq, J = 17.1, 8.4 Hz, 4H), 6.79 (d, J = 5.2 Hz, 1H), 6.52 (q, J = 9.3 Hz, 1H), 4.10-3.98 (m, 1H), 3.23-3.11 (m, 1H), 2.99 (ddd, J = 19.2, 11.0, 7.7 Hz, 1H), 2.91-2.81 (m, 4H), 2.81-2.54 (m, 6H), 2.10 (dq, J = 13.5, 3.9 Hz, 1H), 1.96 (dq, J = 20.1, 4.1 Hz, 4H), 1.81-1.52 (m, 3H), 1.32-1.15 (m, 6H). m/z: 538 [M + H]$^+$ |
| N-[(1S)-1-[4-[(11 rel S)-4-chloro-11-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-tetrahydrothiopyran-4-carboxamide | |

-continued

| Intermediate 152 | Procedure 1 Intermediates 57 and 90 Yield 57% |
| --- | --- |
| 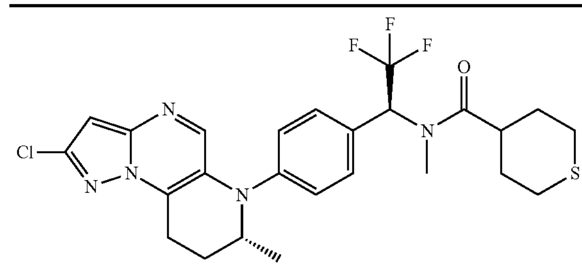 | $^1$H NMR (400 MHz, DMSO) δ ppm 8.22 (s, 1H), 7.40-7.20 (m, 4H), 6.81 (s, 1H), 6.52 (q, J = 9.3 Hz, 1H), 4.11-3.99 (m, 1H), 3.18 (ddd, J = 19.5, 6.2, 2.6 Hz, 1H), 3.00 (ddd, J = 19.2, 11.1, 7.8 Hz, 1H), 2.89 (s, 3H), 2.82-2.57 (m, 5H), 2.02-1.87 (m, 2H), 1.68 (pd, J = 11.4, 3.1 Hz, 2H), 1.24 (d, J = 6.8 Hz, 6H). m/z: 538 [M + H]+ |
| N-[(1S)-1-[4-[(11 rel R)-4-chloro-11-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-tetrahydrothiopyran-4-carboxamide | |

N-[(1S)-1-[4-(4-chloro-2,3,7,10-tetrazatricyclo[7.4.0.02,6]trideca-1(9),3,5,7-tetraen-10-yl)phenyl]-2,2,2-trifluoro-ethyl]-N-methyl-3-methylsulfanyl-cyclobutanecarboxamide (Intermediate 153)

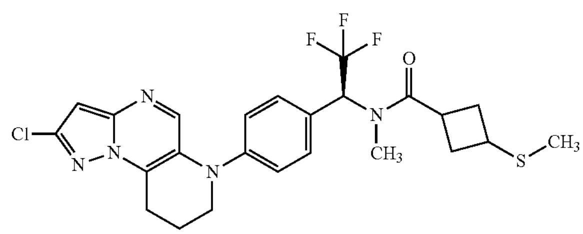 [SMILES: CSC1CC(C(=O)N(C)[C@@H](c2ccc(N3CCCc4c3cnc3cc(Cl)nn43)cc2)C(F)(F)F)C1]

Title compound was prepared according to procedure 2 used to prepare intermediates 144-152. 1H NMR (400 MHz, DMSO-$d_6$) δ ppm 8.30 (s, 1H), 7.35-7.23 (m, 4H), 6.82 (s, 1H), 6.57-6.44 (m, 1H), 3.71 (dd, J=6.3, 4.0 Hz, 2H), 3.66-3.55 (m, 1H), 3.43-3.34 (m, 1H), 3.10 (d, J=6.7 Hz, 2H), 2.75 (d, J=11.0 Hz, 3H), 2.61-2.53 (m, 2H), 2.29-2.08 (m, 2H), 2.03 (s, 3H), 1.96 (dd, J=11.5, 6.6 Hz, 2H). m/z: 524 [M+H]+.

Intermediates 154-159

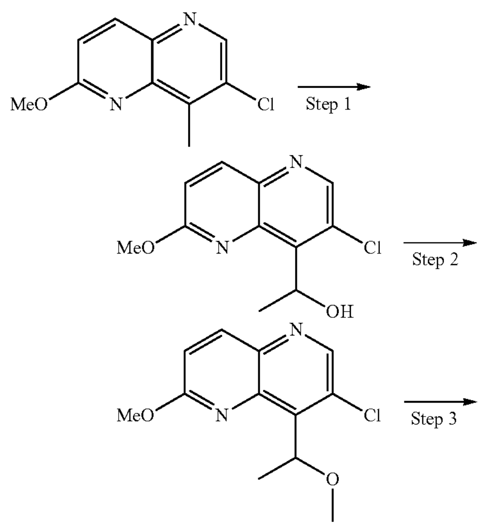

-continued

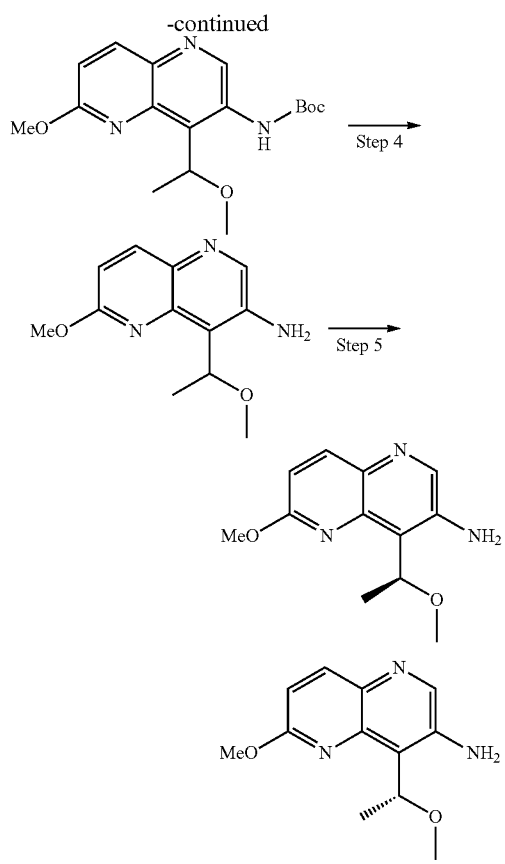

Step 1. 1-(3-chloro-6-methoxy-1,5-naphthyridin-4-yl) ethanol (Intermediate 154)

To a solution of 8-Bromo-7-chloro-2-methoxy-[1,5]naphthyridine (6.00 g, 21.9 mmol) in THF (146 mL) was added 1.6 M butyllithium (21 mL, 32.9 mmol) at −78° C. The reaction mixture was kept at −78° C. for 15 min before addition of acetaldehyde (3.1 mL, 54.8 mmol) and left stirring for 3 h at −78° C. The reaction mixture was quenched with sat $NH_4Cl$ and then diluted with EtOAc. The phases were separated and the aqueous phase was extracted with EtOAc. The organic layers were combined, washed with brine, dried over anhydrous $Na_2SO_4$, filtered and concentrated under reduced pressure. The crude was purified by flash column chromatography (Heptane/EtOAc, 0 to 30% of EtOAc) to obtain intermediate 154 (3.41 g, 64%). m/z: 239 $[M+H]^+$. $^1$H NMR (400 MHz, DMSO-ds) δ ppm 8.76 (s, 1H), 8.34 (d, J=9.1 Hz, 1H), 7.34 (d, J=9.1 Hz, 1H), 5.86-5.79 (m, 1H), 5.77 (d, J=7.7 Hz, 1H), 4.04 (s, 3H), 1.62 (d, J=6.4 Hz, 3H).

Step 2. 7-chloro-2-methoxy-8-(1-methoxyethyl)-1,5-naphthyridine (Intermediate 155)

To a solution of intermediate 154 (1.37 g, 5.74 mmol) in dry THF (29 mL) was added a solution of 1 M LiHMDS in THF (11 mL, 11.5 mmol), the mixture was stirred at rt for 30 min. Then iodomethane (1.1 mL, 17.2 mmol) was added, the mixture was stirred at rt for 6 h and 40° C. overnight. The mixture was poured onto sat. aq. $NH_4Cl$ and then extracted twice with EtOAc (10 ml). The organic layers were combined, washed with brine, dried over anhydrous $MgSO_4$ and concentrated under vacuum. The crude was purified by flash column chromatography (Heptane/EtOAc, 0 to 30% of EtOAc) to afford intermediate 155 (1.14 g, 77%). m/z 253 $[M+H]^+$. $^1$H NMR (400 MHz, DMSO-$d_6$) δ ppm 8.75 (s, 1H), 8.31 (d, J=9.0 Hz, 1H), 7.32 (d, J=9.0 Hz, 1H), 5.90 (q, J=6.7 Hz, 1H), 4.04 (s, 3H), 3.14 (s, 3H), 1.60 (d, J=6.7 Hz, 3H).

Step 3. Tert-butyl N-[6-methoxy-4-(1-methoxyethyl)-1,5-naphthyridin-3-yl]carbamate (Intermediate 156)

Pd Xphos G2 (366 mg, 0.465 mmol), cesium carbonate (1.1 g, 3.26 mmol), tert-butyl carbamate (545 mg, 4.65 mmol) and intermediate 155 (1.20 g, 4.65 mmol) were suspended in dry 1,4-dioxane (18.5 mL). The reaction mixture was degassed with $N_2$ for 10 minutes and stirred at 100° C. overnight and then diluted with EtOAc, sat. aq. $NH_4Cl$ was added. The aqueous layer was extracted twice with EtOAc (2×15 ml). The organic layers were combined, dried over anhydrous $MgSO_4$ and concentrated under vacuum. The crude was purified by flash column chromatography (Heptane/EtOAc, 0 to 50% of EtOAc) to obtain Intermediate 156 (1.24 g, 79%). m/z $[M+H]^+$334. $^1$H NMR (400 MHz, DMSO-$d_6$) δ ppm 9.33 (s, 1H), 8.82 (s, 1H), 8.23 (d, J=9.0 Hz, 1H), 7.17 (d, J=9.0 Hz, 1H), 5.84 (q, J=6.7 Hz, 1H), 4.02 (s, 3H), 3.32 (s, 3H), 1.51 (s, 9H).

Step 4. 6-Methoxy-4-(1-methoxyethyl)-1,5-naphthyridin-3-amine (Intermediate 157)

To a stirred solution of intermediate 156 (1.24 g, 3.65 mmol) in DCM (18 mL) was added TFA (11 mL, 0.146 mol). The reaction mixture was stirred at rt for 2 h. The solvent and TFA were removed under reduced pressure. Water and a sat. aq. $NaHCO_3$ were added until pH 7 and then the aqueous layers were extracted 3 times with EtOAc (3×15 ml). The organic layers were combined, dried over anhydrous $MgSO_4$ and concentrated by vacuum to intermediate 157 (28 mg, 60%). m/z $[M+H]^+$ 234. $^1$H NMR (400 MHz, DMSO-$d_6$) δ ppm 8.32 (s, 1H), 8.00 (d, J=8.8 Hz, 1H), 6.83 (d, J=8.8 Hz, 1H), 5.88 (s, 2H), 5.80-5.63 (m, 1H), 3.96 (s, 3H), 3.22 (s, 3H), 1.44 (d, J=6.7 Hz, 3H).

Step 5 (Intermediates 158-159)

Intermediate 158-159 were obtained by SFC Chiral separation using Chiralpak AD-H 5 μm with a mobile phase 80/20 ($CO_2$/EtOH).

6-Methoxy-4-[rel-(1R)-1-methoxyethyl]-1,5-naphthyridin-3-amine (Intermediate 158)

$^1$H NMR (400 MHz, DMSO-$d_6$) δ ppm 8.31 (s, 1H), 7.99 (d, J=8.9 Hz, 1H), 6.82 (d, J=8.8 Hz, 1H), 5.87 (s, 2H), 5.72 (q, J=6.7 Hz, 1H), 3.95 (s, 3H), 3.21 (s, 3H), 1.44 (d, J=6.7 Hz, 3H). m/z: 234 $[M+H]^+$ 6-Methoxy-4-[rel-(1S)-1-methoxyethyl]-1,5-naphthyridin-3-amine (Intermediate 159)

$^1$H NMR (400 MHz, DMSO-$d_6$) δ ppm 8.31 (s, 1H), 7.99 (d, J=8.8 Hz, 1H), 6.82 (d, J=8.8 Hz, 1H), 5.87 (s, 2H), 5.71 (q, J=6.7 Hz, 1H), 3.95 (s, 3H), 3.21 (s, 3H), 1.44 (d, J=6.7 Hz, 3H). m/z: 234 $[M+H]^+$ Intermediates 160-161

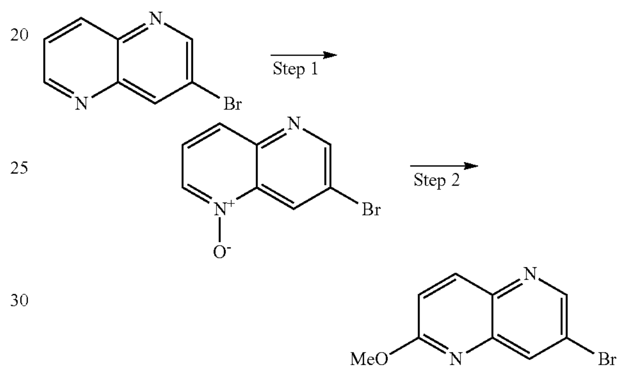

Step 1. 7-bromo-1-oxido-1,5-naphthyridin-1-ium (Intermediate 160)

To a stirred solution of 3-bromo-1,5-naphthyridine (5.0 g, 23.0 mmol) in dry DCM (42.1 mL) at 0° C. was added m-CPBA (4.76 g, 27.6 mmol) in several portions. The resulting mixture was stirred for 1 h at rt. The reaction mixture was washed with a sat. aq. $Na_2SO_3$ solution and a sat. aq. $NaHCO_3$ solution sequentially, and then washed with brine, dried over anhydrous $MgSO_4$ and concentrated under reduced pressure. The crude was purified by flash column chromatography (DCM/MeOH, from 0% to 5% in DCM) to afford intermediate 160 (3.55 g, 69% yield). m/z: 225 $[M+H]^+$. $^1$H NMR (400 MHz, DMSO-$d_6$) δ ppm 9.18 (s, 1H), 9.06 (s, 1H), 8.71 (d, J=6.2 Hz, 1H), 8.03 (d, J=8.6 Hz, 1H), 7.81-7.69 (m, 1H).

Step 2. 7-bromo-2-methoxy-1,5-naphthyridine (Intermediate 161)

To a solution of intermediate 160 (86%, 5.10 g, 19.5 mmol), 4-methylbenzenesulfonyl chloride (4.46 g, 23.4 mmol), dipotassium carbonate (34 mL, 68.2 mmol) in $CHCl_3$ (75 mL), methanol (1.6 mL, 39.0 mmol) was added at rt. The mixture was stirred overnight and filtered. The residue was washed with $CHCl_3$ and water 3 times. Then the aqueous layer was extracted 3 times with $CHCl_3$. The organic layers were combined, washed with brine, dried over anhydrous $MgSO_4$ and concentrated under vacuum. The crude was purified by flash column chromatography (Heptane/EtOAc, from 50 to 100% of EtOAc) to afford intermediate 161 (2.9 g, 62%). m/z: 239 $[M+H]^+$. $^1$H NMR (400 MHz, DMSO-$d_6$) δ ppm 8.88 (d, J=2.2 Hz, 1H), 8.48 (d, J=2.2 Hz, 1H), 8.30 (d, J=9.1 Hz, 1H), 7.33 (d, J=9.1 Hz, 1H), 4.03 (s, 3H).

Intermediates 162-163

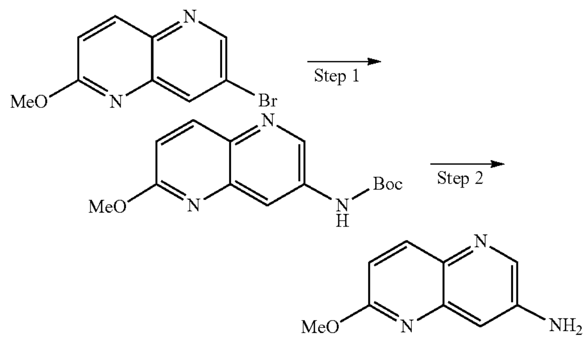

Step 1 tert-butyl N-(6-methoxy-1,5-naphthyridin-3-yl)carbamate: (Intermediate 162)

Pd Xphos G2 (46 mg, 0.058 mmol), cesium carbonate (668 mg, 2.05 mmol), tert-butyl carbamate (206 mg, 1.76 mmol) and intermediate 161 (350 mg, 1.46 mmol) in dry 1,4-dioxane (14.5 mL). The mixture was flushed with nitrogen for 5 min. Then the reaction mixture was stirred at 100° C. under nitrogen gas until aryl halide was consumed (2 h). The reaction mixture was filtered through a pad of Celite and washed with EtOAc. The filtrate was poured in $H_2O$ and then extracted with EtOAc twice. The organic layers were combined, washed with brine, dried over anhydrous $MgSO_4$ and concentrated in vacuo to give intermediate 162 without any further purification (369 mg, 91% yield). m/z: 276 $[M+H]^+$. $^1H$ NMR (400 MHz, DMSO-$d_6$) δ ppm 9.98 (s, 1H), 8.79 (d, J=2.4 Hz, 1H), 8.32 (s, 1H), 8.16 (d, J=9.0 Hz, 1H), 7.08 (d, J=9.0 Hz, 1H), 4.00 (s, 3H), 1.53 (s, 9H).

Step 2. 6-methoxy-1,5-naphthyridin-3-amine: (Intermediate 163)

To a stirred solution of intermediate 162 (200 mg, 0.726 mmol) in DCM (3.6 mL), TFA (2.2 mL, 29.1 mmol) was added. The reaction mixture was stirred at rt overnight. Volatiles were removed under reduce pressure. Water and sat. aq. $NaHCO_3$ were added until pH 7 and then EtOAc was added. The aqueous layer was extracted 3 times with EtOAc. The organic layers were combined, dried over anhydrous $MgSO_4$ and concentrated by vacuum to give intermediate 163 (124 mg, 93%). m/z: 176 $[M+H]^+$. $^1H$ NMR (400 MHz, DMSO-$d_6$) δ ppm 8.28 (d, J=2.5 Hz, 1H), 7.97 (d, J=8.8 Hz, 1H), 7.03 (d, J=2.5 Hz, 1H), 6.79 (d, 8.8 Hz, 1H), 5.92 (s, 2H), 3.93 (s, 3H).

Intermediates 164-165

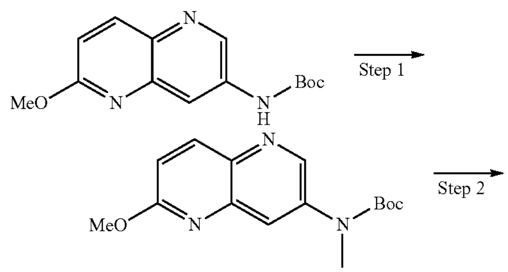

-continued

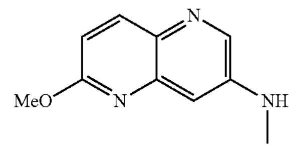

Step 1. tert-butyl N-(6-methoxy-1,5-naphthyridin-3-yl)-N-methyl-carbamate: (Intermediate 164)

To a stirred solution of tert-butyl N-(6-methoxy-1,5-naphthyridin-3-yl)carbamate (230 mg, 0.835 mmol) in THF (2 mL) was added NaH (60%, 60 mg, 1.50 mmol). Iodomethane (0.16 mL, 2.51 mmol) was added. The reaction mixture was stirred at rt until total conversion of starting material. The solvent was removed under reduce pressure. Water and sat. aq. $NH_4Cl$ was added until pH 7 and then EtOAc was added. The aqueous layers were extracted 3 times with EtOAc. The organic layers were combined, dried over anhydrous $MgSO_4$ and concentrated in vacuo. The crude was purified by flash column chromatography (Heptane/EtOAc, from 0 to 50% of EtOAc) to afford intermediate 164 (168 mg, 70%). m/z: 290 $[M+H]^+$. $^1H$ NMR (400 MHz, DMSO-$d_6$) δ ppm 8.82 (d, J=2.4 Hz, 1H), 8.25 (dd, J=9.0, 0.6 Hz, 1H), 8.04 (dd, J=2.4, 0.6 Hz, 1H), 7.21 (d, J=9.0 Hz, 1H), 4.02 (s, 3H), 3.35 (s, 3H), 1.44 (s, 9H).

Step 2. 6-methoxy-N-methyl-1,5-naphthyridin-3-amine (Intermediate 165)

To a solution of intermediate 164 (168 mg, 0.581 mmol) in DCM (2.9 mL) was added TFA (1.7 mL, 23.2 mmol). The reaction mixture was stirred at rt overnight. The reaction mixture was quenched with a sat. aq. $NaHCO_3$ until pH 8. The aqueous layer was extracted twice with DCM (3×10 mL) and then the organic layers were combined, washed with brine, dried over anhydrous $MgSO_4$ and concentrated under vacuum to afford the intermediate 165 (104 mg, 95%). m/z: 190 $[M+H]^+$. $^1H$ NMR (400 MHz, DMSO-$d_6$) δ ppm 8.30 (d, J=2.7 Hz, 1H), 7.99 (d, J=8.8 Hz, 1H), 6.85 (d, J=2.6 Hz, 1H), 6.79 (d, J=8.8 Hz, 1H), 6.60 (d, J=4.9 Hz, 1H), 3.95 (s, 3H), 2.80 (d, J=5.0 Hz, 3H).

6-Chloro-1,5-naphthyridin-3-amine (Intermediate 166)

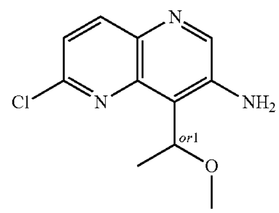 [SMILES: COC(C)c1c(N)cnc2ccc(Cl)nc12]

This intermediate was prepared according to the procedure described in WO2020111087

Scheme 8

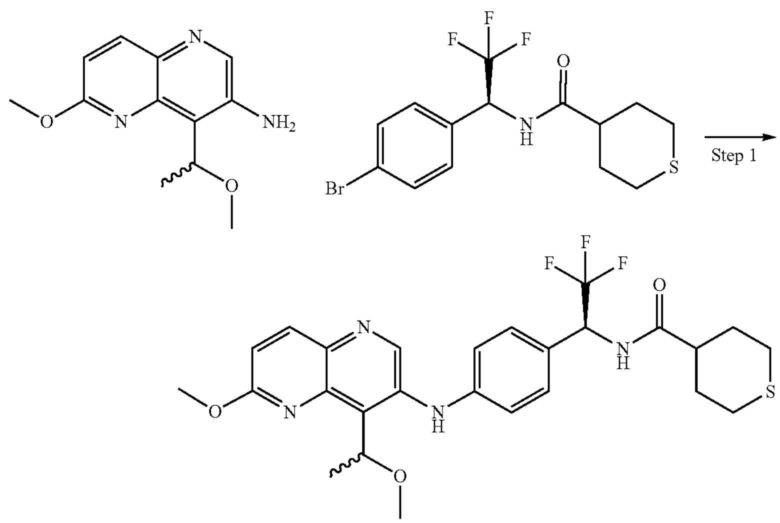

Intermediates 167-170

General Procedure

A solution of intermediates 90-91 (1.2 mmol), intermediates 158-159 (1 mmol) and cesium carbonate (2 mmol) in 1,4-dioxane (28 mL) was degassed with $N_2$ for 5 min prior addition of [2-(2-aminophenyl)phenyl]-chloro-palladium; dicyclohexyl-[3-(2,4,6-triisopropylphenyl)phenyl]phosphane (0.12 mmol) at rt. The reaction mixture was then heated at 100° C. upon completion. The reaction mixture was diluted with EtOAc and a sat. aq. $NH_4Cl$ was added. The aqueous phase was extracted with EtOAc. The combined organic layers were dried over anhydrous $Na_2SO_4$, filtered and concentrated under reduced pressure. The crude was purified by flash column chromatography (Heptane/EtOAc 0% of EtOAc to 100%)

| Intermediate 167 | Intermediates: 159 and 90 | Yield: 93% |
|---|---|---|
| 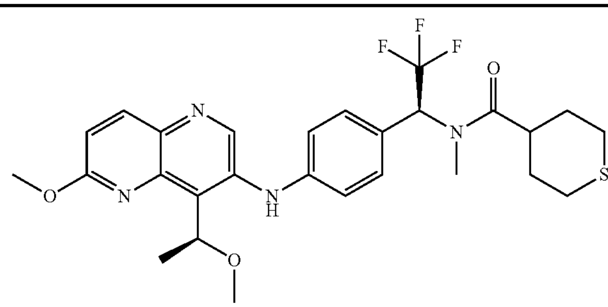 | $^1H$ NMR (400 MHz, DMSO-$d_6$) δ ppm 8.78 (s, 1H), 8.17 (d, J = 9.0 Hz, 1H), 8.05 (s, 1H), 7.30-7.21 (m, 4H), 7.08 (d, J = 8.9 Hz, 1H), 6.50 (q, J = 9.3 Hz, 1H), 5.85 (q, J = 6.7 Hz, 1H), 4.02 (s, 3H), 3.30 (s, 3H), 2.90 (s, 3H), 2.88-2.56 (m, 5H), 2.06-1.93 (m, 2H), 1.69 (p, J = 11.4 Hz, 2H), 1.51 (d, J = 6.7 Hz, 3H). m/z: 549 $[M + H]^+$. | |
| N-methyl-N-[(1S)-2,2,2-trifluoro-1-[4-[6-methoxy-4-[(1 rel S)-1-methoxyethyl]-1,5-naphthyridin-3-yl]amino]phenyl]ethyl]tetrahydrothiopyran-4-carboxamide | | |
| Intermediate 168 | Intermediates: 158 and 90 | Yield: 66% |
| 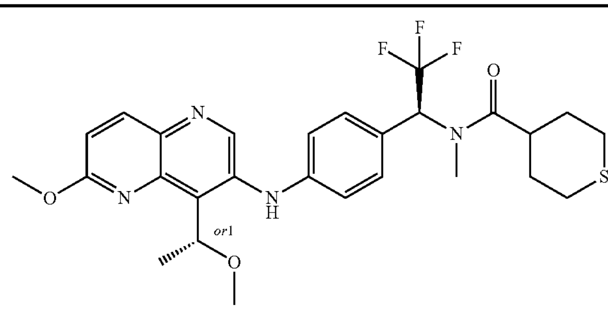 | $^1H$ NMR (400 MHz, DMSO-$d_6$) δ ppm 8.78 (s, 1H), 8.16 (d, J = 8.9 Hz, 1H), 8.04 (s, 1H), 7.33-7.21 (m, 4H), 7.07 (d, J = 8.9 Hz, 1H), 6.49 (t, J = 9.4 Hz, 1H), 5.85 (q, J = 6.7 Hz, 1H), 4.01 (s, 3H), 3.30 (s, 3H), 2.90 (s, 3H), 2.78-2.66 (m, 2H), 2.61 (s, 2H), 2.01 (dd, J = 34.3, 15.4 Hz, 2H), 1.79-1.59 (m, 2H), 1.50 (d, J = 6.7 Hz, 3H). m/z: 549 $[M + H]^+$. | |
| N-methyl-N-[(1S)-2,2,2-trifluoro-1-[4-[6-methoxy-4-[(1 rel R)-1-methoxyethyl]-1,5-naphthyridin-3-yl]amino]phenyl]ethyl]tetrahydrothiopyran-4-carboxamide | | |

-continued

| Intermediate 169 | Intermediates: 159 and 91 | Yield: 90% |
|---|---|---|
| 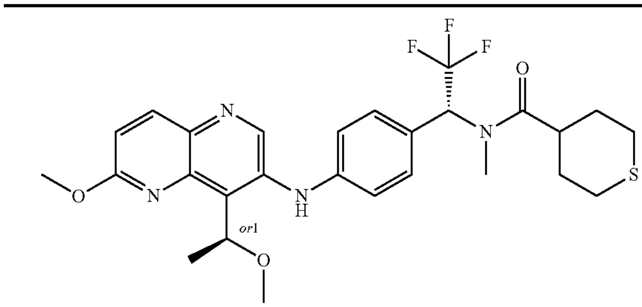 | | $^1H$ NMR (400 MHz, DMSO) δ ppm 8.78 (d, J = 1.5 Hz, 1H), 8.16 (d, J = 8.9 Hz, 1H), 8.04 (s, 1H), 7.34-7.21 (m, 4H), 7.08 (d, J = 9.0 Hz, 1H), 6.50 (q, J = 9.4 Hz, 1H), 5.85 (q, J = 6.7 Hz, 1H), 4.02 (s, 3H), 3.30 (s, 3H), 2.90 (d, J = 2.5 Hz, 3H), 2.89-2.82 (m, 1H), 2.81-2.64 (m, 2H), 2.63-2.56 (m, 2H), 2.06-1.93 (m, 2H), 1.76-1.61 (m, 2H), 1.51 (d, J = 6.7 Hz, 3H). m/z: 549 $[M + H]^+$. |
| N-methyl-N-[(1R)-2,2,2-trifluoro-1-[4-[6-methoxy-4-[(1 rel S)-1-methoxyethyl]-1,5-naphthyridin-3-yl]amino]phenyl]ethyl]tetrahydrothiopyran-4-carboxamide | | |
| Intermediate 170 | Intermediates: 158 and 91 | Yield: 85% |
| 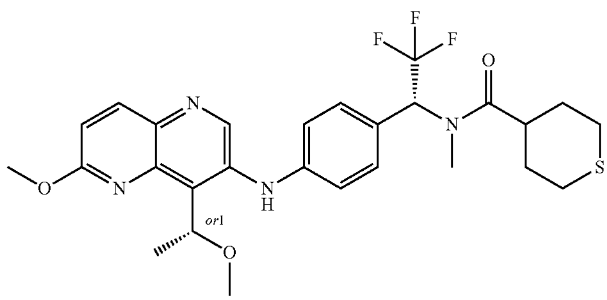 [SMILES: COc1ccc2ncc(Nc3ccc([C@@H](N(C)C(=O)C4CCSCC4)C(F)(F)F)cc3)c([C@@H](C)OC)c2n1] | | $^1H$ NMR (400 MHz, DMSO) δ ppm 8.78 (s, 1H), 8.17 (d, J = 8.8 Hz, 1H), 8.05 (s, 1H), 7.31-7.18 (m, 4H), 7.08 (d, J = 9.0 Hz, 1H), 6.50 (q, J = 9.4 Hz, 1H), 5.85 (q, J = 6.7 Hz, 1H), 4.02 (s, 3H), 3.30 (s, 3H), 2.90 (s, 3H), 2.89-2.54 (m, 2H), 2.00 (t, J = 16.1 Hz, 2H), 1.77-1.60 (m, 2H), 1.51 (d, J = 6.7 Hz, 3H). m/z: 549 $[M + H]^+$ |
| N-methyl-N-[(1R)-2,2,2-trifluoro-1-[4-[6-methoxy-4-[(1 rel R)-1-methoxyethyl]-1,5-naphthyridin-3-yl]amino]phenyl]ethyl]tetrahydrothiopyran-4-carboxamide | | |

Intermediates 171-174

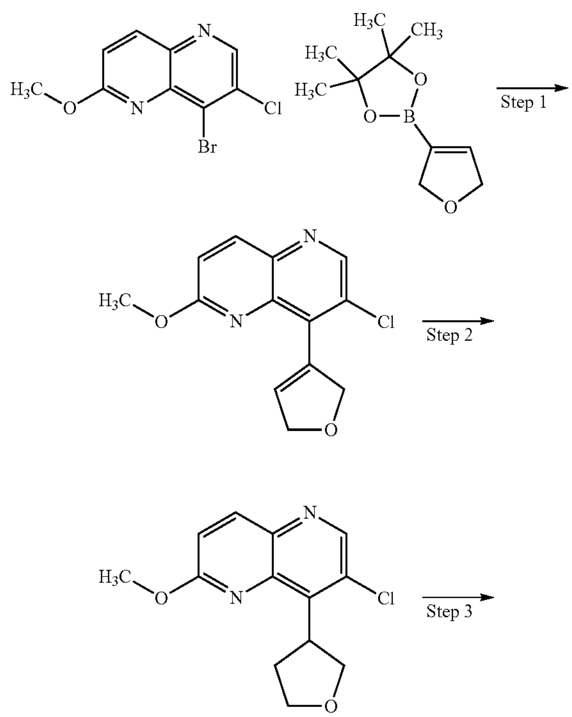

-continued

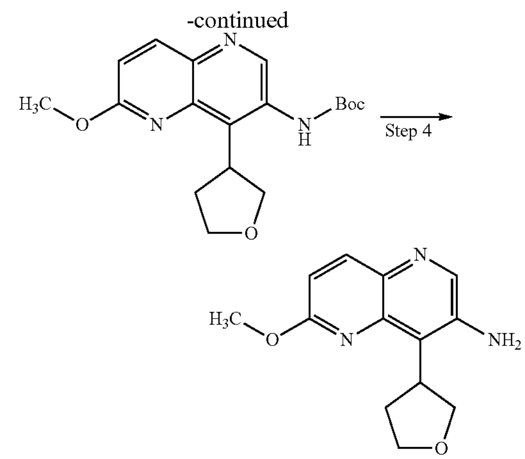

Step 1: 7-chloro-8-(2,5-dihydrofuran-3-yl)-2-methoxy-1,5-naphthyridine (Intermediate 171)

A solution of 8-Bromo-7-chloro-2-methoxy-[1,5]naphthyridine (500 mg, 1.83 mmol), 2-(2,5-dihydrofuran-3-yl)-4,4,5,5-tetramethyl-1,3,2-dioxaborolane (95%, 377 mg, 1.83 mmol) and tripotassium; phosphate (787 mg, 3.66 mmol) in toluene was degassed with $N_2$ for 5 min prior addition of (1{E},4{E})-1,5-diphenylpenta-1,4-dien-3-one palladium (95%, 176 mg, 0.183 mmol) and tricyclohexylphosphane (154 mg, 0.548 mmol). The reaction mixture was heated at 110° C. for 3 h. The reaction mixture was filtered through celite and filtrate was partitioned between water and EtOAc. Phases were separated and aqueous phase was extracted with EtOAc. The combined organic layers were dried over anhydrous $Na_2SO_4$, filtered and concentrated under reduced pressure. The crude was purified by flash column chromatography (Heptane/EtOAc from 0% of EtOAC to 30% of EtOAc) to give intermediate 171 (314 mg, 65% Yield). m/z: 263 $[M+H]^+$. $^1H$ NMR (400 MHz, DMSO-$d_6$) δ ppm 8.86 (s, 1H), 8.31 (d, J=9.0 Hz, 1H), 7.31 (d, J=9.0 Hz, 1H), 6.52 (t, J=2.0 Hz, 1H), 5.12 (td, J=4.9, 2.2 Hz, 2H), 4.84 (td, J=4.9, 1.8 Hz, 2H), 3.99 (s, 3H).

Step 2: 7-chloro-2-methoxy-8-tetrahydrofuran-3-yl-1,5-naphthyridine (Intermediate 172)

To a solution of intermediate 171 (99%, 10 mg, 0.0377 mmol) in dry methanol (1 mL), platinum (10%, 3.7 mg, 1.88 μmol) was added. The reaction mixture was stirred at rt under hydrogen atmosphere overnight. The reaction mixture was filtered through a pad of Celite, washed with MeOH and concentrated under reduced pressure to give intermediate 172 (10 mg, 60.144% Yield). m/z: 265 $[M+H]^+$. $^1H$ NMR (400 MHz, DMSO-$d_6$) δ ppm 8.76 (s, 1H), 8.29 (d, J=9.1 Hz, 1H), 7.29 (d, J=9.0 Hz, 1H), 4.44 (p, J=9.1 Hz, 1H), 4.30 (dd, J=8.8, 7.6 Hz, 1H), 4.18 (td, J=8.4, 4.5 Hz, 1H), 4.03 (s, 3H), 4.01-3.92 (m, 2H), 2.73 (dq, J=11.5, 8.5 Hz, 1H), 2.22 (dddd, J=11.5, 9.6, 7.1, 4.4 Hz, 1H).

Step 3: tert-butyl N-(6-methoxy-4-tetrahydrofuran-3-yl-1,5-naphthyridin-3-yl)carbamate (Intermediate 173)

A solution of intermediate 172 (690 mg, 2.58 mmol), tert-butyl carbamate (617 mg, 5.16 mmol) and cesium carbonate (1.68 g, 5.16 mmol) in dry 1,4-dioxane (13 mL) was degassed for 5 min with $N_2$ prior addition of XPhos Pd G2 (406 mg, 0.258 mmol). The reaction mixture was heated at 100° C. for 1 h30. The reaction mixture was filtered through a pad of Celite, washed with EtOAc. The filtrate was partitioned between EtOAc and sat. aq. $NH_4Cl$, phases were separated and the aqueous phase was extracted with EtOAc. The combined organic layers were dried over $Na_2SO_4$, filtered and concentrated under reduced pressure. The crude was purified by flash column chromatography (Heptane/EtOAc 100:0 to 70:30) to give intermediate 173 (773 mg, 84.9% Yield). m/z: 346.4 $[M+H]^+$. $^1H$ NMR (400 MHz, DMSO) δ ppm 9.26 (s, 1H), 8.68 (s, 1H), 8.22 (d, J=9.0 Hz, 1H), 7.19 (d, J=9.0 Hz, 1H), 4.29 (dd, J=7.9, 6.9 Hz, 1H), 4.17 (td, J=8.4, 4.2 Hz, 1H), 4.04 (t, J=8.5 Hz, 1H), 4.00 (s, 3H), 3.99-3.94 (m, 1H), 3.90 (d, J=7.9 Hz, 1H), 2.68 (dq, J=11.8, 8.5 Hz, 1H), 2.20 (tdd, J=9.3, 7.4, 4.2 Hz, 1H), 1.48 (s, 9H).

Step 4 6-methoxy-4-tetrahydrofuran-3-yl-1,5-naphthyridin-3-amine (Intermediate 174)

To a solution of intermediate 173 (770 mg, 2.18 mmol) in DCM (11 mL) was added TFA (1.7 mL, 21.8 mmol). The reaction mixture was left stirring at rt for 3 h30. The reaction mixture was neutralized with sat. aq. $NaHCO_3$, partitioned with EtOAc. Phases were separated and aqueous phase was extracted with EtOAc. The combined organic layers were dried over $Na_2SO_4$, filtered and concentrated under reduced pressure. The crude was purified by flash column chromatography (Heptane/EtOAc 100:0 to 65:35) to obtain intermediate 174 (435 mg, 81.1% Yield). m/z: 246.4 $[M+H]^+$. $^1H$ NMR (400 MHz, DMSO) δ ppm 8.31 (s, 1H), 7.98 (d, J=8.8 Hz, 1H), 6.81 (d, J=8.9 Hz, 1H), 5.85 (s, 2H), 4.45-4.32 (m, 1H), 4.25-4.15 (m, 2H), 3.95 (s, 3H), 3.89-3.72 (m, 2H), 2.39 (s, 1H), 2.17 (dddd, J=11.8, 10.0, 7.1, 3.3 Hz, 1H).

Intermediates 175-176

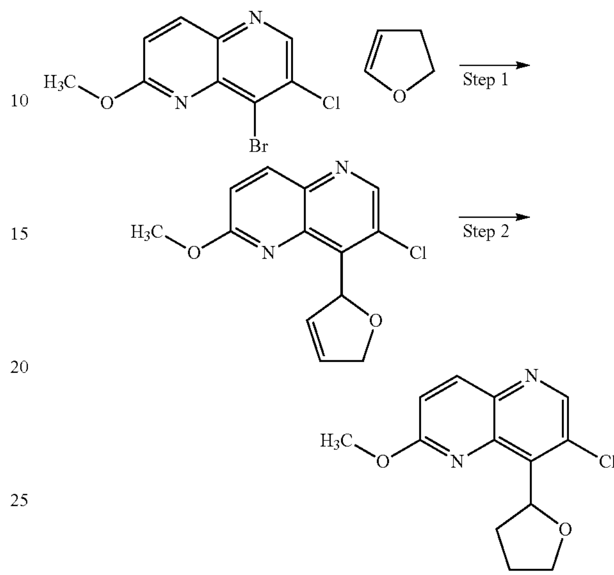

Step 1. 7-chloro-8-(2,5-dihydrofuran-2-yl)-2-methoxy-1,5-naphthyridine (Intermediate 175)

To a stirred solution of 8-bromo-7-chloro-2-methoxy-[1,5]naphthyridine (95%, 300 mg, 1.04 mmol) in dry 1,4-dioxane (4.5 mL) at rt under nitrogen were successively added 2,3-dihydrofuran (0.24 mL, 3.13 mmol), N-ethyl-N-isopropyl-propan-2-amine (0.55 mL, 3.13 mmol) and bis[3,5-bis(trifluoromethyl)phenyl]({2',4',6'-triisopropyl-4,6-dimethoxy-[1,1'-biphenyl]-2-yl})phosphane (95%, 175 mg, 0.208 mmol). The reaction mixture was stirred for 10 min under nitrogen. (1 {E},4 {E})-1,5-diphenylpenta-1,4-dien-3-one palladium (95%, 100 mg, 0.104 mmol) on carbon was added and the reaction mixture was stirred at 90° C. for 3 h. Water (10 mL) was added, phases separated and the aqueous solution extracted with EtOAc (2×10 mL). The organic layers were combined, washed with brine, dried over phase separator and concentrated under vacuum. The crude was purified by flash column chromatography (heptane/EtOAC 100/0 to 0/100) to give intermediate 175 (140 mg, 51% Yield). m/z: 263 $[M+H]^+$. $^1H$ NMR (400 MHz, DMSO) δ ppm 8.83 (s, 1H), 8.33 (d, J=9.1 Hz, 1H), 7.34 (d, J=9.0 Hz, 1H), 6.69 (t, J=11.2 Hz, 1H), 5.18 (q, J=2.5 Hz, 1H), 4.03 (s, 3H), 3.20-2.81 (m, 3H).

Step 2: 7-chloro-2-methoxy-8-tetrahydrofuran-2-yl-1,5-naphthyridine (Intermediate 176)

To a solution of intermediate 175 (140 mg, 0.528 mmol) in dry methanol (14 mL), platinum (10%, 51 mg, 0.026 mmol) was added. The reaction mixture was stirred at rt under a hydrogen atmosphere overnight. The reaction mixture was filtered through a pad of Celite, washed with MeOH and concentrated under reduced pressure. The crude was purified by flash column chromatography (Heptane/EtOAc, from 0% of EtOAc to 30% of EtOAc) to obtain intermediate 176 (70 mg, 48%). m/z: 265 $[M+H]^+$. $^1H$ NMR (400 MHz, DMSO) δ ppm 8.76 (s, 1H), 8.30 (d, J=9.1 Hz, 1H), 7.31 (d, J=9.0 Hz, 1H), 6.20-6.09 (m, 1H), 4.25-4.15 (m, 1H), 4.03 (s, 3H), 3.95 (td, J=7.9, 4.1 Hz, 1H), 2.40-2.03 (m, 4H).

Scheme 9

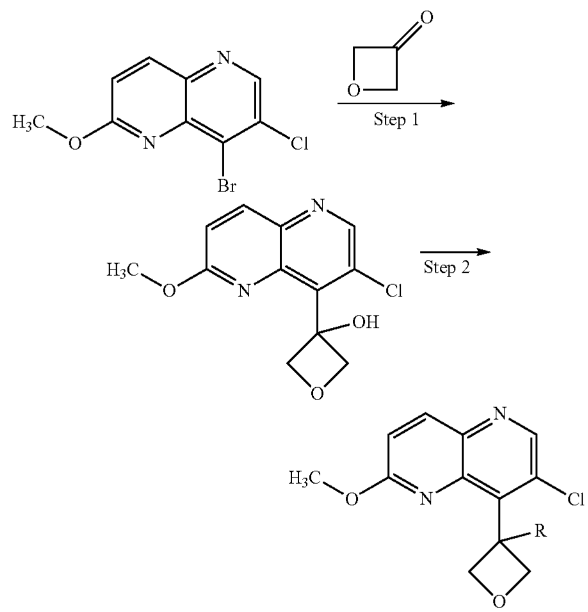

Step 1 3-(3-chloro-6-methoxy-1,5-naphthyridin-4-yl) oxetan-3-ol (Intermediate 177)

To a solution of 8-Bromo-7-chloro-2-methoxy-[1,5]naphthyridine (95%, 500 mg, 1.74 mmol) in dry THF (8.6 mL) at −78° C. was added 1.6 M butyllithium in hexane (1.6 mL, 2.61 mmol). The reaction was stirred for 15 min, then oxetan-3-one (98%, 0.57 mL, 8.68 mmol) was added, the mixture was stirred at −78° C. for 3 h. The mixture was poured in sat. aq. $NH_4Cl$ and then extracted twice with EtOAc (15 ml). The organic layers were combined, washed with brine, dried over $MgSO_4$ and concentrated under vacuum. The crude was purified by flash column chromatography (EtAOc in Heptane from 0% of EtOAc to 30%) to give intermediate 177 (202 mg, 40% Yield) as white solid. m/z: 267 $[M+H]^+$. $^1$H NMR (400 MHz, DMSO) δ ppm 8.78 (s, 1H), 8.31 (d, J=9.1 Hz, 1H), 7.30 (d, J=9.0 Hz, 1H), 6.53 (s, 1H), 5.35-5.27 (m, 2H), 4.86-4.80 (m, 2H), 3.98 (s, 3H).

Step 2 R═OMe 7-chloro-2-methoxy-8-(3-methoxyoxetan-3-yl)-1,5-naphthyridine (Intermediate 178)

To a solution of intermediate 177 (90%, 232 mg, 0.783 mmol) in dry THF (3.9148 mL) was added iodomethane (0.19 mL, 3.13 mmol), then 1 M LiHMDS (1.6 mL, 1.57 mmol) was added at 0° C., the mixture was stirred at rt for 6 h. Then iodomethane (0.19 mL, 3.13 mmol) was added again and the reaction mixture was stirred overnight at rt. The mixture was poured in sat. aq. $NH_4Cl$ and then extracted twice with EtOAc (10 mL). The organic layers were combined, washed with brine, dried over $MgSO_4$ and concentrated under vacuum. The crude was purified by flash column chromatography (EtOAc in Heptane from 0% of EtOAc to 30%) to give intermediate 178 (99 mg, 45%). m/z: 281 $[M+H]^+$. $^1$H NMR (400 MHz, DMSO) δ ppm 8.84 (s, 1H), 8.33 (d, J=9.1 Hz, 1H), 7.32 (d, J=9.1 Hz, 1H), 5.23 (d, J=8.0 Hz, 2H), 4.95 (d, J=8.3 Hz, 2H), 3.98 (s, 3H), 3.18 (s, 3H).

Step 2: R═F 7-chloro-8-(3-fluorooxetan-3-yl)-2-methoxy-1,5-naphthyridine (Intermediate 179)

To a solution of intermediate 178 (99%, 20 mg, 0.0742 mmol) in dry DOM (2.3 mL) was added at −78° C. neat N-ethyl-N-(trifluoro-$\lambda^4$-sulfanyl) ethanamine (0.021 mL, 0.148 mmol) dropwise. The resulting mixture was allowed to stir at −78° C. for 4 h before it was carefully quenched with sat. aq. $NaHCO_3$. The organic layer was separated, dried over anhydrous $MgSO_4$, filtered and the filtrate concentrated in vacuo to give intermediate 179 (16 mg, 77% Yield). m/z: 269. $^1$H NMR (400 MHz, DMSO) δ ppm 8.91 (d, J=0.8 Hz, 1H), 8.37 (d, J=9.1 Hz, 1H), 7.36 (d, J=9.1 Hz, 1H), 5.57-5.50 (m, 1H), 5.48-5.41 (m, 1H), 5.21-5.08 (m, 2H), 3.98 (s, 3H).

Intermediates 180-184

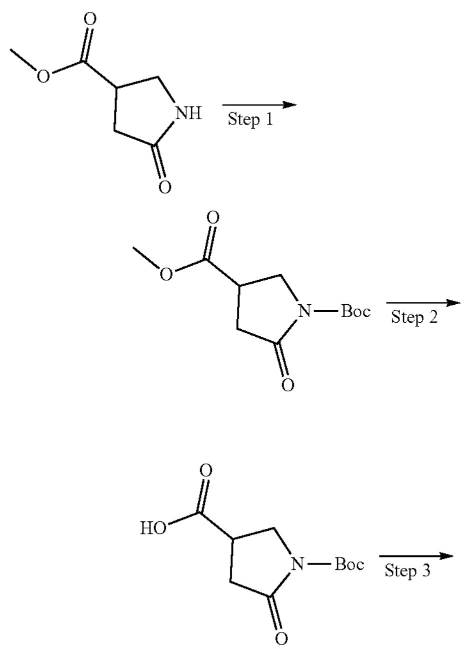

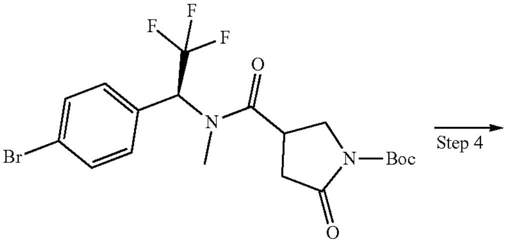

-continued

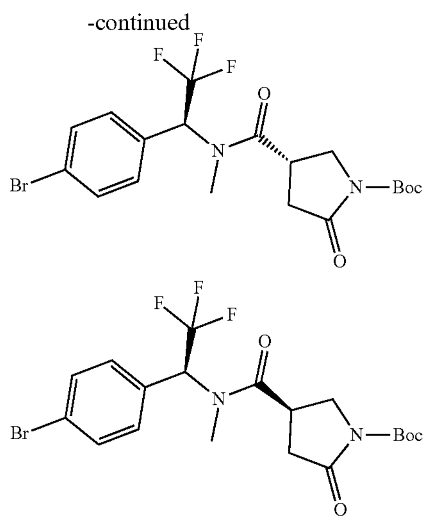

Step 1: 1-tert-butyl 3-methyl 5-oxopyrrolidine-1,3-dicarboxylate (Intermediate 180)

To a solution of methyl 5-oxopyrrolidine-3-carboxylate (97%, 2.0 g, 0.013 mol) in acetonitrile (45.2 mL) was added TEA (5.7 mL, 0.041 mol) and N,N-dimethylpyridin-4-amine (0.166 g, 0.136 mmol). After a few min., tert-butoxycarbonyl tert-butyl carbonate (5.92 g, 0.027 mol) was added. The reaction mixture was stirred at rt for 3 h. The reaction mixture was concentrated under reduced pressure. The residue was purified by flash chromatography [DCM/(DCM/MeOH 98/2)] 10/0 to 7/3, to provide intermediate 180 (2.93 g, 86%). m/z 266 $[M+Na]^+$. $^1H$ NMR (400 MHz, DMSO) δ ppm 3.88 (dd, J=10.7, 8.7 Hz, 1H), 3.76 (dd, J=10.7, 6.1 Hz, 1H), 3.66 (s, 3H), 3.37-3.25 (m, 1H), 2.77-2.58 (m, 2H), 1.45 (s, 9H).

Step 2: 1-[(tert-butoxy) carbonyl]-5-oxopyrrolidine-3-carboxylic acid (Intermediate 181)

To a solution of intermediate 180 (97%, 2.93 g, 0.012 mol) in THF (53 mL) and water (53 mL) was added lithium hydroxide hydrate (0.77 g, 0.017 mol) portion-wise. The reaction mixture was stirred at rt for 1 h30. The reaction mixture was concentrated under reduced pressure to remove THF. The aqueous layer was acidified until pH~4 with citric acid then extracted with EtOAc (3×20 mL). The organic layers were combined, dried over anhydrous $MgSO_4$, filtered and concentrated under reduced pressure. The residue was taken-up in DCM, the insoluble was filtered, washed with DCM and the filtrate concentrated under reduced pressure to provide intermediate 181 (790 mg, 21% Yield). m/z: 252 $[M+Na]^+$. $^1H$ NMR (400 MHz, DMSO) δ ppm 12.58 (s, 1H), 3.84 (dd, J=10.7, 8.5 Hz, 1H), 3.74 (dd, J=10.7, 5.9 Hz, 1H), 3.18 (tt, J=8.6, 5.9 Hz, 1H), 2.68 (dd, J=17.2, 9.2 Hz, 1H), 2.60 (dd, J=17.3, 7.1 Hz, 1H), 1.45 (s, 9H).

Step 3 and Step 4 (Intermediates 182, 183 and 184)

To a solution of intermediate 181 (1.37 g, 4.25 mmol) and (1S)-1-(4-bromophenyl)-2,2,2-trifluoro-N-methyl-ethanamine (1.00 g, 3.54 mmol) in DCM (18 mL) was added TEA (10 mL, 70.9 mmol) and $T_3P$ in EtOAc (50%, 21 mL, 35.4 mmol). The reaction mixture was stirred at rt for 1 h30. The reaction mixture was neutralized with sat. aq. $NaHCO_3$, phases were separated and aqueous phase was extracted with DCM. The combined organic layers were dried over $Na_2SO_4$, filtered and concentrated under reduced pressure. The crude was purified by chiral chromatography chiralpak IG 20 μm, 300×50 mm eluting with methanol to give:

tert-butyl (4rel S)-4-[[(1S)-1-(4-bromophenyl)-2,2,2-trifluoro-ethyl]-methyl-carbamoyl]-2-oxo-pyrrolidine-1-carboxylate (intermediate 183) (900 mg; 53%, Yield). $^1H$ NMR (400 MHz, DMSO) δ ppm 7.75-7.64 (m, 2H), 7.46-7.30 (m, 2H), 6.52 (q, J=9.1 Hz, 1H), 4.00-3.82 (m, 1H), 3.74-3.60 (m, 2H), 2.86 (s, 3H), 2.82-2.54 (m, 2H), 1.45 (s, 9H). m/z; 252 $[M+H]^+$ tert-butyl (4rel R)-4-[[(1S)-1-(4-bromophenyl)-2,2,2-trifluoro-ethyl]-methyl-carbamoyl]-2-oxo-pyrrolidine-1-carboxylate (intermediate 184) (710 mg; 38.9%, Yield). $^1H$ NMR (400 MHz, DMSO) δ ppm 7.74-7.62 (m, 2H), 7.44-7.31 (m, 2H), 6.52 (q, J=9.2 Hz, 1H), 3.87 (ddd, J=10.8, 8.4, 2.7 Hz, 1H), 3.82-3.73 (m, 1H), 3.72-3.66 (m, 1H), 2.92-2.81 (m, 4H), 2.79-2.58 (m, 1H), 1.45 (d, J=2.5 Hz, 9H). m/z: 252 $[M+H]^+$ Intermediate 185

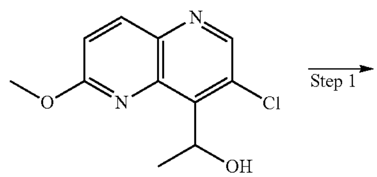

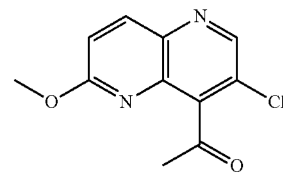

1-(3-chloro-6-methoxy-1,5-naphthyridin-4-yl) ethanone (Intermediate 185)

Intermediate 154 (1.50 g, 6.16 mmol) and dioxomanganese (5.35 g, 61.6 mmol) were suspended in toluene (31 mL) at rt. The black suspension was stirred at 80° C. for 1 hour and then 40° C. overnight and at 80° C. for 8 h and at rt over the week-end. The black solid was removed by filtration and washed with EtOAc. The filtrated was concentrated under reduced pressure to give intermediate 185 (1.4 g, 99%). m/z: 237 $[M+H]^+$. $^1H$ NMR (400 MHz, DMSO-d6) δ ppm 8.89 (s, 1H), 8.36 (d, J=9.1 Hz, 1H), 7.35 (d, J=9.1 Hz, 1H), 3.97 (s, 3H), 2.69 (s, 3H). α1

Intermediates 186-187

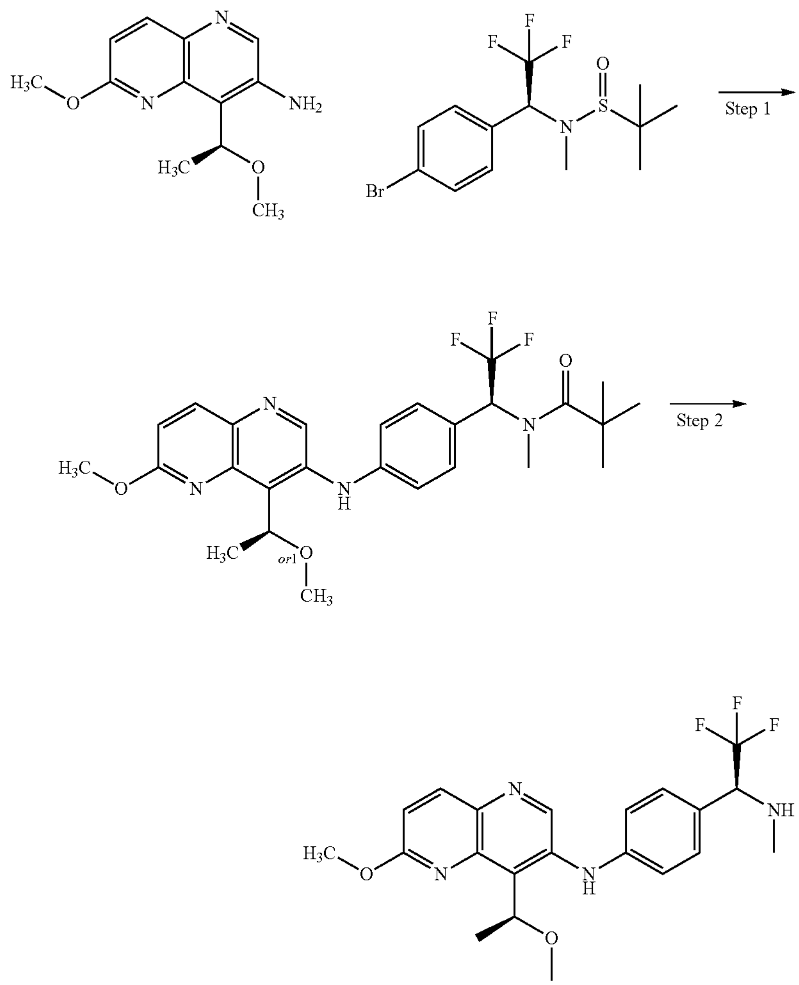

Step 1: (R)—N,2-dimethyl-N-[(1S)-2,2,2-trifluoro-1-[4-[[6-methoxy-4-[(1 rel S)-1-methoxyethyl]-1,5-naphthyridin-3-yl]amino]phenyl]ethyl]propane-2-sulfinamide (Intermediate 186)

A suspension of Intermediate 72 (100%, 1.88 g, 5.05 mmol), Intermediate 155 (98%, 1.00 g, 4.21 mmol) and cesium carbonate (2.74 g, 8.42 mmol) in dry 1,4-dioxane (42.1 mL) was degassed with $N_2$ for 5 min prior addition of XPhos Pd G2 (1.66 g, 1.05 mmol) at rt. The reaction mixture was stirred at 100° C. for 7 h then N-[(1S)-1-(4-bromophenyl)-2,2,2-trifluoro-ethyl]-N,2-dimethyl-propane-2-sulfinamide (100%, 784 mg, 2.10 mmol) was added and the reaction was stirred at 100° C. overnight. The reaction mixture was filtered through a pad of celite and washed with EtOAc. The filtrate was diluted with EtOAc and sat. aq. $NH_4Cl$ was added. The aqueous phase was extracted with EtOAc. The organic layers were combined dried over $Na_2SO_4$, filtered and concentrated under reduced pressure. The crude was purified by flash column chromatography (Heptane/EtOAc, from 0% of EtOAc to 50%) to afford intermediate 186 (925 mg, 38% Yield). m/z: 525 $[M+H]^+$. $^1H$ NMR (400 MHz, DMSO) δ ppm 8.78 (s, 1H), 8.17 (d, J=9.0 Hz, 1H), 8.05 (s, 1H), 7.37 (d, J=8.4 Hz, 2H), 7.28-7.21 (m, 2H), 7.08 (d, J=8.9 Hz, 1H), 5.85 (q, J=6.7 Hz, 1H), 5.47 (q, J=9.2 Hz, 1H), 4.02 (s, 3H), 2.44 (s, 3H), 1.51 (d, J=6.7 Hz, 3H), 1.15 (s, 9H).

Step 2: 6-methoxy-4-[(1 rel S)-1-methoxyethyl]-N-[4-[(1S)-2,2,2-trifluoro-1-(methylamino)ethyl]phenyl]-1,5-naphthyridin-3-amine (Intermediate 187)

Intermediate 186 (0.019 mL, 1.67 mmol) was dissolved in 2-methyltetrahydrofuran (6.2 mL) at 0° C. 12 M hydrogen chloride in water (0.42 mL, 5.00 mmol) was added and the reaction mixture was stirred at 0° C. for 15 minutes. The cooling bath was removed and the reaction mixture was stirred at rt for 1 h30. The reaction mixture was diluted with water and sodium hydrogen carbonate (0.56 g, 6.67 mmol) was slowly added portion-wise under vigorous stirring. When gas evolution ceased, the aqueous layer was isolated and extracted with 2-MeTHF. Organic layers were combined, washed with brine (100 mL), dried over anhydrous $Na_2SO_4$, filtered and concentrated to give intermediate 187 (760 mg, 81% Yield). m/z 421 $[M+H]^+$ $^1H$ NMR (400 MHz, DMSO) δ ppm 8.77 (s, 1H), 8.15 (d, J=8.9 Hz, 1H), 8.00 (s, 1H), 7.40 (d, J=8.6 Hz, 2H), 7.22 (d, J=8.5 Hz, 2H), 7.05 (d, J=9.0 Hz, 1H), 5.86 (q, J=6.6 Hz, 1H), 4.20 (p, J=8.0 Hz, 1H), 4.02 (s, 3H), 3.31 (s, 3H), 2.77-2.69 (m, 1H), 2.25 (d, J=5.4 Hz, 3H), 1.52 (d, J=6.7 Hz, 3H).

Scheme 10

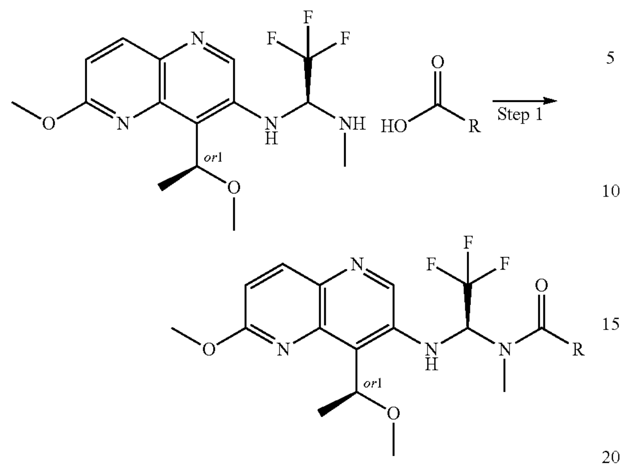

Intermediates 188-191 were prepared according to the general procedure 3 described for preparing the examples 37-127 from either commercially available acids or intermediates.

| Intermediate 188 | Procedure: 3b | Intermediates 187 and 181 | Yield: 64% |
| --- | --- | --- | --- |
| 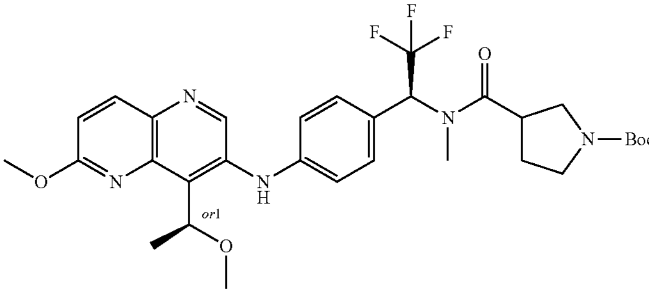 | $^1H$ NMR (500 MHz, DMSO-$d_6$) δ ppm 1.39-1.47 (m, 9 H) 1.51 (d, J = 6.60 Hz, 3 H) 2.57-2.80 (m, 2 H) 2.84-2.92 (m, 3 H) 3.29-3.30 (m, 3 H) 3.55-3.91 (m, 3 H) 3.94-4.05 (m, 3 H) 5.85 (q, J = 6.60 Hz, 1 H) 6.46 (q, J = 9.13 Hz, 1 H) 7.08 (d, J = 8.80 Hz, 1 H) 7.21-7.41 (m, 4 H) 8.03-8.07 (m, 1 H) 8.16 (d, J = 9.05 Hz, 1 H) 8.78 (s, 1 H). m/z 632 $[M + H]^+$ | | |
| tert-butyl 4-[methyl-[(1 S)-2,2,2-trifluoro-1-[4-[6-methoxy-4-[(1 rel S)-1-methoxyethyl]-1,5-naphthyridin-3-yl]amino]phenyl]ethyl]carbamoyl]-2-oxo-pyrrolidine-1-carboxylate | | | |

| Intermediate 189 | Procedure: 3b | Intermediate 187 | Yield: 64.9% |
| --- | --- | --- | --- |
| 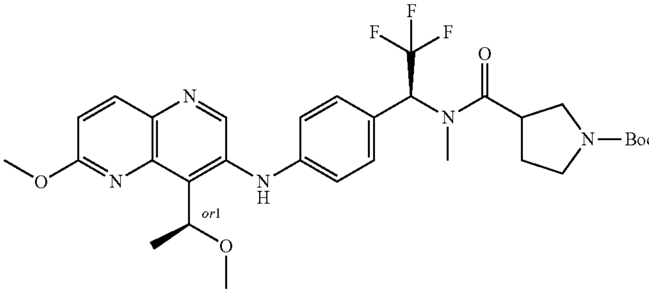 [SMILES: COc1ccc2ncc(Nc3ccc([C@H](N(C)C(=O)C4CCN(C(=O)OC(C)(C)C)C4)C(F)(F)F)cc3)c([C@H](C)OC)c2n1] | $^1H$ NMR (400 MHz, DMSO) δ ppm 8.78 (s, 1H), 8.16 (dd, J = 8.9, 0.7 Hz, 1H), 8.05 (s, 1H), 7.40-7.21 (m, 4H), 7.07 (d, J = 9.0 Hz, 1H), 6.50 (qd, J = 9.3, 3.3 Hz, 1H), 5.85 (q, J = 6.7 Hz, 1H), 4.01 (s, 3H), 3.64-3.32 (m, 4H), 3.30 (s, 4H), 2.92 (d, J = 3.9 Hz, 2H), 2.29-1.78 (m, 2H), 1.50 (d, J = 6.7 Hz, 3H), 1.40 (d, J = 1.3 Hz, 10H). m/z 618 $[M + H]^+$ | | |
| tert-butyl 3-[methyl-[(1 S)-2,2,2-trifluoro-1-[4-[6-methoxy-4-[(1 rel S)-1-methoxyethyl]-1,5-naphthyridin-3-yl]amino]phenyl]ethyl]carbamoyl]pyrrolidine-1-carboxylate | | | |

-continued

| Intermediate 190 | Intermediate Procedure: 3b 187 | Yield: 43% |
|---|---|---|
| 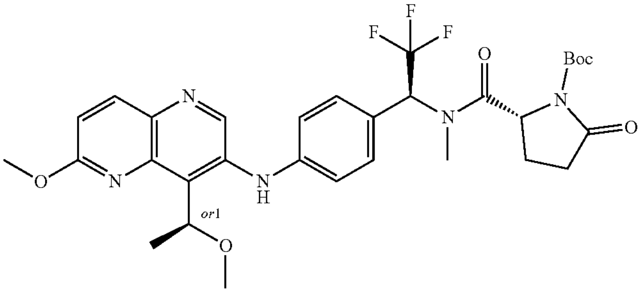 [SMILES: COc1ccc2ncc(Nc3ccc([C@H](N(C)C(=O)[C@H]4CCC(=O)N4C(=O)OC(C)(C)C)C(F)(F)F)cc3)c([C@H](C)OC)c2n1] | $^1$H NMR (400 MHz, DMSO) δ ppm 8.79 (s, 1H), 8.16 (d, J = 8.9 Hz, 1H), 8.06 (s, 1H), 7.34-7.22 (m, 4H), 7.08 (d, J = 9.0 Hz, 1H), 6.42 (q, J = 9.2 Hz, 1H), 5.84 (q, J = 6.7 Hz, 1H), 5.16 (dd, J = 9.3, 2.3 Hz, 1H), 4.01 (s, 3H), 3.30 (s, 3H), 2.90 (s, 3H), 2.46-2.26 (m, 3H), 1.77-1.64 (m, 1H), 1.51 (d, J = 6.7 Hz, 3H), 1.41 (s, 9H). m/z 632 $[M + H]^+$ | |
| tert-butyl (2 rel S)-2-[methyl-[(1S)-2,2,2-trifluoro-1-[4-[6-methoxy-4-[(1 rel S)-1-methoxyethyl]-1,5-naphthyridin-3-yl]amino]phenyl]ethyl]carbamoyl]-5-oxo-pyrrolidine-1-carboxylate | | |

| Intermediate 191 | Intermediate Procedure: 3b 187 | Yield: 38% |
|---|---|---|
| 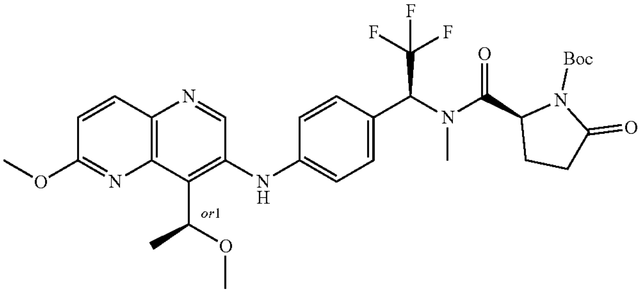 [SMILES: COc1ccc2ncc(Nc3ccc([C@H](N(C)C(=O)[C@@H]4CCC(=O)N4C(=O)OC(C)(C)C)C(F)(F)F)cc3)c([C@H](C)OC)c2n1] | $^1$H NMR (400 MHz, DMSO) δ ppm: 8.75 (s, 1H), 8.17 (d, J = 8.9 Hz, 1H), 8.05 (s, 1H), 7.35 (d, J = 8.4 Hz, 2H), 7.30-7.22 (m, 2H), 7.08 (d, J = 8.9 Hz, 1H), 6.47 (q, J = 9.3 Hz, 1H), 5.85 (q, J = 6.6 Hz, 1H), 5.16 (dd, J = 9.0, 2.6 Hz, 1H), 4.02 (s, 3H), 3.29 (s, 3H), 2.98 (s, 3H), 2.47-2.29 (m, 3H), 1.79-1.67 (m, 1H), 1.51 (d, J = 6.7 Hz, 3H), 1.31 (s, 9H). m/z 632 $[M + H]^+$ | |
| tert-butyl (2 rel R)-2-[methyl-[(1S)-2,2,2-trifluoro-1-[4-[6-methoxy-4-[(1 rel S)-1-methoxyethyl]-1,5-naphthyridin-3-yl]amino]phenyl]ethyl]carbamoyl]-5-oxo-pyrrolidine-1-carboxylate | | |

Intermediates 192-193

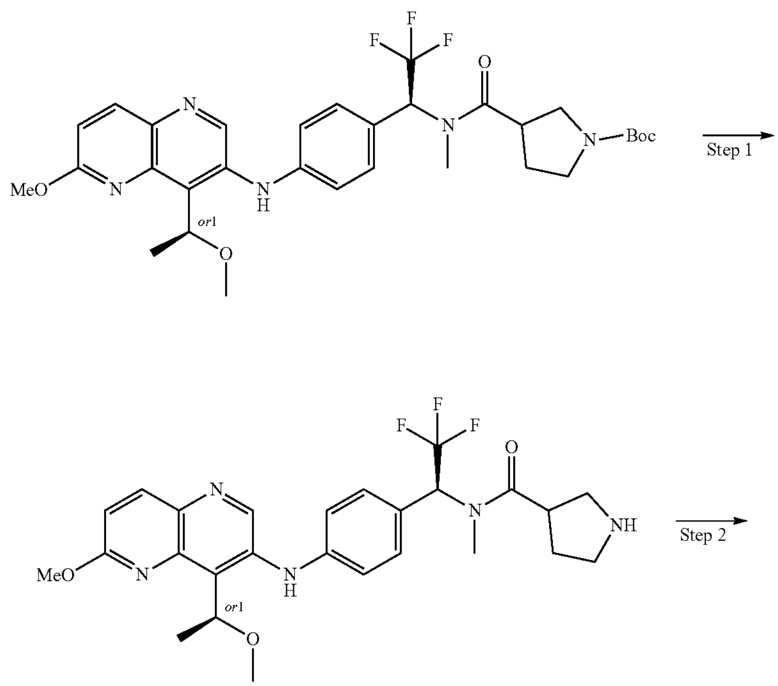

-continued

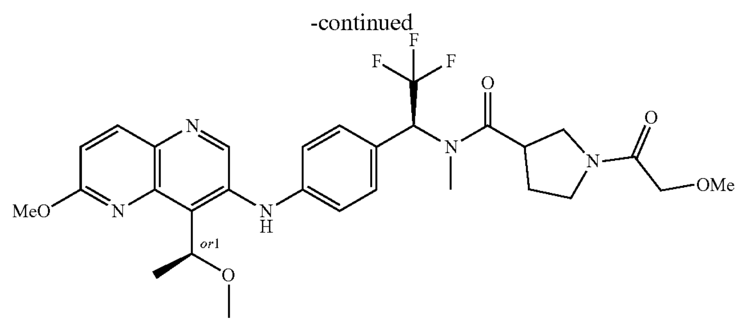

Step 1: N-methyl-N-[(1S)-2,2,2-trifluoro-1-[4-[[6-methoxy-4-[(1 rel S)-1-methoxyethyl]-1,5-naphthyridin-3-yl]amino]phenyl]ethyl]pyrrolidine-3-carboxamide (Intermediate 192)

To a solution of tert-butyl 3-[methyl-[(1S)-2,2,2-trifluoro-1-[4-[[6-methoxy-4-[(1 rel S)-1-methoxyethyl]-1,5-naphthyridin-3-yl]amino]phenyl]ethyl]carbamoyl]pyrrolidine-1-carboxylate (91%, 600 mg, 0.884 mmol) in DCM (4 mL) was added TFA (0.68 mL, 8.84 mmol). The reaction mixture was stirred at rt for 2 h. The reaction mixture was slowly poured over sat. aq. $NaHCO_3$. The aqueous layer was extracted with DCM (2×10 mL). The organic layers were combined, dried over magnesium sulfate, filtered and concentrated under reduced pressure. The residue was purified by flash chromatography eluting with [DCM/(DCM/MeOH 9/1)] 10/0 to 3/7 to provide intermediate 192 (150 mg, 31.5% Yield). m/z 617 $[M+H]^+$. $^1H$ NMR (400 MHz, DMSO) δ ppm 8.78 (s, 1H), 8.16 (d, J=9.0 Hz, 1H), 8.04 (s, 1H), 7.38-7.21 (m, 4H), 7.07 (d, J=9.0 Hz, 1H), 6.51 (q, J=9.4 Hz, 1H), 5.85 (q, J=6.7 Hz, 1H), 4.08 (q, J=5.2 Hz, 1H), 3.30 (s, 3H), 3.17 (d, J=4.8 Hz, 3H), 3.03 (ddd, J=33.6, 11.0, 8.1 Hz, 1H), 2.90 (s, 3H), 2.86-2.65 (m, 4H), 1.91-1.74 (m, 2H), 1.51 (d, J=6.7 Hz, 3H).

Step 2: [2-[3-[methyl-[(1S)-2,2,2-trifluoro-1-[4-[[6-methoxy-4-[(1 rel S)-1-methoxyethyl]-1,5-naphthyridin-3-yl]amino]phenyl]ethyl]carbamoyl]pyrrolidin-1-yl]-2-oxo-ethyl]acetate (Intermediate 193)

This intermediate was prepared according to the general procedure 3b already described for examples 37-127. Yield: 95%. m/z 617 $[M+H]^+$. $^1H$ NMR (400 MHz, DMSO) δ ppm 8.78 (d, J=1.6 Hz, 1H), 8.16 (d, J=9.0 Hz, 1H), 8.05 (s, 1H), 7.33-7.22 (m, 4H), 7.08 (d, J=8.9 Hz, 1H), 5.85 (q, J=6.7 Hz, 1H), 4.69 (d, J=14.4 Hz, 2H), 4.08 (q, J=5.3 Hz, 2H), 3.77-3.33 (m, 5H), 3.30 (s, 4H), 2.98-2.90 (m, 3H), 2.33-2.14 (m, 1H), 2.12-2.03 (m, 4H), 1.51 (d, J=6.7 Hz, 3H)+1H labile proton.

Scheme 11

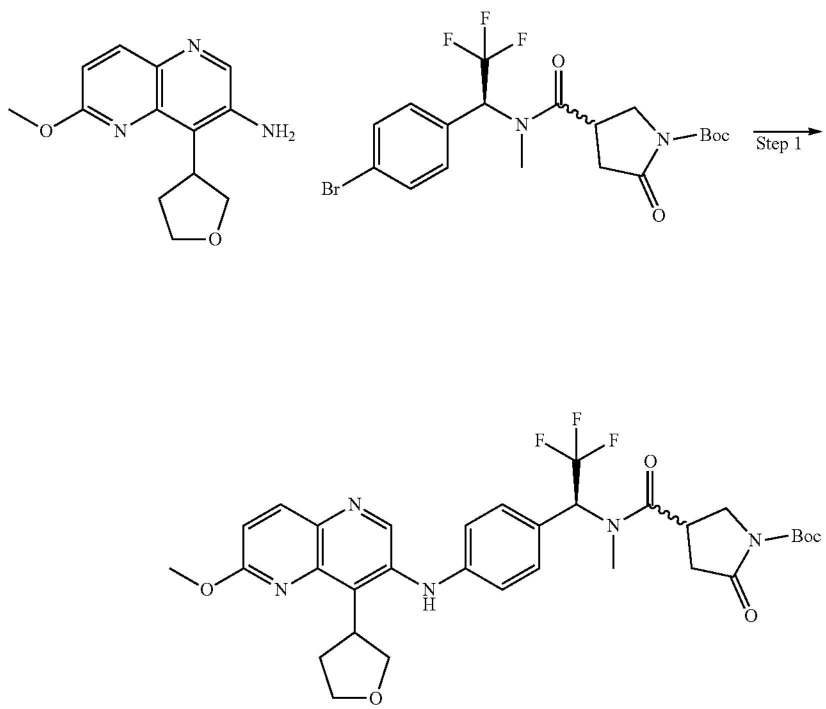

A suspension of intermediate 174 (100 mg, 0.408 mmol), intermediate 183 or 184 (1 mmol) and cesium carbonate (2 mmol) in dry 1,4-dioxane (0.5 M) was degassed with $N_2$ for 5 min prior addition of XPhos Pd G2 (0.2 mmol). The reaction mixture was then heated at 100° C. for 4 h. The reaction mixture was filtered through a pad of Celite, washed with EtOAc. The filtrate was partitioned between EtOAc and sat. aq. $NH_4Cl$, phases were separated and aqueous phase was extracted with EtOAc. The combined organic layers were dried over $Na_2SO_4$, filtered and concentrated under reduced pressure. The crude was purified by flash column chromatography, (Heptane/[EtOAc/EtOH 3:1] 100:0 to 60:40).

| Intermediate 194 | Intermediates 174 and 184 | Yield: 67.8% |
|---|---|---|
| 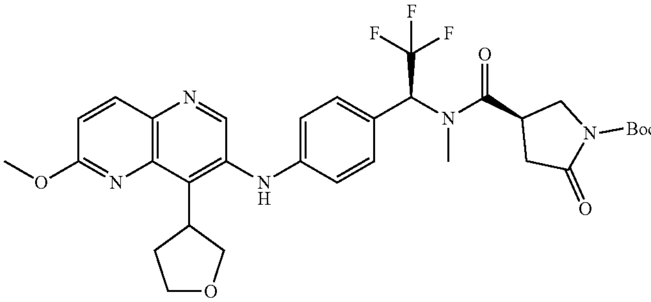 [SMILES: COc1ccc2ncc(Nc3ccc([C@H](N(C)C(=O)[C@@H]4CC(=O)N(C(=O)OC(C)(C)C)C4)C(F)(F)F)cc3)c(C3CCOC3)c2n1] | $^1$H NMR (400 MHz, DMSO) δ ppm 8.63 (s, 1H), 8.32 (d, J = 6.9 Hz, 1H), 8.20 (d, J = 9.0 Hz, 1H), 7.26 (dd, J = 24.4, 8.4 Hz, 2H), 7.14 (d, J = 9.0 Hz, 1H), 6.97-6.88 (m, 2H), 6.41 (q, J = 9.3 Hz, 1H), 4.36-4.28 (m, 1H), 4.21-4.08 (m, 2H), 4.01 (s, 3H), 3.97-3.80 (m, 3H), 3.80-3.60 (m, 2H), 2.88 (s, 3H), 2.87 (s, 1H), 2.72 (d, J = 11.3 Hz, 1H), 2.50 (p, J = 1.9 Hz, 1H), 2.22-2.11 (m, 1H), 1.45 (d, J = 5.8 Hz, 9H). m/z 644.4 [M + H]$^+$ | |
| tert-butyl (4rel R)-4-[methyl-[(1S)-2,2,2-trifluoro-1-[4-[(6-methoxy-4-tetrahydrofuran-3-yl-1,5-naphthyridin-3-yl)amino]phenyl]ethyl]carbamoyl]-2-oxo-pyrrolidine-1-carboxylate | | |

| Intermediate 195 | Intermediates 174 and 183 | Yield: 70.2% |
|---|---|---|
| 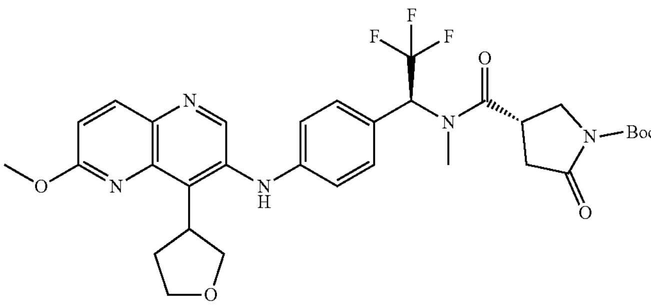 [SMILES: COc1ccc2ncc(Nc3ccc([C@H](N(C)C(=O)[C@H]4CC(=O)N(C(=O)OC(C)(C)C)C4)C(F)(F)F)cc3)c(C3CCOC3)c2n1] | $^1$H NMR (400 MHz, DMSO) δ ppm: 8.63 (s, 1H), 8.31 (s, 1H), 8.20 (d, J = 9.0 Hz, 1H), 7.33-7.18 (m, 2H), 7.14 (d, J = 8.9 Hz, 1H), 6.92 (d, J = 8.7 Hz, 2H), 6.41 (q, J = 9.4 Hz, 1H), 4.32 (t, J = 8.0 Hz, 1H), 4.16 (dd, J = 8.5, 4.2 Hz, 2H), 4.01 (s, 3H), 3.98-3.81 (m, 3H), 3.74-3.63 (m, 2H), 2.89 (s, 3H), 2.75 (dd, J = 16.3, 8.0 Hz, 2H), 2.58 (dd, J = 17.1, 5.4 Hz, 1H), 2.16 (s, 1H), 1.45 (s, 9H). m/z 644.4 [M + H]$^+$ | |
| tert-butyl (4rel S)-4-[methyl-[(1S)-2,2,2-trifluoro-1-[4-[(6-methoxy-4-tetrahydrofuran-3-yl-1,5-naphthyridin-3-yl)amino]phenyl]ethyl]carbamoyl]-2-oxo-pyrrolidine-1-carboxylate | | |

Intermediates 196-201

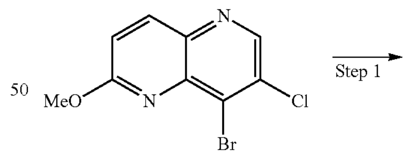

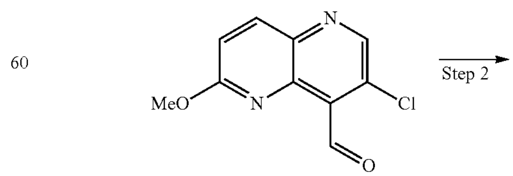

-continued

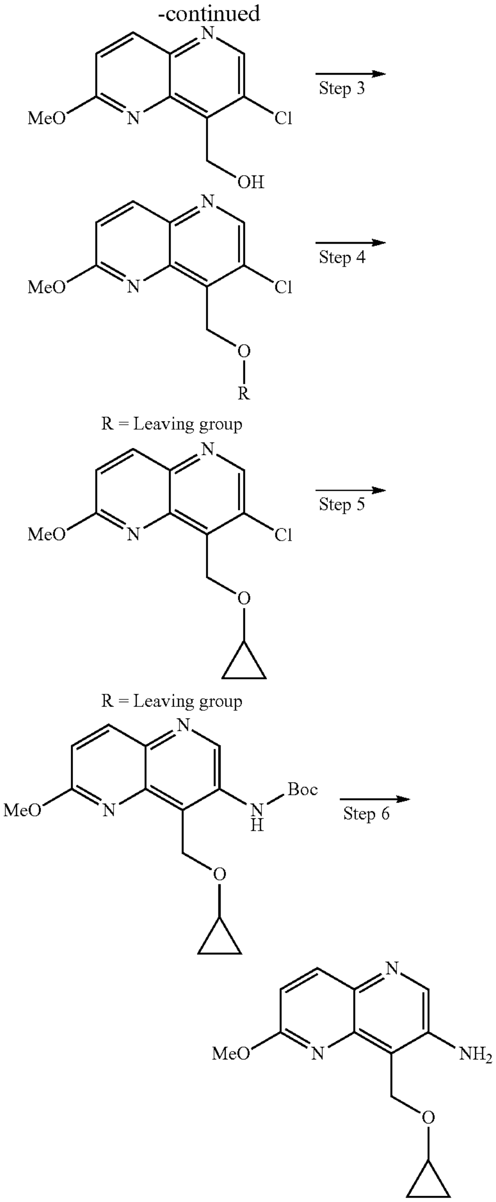

Step 1: 3-chloro-6-methoxy-1,5-naphthyridine-4-carbaldehyde (Intermediate 196)

A suspension of 8-bromo-7-chloro-2-methoxy-[1,5]naphthyridine (3.00 g, 11.0 mmol), ethyltrifluoroborate (95%, 1.55 g, 11.0 mmol) and tripotassium phosphate (4.72 g, 21.9 mmol) in 1,4-dioxane (44 mL)/water (11 mL) was degassed with $N_2$ for 5 min prior addition of [2-(2-aminophenyl) phenyl]-methylsulfonyloxy-palladium-dicyclohexyl-[2-(2,6-diisopropoxyphenyl)phenyl]phosphane (1.84 g, 2.19 mmol). The reaction mixture was heated at 100° C. for 2 h. The reaction mixture was cooled to rt and tetraoxoosmium in water (2.0 mL, 0.329 mmol) was added and stirred for 5 min prior addition of sodium-periodate (5.89 g, 27.4 mmol). The reaction mixture was left stirring at rt for 2 days. The reaction mixture was filtered through a pad of Celite and washed with EtOAc. The filtrate was partitioned between sat $NaHCO_3$ and EtOAc, phases were separated and aqueous phase was extracted with EtOAc. The combined organic layers were dried over $Na_2SO_4$, filtered and concentrated under reduced pressure. The crude was purified by flash column chromatography (Heptane:EtOAc, 100:0 to 70:30) to afford Intermediate 196 (1 g, 40% Yield). m/z: 223 $[M+H]^+$. $^1H$ NMR (400 MHz, DMSO) δ ppm 11.09 (s, 1H), 8.95 (s, 1H), 8.41 (d, J=9.1 Hz, 1H), 7.40 (d, J=9.2 Hz, 1H), 4.06 (s, 3H).

Step 2: (3-chloro-6-methoxy-1,5-naphthyridin-4-yl) methanol (Intermediate 197)

To a solution of Intermediate 196 (300 mg, 1.32 mmol) in methanol (9.4 mL) was added sodium borohydride (55 mg, 1.45 mmol) at 0° C. The reaction mixture was left stirring at 0° C. for 30 min. The reaction mixture was quenched with water and partitioned with EtOAc, phases were separated and aqueous phase was extracted with EtOAc. The combined organic layers were dried over $Na_2SO_4$, filtered and concentrated under reduced pressure. The crude was purified by flash column chromatography (Heptane/EtOAc, 90:10 to 65:35) to obtain Intermediate 197. (295 mg, 99% Yield). m/z: 225.3 $[M+H]^+$. $^1H$ NMR (400 MHz, DMSO) δ ppm 8.81 (s, 1H), 8.31 (d, J=9.1 Hz, 1H), 7.31 (d, J=9.0 Hz, 1H), 5.25 (t, J=5.7 Hz, 1H), 5.12 (d, J=5.4 Hz, 2H), 4.07 (s, 3H).

Step 3: Mixture of 7-chloro-8-(chloromethyl)-2-methoxy-1,5-naphthyridine and (3-chloro-6-methoxy-1,5-naphthyridin-4-yl)methyl methanesulfonate (ratio: 1:1) (Intermediate 198)

To a solution of Intermediate 197 (265 mg, 1.17 mmol) in dry DCM (5.8 mL) was added TEA (0.33 mL, 2.34 mmol) prior addition of methanesulfonyl chloride (0.14 mL, 1.75 mmol) at 0° C. The reaction mixture was allowed to warm to rt and stirred for 45 min. The reaction mixture was partitioned between DCM and $H_2O$, phases were separated and the aqueous phase was extracted with DCM. The combined organic layers were dried over $Na_2SO_4$, filtered and concentrated under reduced pressure to give a mixture of 7-chloro-8-(chloromethyl)-2-methoxy-1,5-naphthyridine and (3-chloro-6-methoxy-1,5-naphthyridin-4-yl)methyl methanesulfonate in a 1:1 ratio which was used as such without further purification. $^1H$ NMR (400 MHz, DMSO) δ ppm 8.94 (s, 1H), 8.36 (dd, J=9.0, 7.0 Hz, 1H), 7.37 (dd, J=9.0, 4.0 Hz, 1H), 5.89 (s, 2H), 4.08 (d, J=1.0 Hz, 3H), 3.34 (s, 3H, under the solvent peak) (mixture). m/z: 303.3 $[M+H]^+$ (product OMs) and m/z: 243.2 $[M+H]^+$ (product Cl)

Step 4: 7-chloro-8-(cyclopropoxymethyl)-2-methoxy-1,5-naphthyridine (Intermediate 199)

To a solution of cyclopropanol (0.11 mL, 1.62 mmol) in dry DMF (3.3 mL) was added NaH (60%, 108 mg, 2.69 mmol) at 0° C. and stirred at this temperature for 25 min. A solution of intermediate 198 in dry DMF (2.5 mL) was then added to the solution and the resulting reaction mixture was warmed to rt and stirred for 30 min. The reaction mixture was neutralized with sat. aq. $NH_4Cl$, extracted with EtOAc. The combined organic layers were dried over $Na_2SO_4$, filtered and concentrated under reduced pressure. The crude was purified by flash column chromatography (Heptane/EtOAc, 100:0 to 85:15) to obtain intermediate 199 (111 mg, 16.8% Yield) $^1H$ NMR (400 MHz, DMSO) δ ppm 8.84 (s, 1H), 8.29 (dd, J=15.0, 9.0 Hz, 1H), 7.34-7.24 (m, 1H), 5.14 (s, 2H), 4.05 (d, J=10.6 Hz, 3H), 3.54-3.39 (m, 1H), 0.61-0.40 (m, 4H). m/z: 265.3 $[M+H]^+$.

Step 5: tert-butyl N-[4-(cyclopropoxymethyl)-6-methoxy-1,5-naphthyridin-3-yl]carbamate (Intermediate 200)

A solution of intermediate 199 (38 mg, 0.0689 mmol), tert-butyl carbamate (16 mg, 0.138 mmol) and cesium carbonate (45 mg, 0.138 mmol) was degassed with $N_2$ for 5 min prior addition of [2-(2-aminophenyl)phenyl]-methylsulfonyloxy-palladium; dicyclohexyl-[2-(2,6-diisopropoxyphenyl)phenyl]phosphane (12 mg, 0.0138 mmol). The reaction mixture was heated at 100° C. for 1 h. The reaction mixture was filtered through a pad of celite and washed with EtOAc. The filtrate was partitioned between sat. aq. $NH_4Cl$ and EtOAc, phases were separated and the aqueous phase was extracted with EtOAc. The combined organic layers were dried over $Na_2SO_4$, filtered and concentrated under reduced pressure. The crude was purified by flash column chromatography (Heptane/EtOAc, 100:0 to 70:30) to obtain intermediate 200 (41.9 mg, quantitative). $^1$H NMR (400 MHz, DMSO) δ ppm 9.01 (s, 1H), 8.87 (s, 1H), 8.23 (d, J=9.0 Hz, 1H), 7.18 (d, J=9.0 Hz, 1H), 5.21 (s, 2H), 4.04 (s, 3H), 3.38 (tt, J=6.0, 2.9 Hz, 1H), 1.50 (s, 9H), 0.59-0.52 (m, 2H), 0.49-0.41 (m, 2H). m/z: 346.4 $[M+H]^+$.

Step 6: 4-(cyclopropoxymethyl)-6-methoxy-1,5-naphthyridin-3-amine (intermediate 201)

To a solution of intermediate 200 (47 mg, 0.116 mmol) in DCM (0.6 mL) was added TFA (90 μL, 1.18 mmol). The reaction mixture was stirred at rt for 3 hours. The reaction mixture was neutralized with $NaHCO_3$ sat and aqueous phase was extracted with EtOAc. The combined organic layers were dried over $Na_2SO_4$, filtered and concentrated under reduced pressure. The product was used as such without further purification. $^1$H NMR (400 MHz, DMSO) δ ppm 8.35 (s, 1H), 7.99 (d, J=8.9 Hz, 1H), 6.81 (d, J=8.8 Hz, 1H), 5.84 (s, 2H), 5.02 (s, 2H), 3.98 (s, 3H), 3.37 (tt, J=6.0, 2.9 Hz, 1H), 0.60-0.54 (m, 2H), 0.47-0.40 (m, 2H). m/z: 246.3 $[M+H]^+$.

Intermediates 202-203

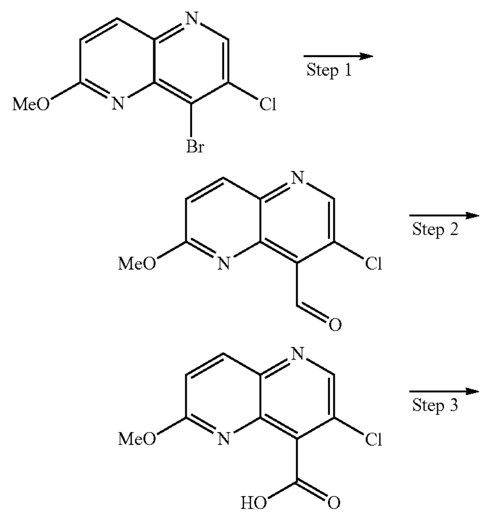

-continued

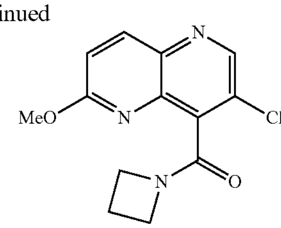

Step 1: 3-chloro-6-methoxy-1,5-naphthyridine-4-carbaldehyde

The compound from step 1 is intermediate 197.

Step 2: 3-chloro-6-methoxy-1,5-naphthyridine-4-carboxylic acid (Intermediate 202)

To a solution of intermediate 197 (500 mg, 2.20 mmol) in tert-butanol (5.5 mL) was added a 2M solution of 2-methylbut-2-ene in THF (5.5 mL, 11.0 mmol) followed by a solution of sodium dihydrogen phosphate (799 mg, 6.60 mmol) in water (5.5 mL). The reaction mixture was stirred 5 min at rt prior addition of sodium chlorite (498 mg, 4.40 mmol). The reaction mixture was left stirring at rt for 1 h30. The reaction mixture was neutralized with 10% $Na_2SO_3$, acidified with 5M HCl and extracted with EtOAc. The organic layers were combined, dried over $Na_2SO_4$, filtered and concentrated under reduced pressure to obtain intermediate 202 which was used as such without further purification (577 mg, 79.1% Yield). $^1$H NMR (400 MHz, DMSO) δ ppm 14.24 (s, 1H), 8.89 (s, 1H), 8.35 (d, J=9.2 Hz, 1H), 7.36 (d, J=9.1 Hz, 1H), 3.98 (s, 3H). m/z: 239.2 $[M+H]^+$.

Step 3: azetidin-1-yl-(3-chloro-6-methoxy-1,5-naphthyridin-4-yl) methanone (intermediate 203)

To a solution of intermediate 202 (72%, 280 mg, 0.845 mmol) and azetidine (0.24 mL, 3.38 mmol) in dry DCM (4.2 mL) was added TEA (2.4 mL, 16.9 mmol) followed by $T_3P$ in 50% in EtOAc (50%, 5.0 mL, 8.45 mmol). The reaction mixture was left stirring at rt overnight. The reaction mixture was partitioned between $H_2O$ and EtOAc, phases were separated and aqueous phase was extracted with EtOAc. The organic layers were combined, dried over $Na_2SO_4$, filtered and concentrated under reduced pressure. The crude was purified by reverse flash column chromatography (water/MeCN, from 100:0 to 0:100) to obtain intermediate 203 (67 mg, 27.7% Yield). $^1$H NMR (400 MHz, DMSO) δ ppm 8.88 (s, 1H), 8.35 (d, J=9.1 Hz, 1H), 7.35 (d, J=9.2 Hz, 1H), 4.28-4.07 (m, 2H), 4.03 (s, 3H), 3.87-3.69 (m, 2H), 2.30 (tq, J=8.9, 6.6 Hz, 2H). m/z: 278.3 $[M+H]^+$.

Intermediates 204-205

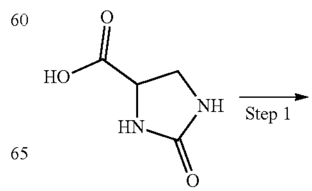

-continued

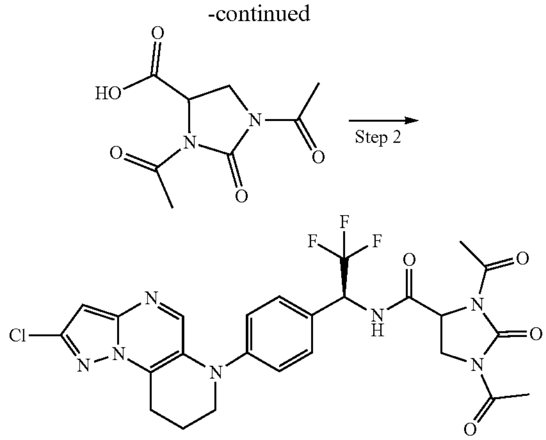

Intermediates 206-207

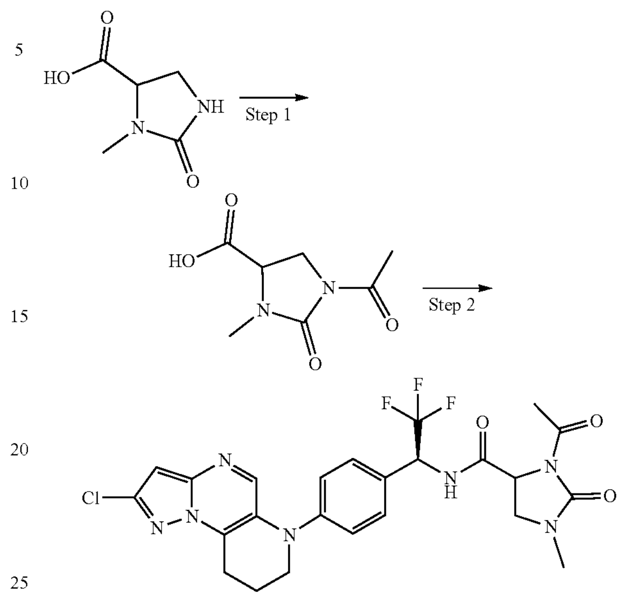

Step 1: 1,3-diacetyl-2-oxo-imidazolidine-4-carboxylic acid (Intermediate 204)

To a stirred solution of 2-oxoimidazolidine-4-carboxylic acid (500 mg, 3.84 mmol) in acetone (22 mL) at rt under nitrogen were successively added acetyl chloride (0.82 mL, 11.5 mmol) and TEA (1.6 mL, 11.5 mmol). The reaction mixture was stirred at rt for 3 h. The reaction mixture was concentrated and the crude dissolved in EtOAc (10 ml). 1M aqueous solution of HCl (10 ml) was added. The phases were separated and the aqueous phase was extracted with AcOEt (3×10 mL). The organic layers were combined, washed with sat. aq. NaCl, dried over $MgSO_4$ and concentrated under vacuum to afford Intermediate 204 (272 mg, 26.1% Yield). $^1H$ NMR (400 MHz, DMSO) δ ppm 7.75 (s, 1H), 4.64 (ddd, J=10.3, 3.4, 2.0 Hz, 1H), 3.70-3.64 (m, 1H), 3.21 (ddd, J=9.9, 3.5, 1.1 Hz, 1H), 2.43 (d, J=11.3 Hz, 3H), 2.34 (d, J=11.9 Hz, 3H). m/z: 215 $[M+H]^+$.

Step 2: 1,3-diacetyl-N-[(1S)-1-[4-(4-chloro-2,3,7,10-tetrazatricyclo[7.4.0.02,6]trideca-1(9),3,5,7-tetraen-10-yl)phenyl]-2,2,2-trifluoro-ethyl]-N-methyl-2-oxo-imidazolidine-4-carboxamide (Intermediate 205)

To a stirred solution of Intermediate 204 (94%, 110 mg, 0.239 mmol) in dry DCM (1 mL) at rt and under nitrogen were added successively 1,3-diacetyl-2-oxo-imidazolidine-4-carboxylic acid (89%, 98 mg, 0.407 mmol), $T_3P$-50% in EtOAc (1.4 mL, 2.39 mmol) and TEA (0.67 mL, 4.78 mmol). The reaction mixture was stirred at rt overnight. The reaction mixture was quenched with water (5 mL) and DCM (5 mL) was added. The aqueous layer was extracted with DCM (3×5 mL). The organic layers were combined, washed with sat. aq. NaCl, dried using a phase separator, evaporated and concentrated under reduced pressure. The crude was purified by flash chromatography on silica gel using a gradient of AcOEt in Heptane from 0% to 100%. The desired fractions were combined to give Intermediate 205 (50 mg, 33.9% Yield). $^1H$ NMR (400 MHz, DMSO) δ ppm 8.33 (d, J=4.6 Hz, 1H), 7.36-7.24 (m, 4H), 6.83 (d, J=1.0 Hz, 1H), 4.04 (d, J=7.1 Hz, 1H), 3.73 (s, 2H), 3.51 (dd, J=11.4, 3.1 Hz, 1H), 3.11 (t, J=6.7 Hz, 2H), 2.98 (s, 3H), 2.48-2.43 (m, 6H), 1.99 (s, 2H), 1.97 (s, 2H), 1.18 (t, J=7.1 Hz, 2H). m/z: 591.7 $[M+H]^+$.

Step 1: 3-acetyl-1-methyl-2-oxo-imidazolidine-4-carboxylic acid (Intermediate 206)

To a stirred solution of 1-methyl-2-oxoimidazolidine-4-carboxylic acid (165 mg, 1.14 mmol) in acetone (6.6 mL) at rt under nitrogen were added successively acetyl chloride (0.18 mL, 2.52 mmol) and TEA (0.48 mL, 3.43 mmol). The reaction mixture was stirred at rt for 3 h. The reaction mixture was concentrated and the crude dissolved in EtOAc (10 ml), 1M aqueous solution of HCl (10 ml) was added. The phases were separated and the aqueous phase was extracted with AcOEt (3 times). The organic layers were combined, washed with sat. aq. NaCl, dried over $MgSO_4$ and concentrated under vacuum to afford Intermediate 206 (178 mg, 80.2% Yield). $^1H$ NMR (400 MHz, DMSO) δ ppm 5.76 (s, 1H), 4.60 (dd, J=10.3, 3.5 Hz, 1H), 3.67 (t, J=10.1 Hz, 1H), 3.33 (dd, J=9.8, 3.5 Hz, 1H), 2.75 (s, 3H), 2.37 (s, 3H).

Step 2: 3-acetyl-N-[(1S)-1-[4-(4-chloro-2,3,7,10-tetrazatricyclo[7.4.0.02,6]trideca-1(9),3,5,7-tetraen-10-yl)phenyl]-2,2,2-trifluoro-ethyl]-N,1-dimethyl-2-oxo-imidazolidine-4-carboxamide (Intermediate 207)

To a stirred solution of intermediate 206 (99%, 250 mg, 0.573 mmol) and 3-acetyl-1-methyl-2-oxo-imidazolidine-4-carboxylic acid (96%, 167 mg, 0.859 mmol) in dry DCM (2.5 mL) at rt and under nitrogen were added successively TEA (1.6 mL, 11.5 mmol) and $T_3P$-50% EtOAc (3.4 mL, 5.73 mmol). The reaction mixture was stirred at rt 18 h. The reaction mixture was quenched with water and DCM was added. The aqueous layer was extracted with DCM. The organic layers were combined, washed with sat. aq. NaCl, dried using a phase separator and evaporated and concentrated under reduced pressure. The crude was purified by flash chromatography on silica gel using a gradient of AcOEt in Heptane (0 to 100%). The desired fractions were combined and concentrated to afford Intermediate 207 (180 mg, 52.4% Yield). $^1H$ NMR (400 MHz, DMSO) δ ppm 8.32 (d, J=4.3 Hz, 1H), 7.35-7.23 (m, 4H), 6.82 (d, J=1.0 Hz, 1H), 6.48-6.30 (m, 1H), 5.22 (dt, J=10.1, 3.9 Hz, 1H), 3.79 (t, J=9.9 Hz, 1H), 3.72 (d, J=5.0 Hz, 2H), 3.16 (dd, J=9.6, 3.8 Hz, 1H), 3.13-3.07 (m, 2H), 2.92 (d, J=2.2 Hz, 3H), 2.78 (d, J=10.9 Hz, 3H), 2.38 (s, 3H), 1.95 (d, J=4.9 Hz, 2H). m/z: 564.3 $[M+H]^+$.

Intermediates 208-209

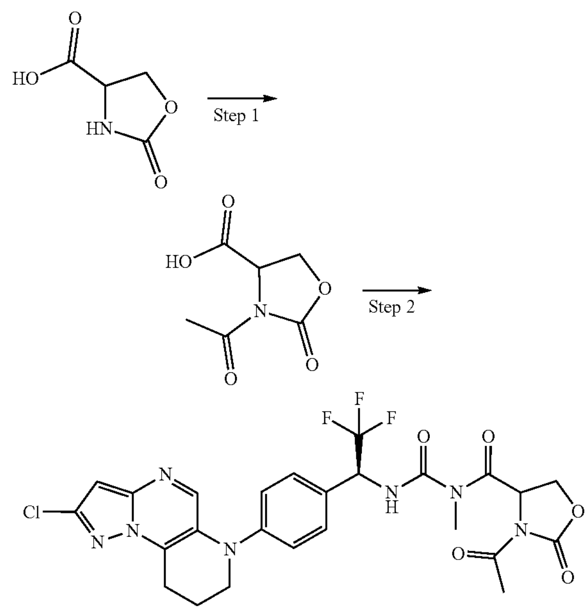

Step 1: 3-Acetyl-2-oxo-oxazolidine-4-carboxylic acid (Intermediate 208)

To a stirred solution of 2-oxo-1,3-oxazolidine-4-carboxylic acid (95%, 100 mg, 0.725 mmol) in acetone (4 mL) at rt under nitrogen were successively added acetyl chloride (0.11 mL, 1.59 mmol) and TEA (0.30 mL, 2.17 mmol). The reaction mixture was stirred at RT for 18 h.

The reaction mixture was concentrated under reduced pressure and dried under vacuum. 1M aqueous solution of HCl was added and the aqueous layer was extracted with AcOEt (3×10 mL). The organic layers were combined, washed with sat. aq. NaCl, dried and concentrated under vacuum to afford Intermediate 208 (138 mg, 97.9% Yield). $^1$H NMR (400 MHz, DMSO) δ ppm 4.80 (dd, J=9.5, 3.4 Hz, 1H), 4.58 (t, J=9.3 Hz, 1H), 4.39 (dd, J=9.1, 3.4 Hz, 1H), 2.41 (s, 3H).

Step 2: 3-acetyl-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-2-oxo-oxazolidine-4-carboxamide (Intermediate 209)

To a stirred solution of intermediate 208 (90%, 207 mg, 0.431 mmol) in dry DCM (2 mL) at rt, under nitrogen were successively added 3-acetyl-2-oxo-oxazolidine-4-carboxylic acid (92%, 138 mg, 0.733 mmol), $T_3P$ in AcOEt (50% 2.6 mL, 4.31 mmol) and TEA (1.2 mL, 8.62 mmol). The reaction mixture was stirred at rt for 18 h. The reaction mixture was quenched with water and DCM was added. The aqueous layer was extracted twice with DCM. The organic layers were combined, washed with sat. aq. NaCl, dried and concentrated under reduced pressure. The crude was purified by flash chromatography on silica gel using a gradient of AcOEt in Heptane from 0% to 100%. The desired fractions were combined to afford Intermediate 209 (27 mg; 11% Yield). m/z: 551.3 $[M+H]^+$ $^1$H NMR (400 MHz, DMSO) δ ppm 8.32 (d, J=8.1 Hz, 1H), 7.43-7.22 (m, 4H), 6.82 (s, 1H), 6.41 (p, J=9.2 Hz, 1H), 5.43 (ddd, J=9.1, 5.8, 3.3 Hz, 1H), 4.63 (dt, J=31.9, 9.1 Hz, 1H), 4.25 (ddd, J=22.4, 9.1, 3.3 Hz, 1H), 3.76-3.69 (m, 2H), 3.10 (t, J=6.6 Hz, 2H), 2.93 (s, 3H), 2.43 (s, 3H), 1.97 (d, J=5.3 Hz, 2H).

Intermediates 210-212

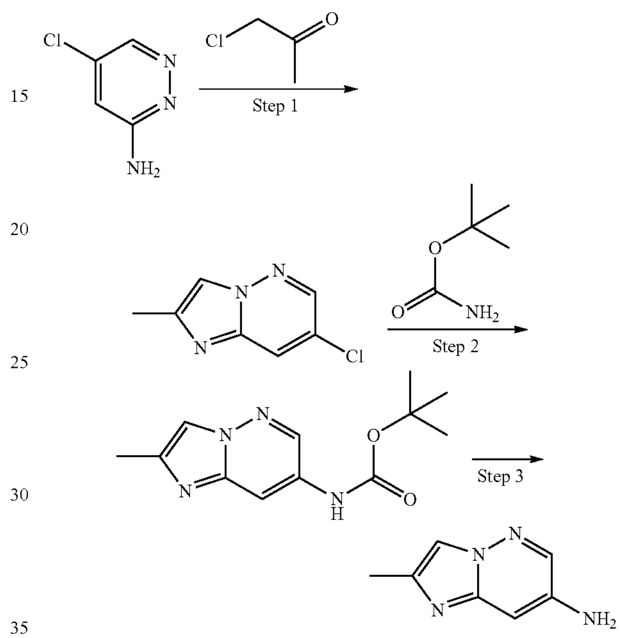

Step 1. 7-chloro-2-methyl-imidazo[1,2-b]pyridazine: (Intermediate 210)

To a stirred solution of 1-chloropropan-2-one (2.0 mL, 25.7 mmol) in ethanol (16 mL) at rt under nitrogen was added 5-chloropyridazin-3-amine (1.00 g, 7.33 mmol). The reaction mixture was stirred at 100° C. overnight. Additional 1-chloropropan-2-one (2.0 mL, 25.7 mmol) was added at rt and the reaction mixture was stirred at 100° C. for 4 h. The reaction mixture was concentrated under reduced pressure and dried under vacuum. The residue was dissolved in EtOAc and filtered through a pad of basic alumina and the filtrate was concentrated under reduced pressure to afford Intermediate 210 (200 mg, 14%) m/z: 168 $[M+H]^+$. $^1$H NMR (400 MHz, DMSO-$d_6$) δ ppm 8.55 (d, J=2.4 Hz, 1H), 8.27 (d, J=2.4 Hz, 1H), 8.10 (s, 1H), 2.38 (s, 3H).

Step 2. tert-butyl N-(2-methylimidazo[1,2-b]pyridazin-7-yl)carbamate: (Intermediate 211)

To a stirred solution of intermediate 209 (150 mg, 0.895 mmol) in dry 1,4-dioxane (4.5 mL) were added tert-butyl carbamate (210 mg, 1.79 mmol) and cesium carbonate (962 mg, 2.95 mmol). The reaction mixture was degassed with argon for 5 min and then diacetoxypalladium (20 mg, 0.089 mmol) and (5-diphenylphosphanyl-9,9-dimethyl-xanthen-4-yl)-diphenyl-phosphane (104 mg, 0.18 mmol) were added. The reaction mixture was stirred at 100° C. overnight. The reaction mixture was filtered on a pad of celite, rinsed with EtOAc and water was added into the filtrate. Phases were separated. The organic layers were combined, washed with a brine, dried using a phase separator and evaporated and concentrated under reduced pressure. The crude was purified by flash chromatography (DCM/MeOH from 0% to 10% of MeOH). The desired fractions were combined and concentrated to afford Intermediate 211 (70 mg, 30%). m/z: 249 $[M+H]^+$. $^1$H NMR (400 MHz, DMSO-$d_6$) δ ppm 9.86 (s, 1H), 8.40 (d, J=2.4 Hz, 1H), 7.89 (d, J=36.5 Hz, 2H), 3.17 (d, J=5.3 Hz, 6H), 1.50 (s, 9H).

Step 3. 2-methylimidazo[1,2-b]pyridazin-7-amine: (Intermediate 212)

To a stirred solution of intermediate 211 (70 mg, 0.273 mmol) in DCM (3 mL) at rt under nitrogen was added 4M hydrogen chloride in 1,4-dioxane (137 μL, 0.547 mmol). The reaction mixture was stirred at rt overnight. The reaction mixture was quenched with sat. aq. $NaHCO_3$ (10 mL) and DCM (10 mL) was added. The aqueous layer was extracted with DCM (3×10 mL). The organic layers were combined, washed with sat. aq. NaCl, dried using a phase separator and evaporated and concentrated under reduced pressure. The crude was purified by flash chromatography (DCM/MeOH from 0% to 10% of MeOH). The desired fractions were combined and concentrated to afford Intermediate 212 (40 mg, 99%). m/z: 149 $[M+H]^+$. $^1$H NMR (400 MHz, DMSO-$d_6$) δ ppm 7.97 (d, J=2.5 Hz, 1H), 7.54 (s, 1H), 6.65 (d, J=2.5 Hz, 1H), 5.79 (s, 2H), 2.22 (s, 3H).

Intermediates 213-219 were prepared following a stereo-selective synthesis where the enantiomer (S) was the major enantiomer

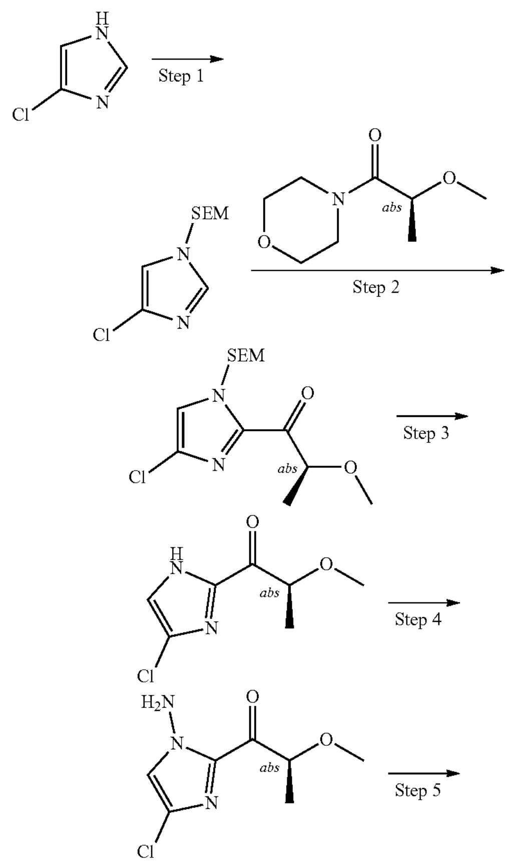

-continued

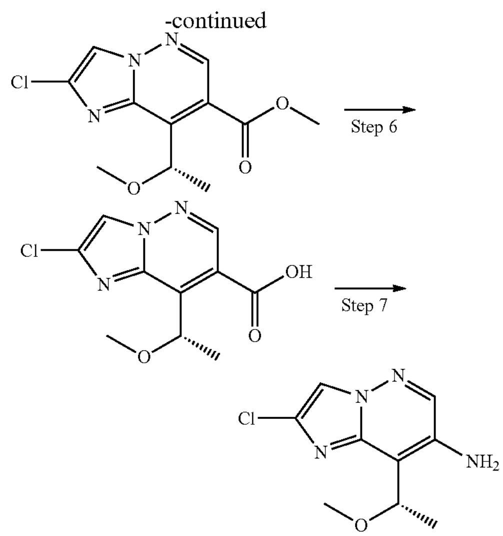

Step 1: 2-[(4-chloroimidazol-1-yl)methoxy]ethyl-trimethyl-silane (Intermediate 213)

Under nitrogen atmosphere 4-chloro-1H-imidazole (4.00 g, 0.04 mol) was dissolved in 1,4-dioxane (32 mL) at rt. N-ethyl-N-isopropyl-propan-2-amine (9.2 mL, 0.053 mol) was added and the light yellow homogeneous solution was heated at 40° C. When the temperature was reached [2-(chloromethoxy)ethyl](trimethyl) silane (95%, 8.3 mL, 0.045 mol) was added at once. The reaction mixture was cooled to 15° C., water (40 mL) was added followed by cyclohexane (50 mL). The biphasic mixture was stirred for 15 minutes. The two layers were separated, the organic layer was washed with water (3×30 mL), dried over $MgSO_4$, filtered and concentrated to dryness to obtain Intermediate 213 (8.6 g, 94.5% Yield). m/z 233 $[M+H]^+$. $^1$H NMR (DMSO-$d_6$, 500 MHz): δ ppm 7.78 (d, J=1.5 Hz, 1H), 7.39 (d, J=1.5 Hz, 1H), 5.28 (s, 2H), 3.45-3.50 (m, 2H), 0.82-0.87 (m, 2H), −0.04 (s, 9H).

Step 2: (2S)-1-[4-chloro-1-(2-trimethylsilylethoxymethyl) imidazol-2-yl]-2-methoxy-propan-1-one (Intermediate 214)

To a solution of intermediate 213 (80%, 1.00 g, 4.62 mmol, previously prepared through an amide coupling using $T_3P$ as coupling agent) in 2-Methyltetrahydrofuran (16 mL) at −20° C., 1M (diisopropylamino) lithium (4.9 mL, 4.87 mmol) was added. After that, a solution of 2-[(4-chloroimidazol-1-yl)methoxy]ethyl-trimethyl-silane (87%, 1.08 g, 4.06 mmol) in 2-Me-THF (3.2 mL) was added over a period of 2 minutes and the reaction stirred at the same temperature for 2 hours. The reaction was quenched with sat. aq. $NH_4Cl$ (4 ml). The mixture was decanted and washed with water (3×5 mL). The organic layer was dried over $MgSO_4$, filtered and concentrated under reduce pressure to afford Intermediate 214 (1.4 g; 62.6% yield). $^1$H NMR (500 MHz, DMSO-$d_6$) δ ppm 7.29 (s, 1H), 7.27 (s, 1H), 6.36 (s, 1H), 5.51 (d, J=10.3 Hz, 1H), 5.43 (d, J=10.3 Hz, 1H), 5.22 (d, J=10.3 Hz, 1H), 5.13 (d, J=10.3 Hz, 1H), 4.17 (d, J=6.4 Hz, 1H), 3.37 (m, 2H), 3.23 (s, 2H), 3.17 (s, 3H), 1.10 (d, J=6.1 Hz, 3H), 0.78 (m, 4H), −0.03 (d, J=1.7 Hz, 18H).

Step 3: (2S)-1-(4-chloro-1H-imidazol-2-yl)-2-methoxy-propan-1-one (Intermediate 215)

To a stirred solution of intermediate 214 (860 mg, 2.70 mmol) in dry DCM (3 mL) at rt, under nitrogen, TFA (1.7 mL, 21.6 mmol) was added. The reaction mixture was stirred at the same temperature for 4 h. The reaction mixture was concentrated under reduced pressure and dried under vacuum. The resulting oil was then basified with sat. aq. $NaHCO_3$ (10 mL) and $CHCl_3$/i-PrOH (3/1) (10 mL) was added. The aqueous layer was extracted with $CHCl_3$/i-PrOH (3/1) (3×10 mL). The organic layers were combined, washed with brine, dried over $MgSO_4$ and concentrated under reduced pressure to afford Intermediate 215 (490 mg, 91.5% Yield). m/z $[M+H]^+$: 189.1. $^1H$ NMR (400 MHz, DMSO-$d_6$) δ ppm 13.80 (s, 1H), 7.63 (s, 1H), 4.85 (q, J=6.8 Hz, 1H), 3.25 (s, 3H), 1.33 (d, J=6.8 Hz, 3H).

Step 4: (2S)-1-(1-amino-4-chloro-imidazol-2-yl)-2-methoxy-propan-1-one (Intermediate 216)

To a solution of intermediate 215 (95%, 490 mg, 2.47 mmol) in DMF (30 mL) at rt under $N_2$ atmosphere, potassium 2-methylpropan-2-olate (360 mg, 3.21 mmol) was added and the reaction mixture was stirred at rt for 1 hour. A solution of O-(4-Nitrobenzoyl) hydroxylamine (98%, 550 mg, 2.96 mmol) in DMF (30 mL) was slowly added dropwise and the suspension was vigorously stirred at rt under $N_2$ atmosphere overnight. The reaction mixture was concentrated under reduced pressure to a minimum volume of DMF (10 ml). The solid was removed by filtration and washed with DCM. The filtrate was concentrated under reduced pressure. The resulting residue was triturated in DCM, the solid was removed by filtration and the filtrate was concentrated under reduced pressure. The crude was purified by flash chromatography on basic alumina gel using a gradient of EtOAc in heptane from 50% to 100%. The desired fractions were combined and concentrated to afford Intermediate 216 (250 mg, 48% Yield). m/z $[M+H]^+$: 204.1. $^1H$ NMR (DMSO-$d_6$, 500 MHz): δ ppm 7.65 (s, 1H), 6.98 (s, 2H), 4.84 (q, J=6.8 Hz, 1H), 3.24-3.25 (m, 3H), 1.31 (d, J=6.8 Hz, 3H).

Step 5: Methyl 2-chloro-8-[rac-(1S)-1-methoxyethyl]imidazo[1,2-b]pyridazine-7-carboxylate (Intermediate 217)

To a suspension of intermediate 216 (97%, 258 mg, 1.23 mmol), diacetoxypalladium (56 mg, 0.246 mmol) and lithium bromide (0.43 g, 4.91 mmol) in dry THF (10 ml) at rt under air atmosphere, methyl prop-2-enoate (221 μL, 2.46 mmol) was added and the reaction mixture was stirred at 50° C. overnight under air atmosphere (with an open condenser). The reaction mixture was allowed to cool to rt then filtered onto a microfiber filter, concentrated and the crude purified by flash chromatography on silica gel using a gradient of DCM/EtOAc from 100/0 to 90/10. Relevant fractions were combined and concentrated to obtain title compound (130 mg, 38.1% Yield). m/z 270 $[M+H]^+$. $^1H$ NMR (DMSO-$d_6$, 500 MHz) δ ppm 8.69 (s, 1H), 8.64 (s, 1H), 5.15 (q, 1H, J=6.8 Hz), 3.87 (s, 3H), 3.15 (s, 3H), 1.59 (d, 3H, J=6.6 Hz).

Step 6: 2-Chloro-8-[rac-(1S)-1-methoxyethyl]imidazo[1,2-b]pyridazine-7-carboxylic acid (Intermediate 218)

To a stirred solution of intermediate 217 (97%, 130 mg, 0.468 mmol) in methanol (2 mL) at rt and under nitrogen was added lithium hydroxide (98%, 13 mg, 0.514 mmol). The reaction mixture was stirred at rt for 4 h. Organic volatiles were evaporated off and the crude was purified by reverse-phase preparative chromatography using a gradient of acetonitrile in water from 0% to 100% (0.1% AcOH in water). The desired fractions were combined and concentrated to afford Intermediate 218 (70 mg, 58.6% Yield). m/z $[M+H]^+$: 256 (1Cl). $^1H$ NMR (DMSO-$d_6$, 600 MHz): δ ppm 13.80 (br s, 1H), 8.69 (s, 1H), 8.60 (s, 1H), 5.28 (q, J=6.7 Hz, 1H), 3.15 (s, 3H), 1.61 (d, J=6.6 Hz, 3H).

Step 7: 2-chloro-8-[rac-(1R)-1-methoxyethyl]imidazo[1,2-b]pyridazin-7-amine (intermediate 219)

To a suspension of intermediate 218 (70 mg, 0.274 mmol) in dry toluene (4 mL) at rt, TEA (0.06 mL, 0.411 mmol) was added, followed by diphenyl phosphorazidate (97%, 0.12 mL, 0.548 mmol). The reaction mixture was stirred at 40° C. for 3 hours. The reaction mixture was allowed to reach rt and then partitioned between sat. aq. $NaHCO_3$ (5 ml) and EtOAc (10 ml). Aqueous phase was separated and extracted with EtOAc (3×10 ml). Organic layers were combined, washed with brine, dried over anhydrous $Na_2SO_4$, filtered and concentrated. The residue was purified by flash column chromatography ($SiO_2$; EtOAc:heptane 0:100 to 70:30) to afford intermediate 219 (20 mg, 32.2% Yield). m/z $[M+H]^+$: 227.2 $^1H$ NMR (DMSO-$d_6$, 500 MHz) δ ppm 8.12 (s, 1H), 7.98 (s, 1H), 5.89 (s, 2H), 4.99 (q, 1H, J=6.6 Hz), 3.21 (s, 3H), 1.42 (d, 3H, J=6.6 Hz).

Alternatively, racemic intermediate 219-b was synthesised as described in the patent WO2020/111087A1.

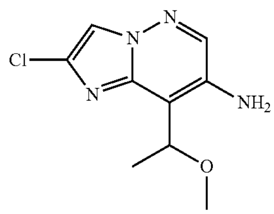

Intermediates 220-223

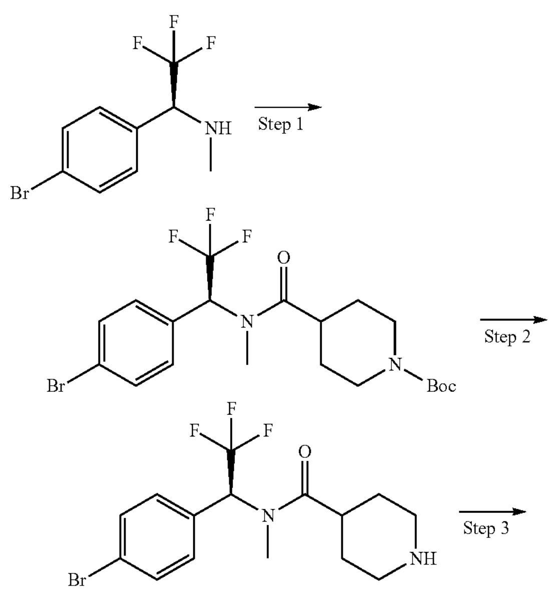

-continued

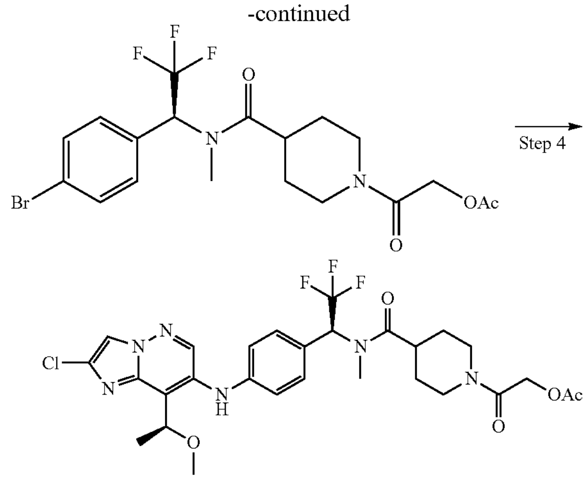

Step 1: tert-butyl 4-[[(1S)-1-(4-bromophenyl)-2,2,2-trifluoro-ethyl]-methyl-carbamoyl]piperidine-1-carboxylate (Intermediate 220)

(1S)-1-(4-bromophenyl)-2,2,2-trifluoro-N-methyl-ethanamine (95%, 500 mg, 1.77 mmol), 1-(tert-butoxycarbonyl) piperidine-4-carboxylic acid (98%, 497 mg, 2.13 mmol) and TEA (4.9 mL, 35.4 mmol) were dissolved in DCM (8.8 mL) at room temperature. $T_3P$ (50%, 11.28 g, 17.7 mmol) was added and the reaction mixture was stirred at room temperature for 2 days. The reaction mixture was quenched with sat. aq. $NaHCO_3$. Layers were separated and the aqueous phase was extracted twice with DCM. Organic layers were combined, dried over anhydrous $Na_2SO_4$, filtered and concentrated. The residue was purified by flash column chromatography ($SiO_2$; EtOAc:heptane 0:100 to 30:700) to give intermediate 220 (493 mg, 56.3% Yield). m/z $[M+Na]^+$ 503.4. $^1H$ NMR (400 MHz, DMSO) δ ppm 7.71-7.64 (m, 2H), 7.30 (d, J=8.3 Hz, 2H), 6.55 (q, J=9.2 Hz, 1H), 4.04-3.85 (m, 2H), 2.95 (tt, J=11.3, 3.6 Hz, 1H), 2.88 (s, 3H), 2.86-2.68 (m, 2H), 1.75-1.62 (m, 2H), 1.50-1.32 (m, 11H).

Step 2: N-[(1S)-1-(4-bromophenyl)-2,2,2-trifluoro-ethyl]-N-methyl-piperidine-4-carboxamide (Intermediate 221)

Intermediate 220 (97%, 493 mg, 0.998 mmol) was dissolved in DCM (5 mL) at room temperature. TFA (0.76 mL, 9.98 mmol) was added and the reaction mixture was stirred at room temperature for 2 hours. The reaction mixture was diluted with DCM and carefully quenched by addition of sat. aq. $NaHCO_3$. pH of the aqueous layer was brought to 10 by addition of solid $K_2CO_3$. The aqueous phase was isolated and extracted twice with DCM. Organic layers were combined, washed with brine, dried over anhydrous $Na_2SO_4$, filtered and concentrated to give Intermediate 221 (375 mg, 95.1% Yield). m/z 381.3 $[M+H]^+$. $^1H$ NMR (400 MHz, DMSO) δ ppm 7.68 (d, J=8.6 Hz, 2H), 7.29 (d, J=8.6 Hz, 2H), 6.56 (q, J=9.3 Hz, 1H), 3.00-2.90 (m, 2H), 2.85 (s, 3H), 2.81 (tt, J=11.5, 3.9 Hz, 1H), 2.62-2.52 (m, 2H), 1.67-1.54 (m, 2H), 1.47 (pd, J=12.0, 3.9 Hz, 2H).

Step 3: [2-[4-[[(1S)-1-(4-bromophenyl)-2,2,2-trifluoro-ethyl]-methyl-carbamoyl]-1-piperidyl]-2-oxo-ethyl]acetate (Intermediate 222)

(Acetyloxy) acetic acid (99%, 134 mg, 1.12 mmol), Intermediate 221 (96%, 370 mg, 0.94 mmol) and TEA (0.65 mL, 4.68 mmol) were dissolved in DCM (4.6833 mL) at rt. $T_3P$ (50%, 894 mg, 1.40 mmol) was added and the reaction mixture was stirred at room temperature for 2 h. The reaction mixture was stirred at rt for 1 h. The pale yellow solution was patitioned between sat. aq. $NH_4Cl$ and EtOAc. The aqueous phase was isolated and extracted twice with EtOAc. Organic layers were combined, washed with brine, dried over anhydrous $Na_2SO_4$, filtered and concentrated. The residue was purified by flash column chromatography ($SiO_2$; MeOH:DCM 0:100 to 5:95) to give Intermediate 222 (336 mg, 73.4% Yield). m/z: 481.4 $[M+H]^+$. $^1H$ NMR (400 MHz, DMSO) δ ppm 7.73-7.64 (m, 2H), 7.39-7.27 (m, 2H), 6.61-6.34 (m, 1H), 4.86-4.71 (m, 2H), 4.29 (d, J=13.1 Hz, 1H), 3.72 (d, J=13.5 Hz, 1H), 3.15-2.99 (m, 2H), 2.89 (s, 3H), 2.76-2.61 (m, 1H), 2.07 (s, 3H), 1.82-1.66 (m, 2H), 1.57 (q, J=10.9 Hz, 1H), 1.39 (t, J=13.1 Hz, 1H).

Step 4: [2-[4-[[(1S)-1-[4-[[2-chloro-8-[(1S)-1-methoxyethyl]imidazo[1,2-b]pyridazin-7-yl]amino]phenyl]-2,2,2-trifluoro-ethyl]-methyl-carbamoyl]-1-piperidyl]-2-oxo-ethyl]acetate (Intermediate 223)

Intermediate 222 (98%, 68 mg, 0.139 mmol), Intermediate 219 (99%, 32 mg, 0.139 mmol) and cesium carbonate (91 mg, 0.278 mmol) were suspended in dry toluene (0.7 mL) at room temperature under $N_2$ atmosphere. The suspension was bubbled with $N_2$ for 10 minutes, diacetoxypalladium (3.1 mg, 0.0139 mmol) and dicyclohexyl-[2-(2,6-diisopropoxyphenyl)phenyl]phosphane (7.8 mg, 0.0167 mmol) were added, the vial was capped and the suspension was bubbled with $N_2$ for 10 minutes. The vial was transferred onto a pre-heated stirring plate and the reaction mixture was stirred at 100° C. for 4 hours. The reaction mixture was diluted with water and extracted three times with EtOAc. Organic layers were combined, washed with brine, dried over anhydrous $Na_2SO_4$, filtered and concentrated. The residue was purified by flash column chromatography ($SiO_2$; EtOAc:heptane 0:100 to 100:0) to give Intermediate 223 (51 mg, 55.7% Yield). m/z: 625.6 $[M+H]^+$. $^1H$ NMR (400 MHz, DMSO) δ ppm 8.48 (s, 1H), 8.29 (s, 1H), 8.01 (s, 1H), 7.36-7.23 (m, 2H), 7.16 (d, J=8.7 Hz, 2H), 6.56-6.20 (m, 1H), 5.09 (q, J=6.6 Hz, 1H), 4.86-4.71 (m, 2H), 4.29 (d, J=13.1 Hz, 1H), 3.73 (d, J=13.4 Hz, 1H), 3.22 (s, 3H), 3.16-2.99 (m, 2H), 2.93 (s, 3H), 2.77-2.61 (m, 1H), 2.07 (s, 3H), 1.81-1.67 (m, 2H), 1.65-1.55 (m, 1H), 1.54 (d, J=6.7 Hz, 3H), 1.48-1.31 (m, 1H).

Intermediate 224

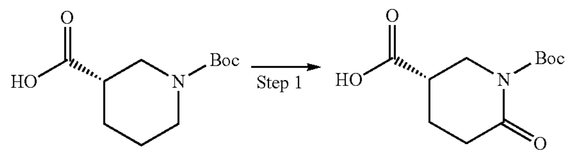 [SMILES: CC(C)(C)OC(=O)N1CCC[C@H](C(=O)O)C1 ; CC(C)(C)OC(=O)N1C[C@@H](C(=O)O)CCC1=O]

Step 1: (3S)-1-tert-butoxycarbonyl-6-oxo-piperidine-3-carboxylic acid (Intermediate 224)

(3S)-1-(tert-butoxycarbonyl) piperidine-3-carboxylic acid (98%, 1.00 g, 4.27 mmol) was partitioned between ethyl acetate (30 mL) and water (30 mL) prior addition of sodium periodate (99%, 3.69 g, 17.1 mmol) and ruthenium (III) chloride hydrate (95%, 101 mg, 0.427 mmol). The reaction mixture was stirred at room temperature for 18 h. Water was added (15 mL) to dissolve the white solid, the organic phase was separated. The aqueous layer was extracted with EtOAc (3×20 mL), The organic layers were combined, washed with brine, dried over anhydrous $Na_2SO_4$ and concentrated under vacuum. The crude was purified by reverse phase chromatography using a gradient of acetonitrile in water from 0% to 100% (0.1% AcOH). Relevant fractions were collected and evaporated to afford Intermediate 224 (627 mg, 54% Yield). m/z $[M+Na]^+$: 266 $^1H$ NMR (400 MHz, DMSO) δ ppm 12.39 (s, 1H), 3.82-3.69 (m, 1H), 3.47-2.82 (m, 1H), 2.76-1.57 (m, 5H), 1.41 (d, J=27.4 Hz, 9H) (mixture of conformers)

Intermediate 225-226

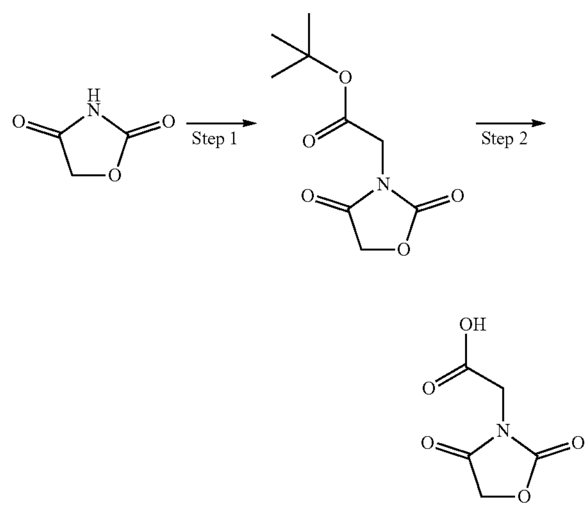

Step 1: tert-butyl 2-(2,4-dioxooxazolidin-3-yl)acetate (Intermediate 225)

To a stirred solution of 1,3-oxazolidine-2,4-dione (97%, 50 mg, 0.480 mmol) in dry DMF (1 mL) at rt and under nitrogen were successively added tert-butyl bromoacetate (106 uL, 0.720 mmol) and dipotassium carbonate (199 mg, 1.44 mmol). The reaction mixture was stirred at rt for 18 h. The reaction mixture was quenched with sat $NH_4Cl$ (10 mL) and AcOEt (10 mL) was added. The aqueous layer was extracted with AcOEt (3×10 mL). The organic layers were combined, washed with sat. aq. NaCl, dried and concentrated under reduced pressure to afford intermediate 225 (105 mg, quantitative Yield). $^1H$ NMR (400 MHz, DMSO) δ ppm 5.03 (s, 2H), 4.16 (s, 2H), 1.42 (s, 9H).

Step 2: 2-(2,4-dioxooxazolidin-3-yl) acetic acid (Intermediate 226)

To a stirred solution of tert-butyl 2-(2,4-dioxooxazolidin-3-yl)acetate (105 mg, 0.488 mmol) was added TFA (0.19 mL, 2.44 mmol) at rt and under nitrogen. The reaction mixture was stirred at rt for 3 h. The reaction mixture was concentrated under reduced pressure and dried under vacuum to afford Intermediate 226 (80 mg, 100% Yield). $^1H$ NMR (400 MHz, DMSO) δ ppm 13.38 (s, 1H), 5.02 (s, 2H), 4.17 (s, 2H).

Intermediate 227-228

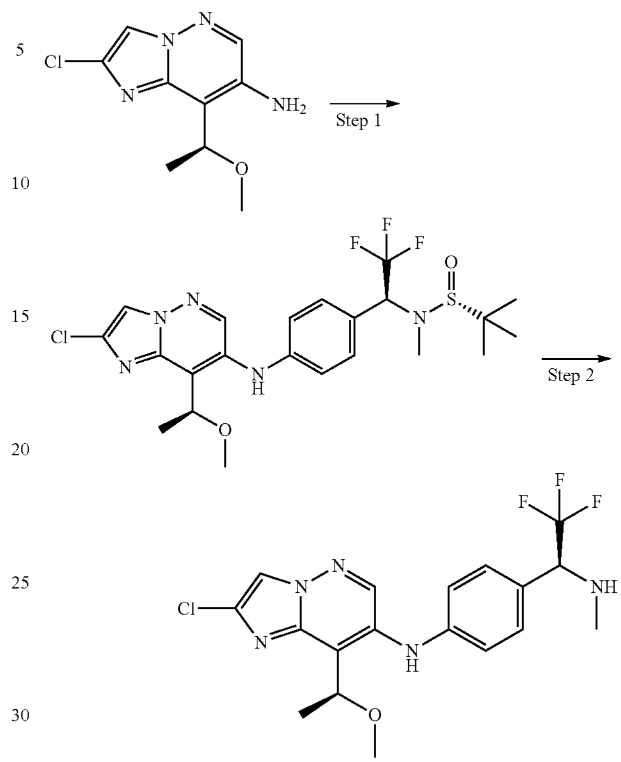

Step 1: (R)—N-[(1S)-1-[4-[[2-chloro-8-[(1S)-1-methoxyethyl]imidazo[1,2-b]pyridazin-7-yl]amino]phenyl]-2,2,2-trifluoro-ethyl]-N,2-dimethyl-propane-2-sulfinamide (Intermediate 227)

To a stirred heterogeneous solution of Intermediate 72 (100%, 5.42 g, 14.6 mmol), intermediate 219 (99%, 3.03 g, 13.2 mmol) and cesium carbonate (8.62 g, 26.5 mmol) in dry toluene (32 mL) was degassed for 20 min. Then, diacetoxypalladium (98%, 0.31 g, 1.32 mmol) and dicyclohexyl-[2-(2,6-diisopropoxyphenyl)phenyl]phosphane (0.74 g, 1.59 mmol) were added. The reaction mixture was stirred at 100° C. for 2 h. The reaction mixture was filtered through a pad of celite and the filtrate was concentrated under reduced pressure. The crude was purified by flash chromatography on silica gel using a gradient of AcOEt in heptane from 5% to 100%. The desired fractions were combined and concentrated to afford Intermediate 227 (5.19 g, 75.7% Yield) $^1H$ NMR (400 MHz, DMSO) δ ppm 8.48 (s, 1H), 8.30 (s, 1H), 8.01 (s, 1H), 7.35 (d, J=8.4 Hz, 2H), 7.20-7.13 (m, 2H), 5.45 (q, J=9.2 Hz, 1H), 5.09 (q, J=6.6 Hz, 1H), 3.23 (s, 3H), 2.42 (s, 3H), 1.55 (d, J=6.6 Hz, 3H), 1.31-1.23 (m, 2H), 1.15 (s, 9H), 0.90-0.82 (m, 1H).

Step 2: 2-chloro-8-[(1S)-1-methoxyethyl]-N-[4-[(1S)-2,2,2-trifluoro-1-(methylamino)ethyl]phenyl]imidazo[1,2-b]pyridazin-7-amine (Intermediate 228)

Intermediate 227 (100%, 5.09 g, 9.83 mmol) in ethyl acetate (49 mL) at room temperature. 4M hydrogen chloride (10 mL, 39.3 mmol) was added and the orange suspension was stirred at room temperature for 2 hours. The suspension was carefully partitioned between sat. aq. $NaHCO_3$ and EtOAc. The aqueous phase was isolated and extracted twice with EtOAc. Organic layers were combined, washed with brine, dried over anhydrous $Na_2SO_4$, filtered and concentrated. The residue was purified by flash column chromatography ($SiO_2$; EtOAc:heptane 0:100 to 50:50) to give expected (2.5 g, 60.8% Yield). m/z $[M+H]^+$=413.82. $^1$H NMR (400 MHz, DMSO) δ ppm 8.46 (s, 1H), 8.27 (s, 1H), 7.92 (s, 1H), 7.38 (d, J=8.3 Hz, 2H), 7.18-7.11 (m, 2H), 5.10 (q, J=6.6 Hz, 1H), 4.21 (s, 1H), 3.25 (d, J=0.6 Hz, 4H), 2.24 (s, 3H), 1.54 (d, J=6.6 Hz, 3H).

Intermediates 229-234

Procedure 1

Intermediate 219 (1 mmol), Br-aryl derivatives (1 mmol) and cesium carbonate (3.5 mmol) were suspended in dry toluene (0.2 M) at rt under $N_2$ atmosphere. The suspension was degassed with $N_2$ for 10 minutes, diacetoxypalladium (0.1 mol) and Ru-Phos (0.12 mmol) were added and the suspension was degassed with $N_2$ for 10 minutes. The reaction mixture was stirred on a pre-heated plate at 100° C. for 1 hour. The reaction mixture was allowed to cool to rt and partitioned between water and EtOAc. The organic layer was extracted twice with EtOAc. Organic layers were combined, washed with brine, dried over anhydrous $Na_2SO_4$, filtered and concentrated. The residue was purified by flash column chromatography (SiO2 EtOAc:Heptane 0:100 to 75:25).

Procedure 2

Intermediates 228 (1 mmol) was suspended in DCM (500 mL) at rt, TEA (20 mol) and corresponding acid (1.2 mmol) were added followed by $T_3P$ (53% in EtOAc, 10 mmol). The reaction mixture was stirred at room 2 hours. The reaction mixture was quenched by addition of water. The organic layer was washed twice with water, dried over anhydrous $Na_2SO_4$, filtered and concentrated to dryness. The crude was purified by reverse-phase flash chromatography using a gradient of acetonitrile in water from 0% to 100% (0.1% AcOH).

Procedure 3

To a solution of commercially available carboxylic acid (83 mg, 0.362 mmol) in dry DCM (1 mL) was added pyridine (97 μL, 1.21 mmol) followed by phosphoryl trichloride (27 μL, 0.290 mmol). The reaction mixture was left stirring at room temperature upon completion prior addition of Intermediate 219 (100%, 100 mg, 0.242 mmol). The reaction mixture was then stirred at room temperature for 18 h. The reaction mixture was quenched by addition of a sat. $NaHCO_3$. The aqueous layer was extracted twice with EtOAc, dried over anhydrous $Na_2SO_4$, filtered and concentrated to dryness. The crude was purified by flash chromatography eluting with DCM/MeOH.

| Intermediate 229 | Procedure 1 | Intermediates 219 and 184 | Yield: 62.4% |
|---|---|---|---|
| 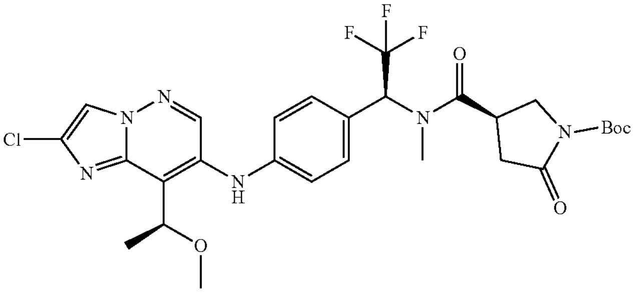 [SMILES: CO[C@@H](C)c1c(Nc2ccc([C@H](N(C)C(=O)[C@@H]3CC(=O)N(C(=O)OC(C)(C)C)C3)C(F)(F)F)cc2)cnn2cc(Cl)nc12] tert-butyl (4 rel-R)-4-[[(1S)-1-[4-[[2-chloro-8-[(1S)-1-methoxyethyl]imidazo[1,2-b]pyridazin-7-yl]amino]phenyl]-2,2,2-trifluoro-ethyl]-methyl-carbamoyl]-2-oxo-pyrrolidine-1-carboxylate | $^1$H NMR (400 MHz, DMSO) δ ppm 8.48 (s, 1H), 8.29 (s, 1H), 8.03 (d, J = 6.9 Hz, 1H), 7.39-7.26 (m, 2H), 7.16 (d, J = 8.7 Hz, 2H), 6.54-6.04 (m, 1H), 5.08 (q, J = 6.6 Hz, 1H), 3.87 (dd, J = 10.5, 8.2 Hz, 1H), 3.77 (dd, J = 10.6, 5.2 Hz, 1H), 3.74-3.62 (m, 1H), 3.22 (s, 3H), 2.89 (s, 3H), 2.87 (dd, J = 17.2, 9.3 Hz, 1H), 2.49 (dd, J = 17.2, 5.9 Hz, 1H), 1.54 (d, J = 6.6 Hz, 3H), 1.45 (s, 9H). m/z 625.5 $[M + H]^+$ | | |

| Intermediate 230 | Procedure 1 | Intermediates 219 and 183 | Yield: 88% |
|---|---|---|---|
| 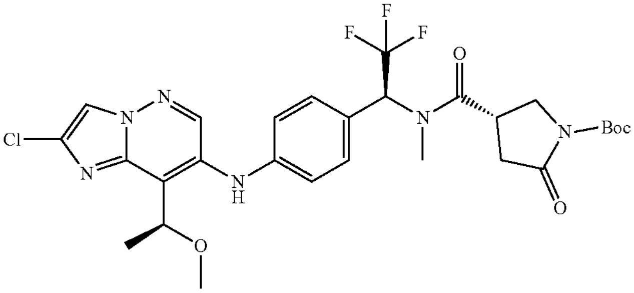 [SMILES: CO[C@@H](C)c1c(Nc2ccc([C@H](N(C)C(=O)[C@H]3CC(=O)N(C(=O)OC(C)(C)C)C3)C(F)(F)F)cc2)cnn2cc(Cl)nc12] tert-butyl (4 rel-S)-4-[[(1S)-1-[4-[2-chloro-8-[(1S)-1-methoxyethyl]imidazo[1,2-b]pyridazin-7-yl]amino]phenyl]-2,2,2-trifluoro-ethyl]-methyl-carbamoyl]-2-oxo-pyrrolidine-1-carboxylate | $^1$H NMR (600 MHz, DMSO) δ ppm 8.48 (s, 1H), 8.29 (s, 1H), 8.02 (s, 1H), 7.40-7.25 (m, 2H), 7.22-7.13 (m, 2H), 6.51-6.05 (m, 1H), 5.08 (q, J = 6.5 Hz, 1H), 4.00-3.92 (m, 1H), 3.74-3.64 (m, 2H), 3.22 (s, 3H), 2.89 (s, 3H), 2.75 (dd, J = 17.3, 8.7 Hz, 1H), 2.59 (dd, J = 17.2, 5.9 Hz, 1H), 1.54 (d, J = 6.7 Hz, 3H), 1.46 (s, 9H). m/z 625.3 $[M + H]^+$ | | |

-continued

| Intermediate 231 | Procedure 3 | Intermediates 228 | Yield: 45% |
|---|---|---|---|
| 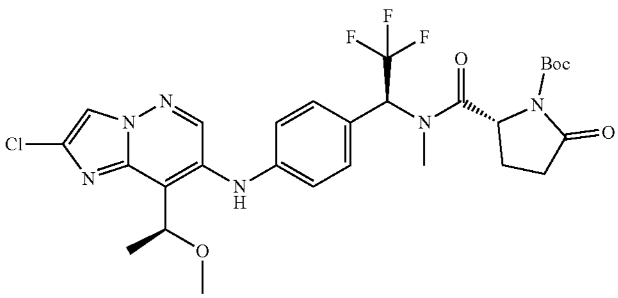 [SMILES: CO[C@@H](C)c1c(Nc2ccc([C@H](N(C)C(=O)[C@H]3CCC(=O)N3C(=O)OC(C)(C)C)C(F)(F)F)cc2)cnn2cc(Cl)nc12] | $^1$H NMR (400 MHz, DMSO) δ ppm: $^1$H NMR (400 MHz, DMSO) δ 8.48 (d, J = 13.5 Hz, 1H), 8.30 (s, 1H), 8.04 (s, 1H), 7.29 (d, J = 8.4 Hz, 2H), 7.25-7.08 (m, 2H), 6.41 (q, J = 9.2 Hz, 1H), 5.08 (t, J = 6.7 Hz, 1H), 4.50 (dd, J = 9.3, 3.3 Hz, 1H), 3.23 (s, 3H), 2.90 (s, 3H), 2.49-1.59 (m, 4H), 1.55 (d, J = 6.6 Hz, 3H), 1.41 (d, J = 2.5 Hz, 9H). m/z: 625.5 [M + H]$^+$ | | |
| tert-butyl (2S)-2-[[(1S)-1-[4-[[2-chloro-8-[(1S)-1-methoxyethyl]imidazo[1,2-b]pyridazin-7-yl]amino]phenyl]-2,2,2-trifluoro-ethyl]-methyl-carbamoyl]-5-oxo-pyrrolidine-1-carboxylate | | | |

| Intermediate 232 | Procedure 3 | Intermediates 228 | Yield: 40% |
|---|---|---|---|
| 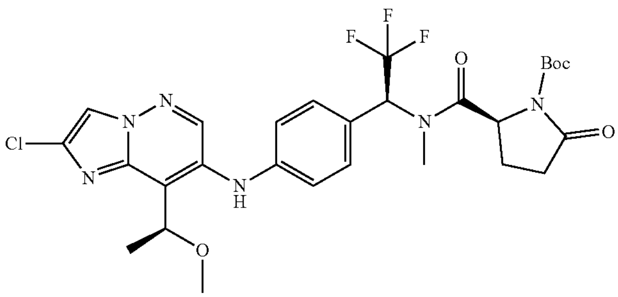 [SMILES: CO[C@@H](C)c1c(Nc2ccc([C@H](N(C)C(=O)[C@@H]3CCC(=O)N3C(=O)OC(C)(C)C)C(F)(F)F)cc2)cnn2cc(Cl)nc12] | $^1$H NMR (400 MHz, DMSO) δ ppm: 8.43 (s, 1H), 8.30 (s, 1H), 8.04 (s, 1H), 7.33 (d, J = 8.5 Hz, 2H), 7.27-7.08 (m, 2H), 6.46 (q, J = 9.3 Hz, 1H), 5.16 (dd, J = 9.0, 2.7 Hz, 1H), 5.09 (q, J = 6.6 Hz, 1H), 3.22 (s, 3H), 2.97 (s, 3H), 2.50-1.67 (m, 4H), 1.55 (d, J = 6.7 Hz, 3H), 1.47-1.25 (m, 9H). m/z: 625.5 M + H]$^+$ | | |
| tert-butyl (2S)-2-[[(1S)-1-[4-[[2-chloro-8-[(1R)-1-methoxyethyl]imidazo[1,2-b]pyridazin-7-yl]amino]phenyl]-2,2,2-trifluoro-ethyl]-methyl-carbamoyl]-5-oxo-pyrrolidine-1-carboxylate | | | |

| Intermediate 233 | Procedure 2 | Intermediates 228 and 224 | Yield: 48% |
|---|---|---|---|
| 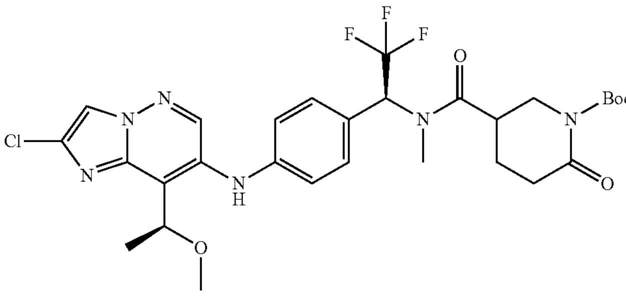 [SMILES: CO[C@@H](C)c1c(Nc2ccc([C@H](N(C)C(=O)C3CCC(=O)N(C(=O)OC(C)(C)C)C3)C(F)(F)F)cc2)cnn2cc(Cl)nc12] | $^1$H NMR (400 MHz, DMSO) δ ppm 8.49 (d, J = 1.5 Hz, 1H), 8.29 (s, 1H), 8.03 (d, J = 1.9 Hz, 1H), 7.29 (dd, J = 12.1, 8.4 Hz, 2H), 7.17 (d, J = 8.4 Hz, 2H), 6.47 (p, J = 9.0 Hz, 1H), 5.09 (q, J = 6.5 Hz, 1H), 3.89-3.54 (m, 2H), 3.38 (qd, J = 7.4, 5.3 Hz, 1H), 3.23 (s, 3H), 2.95-2.64 (m, 3H), 2.64-2.31 (m, 1H, under the solvent peak), 2.21-1.68 (m, 2H), 1.55 (dd, J = 6.7, 1.7 Hz, 3H), 1.45 (d, J = 2.9 Hz, 9H). m/z 661 [M + H]$^+$ Mixture of diastereomers (epimerisation occurred) | | |
| tert-butyl 5-[(1S)-1-[4-[[2-chloro-8-[(1S)-1-methoxyethyl]imidazo[1,2-b]pyridazin-7-yl]amino]phenyl]-2,2,2-trifluoro-ethyl]-methyl-carbamoyl]-2-oxo-piperidine-1-carboxylate | | | |

| Intermediate 234 | Procedure 1 | Intermediates 219 and 90 | Yield: 26% |
|---|---|---|---|
| 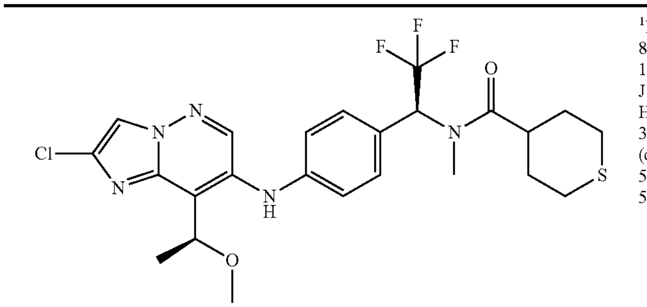 | $^1$H NMR (400 MHz, DMSO) δ ppm 8.48 (s, 1H), 8.29 (s, 1H), 8.02 (s, 1H), 7.26 (d, J = 8.4 Hz, 2H), 7.17 (d, J = 8.7 Hz, 2H), 6.49 (q, J = 9.4 Hz, 1H), 5.09 (q, J = 6.5 Hz, 1H), 3.23 (s, 3H), 2.89 (s, 3H), 2.69 (dq, J = 43.9, 13.1 Hz, 4H), 1.99 (s, 5H), 1.54 (d, J = 6.8 Hz, 3H). m/z 542.1 [M + H]$^+$ | | |

-continued

| N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-tetrahydrothiopyran-4-carboxamide |
|---|

Intermediate 235-237

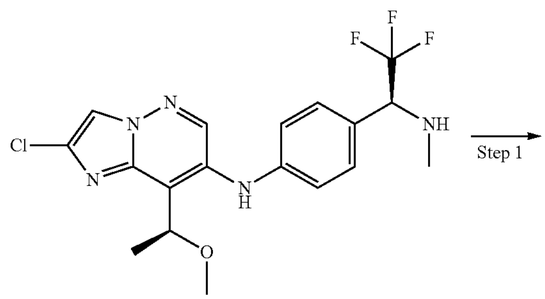

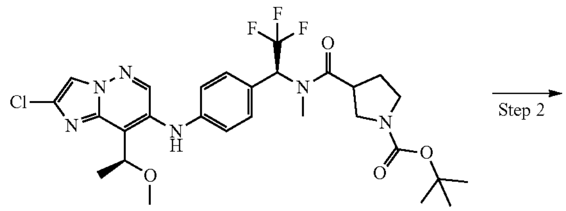

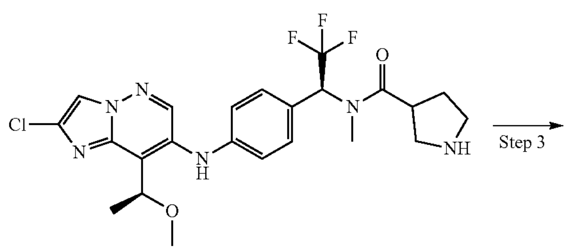

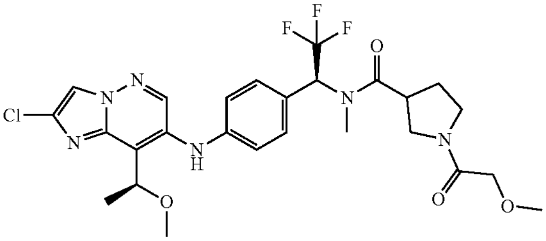

Step 1: tert-butyl 3-[[(1S)-1-[4-[[2-chloro-8-[(1S)-1-methoxyethyl]imidazo[1,2-b]pyridazin-7-yl]amino] phenyl]-2,2,2-trifluoro-ethyl]-methyl-carbamoyl] pyrrolidine-1-carboxylate (Intermediate 235)

To a stirred solution of Intermediate 117 (100%, 300 mg, 0.725 mmol) in dry DCM (3.1 mL) at rt were successively added (3R)-1-(tert-butoxycarbonyl) pyrrolidine-3-carboxylic acid (97%, 273 mg, 1.23 mmol), $T_3P$ 50% (4.3 mL, 7.25 mmol) and TEA (2.0 mL, 14.5 mmol) and the mixture stirred at rt for 18 h. The reaction mixture was quenched with water (5 mL) and DCM (5 mL) was added. The aqueous layer was extracted with DCM (3×5 mL). The organic layers were combined washed with sat. aq. aq. NaCl, dried over anhydrous $MgSO_4$ and concentrated under reduced pressure. The crude was purified by flash chromatography using a gradient of AcOEt in Heptane from 0% to 100%. Relevant fractions were combined and concentrated to afford intermediate 235 (379 mg, 82.1% Yield). m/z 612=$[M+H]^+$. $^1$H NMR (400 MHz, DMSO) δ ppm 8.49 (s, 1H), 8.29 (s, 1H), 8.03 (s, 1H), 7.32-7.24 (m, 2H), 7.17 (d, J=8.6 Hz, 2H), 5.09 (q, J=6.6 Hz, 1H), 3.53 (s, 1H), 3.23 (s, 3H), 2.92 (d, J=3.4 Hz, 3H), 1.55 (d, J=6.6 Hz, 3H), 1.41 (d, J=1.5 Hz, 9H), 1.31-0.79 (m, 2H).

Step 2: N-[(1S)-1-[4-[[2-chloro-8-[(1S)-1-methoxyethyl]imidazo[1,2-b]pyridazin-7-yl]amino]phenyl]-2,2,2-trifluoro-ethyl]-N-methyl-pyrrolidine-3-carboxamide (Intermediate 236)

To a solution of Intermediate 235 (96%, 379 mg, 0.595 mmol) in DCM (3 mL) was added TFA (0.46 mL, 5.95 mmol). The reaction mixture was stirred at rt for 1 h and then slowly poured in sat. aq. $NaHCO_3$. The aqueous layer was extracted with DCM (2×5 mL). The organic layers were combined, dried over anhydrous $MgSO_4$, filtered and concentrated under reduced pressure to afford intermediate 236 (293 mg, 93.4% Yield). m/z 511.9 [M+H]+. $^1$H NMR (400 MHz, DMSO) δ ppm 8.48 (d, J=1.2 Hz, 1H), 8.30 (s, 1H), 8.02 (s, 1H), 7.38-7.14 (m, 4H), 6.49 (q, J=9.3 Hz, 1H), 5.76 (s, 2H), 5.09 (q, J=6.6 Hz, 1H), 3.23 (s, 3H), 2.91 (s, 3H), 2.72-2.67 (m, 1H), 2.35-1.75 (m, 2H), 1.58-1.49 (m, 3H), 1.12 (s, 1H).

Step 3: [2-[3-[[(1S)-1-[4-[[2-chloro-8-[(1S)-1-methoxyethyl]imidazo[1,2-b]pyridazin-7-yl]amino] phenyl]-2,2,2-trifluoro-ethyl]-methyl-carbamoyl] pyrrolidin-1-yl]-2-oxo-ethyl]acetate (Intermediate 237)

To a stirred solution of Intermediate 236 (97%, 293 mg, 0.556 mmol) in dry DCM (2.2 mL) were added successively $T_3P$ 50% (1.7 mL, 5.56 mmol) and TEA (1.6 mL, 11.1 mmol). The reaction mixture was stirred at rt for 18 h then was quenched with water (15 mL). DCM (15 mL) was added. The aqueous layer was extracted with DCM (3×15 mL). The organic layers were combined washed with sat. aq. NaCl, dried over anhydrous $MgSO_4$ and concentrated under reduced pressure. The crude was purified by flash chromatography using a gradient of AcOEt in Heptane from 0% to 100%. Relevant fractions were combined and concentrated to give intermediate 237 (299 mg, 87.9% Yield). m/z 612 [M+H]+. $^1$H NMR (400 MHz, DMSO) δ ppm 8.49 (d, J=2.3 Hz, 1H), 8.30 (s, 1H), 8.03 (s, 1H), 7.28 (d, J=7.5 Hz, 2H), 7.17 (d, J=8.5 Hz, 2H), 6.49 (d, J=9.2 Hz, 1H), 5.09 (q, J=6.6 Hz, 1H), 4.67 (d, J=4.2 Hz, 2H), 3.84-3.32 (m, 3H), 3.23 (s, 3H), 2.97-2.91 (m, 2H), 2.70 (s, 1H), 2.08 (d, J=1.9 Hz, 3H), 1.55 (d, J=6.6 Hz, 3H).

Examples 1-32

Scheme 12

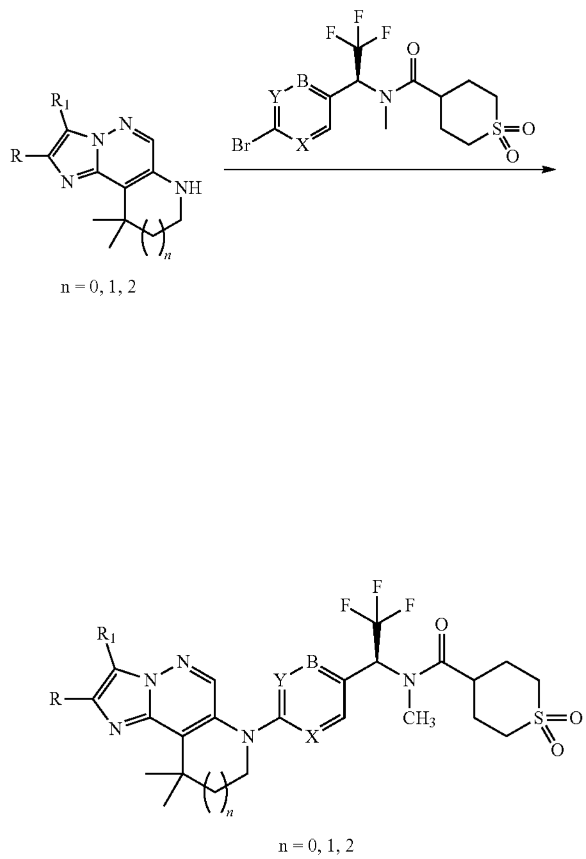

General Procedure 1

A solution of Intermediates 41-60 and 60-b (1 mmol), the Br-aryl intermediate (1.1 mmol) and cesium carbonate (2 mmol) in dry 1,4-dioxane (0.2 M) was degassed with $N_2$ for 5 min prior addition of XPhos Pd G2 (0.02 mmol) at rt. The reaction mixture was then heated at 100° C. for 3 h. The reaction mixture was diluted with EtOAc and a sat. aq. $NH_4Cl$ solution was added. The aqueous phase was extracted with EtOAc. The organic layers were combined, dried over anhydrous $Na_2SO_4$, filtered and concentrated under reduced pressure. The crude was:

a) purified by flash column chromatography (heptane/EtOAc, from 0% to 100% of EtOAc)

b) reverse phase column chromatography (water/MeCN, 100/0 to 0/100)

General Procedure 2

A solution of Br-aryl intermediate (1 mmol), Intermediates 41-60 and 60-b (1 mmol), Rac-BINAP (0.05 mmol) and cesium carbonate (5 mmol) in dry toluene (0.2 M) was degassed with nitrogen for 5 min prior addition of diacetoxypalladium (0.05 mmol). The reaction mixture was then heated at 100° C. and stirred for 3 h. The reaction mixture was partitioned between EtOAc and a sat. aq. $NH_4Cl$. Phases were separated and aqueous phase was extracted twice with EtOAc. The organic layers were combined, washed with water, brine and concentrated under reduced pressure. The crude was:

a) Purified by reverse column chromatography (water/MeCN from water 100% (with 0.1% of AcOH) to acetonitrile 100% (with 0.1% of AcOH)).

b) Purified by flash chromatography (Heptane/EtOAc from 0% to 40% of EtOAc)

c) Purified by reverse column chromatography (water/MeCN, 100/0 to 0/100)

d) Preparative HPLC XBridge BEH C18 10 μm, 250×50 mm, ($H_2O/NH_4OH$ 0.1%)/(acetonitrile/$NH_4OH$ 0.1%) from 50/50 to 5/95)

e) Preparative Chiralpak AD-H 5 μm, 250×20 mm ($CO_2$/MeOH 70/30)

General Procedure 3

To a solution of Intermediates 41-60 or 60-b (1 mmol), Br-aryl intermediate (1.1 mmol) and cesium carbonate (2 mmol) were dissolved in dry 1,4-dioxane (0.2 M) and the vial evacuated and backfilled with nitrogen (three times) after that XPhos Pd G2 (0.02 mmol) was added and the vial evacuated and backfilled with nitrogen again. The reaction was heated at 110° C. for 18 h. The reaction was allowed to reach rt and diluted with EtOAc, filtered and the filtrated solution washed with water (2×10 ml), dried over anhydrous $Na_2SO_4$ and concentrated to dryness. The crude was:

a) purified by reverse-phase chromatography (water/acetonitrile from water 100% (with 0.1% AcOH) to acetonitrile 100% (with 0.1% AcOH))

b) purified by flash chromatography on silica gel (DCM/Acetone 85/15)

General Procedure 4

To a solution of Intermediates 41-60 or 60-b (1 mmol), Br-intermediate (1.1 mmol) and cesium carbonate (2 mmol) were dissolved in dry 1,4-dioxane (0.2 M) and the vial evacuated and backfilled with nitrogen (three times) after diacetoxypalladium (0.02 mmol), tritert-butylphosphane (0.02 mmol) was added and the vial evacuated and backfilled with nitrogen (three times) again. The reaction was heated at 110° C. for 18 h. The reaction was allowed to reach rt and diluted with EtOAc, filtered and the filtered solution washed with water (2×10 ml), dried over anhydrous $Na_2SO_4$ and concentrated to dryness. The crude was purified by reverse-phase chromatography (water/acetonitrile from water 100% (with 0.1% AcOH) to acetonitrile 100% (with 0.1% AcOH)).

General Procedure 5

To a solution of Intermediates 41-60 or 60-b (1 mmol), Br-aryl intermediate (1.1 mmol) and cesium carbonate (2 mmol) were dissolved in dry 1,4-dioxane (0.2 M) and the vial evacuated and backfilled with nitrogen (three times) after that RuPhos Pd G3 (0.02 mmol) was added and the vial evacuated and backfilled with nitrogen (three times) again. The reaction was heated at 110° C. for 18 h. The reaction was allowed to reach rt and diluted with EtOAc, filtered and the filtrated solution washed with water (2×10 ml), dried over anhydrous $Na_2SO_4$ and concentrated to dryness. The crude was purified:

a) by chiral separation $CO_2$/(MeOH+0.5% IPAm) 72/28 b) by reverse-phase chromatography (water/acetonitrile from water 100% (with 0.1% AcOH) to acetonitrile 100% (with 0.1% AcOH)).

Examples 1-32

| EXAMPLE 1 CPD0019184 | Procedure: 1a-b | Intermediates 41; 86 | Yield: 30% |
|---|---|---|---|
| 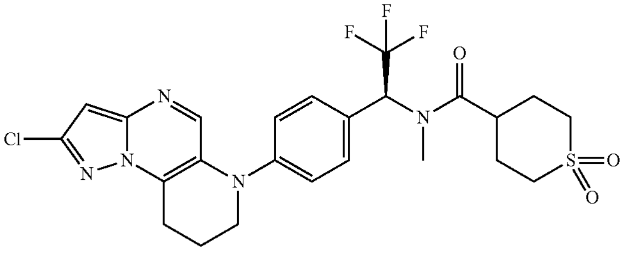 | $^1$H NMR (600 MHz, DMSO-$d_6$) δ ppm 8.30 (s, 1H), 7.19-7.48 (m, 4H), 6.82 (s, 1H), 6.13-6.54 (m, 1H), 3.66-3.78 (m, 2H), 3.03-3.28 (m, 7H), 2.92 (s, 1H), 2.67 (s, 1H), 2.65-2.96 (m, 1H), 1.93-2.12 (m, 6H). m/z: 556 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiane-4-carboxamide

| EXAMPLE 2 CPD0019194 | Procedure 2a | Intermediate 51-87 | Yield: 7% |
|---|---|---|---|
| 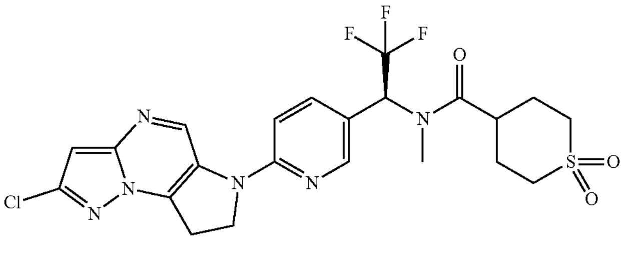 [SMILES: CN(C(=O)C1CCS(=O)(=O)CC1)[C@@H](c1ccc(N2CCc3c2cnc2cc(Cl)nn32)nc1)C(F)(F)F] | $^1$H NMR (600 MHz, DMSO-$d_6$) δ ppm 9.72 (s, 1H), 8.47-8.30 (m, 1H), 7.87-7.72 (m, 1H), 6.93(d, J = 8.9 Hz, 1H), 6.86(s, 1H), 6.54 (q, J = 9.2 Hz, 1H), 4.25 (t, J = 9.1 Hz, 2H), 3.72 (t, J = 9.1 Hz, 2H), 3.28-3.06 (m,5H), 2.96 (s, 3H), 2.21-1.94 (m, 4H). m/z: 543 [M + H]$^+$ | | |

N-[(1S)-1-(6-{11-chloro-1,5,8,12-tetraazatricyclo[7.3.0.0$^{2,6}$]dodeca-2(6),7,9,11-tetraen-5-yl}pyridin-3-yl)-2,2,2-trifluoroethyl]-N-methyl-1,1-dioxo-1λ$^6$-thiane-4-carboxamide

| EXAMPLE 3 CPD0019212 | Procedure 3a-b | Intermediate 41; 87 | Yield: 12% |
|---|---|---|---|
| 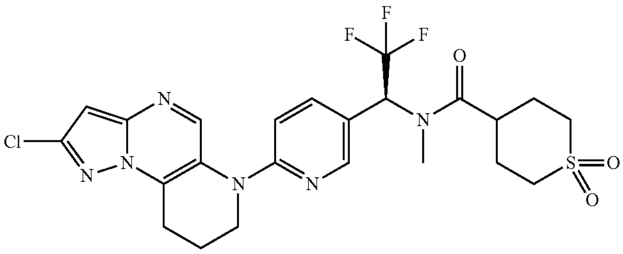 | $^1$H NMR (DMSO-$d_6$, 600 MHz): δ ppm 8.69 (s, 1H), 8.18 (d, J = 2.2 Hz, 1H), 7.71 (dd, J = 8.8, 2.3 Hz, 1H), 7.24 (d, J = 8.8 Hz, 1H), 6.83-6.88 (m, 1H), 6.46-6.55 (m, 1H), 3.90-4.04 (m, 2H), 3.08-3.28 (m, 7H), 2.92-2.99 (m, 3H), 1.94-2.17 (m, 6H). m/z: 357 [M + H]$^+$ | | |

N-[(1S)-1-(6-{4-chloro-2,3,7,10-tetraazatricyclo[7.4.0.0$^{2,6}$]trideca-1(9),3,5,7-tetraen-10-yl}pyridin-3-yl)-2,2,2-trifluoroethyl]-N-methyl-1,1-dioxo-1λ$^6$-thiane-4-carboxamide

| EXAMPLE 4 CPD0019494 | Procedure 2a | Intermediate 52; 86 | Yield: 34% |
|---|---|---|---|
| 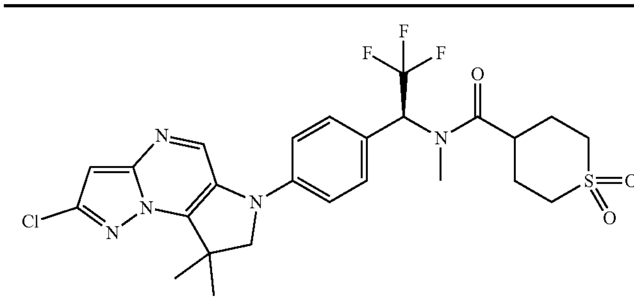 | $^1$H NMR (500 MHz, DMSO-$d_6$) δ ppm 8.82 (s, 1H), 7.32-7.38 (m,4H), 6.86 (s, 1H), 6.51 (q, J = 9.46 Hz, 1H), 3.92-3.97 (m, 2H), 3.08-3.27 (m, 5H), 2.93 (s, 3H), 1.97-2.15 (m, 4H), 1.62 (d, J = 1.71 Hz, 6H). m/z: 570 [M + H]$^+$ | | |

N-[(1S)-1-(4-{11-chloro-3,3-dimethyl-1,5,8,12-tetraazatricyclo[7.3.0.0$^{2,6}$]dodeca-2(6),7,9,11-tetraen-5-yl}phenyl)-2,2,2-trifluoroethyl]-N-methyl-1,1-dioxo-1λ$^6$-thiane-4-carboxamide -continued

| EXAMPLE 5 CPD0019574 | Procedure 2a-b | Intermediates 53; 86 | Yield: 10% |
|---|---|---|---|
| 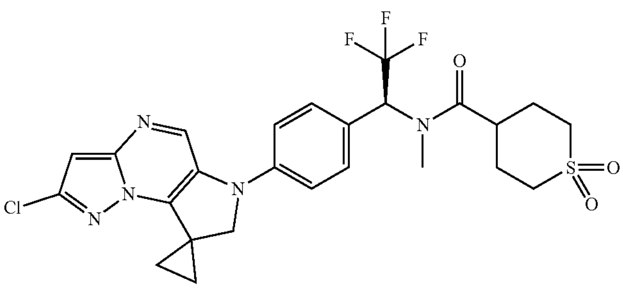 [SMILES: CN(C(=O)C1CCS(=O)(=O)CC1)[C@@H](c1ccc(N2CC3(CC3)c3c2cnc2cc(Cl)nn32)cc1)C(F)(F)F] | $^{1}H$ NMR (DMSO-$d_6$, 600 MHz): δ ppm 8.63 (s, 1H), 7.39 (s, 4H), 6.55 (s, 1H), 6.50-6.54 (m, 1H), 4.21 (d, J = 2.8 Hz, 2H), 3.09-3.28 (m, 5H), 2.92 (s, 3H), 1.95-2.19 (m, 4H), 1.38-1.44 (m, 4H)m/z: 569 $[M + H]^+$ | | |
| N-[(1S)-1-(4-{11'-chloro-1',5',8',12'-tetraazaspiro[cyclopropane-1,3'-tricyclo[7.3.0.0$^{2,6}$]dodecane]-2'(6'),7',9',11'-tetraen-5'-yl}phenyl)-2,2,2-trifluoroethyl]-N-methyl-1,1-dioxo-1λ$^6$-thiane-4-carboxamide | | | |
| EXAMPLE 6 CPD0019576 | Procedure 2b | Intermediates 42; 86 | Yield: 35% |
| 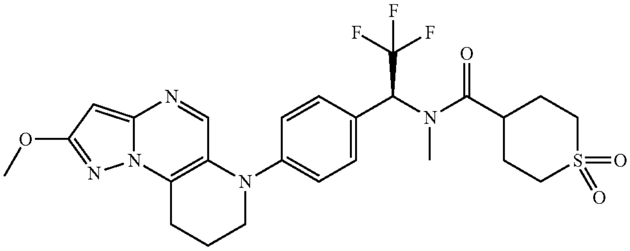 [SMILES: COc1cc2ncc3c(n2n1)CCCN3c1ccc([C@H](N(C)C(=O)C2CCS(=O)(=O)CC2)C(F)(F)F)cc1] | $^{1}H$ NMR (500 MHz, DMSO-$d_6$) δ ppm 8.17 (s, 1H), 0.00 (d, J = 8.1 Hz, 2H), 0.00 (d, J = 8.6 Hz, 2H), 6.54-6.38 (m, 1H), 6.11 (s, 1H), 3.94 (s, 3H), 3.80-3.64 (m, 2H), 3.28-3.08 (m, 5H), 3.08-3.01 (m, 2H), 2.89 (s, 3H), 2.16-1.97 (m, 4H), 1.95-1.86 (m, 2H) m/z: 552 $[M + H]^+$ | | |
| N-methyl-1,1-dioxo-N-[(1S)-2,2,2-trifluoro-1-(4-{4-methoxy-2,3,7,10-tetraazatricyclo[7.4.0.0$^{2,6}$]trideca-1(9),3,5,7-tetraen-10-yl}phenyl)ethyl]-1λ$^6$-thiane-4-carboxamide | | | |
| EXAMPLE 7 CPD0021663 | Procedure 2a | Intermediates 42; 87 | Yield: 45% |
| 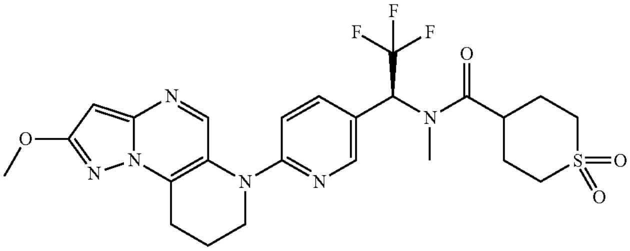 [SMILES: COc1cc2ncc3c(n2n1)CCCN3c1ccc([C@H](N(C)C(=O)C2CCS(=O)(=O)CC2)C(F)(F)F)cn1] | $^{1}H$ NMR (500 MHz, DMSO-$d_6$) δ ppm 8.53 (s, 1H), 8.17 (d, J = 2.2 Hz, 1H), 7.67 (dd, J = 8.8, 2.0 Hz, 1H), 7.18 (d, J = 8.8 Hz, 1H), 6.50 (q, J = 9.3 Hz, 1H), 6.14 (s, 1H), 3.94 (s, 5H), 3.29-3.03 (m, 7H), 2.95 (s, 3H), 2.30-1.77 (m, 6H) m/z: 553 $[M + H]^+$ | | |
| N-methyl-1,1-dioxo-N-[(1S)-2,2,2-trifluoro-1-(6-{4-methoxy-2,3,7,10-tetraazatricyclo[7.4.0.0$^{2,6}$]trideca-1(9),3,5,7-tetraen-10-yl}pyridin-3-yl)ethyl]-1λ$^6$-thiane-4-carboxamide | | | |
| EXAMPLE 8 CPD0019589 | Procedure 2b | Intermediates 48; 86 | Yield: 11% |
| 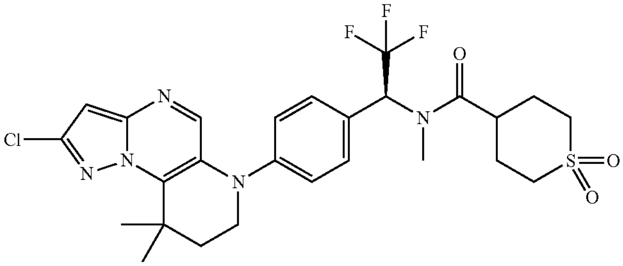 [SMILES: CN(C(=O)C1CCS(=O)(=O)CC1)[C@@H](c1ccc(N2CCC(C)(C)c3c2cnc2cc(Cl)nn32)cc1)C(F)(F)F] | $^{1}H$ NMR (600 MHz, DMSO-$d_6$) δ ppm 8.25 (s, 1H), 7.41-7.29 (m, 2H), 7.24 (d, J = 8.7 Hz, 2H), 6.81 (s, 1H), 6.55-6.14 (m, 1H), 3.69 (dt, J = 5.3, 2.5 Hz, 2H), 3.29-3.08 (m, 5H), 2.92 (s, 3H), 2.17-1.96 (m, 4H), 1.80 (dt, J = 5.4, 2.5 Hz, 2H), 1.63 (s, 6H). m/z: 584 $[M + H]^+$ | | |
| N-[(1S)-1-(4-{4-chloro-13,13-dimethyl-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiane-4-carboxamide | | | |

-continued

| EXAMPLE 9 CPD0019590 | Procedure 2b | Intermediates 49; 86 | Yield: 41% |
|---|---|---|---|
| 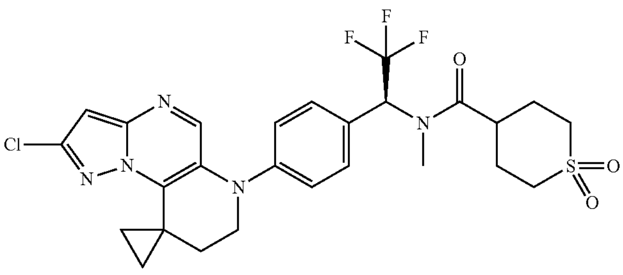 [SMILES: CN(C(=O)C1CCS(=O)(=O)CC1)[C@@H](c1ccc(N2CCC3(CC3)c3c2cnc2cc(Cl)nn32)cc1)C(F)(F)F] | $^1H$ NMR (500 MHz, DMSO-$d_6$) δ 8.20 (s, 1H), 7.31 (d, J = 8.3 Hz, 2H), 7.25 (d, J = 8.8 Hz, 2H), 6.75 (s, 1H), 6.57-6.40 (m, 1H), 3.84-3.71 (m, 2H), 3.28-3.06 (m, 5H), 2.92 (s, 3H), 2.60-2.53 (m, 2H), 2.17-1.94 (m, 4H), 1.86-1.73 (m, 2H), 1.00-0.83 (m, 2H). m/z: 582 $[M + H]^+$ | | |
| N-[(1S)-1-(4-{4'-chloro-2',3',7', 10'-tetraazaspiro[cyclopropane-1,13'-tricyclo[7.4.0.0$^{2,6}$]tridecane]-1'(9'),3',5',7'-tetraen-10'-yl}phenyl)-2,2,2-trifluoroethyl]-N-methyl-1,1-dioxo-1λ$^6$-thiane-4-carboxamide | | | |
| EXAMPLE 10 CPD0021811 | Procedure 2c | Intermediates 50; 86 | Yield: 37% |
| 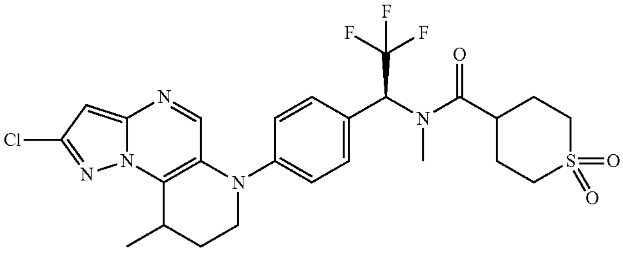 [SMILES: CC1CCN(c2ccc([C@H](N(C)C(=O)C3CCS(=O)(=O)CC3)C(F)(F)F)cc2)c2cnc3cc(Cl)nn3c21] | $^1H$ NMR (600 MHz, DMSO-$d_6$) δ 1.44 (d, J = 7.0 Hz, 3 H), 1.69-1.81 (m, 1 H), 1.92-2.20 (m, 5 H), 2.92 (d, J = 4.5 Hz, 3 H), 3.03-3.29 (m, 5 H), 3.52 (br d, J = 2.3 Hz, 1 H), 3.64-3.80 (m, 2 H), 6.51 (q, J = 9.2 Hz, 1 H), 6.79 (s, 1 H), 7.23-7.50 (m, 4 H), 8.27 (d, J = 2.1 Hz, 1 H). m/z: 570 $[M + H]^+$ Mixture of 2 diastereomers 1/1 | | |
| N-[(1S)-1-(4-{4-chloro-13-methyl-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiane-4-carboxamide | | | |
| EXAMPLE 11 CPD0021812 | Procedure 2c | Intermediates 50; 87 | Yield: 26% |
| 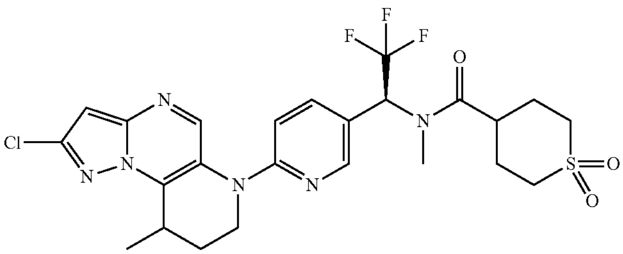 [SMILES: CC1CCN(c2ccc([C@H](N(C)C(=O)C3CCS(=O)(=O)CC3)C(F)(F)F)cn2)c2cnc3cc(Cl)nn3c21] | $^1H$ NMR (600 MHz, DMSO-$d_6$) δ 1.43 (d, J = 6.9 Hz, 3 H), 1.73-1.88 (m, 1 H), 1.93-2.25 (m, 5 H), 2.96 (d, J = 2.9 Hz, 3 H), 3.01-3.28 (m, 5 H), 3.54 (td, J = 6.6, 3.4 Hz, 1 H), 3.77-3.93 (m, 1 H), 3.98-4.14 (m, 1 H), 6.52 (br d, J = 9.2 Hz, 1 H), 6.83 (s, 1 H), 7.25 (d, J = 8.8 Hz, 1 H), 7.73 (br d, J = 8.8 Hz, 1 H), 8.18 (d, J = 2.2 Hz, 1 H), 8.69 (d, J = 2.5 Hz, 1 H) m/z: 571 $[M + H]^+$ Mixture of 2 diastereomers 1/1 | | |
| N-[(1S)-1-(6-{4-chloro-13-methyl-2,3,7,10-tetraazatricyclo[7.4.0.0$^{2,6}$]trideca-1(9),3,5,7-tetraen-10-yl}pyridin-3-yl)-2,2,2-trifluoroethyl]-N-methyl-1,1-dioxo-1λ$^6$-thiane-4-carboxamide | | | |
| EXAMPLE 12 CPD0021562 | Procedure 2b | Intermediates 48; 87 | Yield: 42% |
| 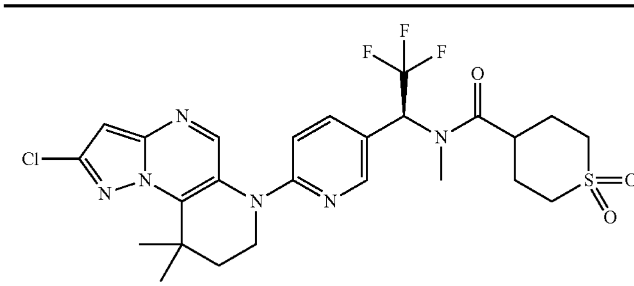 | $^1H$ NMR (600 MHz, DMSO-$d_6$) δ 8.58 (s, 1H), 8.19 (d, J = 2.3 Hz, 1H), 7.72 (dd, J = 8.8, 2.3 Hz, 1H), 7.25 (d, J = 8.8 Hz, 1H), 6.84 (s, 1H), 6.52 (q, J = 9.2 Hz, 1H), 3.97 (dt, J = 5.3, 2.5 Hz, 2H), 3.28-3.07 (m, 5H), 2.96 (s, 3H), 2.17-1.96 (m, 4H), 1.84 (dt, J = 5.2, 2.5 Hz, 2H), 1.62 (s, 6H). m/z: 586 $[M + H]^+$ | | |
| N-[(1S)-1-(6-{4-chloro-13,13-dimethyl-2,3,7,10-tetraazatricyclo[7.4.0.0$^{2,6}$]trideca-1(9),3,5,7-tetraen-10-yl}pyridin-3-yl)-2,2,2-trifluoroethyl]-N-methyl-1,1-dioxo-1λ$^6$-thiane-4-carboxamide | | | |

-continued

| EXAMPLE 13 CPD0021660 | Procedure 2b | Intermediates 49; 87 | Yield: 65% |
|---|---|---|---|
| 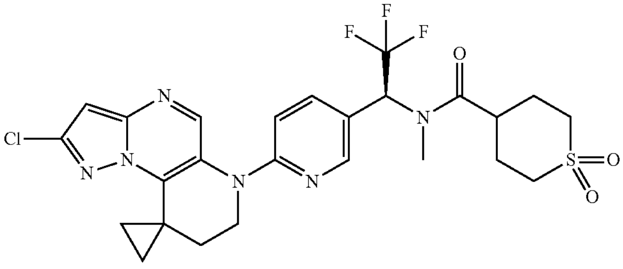 [SMILES: CN(C(=O)C1CCS(=O)(=O)CC1)[C@@H](c1ccc(N2CCC3(CC3)c3c2cnc2cc(Cl)nn32)nc1)C(F)(F)F] | $^1$H NMR (600 MHz, DMSO-$d_6$) δ ppm 8.50-8.53 (m, 1H), 8.19 (d, J = 2.20 Hz, 1H), 7.67-7.81 (m, 1H), 7.24 (d, J = 8.80 Hz, 1H), 6.77 (s, 1H), 6.11-6.59 (m, 1H), 4.00-4.07 (m, 2H), 3.22-3.28 (m, 1H), 3.08-3.20 (m, 4H), 2.95 (s, 3H), 2.52-2.59 (m, 2H), 1.93-2.13 (m, 4H), 1.84 (br dd, J = 3.23, 6.60 Hz, 2H), 0.91-0.98 (m, 2H). m/z: 584 [M + H]$^+$ | | |

N-[(1S)-1-(6-{4'-chloro-2',3',7',10'-tetraazaspiro[cyclopropane-1,13'-tricyclo[7.4.0.0$^{2,6}$]tridecane]-1'(9'),3',5',7'-tetraen-10'-yl}pyridin-3-yl)-2,2,2-trifluoroethyl]-N-methyl-1,1-dioxo-1λ$^6$-thiane-4-carboxamide

| EXAMPLE 14 CPD0021664 | Procedure 2a | Intermediates 45; 86 | Yield: 34% |
|---|---|---|---|
| 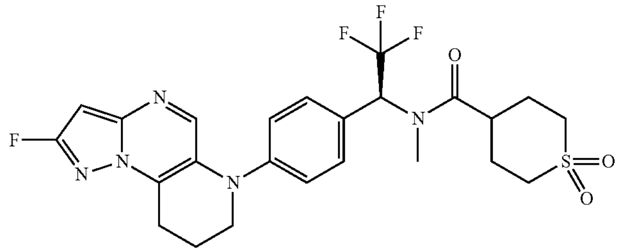 [SMILES: CN(C(=O)C1CCS(=O)(=O)CC1)[C@@H](c1ccc(N2CCCc3c2cnc2cc(F)nn32)cc1)C(F)(F)F] | $^1$H NMR (500 MHz, DMSO-$d_6$) δ ppm 8.30 (s, 1H), 0.00 (d, J = 8.3 Hz, 2H), 7.26 (d, J = 8.8 Hz, 2H), 6.54-6.46 (m, 1H), 6.45-6.41 (m, 1H), 3.75-3.64 (m, 2H), 3.29-3.08 (m, 5H), 3.05 (t, J = 6.7 Hz, 2H), 2.92 (s, 3H), 2.17-1.99 (m, 4H), 1.98-1.85 (m, 2H). m/z: 540 [M + H]$^+$ | | |

N-methyl-1,1-dioxo-N-[(1S)-2,2,2-trifluoro-1-(4-{4-fluoro-2,3,7,10-tetraazatricyclo[7.4.0.0$^{2,6}$]trideca-1(9),3,5,7-tetraen-10-yl}phenyl)ethyl]-1λ$^6$-thiane-4-carboxamide

| EXAMPLE 15 CPD0021665 | Procedure 2a | Intermediates 45; 87 | Yield: 22% |
|---|---|---|---|
| 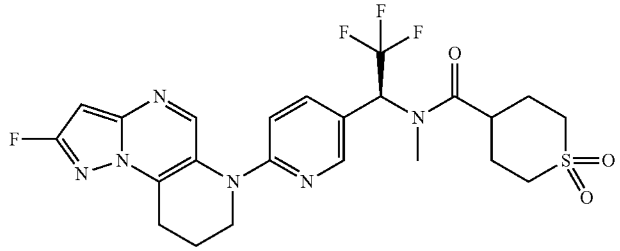 [SMILES: CN(C(=O)C1CCS(=O)(=O)CC1)[C@@H](c1ccc(N2CCCc3c2cnc2cc(F)nn32)nc1)C(F)(F)F] | $^1$H NMR (DMSO-$d_6$, 500 MHz): δ ppm 8.69 (s, 1H), 8.17 (d, J = 2.0 Hz, 1H), 0.00 (dd, J = 8.6, 2.0 Hz, 1H), 7.24 (d, J = 8.8 Hz, 1H), 6.55-6.48 (m, 1H), 6.47 (d, J = 5.1 Hz, 1H), 4.02-3.92 (m, 2H), 3.29-3.02 (m, 7H), 2.96 (s, 3H), 2.14-1.93 (m, 6H). m/z: 541 [M + H]$^+$ | | |

N-methyl-1,1-dioxo-N-[(1S)-2,2,2-trifluoro-1-(6-{4-fluoro-2,3,7,10-tetraazatricyclo[7.4.0.0$^{2,6}$]trideca-1(9),3,5,7-tetraen-10-yl}pyridin-3-yl)ethyl]-1λ$^6$-thiane-4-carboxamide

| EXAMPLE 16 CPD0021815 | Procedure 2b | Intermediates 44; 86 | Yield: 25% |
|---|---|---|---|
| 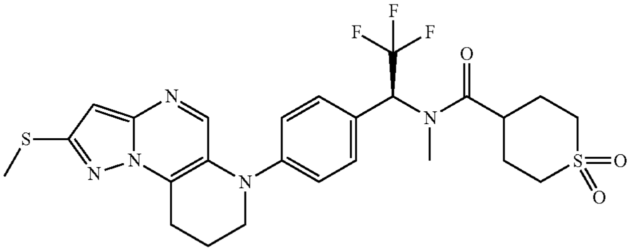 | $^1$H NMR (500 MHz, DMSO-$d_6$) δ ppm 8.21 (s, 1H), 7.29 (d, J = 8.6 Hz, 2H), 7.23 (d, J = 9.0 Hz, 2H), 6.68 (s, 1H), 6.58-6.09 (m, 1H), 3.80-3.66 (m, 2H), 3.29-3.06 (m, 7H), 2.92 (s, 3H), 2.58 (s, 3H), 2.17-1.99 (m, 4H), 1.98-1.88 (m, 2H). m/z: [M + H]$^+$. | | |

N-methyl-1,1-dioxo-N-[(1S)-2,2,2-trifluoro-1-{4-[4-(methylsulfanyl)-2,3,7,10-tetraazatricyclo[7.4.0.0$^{2,6}$]trideca-1(9),3,5,7-tetraen-10-yl]phenyl}ethyl]-1λ$^6$-thiane-4-carboxamide -continued

| EXAMPLE 17 CPD0021751 | Procedure 2c | Intermediates 47; 86 | Yield: 30% |
|---|---|---|---|
| 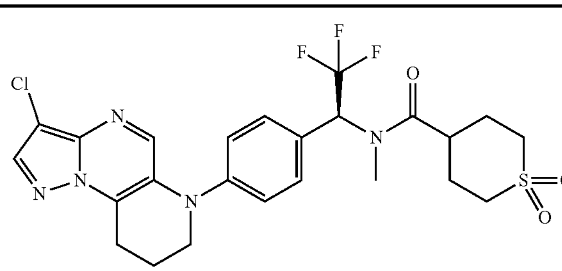 | $^1$H NMR (500 MHz, DMSO-$d_6$, 300K) δ ppm 8.33 (s, 1 H), 8.26 (s, 1 H), 7.29 (br d, J = 14.2 Hz, 4 H), 6.51 (q, J = 9.1 Hz, 1 H), 3.67-3.80 (m, 2 H), 3.04-3.30 (m, 7 H), 2.93 (s, 3 H), 1.90-2.22 (m, 6 H). m/z: 557 $[M + H]^+$ | | |
| N-[(1S)-1-(4-{5-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiane-4-carboxamide | | | |

| EXAMPLE 18 CPD0021752 | Procedure 2c | Intermediates 47; 87 | Yield: 45% |
|---|---|---|---|
| 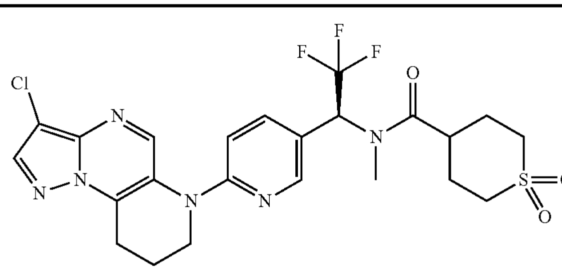 | $^1$H NMR (500 MHz, DMSO-$d_6$, 300K) δ ppm 8.71 (s, 1 H), 8.30 (s, 1 H), 8.18 (d, J = 2.0 Hz, 1 H), 7.72 (dd, J = 8.8, 2.0 Hz, 1 H), 7.26 (d, J = 8.8 Hz, 1 H), 6.52 (br d, J = 9.3 Hz, 1 H), 3.99 (br d, J = 2.9 Hz, 2 H), 3.05-3.29 (m, 7 H), 2.96 (s, 3 H), 2.01 (br d, J = 4.6 Hz, 6 H). m/z: 558 $[M + H]^+$ | | |
| N-[(1S)-1-(6-{5-chloro-2,3,7,10-tetraazatricyclo[7.4.0.0$^{2,6}$]trideca-1(9),3,5,7-tetraen-10-yl}pyridin-3-yl)-2,2,2-trifluoroethyl]-N-methyl-1,1-dioxo-1λ$^6$-thiane-4-carboxamide | | | |

| EXAMPLE 19 CPD0022149 | Procedure 2d | Intermediates 54; 86 | Yield: 17% |
|---|---|---|---|
| 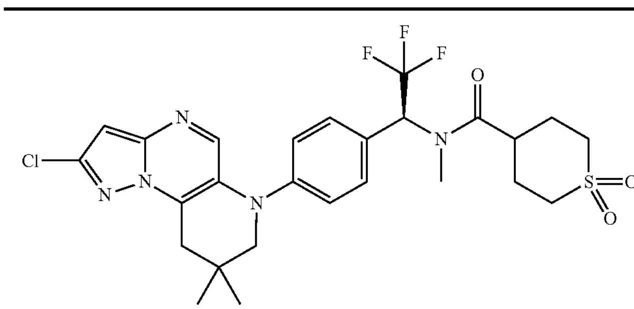 | $^1$H NMR (600 MHz, DMSO-$d_6$) δ ppm 8.40 (s, 1H), 7.44-7.23 (m, 4H), 6.80 (s, 1H), 6.58-6.12 (m, 1H), 3.46 (s, 2H), 3.28-3.06 (m, 5H), 2.97-2.65 (m, J = 2.8 Hz, 5H), 2.18-1.93 (m, 4H), 1.02 (s, 6H). m/z: 584 $[M + H]^+$ | | |
| N-[(1S)-1-(4-{4-chloro-12,12-dimethyl-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiane-4-carboxamide | | | |

| EXAMPLE 20 CPD0022148 | Procedure: 4 | Intermediates 55; 86 | Yield: 24% |
|---|---|---|---|
| 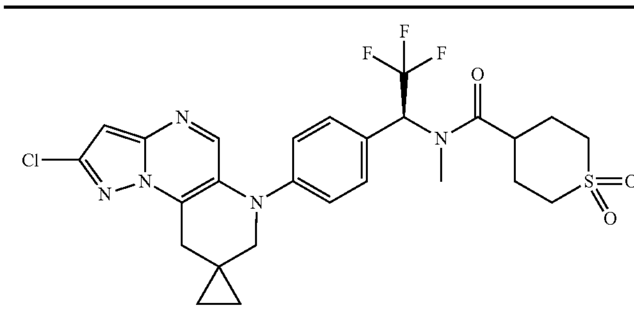 | $^1$H NMR (500 MHz, DMSO-$d_6$) δ ppm 8.35 (s, 1H), 7.19-7.49 (m, 4H), 6.83 (s, 1H), 6.50 (q, J = 9.2 Hz, 1H), 3.56 (d, J = 2.0 Hz, 2H), 3.08- 3.28 (m, 5H), 3.06 (d, J = 1.5 Hz, 2H), 2.91 (s, 3H), 1.94-2.17 (m, 4H), 0.51-0.66 (m, 2H), 0.32-0.48 (m, 2H). m/z: 582 $[M + H]^+$ | | |
| N-[(1S)-1-(4-{4'-chloro-2',3',7',10'-tetraazaspiro[cyclopropane-1,12'-tricyclo[7.4.0.0$^{2,6}$]tridecane]-1'(9'),3',5',7'-tetraen-10'-yl}phenyl)-2,2,2-trifluoroethyl]-N-methyl-1,1-dioxo-1λ$^6$-thiane-4-carboxamide | | | |

-continued

| EXAMPLE 21 CPD0072805 | Procedure: 5b | Intermediates 56; 86 | Yield: 29% |
|---|---|---|---|
| 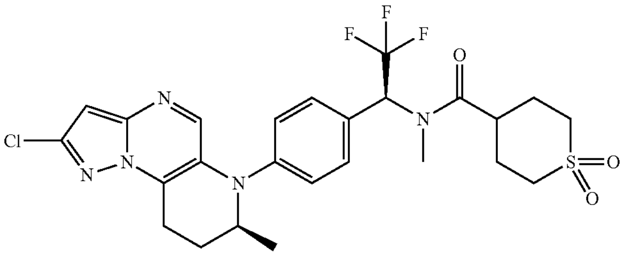 [SMILES: C[C@H]1CCc2c(cnc3cc(Cl)nn23)N1c1ccc([C@H](N(C)C(=O)C2CCS(=O)(=O)CC2)C(F)(F)F)cc1] | $^1H$ NMR (600 MHz, DMSO-$d_6$) δ ppm 8.22 (s, 1 H), 7.24-7.44 (m, 4 H), 6.80 (s, 1 H), 6.51 (br d, = 9.2 Hz, 1 H), 4.07 (td, = 6.9, 3.3 Hz, 1 H), 2.96-3.28 (m, 7 H), 2.93 (s, 3 H), 1.78-2.26 (m, 6 H), 1.13-1.30 (m, 3 H). m/z: 571 $[M + H]^+$ | | |

N-[(1S)-1-{4-[(11rel-S)-4-chloro-11-methyl-2,3,7,10-tetraazatricyclo[7.4.0.0$^{2,6}$]trideca-1(9),3,5,7-tetraen-10-yl]phenyl}-2,2,2-trifluoroethyl]-N-methyl-1,1-dioxo-1λ$^6$-thiane-4-carboxamide

| EXAMPLE 22 CPD0072806 | Procedure 5b | Intermediates 57; 86 | Yield:14% |
|---|---|---|---|
| 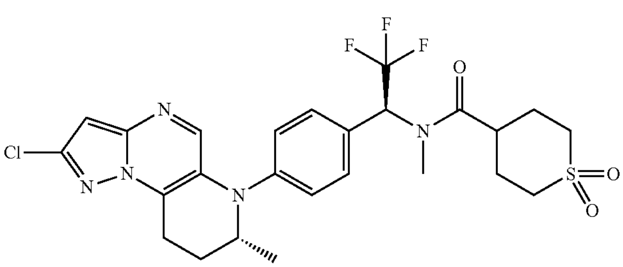 [SMILES: C[C@@H]1CCc2c(cnc3cc(Cl)nn23)N1c1ccc([C@H](N(C)C(=O)C2CCS(=O)(=O)CC2)C(F)(F)F)cc1] | $^1H$ NMR (600 MHz, DMSO-$d_6$) δ ppm 8.21 (s, 1 H), 7.17-7.52 (m, 4 H), 6.80 (s, 1 H), 6.46-6.57 (m, 1 H), 4.05-4.11 (m, 1 H), 2.95-3.28 (m, 7 H), 2.91 (s, 2 H), 1.86-2.19 (m, 7 H), 1.24 (d, =6.7 Hz, 3 H). m/z: 571 $[M + H]^+$ | | |

N-[(1S)-1-{4-[(11rel-R)-4-chloro-11-methyl-2,3,7,10-tetraazatricyclo[7.4.0.0$^{2,6}$]trideca-1(9),3,5,7-tetraen-10-yl]phenyl}-2,2,2-trifluoroethyl]-N-methyl-1,1-dioxo-1λ$^6$-thiane-4-carboxamide

| EXAMPLE 23 CPD0073056 | Procedure 4 | Intermediates 41; 134 | Yield: 38% |
|---|---|---|---|
| 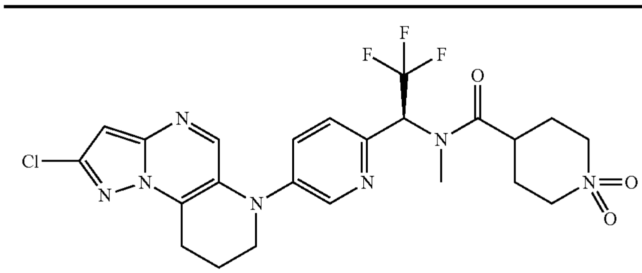 | $^1H$ NMR (DMSO-$d_6$, 500 MHz): δ ppm 8.55 (d, J = 2.7 Hz, 1H), 8.38 (s, 1H), 7.68 (dd, J = 8.6, 2.9 Hz, 1H), 7.36 (d, J = 8.6 Hz, 1H), 6.85 (s, 1H), 6.53 (q, J = 8.9 Hz, 1H), 3.69-3.81 (m, 2H), 3.15-3.30 (m, 3H), 3.11 (br t, J = 6.7 Hz, 4H), 3.04 (s, 3H), 1.95-2.22 (m, 6H).m/z: 557 $[M + H].^+$ | | |

N-[(1S)-1-[5-(4-chloro-2,3,7,10-tetrazatricyclo[7.4.0.0$^{2,6}$]trideca-1(9),3,5,7-tetraen-10-yl)-2-pyridyl]-2,2,2-trifluoro-ethyl]-N-methyl-1,1-dioxo-thiane-4-carboxamide

| EXAMPLE 24 CPD0073969 | Procedure 2 | Intermediates 41; 88 | Yield: 42% |
|---|---|---|---|
| 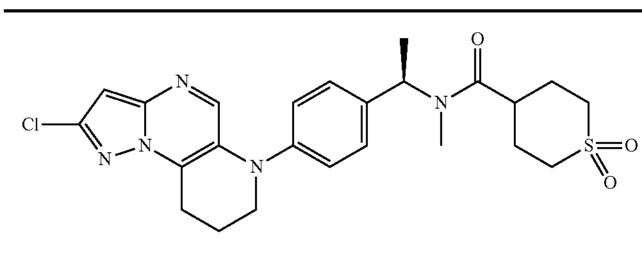 | $^1H$ NMR (400 MHz, DMSO-$d_6$) δ ppm 8.30 (s, 1H), 7.40 (d, J = 8.5 Hz, 2H), 7.26 (d, J = 8.7 Hz, 2H), 6.83 (s, 1H), 5.51 (q, J = 9.2 Hz, 1H), 3.76-3.69 (m, 2H), 3.10 (t, J = 6.7 Hz, 2H), 2.42 (s, 3H), 1.97 (dd, J = 11.1, 6.0 Hz, 2H), 1.15 (s, 9H). m/z: 502 $[M + H]^+$. | | |

N-[(1R)-1-(4-{4-chloro-2,3,7,10-tetraazatricyclo[7.4.0.0$^{2,6}$]trideca-1(9),3,5,7-tetraen-10-yl}phenyl)ethyl]-N-methyl-1,1-dioxo-1λ$^6$-thiane-4-carboxamide -continued

| EXAMPLE 25 CPD0073041 | Procedure 3 | Intermediates 41; 87-b | Yield: 31% |
|---|---|---|---|
| 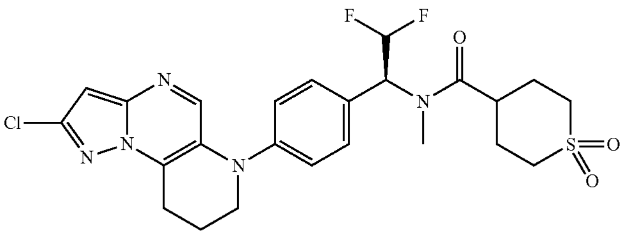 [SMILES: CN(C(=O)C1CCS(=O)(=O)CC1)[C@@H](c1ccc(N2CCCc3c2cnc2cc(Cl)nn32)cc1)C(F)F] | $^1$H NMR (600 MHz, DMSO-$d_6$) δ ppm 8.26 (s, 1H), 7.1-7.5 (m, 4H), 6.6-7.0 (m, 2H), 5.79 (dt, 1H, J = 5.4, 13.4 Hz), 3.6-3.8 (m, 2H), 3.0-3.4 (m, 7H), 2.95 (s, 3H), 1.8-2.2 (m, 6H). m/z: 538 $[M + H]^+$. | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2-difluoroethyl]-N-methyl-1,1-dioxo-1λ$^6$-thiane-4-carboxamide | | | |
| EXAMPLE 26 CPD0072774 | Procedure 2 | Intermediates 41; 89 | Yield: 12% |
| 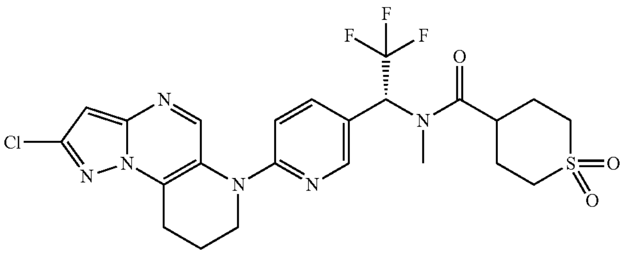 [SMILES: CN(C(=O)C1CCS(=O)(=O)CC1)[C@H](c1ccc(N2CCCc3c2cnc2cc(Cl)nn32)nc1)C(F)(F)F] | $^1$H NMR (DMSO-$d_6$, 600 MHz): δ ppm 8.69 (s, 1H), 8.18 (d, J = 2.3 Hz, 1H), 7.71 (dd, J = 8.9, 2.3 Hz, 1H), 7.24 (d, J = 9.0 Hz, 1H), 6.85 (s, 1H), 6.51 (q, J = 9.2 Hz, 1H), 3.92-4.01 (m, 2H), 3.07-3.30 (m, 7H), 2.95 (s, 3H), 1.95-2.16 (m, 6H). m/z: 557 $[M + H]^+$ | | |
| N-[(1R)-1-[6-(4-chloro-2,3,7,10-tetrazatricyclo[7.4.0.0$^{2,6}$]trideca-1(9),3,5,7-tetraen-10-yl)-3-pyridyl]-2,2,2-trifluoro-ethyl]-N-methyl-1,1-dioxo-1λ$^6$-thiane-4-carboxamide | | | |
| EXAMPLE 27 CPD0073762 | Procedure 5a | Intermediates 58; 86 | Yield: 14% |
| 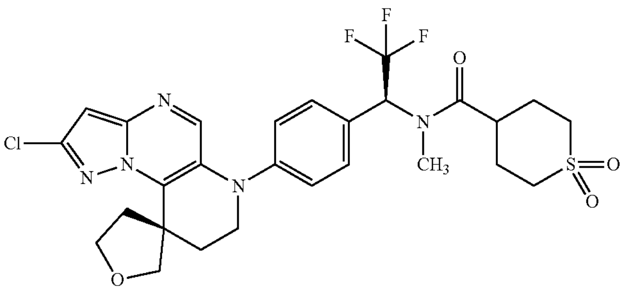 [SMILES: CN(C(=O)C1CCS(=O)(=O)CC1)[C@@H](c1ccc(N2CC[C@@]3(CCOC3)c3c2cnc2cc(Cl)nn32)cc1)C(F)(F)F] | $^1$H NMR (500 MHz, DMSO-$d_6$) δ ppm 8.29 (s, 1H), 7.36-7.31 (m, 2H), 7.30-7.25 (m, 2H), 6.85 (s, 1H), 6.57-6.03 (m, 1H), 4.42-4.32 (m, 1H), 4.13 (s, 2H), 3.81-3.62 (m, 2H), 3.59 (d, J = 8.3 Hz, 1H), 3.28-3.03 (m, 6H), 2.93 (s, 3H), 2.05 (s, 7H). m/z: 612 $[M + H]^+$. | | |
| N-[(1S)-1-[4-[(13rel-R)-4-chlorospiro[2,3,7,10-tetrazatricyclo[7.4.0.0$^{2,6}$]trideca-1(9),3,5,7-tetraene-13,3'-tetrahydrofuran]-10-yl]phenyl]-2,2,2-trifluoro-ethyl]-N-methyl-1,1-dioxo-1λ$^6$-thiane-4-carboxamide | | | |
| EXAMPLE 28 CPD0073763 | Procedure 5a | Intermediates 58; 86 | Yield: 15% |
| 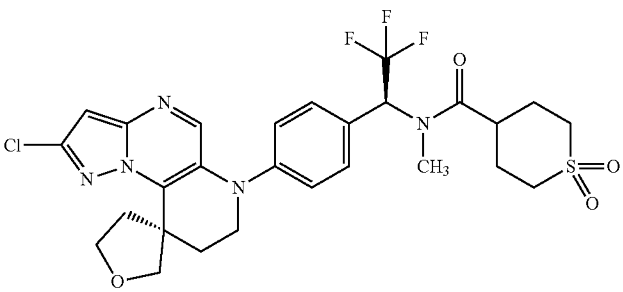 [SMILES: CN(C(=O)C1CCS(=O)(=O)CC1)[C@@H](c1ccc(N2CC[C@]3(CCOC3)c3c2cnc2cc(Cl)nn32)cc1)C(F)(F)F] | $^1$H NMR (500 MHz, DMSO-$d_6$) δ ppm 8.28 (s, 1H), 7.32 (s, 2H), 7.29 (s, 2H), 6.85 (s, 1H), 6.63-5.97 (m, 1H), 4.36 (d, J = 7.8 Hz, 1H), 4.26-4.02 (m, 2H), 3.84-3.62 (m, 2H), 3.59 (d, J = 8.3 Hz, 1H), 3.29-3.02 (m, 6H), 2.92 (s, 3H), 2.20-1.68 (m, 7H). m/z: 612 $[M + H]^+$. | | |
| N-[(1S)-1-[4-[(13rel-S)-4-chlorospiro[2,3,7,10-tetrazatricyclo[7.4.0.0$^{2,6}$]trideca-1(9),3,5,7-tetraene-13,3'-tetrahydrofuran]-10-yl]phenyl]-2,2,2-trifluoro-ethyl]-N-methyl-1,1-dioxo-1λ$^6$-thiane-4-carboxamide | | | |

-continued

| EXAMPLE 29 CPD0073503 | Procedure 2e | Intermediates 59; 86 | Yield: 10% |
|---|---|---|---|

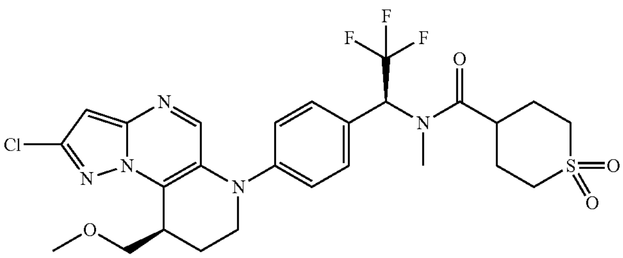 [SMILES: COC[C@@H]1CCN(c2ccc([C@H](N(C)C(=O)C3CCS(=O)(=O)CC3)C(F)(F)F)cc2)c2cnc3cc(Cl)nn3c21]

$^1$H NMR (DMSO-$d_6$, 600 MHz) δ ppm 8.27 (s, 1H), 7.2-7.5 (m, 4H), 6.80 (s, 1H), 6.51 (q, 1H, J = 9.4 Hz), 3.6-4.0 (m, 5H), 3.27 (s, 8H), 2.92 (s, 3H), 1.8-2.2 (m, 6H). m/z: 600 $[M + H]^+$.

N-[(1S)-1-[4-[(13rel-R)-4-chloro-13-(methoxymethyl)-2,3,7,10-tetrazatricyclo[7.4.0.0$^{2,6}$]trideca-1(9),3,5,7-tetraen-10-yl]phenyl]-2,2,2-trifluoro-ethyl]-N-methyl-1,1-dioxo-16-thiane-4-carboxamide

| EXAMPLE 30 CPD0073504 | Procedure 2e | Intermediates 59; 86 | Yield: 10% |
|---|---|---|---|

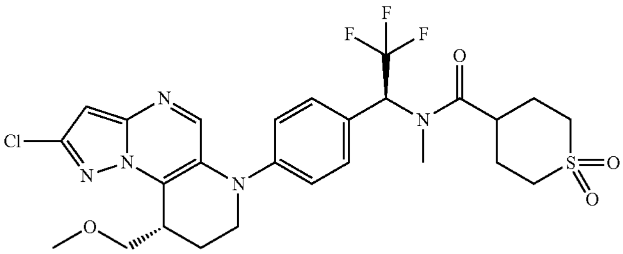 [SMILES: COC[C@H]1CCN(c2ccc([C@H](N(C)C(=O)C3CCS(=O)(=O)CC3)C(F)(F)F)cc2)c2cnc3cc(Cl)nn3c21]

$^1$H NMR (DMSO-$d_6$, 600 MHz) δ ppm 8.27 (s, 1H), 7.1-7.5 (m, 4H), 6.80 (s, 1H), 6.51 (q, 1H, J = 9.1 Hz), 3.6-4.0 (m, 5H), 3.1-3.3 (m, 8H), 2.93 (s, 3H), 1.8-2.1 (m, 6H). m/z: 600 $[M + H]^+$.

N-[(1S)-1-[4-[(13rel-S)-4-chloro-13-(methoxymethyl)-2,3,7,10-tetrazatricyclo[7.4.0.0$^{2,6}$]trideca-1(9),3,5,7-tetraen-10-yl]phenyl]-2,2,2-trifluoro-ethyl]-N-methyl-1,1-dioxo-1λ$^6$-thiane-4-carboxamide

| EXAMPLE 31 CPD0073139 | Procedure 2d | Intermediates 60; 86 | Yield: 8% |
|---|---|---|---|

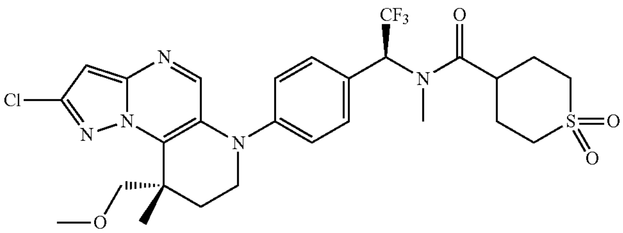 [SMILES: COC[C@@]1(C)CCN(c2ccc([C@H](N(C)C(=O)C3CCS(=O)(=O)CC3)C(F)(F)F)cc2)c2cnc3cc(Cl)nn3c21]

$^1$H NMR (600 MHz, DMSO-$d_6$, 300K) δ ppm 8.24 (s, 1 H), 7.32 (d, J = 8.5 Hz, 2 H), 7.20 (d, J = 8.7 Hz, 2 H), 6.81 (s, 1 H), 6.50 (q, J = 8.9 Hz, 1 H), 4.49 (d, J = 8.8 Hz, 1 H), 3.75-3.89 (m, 1 H), 3.64 (ddd, J = 12.9, 10.3, 2.3 Hz, 1 H), 3.54 (d, J = 8.8 Hz, 1 H), 3.12 (s, 8 H), 2.92 (s, 3 H), 2.16-2.23 (m, 1 H), 1.92-2.14 (m, 4 H), 1.65 (ddd, J = 13.6, 6.2, 2.3 Hz, 1 H), 1.52 (s, 3 H). m/z: 613 $[M + H]^+$.

N-[(1S)-1-[4-[(13rel-S)-4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-1,1-dioxo-1λ$^6$-thiane-4-carboxamide

| EXAMPLE 32 CPD0073140 | Procedure 2d | Intermediates 60; 86 | Yield: 7% |
|---|---|---|---|

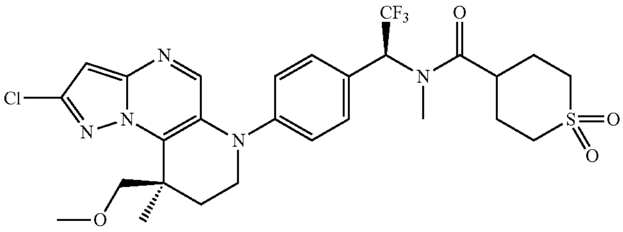 [SMILES: COC[C@]1(C)CCN(c2ccc([C@H](N(C)C(=O)C3CCS(=O)(=O)CC3)C(F)(F)F)cc2)c2cnc3cc(Cl)nn3c21]

$^1$H NMR (600 MHz, DMSO-$d_6$, 300K) δ ppm 8.25 (s, 1 H), 7.33 (d, J = 8.4 Hz, 2 H), 7.20 (d, J = 8.8 Hz, 2 H), 6.81 (s, 1 H), 6.46-6.54 (m, 1 H), 4.49 (d, J = 8.8 Hz, 1 H), 3.80 (br s, 1 H), 3.59-3.70 (m, 1 H), 3.55 (d, J = 8.8 Hz, 1 H), 3.12 (s, 8 H), 2.93 (s, 3 H), 2.19 (ddd, J = 13.4, 10.2, 2.9 Hz, 1 H), 1.95-2.15 (m, 4 H), 1.61-1.72 (m, 1 H), 1.52 (s, 3 H). m/z: 613 $[M + H]^+$.

N-[(1S)-1-[4-[(13rel-R)-4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-1,1-dioxo-1λ$^6$-thiane-4-carboxamide Example 33 (CPD0019575)

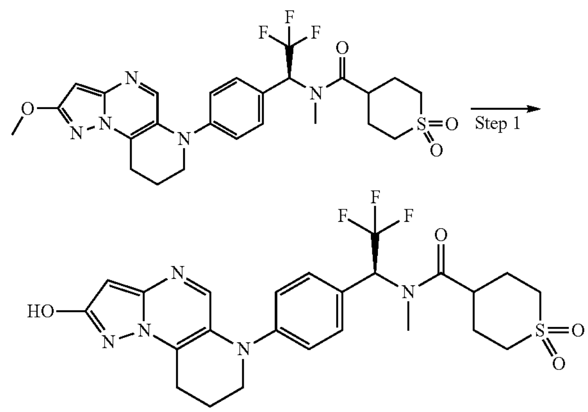

N-methyl-1,1-dioxo-N-[(1S)-2,2,2-trifluoro-1-(4-{4-hydroxy-2,3,7,10-tetraazatricyclo[7.4.0.0$^{2,6}$]trideca-1(9),3,5,7-tetraen-10-yl}phenyl)ethyl]-1λ$^6$-thiane-4-carboxamide To of N-methyl-1,1-dioxo-N-[(1S)-2,2,2-trifluoro-1-(4-{4-methoxy-2,3,7,10-a solution tetraazatricyclo[7.4.0.0$^{2,6}$]trideca-1(9),3,5,7-tetraen-10-yl}phenyl)ethyl]-1λ$^6$-thiane-4-carboxamide (36 mg, 0.046 mmol) in dry DCM (1.5 mL) was added 1M tribromoborane in DCM (0.28 mL, 0.28 mmol). The reaction mixture was stirred at rt overnight, then was heated at 40° C. for 48 h. A second amount of 1M tribromoborane in DCM (0.14 mL, 0.140 mmol) was added to the reaction mixture and left stirring at 40° C. for 6 h and then at rt over the weekend. A third amount of 1M tribromoborane in DCM (0.14 mL, 0.140 mmol) was added and the reaction mixture left stirring at 40° C. overnight. $H_2O$ and DCM were added and phases were separated. The aqueous phase was extracted twice with DCM. The organic layers were combined, dried over anhydrous $Na_2SO_4$, filtered and concentrated under reduced pressure. The crude was purified by a flash reverse column chromatography (water/acetonitrile with 0.1% of AcOH from water 100% to acetonitrile 100%) to afford the expected compound as a yellow solid (3.5 mg, 14%). m/z: 538 [M+H]. $^+$ $^1$H NMR (600 MHz, DMSO-d$_6$) δ ppm 10.51-11.09 (m, 1H), 8.08 (s, 1H), 7.27 (d, J=8.5 Hz, 2H), 7.17 (d, J=8.8 Hz, 2H), 6.47 (q, J=9.3 Hz, 1H), 5.80 (s, 1H), 3.64-3.76 (m, 2H), 3.09-3.27 (m, 5H), 3.01 (t, J=6.7 Hz, 2H), 2.91 (s, 3H), 1.95-2.17 (m, 4H), 1.87-1.94 (m, 2H).

Example 34 (CPD0021662)

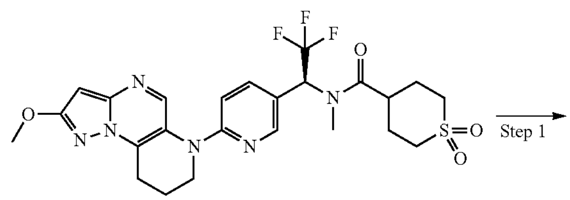

-continued

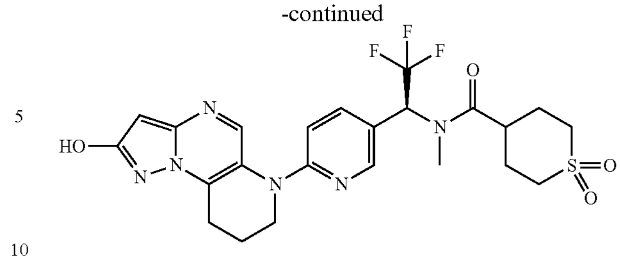

N-methyl-1,1-dioxo-N-[(1S)-2,2,2-trifluoro-1-(6{-4-hydroxy-2,3,7,10-tetraazatricyclo[7.4.0.0$^{2,6}$]trideca-1(9),3,5,7-tetraen-10-yl}pyridin-3-yl)ethyl]-1λ$^6$-thiane-4-carboxamide To a solution of N-methyl-1,1-dioxo-N-[(1S)-2,2,2-trifluoro-1-(6-{4-methoxy-2,3,7,10-tetraazatricyclo[7.4.0.0$^{2,6}$]trideca-1(9),3,5,7-tetraen-10-yl}pyridin-3-yl)ethyl]-1λ$^6$-thiane-4-carboxamide (75 mg, 0.122 mmol) in dry DCM (4.1 mL) was added 1M tribromoborane in DCM (0.73 mL, 0.733 mmol). The reaction mixture was heated at 40° C. and stirred for 48 h. $H_2O$ and DCM were added and phases were separated. The aqueous phase was extracted twice with DCM. The organic layers were combined, dried over anhydrous $Na_2SO_4$, filtered and concentrated under reduced pressure. The crude was purified by a flash reverse column chromatography (water/acetonitrile with 0.1% of TFA from water 100% to acetonitrile 100%) to afford the expected compound as an orange solid (17.9 mg, 27%). m/z: 539 [M+H]. $^+$ $^1$H NMR (600 MHz, DMSO-d$_6$) δ ppm 10.55-11.07 (m, 1H), 8.44 (s, 1H), 8.16 (d, J=2.2 Hz, 1H), 7.66 (dd, J=8.9, 2.3 Hz, 1H), 7.16 (d, J=8.8 Hz, 1H), 6.11-6.54 (m, 1H), 5.84 (s, 1H), 3.97 (br dd, J=8.6, 4.3 Hz, 2H), 3.06-3.29 (m, 5H), 3.03 (t, J=6.9 Hz, 2H), 2.95 (s, 3H), 1.93-2.16 (m, 6H).

Example 35-36 (CPD0021128/CPD0072401)

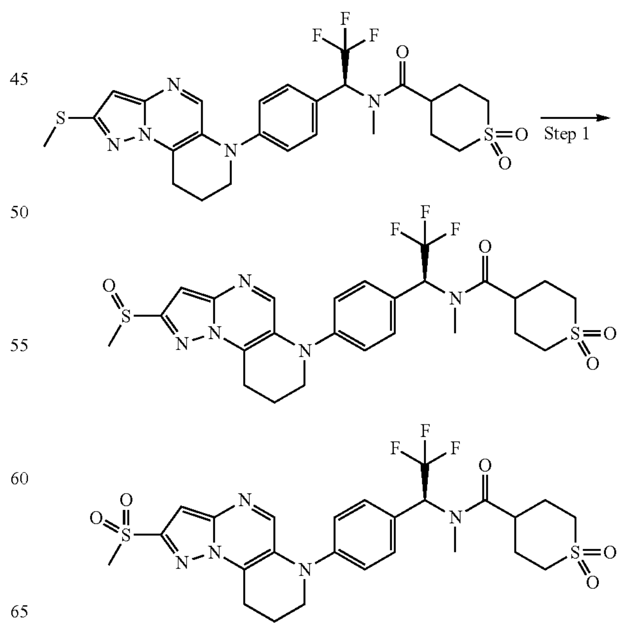

Example 35 N-methyl-1,1-dioxo-N-[(1S)-2,2,2-trifluoro-1-(4-{4-methanesulfinyl-2,3,7,10-tetraazatricyclo[7.4.0.0$^{2,6}$]trideca-1(9),3,5,7-tetraen-10-yl}phenyl)ethyl]-1λ$^6$-thiane-4 carboxamide N-methyl-1,1-dioxo-N-[(1S)-2,2,2-trifluoro-1-{4-[4-(methylsulfanyl)-2,3,7,10-tetraazatricyclo[7.4.0.0$^{2,6}$]trideca-1(9),3,5,7-tetraen-10-yl]phenyl}ethyl]-1λ$^6$-thiane-4-carboxamide (20 mg, 0.035 mmol) was dissolved in dry DCM (0.7 mL), m-CPBA (50% purity, 12 mg, 0.033 mmol) was added at 0° C. The reaction mixture was stirred for 2 h. The reaction mixture was quenched with a sat. aq. $NaHCO_3$. The aqueous phase was extracted twice with EtOAc. The organic layers were combined, dried over anhydrous $Na_2SO_4$, filtered and concentrated under reduced pressure. The crude was purified by a flash reverse column chromatography (water/acetonitrile with 0.1% of TFA from water 100% to acetonitrile 100%) to afford the expected compound (13.1 mg, 61%). m/z: 584 $[M+H]^+$. $^1$H NMR (600 MHz, DMSO-$d_6$) δ ppm 8.36 (s, 1H), 7.32 (s, 2H), 7.30-7.25 (m, 2H), 7.18 (s, 1H), 6.58-6.13 (m, J=9.1 Hz, 1H), 3.78-3.67 (m, 2H), 3.28-3.06 (m, 7H), 2.99 (s, 3H), 2.93 (s, 3H), 2.17-1.95 (m, 6H).

Example 36 N-methyl-1,1-dioxo-N-[(1S)-2,2,2-trifluoro-1-(4-{4-methanesulfonyl-2,3,7,10 tetraazatricyclo[7.4.0.0$^{2,6}$]trideca-1(9),3,5,7-tetraen-10-yl}phenyl)ethyl]-1λ$^6$-thiane-4 carboxamide The title compound was obtained from the previous purification (7.2 mg, 32%). m/z: 600 [M+H]. $^+$ $^1$H NMR (600 MHz, DMSO-$d_6$) δ ppm 8.42 (s, 1H), 7.46-7.28 (m, J=7.3 Hz, 4H), 7.24 (s, 1H), 6.58-6.43 (m, 1H), 3.81-3.65 (m, 2H), 3.35 (s, 3H), 3.28-3.06 (m, 7H), 2.93 (s, 3H), 2.18-1.93 (m, 6H).

Examples 37-127

Scheme 13

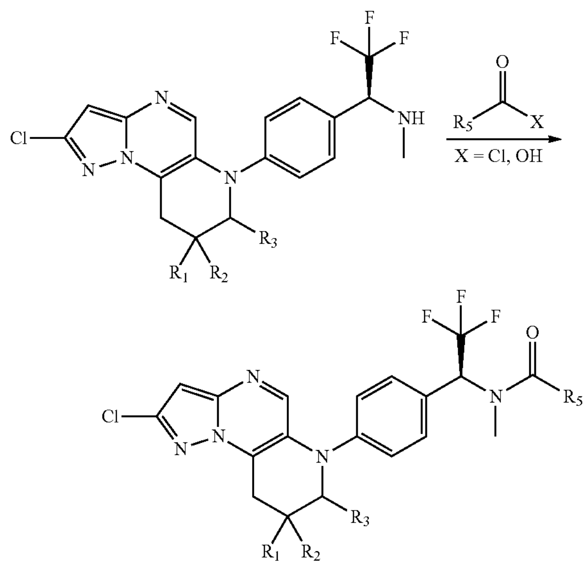

General Procedure 1

To a solution of either commercially available or prepared carboxylic acid (2 mmol) in dry DCM (0.1 M) at rt, under nitrogen atmosphere, was added pyridine (5 eq), followed by phosphoryl trichloride (1.5 eq). The solution was stirred at rt for 10 min and then Intermediates 117-128 (1 mmol) was added and the reaction left stirring until complete conversion (2-5 h). (If the reaction was not proceeding, further carboxylic acid (1.5 mmol), pyridine (20 mmol) and phosphoryl trichloride (1.1 mmol) were added). The reaction mixture was quenched by slow addition of sat. aq. $NaHCO_3$. Layers were separated and the aqueous phase was extracted twice with DCM. Organic layers were combined, dried over anhydrous $Na_2SO_4$, filtered and evaporated. The crude was:

a) purified by flash column chromatography (Heptane/EtOAc)
b) purified by reverse preparative chromatography (water/acetonitrile from water 100% (with 0.1% TFA) to acetonitrile 100%)
c) purified by reverse chromatography (water/acetonitrile from water 100% to acetonitrile 100%)
d) purified by reverse chromatography (water/acetonitrile from water 100% (with 0.1% AcOH) to acetonitrile 100%)
e) Chiral separation (Chiralpak IB 5 μM, 250×20 mm, CO2/MeOH+0.5 IPAm 7/3)

General Procedure 2

To a solution of Intermediates 117-128 (1 mmol) in dry THF (0.16 M) at 0° C. under nitrogen atmosphere was added the corresponding acyl/sulphonyl chloride (2 mmol), followed by sodium hydride—60% dispersion in mineral oil (3 mmol). The reaction mixture was stirred at rt upon completion then was quenched with sat. aq. $NH_4Cl$ and diluted in DCM, the phases were separated, and the aqueous phase extracted with DCM (2 times), dried over anhydrous $Na_2SO_4$ and concentrated under reduced pressure. The crude was purified by reverse-phase column (water/acetonitrile from water 100% to acetonitrile 100%).

General Procedure 3

To a solution of Intermediates 117-128 (1 mmol) in dry DCM (0.2 M) at rt under nitrogen atmosphere, was added TEA (20 mmol) and T3P-50% in EtOAc (10 mmol), followed by the corresponding either commercially available or prepared carboxylic acid (1.5 mmol). The reaction mixture was stirred at rt upon completion. The reaction mixture was quenched with sat. aq. $NaHCO_3$. The reaction mixture was diluted in DCM, the phases were separated, and the aqueous phase extracted with DCM (2 times), dried over anhydrous $Na_2SO_4$ and concentrated under reduced pressure. The crude was:

a) purified by reverse-phase column chromatography (water/acetonitrile from water 100% to acetonitrile 100%)
b) purified by flash column chromatography (Heptane/EtOAc or DCM/MeOH)
c) purified by reverse chromatography (water/acetonitrile from water 100% (with 0.1% AcOH) to acetonitrile 100%)
d) Chiral separation (Chiralpak IB 5 μm, 250×4.6 mm, $CO_2$/EtOH 70/30)
e) Chiral separation (Chiralcel OJ-H 5 μm, 250×21 mm, $CO_2$/EtOH 80/20)
f) Chiral separation (Pirkle (R, R) Whelk-01 5 μm, 250×21.1 mm, $CO_2$/EtOH 65/35)
g) Chiral separation (Xbridge BEH C18 10 μm, 250×50 mm, $H_2O$/MeCN+$HCOONH_4$)

General Procedure 4

To a solution of Intermediates 117-128 (1 mmol) in dry DCM (0.1 M) at rt under nitrogen atmosphere was added pyridine (20 mmol), followed by the corresponding commercially available acyl chloride (1.5 mmol). The reaction mixture was stirred at rt upon completion. Sat. aq. $NaHCO_3$ was carefully added and the biphasic mixture was vigorously stirred for 1 h. Layers were separated and the aqueous phase was extracted twice with EtOAc. Organic layers were combined, washed with brine, dried over anhydrous $Na_2SO_4$, filtered and concentrated. The crude was:

a) Purified by flash column chromatography (Heptane/EtOAc or DCM/MeOH)

b) Purified by reverse-phase column (water/acetonitrile from 100/0 to 0/100% with 0.1% AcOH).

General Procedure 5

To a solution of starting acetyl-protected intermediates (96%, 50 mg, 0.0811 mmol) in methanol (0.12 M), was added dipotassium carbonate (3 mmol) and the mixture was stirred at 0° C. for 50 min. The reaction was quenched at 0° C. with sat. aq. $NH_4Cl$ and then stirred for 5 min, DCM was added, phases were separated and the organic layer was washed with sat. aq. $NH_4Cl$, then dried over $MgSO_4$ and concentrate under reduce pressure. The crude was purified by SFC (eluent: CO2/(MeOH+0.5% IPAm) 70/30 to give the two diastereomers.

Examples 37-125

| EXAMPLES 37 CPD0019342 | Procedure 1b | Intermediate 117 | Yield 52% |
|---|---|---|---|
| 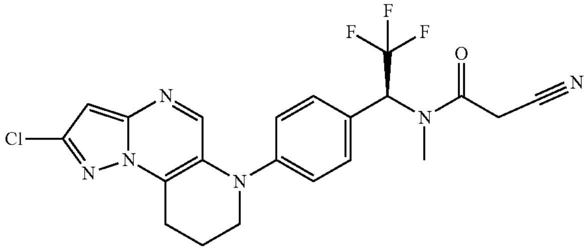 [SMILES: CN(C(=O)CC#N)[C@@H](c1ccc(N2CCCc3c2cnc2cc(Cl)nn32)cc1)C(F)(F)F] | $^1$H NMR (DMSO-d$_6$, 500 MHz): δ ppm 8.30 (s, 1H), 7.36 (d, J = 8.6 Hz, 2H), 7.27 (d, J = 8.8 Hz, 2H), 6.82 (s, 1H), 6.40 (q, J = 9.1 Hz, 1H), 4.20-4.34 (m, 2H), 3.67-3.76 (m, 2H), 3.10 (t, J = 6.7 Hz, 2H), 2.82 (s, 3H), 1.92-2.00 (m, 2H) m/z: 463 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-cyano-N-methylacetamide

| EXAMPLES 38 CPD0019346 | Procedure 1b | Intermediate 117 | Yield 15% |
|---|---|---|---|
| 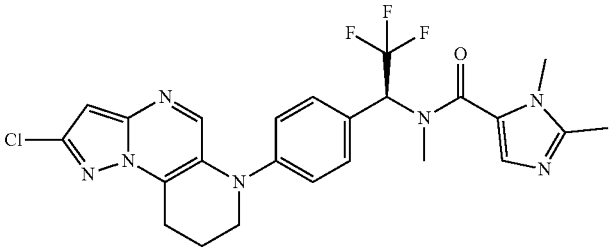 [SMILES: Cc1ncc(C(=O)N(C)[C@@H](c2ccc(N3CCCc4c3cnc3cc(Cl)nn43)cc2)C(F)(F)F)n1C] | $^1$H NMR (600 MHz, DMSO-d$_6$) δ ppm 8.32 (s, 1 H) 7.41 (d, J = 8.51 Hz, 2 H) 7.30-7.34 (m, 1 H) 7.28 (d, J = 8.80 Hz, 2 H) 6.82 (s, 1 H) 6.32-6.67 (m, 1 H) 3.70-3.74 (m, 2 H) 3.62 (s, 3 H) 0.00 (t, J = 6.75 Hz, 2 H) 3.02 (s, 3 H) 2.34 (s, 3 H) 1.93-1.99 (m, 2 H). m/z: 517 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1,2-trimethyl-1H-imidazole-5-carboxamide

| EXAMPLES 39 CPD0019347 | Procedure 1b | Intermediate 117 | Yield 19% |
|---|---|---|---|
| 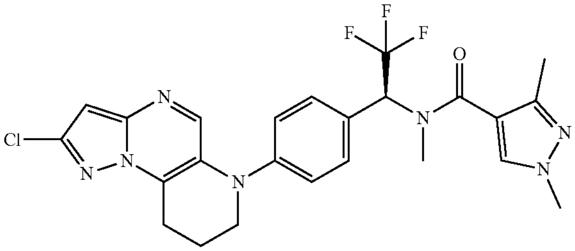 [SMILES: Cc1nn(C)cc1C(=O)N(C)[C@@H](c1ccc(N2CCCc3c2cnc2cc(Cl)nn32)cc1)C(F)(F)F] | $^1$H NMR (DMSO-d$_6$, 500 MHz): δ ppm 8.32 (s, 1H), 7.99-8.13 (m, 1H), 7.38 (d, J = 8.6 Hz, 2H), 7.28 (d, J = 8.6 Hz, 2H), 6.82 (s, 1H), 6.36-6.73 (m, 1H), 3.78 (s, 3H), 3.72 (dt, J = 5.0, 2.8 Hz, 2H), 3.10 (t, J = 6.7 Hz, 2H), 2.93 (s, 3H), 2.23 (s, 3H), 1.93-2.01 (m, 2H). m/z: 517 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1,3-trimethyl-1H-pyrazole-4-carboxamide -continued

| EXAMPLES 40 CPD0019348 | Procedure 1b | Intermediate 117 | Yield 30% |
|---|---|---|---|
| 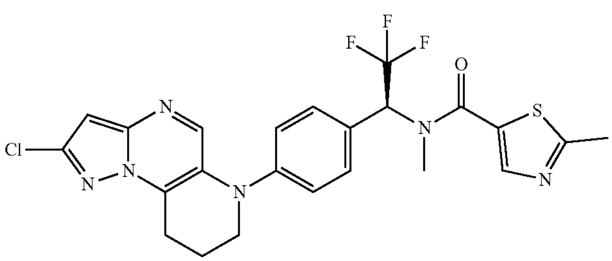 [SMILES: Cc1ncc(C(=O)N(C)[C@@H](c2ccc(N3CCCc4c3cnc3cc(Cl)nn43)cc2)C(F)(F)F)s1] | $^1$H NMR (DMSO-$d_6$, 600 MHz): δ ppm 8.32 (s, 1H), 8.04-8.22 (m, 1H), 7.41 (d, J = 8.5 Hz, 2H), 7.24-7.33 (m, 2H), 6.82 (s, 1H), 6.33-6.69 (m, 1H), 3.61-3.80 (m, 2H), 3.10 (br t, J = 6.7 Hz, 5H), 2.69 (s, 3H), 1.92-2.06 (m, 2H).m/z: 521 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,2-dimethyl-1,3-thiazole-5-carboxamide

| EXAMPLES 41 CPD0019349 | Procedure 2 | Intermediate 117 | Yield 55% |
|---|---|---|---|
| 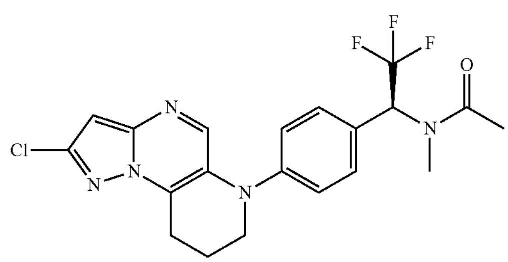 [SMILES: CC(=O)N(C)[C@@H](c1ccc(N2CCCc3c2cnc2cc(Cl)nn32)cc1)C(F)(F)F] | $^1$H NMR (DMSO-$d_6$, 500 MHz): δ ppm 8.30 (s, 1H), 7.30-7.43 (m, 2H), 7.20-7.30 (m, 2H), 6.82 (s, 1H), 6.49 (q, J = 9.5 Hz, 1H), 3.68-3.75 (m, 2H), 3.10 (t, J = 6.7 Hz, 2H), 2.86 (s, 3H), 2.15 (s, 3H), 1.92-2.01 (m, 2H). m/z: 438 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylacetamide

| EXAMPLES 42 CPD0019351 | Procedure 1c | Intermediate 117 | Yield 7% |
|---|---|---|---|
| 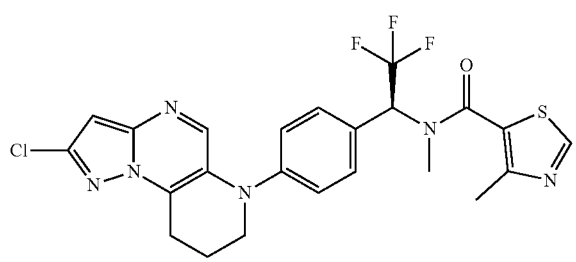 [SMILES: Cc1ncsc1C(=O)N(C)[C@@H](c1ccc(N2CCCc3c2cnc2cc(Cl)nn32)cc1)C(F)(F)F] | $^1$H NMR (DMSO-$d_6$, 600 MHz): δ ppm 9.16 (s, 1H), 8.33 (s, 1H), 7.43 (d, J = 8.5 Hz, 2H), 7.30 (d, J = 8.8 Hz, 2H), 6.82 (s, 1H), 6.24-6.72 (m, 1H), 3.65-3.86 (m, 2H), 3.10 (t, J = 6.7 Hz, 2H), 2.84 (s, 3H), 2.38 (s, 3H), 1.92-2.05 (m, 2H). m/z: 521 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,4-dimethyl-1,3-thiazole-5-carboxamide

| EXAMPLES 43 CPD0019352 | Procedure 1a | Intermediate 117 | Yield: 23% |
|---|---|---|---|
| 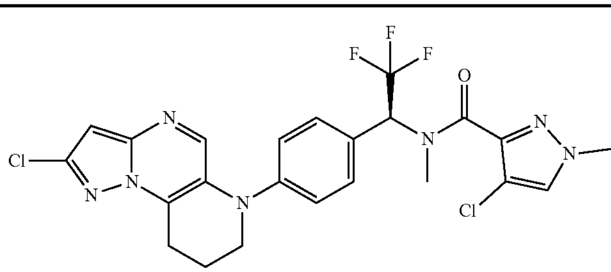 | $^1$H NMR (600 MHz, DMSO-$d_6$) δ ppm 8.33 (s, 1H), 8.05-8.16 (m, 1H), 7.37-7.52 (m, 2H), 7.30 (br d, J = 8.51 Hz, 2H), 6.82 (s, 1H), 6.31-6.67 (m, 1H), 3.84-3.91 (m, 3H), 3.69-3.76 (m, 2H), 3.10 (t, J = 6.68 Hz, 2H), 2.77-2.94 (m, 3H), 1.94-1.99 (m, 2H). m/z: 538 $[M + H]^+$ | | |

4-chloro-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-1H-pyrazole-3-carboxamide -continued

| EXAMPLES 44 CPD0019353 | Procedure 1a | Intermediate 117 | Yield: 34% |
|---|---|---|---|
| 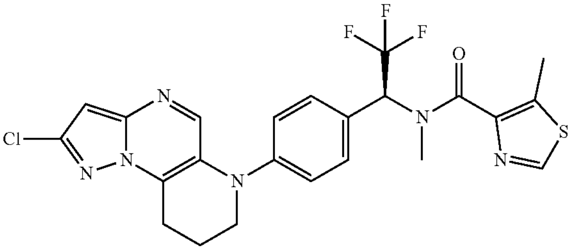 [SMILES: Cc1scnc1C(=O)N(C)[C@@H](c1ccc(N2CCCc3c2cnc2cc(Cl)nn32)cc1)C(F)(F)F] | $^1$H NMR (600 MHz, DMSO-$d_6$) 2 conformers (60/40): δ ppm 8.91-9.07 (m, 1H), 8.30-8.34 (m, 1H), 7.38-7.53 (m, 2H), 7.30 (br d, J = 8.36 Hz, 2H), 6.82 (s, 1H), 6.65 (q, J = 9.15 Hz, 0.6H), 6.15 (q, J = 8.27 Hz, 0.4H), 3.70-3.76 (m, 2H), 3.10 (t, J = 6.68 Hz, 2H), 2.76-2.87 (m, 3H), 2.50-2.54 (m, 3H), 1.94-1.99 (m, 2H). m/z: 521 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,5-dimethyl-1,3-thiazole-4-carboxamide

| EXAMPLES 45 CPD0019354 | Procedure 2 | Intermediate 117 | Yield: 55% |
|---|---|---|---|
| 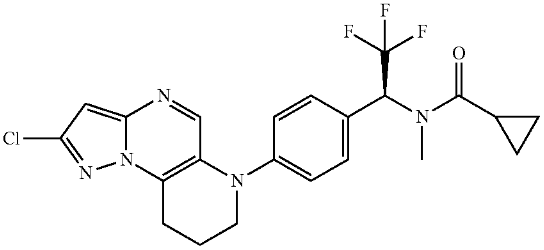 [SMILES: CN(C(=O)C1CC1)[C@@H](c1ccc(N2CCCc3c2cnc2cc(Cl)nn32)cc1)C(F)(F)F] | $^1$H NMR (600 MHz, DMSO-$d_6$) 2 conformer (80/20): δ ppm 8.31 (s, 1H), 7.23-7.41 (m, 4H), 6.82 (s, 1H), 6.42-6.54 (m, 1H), 3.68-3.75 (m, 2H), 3.10 (t, J = 6.68 Hz, 2H), 3.02 (s, 2.4H), 2.63-2.68 (br s, 0.6H), 2.28-2.37 (br s, 0.2H), 2.00-2.07 (m, 0.8H), 1.93-1.99 (m, 2H), 0.80-0.88 (m, 4H). m/z: 464 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylcyclopropanecarboxamide

| EXAMPLES 46 CPD0019344 | Procedure 1d | Intermediate 117 | Yield: 28% |
|---|---|---|---|
| 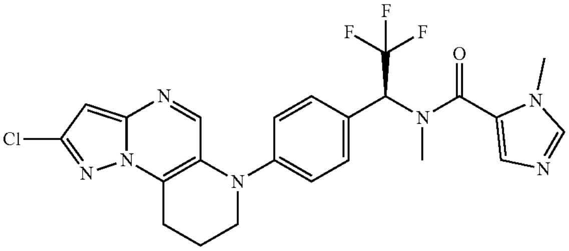 [SMILES: CN(C(=O)c1cncn1C)[C@@H](c1ccc(N2CCCc3c2cnc2cc(Cl)nn32)cc1)C(F)(F)F] | $^1$H NMR (500 MHz, DMSO-$d_6$) δ ppm 8.32 (s, 1H), 7.85 (s, 1H), 7.47 (br s, 1H), 7.42 (d, J = 8.56 Hz, 2H), 7.29 (d, J = 8.56 Hz, 2H), 6.83 (s, 1H), 6.47-6.61 (m, 1H), 3.71-3.76 (m, 5H), 3.10 (t, J = 6.72 Hz, 2H), 3.04 (s, 3H), 1.93-1.99 (m, 2H). m/z: 504 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-1H-imidazole-5-carboxamide

| EXAMPLES 47 CPD0019482 | Procedure 4a-b | Intermediate 117 | Yield: 25% |
|---|---|---|---|
| 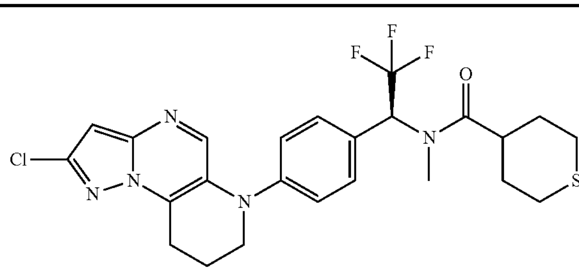 | $^1$H NMR (500 MHz, DMSO-$d_6$) δ ppm 8.30 (s, 1H), 7.44-7.20 (m, 4H), 6.82 (s, 1H), 6.51 (q, J = 9.4 Hz, 1H), 3.75-3.65 (m, 2H), 3.10 (t, J = 6.7 Hz, 2H), 2.89 (s, 3H), 2.87-2.83 (m, 1H), 2.79-2.57 (m, 4H), 2.06-1.61 (m, 6H). m/z: 524 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylthiane-4-carboxamide -continued

| EXAMPLES 48 CPD0021569 | Procedure 1d | Intermediate 117 | Yield:42% |
|---|---|---|---|
| 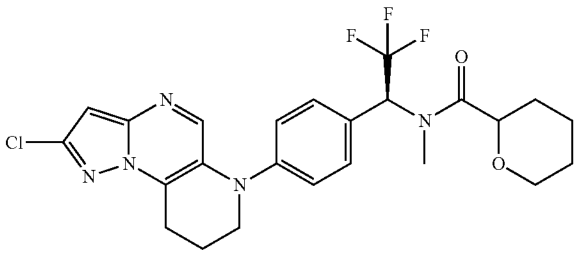 [SMILES: CN(C(=O)C1CCCCO1)[C@@H](c1ccc(N2CCCc3c2cnc2cc(Cl)nn32)cc1)C(F)(F)F] | $^1$H NMR (500 MHz, DMSO-$d_6$) δ ppm 8.69 (s, 1H), 8.17 (d, J = 2.0 Hz, 1H), 0.00 (dd, J = 8.6, 2.0 Hz, 1H), 7.24 (d, J = 8.8 Hz, 1H), 6.55-6.48 (m, 1H), 6.47 (d, J = 5.1 Hz, 1H), 4.02-3.92 (m, 2H), 3.29-3.02 (m, 7H), 2.96 (s, 3H), 2.14-1.93 (m, 6H) m/z: 508 [M + H]$^+$ Mixture of dias in proportion 1/1 | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyloxane-2-carboxamide | | | |

| EXAMPLES 49 CPD0021572 | Procedure 1c | Intermediate 117 | Yield: 30% |
|---|---|---|---|
| 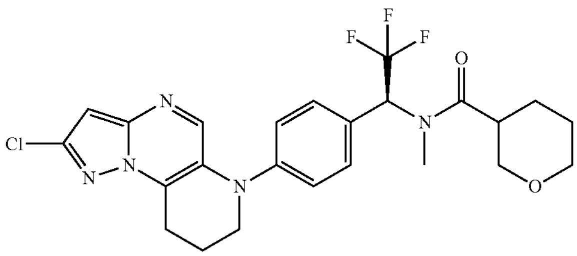 [SMILES: CN(C(=O)C1CCCOC1)[C@@H](c1ccc(N2CCCc3c2cnc2cc(Cl)nn32)cc1)C(F)(F)F] | $^1$H NMR (500 MHz, DMSO-$d_6$) δ ppm 8.30 (s, 1 H), 7.15-7.48 (m, 4 H), 6.82 (s, 1 H), 6.48 (br dd, J = 9.2, 2.6 Hz, 1 H), 3.78-3.97 (m, 2 H), 3.66-3.76 (m, 2 H), 3.32-3.46 (m, 2 H), 3.10 (t, J = 6.7 Hz, 2H), 2.93-3.02 (m, 1 H), 2.92 (s, 3 H), 1.41-2.10 (m, 6 H). m/z: 508 [M + H]$^+$ Mixture of dias in proportion 1/1 | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyloxane-3-carboxamide | | | |

| EXAMPLES 50 CPD0021574 | Procedure 1c | Intermediate 117 | Yield: 10% |
|---|---|---|---|
| 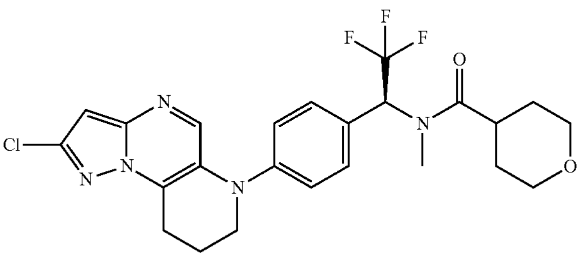 [SMILES: CN(C(=O)C1CCOCC1)[C@@H](c1ccc(N2CCCc3c2cnc2cc(Cl)nn32)cc1)C(F)(F)F] | $^1$H NMR (500 MHz, DMSO-$d_6$) δ ppm 8.30 (s, 1 H), 7.18-7.42 (m, 4 H), 6.82 (s, 1 H), 6.53 (q, J = 9.4 Hz, 1 H), 3.80-3.94 (m, 2 H), 3.66-3.76 (m, 2 H), 3.39 (qd, J = 11.7, 2.4 Hz, 2 H), 3.10 (t, J = 6.7 Hz, 2H), 3.01 (br s, 1 H), 2.92 (s, 3 H), 1.92-2.04 (m, 2 H), 1.43-1.77 (m, 4 H). m/z: 508 [M + H]$^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyloxane-4-carboxamide | | | |

| EXAMPLES 51 CPD0021568 | Procedure 1c | Intermediate 117 | Yield: 33% |
|---|---|---|---|
| 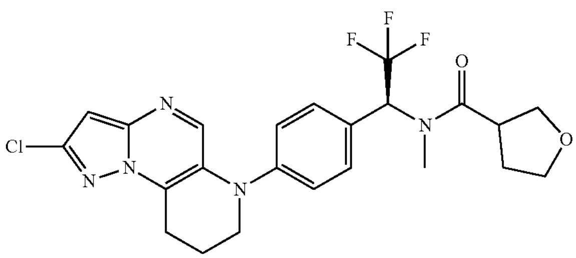 [SMILES: CN(C(=O)C1CCOC1)[C@@H](c1ccc(N2CCCc3c2cnc2cc(Cl)nn32)cc1)C(F)(F)F] | $^1$H NMR (500 MHz, DMSO-$d_6$) δ ppm 8.31 (d, J = 1.0 Hz, 1H), 7.29-7.39 (m, 2H), 7.19-7.29 (m, 2H), 6.82 (s, 1H), 6.52 (q, J = 9.2 Hz, 1H), 3.85-4.04 (m, 1H), 3.60-3.82 (m, 5H), 3.45-3.56 (m, 1H), 3.10 (t, J = 6.6 Hz, 2H), 2.90 (d, J = 2.7 Hz, 3H), 1.86-2.26 (m, 4H). m/z: 494 [M + H]$^+$ Mixture of dias in proportion 1/1 | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyloxolane-3-carboxamide | | | |

-continued

| EXAMPLES 52 CPD0021570 | Procedure 1c | Intermediate 117 | Yield: 50% |
|---|---|---|---|

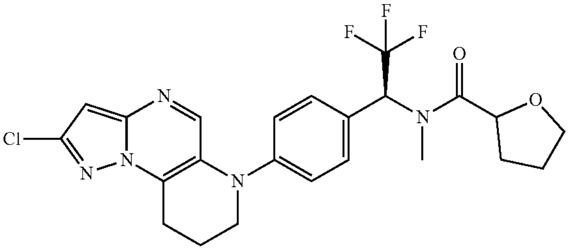 [SMILES: CN(C(=O)C1CCCO1)[C@@H](c1ccc(N2CCCc3c2cnc2cc(Cl)nn32)cc1)C(F)(F)F]

$^1$H NMR (500 MHz, DMSO-$d_6$) δ ppm 8.31 (d, J = 3.91 Hz, 1H), 7.18-7.51 (m, 4H), 6.82 (s, 1H), 6.41-6.49 (m, 1H), 4.78-4.91 (m, 1H), 3.75-3.86 (m, 2H), 3.72 (br s, 2H), 3.10 (t, J = 6.72 Hz, 2H), 2.90 (d, J = 2.93 Hz, 3H), 1.70-2.31 (m, 6H). m/z: 494 $[M + H]^+$ Mixture of dias in proportion 55/45

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyloxolane-2-carboxamide

| EXAMPLES 53 CPD0021571 | Procedure 1c | Intermediate 117 | Yield: 8% |
|---|---|---|---|

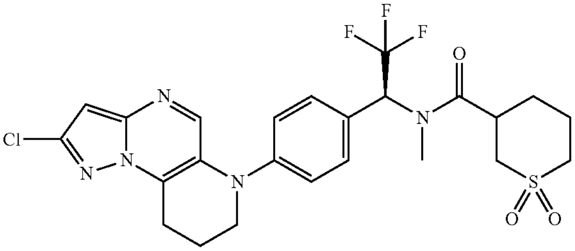 [SMILES: CN(C(=O)C1CCCS(=O)(=O)C1)[C@@H](c1ccc(N2CCCc3c2cnc2cc(Cl)nn32)cc1)C(F)(F)F]

$^1$H NMR (600 MHz, DMSO-$d_6$) δ ppm 8.30 (d, J = 2.3 Hz, 1H), 7.24-7.36 (m, 4H), 6.82 (s, 1H), 6.41-6.49 (m, 1H), 3.71 (br dd, J = 6.3, 4.1 Hz, 2H), 3.15-3.28 (m, 4H), 3.10 (t, J = 6.6 Hz, 2H), 3.02-3.08 (m, 1H), 2.90-2.94 (m, 3H), 2.03-2.12 (m, 1H), 1.79-1.99 (m, 4H), 1.50-1.62 (m, 1H). m/z: 555 $[M + H]^+$ Mixture of dias in proportion 55/45

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiane-3-carboxamide

| EXAMPLES 54 CPD0022134 | Procedure 1e | Intermediate 117 | Yield: 8% |
|---|---|---|---|

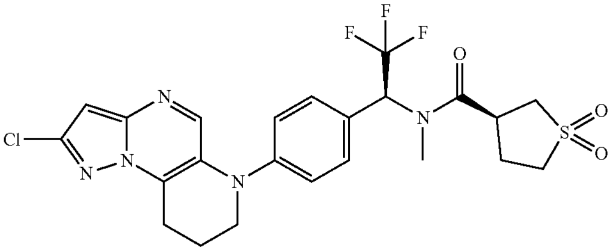 [SMILES: CN(C(=O)[C@@H]1CCS(=O)(=O)C1)[C@@H](c1ccc(N2CCCc3c2cnc2cc(Cl)nn32)cc1)C(F)(F)F]

$^1$H NMR (600 MHz, DMSO-$d_6$) δ ppm 8.31 (s, 1H), 7.23-7.34 (m, 4H), 6.82 (s, 1H), 6.47 (q, J = 9.2 Hz, 1H), 3.79-3.86 (m, 1H), 3.78-4.06 (m, 1H), 3.69-3.75 (m, 2H), 3.44-3.51 (m, 1H), 3.22-3.29 (m, 1H), 3.08-3.20 (m, 4H), 2.93 (s, 2H), 2.33-2.41 (m, 1H), 2.06-2.17 (m, 1H), 1.93-1.99 (m, 2H). m/z: 541 $[M + H]^+$ (3rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiolane-3-carboxamide

| EXAMPLES 55 CPD0022135 | Procedure 1e | Intermediate 117 | Yield: 6% |
|---|---|---|---|

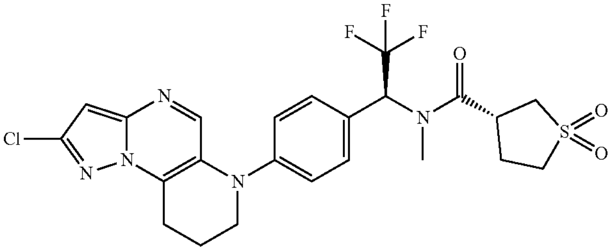 [SMILES: CN(C(=O)[C@H]1CCS(=O)(=O)C1)[C@@H](c1ccc(N2CCCc3c2cnc2cc(Cl)nn32)cc1)C(F)(F)F]

$^1$H NMR (600 MHz, DMSO-$d_6$) δ ppm 8.29-8.32 (m, 1H), 7.22-7.45 (m, 4H), 6.82 (s, 1H), 6.49 (q, J = 9.1 Hz, 1H), 3.78-4.09 (m, 1H), 3.68-3.74 (m, 2H), 3.31-3.38 (m, 1H), 3.21-3.28 (m, 2H), 3.05-3.17 (m, 3H), 2.94 (s, 3H), 2.42-2.48 (m, 1H), 1.94-2.11 (m, 3H). m/z: 541 $[M + H]^+$ (3rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiolane-3-carboxamide -continued

| EXAMPLES 56 CPD0021575 | Procedure 1c | Intermediate 117 | Yield: 20% |
|---|---|---|---|
| 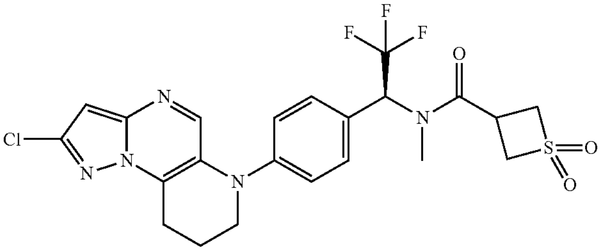 [SMILES: CN(C(=O)C1CS(=O)(=O)C1)[C@@H](c1ccc(N2CCCc3c2cnc2cc(Cl)nn32)cc1)C(F)(F)F] | $^{1}$H NMR (600 MHz, DMSO-$d_6$) δ ppm 8.30 (s, 1 H), 7.35 (d, J = 8.7 Hz, 2 H), 7.25 (d, J = 8.7 Hz, 2 H), 6.82 (s, 1 H), 6.42-6.50 (m, 1 H), 4.25-4.63 (m, 4 H), 3.87 (s, 1 H), 3.65-3.79 (m, 2 H), 3.10 (t, J = 6.7 Hz, 2 H), 2.84 (s, 3 H), 1.89-2.02 (m, 2 H). m/z: 527 $[M + H]^+$ | | |

N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N-methyl-1,1-dioxo-1$\lambda^6$-thietane-3-carboxamide

| EXAMPLES 57 CPD0073083 | Procedure 3b | Intermediate 117 | Yield: 22% |
|---|---|---|---|
| 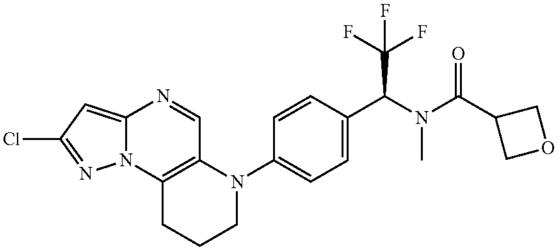 [SMILES: CN(C(=O)C1COC1)[C@@H](c1ccc(N2CCCc3c2cnc2cc(Cl)nn32)cc1)C(F)(F)F] | $^{1}$H NMR (500 MHz, DMSO-$d_6$) δ ppm 8.30 (s, 1H), 7.31-7.38 (m, 2H), 7.23-7.29 (m, 2H), 6.82 (s, 1H), 5.62-6.63 (m, 1H), 4.61-4.82 (m, 4H), 4.31 (ddd, J = 8.6, 6.9, 1.8 Hz, 1H), 3.71 (dt, J = 4.9, 2.7 Hz, 2H), 3.10 (t, J = 6.7 Hz, 2H), 2.65 (s, 3H), 1.91-2.02 (m, 2H). m/z: 480 $[M + H]^+$ | | |

N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N-methyloxetane-3-carboxamide

| EXAMPLES 58 CPD0021746 | Procedure 3a | Intermediate Example 151 | Yield: 44% |
|---|---|---|---|
| 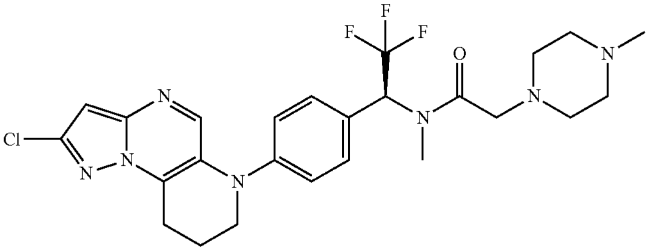 [SMILES: CN1CCN(CC(=O)N(C)[C@@H](c2ccc(N3CCCc4c3cnc3cc(Cl)nn43)cc2)C(F)(F)F)CC1] | $^{1}$H NMR (600 MHz, DMSO-$d_6$) δ ppm 8.40-8.23 (m, 1H), 7.51-7.21 (m, 4H), 6.81 (s, 1H), 6.53-6.32 (m, 1H), 3.77-3.66 (m, 2H), 3.36-3.31 (m, 1H), 3.27-3.21 (m, 1H), 3.14-3.06 (m, 2H), 2.92 (s, 3H), 2.49-2.15 (m, 8H), 2.14 (s, 3H), 2.01-1.90 (m, 2H). m/z: 536 $[M + H]^+$ | | |

N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N-methyl-2-(4-methylpiperazin-1-yl)acetamide

| EXAMPLES 59 CPD0021874 | Procedure 3a | Intermediate 117 | Yield: 36% |
|---|---|---|---|
| 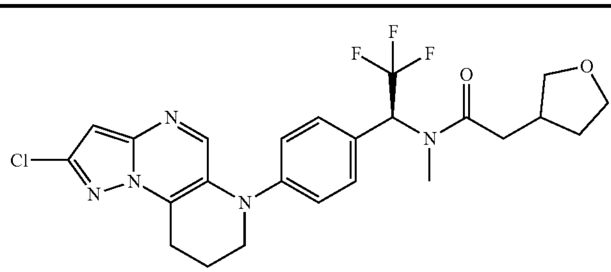 | $^{1}$H NMR (600 MHz, DMSO-$d_6$) δ ppm 8.30 (s, 1H), 7.29-7.41 (m, 2H), 7.24-7.29 (m, 2H), 6.82 (s, 1H), 5.98-6.59 (m, 1H), 3.85 (ddd, = 8.3, 6.5, 5.0 Hz, 1H), 3.68-3.76 (m, 3H), 3.63 (q, = 7.6 Hz, 1H), 3.24-3.29 (m, 1H), 3.10 (t, J = 6.7 Hz, 2H), 2.86 (s, 3H), 2.53-2.69 (m, 3H), 1.99-2.10 (m, 1H), 1.92-1.99 (m, 2H), 1.46-1.55 (m, 1H). m/z: 508 $[M + H]^+$ Mixture of diastereomers in proportion 1/1 | | |

N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N-methyl-2-(oxolan-3-yl)acetamide -continued

| EXAMPLES 60 CPD0021934 | Procedure 3a | Intermediate 117 | Yield: 28% |
|---|---|---|---|
| 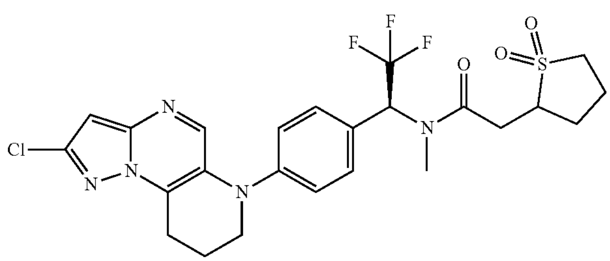 [SMILES: CN(C(=O)CC1CCCS1(=O)=O)[C@@H](c1ccc(N2CCCc3c2cnc2cc(Cl)nn32)cc1)C(F)(F)F] | $^1H$ NMR (500 MHz, DMSO-$d_6$) δ ppm 8.36-8.22 (m, J = 3.2 Hz, 1H), 7.38-7.30 (m, 2H), 7.29-7.21 (m, 2H), 6.82 (s, 1H), 6.55-6.41 (m, 1H), 3.81-3.63 (m, 2H), 3.52-3.42 (m, 1H), 3.18-3.04 (m, 3H), 3.04-2.92 (m, 2H), 2.91-2.85 (m, 3H), 2.84-2.74 (m, 1H), 2.46-2.33 (m, 1H), 2.12-2.03 (m, 1H), 2.02-1.92 (m, 3H), 1.82-1.70 (m, 1H). m/z: 556 $[M + H]^+$ Mixture of dias 1/1 ratio | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1λ$^6$-thiolan-2-yl)-N-methylacetamide | | | |
| EXAMPLES 61 CPD0072799 | Procedure 3d | Intermediate 117 | Yield 27% |
| 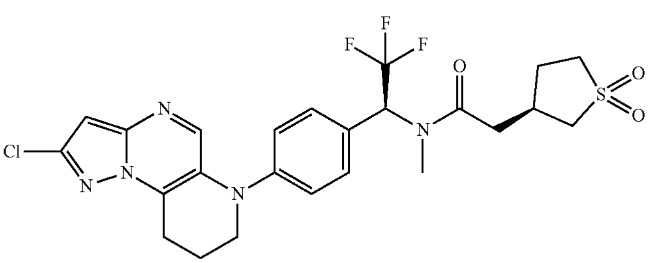 [SMILES: CN(C(=O)C[C@H]1CCS(=O)(=O)C1)[C@@H](c1ccc(N2CCCc3c2cnc2cc(Cl)nn32)cc1)C(F)(F)F] | $^1H$ NMR (500 MHz, DMSO-$d_6$) δ ppm 8.30 (s, 1H), 7.32 (s, 2H), 7.27 (s, 2H), 6.82 (s, 1H), 6.57-5.95 (m, 1H), 3.81-3.61 (m, 2H), 3.30-3.24 (m, 1H), 3.23-3.15 (m, 1H), 3.10 (br t, J = 6.7 Hz, 3H), 2.87-2.79 (m, 3H), 2.79-2.62 (m, 4H), 2.38-2.25 (m, 1H), 2.02-1.90 (m, 2H), 1.89-1.69 (m, 1H).m/z: 556 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-[(3rel-S)-1,1-dioxo-1λ$^6$-thiolan-3-yl]-N-methylacetamide | | | |
| EXAMPLES 62 CPD0072800 | Procedure 3d | Intermediate 117 | Yield 28% |
| 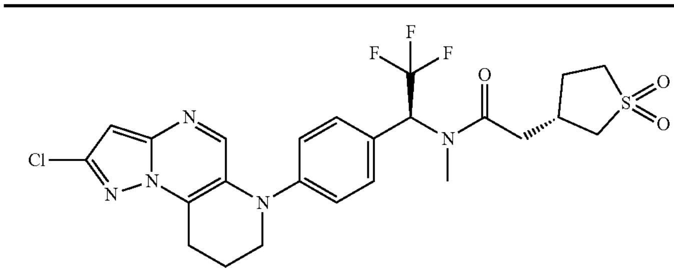 | $^1H$ NMR (500 MHz, DMSO-$d_6$) δ ppm 8.30 (s, 1H), 7.40-7.31 (m, 2H), 7.29-7.21 (m, 2H), 6.82 (s, 1H), 6.04 (br d, J = 7.8 Hz, 1H), 3.79-3.63 (m, 2H), 3.29-3.15 (m, 2H), 3.14-3.02 (m, 3H), 2.85 (s, 3H), 2.75 (br s, 4H), 2.38-2.24 (m, 1H), 2.06-1.91 (m, 2H), 1.89-1.71 (m, 1H). m/z: 556 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-[(3rel-R)-1,1-dioxo-1λ$^6$-thiolan-3-yl]-N-methylacetamide | | | |
| EXAMPLES 63 CPD0072798 | Procedure 3a | Intermediate 117 | Yield: 69% |
| 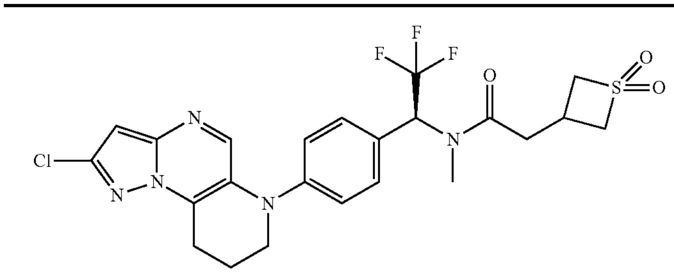 | $^1H$ NMR (500 MHz, DMSO-$d_6$) δ ppm 8.30 (s, 1H), 7.18-7.49 (m, 4H), 6.82 (s, 1H), 5.91-6.54 (m, 1H), 4.19-4.36 (m, 2H), 3.79-3.98 (m, 2H), 3.67-3.76 (m, 2H), 3.10 (t, J = 6.6 Hz, 2H), 2.96 (dd, J = 7.2, 2.6 Hz, 2H), 2.85 (s, 3H), 2.77-2.83 (m, 1H), 1.87-2.02 (m, 2H). m/z: 541 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1λ$^6$-thietan-3-yl)-N-methylacetamide | | | |

-continued

| EXAMPLES 64 CPD0072801 | Procedure 3b | Intermediate 117 | Yield 41% |
|---|---|---|---|
| 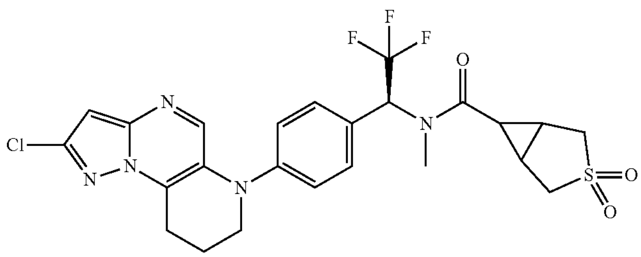 [SMILES: CN(C(=O)C1C2CS(=O)(=O)CC21)[C@@H](c1ccc(N2CCCc3c2cnc2cc(Cl)nn32)cc1)C(F)(F)F] | $^1$H NMR (600 MHz, DMSO-$d_6$) δ ppm 8.29-8.32 (m, 1H), 7.22-7.47 (m, 4H), 6.82 (s, 1H), 6.31-6.50 (m, 1H), 3.71 (br d, J = 3.2 Hz, 2H), 3.52-3.62 (m, 2H), 2.95-3.12 (m, 7H), 2.44 (t, J = 3.9 Hz, 1H), 2.14-2.22 (m, 2H), 1.93-1.99 (m, 2H). m/z: 554 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-3,3-dioxo-3λ$^6$-thiabicyclo[3.1.0]hexane-6-carboxamide | | | |

| EXAMPLES 65 CPD0072937 | Procedure 3a | Intermediate 117 | Yield: 34% |
|---|---|---|---|
| 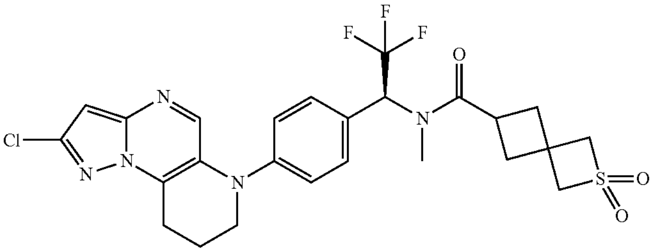 [SMILES: CN(C(=O)C1CC2(C1)CS(=O)(=O)C2)[C@@H](c1ccc(N2CCCc3c2cnc2cc(Cl)nn32)cc1)C(F)(F)F] | $^1$H NMR (600 MHz, DMSO-$d_6$) δ ppm 8.30 (s, 1H), 7.1-7.5 (m, 4H), 6.8-6.9 (m, 1H), 6.4-6.6 (m, 1H), 4.2-4.4 (m, 2H), 4.1-4.2 (m, 2H), 3.7-3.8 (m, 2H), 3.49 (quin, 1H, J = 8.5 Hz), 3.09 (t, 2H, J = 6.7 Hz), 2.76 (s, 3H), 2.4-2.6 (m, 4H), 1.9-2.0 (m, 2H). m/z: 568 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-2,2-dioxo-2λ$^6$-thiaspiro[3.3]heptane-6-carboxamide | | | |

| EXAMPLES 66 CPD0072938 | Procedure 3b | Intermediate 117 | Yield: 48% |
|---|---|---|---|
| 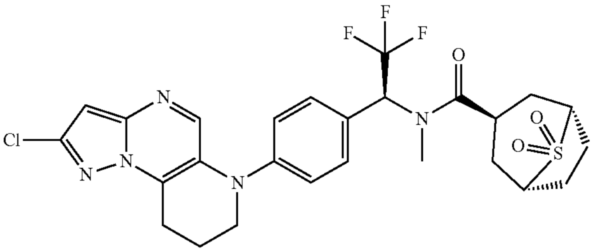 [SMILES: CN(C(=O)[C@@H]1C[C@H]2CC[C@@H](C1)S2(=O)=O)[C@@H](c1ccc(N2CCCc3c2cnc2cc(Cl)nn32)cc1)C(F)(F)F] | $^1$H NMR (600 MHz, DMSO-$d_6$) δ ppm 8.29 (s, 1H), 7.1-7.4 (m, 4H), 6.82 (s, 1H), 6.51 (q, 1H, J = 9.2 Hz), 3.71 (br dd, 2H, J = 3.7, 6.8 Hz), 3.10 (s, 5H), 2.96 (s, 3H), 2.3-2.4 (m, 2H), 1.9-2.2 (m, 8H). m/z: 582 $[M + H]^+$ | | |
| (1R,3R,5S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-8,8-dioxo-8λ$^6$-thiabicyclo[3.2.1]octane-3-carboxamide | | | |

| EXAMPLES 67 CPD0073085 | Procedure 3a | Intermediate 117 | Yield: 88% |
|---|---|---|---|
| 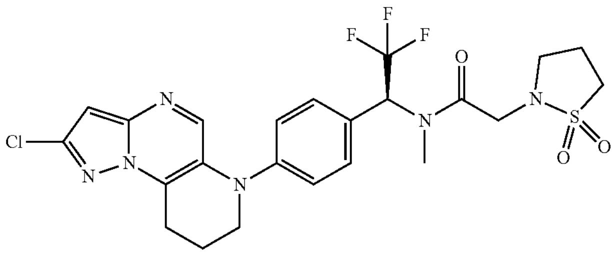 [SMILES: CN(C(=O)CN1CCCS1(=O)=O)[C@@H](c1ccc(N2CCCc3c2cnc2cc(Cl)nn32)cc1)C(F)(F)F] | $^1$H NMR (600 MHz, DMSO-$d_6$) δ ppm 8.36-8.17 (m, 1H), 7.33 (s, 2H), 7.26 (d, J = 8.7 Hz, 2H), 6.82 (s, 1H), 6.49-5.92 (m, 1H), 4.08 (s, 2H), 3.83-3.63 (m, 2H), 3.38-3.31 (m, 2H), 3.21 (t, J = 7.6 Hz, 2H), 3.14-3.03 (m, 2H), 2.87 (s, 3H), 2.33-2.23 (m, 2H), 2.02-1.89 (m, 2H).m/z: 557 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1λ$^6$,2-thiazolidin-2-yl)-N-methylacetamide | | | |

-continued

| EXAMPLES 68 CPD0073087 | Procedure 3a | Intermediate 117 | Yield: 69% |
|---|---|---|---|
| 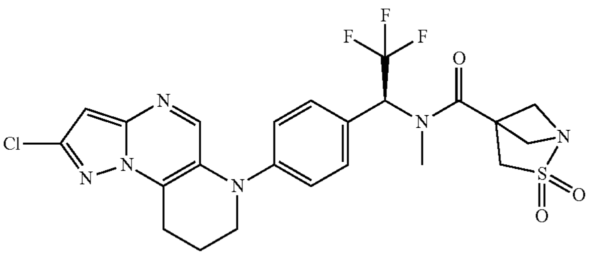 [SMILES: CN(C(=O)C12CN(C1)S(=O)(=O)C2)[C@@H](c1ccc(N2CCCc3c2cnc2cc(Cl)nn32)cc1)C(F)(F)F] | $^1$H NMR (500 MHz, DMSO-$d_6$) δ ppm 8.30 (s, 1H), 7.35 (s, 2H), 7.31-7.22 (m, 2H), 6.83 (s, 1H), 6.47-6.18 (m, 1H), 4.46-4.35 (m, 2H), 3.79-3.65 (m, 4H), 3.51-3.41 (m, 2H), 3.16-3.04 (m, 2H), 2.77 (s, 3H), 2.05-1.77 (m, 2H).m/z: 555 [M + H]$^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-2,2-dioxo-2λ$^6$-thia-1-azabicyclo[2.1.1]hexane-4-carboxamide | | | |

| EXAMPLES 69 CPD0073088 | Procedure 3b | Intermediate 117 | Yield: 81% |
|---|---|---|---|
| 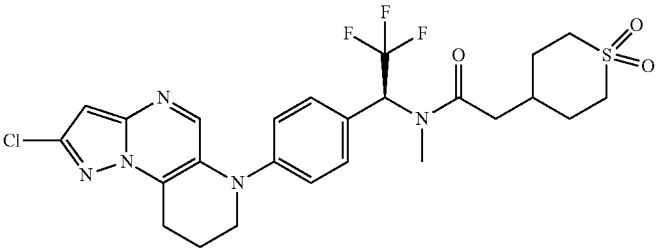 [SMILES: CN(C(=O)CC1CCS(=O)(=O)CC1)[C@@H](c1ccc(N2CCCc3c2cnc2cc(Cl)nn32)cc1)C(F)(F)F] | $^1$H NMR (600 MHz, DMSO-$d_6$) δ ppm 8.30 (s, 1H), 7.1-7.5 (m, 4H), 6.82 (s, 1H), 6.52 (q, 1H, J = 9.4 Hz), 3.6-3.8 (m, 2H), 3.1-3.2 (m, 4H), 3.0-3.1 (m, 2H), 2.86 (s, 3H), 2.50 (td, 2H, J = 1.8, 3.7 Hz), 2.1-2.3 (m, 1H), 1.9-2.1 (m, 4H), 1.6-1.8 (m, 2H).m/z: 570 [M + H]$^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1)6-thian-4-yl)-N-methylacetamide | | | |

| EXAMPLES 70 CPD0073089 | Procedure 3b | Intermediate 117 | Yield: Quant. |
|---|---|---|---|
| 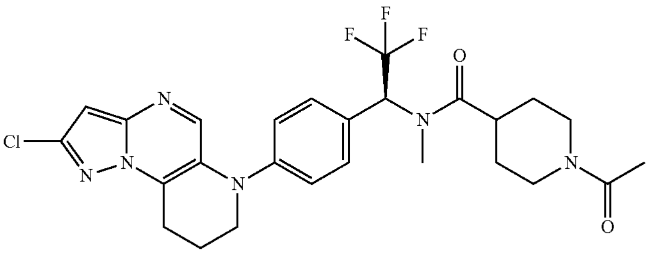 [SMILES: CC(=O)N1CCC(C(=O)N(C)[C@@H](c2ccc(N3CCCc4c3cnc3cc(Cl)nn43)cc2)C(F)(F)F)CC1] | $^1$H NMR (600 MHz, DMSO-$d_6$) δ ppm 8.30 (s, 1H), 7.2-7.5 (m, 4H), 6.82 (s, 1H), 6.4-6.6 (m, 1H), 4.37 (br d, 1H, J = 13.1 Hz), 3.83 (br dd, 1H, J = 3.7, 9.7 Hz), 3.6-3.8 (m, 2H), 3.10 (br t, 3H, J = 6.7 Hz), 3.01 (tt, 1H, J = 3.7, 11.2 Hz), 2.93 (s, 3H), 2.5-2.6 (m, 1H), 1.9-2.1 (m, 5H), 1.6-1.8 (m, 2H), 1.5-1.6 (m, 1H), 1.3-1.4 (m, 1H). m/z: 549 [M + H]$^+$ | | |
| 1-acetyl-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylpiperidine-4-carboxamide | | | |

| EXAMPLES 71 CPD0073141 | Procedure 3a-d | Intermediate 117 | Yield: 26% |
|---|---|---|---|
| 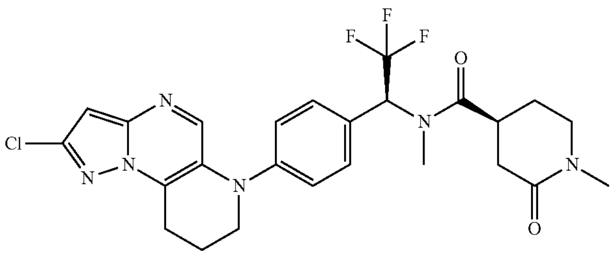 [SMILES: CN1CC[C@H](C(=O)N(C)[C@@H](c2ccc(N3CCCc4c3cnc3cc(Cl)nn43)cc2)C(F)(F)F)CC1=O] | $^1$H NMR (600 MHz, DMSO-$d_6$) δ ppm 8.30 (s, 1H), 7.1-7.5 (m, 4H), 6.82 (s, 1H), 6.4-6.6 (m, 1H), 3.6-3.8 (m, 2H), 3.30 (s, 3H), 3.10 (t, 2H, J = 6.7 Hz), 2.92 (s, 3H), 2.80 (s, 3H), 2.2-2.4 (m, 2H), 1.7-2.1 (m, 4H). m/z: 535 [M + H]$^+$ | | |
| (4rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-2-oxopiperidine-4-carboxamide | | | |

-continued

| EXAMPLES 72 CPD0073142 | Procedure 3a-d | Intermediate 117 | Yield: 32% |
|---|---|---|---|
| 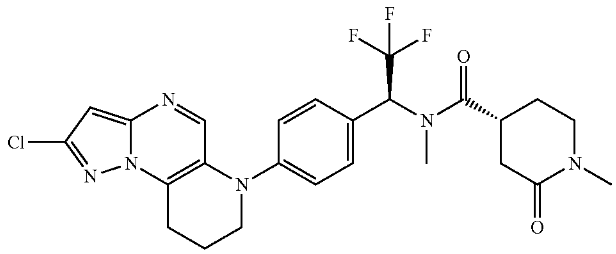 [SMILES: CN1CC[C@@H](C(=O)N(C)[C@@H](c2ccc(N3CCCc4c3cnc3cc(Cl)nn43)cc2)C(F)(F)F)CC1=O] | $^1$H NMR (600 MHz, DMSO-$d_6$) δ ppm 8.31 (s, 1H), 7.30-7.41 (m, 2H), 7.23-7.30 (m, 2H), 6.82 (s, 1H), 6.14-6.59 (m, 1H), 3.67-3.75 (m, 2H), 3.32-3.39 (m, 2H), 3.20 (dt, J = 12.1, 5.3 Hz, 1H), 3.10 (t, J = 6.7 Hz, 2H), 2.92 (s, 3H), 2.80 (s, 3H), 2.23-2.42 (m, 2H), 1.92-2.06 (m, 3H), 1.72-1.87 (m, 1H). m/z: 535 [M + H]$^+$ | | |
| (4rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-2-oxopiperidine-4-carboxamide | | | |
| EXAMPLES 73 CPD0073143 | Procedure 3b-d | Intermediate 136 | Yield: 27% |
| 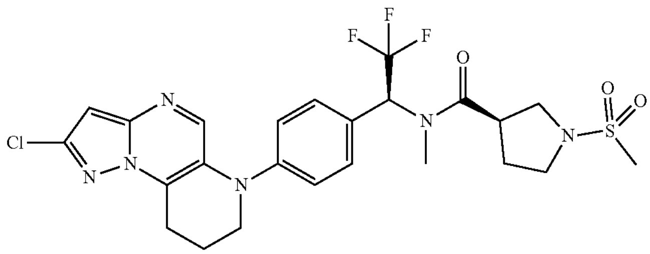 [SMILES: CN(C(=O)[C@@H]1CCN(S(C)(=O)=O)C1)[C@@H](c1ccc(N2CCCc3c2cnc2cc(Cl)nn32)cc1)C(F)(F)F] | $^1$H NMR (600 MHz, DMSO-$d_6$) δ ppm 8.31 (s, 1H), 7.21-7.43 (m, 4H), 6.82 (s, 1H), 6.15-6.56 (m, 1H), 3.69-3.74 (m, 2H), 3.56-3.62 (m, 2H), 3.32-3.43 (m, 2H), 3.25-3.30 (m, 1H), 3.10 (t, J = 6.7 Hz, 2H), 2.92 (s, 6H), 2.14-2.21 (m, 1H), 1.94-2.07 (m, 3H). m/z: 571 [M + H]$^+$ | | |
| (3rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-methanesulfonyl-N-methylpyrrolidine-3-carboxamide | | | |
| EXAMPLES 74 CPD0073144 | Procedure 3b-d | Intermediate 136 | Yield: 26% |
| 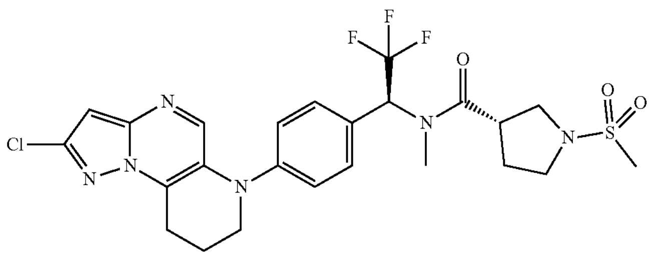 [SMILES: CN(C(=O)[C@H]1CCN(S(C)(=O)=O)C1)[C@@H](c1ccc(N2CCCc3c2cnc2cc(Cl)nn32)cc1)C(F)(F)F] | $^1$H NMR (600 MHz, DMSO-$d_6$) δ ppm 8.30 (s, 1H), 7.24-7.41 (m, 4H), 6.82 (s, 1H), 6.17-6.56 (m, 1H), 3.69-3.74 (m, 2H), 3.59 (quin, J = 7.3 Hz, 1H), 3.46-3.51 (m, 1H), 3.31-3.43 (m, 2H), 3.24-3.29 (m, 1H), 3.10 (t, J = 6.7 Hz, 2H), 2.91-2.96 (m, 6H), 2.20-2.30 (m, 1H), 1.90-2.02 (m, 3H) m/z: 571 [M + H]$^+$ | | |
| (3rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-methanesulfonyl-N-methylpyrrolidine-3-carboxamide | | | |
| EXAMPLES 75 CPD0073188 | Procedure 3b-d | Intermediate 136 | Yield: 34% |
| 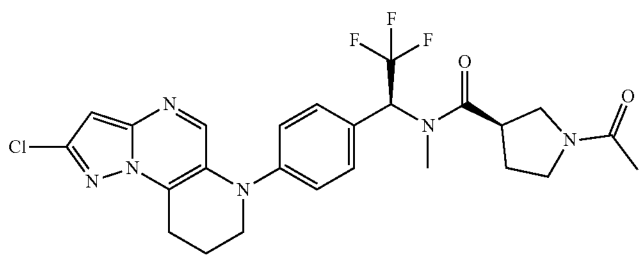 [SMILES: CC(=O)N1CC[C@@H](C(=O)N(C)[C@@H](c2ccc(N3CCCc4c3cnc3cc(Cl)nn43)cc2)C(F)(F)F)C1] | $^1$H NMR (600 MHz, DMSO-$d_6$) δ ppm 8.31 (s, 1H), 7.34-7.29 (m, 2H), 7.28-7.24 (m, 2H), 6.82 (s, 1H), 6.60-6.14 (m, 1H), 3.80-3.63 (m, 3H), 3.61-3.38 (m, 3H), 3.37-3.31 (m, 1H), 3.10 (t, J = 6.7 Hz, 2H), 2.93 (d, J = 9.4 Hz, 3H), 2.18-1.84 (m, 7H). m/z: 535 [M + H]$^+$ | | |
| (3rel-R)-1-acetyl-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylpyrrolidine-3-carboxamide | | | |

-continued

| EXAMPLES 76 CPD0073189 | Procedure 3b-d | Intermediate 136 | Yield: 27% |
|---|---|---|---|
| 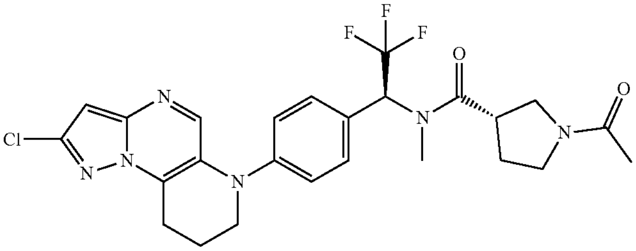 [SMILES: CC(=O)N1CC[C@H](C(=O)N(C)[C@@H](c2ccc(N3CCCc4c3cnc3cc(Cl)nn43)cc2)C(F)(F)F)C1] | $^{1}H$ NMR (600 MHz, DMSO-$d_6$) δ ppm 8.21-8.39 (m, 1H), 7.19-7.46 (m, 4H), 6.73-6.93 (m, 1H), 6.17-6.56 (m, 1H), 3.70-3.76 (m, 2H), 3.36-3.69 (m, 5H), 3.06-3.14 (m, 2H), 2.88-2.98 (m, 3H), 2.11-2.27 (m, 1H), 1.79-2.05 (m, 6H) m/z: 535 $[M + H]^+$ | | |
| (3rel-S)-1-acetyl-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylpyrrolidine-3-carboxamide | | | |
| EXAMPLES 77 CPD0073196 | Procedure 3b-d | Intermediate 117 | Yield: 21% |
| 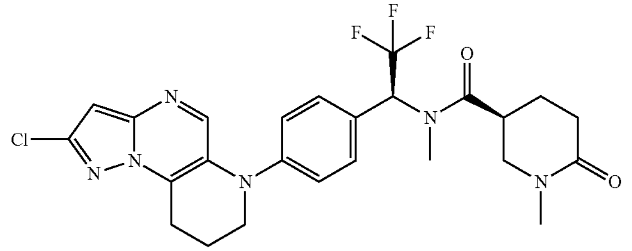 [SMILES: CN1C[C@@H](C(=O)N(C)[C@@H](c2ccc(N3CCCc4c3cnc3cc(Cl)nn43)cc2)C(F)(F)F)CCC1=O] | $^{1}H$ NMR (600 MHz, DMSO-$d_6$) δ ppm 8.30 (s, 1H), 7.24-7.39 (m, 4H), 6.82 (s, 1H), 6.22-6.56 (m, 1H), 3.68-3.75 (m, 2H), 3.43-3.58 (m, 1H), 3.31-3.35 (m, 2H), 3.10 (t, J = 6.7 Hz, 2H), 2.95 (s, 3H), 2.83 (s, 1H), 2.81 (s, 2H), 2.30-2.38 (m, 1H), 2.20-2.26 (m, 1H), 1.92-1.99 (m, 3H), 1.78-1.89 (m, 1H) m/z: 535 $[M + H]^+$ | | |
| (3rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-6-oxopiperidine-3-carboxamide | | | |
| EXAMPLES 78 CPD0073197 | Procedure 3b-d | Intermediate 117 | Yield: 13% |
| 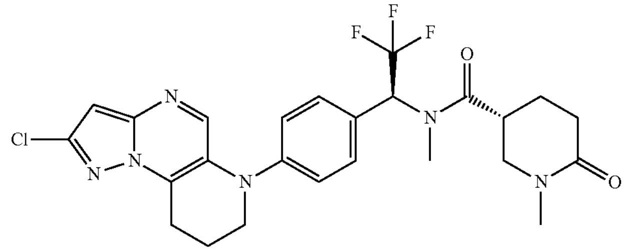 [SMILES: CN1C[C@H](C(=O)N(C)[C@@H](c2ccc(N3CCCc4c3cnc3cc(Cl)nn43)cc2)C(F)(F)F)CCC1=O] | $^{1}H$ NMR (600 MHz, DMSO-$d_6$) δ ppm 8.30 (s, 1H), 7.24-7.41 (m, 4H), 6.82 (s, 1H), 6.25-6.58 (m, 1H), 3.68-3.75 (m, 2H), 3.38-3.46 (m, 2H), 3.31-3.35 (m, 1H), 3.10 (t, J = 6.7 Hz, 2H), 2.95 (s, 3H), 2.78-2.84 (m, 3H), 2.22-2.38 (m, 2H), 1.93-1.98 (m, 2H), 1.77-1.91 (m, 2H) m/z: 535 $[M + H]^+$ | | |
| (3rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-6-oxopiperidine-3-carboxamide | | | |
| EXAMPLES 79 CPD0073237 | Procedure 3a | Intermediate 117 and 226 | Yield: 96% |
| 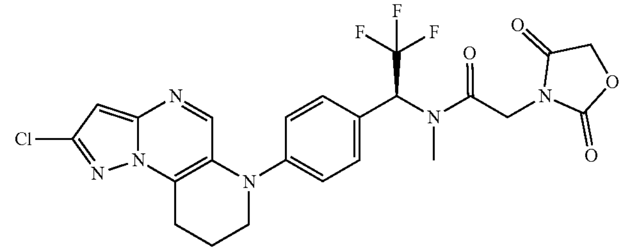 [SMILES: CN(C(=O)CN1C(=O)COC1=O)[C@@H](c1ccc(N2CCCc3c2cnc2cc(Cl)nn32)cc1)C(F)(F)F] | $^{1}H$ NMR (600 MHz, DMSO-$d_6$) δ ppm 8.30-8.33 (m, 1H), 7.22-7.47 (m, 4H), 6.82 (s, 1H), 6.14-6.41 (m, 1H), 5.03-5.06 (m, 2H), 4.58 (d, J = 3.4 Hz, 1H), 3.69-3.76 (m, 2H), 3.10 (t, J = 6.7 Hz, 2H), 2.98 (s, 3H), 2.51-2.52 (m, 1H), 1.92-1.99 (m, 2H). m/z: 537 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(2,4-dioxo-1,3-oxazolidin-3-yl)-N-methylacetamide | | | |

-continued

| EXAMPLES 80 CPD0073238 | Procedure 3b | Intermediate 117 | Yield: 79% |
|---|---|---|---|
| 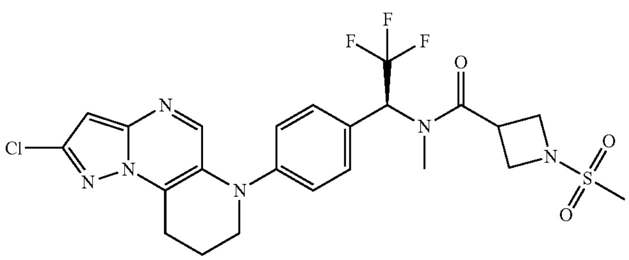 [SMILES: CN(C(=O)C1CN(S(C)(=O)=O)C1)[C@@H](c1ccc(N2CCCc3c2cnc2cc(Cl)nn32)cc1)C(F)(F)F] | $^1$H NMR (600 MHz, DMSO-$d_6$) δ ppm 8.29-8.31 (m, 1H), 7.19-7.44 (m, 4H), 6.81-6.83 (m, 1H), 5.75-6.57 (m, 1H), 3.96-4.15 (m, 4H), 3.88-3.94 (m, 1H), 3.68-3.75 (m, 2H), 3.10 (t, J = 6.7 Hz, 2H), 2.99-3.02 (m, 3H), 2.71-2.76 (m, 3H), 1.93-1.99 (m, 2H). m/z: 557 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-methanesulfonyl-N-methylazetidine-3-carboxamide

| EXAMPLES 81 CPD0073243 | Procedure 3a Intermediate 117 | | Yield: 66% |
|---|---|---|---|
| 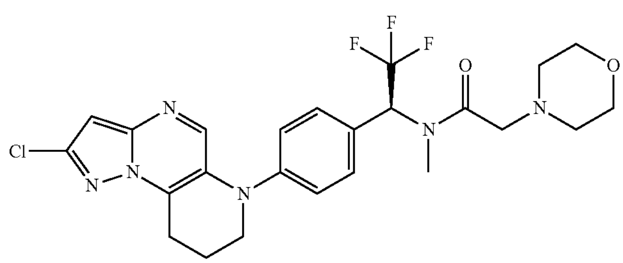 [SMILES: CN(C(=O)CN1CCOCC1)[C@@H](c1ccc(N2CCCc3c2cnc2cc(Cl)nn32)cc1)C(F)(F)F] | $^1$H NMR (600 MHz, DMSO-$d_6$) δ ppm 8.30 (s, 1 H), 7.29-7.35 (m, 2 H), 7.27 (s, 2 H), 6.82 (s, 1 H), 6.40-6.53 (m, 1 H), 3.67-3.76 (m, 2 H), 3.49-3.65 (m, 4 H), 3.34-3.41 (m, 1 H), 3.29 (s, 1 H), 3.10 (t, J = 6.7 Hz, 2 H), 2.92 (s, 3 H), 2.46 (br d, J = 2.3 Hz, 4 H), 1.91-2.05 (m, 2 H). m/z: 523 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-2-(morpholin-4-yl)acetamide

| EXAMPLES 82 CPD0073572 | Procedure 3b | Intermediate 117 | Yield: 50% |
|---|---|---|---|
| 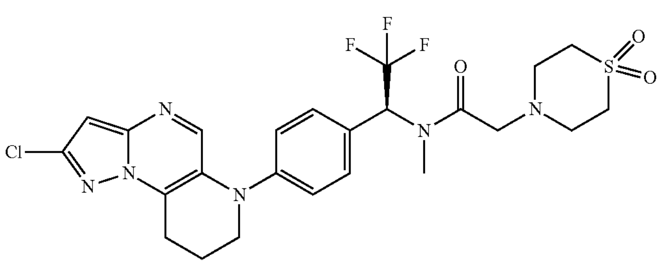 [SMILES: CN(C(=O)CN1CCS(=O)(=O)CC1)[C@@H](c1ccc(N2CCCc3c2cnc2cc(Cl)nn32)cc1)C(F)(F)F] | $^1$H NMR (600 MHz, DMSO-$d_6$) δ ppm 8.30 (s, 1H), 7.19-7.50 (m, 4H), 6.82 (s, 1H), 6.03-6.57 (m, 1H), 3.69-3.75 (m, 2H), 3.57-3.68 (m, 2H), 2.93-3.19 (m, 10H), 2.87 (s, 3H), 1.91-2.00 (m, 2H). m/z: 571 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1λ$^6$-thiomorpholin-4-yl)-N-methylacetamide

| EXAMPLES 83 CPD0073499 | Procedure 3b-e | Intermediate 117 | Yield: 13% |
|---|---|---|---|
| 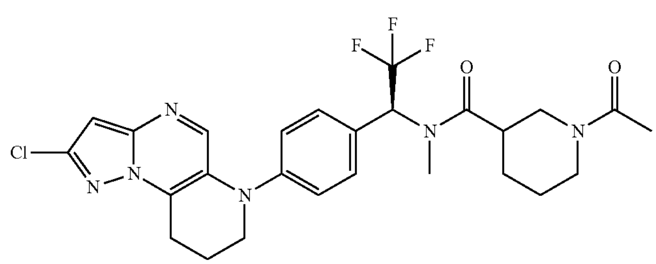 [SMILES: CC(=O)N1CCCC(C(=O)N(C)[C@@H](c2ccc(N3CCCc4c3cnc3cc(Cl)nn43)cc2)C(F)(F)F)C1] | $^1$H NMR (500 MHz, DMSO-$d_6$) δ ppm 8.31 (d, J = 13.4 Hz, 1H), 7.15-7.54 (m, 4H), 6.82 (d, J = 2.2 Hz, 1H), 6.07-6.64 (m, 1H), 4.17-4.49 (m, 1H), 3.61-3.85 (m, 3H), 2.99-3.26 (m, 3H), 2.85-2.97 (m, 3H), | | |

(3rel-R)-1-acetyl-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylpiperidine-3-carboxamide -continued

| EXAMPLES 84 CPD0073500 | Procedure 3b-e | Intermediate 117 | Yield: 12% |
|---|---|---|---|
| 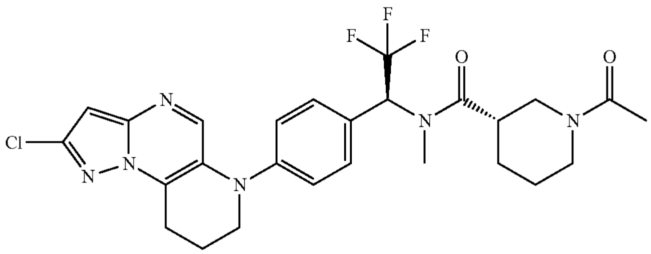 [SMILES: CC(=O)N1CCC[C@H](C(=O)N(C)[C@@H](c2ccc(N3CCCc4c3cnc3cc(Cl)nn43)cc2)C(F)(F)F)C1] | $^{1}H$ NMR (500 MHz, DMSO-$d_6$) δ ppm 8.31 (s, 1H), 7.16-7.56 (m, 4H), 6.82 (s, 1H), 6.11-6.56 (m, 1H), 4.21-4.48 (m, 1H), 3.65-3.86 (m, 3H), 3.10 (t, J = 6.7 Hz, 2H), 2.98-3.06 (m, 1H), 2.92 (d, J = 6.1 Hz, 3H), 2.69-2.77 (m, 1H), 2.54-2.62 (m, 1H), 1.98-2.09 (m, 3H), 1.93-1.98 (m, 2H), 1.76-1.90 (m, 1H), 1.41-1.74 (m, 3H). m/z: 549 $[M + H]^+$ | | |
| (3rel-S)-1-acetyl-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylpiperidine-3-carboxamide | | | |
| EXAMPLES 85 CPD0073501 | Procedure 3b | Intermediate 117 | Yield: 43% |
| 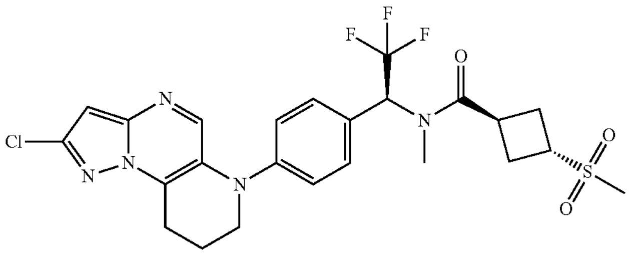 [SMILES: CN(C(=O)[C@H]1C[C@H](S(C)(=O)=O)C1)[C@@H](c1ccc(N2CCCc3c2cnc2cc(Cl)nn32)cc1)C(F)(F)F] | $^{1}H$ NMR (600 MHz, DMSO-$d_6$) δ ppm 8.30 (s, 1H), 7.2-7.5 (m, 4H), 6.8-6.9 (m, 1H), 6.45 (q, 1H, J = 9.5 Hz), 3.8-4.0 (m, 1H), 3.7-3.8 (m, 2H), 3.51 (t, 1H, J = 8.9 Hz), 3.10 (t, 2H, J = 6.7 Hz), 2.9-3.0 (m, 3H), 2.7-2.8 (m, 3H), 2.50 (td, 4H, J = 1.8, 3.7 Hz), 1.9-2.0 (m, 2H). m/z: 556 $[M + H]^+$ | | |
| trans-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-methanesulfonyl-N-methylcyclobutane-1-carboxamide | | | |
| EXAMPLES 86 CPD0073502 | Procedure 3b | Intermediate 117 | Yield: 17% |
| 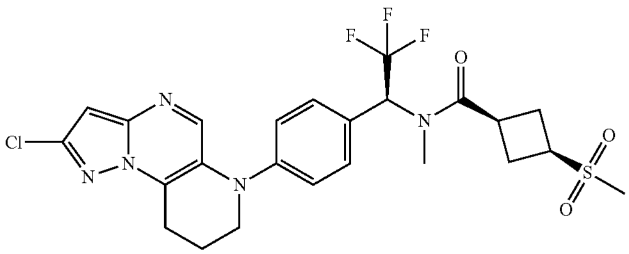 [SMILES: CN(C(=O)[C@H]1C[C@@H](S(C)(=O)=O)C1)[C@@H](c1ccc(N2CCCc3c2cnc2cc(Cl)nn32)cc1)C(F)(F)F] | $^{1}H$ NMR (600 MHz, DMSO-$d_6$) δ ppm 8.30 (s, 1H), 7.2-7.5 (m, 4H), 6.82 (s, 1H), 6.49 (br d, 1H, J = 9.1 Hz), 3.8-4.0 (m, 1H), 3.6-3.8 (m, 2H), 3.5-3.6 (m, 1H), 3.10 (t, 2H, J = 6.7 Hz), 2.9-3.0 (m, 3H), 2.7-2.8 (m, 3H), 2.5-2.7 (m, 4H), 1.9-2.0 (m, 2H) m/z: 556 $[M + H]^+$ | | |
| cis-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-methanesulfonyl-N-methylcyclobutane-1-carboxamide | | | |
| EXAMPLES 87 CPD0073553 | Procedure 3b | Intermediate 117 | Yield: 23% |
| 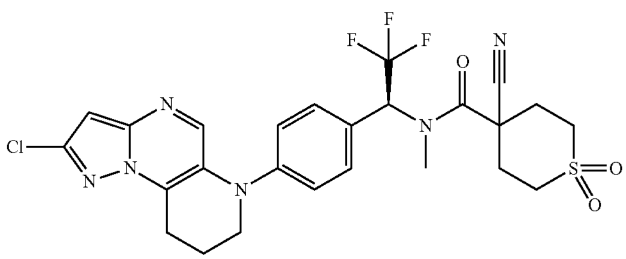 [SMILES: CN(C(=O)C1(C#N)CCS(=O)(=O)CC1)[C@@H](c1ccc(N2CCCc3c2cnc2cc(Cl)nn32)cc1)C(F)(F)F] | $^{1}H$ NMR (600 MHz, DMSO-$d_6$) δ ppm 8.32 (s, 1H), 7.38 (d, 2H, J = 8.5 Hz), 7.28 (d, 2H, J = 8.8 Hz), 6.82 (s, 1H), 6.50 (br d, 1H, J = 8.7 Hz), 3.6-3.9 (m, 2H), 3.3-3.4 (m, 2H), 3.30 (s, 5H), 3.0-3.2 (m, 2H), 2.6-2.7 (m, 2H), 2.5-2.6 (m, 2H), 1.9-2.0 (m, 2H). m/z: 581 $[M + H]^+$ | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-4-cyano-N-methyl-1,1-dioxo-1λ$^6$-thiane-4-carboxamide | | | |

-continued

| EXAMPLES 88 CPD0073556 | Procedure 3b-f | Intermediate 117 | Yield: 38% |
|---|---|---|---|
| 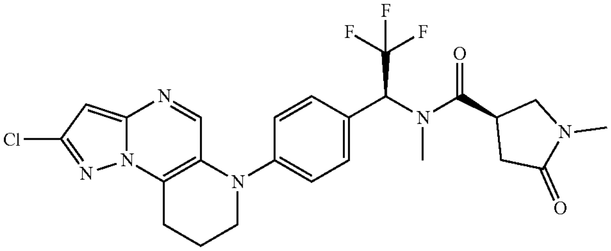 [SMILES: CN1C[C@H](C(=O)N(C)[C@@H](c2ccc(N3CCCc4c3cnc3cc(Cl)nn43)cc2)C(F)(F)F)CC1=O] | $^1$H NMR (600 MHz, DMSO-$d_6$) δ ppm 8.31 (s, 1H), 7.22-7.43 (m, 4H), 6.82 (s, 1H), 6.11-6.56 (m, 1H), 3.60-3.97 (m, 4H), 3.32-3.47 (m, 1H), 3.10 (t, J = 6.7 Hz, 2H), 2.89 (s, 2H), 2.72 (s, 3H), 2.71 (br s, 1H), 2.51-2.55 (m, 1H), 2.44-2.48 (m, 1H), 1.93-1.99 (m, 2H). m/z: 521 $[M + H]^+$ | | |
| (3rel-R)-N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N,1-dimethyl-5-oxopyrrolidine-3-carboxamide | | | |
| EXAMPLES 89 CPD0073557 | Procedure 3b-f | Intermediate 117 | Yield: 26% |
| 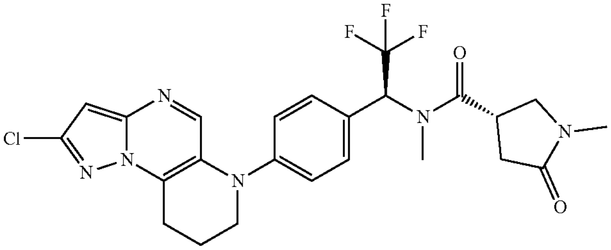 [SMILES: CN1C[C@@H](C(=O)N(C)[C@@H](c2ccc(N3CCCc4c3cnc3cc(Cl)nn43)cc2)C(F)(F)F)CC1=O] | $^1$H NMR (600 MHz, DMSO-$d_6$) δ ppm 8.30 (s, 1H), 8.11-8.48 (m, 1H), 7.17-7.45 (m, 4H), 6.82 (s, 1H), 6.09-6.56 (m, 1H), 3.63-4.04 (m, 3H), 3.57 (t, J = 9.2 Hz, 1H), 3.43-3.52 (m, 1H), 3.10 (t, J = 6.7 Hz, 2H), 2.89 (s, 2H), 2.70-2.74 (m, 3H), 2.60-2.66 (m, 1H), 2.33-2.44 (m, 1H), 1.93-1.99 (m, 2H) m/z: 521 $[M + H]^+$ | | |
| (3rel-S)-N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N,1-dimethyl-5-oxopyrrolidine-3-carboxamide | | | |
| EXAMPLES 90 CPD0073560 | Procedure 3c-e | Intermediate 117 | Yield: 44% |
| 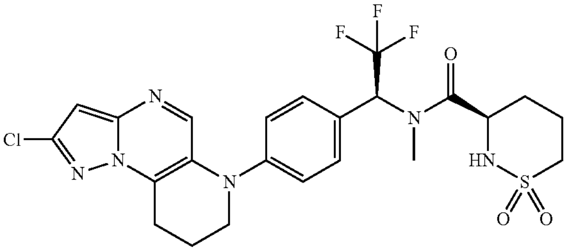 [SMILES: CN(C(=O)[C@H]1CCCS(=O)(=O)N1)[C@@H](c1ccc(N2CCCc3c2cnc2cc(Cl)nn32)cc1)C(F)(F)F] | $^1$H NMR (600 MHz, DMSO-$d_6$) δ ppm 8.32 (s, 1H), 7.33 (s, 2H), 7.30-7.24 (m, 2H), 6.87-6.83 (m, 1H), 6.82 (s, 1H), 6.58-6.06 (m, 1H), 4.41 (td, J = 11.0, 2.4 Hz, 1H), 3.82-3.65 (m, 2H), 3.18 (dt, J = 13.4, 3.6 Hz, 1H), 3.12-3.06 (m, 2H), 3.00-2.73 (m, 4H), 2.25-2.00 (m, 2H), 1.99-1.89 (m, 2H), 1.84-1.53 (m, 2H). m/z: 557 $[M + H]^+$ | | |
| (3rel-R)-N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N-methyl-1,1-dioxo-1$\lambda^6$,2-thiazinane-3-carboxamide | | | |
| EXAMPLES 91 CPD0073568 | Procedure 3d | Intermediate 117 | Yield: 4% |
| 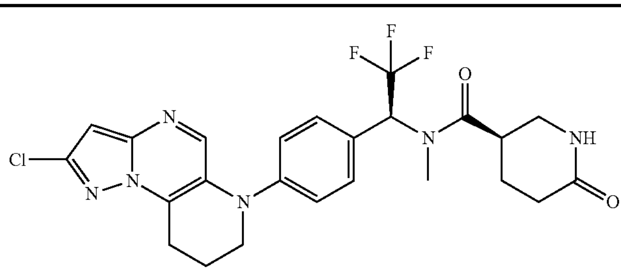 | $^1$H NMR (600 MHz, DMSO-$d_6$) δ ppm 8.30 (s, 1H), 7.48 (br s, 1H), 7.2-7.4 (m, 4H), 6.82 (s, 1H), 6.50 (q, 1H, J = 9.2 Hz), 3.6-3.8 (m, 2H), 3.1-3.4 (m, 9H), 3.10 (t, 2H, J = 6.7 Hz), 2.94 (s, 3H). m/z: 521 $[M + H]^+$ | | |
| (3rel-R)-N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-N-methyl-6-oxopiperidine-3-carboxamide | | | |

-continued

| EXAMPLES 92 CPD0073569 | Procedure 3d | Intermediate 117 | Yield: 4% |
|---|---|---|---|
| 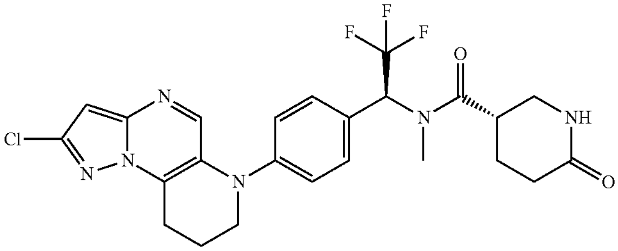 [SMILES: CN(C(=O)[C@H]1CCC(=O)NC1)[C@@H](c1ccc(N2CCCc3c2cnc2cc(Cl)nn32)cc1)C(F)(F)F] | $^{1}H$ NMR (600 MHz, DMSO-$d_6$) δ ppm 8.30 (s, 1H), 7.4-7.7 (m, 1H), 7.2-7.4 (m, 4H), 6.82 (s, 1H), 6.4-6.6 (m, 1H), 3.6-3.8 (m, 2H), 3.30 (s, 3H), 3.10 (t, 2H, J = 6.7 Hz), 2.94 (s, 3H), 2.1-2.3 (m, 2H), 1.6-2.0 (m, 4H). m/z: 521 $[M + H]^+$ | | |
| (3rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-6-oxopiperidine-3-carboxamide | | | |
| EXAMPLES 93 CPD0073570 | Procedure 3b-e | Intermediate 117 | Yield: 5% |
| 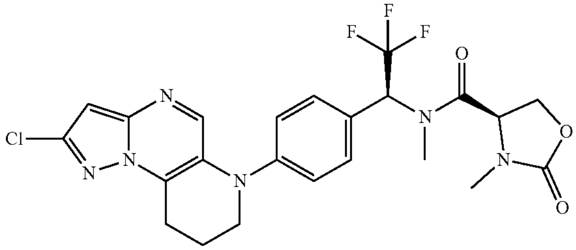 [SMILES: CN1C(=O)OC[C@@H]1C(=O)N(C)[C@@H](c1ccc(N2CCCc3c2cnc2cc(Cl)nn32)cc1)C(F)(F)F] | $^{1}H$ NMR (600 MHz, DMSO-$d_6$) δ ppm 8.30 (s, 1H), 7.37 (d, 2H, J = 8.7 Hz), 7.28 (d, 2H, J = 8.8 Hz), 6.82 (s, 1H), 6.46 (q, 1H, J = 9.0 Hz), 5.02 (dd, 1H, J = 4.3, 9.2 Hz), 4.59 (t, 1H, J = 9.1 Hz), 4.03 (dd, 1H, J = 4.2, 8.9 Hz), 3.6-3.8 (m, 2H), 3.10 (t, 2H, J = 6.7 Hz), 2.86 (s, 3H), 2.76 (s, 3H), 1.9-2.1 (m, 2H). m/z: 523 $[M + H]^+$ | | |
| (4rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,3-dimethyl-2-oxo-1,3-oxazolidine-4-carboxamide | | | |
| EXAMPLES 94 CPD0073571 | Procedure 3b-e | Intermediate 117 | Yield: 10% |
| 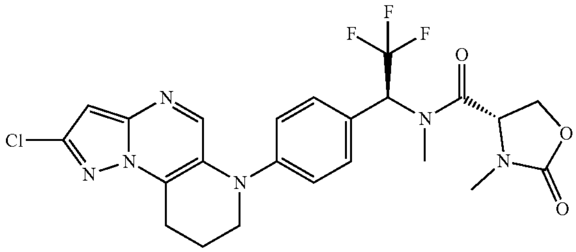 [SMILES: CN(C(=O)[C@@H]1COC(=O)N1C)[C@@H](c1ccc(N2CCCc3c2cnc2cc(Cl)nn32)cc1)C(F)(F)F] | $^{1}H$ NMR (600 MHz, DMSO-$d_6$) δ ppm 8.30 (s, 1H), 7.37 (d, 2H, J = 8.7 Hz), 7.28 (d, 2H, J = 8.8 Hz), 6.82 (s, 1H), 6.46 (q, 1H, J = 9.0 Hz), 5.02 (dd, 1H, J = 4.3, 9.2 Hz), 4.59 (t, 1H, J = 9.1 Hz), 4.03 (dd, 1H, J = 4.2, 8.9 Hz), 3.6-3.8 (m, 2H), 3.10 (t, 2H, J = 6.7 Hz), 2.86 (s, 3H), 2.76 (s, 3H), 1.9-2.1 (m, 2H). m/z: 523 $[M + H]^+$ | | |
| (4rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,3-dimethyl-2-oxo-1,3-oxazolidine-4-carboxamide | | | |
| EXAMPLES 95 CPD0073691 | Procedure 3b | Intermediate 117 | Yield: 47% |
| 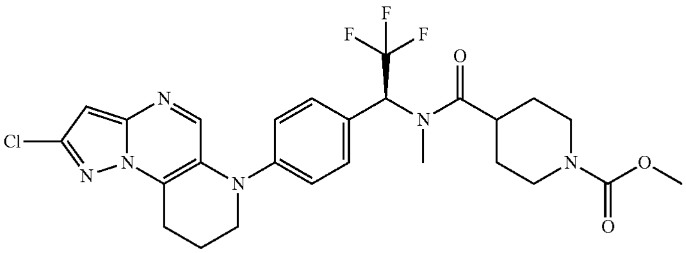 [SMILES: COC(=O)N1CCC(C(=O)N(C)[C@@H](c2ccc(N3CCCc4c3cnc3cc(Cl)nn43)cc2)C(F)(F)F)CC1] | $^{1}H$ NMR (600 MHz, DMSO-$d_6$) δ ppm 8.31 (s, 1H), 7.1-7.5 (m, 4H), 6.7-6.9 (m, 1H), 6.3-6.5 (m, 1H), 5.03 (dd, 1H, J = 4.3, 9.2 Hz), 4.49 (t, 1H, J = 9.0 Hz), 4.10 (dd, 1H, J = 4.3, 8.9 Hz), 3.6-3.8 (m, 2H), 3.10 (t, 2H, J = 6.7 Hz), 2.86 (s, 3H), 2.75 (s, 3H), 1.9-2.1 (m, 2H). m/z: 565 $[M + H]^+$ | | |
| methyl 4-{[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl](methyl) carbamoyl}piperidine-1-carboxylate | | | |

-continued

| EXAMPLES 96 CPD0073919 | Procedure 3b-e | Intermediate 117 | Yield: 40% |
|---|---|---|---|
| 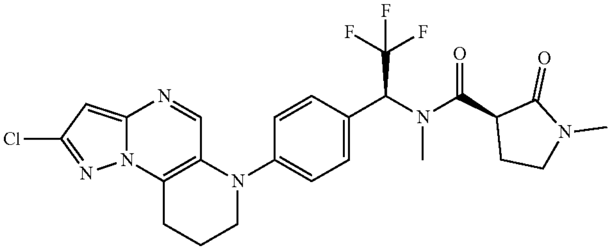 [SMILES: CN1CC[C@@H](C(=O)N(C)[C@@H](c2ccc(N3CCCc4c3cnc3cc(Cl)nn43)cc2)C(F)(F)F)C1=O] | $^1H$ NMR (500 MHz, DMSO-$d_6$) δ ppm 8.65-8.16 (m, 1H), 7.28 (s, 4H), 6.88-6.79 (m, 1H), 6.48 (br t, J = 9.2 Hz, 1H), 5.10-4.64 (m, 1H), 3.82-3.63 (m, 2H), 3.10 (t, J = 6.6 Hz, 2H), 2.90 (d, J = 13.0 Hz, 3H), 2.66 (d, J = 4.2 Hz, 3H), 2.45-2.28 (m, 1H), 2.25 (s, 2H), 1.96 (br s, 2H), 1.82-1.68 (m, 1H). m/z: 521 $[M + H]^+$ | | |

(2S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-5-oxopyrrolidine-2-carboxamide

| EXAMPLES 97 CPD0073920 | Procedure 3a-e | Intermediate 117 | Yield: 39% |
|---|---|---|---|
| 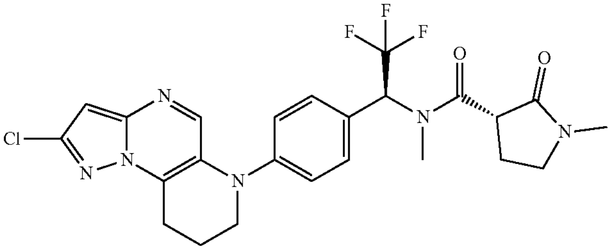 [SMILES: CN1CC[C@H](C(=O)N(C)[C@@H](c2ccc(N3CCCc4c3cnc3cc(Cl)nn43)cc2)C(F)(F)F)C1=O] | $^1H$ NMR (500 MHz, DMSO-$d_6$) δ ppm 8.37-8.25 (m, 1H), 7.45-7.18 (m, 4H), 6.82 (s, 1H), 6.54-6.10 (m, 1H), 4.82-4.62 (m, 1H), 3.88-3.61 (m, 2H), 3.15-3.04 (m, 2H), 2.95-2.70 (m, 3H), 2.68-2.58 (m, 3H), 2.45-2.29 (m, 1H), 2.25 (s, 2H), 2.03-1.91 (m, 2H), 1.84-1.68 (m, 1H). m/z: 521 $[M + H]^+$ | | |

(2R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,1-dimethyl-5-oxopyrrolidine-2-carboxamide

| EXAMPLES 98 CPD0073921 | Procedure 3b-d | Intermediate 117 | Yield: 19% |
|---|---|---|---|
| 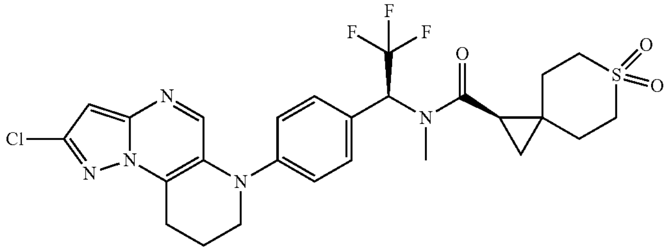 [SMILES: CN(C(=O)[C@@H]1CC12CCS(=O)(=O)CC2)[C@@H](c1ccc(N2CCCc3c2cnc2cc(Cl)nn32)cc1)C(F)(F)F] | $^1H$ NMR (600 MHz, DMSO-$d_6$) δ ppm 8.31 (s, 1H), 7.1-7.5 (m, 4H), 6.82 (s, 1H), 6.54 (q, 1H, J = 9.4 Hz), 3.6-3.8 (m, 2H), 3.0-3.2 (m, 6H), 2.98 (s, 3H), 2.19 (dd, 1H, J = 5.4, 7.8 Hz), 1.6-2.1 (m, 6H), 1.20 (br t, 1H, J = 4.8 Hz), 0.99 (dd, 1H, J = 4.2, 7.7 Hz). m/z: 582 $[M + H]^+$ | | |

(1rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-6,6-dioxo-6λ$^6$-thiaspiro[2.5]octane-1-carboxamide

| EXAMPLES 99 CPD0073922 | Procedure 3b-d | Intermediate 117 | Yield: 36% |
|---|---|---|---|
| 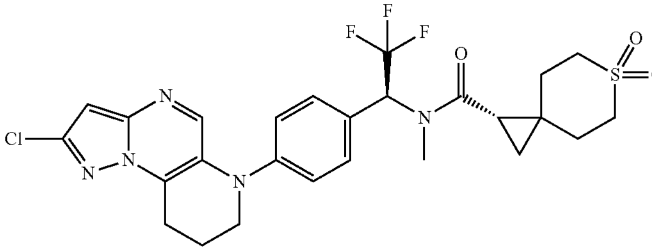 | $^1H$ NMR (600 MHz, DMSO-$d_6$) δ ppm 8.1-8.4 (m, 1H), 7.35 (d, 2H, J = 8.5 Hz), 7.27 (d, 2H, J = 8.7 Hz), 6.82 (s, 1H), 6.50 (q, 1H, J = 9.3 Hz), 3.6-3.8 (m, 2H), 3.1-3.2 (m, 5H), 3.01 (s, 3H), 2.21 (dd, 1H, J = 5.6, 7.8 Hz), 1.6-2.1 (m, 7H), 1.20 (t, 1H, J = 4.8 Hz), 0.97 (dd, 1H, J = 4.3, 7.8 Hz). m/z: 582 $[M + H]^+$ | | |

(1rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-6,6-dioxo-6λ$^6$-thiaspiro[2.5]octane-1-carboxamide -continued

| EXAMPLES 100 CPD0073968 | Procedure 3d | Intermediate 117 | Yield: 3% |
|---|---|---|---|

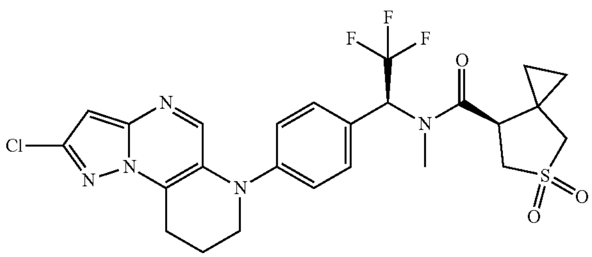 [SMILES: CN(C(=O)[C@@H]1CS(=O)(=O)CC12CC2)[C@@H](c1ccc(N2CCCc3c2cnc2cc(Cl)nn32)cc1)C(F)(F)F]

$^1H$ NMR (600 MHz, DMSO-$d_6$) δ ppm 8.31 (s, 1H), 7.50-7.12 (m, 4H), 6.82 (s, 1H), 6.58-5.96 (m, 1H), 3.81-3.66 (m, 3H), 3.62-3.51 (m, 1H), 3.47-3.40 (m, 1H), 3.29-3.21 (m, 1H), 3.10 (s, 2H), 3.02 (d, J = 12.6 Hz, 1H), 2.85 (s, 3H), 2.04-1.91 (m, 2H), 0.87-0.54 (m, 4H). m/z: 568 $[M + H]^+$ (7rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-5,5-dioxo-5λ$^6$-thiaspiro[2.4]heptane-7-carboxamide

| EXAMPLES 101 CPD0073969 | Procedure: 3d | Intermediate 117 | Yield: 11% |
|---|---|---|---|

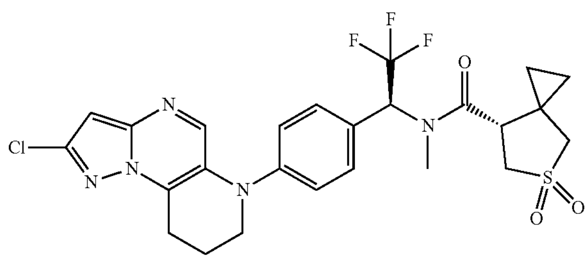 [SMILES: CN(C(=O)[C@H]1CS(=O)(=O)CC12CC2)[C@@H](c1ccc(N2CCCc3c2cnc2cc(Cl)nn32)cc1)C(F)(F)F]

$^1H$ NMR (600 MHz, DMSO-$d_6$) δ ppm 8.29 (s, 1H), 7.32 (s, 2H), 7.25 (d, J = 8.8 Hz, 2H), 6.82 (s, 1H), 6.55-6.15 (m, 1H), 3.82-3.75 (m, 1H), 3.74-3.67 (m, 2H), 3.50-3.41 (m, 1H), 3.39-3.33 (m, 2H), 3.09 (s, 3H), 2.85 (s, 3H), 2.02-1.88 (m, 2H), 0.89-0.58 (m, 4H). m/z: 568 $[M + H]^+$ (7rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-5,5-dioxo-5λ$^6$-thiaspiro[2.4]heptane-7-carboxamide

| EXAMPLES 102 CPD0073974 | Procedure: 3b-d | Intermediate 117 | Yield: 2% |
|---|---|---|---|

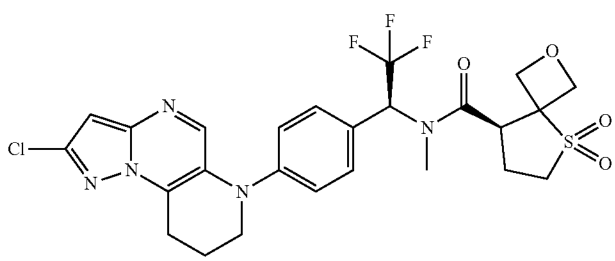 [SMILES: CN(C(=O)[C@@H]1CCS(=O)(=O)C12COC2)[C@@H](c1ccc(N2CCCc3c2cnc2cc(Cl)nn32)cc1)C(F)(F)F]

$^1H$ NMR (500 MHz, DMSO-$d_6$) δ ppm 8.31 (s, 1H), 7.36 (d, J = 8.6 Hz, 2H), 7.28 (d, J = 8.8 Hz, 2H), 6.82 (s, 1H), 6.49 (q, J = 9.2 Hz, 1H), 4.50-4.61 (m, 4H), 4.41 (dd, J = 9.7, 4.3 Hz, 1H), 3.80 (d, J = 13.0 Hz, 1H), 3.72 (dt, J = 5.0, 2.8 Hz, 2H), 3.62-3.72 (m, 2H), 3.16 (dd, J = 14.2, 4.4 Hz, 1H), 3.10 (t, J = 6.7 Hz, 2H), 2.96 (s, 3H), 1.92-2.00 (m, 2H). m/z: 584 $[M + H]^+$ (8rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-6,6-dioxo-2-oxa-6λ$^6$-thiaspiro[3.4]octane-8-carboxamide

| EXAMPLES 103 CPD0073975 | Procedure: 3b-d | Intermediate 117 | Yield: 3% |
|---|---|---|---|

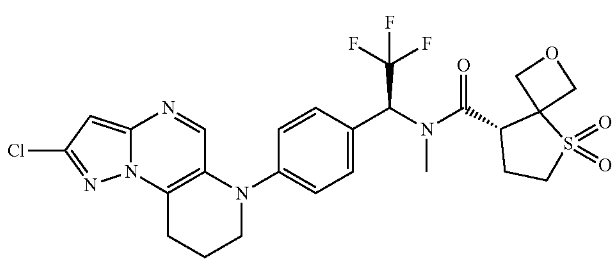 [SMILES: CN(C(=O)[C@H]1CCS(=O)(=O)C12COC2)[C@@H](c1ccc(N2CCCc3c2cnc2cc(Cl)nn32)cc1)C(F)(F)F]

$^1H$ NMR (500 MHz, DMSO-$d_6$) δ ppm 8.36-8.27 (m, 1H), 7.40-7.30 (m, 2H), 7.27 (d, J = 8.8 Hz, 2H), 6.82 (s, 1H), 6.50 (q, J = 9.0 Hz, 1H), 4.72-4.46 (m, 4H), 4.43-4.30 (m, 1H), 3.84-3.63 (m, 4H), 3.61-3.52 (m, 1H), 3.27-3.19 (m, 1H), 3.10 (s, 2H), 3.02-2.75 (m, 3H), 2.01-1.88 (m, 2H). m/z: 584 $[M + H]^+$ (8rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-6,6-dioxo-2-oxa-6λ$^6$-thiaspiro[3.4]octane-8-carboxamide -continued

| EXAMPLES 104 CPD0074050 | Procedure: 3c | Intermediate 118 | Yield: 51% |
|---|---|---|---|
| 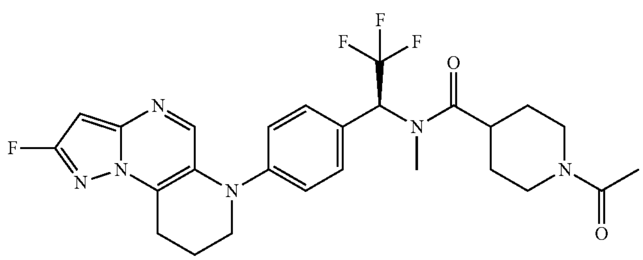 [SMILES: CC(=O)N1CCC(C(=O)N(C)[C@@H](c2ccc(N3CCCc4c3cnc3cc(F)nn43)cc2)C(F)(F)F)CC1] | $^{1}H$ NMR (500 MHz, DMSO-$d_6$) δ ppm 8.30 (s, 1H), 7.19-7.40 (m, 4H), 6.47-6.56 (m, 1H), 6.43 (d, J = 5.1 Hz, 1H), 4.31-4.45 (m, 1H), 3.79-3.89 (m, 1H), 3.64-3.77 (m, 2H), 2.96-3.23 (m, 4H), 2.93 (s, 2H), 2.54-2.69 (m, 2H), 2.00 (s, 3H), 1.88-1.98 (m, 2H), 1.29-1.84 (m, 4H). m/z: 533 $[M + H]^+$ | | |

1-acetyl-N-methyl-N-[(1S)-2,2,2-trifluoro-1-(4-{4-fluoro-2,3,7,10-tetraazatricyclo[7.4.0.0$^{2,6}$]trideca-1(9),3,5,7-tetraen-10-yl}phenyl)ethyl]piperidine-4-carboxamide

| EXAMPLES 105 CPD0021750 | Procedure 3b | Intermediate 123 | Yield: 24% |
|---|---|---|---|
| 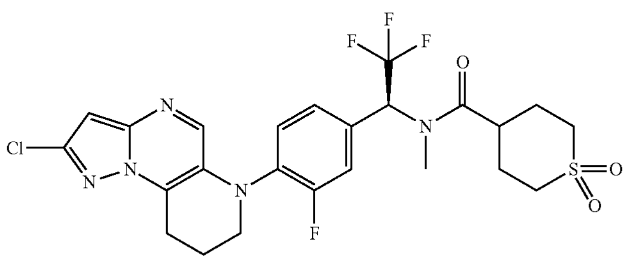 [SMILES: CN(C(=O)C1CCS(=O)(=O)CC1)[C@@H](c1ccc(N2CCCc3c2cnc2cc(Cl)nn32)c(F)c1)C(F)(F)F] | $^{1}H$ NMR (500 MHz, DMSO-$d_6$) δ ppm 8.11 (d, J = 1.2 Hz, 1H), 7.38 (t, J = 8.6 Hz, 1H), 7.29 (br d, J = 12.7 Hz, 1H), 7.19 (br d, J = 8.6 Hz, 1H), 6.80 (s, 1H), 6.17-6.60 (m, 1H), 3.57-3.66 (m, 2H), 3.07-3.29 (m, 7H), 2.96 (s, 3H), 1.95-2.19 (m, 6H).m/z: 574 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}-3-fluorophenyl)-2,2,2-trifluoroethyl]-N-methyl-1,1-dioxo-1λ$^6$-thiane-4-carboxamide

| EXAMPLES 106 CPD0072808 | Procedure: 3b | Intermediate 124 | Yield: 52% |
|---|---|---|---|
| 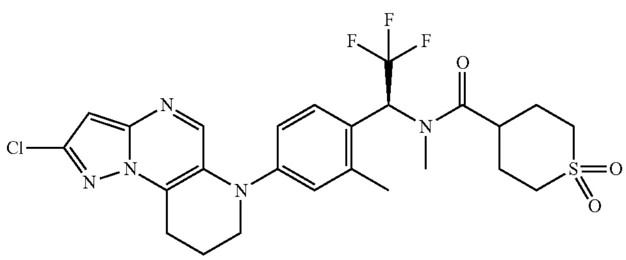 [SMILES: Cc1cc(N2CCCc3c2cnc2cc(Cl)nn32)ccc1[C@H](N(C)C(=O)C1CCS(=O)(=O)CC1)C(F)(F)F] | $^{1}H$ NMR (500 MHz, DMSO-$d_6$) δ ppm 8.30 (s, 1H), 7.43 (br d, J = 8.3 Hz, 1H), 7.14 (d, J = 2.2 Hz, 1H), 7.11 (dd, J = 8.6, 2.4 Hz, 1H), 6.82 (s, 1H), 6.51 (q, J = 9.1 Hz, 1H), 3.64-3.77 (m, 2H), 3.06-3.28 (m, 7H), 2.83 (s, 3H), 2.09 (s, 3H), 1.92-2.08 (m, 6H). m/z: 570 $[M + H].^+$ | | |

N-[(1S)-1-(4-{4-chloro-2,3,7,10-tetraazatricyclo[7.4.0.0$^{2,6}$]trideca-1(9),3,5,7-tetraen-10-yl}-2-methylphenyl)-2,2,2-trifluoroethyl]-N-methyl-1,1-dioxo-1λ$^6$-thiane-4-carboxamide

| EXAMPLES 107 CPD0073040 | Procedure: 3b | Intermediate 125 | Yield: 52% |
|---|---|---|---|
| 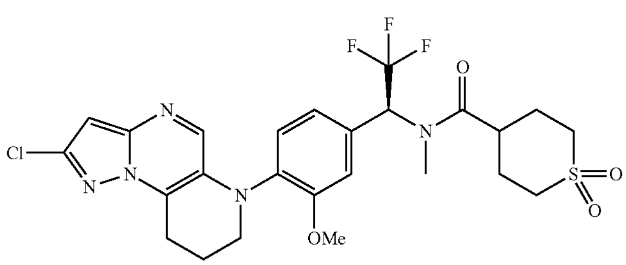 [SMILES: COc1cc([C@H](N(C)C(=O)C2CCS(=O)(=O)CC2)C(F)(F)F)ccc1N1CCCc2c1cnc1cc(Cl)nn21] | $^{1}H$ NMR (500 MHz, DMSO-$d_6$) δ ppm 7.84 (s, 1 H), 7.26 (d, J = 8.2 Hz, 1 H), 6.97-7.02 (m, 1 H), 6.93 (d, J = 1.6 Hz, 1 H), 6.73 (s, 1 H), 6.50-6.60 (m, 1 H), 3.79 (s, 3 H), 3.54 (br d, J = 5.3 Hz, 2 H), 3.08-3.29 (m, 6 H), 2.95 (s, 3 H), 2.51-2.54 (m, 1 H), 1.93-2.23 (m, 6 H). m/z: 586 $[M + H]^+$ | | |

N-[(1S)-1-(4-{4-chloro-2,3,7,10-tetraazatricyclo[7.4.0.0$^{2,6}$]trideca-1(9),3,5,7-tetraen-10-yl}-3-methoxyphenyl)-2,2,2-trifluoroethyl]-N-methyl-1,1-dioxo-1λ$^6$-thiane-4-carboxamide -continued

| EXAMPLES 108 CPD0072803 | Procedure: 3c | Intermediate 126 | Yield: 11% |
|---|---|---|---|
| 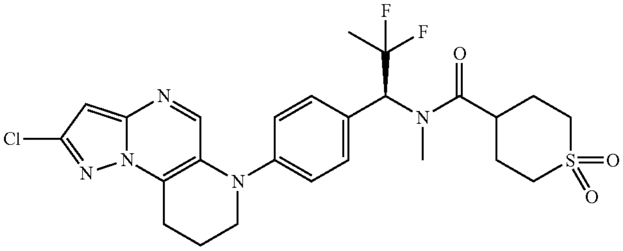 [SMILES: CN(C(=O)C1CCS(=O)(=O)CC1)[C@@H](c1ccc(N2CCCc3c2cnc2cc(Cl)nn32)cc1)C(C)(F)F] | $^1$H NMR (500 MHz, DMSO-$d_6$) δ ppm 8.2-8.4 (m, 1H), 7.0-7.6 (m, 4H), 6.81 (s, 1H), 6.11 (dd, 1H, J = 11.5, 19.8 Hz), 3.6-3.8 (m, 2H), 3.0-3.3 (m, 7H), 2.90 (s, 3H), 1.9-2.2 (m, 6H), 1.5-1.8 (m, 3H). m/z: 552 [M + H]$^+$. | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2-difluoropropyl]-N-methyl-1,1-dioxo-1λ$^6$-thiane-4-carboxamide

| EXAMPLES 109 CPD0073918 | Procedure: 3c | Intermediate 127 | Yield: 22% |
|---|---|---|---|
| 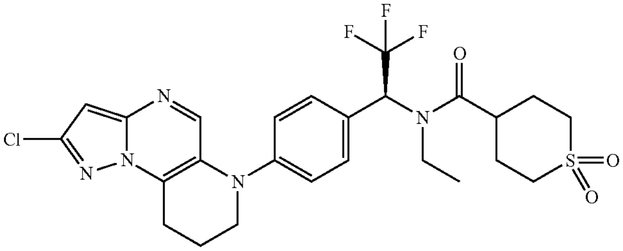 [SMILES: CCN(C(=O)C1CCS(=O)(=O)CC1)[C@@H](c1ccc(N2CCCc3c2cnc2cc(Cl)nn32)cc1)C(F)(F)F] | $^1$H NMR (500 MHz, DMSO-$d_6$) δ ppm 8.28 (s, 1H), 7.19-7.45 (m, 4H), 6.82 (s, 1H), 6.10-6.58 (m, 1H), 3.67-3.75 (m, 2H), 3.34-3.45 (m, 2H), 3.01-3.28 (m, 7H), 1.92-2.21 (m, 6H), 0.69-0.91 (m, 3H). m/z: 570 [M + H]$^+$. | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-ethyl-1,1-dioxo-1λ$^6$-thiane-4-carboxamide

| EXAMPLES 110 CPD0021581 | Procedure: 2 | Intermediate 117 | Yield: 11% |
|---|---|---|---|
| 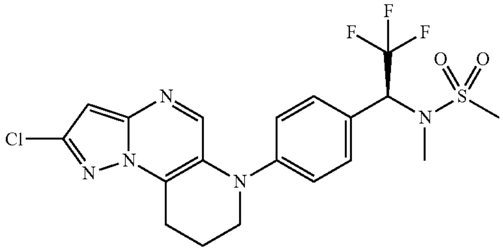 [SMILES: CN([C@@H](c1ccc(N2CCCc3c2cnc2cc(Cl)nn32)cc1)C(F)(F)F)S(C)(=O)=O] | $^1$H NMR (600 MHz, DMSO-$d_6$) δ ppm 8.33 (s, 1H), 7.44 (d, J = 8.7 Hz, 2H), 7.28 (d, J = 8.7 Hz, 2H), 6.82 (s, 1H), 5.72 (q, J = 8.8 Hz, 1H), 3.85-3.63 (m, 2H), 3.10 (t, J = 6.7 Hz, 2H), 3.04 (s, 3H), 2.76 (s, 3H), 2.07-1.92 (m, 2H). m/z: 474 [M + H]$^+$ | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylmethanesulfonamide

| EXAMPLES 111 CPD0021733 | Procedure: 2 | Intermediate 117 | Yield: 26% |
|---|---|---|---|
| 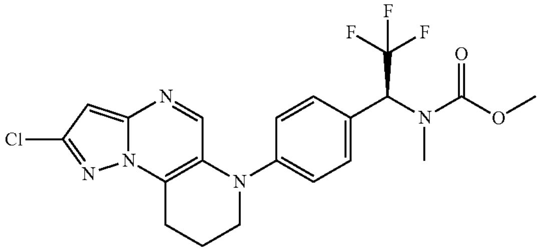 [SMILES: COC(=O)N(C)[C@@H](c1ccc(N2CCCc3c2cnc2cc(Cl)nn32)cc1)C(F)(F)F] | $^1$H NMR (500 MHz, DMSO-$d_6$) δ ppm 8.31 (s, 1H), 7.36 (d, J = 8.3 Hz, 2H), 7.27 (d, J = 8.8 Hz, 2H), 6.82 (s, 1H), 6.15-5.91 (m, 1H), 3.72 (s, 5H), 3.10 (t, J = 6.7 Hz, 2H), 2.73 (s, 3H), 2.01-1.88 (m, 2H). m/z: 454 [M + H]$^+$. | | |

Methyl N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methylcarbamate -continued

| EXAMPLES 112 CPD0021731 | Procedure: 2 | Intermediate 117 | Yield: 65% |
|---|---|---|---|
| 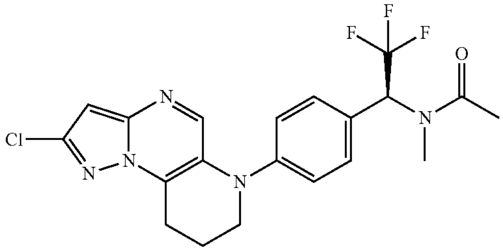 | $^1$H NMR (600 MHz, DMSO-$d_6$) δ ppm 9.06 (d, J = 9.7 Hz, 1H), 8.27 (s, 1H), 7.51-7.47 (m, 2H), 7.24-7.21 (m, 2H), 6.81 (s, 1H), 5.72 (dq, J = 8.9, 1.0 Hz, 1H), 3.70 (dd, J = 6.5, 4.1 Hz, 2H), 3.09 (t, J = 6.7 Hz, 2H), 1.99-1.92 (m, 5H). m/z: 424 [M + H]$^+$. | | |

N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]acetamide

| EXAMPLES 113 CPD0074566 | Procedure 3 d | Intermediate 122 | Yield: 19% |
|---|---|---|---|
| 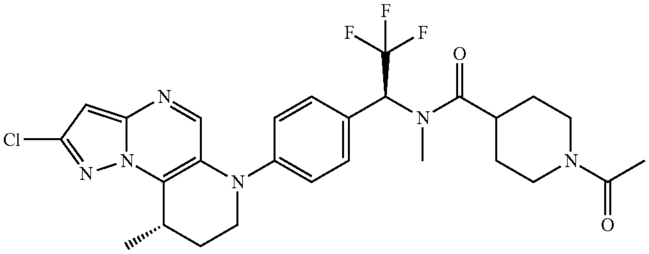 [SMILES: CC(=O)N1CCC(C(=O)N(C)[C@@H](c2ccc(N3CC[C@H](C)c4c3cnc3cc(Cl)nn43)cc2)C(F)(F)F)CC1] | $^1$H NMR (DMSO-$d_6$, 500 MHz) δ ppm 8.28 (s, 1H), 7.2-7.5 (m, 4H), 6.79 (s, 1H), 6.53 (q, 1H, J = 9.2 Hz), 4.37 (br d, 1H, J = 13.0 Hz), 3.8-4.0 (m, 1H), 3.6-3.8 (m, 2H), 3.52 (dt, 1H, J = 2.6, 6.5 Hz), 3.0-3.2 (m, 2H), 2.93 (s, 3H), 2.5-2.7 (m, 1H), 2.0-2.1 (m, 1H), 2.00 (s, 3H), 1.3-1.8 (m, 8H). m/z: 563 [M + H]$^+$. | | |

1-Acetyl-N-[(1S)-1-[4-[(13rel-R)-4-chloro-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-piperidine-4-carboxamide

| EXAMPLES 114 CPD0074568 | Procedure 3 d | Intermediate 122 | Yield: 22% |
|---|---|---|---|
| 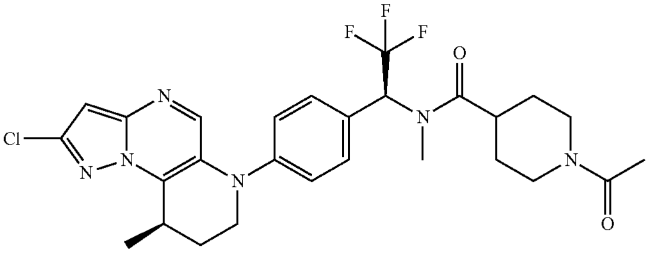 [SMILES: CC(=O)N1CCC(C(=O)N(C)[C@@H](c2ccc(N3CC[C@@H](C)c4c3cnc3cc(Cl)nn43)cc2)C(F)(F)F)CC1] | $^1$H NMR (DMSO-$d_6$, 500 MHz) δ ppm 8.28 (s, 1H), 7.1-7.5 (m, 4H), 6.79 (s, 1H), 6.53 (d, 1H, J = 9.5 Hz), 6.2-6.4 (m, 1H), 4.37 (br d, 1H, J = 13.2 Hz), 3.8-3.9 (m, 1H), 3.6-3.8 (m, 2H), 3.4-3.6 (m, 1H), 3.0-3.2 (m, 2H), 2.94 (s, 2H), 2.5-2.7 (m, 1H), 1.9-2.1 (m, 4H), 1.3-1.9 (m, 8H). m/z: 563 [M + H]$^+$. | | |

1-Acetyl-N-[(1S)-1-[4-[(13rel-S)-4-chloro-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-piperidine-4-carboxamide

| EXAMPLES 115 CPD0074567 | Procedure 3c-f | Intermediate 122 | Yield: 2% |
|---|---|---|---|
| 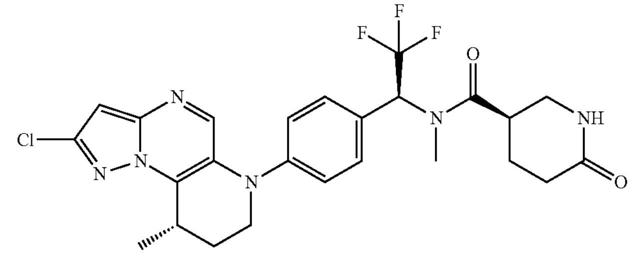 [SMILES: C[C@H]1CCN(c2ccc([C@H](N(C)C(=O)[C@@H]3CCC(=O)NC3)C(F)(F)F)cc2)c2cnc3cc(Cl)nn3c21] | $^1$H NMR (500 MHz, DMSO-$d_6$) δ ppm 8.28 (s, 1H), 7.47 (br d, J = 2.4 Hz, 1H), 7.42-7.33 (m, 2H), 7.32-7.25 (m, 2H), 6.79 (s, 1H), 6.61-6.22 (m, 1H), 3.79-3.63 (m, 2H), 3.57-3.48 (m, 1H), 3.28 (s, 1H), 3.25-3.12 (m, 2H), 3.01-2.65 (m, 3H), 2.34-2.13 (m, 2H), 2.10-2.01 (m, 1H), 1.99-1.87 (m, 1H), 1.84-1.68 (m, 2H), 1.53-1.41 (m, 3H). m/z: 535 [M + H]$^+$. | | |

(3rel-R)-N-[(1S)-1-[4-[(13rel-S)-4-chloro-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-6-oxo-piperidine-3-carboxamide -continued

| EXAMPLES 116 CPD0074549 | Procedure 3c-f | Intermediate 122 | Yield: 3.3% |
|---|---|---|---|
| 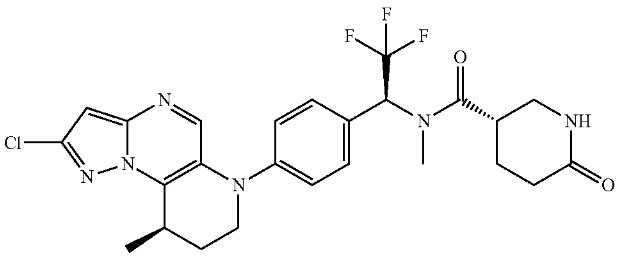 [SMILES: C[C@@H]1CCN(c2ccc([C@H](N(C)C(=O)[C@H]3CCC(=O)NC3)C(F)(F)F)cc2)c2cnc3cc(Cl)nn3c21] | $^1$H NMR (600 MHz, DMSO-$d_6$) δ ppm 8.28 (s, 1 H), 7.48 (br d, J = 2.8 Hz, 1 H), 7.34 (m, 2 H), 7.28 (m, 2 H), 6.79 (s, 1 H), 6.53 (q, J = 9.3 Hz, 1 H), 3.72 (m, 2 H), 3.52 (td, J = 6.5, 2.4 Hz, 1 H), 3.21 (m, 2 H), 2.94 (s, 3 H), 2.22 (m, 2 H), 1.89 (m, 5 H), 1.44 (d, J = 7.0 Hz, 3 H). m/z: 535 [M + H]$^+$. | | |
| (3rel-S)-N-[(1S)-1-[4-[(13rel-R)-4-chloro-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-6-oxo-piperidine-3-carboxamide | | | |
| EXAMPLES 117 CPD0074561 | Procedure 3c-f | Intermediate 122 | Yield: 3% |
| 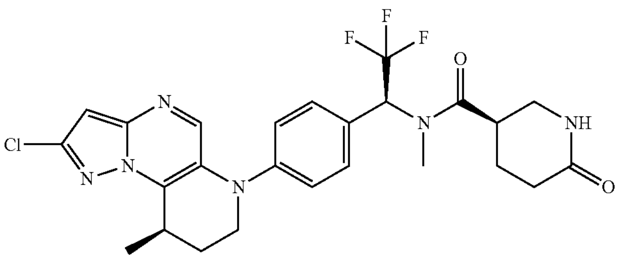 [SMILES: C[C@@H]1CCN(c2ccc([C@H](N(C)C(=O)[C@@H]3CCC(=O)NC3)C(F)(F)F)cc2)c2cnc3cc(Cl)nn3c21] | $^1$H NMR (600 MHz, DMSO-$d_6$) δ ppm 8.28 (s, 1 H), 7.48 (br d, J = 2.8 Hz, 1 H), 7.34 (m, 2 H), 7.28 (m, 2 H), 6.79 (s, 1 H), 6.53 (q, J = 9.3 Hz, 1 H), 3.72 (m, 2 H), 3.52 (td, J = 6.5, 2.4 Hz, 1 H), 3.21 (m, 2 H), 2.94 (s, 3 H), 2.22 (m, 2 H), 1.89 (m, 5 H), 1.44 (d, J = 7.0 Hz, 3 H). m/z: 535 [M + H]$^+$ | | |
| (3rel-R)-N-[(1S)-1-[4-[(13rel-R)-4-chloro-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-6-oxo-piperidine-3-carboxamide | | | |
| EXAMPLES 118 CPD0074051 | Procedure 3c | Intermediate 128 | Yield: 58% |
| 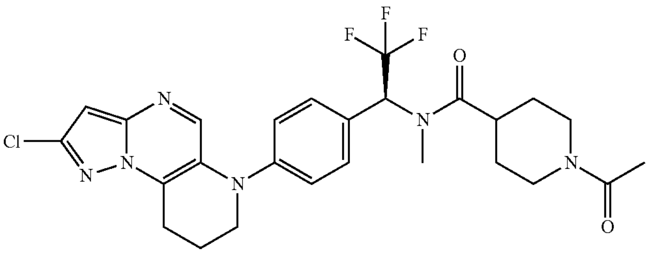 [SMILES: CC(=O)N1CCC(C(=O)N(C)[C@@H](c2ccc(N3CCCc4c3cnc3cc(Cl)nn43)cc2)C(F)(F)F)CC1] | $^1$H NMR (500 MHz, DMSO-$d_6$) δ ppm 1.28-1.82 (m, 4 H) 1.97-2.03 (m, 5 H) 2.55-2.72 (m, 1 H) 2.97 (s, 3 H) 2.98-3.14 (m, 4 H) 3.78-3.87 (m, 1 H) 3.97 (br dd, J = 7.21, 3.30 Hz, 2 H) 4.37 (br d, J = 12.72 Hz, 1 H) 6.53 (q, J = 9.54 Hz, 1 H) 6.85 (s, 1 H) 7.25 (d, J = 8.80 Hz, 1 H) 7.70 (br d, J = 8.56 Hz, 1 H) 8.17 (s, 1 H) 8.67-8.72 (m, 1 H). m/z: 550 [M + H]$^+$. | | |
| 1-acetyl-N-[(1S)-1-[6-(4-chloro-2,3,7,10-tetrazatricyclo[7.4.0.0$^{2,6}$]trideca-1(9),3,5,7-tetraen-10-yl)-3-pyridyl]-2,2,2-trifluoro-ethyl]-N-methyl-piperidine-4-carboxamide | | | |
| EXAMPLES 119 CPD0073535 | Procedure 3a | Intermediate 117 | Yield: 51% |
| 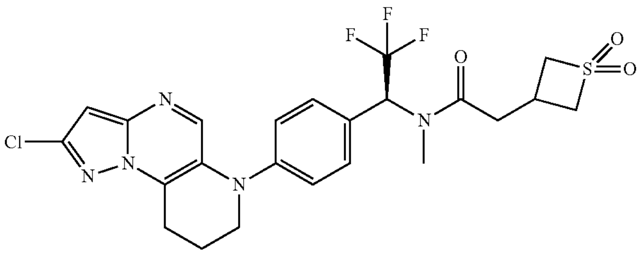 | $^1$H NMR (600 MHz, DMSO-$d_6$) δ ppm 9.23 (d, 1H, J = 9.7 Hz), 8.27 (s, 1H), 7.49 (d, 2H, J = 8.7 Hz), 7.23 (d, 2H, J = 8.8 Hz), 6.81 (s, 1H), 5.72 (br t, 1H, J = 8.8 Hz), 4.1-4.3 (m, 2H), 3.85 (dd, 2H, J = 6.2, 14.6 Hz), 3.6-3.7 (m, 2H), 3.09 (t, 2H, J = 6.7 Hz), 2.6-2.9 (m, 3H), 1.8-2.0 (m, 2H). m/z: 528 [M + H]$^+$. | | |
| N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1)6-thietan-3-yl)acetamide | | | |

-continued

| EXAMPLES 120 CPD0075573 | Procedure: 3b-g | Intermediate 117 | Yield: 6% |
|---|---|---|---|
| 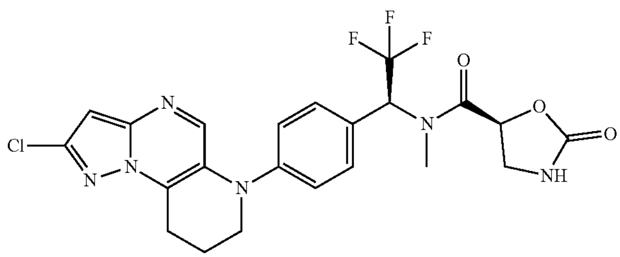 [SMILES: CN(C(=O)[C@@H]1CNC(=O)O1)[C@@H](c1ccc(N2CCCc3c2cnc2cc(Cl)nn32)cc1)C(F)(F)F] | $^1$H NMR (DMSO-$d_6$, 600 MHz): δ ppm 8.30 (s, 1H), 7.19-7.40 (m, 4H), 6.47-6.56 (m, 1H), 6.43 (d, J = 5.1 Hz, 1H), 4.31-4.45 (m, 1H), 3.79-3.89 (m, 1H), 3.64-3.77 (m, 2H), 2.96-3.23 (m, 4H), 2.93 (s, 2H), 2.54-2.69 (m, 2H), 2.00 (s, 3H), 1.88-1.98 (m, 2H), 1.29-1.84 (m, 4H). m/z: 509 [M + H]$^+$. | | |
| N-methyl-2-oxo-N-[rel-(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]oxazolidine-5-carboxamide | | | |

| EXAMPLES 121 CPD0075576 | Procedure: 3b-g | Intermediate 117 | Yield: 9% |
|---|---|---|---|
| 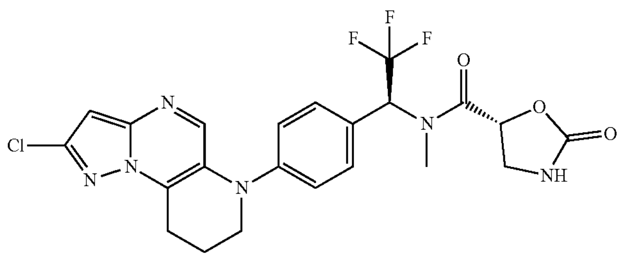 [SMILES: CN(C(=O)[C@H]1CNC(=O)O1)[C@@H](c1ccc(N2CCCc3c2cnc2cc(Cl)nn32)cc1)C(F)(F)F] | $^1$H NMR (DMSO-$d_6$, 600 MHz): δ ppm 8.30 (s, 1H), 7.19-7.40 (m, 4H), 6.47-6.56 (m, 1H), 6.43 (d, J = 5.1 Hz, 1H), 4.31-4.45 (m, 1H), 3.79-3.89 (m, 1H), 3.64-3.77 (m, 2H), 2.96-3.23 (m, 4H), 2.93 (s, 2H), 2.54-2.69 (m, 2H), 2.00 (s, 3H), 1.88-1.98 (m, 2H), 1.29-1.84 (m, 4H). m/z: 509 [M + H]$^+$ | | |
| N-methyl-2-oxo-N-[rel-(1R)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]oxazolidine-5-carboxamide | | | |

| EXAMPLE 122 CPD0075578 | Procedure: 5 | Intermediate 205 | Yield: 12.9% |
|---|---|---|---|
| 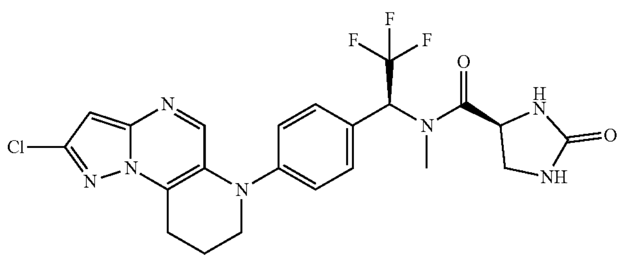 [SMILES: CN(C(=O)[C@@H]1CNC(=O)N1)[C@@H](c1ccc(N2CCCc3c2cnc2cc(Cl)nn32)cc1)C(F)(F)F] | $^1$H NMR (600 MHz, DMSO-$d_6$, 600 MHz) δ ppm 8.31 (s, 1H), 7.36-7.29 (m, 2H), 7.29-7.21 (m, 2H), 6.82 (s, 1H), 6.66 (s, 1H), 6.54-6.39 (m, 1H), 6.28 (s, 1H), 4.70 (dd, J = 9.7, 4.8 Hz, 1H), 3.81-3.66 (m, 2H), 3.60 (t, J = 9.3 Hz, 1H), 3.27-3.21 (m, 1H), 3.09 (t, J = 6.7 Hz, 2H), 2.94-2.75 (m, 1H), 2.84 (s, 2H), 2.04-1.88 (m, 2H). m/z: 508 [M + H]$^+$. | | |
| (4rel S)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-2-oxo-imidazolidine-4-carboxamide | | | |

| EXAMPLE 123 CPD0075579 | Procedure: 5 | Intermediate 205 | Yield: 21% |
|---|---|---|---|
| 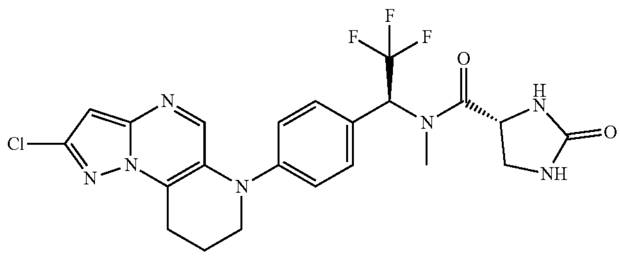 [SMILES: CN(C(=O)[C@H]1CNC(=O)N1)[C@@H](c1ccc(N2CCCc3c2cnc2cc(Cl)nn32)cc1)C(F)(F)F] | $^1$H NMR (600 MHz, DMSO-$d_6$, 600 MHz) δ ppm 1.83-2.06 (m, 2 H) 2.86 (s, 3 H) 3.09 (t, J = 6.68 Hz, 2 H) 3.26 (dd, J = 8.80, 4.70 Hz, 1 H) 3.68 (t, J = 9.39 Hz, 1 H) 3.70-3.74 (m, 2 H) 4.70 (dd, J = 9.76, 4.62 Hz, 1 H) 6.32 (s, 1 H) 6.48 (q, J = 9.34 Hz, 1 H) 6.51 (s, 1 H) 6.82 (s, 1 H) 7.13-7.30 (m, 2 H) 7.33 (d, J = 8.51 Hz, 2 H) 8.30 (s, 1 H). m/z: 508 [M + H]$^+$. | | |
| (4rel R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-2-oxo-imidazolidine-4-carboxamide | | | |

-continued

| EXAMPLE 124 CPD0075577 | Procedure 5 | Intermediate 207 | Yield: 32.5% |
|---|---|---|---|
| 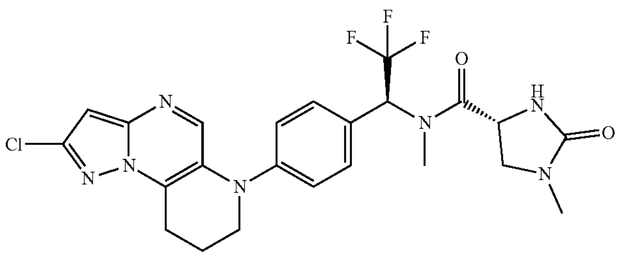 [SMILES: CN1C[C@H](C(=O)N(C)[C@@H](c2ccc(N3CCCc4c3cnc3cc(Cl)nn43)cc2)C(F)(F)F)NC1=O] | $^1$H NMR (600 MHz, DMSO-$d_6$, 600 MHz) δ ppm 1.93-1.98 (m, 2 H) 2.62 (s, 3 H) 2.88 (s, 3 H) 3.09 (t, J = 6.68 Hz, 2 H) 3.31-3.33 (m, 1 H) 3.63-3.75 (m, 3 H) 4.65 (dd, J = 9.76, 4.92 Hz, 1 H) 6.47 (q, J = 9.15 Hz, 1 H) 6.69 (s, 1 H) 6.82 (s, 1 H) 7.27 (m, J = 8.51 Hz, 2 H) 7.34 (m, J = 8.51 Hz, 2 H) 8.30 (s, 1 H) m/z: 522 [M + H]$^+$. | | |
| (4rel R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-2-oxo-imidazolidine-4-carboxamide | | | |

| EXAMPLE 125 CPD0075574 | Procedure 5 | Intermediate 207 | Yield: 12.7% |
|---|---|---|---|
| 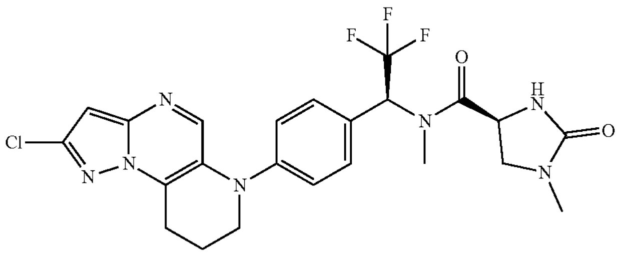 [SMILES: CN1C[C@@H](C(=O)N(C)[C@@H](c2ccc(N3CCCc4c3cnc3cc(Cl)nn43)cc2)C(F)(F)F)NC1=O] | $^1$H NMR (600 MHz, DMSO-$d_6$, 600 MHz) δ ppm 1.93-1.98 (m, 2 H) 2.61 (s, 3 H) 2.86 (s, 3 H) 3.10 (t, J = 6.68 Hz, 2 H) 3.31-3.34 (m, 1 H) 3.60 (t, J = 9.24 Hz, 1 H) 3.69-3.74 (m, 2 H) 4.64 (dd, J = 9.76, 4.92 Hz, 1 H) 6.44 (q, J = 9.29 Hz, 1 H) 6.82 (s, 2 H) 7.26 (m, J = 8.51 Hz, 2 H) 7.29-7.37 (m, 2 H) 8.31 (s, 1 H) m/z: 522 [M + H]$^+$. | | |
| (4rel S)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N,1-dimethyl-2-oxo-imidazolidine-4-carboxamide | | | |

Examples 128-135

Scheme 14

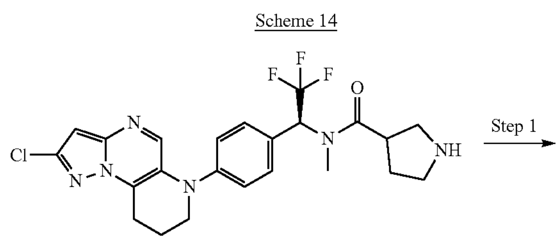

-continued

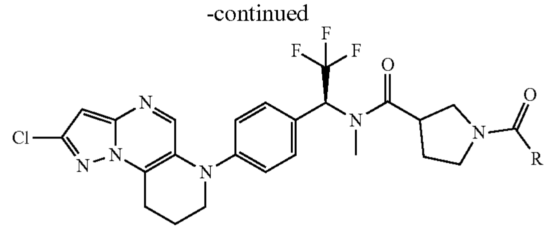

The following examples were prepared from intermediate 136 according to the general procedure 3 already described in examples 37-127

| Example 128 CPD0075877 | Procedure: 3b then chiral separation using CO2/(MeOH + 0.5% IPAm) 70/30 | Yield: 24% |
|---|---|---|
| 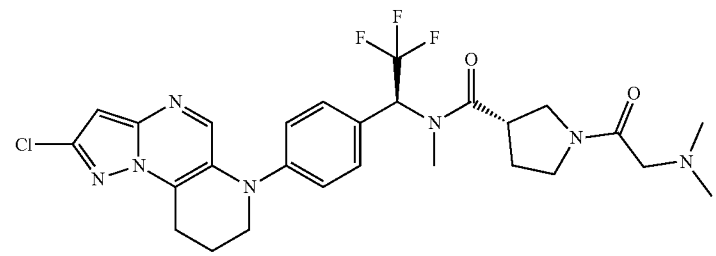 [SMILES: CN(C)CC(=O)N1CC[C@H](C(=O)N(C)[C@@H](c2ccc(N3CCCc4c3cnc3cc(Cl)nn43)cc2)C(F)(F)F)C1] | $^1$H NMR (500 MHz, DMSO-$d_6$) δ ppm 8.31 (d, J = 3.4 Hz, 1H), 7.45-7.31 (m, 2H), 7.30-7.17 (m, 2H), 6.82 (d, J = 1.2 Hz, 1H), 6.52 (br d, J = 9.3 Hz, 1H), 3.83-3.33 (m, 7H), 3.14-3.07 (m, 2H), 3.06-2.98 (m, 2H), 2.96-2.66 (m, 3H), 2.21-1.77 (m, 10H). m/z: 578 [M + H]$^+$. | |
| (3rel-S)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-[2-(dimethylamino)acetyl]-N-methyl-pyrrolidine-3-carboxamide | | |

-continued

| Example 129 CPD0075876 | Procedure: 3b then chiral separation using CO2/(MeOH + 0.5% IPAm) 70/30 | Yield: 45% |
|---|---|---|
| 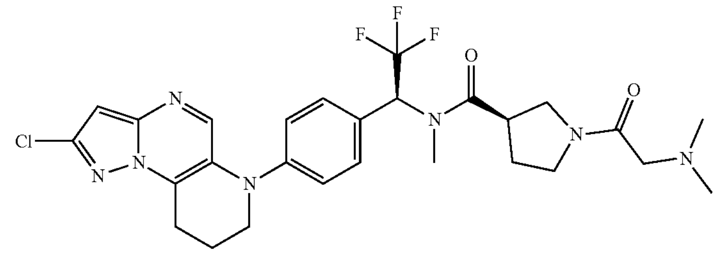 [SMILES: CN(C)CC(=O)N1CC[C@@H](C(=O)N(C)[C@@H](c2ccc(N3CCCc4c3cnc3cc(Cl)nn43)cc2)C(F)(F)F)C1] | $^1$H NMR (500 MHz, DMSO-$d_6$) δ ppm 8.31 (s, 1H), 7.42-7.30 (m, 2H), 7.29-7.17 (m, 2H), 6.82 (s, 1H), 6.59-6.09 (m, 1H), 3.85-3.35 (m, 7H), 3.10 (t, J = 6.6 Hz, 2H), 3.04-2.97 (m, 2H), 2.70 (d, J = 7.3 Hz, 3H), 2.22-2.16 (m, 6H), 2.15-1.83 (m, 4H). m/z: 578 $[M + H]^+$. | |
| (3rel-R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-[2-(dimethylamino)acetyl]-N-methyl-pyrrolidine-3-carboxamide | | |
| Example 130 CPD0075875 | Procedure 3b then chiral separation using CO2/(MeOH + 0.5% IPAm) 70/30 | Yield: 39% |
| 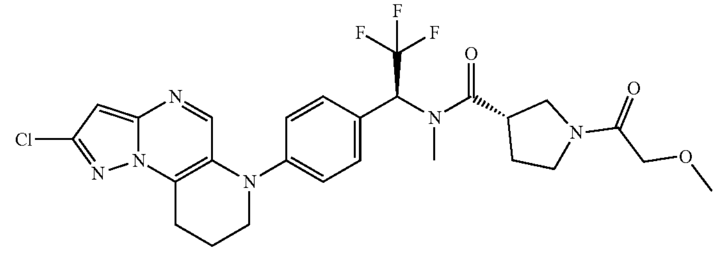 [SMILES: COCC(=O)N1CC[C@H](C(=O)N(C)[C@@H](c2ccc(N3CCCc4c3cnc3cc(Cl)nn43)cc2)C(F)(F)F)C1] | $^1$H NMR (600 MHz, DMSO-$d_6$) δ ppm 1.81-2.27 (m, 4 H) 2.68-2.96 (m, 3 H) 3.10 (t, J = 6.53 Hz, 2 H) 3.28-3.30 (m, 3 H) 3.34-3.64 (m, 5 H) 3.68-3.75 (m, 2 H) 3.97-4.02 (m, 2 H) 6.51 (br d, J = 9.24 Hz, 1 H) 6.82 (s, 1 H) 7.23-7.41 (m, 4 H) 8.31 (d, J = 3.30 Hz, 1 H). m/z: 565 $[M + H]^+$ | |
| (3rel-S)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-(2-methoxyacetyl)-N-methyl-pyrrolidine-3-carboxamide | | |
| Example 131 CPD0075874 | Procedure 3b then chiral separation using CO2/(MeOH + 0.5% IPAm) 70/30 | Yield: 37% |
| 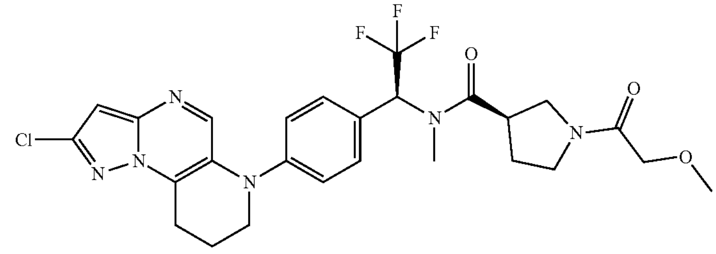 [SMILES: COCC(=O)N1CC[C@@H](C(=O)N(C)[C@@H](c2ccc(N3CCCc4c3cnc3cc(Cl)nn43)cc2)C(F)(F)F)C1] | $^1$H NMR (DMSO-$d_6$, 600 MHz): δ ppm 8.31 (s, 1H), 7.22-7.41 (m, 4H), 6.82 (s, 1H), 6.20-6.56 (m, 1H), 4.01 (d, J = 10.3 Hz, 2H), 3.71 (dt, J = 5.0, 2.7 Hz, 2H), 3.33-3.69 (m, 5H), 3.28-3.30 (m, 3H), 3.10 (t, J = 6.7 Hz, 2H), 2.93 (d, J = 2.9 Hz, 3H), 1.80-2.21 (m, 4H). m/z: 565 $[M + H]^+$ | |
| (3rel-R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-(2-methoxyacetyl)-N-methyl-pyrrolidine-3-carboxamide | | |
| Example 132 CPD0073979 | Procedure 3b then chiral separation using CO2/(MeOH + 0.5% IPAm) 70/30 | Yield: 6% |
| 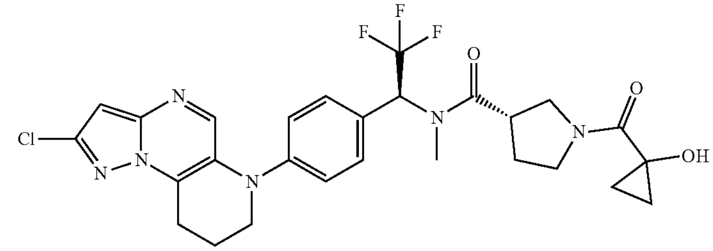 [SMILES: CN(C(=O)[C@H]1CCN(C(=O)C2(O)CC2)C1)[C@@H](c1ccc(N2CCCc3c2cnc2cc(Cl)nn32)cc1)C(F)(F)F] | $^1$H NMR (500 MHz, DMSO-$d_6$) δ ppm 8.31 (s, 1H), 7.43-7.31 (m, 2H), 7.30-7.22 (m, 2H), 6.82 (s, 1H), 6.59-6.18 (m, 1H), 6.09 (s, 1H), 4.14-3.76 (m, 2H), 3.74-3.66 (m, 2H), 3.63-3.33 (m, 3H), 3.10 (t, J = 6.6 Hz, 2H), 2.99-2.67 (m, 3H), 2.31-2.08 (m, 1H), 1.99-1.92 (m, 2H), 1.92-1.77 (m, 1H), 1.05-0.89 (m, 2H), 0.82-0.70 (m, 2H). m/z: 577 $[M + H]^+$ | |
| (3rel-S)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-(1-hydroxycyclopropanecarbonyl)-N-methyl-pyrrolidine-3-carboxamide | | |

-continued

| Example 133 CPD0073978 | Procedure 3b then chiral separation using CO2/(MeOH + 0.5% IPAm) 70/30 | Yield: 7% |
|---|---|---|
| 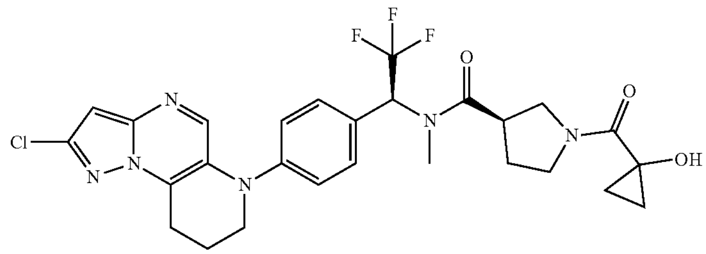 [SMILES: CN(C(=O)[C@@H]1CCN(C(=O)C2(O)CC2)C1)[C@@H](c1ccc(N2CCCc3c2cnc2cc(Cl)nn32)cc1)C(F)(F)F] (3rel-R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-(1-hydroxycyclopropanecarbonyl)-N-methyl-pyrrolidine-3-carboxamide | $^1$H NMR (500 MHz, DMSO-$d_6$) δ ppm 8.31 (s, 1H), 7.42-7.30 (m, 2H), 7.30-7.13 (m, 2H), 6.82 (s, 1H), 6.58-6.22 (m, 1H), 6.16-6.03 (m, 1H), 4.17-3.76 (m, 2H), 3.74-3.69 (m, 2H), 3.68-3.32 (m, 3H), 3.10 (t, J = 6.7 Hz, 2H), 2.94 (s, 3H), 2.22-1.93 (m, 4H), 1.07-0.90 (m, 2H), 0.82-0.68 (m, 2H). m/z: 577 $[M + H]^+$ | |
| Example 134 CPD0073191 | Procedure: 3b then chiral separation then chiral separation using $CO_2$/EtOH 70/30 | Yield: 12% |
| 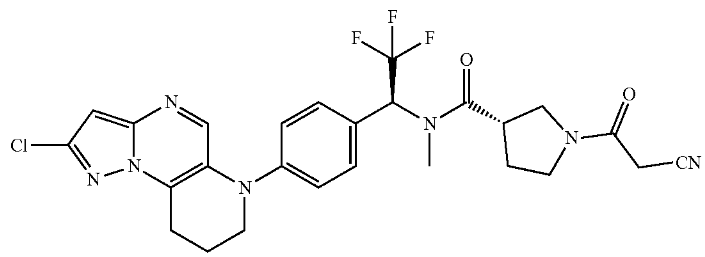 [SMILES: CN(C(=O)[C@H]1CCN(C(=O)CC#N)C1)[C@@H](c1ccc(N2CCCc3c2cnc2cc(Cl)nn32)cc1)C(F)(F)F] (3rel-S)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-(2-cyanoacetyl)-N-methyl-pyrrolidine-3-carboxamide | $^1$H NMR (DMSO-$d_6$, 600 MHz): δ ppm 8.23-8.38 (m, 1H), 7.19-7.43 (m, 4H), 6.75-6.88 (m, 1H), 6.12-6.59 (m, 1H), 3.88-4.01 (m, 2H), 3.68-3.76 (m, 2H), 3.33-3.67 (m, 5H), 3.04-3.16 (m, 2H), 2.66-2.96 (m, 3H), 2.14-2.32 (m, 1H), 1.82-2.05 (m, 3H). m/z: 560 $[M + H]^+$ | |
| Example 135 CPD0073190 | Procedure: 3b then chiral separation using $CO_2$/EtOH 70/30 | Yield: 14% |
| 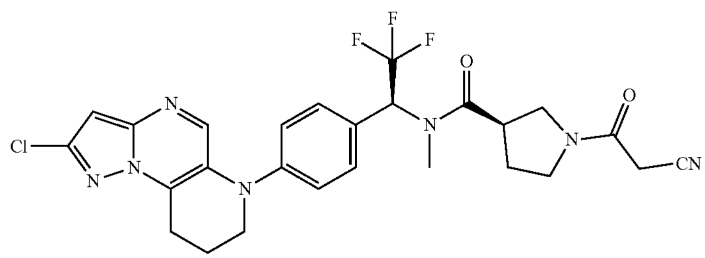 [SMILES: CN(C(=O)[C@@H]1CCN(C(=O)CC#N)C1)[C@@H](c1ccc(N2CCCc3c2cnc2cc(Cl)nn32)cc1)C(F)(F)F] (3rel-R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-1-(2-cyanoacetyl)-N-methyl-pyrrolidine-3-carboxamide | $^1$H NMR (DMSO-$d_6$, 600 MHz): δ ppm 8.31 (s, 1H), 7.29-7.45 (m, 2H), 7.21-7.29 (m, 2H), 6.82 (s, 1H), 6.15-6.55 (m, 1H), 3.89-4.03 (m, 2H), 3.64-3.77 (m, 3H), 3.51-3.63 (m, 2H), 3.31-3.50 (m, 2H), 3.10 (t, J = 6.7 Hz, 2H), 2.93 (d, J = 4.1 Hz, 3H), 1.85-2.22 (m, 4H). m/z: 560 $[M + H]^+$ | |

Examples 136-137

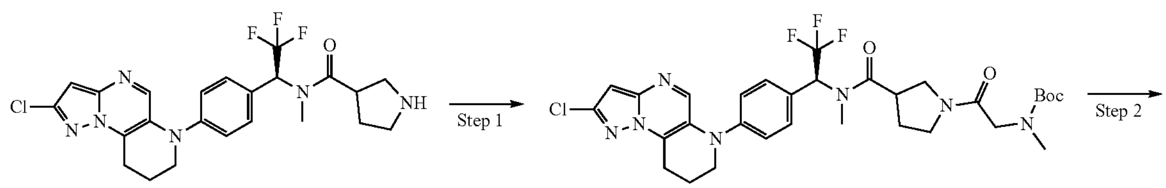

-continued

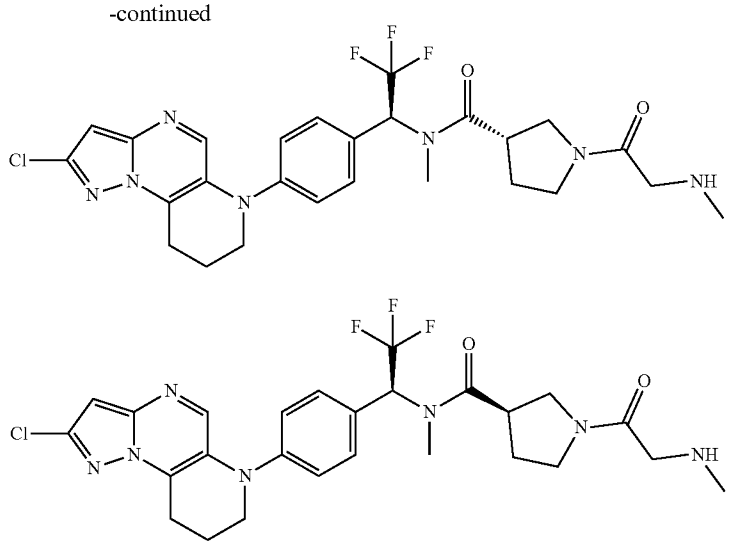

Step 1: Tert-butyl N-[2-(3-{[(1S)-1-[4-(4-chloro-2,3,7,10-tetrazatricyclo[7.4.0.0$^{2,6}$]trideca-1(9),3,5,7-tetraen-10-yl)phenyl}-2,2,2-trifluoro-ethyl]-methyl-carbamoyl]pyrrolidin-1-yl]-2-oxo-ethyl]-N-methyl-carbamate To a stirred solution of N-[(1S)-1-[4-(4-chloro-2,3,7,10-tetrazatricyclo[7.4.0.0$^{2,6}$]trideca-1(9),3,5,7-tetraen-10-yl) phenyl]-2,2,2-trifluoro-ethyl]-N-methyl-pyrrolidine-3-carboxamide (95%, 120 mg, 0.231 mmol) in DCM (2.5 mL) at rt under nitrogen were added successively TEA (645 μL, 4.63 mmol), N-(tert-butoxycarbonyl)-N-methylglycine (53 mg, 0.278 mmol) and $T_3P$ (50% in EtOAc, 1.38 mL, 2.31 mmol). The reaction mixture was stirred at rt overnight. The reaction mixture was quenched with sat. aq. $NH_4Cl$ (5 mL) and DCM (10 mL) was added. The aqueous layer was extracted with DCM (3×10 mL). The organic layers were combined, washed with sat. aq. NaCl, dried using a phase separator and evaporated and concentrated under reduced pressure. The crude was purified by flash chromatography on silica gel (MeOH in DCM from 0% to 10%. The desired fractions were combined and concentrated to afford the expected compound as a yellow oil (150 mg, 95%). m/z 664 $[M+H]^+$. $^1H$ NMR (500 MHz, DMSO-$d_6$) δ ppm 8.31 (s, 1H), 7.32 (br d, J=8.1 Hz, 2H), 7.30-7.21 (m, 2H), 6.82 (s, 1H), 4.03-3.81 (m, 2H), 3.74-3.71 (m, 2H), 3.70-3.33 (m, 5H), 3.10 (s, 2H), 2.99-2.66 (m, 6H), 2.41-1.75 (m, 4H), 1.49-1.16 (m, 9H).

Step 2

To a stirred solution of tert-butyl N-[2-[3-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]pyrrolidin-1-yl]-2-oxo-ethyl]-N-methyl-carbamate (97%, 150 mg, 0.219 mmol) in dry DCM (2 mL) at rt under nitrogen, 4 M HCl in 1,4-dioxane (137 uL, 0.548 mmol) was added. The reaction mixture was stirred at rt for 5 h. Additional 4 M HCl in 1,4-dioxane (137 uL, 0.548 mmol) was added at rt and the reaction mixture was stirred at rt overnight. The reaction mixture was quenched with sat. aq. $NaHCO_3$ (10 mL) and DCM (10 mL) was added. The aqueous layer was extracted with DCM (3×10 mL). The organic layers were combined, washed with brine, dried using a phase separator and evaporated and concentrated under reduced pressure and separated by preparative chiral separation SFC ($CO_2$/(MeOH+0.5% IPAm) 70/30) to afford: Example 136: CPD0075880 (3 rel-R)—N-[(1S)-1-[4-(4-chloro-2,3,7,10-tetrazatricyclo[7.4.0.0$^{2,6}$]trideca-1(9), 3,5,7-tetraen-10-yl)phenyl]-2,2,2-trifluoro-ethyl]-N-methyl-1-[2-(methylamino) acetyl]pyrrolidine-3-carboxamide hydrochloride. (33 mg; 24.34% Yield). m/z: 564 $[M+H]^+$. $^1H$ NMR (500 MHz, DMSO-$d_6$) δ 8.36-8.24 (m, 1H), 7.43-7.21 (m, 4H), 6.87-6.74 (m, 1H), 6.73-6.56 (m, 1H), 6.50 (q, J=8.8 Hz, 1H), 3.71 (br d, J=3.7 Hz, 7H), 3.28-3.13 (m, 2H), 3.10 (q, J=6.1 Hz, 2H), 2.98-2.65 (m, 3H), 2.45-2.23 (m, 3H), 1.95 (br d, J=5.1 Hz, 4H) Example 137: CPD0075881 (3 rel-S)—N-[(1S)-1-[4-(4-chloro-2,3,7,10-tetrazatricyclo[7.4.0.0$^{2,6}$]trideca-1(9),3,5,7-tetraen-10-yl) phenyl]-2,2,2-trifluoro-ethyl]-N-methyl-1-[2-(methyl-amino) acetyl]pyrrolidine-3-carboxamide hydrochloride. (33 mg; 24%). m/z: 564 $[M+H]^+$. $^1H$ NMR (500 MHz, DMSO-$d_6$) δ 8.33-8.25 (m, 1H), 7.48-7.12 (m, 4H), 6.84-6.75 (m, 1H), 6.72-6.63 (m, 1H), 6.51 (br dd, J=8.7, 3.8 Hz, 1H), 3.80-3.47 (m, 7H), 3.45-3.38 (m, 1H), 3.26-3.14 (m, 1H), 3.13-3.02 (m, 2H), 2.99-2.60 (m, 3H), 2.44-1.75 (m, 7H)

Examples 138-141

Scheme 15

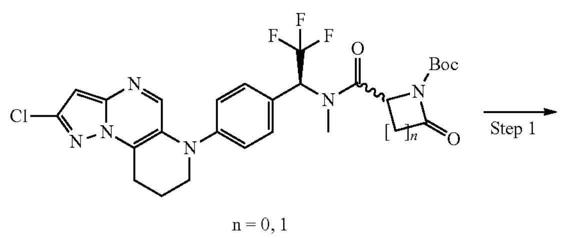

n = 0, 1

-continued

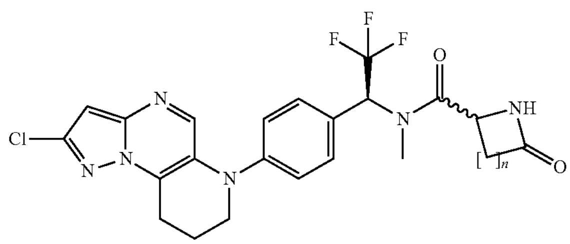

Step 1:

To a solution of intermediates 141-143 (1 mmol) in dry DCM (0.1 M) was added TFA (1 mmol). The reaction mixture was stirred at rt upon completion (2-4 h). Once the reaction was complete the reaction was quenched with a sat. aq. $NaHCO_3$ and diluted with EtOAc. The phases were separated and aqueous phase was extracted with EtOAc (3 times), the organic phases were combined, dried over $Na_2SO_4$ concentrated and then a) Purified by flash chromatography b) separated by SFC preparative chromatography (Chiralpak IB 5 μm, 250×20 mm, $CO_2$/MeOH+0.5% IPAm 70/30)

| Example 138 CPD0075869 | Procedure a | Intermediate 141 | Yield: 56% |
|---|---|---|---|

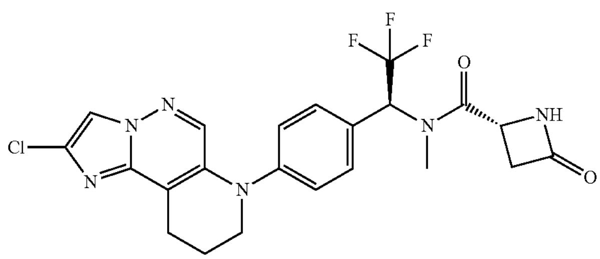 [SMILES: CN(C(=O)[C@H]1CC(=O)N1)[C@@H](c1ccc(N2CCCc3c2cnn2cc(Cl)nc32)cc1)C(F)(F)F]

$^1$H NMR (DMSO-$d_6$, 600 MHz) δ 8.40 (s, 1H), 8.31 (s, 1H), 7.2-7.5 (m, 4H), 6.82 (s, 1H), 6.45 (q, 1H, J = 9.1 Hz), 4.56 (dd, 1H, J = 2.8, 5.7 Hz), 3.6-3.9 (m, 2H), 3.26 (ddd, 1H, J = 1.0, 5.7, 14.4 Hz), 3.09 (t, 2H, J = 6.7 Hz), 2.8-2.9 (m, 1H), 2.79 (s, 3H), 1.9-2.0 (m, 2H). m/z: 493 $[M + H]^+$ (2R)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-4-oxo-azetidine-2-carboxamide

| Example 139 CPD0075670 | Procedure a | Intermediate 142 | Yield: 20% |
|---|---|---|---|

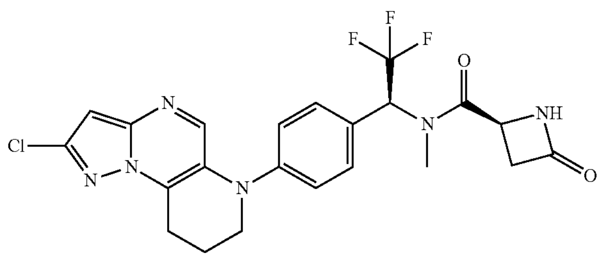 [SMILES: CN(C(=O)[C@@H]1CC(=O)N1)[C@@H](c1ccc(N2CCCc3c2cnc2cc(Cl)nn32)cc1)C(F)(F)F]

$^1$H NMR (DMSO-$d_6$, 600 MHz) δ 8.36 (s, 1H), 8.30 (s, 1H), 7.35 (d, 2H, J = 8.5 Hz), 7.1-7.3 (m, 2H), 6.82 (s, 1H), 6.46 (q, 1H, J = 9.2 Hz), 4.57 (s, 1H), 3.6-3.8 (m, 2H), 3.31 (s, 1H), 3.10 (t, 2H, J = 6.7 Hz), 2.83 (s, 4H), 1.9-2.0 (m, 2H). m/z: 493 [M + H]+

(2S)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-4-oxo-azetidine-2-carboxamide

| Example 140 CPD0073566 | Procedure: b | Intermediate 143 | Yield: 20% |
|---|---|---|---|

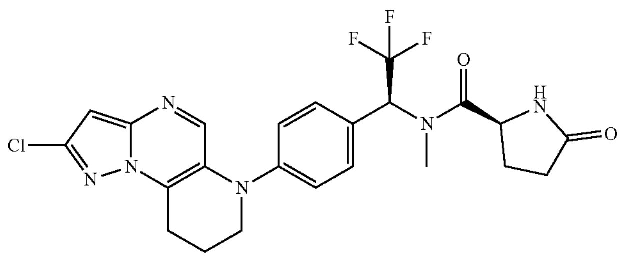 [SMILES: CN(C(=O)[C@@H]1CCC(=O)N1)[C@@H](c1ccc(N2CCCc3c2cnc2cc(Cl)nn32)cc1)C(F)(F)F]

$^1$H NMR (600 MHz, DMSO-$d_6$) δ ppm 8.31 (s, 1H), 7.92 (s, 1H), 7.34-7.29 (m, 2H), 7.29-7.22 (m, 2H), 6.87-6.70 (m, 1H), 6.14 (br s, 1H), 4.65 (dd, J = 9.0, 3.7 Hz, 1H), 3.89-3.58 (m, 2H), 3.15-3.05 (m, 2H), 2.93-2.66 (m, 3H), 2.42-2.28 (m, 1H), 2.22-2.05 (m, 2H), 2.02-1.92 (m, 2H), 1.82 (ddt, J = 13.2, 8.8, 4.5 Hz, 1H). m/z: 507 $[M + H]^+$.

(2rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-5-oxopyrrolidine-2-carboxamide -continued

| Example 141 CPD0073567 | Procedure: b | Intermediate 143 | Yield: 15% |
|---|---|---|---|
| 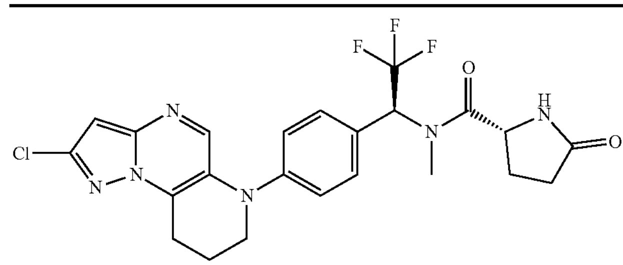 | $^1H$ NMR (600 MHz, DMSO-$d_6$) δ ppm 8.30 (s, 1H), 7.79 (s, 1H), 7.47-7.17 (m, 5H), 6.82 (s, 1H), 6.55-5.97 (m, 1H), 4.66 (br d, J = 5.0 Hz, 1H), 3.76-3.68 (m, 2H), 3.16-3.03 (m, 2H), 2.91 (s, 3H), 2.19-2.10 (m, 2H), 2.01-1.91 (m, 2H), 1.89-1.75 (m, 1H). m/z: 507 [M + H]+. | | |
| (2rel-R)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-5-oxopyrrolidine-2-carboxamide | | | |

Example 142 CPD0019341

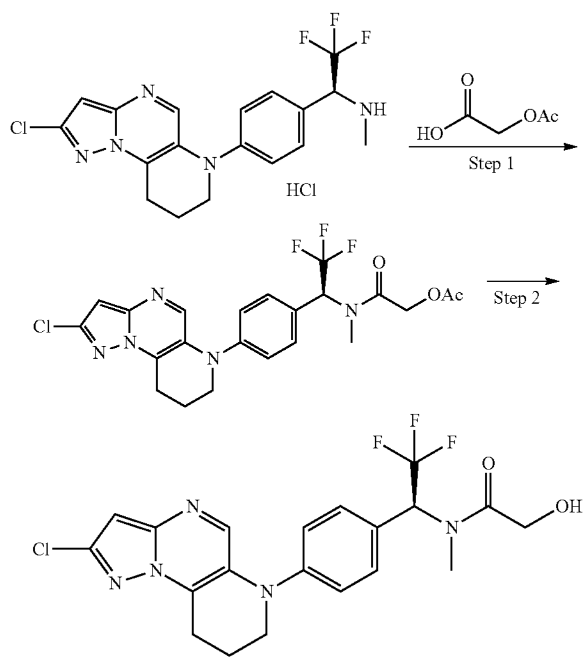

Step 1. [2-[[(1S)-1-[4-(4-chloro-2,3,7,10-tetrazatricyclo[7.4.0.0$^{2,6}$]trideca-1(9),3,5,7-tetraen-10-yl) phenyl]-2,2,2-trifluoro-ethyl]-methyl-amino]-2-oxo-ethyl]acetate Prepared from intermediate 117 according to the general procedure 3b described for preparing examples 37-127 to afford title compound (79 mg, 71%). The crude was used as such in the next step. m/z: 496.0 $[M+H]^+$.

Example 142 Step 2. N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-2-hydroxy-N-methyl-acetamide (CPD0019341)

To a solution of [2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-amino]-2-oxo-ethyl]acetate (72 mg, 0.0973 mmol) in a methanol (0.5 mL)/water (0.5 mL) was added lithium hydroxide hydrate (8.2 mg, 0.195 mmol). The mixture was stirred at rt for 45 min. EtOAc was added to the mixture. An aqueous solution of 10% citric acid was added and the aqueous layer was extracted 3 times with EtOAc. The organic layer was washed with brine, dried over anhydrous $MgSO_4$, filtered and concentrated in vacuo. The crude was purified by reverse phase column chromatography (water/acetonitrile from water 100% to acetonitrile 100%) to afford the expected compound as a light yellow solid (26 mg, 19%). m/z: 454 $[M+H]^+$. $^1H$ NMR (DMSO-$d_6$, 600 MHz): δ ppm 8.30 (s, 1H), 7.34 (br d, =7.3 Hz, 2H), 7.23-7.31 (m, 2H), 6.82 (s, 1H), 6.46 (q, J=9.4 Hz, 1H), 4.88 (t, J=5.9 Hz, 1H), 4.23 (d, J=5.7 Hz, 2H), 3.67-3.76 (m, 2H), 3.10 (t, J=6.7 Hz, 2H), 2.79 (s, 3H), 1.91-2.00 (m, 2H).

Examples 143-144 CPD0021561, CPD0019350

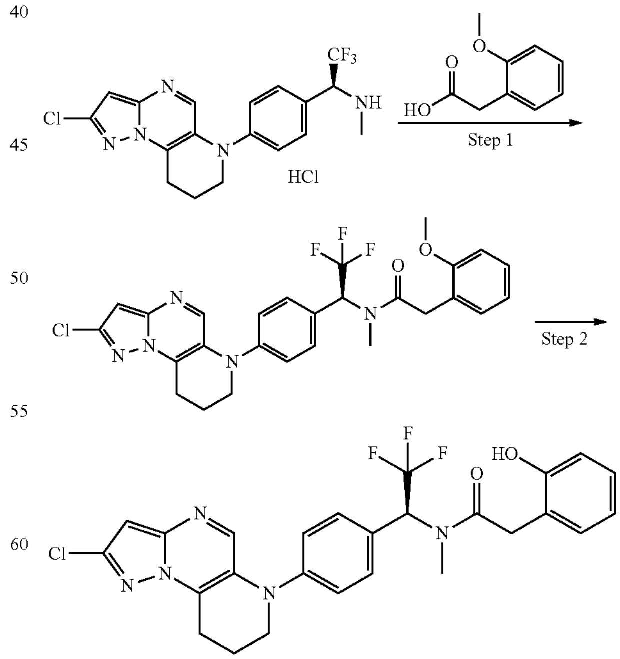

Example 143 Step 1. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(2-methoxyphenyl)-N-methylacetamide (CPD0021561)

Prepared from intermediate 117 according to the general procedure 3b described for examples 37-127 (26 mg, 19%). m/z: 544 $[M+H].^{+}$ $^1$H NMR (600 MHz, DMSO-$d_6$) δ ppm 8.30 (s, 1H) 7.32 (d, J=8.66 Hz, 2H) 7.28 (d, J=8.66 Hz, 2H) 7.22-7.26 (m, 1H) 7.12-7.16 (m, 1H) 6.98 (d, J=7.78 Hz, 1H) 6.88-6.93 (m, 1H) 6.82 (s, 1H) 6.46-6.55 (m, 1H) 3.73-3.76 (m, 5H) 3.70-3.73 (m, 2H) 3.10 (t, J=6.60 Hz, 2H) 2.91 (s, 3H) 1.92-2.02 (m, 2H).

Example 144 Step 2. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(2-hydroxyphenyl)-N-methylacetamide (CPD0019350)

To a solution of N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(2-methoxyphenyl)-N-methylacetamide (51 mg, 0.0846 mmol) in dry DCM (2.8 mL) was added 1 M tribromoborane (0.25 mL, 0.254 mmol). The reaction mixture was left stirring at rt overnight. The reaction mixture was quenched with $H_2O$ and phases were separated. Aqueous phase was extracted with DCM. The combined organic layers were washed with brine, dried over anhydrous $Na_2SO_4$, filtered and concentrated under reduced pressure. The crude was purified by reverse phase column chromatography (water/acetonitrile with 0.1% of AcOH from water 100% to acetonitrile 100%) to afford title compound (14 mg, 30%). m/z: 530 $[M+H]^+$. $^1$H NMR (600 MHz, DMSO-$d_6$) δ ppm 9.46 (s, 1H), 8.31 (s, 1H), 7.40-7.29 (m, 2H), 7.25 (d, J=8.8 Hz, 2H), 7.05 (d, J=7.5 Hz, 2H), 6.82 (s, 1H), 6.80 (d, J=7.6 Hz, 1H), 6.76-6.72 (m, 1H), 6.58-6.03 (m, 1H), 3.71 (s, 2H), 3.75-3.67 (m, 2H), 3.10 (t, J=6.7 Hz, 2H), 2.90 (s, 3H), 2.00-1.91 (m, 2H).

Example 145 CPD0021565

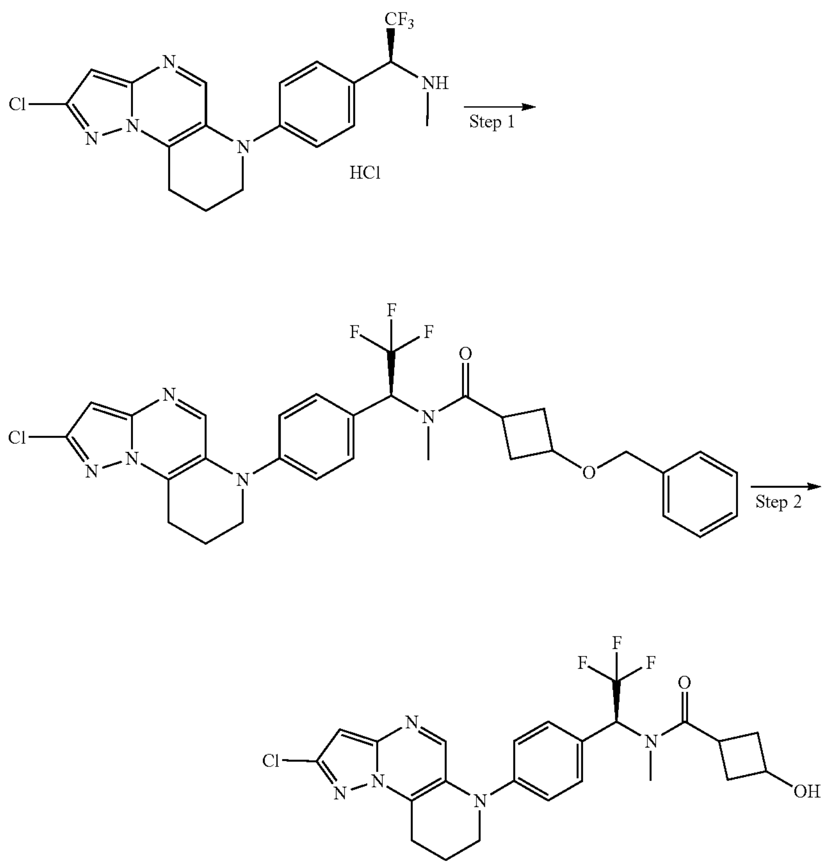

Step 1. 3-benzyloxy-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-cyclobutanecarboxamide The compound was prepared from intermediate 117 according to the procedure 3c described for examples 37-127. (30.5 mg; 76.2% yield). m/z: 584 $[M+H]^+$. $^1$H NMR (400 MHz, DMSO-$d_6$) δ ppm 8.31 (s, 1H), 7.39-7.19 (m, 9H), 6.83 (s, 1H), 6.49 (d, J=9.4 Hz, 1H), 4.39 (s, 2H), 4.15-3.92 (m, 1H), 3.72 (s, 2H), 3.16-2.98 (m, 3H), 2.85-2.58 (m, 3H), 2.33 (s, 2H), 2.12-1.87 (m, 3H).

Example 145 Step 2. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-hydroxy-N-methylcyclobutane-1-carboxamide (CPD0021565)

To a mixture of 3-benzyloxy-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-cyclobutanecarboxamide (86 mg, 0.103 mmol) in DCM (1 mL) at −78° C. was added trichloroborane (0.040 mL, 0.309 mmol). The mixture was then stirred at rt for 8 h. The reaction mixture was quenched with water and extracted twice with DCM. The organic layers were combined, dried over anhydrous $Na_2SO_4$, filtered, and concentrated under reduced pressure. The crude was purified by reverse-phase column (water/acetonitrile from water 100% to acetonitrile 100%) to afford the expected product (46 mg, 88%) with the presence of two diastereomers in proportion 71/29. m/z: 493 $[M+H]^+$. $^1H$ NMR (DMSO-$d_6$, 500 MHz): δ ppm 8.30 (s, 1H), 7.47-7.08 (m, 4H), 6.82 (s, 1H), 6.58-6.41 (m, 1H), 5.16-5.03 (m, 1H), 4.22-3.94 (m, 1H), 3.78-3.64 (m, 2H), 3.13-3.06 (m, 2H), 2.95-2.83 (m, 1H), 2.77 (s, 3H), 2.48-2.31 (m, 2H), 2.18-1.90 (m, 4H).

Example 146 CPD0021576

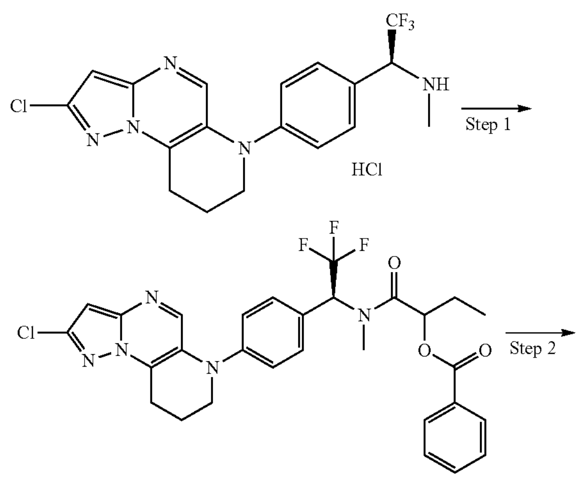

-continued

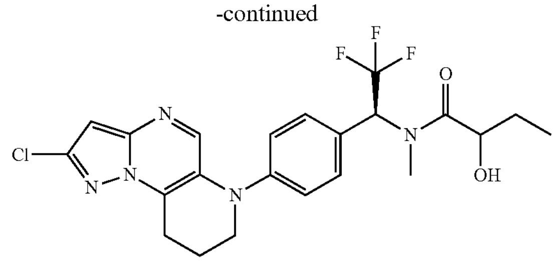

Step 1. 1-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoy]propyl benzoate The compound was prepared from intermediate 117 according to the procedure 3c described for examples 37-127 to afford title compound (108 mg, 38%) as a mixture of 2 diastereomers in proportion 58/42. m/z: 586 $[M+H]^+$. $^1H$ NMR (400 MHz, DMSO-$d_6$) δ ppm 8.33 (d, J=7.0 Hz, 1H), 8.05-8.00 (m, 2H), 7.75-7.52 (m, 4H), 7.36-7.26 (m, 4H), 6.50 (s, 1H), 5.62-5.46 (m, 1H), 3.74 (dd, J=6.4, 3.9 Hz, 2H), 3.11 (t, J=6.6 Hz, 2H), 3.00 (d, J=4.2 Hz, 3H), 1.99-1.80 (m, 4H), 1.07-0.99 (m, 3H).

Example 147 Step 2. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-hydroxy-N-methylbutanamide (CPD0021576)

To a solution of 1-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]propyl benzoate (97 mg, 0.166 mmol) in a methanol (0.8 mL)/water (0.8 mL) was added lithium hydroxide (4.1 mg, 0.166 mmol). The mixture was stirred at rt for 30 min. The mixture was concentrated in vacuo. EtOAc and a sat. aq. $NH_4Cl$ sat were added to the residue. The aqueous layer was extracted 3 times with EtOAc. The organic layer was washed with brine, dried over anhydrous $Na_2SO_4$, filtered and concentrated under vacuo. The crude was purified by flash column chromatography (Cyclohexane/EtOAc, from 0% to 30% of EtOAc) to afford the expected compound (13 mg, 16%) with the presence of two diastereoisomeres en proportion 70/30. m/z: 481 $[M+H]^+$. $^1H$ NMR (DMSO-$d_6$, 500 MHz): δ ppm 8.31 (s, 1H), 7.1-7.5 (m, 4H), 6.82 (s, 1H), 6.2-6.6 (m, 1H), 5.0-5.2 (m, 1H), 4.2-4.5 (m, 1H), 3.6-3.8 (m, 2H), 3.10 (t, 2H, J=6.6 Hz), 2.9-3.0 (m, 3H), 1.8-2.1 (m, 2H), 1.5-1.8 (m, 2H), 0.7-1.0 (m, 3H).

Examples 148-149 CPD0073972/CPD0073973

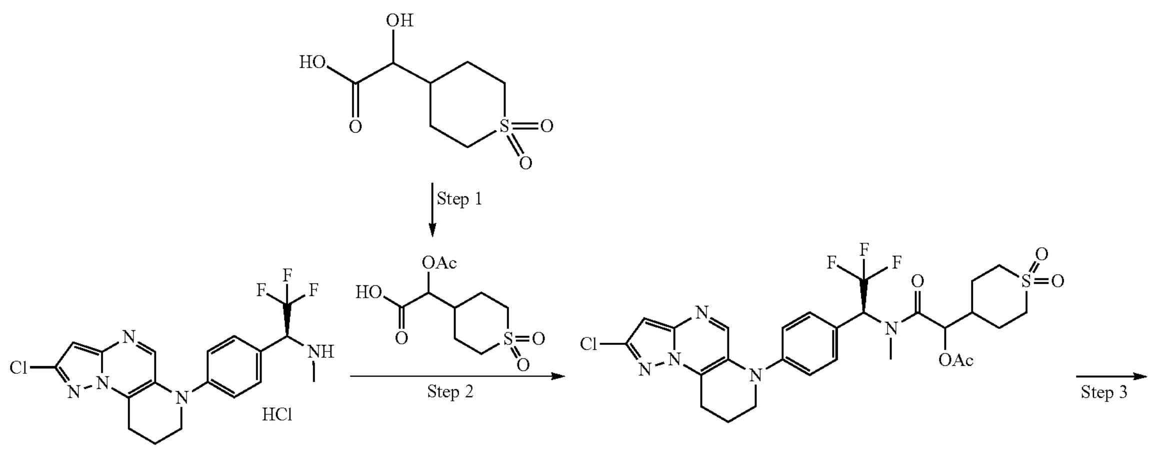

-continued

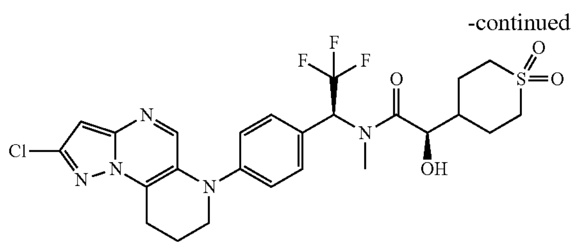

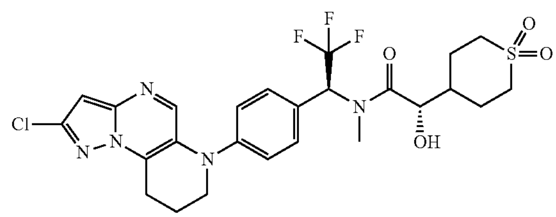

Step 1. 2-(acetyloxy)-2-(1,1-dioxo-1λ[6]-thian-4-yl) acetic acid

To a solution of 2-(1,1-dioxo-1) 6-thian-4-yl)-2-hydroxy-acetic acid (500 mg, 2.28 mmol) in pyridine (11.4 mL) was added acetic anhydride (0.32 mL, 3.42 mmol) at 0° C. The reaction mixture was left stirring at rt overnight. The reaction mixture was quenched with water and the solution was acidified until pH~1-2 with a solution of HCl 37%. Aqueous phase was extracted with EtOAc, the combined organic layers were dried over anhydrous $Na_2SO_4$, filtered and concentrated under reduced pressure to obtain the title compound as a light yellow solid (299 mg, 51%). $^1$H NMR (400 MHz, DMSO-$d_6$) δ ppm 13.24 (s, 1H), 4.82 (d, J=4.1 Hz, 1H), 3.22 (qd, J=12.9, 12.4, 4.9 Hz, 2H), 3.04 (dd, J=14.8, 3.5 Hz, 2H), 2.24 (ddt, J=11.6, 8.4, 3.7 Hz, 1H), 2.09 (s, 3H), 2.05 (d, J=12.2 Hz, 1H), 1.90 (dd, J=8.7, 2.3 Hz, 2H), 1.85-1.70 (m, 1H).

Step 2. [2-[[(1S)-1-[4-(4-chloro-2,3,7,10-tetrazatricyclo[7.4.0.0$^{2,6}$]trideca-1(9),3,5,7-tetraen-10-yl) phenyl]-2,2,2-trifluoro-ethyl]-methyl-amino]-1-(1,1-dioxothian-4-yl)-2-oxo-ethyl]acetate To a solution of Intermediate 117 (100%, 200 mg, 0.463 mmol) and 2-(acetyloxy)-2-(1,1-dioxo-1λ[6]-thian-4-yl) acetic acid (143 mg, 0.555 mmol) in dry DCM (2.3 mL) was added TEA (1.3 mL, 9.25 mmol) followed by T3P-50% in EtOAc (2.8 mL, 4.63 mmol). The reaction mixture was stirred at rt overnight. LCMS showed still unreacted starting material so 2-(acetyloxy)-2-(1,1-dioxo-1\6-thian-4-yl) acetic acid (24 mg, 0.0925 mmol) was added to the reaction mixture and stirred for 4 h. The reaction mixture was quenched with water and diluted with EtOAc. Aqueous phase was extracted with EtOAc. The organic layers were combined, washed with brine, dried over anhydrous $Na_2SO_4$, filtered and concentrated under reduced pressure. The crude was purified by flash column chromatography (Heptane/EtOAc, from 25% to 60% of EtOAc) to obtain the title compound (202 mg, 69%). m/z: 628 $[M+H]^+$. $^1$H NMR (400 MHz, DMSO-$d_6$) δ ppm 8.32 (d, J=1.5 Hz, 1H), 7.28 (d, J=5.0 Hz, 4H), 6.82 (d, J=1.9 Hz, 1H), 6.43 (dt, J=42.4, 9.2 Hz, 1H), 5.28 (dd, J=12.3, 5.3 Hz, 1H), 3.79-3.65 (m, 2H), 3.28-3.14 (m, 2H), 3.10 (dt, J=6.7, 3.3 Hz, 3H), 3.05 (s, 1H), 2.96 (d, J=11.2 Hz, 3H), 2.09 (s, 3H), 1.99 (s, 3H), 1.95 (d, J=3.8 Hz, 4H).

Example 148 (CPD0073972) Step 3. (2rel-R)—N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1λ[6]-thian-4-yl)-2-hydroxy-N-methylacetamide To a solution of [2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-amino]-1-(1,1-dioxothian-4-yl)-2-oxo-ethyl] acetate (175 mg, 0.276 mmol) in water (3.5 mL)/methanol (3.5 mL) was added lithium hydroxide hydrate (24 mg, 0.552 mmol). The reaction mixture was left stirring for 3 h. The reaction mixture was partitioned between water and EtOAc. Phases were separated and aqueous phase was extracted with EtOAc. The organic layers were combined, washed with brine, dried over anhydrous $Na_2SO_4$, filtered and concentrated under reduced pressure. The crude was purified by reverse phase preparative chromatography (water/acetonitrile (with 0.1% AcOH) from water 100% to acetonitrile 100%) to afford a mixture of the 2 diastereomers. The mixture was purified by SFC preparative chromatography (Chiralpak IB 5 μm, 250×20 mm, $CO_2$/MeOH+0.5% IPAm 80/20) to afford title compound (13.8 mg, 8%). m/z: 586 $[M+H]^+$. $^1$H NMR (600 MHz, DMSO-$d_6$) δ ppm 8.30 (s, 1H), 7.21-7.50 (m, 4H), 6.82 (s, 1H), 6.16-6.59 (m, 1H), 5.40-6.02 (m, 1H), 4.29 (t, J=6.7 Hz, 1H), 3.67-3.82 (m, 2H), 2.97-3.19 (m, 6H), 2.95 (s, 3H), 1.59-2.28 (m, 7H).

Example 149 (CPD0073973) (2rel-S)—N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-2-(1,1-dioxo-1λ[6]-thian-4-yl)-2-hydroxy-n-methylacetamide The expected product was obtained from the same purification conditions as the previous compound (15.4 mg, 9%). m/z: 563 $[M+H]^+$. $^1$H NMR (600 MHz, DMSO-$d_6$) δ ppm 8.31 (s, 1H), 7.22-7.44 (m, 4H), 6.82 (s, 1H), 6.23-6.60 (m, 1H), 5.32 (d, J=7.3 Hz, 1H), 4.34 (t, J=6.7 Hz, 1H), 3.64-3.80 (m, 2H), 3.00-3.23 (m, 6H), 2.93 (s, 3H), 1.72-2.14 (m, 7H).

Example 150 CPD0019340

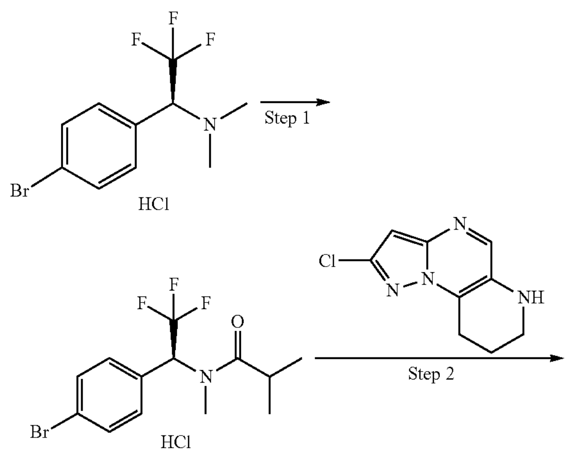

-continued

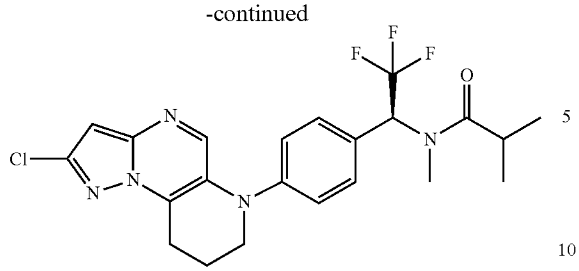

Step 1. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,2-dimethylpropanamide To a solution of Intermediate 80 (100 mg, 0.328 mmol) in dry THF (3.3 mL) was added N-ethyl-N-isopropyl-propan-2-amine (0.14 mL, 0.821 mmol) prior addition of 2-methylpropanoyl chloride (0.069 mL, 0.657 mmol). The reaction mixture was left stirring at rt for 2 h. The solvent was removed and the crude was poured in DCM and sat. aq. $NH_4Cl$. The aqueous layers were extracted twice with DCM. The organic layers were combined, washed with brine, dried over anhydrous $MgSO_4$ and concentrated under vacuum. The crude was purified by flash column chromatography (heptane/EtOAc, from 0% to 50% of EtOAc) to afford the title compound (83 mg, 58%). m/z: 439 $[M+H]^+$. $^1H$ NMR (400 MHz, DMSO-$d_6$) δ ppm 7.69 (d, J=8.5 Hz, 2H), 7.31 (d, J=8.3 Hz, 2H), 6.57 (q, J=9.2 Hz, 1H), 2.99 (p, J=6.7 Hz, 1H), 2.86 (s, 3H), 1.08 (d, J=5.5 Hz, 6H).

Example 150 Step 2. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N,2-dimethylpropanamide (CPD0019340)

The compound was prepared according to the procedure described for examples 1-32 (10 mg, 12%). m/z: 466 $[M+H]^+$. $^1H$ NMR (DMSO-$d_6$, 500 MHz): δ ppm 8.31 (s, 1H), 7.23-7.39 (m, 4H), 6.82 (s, 1H), 6.54 (q, J=9.5 Hz, 1H), 3.68-3.76 (m, 2H), 3.10 (t, J=6.6 Hz, 2H), 2.98 (dt, J=13.3, 6.7 Hz, 1H), 2.90 (s, 3H), 1.92-2.00 (m, 2H), 1.08 (d, J=6.8 Hz, 3H), 1.05 (d, J=6.6 Hz, 3H).

Examples 151 CPD0021745

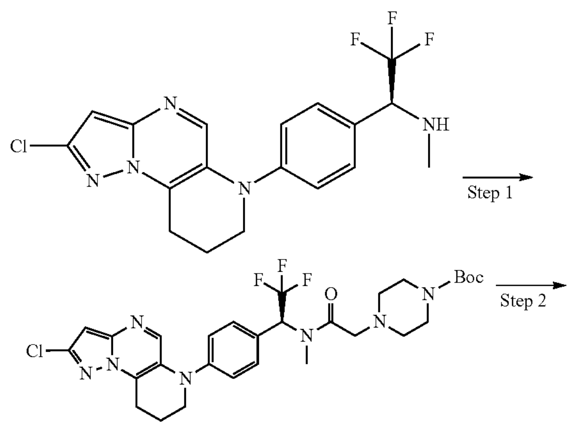

-continued

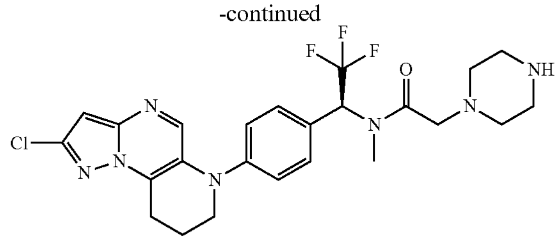

Step 1. tert-butyl 4-[2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-amino]-2-oxo-ethyl]piperazine-1-carboxylate To a solution of Intermediate 117 (130 mg, 0.301 mmol) and T3P-50% in EtOAc (1.8 mL, 3.01 mmol) in dry DCM (1.5 mL) was added TEA (0.84 mL, 6.01 mmol) followed by [4-(tert-butoxycarbonyl) piperazin-1-yl]acetic acid (75 mg, 0.301 mmol) The reaction mixture was left stirring at rt for 18 h. The reaction mixture was partitioned between DCM and a saturated $NaHCO_3$ solution. The phases were separated and the aqueous phase was extracted twice with DCM. The organic layers were combined, washed with brine, dried over anhydrous $Na_2SO_4$, filtered and concentrated under reduced pressure. The crude was purified by reverse-phase column chromatography (water/acetonitrile from water 100% to acetonitrile 100%) to afford the title compound (86 mg, 46%). m/z: 622 $[M+H]^+$. $^1H$ NMR (400 MHz, DMSO-$d_6$) δ ppm 8.31 (s, 1H), 7.50-7.23 (m, 4H), 6.82 (s, 1H), 6.46 (t, J=9.4 Hz, 1H), 3.73 (d, J=4.8 Hz, 2H), 3.45-3.34 (m, 2H), 3.11 (t, J=6.7 Hz, 2H), 2.82 (d, J=79.1 Hz, 3H), 2.47-2.31 (m, 4H), 1.96 (d, J=5.0 Hz, 2H), 1.40 (s, 9H).

Example 151 Step 2. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-2-(piperazin-1-yl) acetamide To a solution of tert-butyl 4-[2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-amino]-2-oxo-ethyl]piperazine-1-carboxylate (70 mg, 0.110 mmol) in dry DCM (0.5 mL) was added TFA (0.082 mL, 1.10 mmol). The mixture was stirred at rt for 5 h. The reaction mixture was quenched with sat. aq. $NaHCO_3$ (5 mL) and DCM (5 mL) was added. The aqueous layer was extracted with DCM (3×5 mL). The organic layers were combined, washed with brine, dried with anhydrous $Na_2SO_4$ and concentrated under reduced pressure The crude was purified by reverse-phase column (water/acetonitrile from water 100% to acetonitrile 100%) to afford the title compound (45 mg, 74%). m/z: 522 $[M+H]^+$. $^1H$ NMR (600 MHz, DMSO-$d_6$) δ ppm 8.31 (s, 1H), 7.50-7.22 (m, 4H), 6.82 (s, 1H), 6.53-6.36 (m, 1H), 3.77-3.67 (m, 2H), 3.43-3.33 (m, 1H), 3.28-3.17 (m, 2H), 3.10 (t, J=6.7 Hz, 2H), 2.93 (s, 3H), 2.69-2.63 (m, 4H), 2.45-2.19 (m, 4H), 1.98 (br s, 2H).

Example 152 CPD0021849

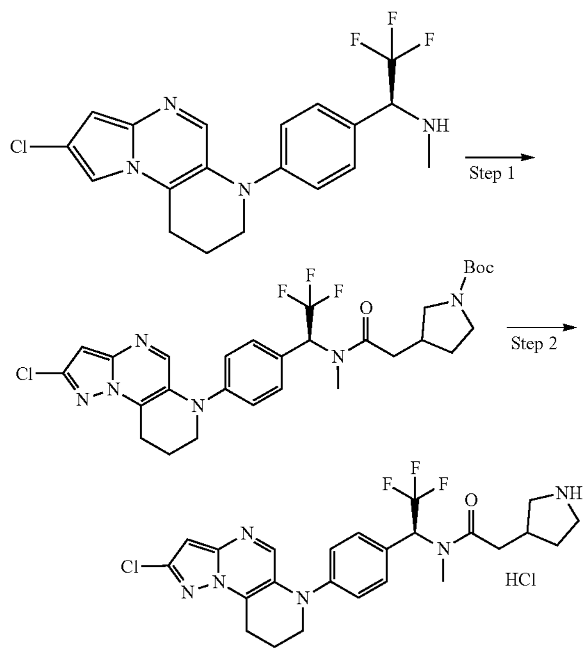

Step 1. tert-butyl 3-[2-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-amino]-2-oxo-ethyl]pyrrolidine-1-carboxylate The compound was prepared from intermediate 117 according to the general procedure 3a described for examples 37-127 (63 mg, 71%). m/z: 607 $[M+H]^+$. $^1H$ NMR (600 MHz, DMSO-$d_6$) δ ppm 8.30 (s, 1H), 7.30-7.42 (m, 2H), 7.23-7.29 (m, 2H), 6.82 (s, 1H), 5.99-6.59 (m, 1H), 3.67-3.75 (m, 2H), 3.40-3.55 (m, 1H), 3.32-3.37 (m, 1H), 3.13-3.23 (m, 1H), 3.09 (t, J=6.7 Hz, 2H), 2.85 (s, 3H), 2.78-2.85 (m, 1H), 2.54-2.65 (m, 2H), 2.51-2.53 (m, 1H), 1.99-2.07 (m, 1H), 1.93-1.98 (m, 2H), 1.44-1.57 (m, 1H), 1.39 (d, J=4.7 Hz, 9H).

Example 152 Step 2. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-2-(pyrrolidin-3-yl) acetamide To a stirred solution of tert-butyl 3-[2-[[(1S)-1-[4-(4-chloro-2,3,7,10-tetrazatricyclo[7.4.0.0$^{2,6}$]trideca-1(9), 3,5,7-tetraen-10-yl)phenyl]-2,2,2-trifluoro-ethyl]-methyl-amino]-2-oxo-ethyl]pyrrolidine-1-carboxylate (55 mg, 0.0861 mmol) in dry 1,4-dioxane (0.4 mL) was added 4M HCl in 1,4-dioxane (0.22 mL, 0.861 mmol). The reaction mixture was stirred at rt for 3 h. The reaction mixture was concentrated under reduced pressure. The crude was purified by flash reverse column (water/acetonitrile from water 100% to acetonitrile 100%) to afford the title compound (14 mg, 30%) as a mixture of two diastereomers in proportion 1/1. m/z: 507 $[M+H]^+$. $^1H$ NMR (500 MHz, DMSO-$d_6$) δ ppm 8.65-8.91 (m, 2H), 8.29 (s, 1H), 7.30-7.43 (m, 2H), 7.25-7.29 (m, 2H), 6.82 (s, 1H), 6.50 (q, J=9.2 Hz, 1H), 3.68-3.76 (m, 2H), 3.35-3.44 (m, 1H), 3.18-3.27 (m, 1H), 3.06-3.15 (m, 1H), 3.10 (br t, J=6.6 Hz, 2H), 2.86 (s, 3H), 2.56-2.81 (m, 4H), 2.05-2.20 (m, 1H), 1.90-2.01 (m, 2H), 1.50-1.63 (m, 1H).

Examples 153-154 CPD0072439/CPD0072934

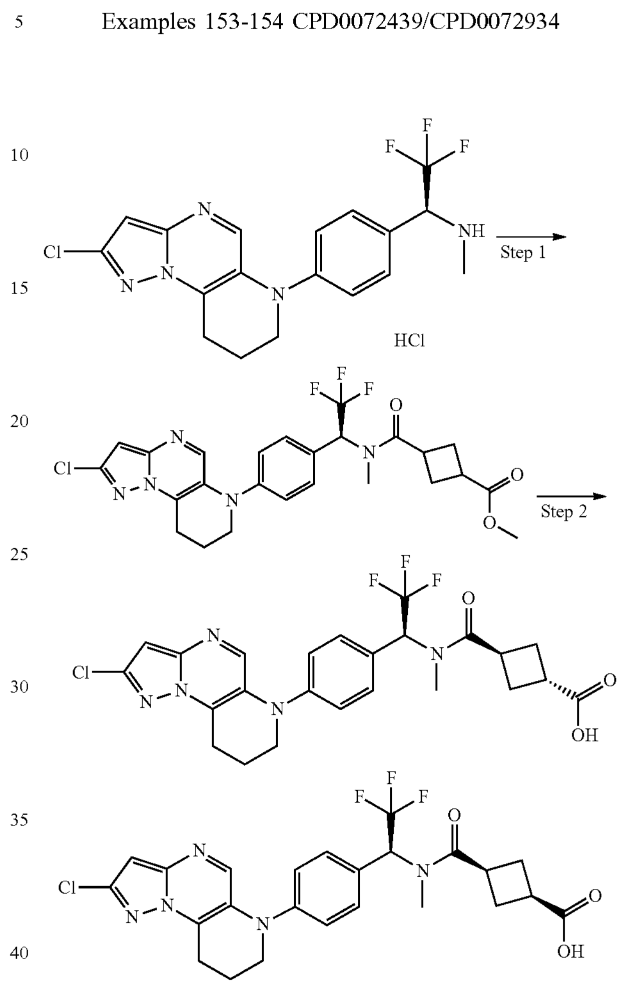

Step 1. methyl 3-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]cyclobutanecarboxylate The compound was prepared from intermediate 117 according to the general procedure 3b described for examples 37-127 to afford the title compound (77.5 mg, 61%) as a mixture of diastereomers. m/z: 536 $[M+H]^+$. $^1H$ NMR (400 MHz, DMSO-$d_6$) δ ppm 8.31 (s, 1H), 7.35-7.23 (m, 4H), 6.82 (s, 1H), 6.56-6.40 (m, 1H), 3.76-3.69 (m, 2H), 3.62 (d, J=13.4 Hz, 3H), 3.58-3.40 (m, 1H), 3.10 (t, J=6.7 Hz, 3H), 2.76 (d, J=14.0 Hz, 2H), 2.49-2.23 (m, 4H), 1.96 (s, 2H).

Example 153 Step 2. (trans)-3-{[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl](methyl)carbamoyl}cyclobutane-1-carboxylic acid (CPD0072439)

To a solution of methyl 3-[[(1S)-1-[4-(4-chloro-2,3,7,10-tetrazatricyclo[7.4.0.0$^{2,6}$]trideca-1(9),3,5,7-tetraen-10-yl) phenyl]-2,2,2-trifluoro-ethyl]-methyl-carbamoyl]cyclobutanecarboxylate (78 mg, 0.145 mmol) in a methanol (2 mL)/water (2 mL) mixture was added lithium hydroxide hydrate (18 mg, 0.434 mmol). The reaction mixture was stirred at rt for 1 h. The mixture was concentrated in vacuo. EtOAc was added to the residue. An aqueous solution of citric acid 10% was added and the aqueous layer was extracted 3 times with EtOAc. The organic layer was washed with brine, dried over anhydrous $MgSO_4$, filtered and concentrated in vacuo. The crude was purified by SFC chromatography (Chiralpak IB 5 μm, 250×20 mm, CO2/(EtOH+0.5% IPAm) 75/25) to afford the expected compound as a light yellow powder (8.3 mg, 11%) with the trans configuration. m/z: 522 $[M+H]^+$. $^1H$ NMR (600 MHz, DMSO-$d_6$) δ ppm 11.81-12.67 (m, 1H), 8.30 (s, 1H), 7.29-7.35 (m, 2H), 7.23-7.28 (m, 2H), 6.81 (s, 1H), 6.49 (q, J=9.2 Hz, 1H), 3.68-3.74 (m, 2H), 3.50 (quin, J=8.1 Hz, 1H), 3.09 (t, J=6.7 Hz, 2H), 2.93-3.01 (m, 1H), 2.73 (s, 3H), 2.34-2.47 (m, 4H), 1.93-1.98 (m, 2H).

Example 154 (cis)-3-{[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl](methyl)carbamoyl}cyclobutane-1-carboxylic acid (CPD0072934)

The expected product was obtained from the same purification as the previous compound (11.1 mg, 14%) with the cis configuration. m/z: 522 $[M+H]^+$. $^1H$ NMR (600 MHz, DMSO-$d_6$) δ ppm 11.92-12.43 (m, 1H), 8.30 (s, 1H), 7.24-7.36 (m, 4H), 6.81 (s, 1H), 6.46 (br d, J=9.1 Hz, 1H), 3.69-3.73 (m, 2H), 3.36-3.43 (m, 1H), 3.09 (t, J=6.7 Hz, 2H), 2.96 (br d, J=8.4 Hz, 1H), 2.64-2.80 (m, 3H), 2.22-2.42 (m, 4H), 1.93-1.98 (m, 2H).

Example 155 CPD0072442

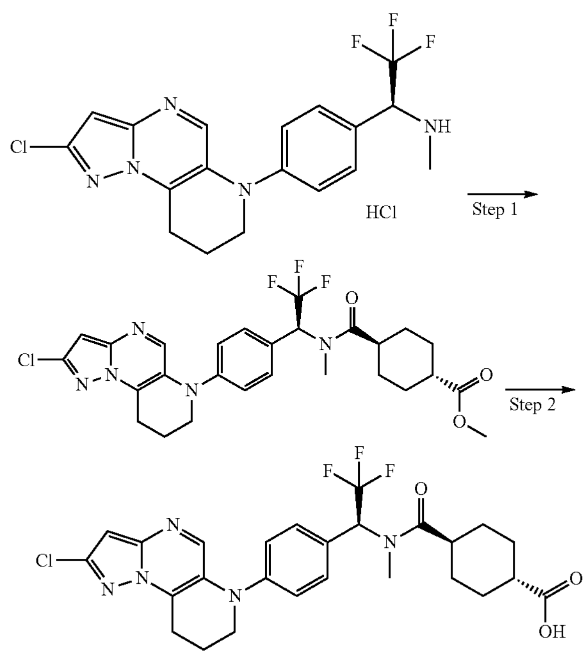

Step 1. methyl (1r,4r)-4-{[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl](methyl)carbamoyl}cyclohexane-1 carboxylate The compound was prepared from intermediate 117 according to the general procedure 3b described for examples 37-127 to afford title compound (45 mg, 49%) with the trans configuration. m/z: 565 $[M+H]^+$. $^1H$ NMR (400 MHz, DMSO-$d_6$) δ ppm 8.30 (s, 1H), 7.32-7.19 (m, 4H), 6.82 (s, 1H), 6.52 (q, J=9.4 Hz, 1H), 3.76-3.67 (m, 2H), 3.59 (s, 3H), 3.17 (d, J=5.3 Hz, 1H), 3.10 (t, J=6.7 Hz, 2H), 2.89 (s, 3H), 2.78-2.60 (m, 2H), 2.33 (s, 1H), 2.03-1.87 (m, 4H), 1.78 (d, J=33.9 Hz, 2H), 1.52-1.36 (m, 4H), 1.14 (s, 1H).

Example 155 Step 2. (1r,4r)-4-{[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl](methyl)carbamoyl}cyclohexane-1-carboxylic acid (CPD0072442)

To a stirred solution of methyl (1r,4r)-4-{[(1S)-1-(4-{4-chloro-2,3,7,10-tetraazatricyclo[7.4.0.0$^{2,6}$]trideca-1(9),3,5,7-tetraen-10-yl}phenyl)-2,2,2 trifluoroethyl](methyl)carbamoyl}cyclohexane-1 carboxylate (40 mg, 0.0709 mmol) in dry 1,4-dioxane (1 mL) and water (1 mL) at rt under nitrogen was added lithium hydroxide hydrate (15 mg, 0.355 mmol). The reaction mixture was stirred at rt for 1 h. The reaction mixture was acidified with a 10% aqueous solution of citric acid (1 mL) and EtOAc (5 mL) was added. The aqueous layer was extracted with EtOAc (3×5 mL). The organic layers were combined, washed with brine, dried over $MgSO_4$ and concentrated under reduced pressure. The crude was purified by reverse-phase preparative chromatography (acetonitrile in water from 0% to 100%) to afford the expected compound as a yellow powder (14.2 mg, 35%) with a trans configuration. m/z: 550 $[M+H]^+$. $^1H$ NMR (600 MHz, DMSO-$d_6$) δ ppm 11.45-12.63 (m, 1H), 8.30 (s, 1H), 7.15-7.56 (m, 4H), 6.81 (s, 1H), 6.52 (br q, J=9.4 Hz, 1H), 3.65-3.81 (m, 2H), 3.09 (t, J=6.7 Hz, 2H), 2.89 (s, 3H), 2.70 (ddd, J=11.0, 7.9, 3.1 Hz, 1H), 2.13-2.26 (m, 1H), 1.87-2.02 (m, 4H), 1.68-1.87 (m, 2H), 1.30-1.52 (m, 4H).

Example 156 CPD0072441

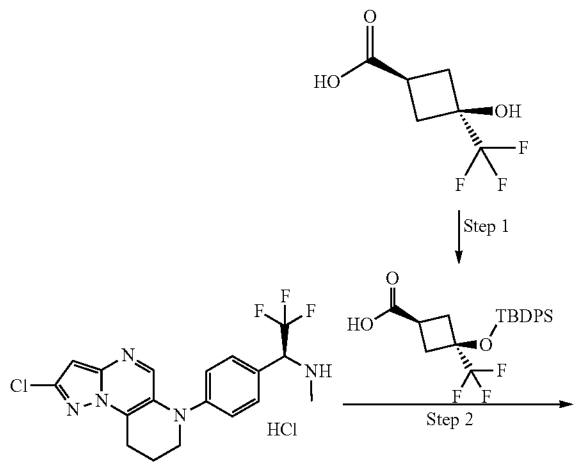

-continued

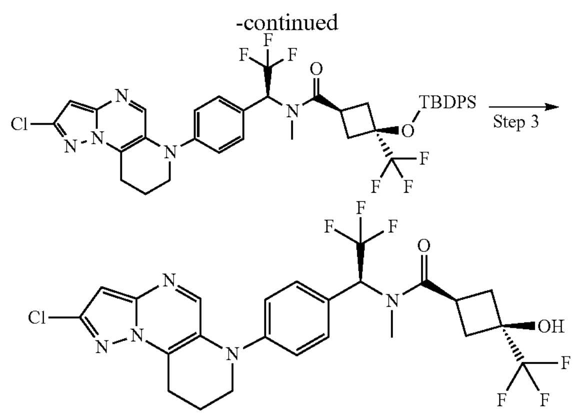

Step 1. (1s,3s)-3-[(tert-butyldiphenylsilyl)oxy]-3-(trifluoromethyl)cyclobutane-1-carboxylic acid (1s,3s)-3-hydroxy-3-(trifluoromethyl)cyclobutanecarboxylic acid (50 mg, 0.272 mmol) was dissolved in DMF (0.5 mL) prior addition of imidazole (92 mg, 1.36 mmol) and tert-butyl-chloro-diphenyl-silane (0.13 mL, 0.597 mmol). The reaction mixture was stirred at rt for 24 h. A second amount of imidazole (92 mg, 1.36 mmol) and tert-butyl-chloro-diphenyl-silane (98%, 0.13 mL, 0.597 mmol) were added and the reaction mixture heated at 70° C. for 24 h. The reaction mixture was quenched with a saturated $NH_4Cl$ solution (10 mL), left stirring for 30 minutes and then extracted with EtOAc (3×10 mL). The organic layers were combined, washed with brine, dried over anhydrous $Na_2SO_4$, filtered and concentrated under reduced pressure. The crude was purified by flash chromatography (DCM/EtOAC 8/2) to obtain the title compound (41 mg, 36%). m/z: no corresponding mass. $^1H$ NMR (400 MHz, DMSO-$d_6$) δ ppm 12.27 (s, 1H), 7.62 (dd, J=8.0, 1.5 Hz, 4H), 7.55-7.37 (m, 6H), 2.61 (s, 1H), 2.42 (d, J=9.1 Hz, 2H), 2.33 (s, 2H), 1.02 (s, 9H).

Step 2. (1s,3s)-3-[tert-butyl(diphenyl)silyl]oxy-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-3-(trifluoromethyl)cyclobutanecarboxamide The compound was prepared from intermediate 117 according to the general procedure 3c described for examples 37-127 to afford the title compound (41.2 mg, 53%). m/z: 800 $[M+H]^+$. $^1H$ NMR (400 MHz, DMSO-$d_6$) δ ppm 8.29 (d, J=11.6 Hz, 1H), 7.64-7.36 (m, 10H), 7.28-7.15 (m, 4H), 6.84 (d, J=4.5 Hz, 1H), 6.31 (d, J=9.2 Hz, 1H), 3.78-3.67 (m, 2H), 3.17-2.96 (m, 3H), 2.61 (d, J=7.3 Hz, 4H), 2.50 (s, 7H), 1.98 (d, J=12.5 Hz, 3H), 1.01 (s, 9H).

Example 156 Step 3. (1s,3s)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-hydroxy-N-methyl-3-(trifluoromethyl)cyclobutane-1-carboxamide (CPD0072441)

(1s,3s)-3-[tert-butyl(diphenyl)silyl]oxy-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-3-(trifluoromethyl)cyclobutanecarboxamide (39 mg, 0.0487 mmol) was dissolved in dry THF (0.5 mL) at rt. A solution of 1 M tetrabutylammonium fluoride in THF (0.073 mL, 0.0731 mmol) was added and the reaction mixture was stirred at 0° C. for 1 h. The reaction mixture was partitioned between EtOAc (5 ml) and water (5 ml). The layers were separated and the aqueous phase was extracted twice with EtOAc (5 ml). Organic layers were combined, washed with brine, dried over anhydrous $Na_2SO_4$, filtered and concentrated. The crude was purified by flash chromatography (Heptane/EtOAc from 20% to 50% of EtOAc) to yield the title compound (9.1 mg, 31%). m/z: 562 $[M+H]^+$. $^1H$ NMR (600 MHz, DMSO-$d_6$) δ ppm 8.29 (s, 1H), 7.37-7.30 (m, 2H), 7.29-7.21 (m, 2H), 6.81 (s, 1H), 6.63 (s, 1H), 6.53-5.82 (m, 1H), 3.78-3.62 (m, 2H), 3.23-3.12 (m, 1H), 3.12-3.03 (m, 2H), 2.77 (s, 3H), 2.73-2.57 (m, 2H), 2.47-2.26 (m, 2H), 2.03-1.91 (m, 2H).

Example 157 CPD0072437

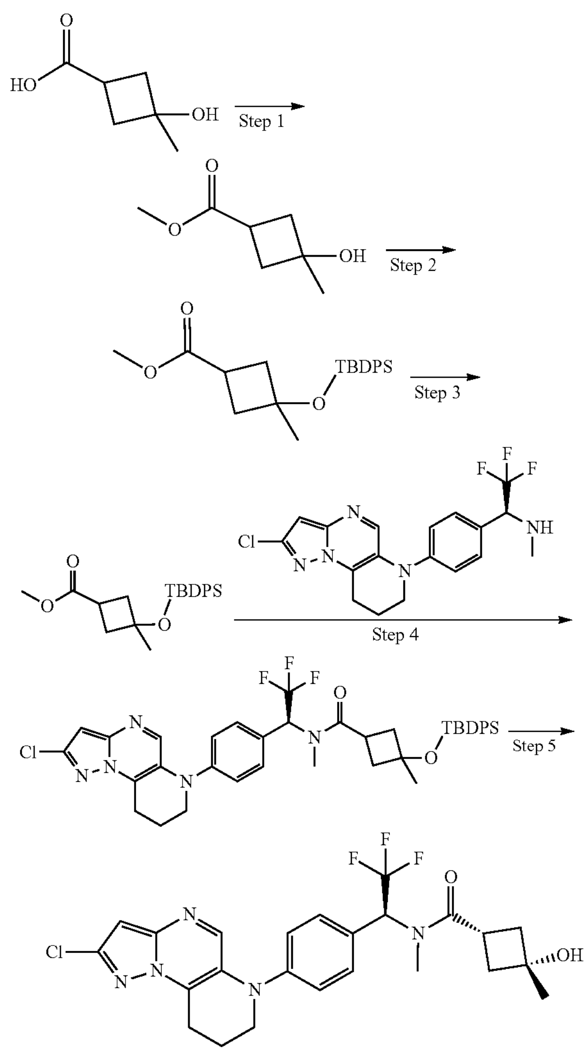

Step 1. Methyl 3-hydroxy-3-methylcyclobutanecarboxylate

To a solution of 3-hydroxy-3-methylcyclobutanecarboxylic acid (500 mg, 3.65 mmol) in methanol (8.5 mL) was added sulfuric acid (0.078 mL, 1.46 mmol). The mixture was refluxed overnight. The reaction mixture was cooled to rt and then concentrated under reduced pressure. The residue was dissolved in water and the mixture was extracted with EtOAc. The combined organic phases were washed with sat. aq. $NaHCO_3$, dried over anhydrous $MgSO_4$, filtered and concentrated in vacuo to provide the title compound (526 mg, 92%). m/z: 167 $[M+Na]^+$. $^1H$ NMR (400 MHz, DMSO-$d_6$) δ ppm 5.07 (s, 1H), 3.59 (s, 3H), 2.74-2.59 (m, 1H), 2.25-1.98 (m, 4H), 1.23 (s, 3H).

Step 2. methyl 3-[tert-butyl(diphenyl)silyl]oxy-3-methyl-cyclobutanecarboxylate

Tert-butyl(chloro)diphenylsilane (3.8 mL, 14.6 mmol) was added to a mixture of methyl 3-hydroxy-3-methyl-cyclobutanecarboxylate (526 mg, 3.65 mmol) in dry DMF (12 mL) and 1H-imidazole (994 mg, 14.6 mmol). The reaction mixture was heated at 80° C. for 30 h. After cooling to rt, the mixture was partitioned between water and EtOAc. The aqueous layer was extracted 3 times with EtOAc. The organic layers were combined, washed with brine, dried over anhydrous $MgSO_4$, filtered and concentrated under reduced pressure. The crude product was purified twice, first by flash column chromatography (DCM/MeOH, from 0% to 10% of MeOH) and then by reverse-phase chromatography (acetonitrile (+0.1% AcOH) in water (+0.1% AcOH) from 0% to 100%) to provide the title compound 368 mg, 22%, purity 85%). m/z: 383.5 $[M+H]^+$. $^1H$ NMR (400 MHz, DMSO-$d_6$) δ ppm 7.64 (dd, J=7.8, 1.7 Hz, 4H), 7.55-7.33 (m, 6H), 3.53 (s, 3H), 2.71-2.55 (m, 1H), 2.27 (td, J=9.4, 2.2 Hz, 2H), 2.06-1.88 (m, 2H), 1.23 (s, 3H), 0.98 (s, 9H).

Step 3. 3-[tert-butyl(diphenyl)silyl]oxy-3-methylcyclobutanecarboxylic acid

To a stirred solution of methyl 3-[tert-butyl(diphenyl)silyl]oxy-3-methyl-cyclobutanecarboxylate (368 mg, 0.962 mmol) in methanol (2.7 mL) and water (0.2 mL) was added lithium hydroxide (69 mg, 2.89 mmol). The reaction mixture was stirred overnight at rt. The solvent was removed under reduced pressure. The crude product was purified by flash column chromatography (DCM/(DCM-MeOH 90/10), from 0 to 20% of DCM-MeOH 10%) to afford the title compound (221 mg, 57%). m/z: 369 $[M+H]^+$. $^1H$ NMR (400 MHz, DMSO-$d_6$) δ ppm 12.13 (s, 1H), 7.64 (dd, J=7.8, 1.6 Hz, 4H), 7.50-7.29 (m, 6H), 2.86-2.60 (m, 1H), 2.36-2.20 (m, 2H), 1.93 (td, J=8.2, 2.5 Hz, 2H), 1.22 (s, 3H), 0.98 (s, 9H).

Step 4. 3-[tert-butyl(diphenyl)silyl]oxy-N-[(1S)-1-[4-(4-chloro-2,3,7,10-tetrazatricyclo[7.4.0.$0^{2,6}$]trideca-1(9),3,5,7-tetraen-10-yl)phenyl]-2,2,2-trifluoroethyl]-N,3-dimethyl-cyclobutanecarboxamide Prepared from intermediate 117 according to the general procedure 3 described for examples 37-127. The crude product was purified by flash column chromatography (DCM/(DCM-MeOH 9/1), from 0% to 40% of DCM-MeOH 9/1) to provide the title compound (225 mg, 95%). m/z: 746 $[M+H]^+$. $^1H$ NMR (400 MHz, DMSO-$d_6$) δ ppm 8.30 (s, 1H), 7.74-7.56 (m, 4H), 7.52-7.33 (m, 6H), 7.24 (s, 4H), 6.83 (s, 1H), 5.76 (s, 9H), 3.82-3.62 (m, 2H), 3.10 (t, J=6.7 Hz, 2H), 2.65 (d, J=20.5 Hz, 3H), 2.31 (dt, J=20.1, 10.2 Hz, 2H), 2.15-2.03 (m, 1H), 2.04-1.89 (m, 3H), 1.28 (d, J=6.5 Hz, 3H), 0.98 (s, 9H).

Example 157 Step 5. (1r,3s)-N-[(1S)-1-(4-{4-chloro-2,3,7,10-tetraazatricyclo[7.4.0.$0^{2,6}$]trideca-1(9),3,5,7-tetraen-10-yl}phenyl)-2,2,2-trifluoroethyl]-3-hydroxy-N,3-dimethylcyclobutane-1-carboxamide (CPD0072437)

To a stirred solution of 3-[tert-butyl(diphenyl)silyl]oxy-N-[(1S)-1-[4-(4-chloro-2,3,7,10-tetrazatricyclo[7.4.0.$0^{2,6}$]trideca-1(9),3,5,7-tetraen-10-yl)phenyl]-2,2,2-trifluoroethyl]-N,3-dimethyl-cyclobutanecarboxamide (215 mg, 0.271 mmol) in DCM (2 mL) at rt under nitrogen was added TFA (1.0 mL, 13.5 mmol). The reaction mixture was stirred at rt for 5 h. Additional TFA (1.0 mL, 13.5 mmol) was added at rt and the reaction mixture was stirred for 18 h. Additional TFA (1.0 mL, 13.5 mmol) was added at rt and the reaction mixture was stirred for 5 h. Finally, additional TFA (1.0 mL, 13.5 mmol) was added at rt and the reaction mixture was stirred for 18 h. The reaction mixture was concentrated under reduced pressure and dried under vacuum. The crude was purified by reverse-phase preparative chromatography (acetonitrile in water from 0% to 100% (0.1% AcOH in water)) to afford the title compound (60 mg, 41%) as a single diastereomer. The second diastereomer couldn't be found after the purification. m/z: 508 $[M+H]^+$. $^1H$ NMR (400 MHz, DMSO-$d_6$) δ ppm 8.30 (s, 1H), 7.19-7.38 (m, 4H), 6.81 (s, 1H), 6.46-6.53 (m, 1H), 5.01 (s, 1H), 3.68-3.74 (m, 2H), 3.09 (t, =6.7 Hz, 2H), 2.99 (quin, J=8.8 Hz, 1H), 2.64-2.79 (m, 3H), 2.07-2.27 (m, 4H), 1.89-2.03 (m, 2H), 1.21-1.33 (m, 3H).

Example 158 CPD0073091

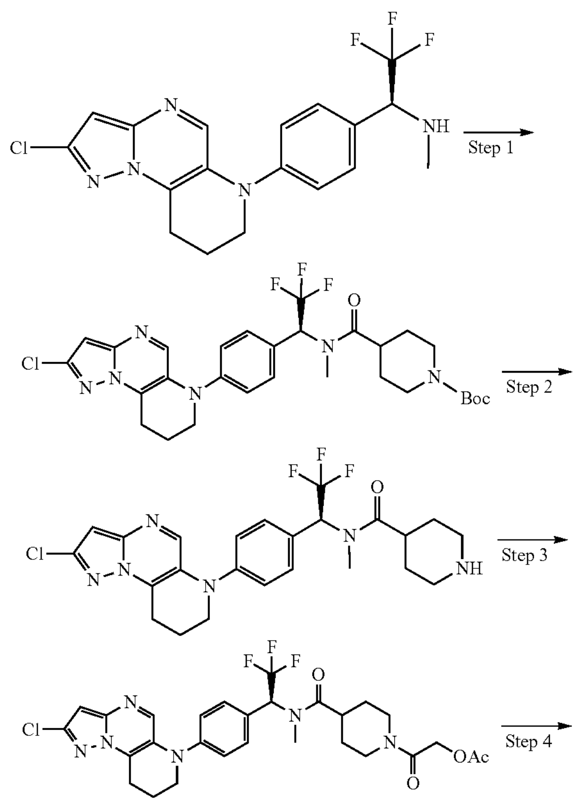

-continued

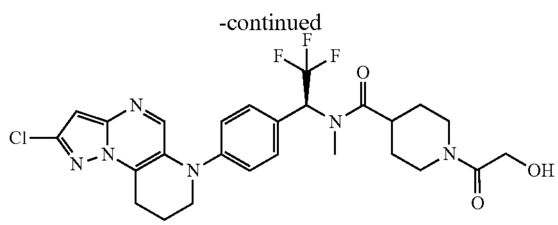

Step 1. tert-butyl 4-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]piperidine-1-carboxylate The compound was prepared from intermediate 117 according to the general procedure 3b used for examples 37-127 to obtain the expected compound as a brown oil (158 mg, 55%). m/z: 607 $[M+H]^+$. $^1$H NMR (400 MHz, DMSO-$d_6$) δ ppm 7.41-7.20 (m, 4H), 6.83 (s, 1H), 6.52 (d, J=8.5 Hz, 1H), 4.03 (d, J=42.7 Hz, 2H), 3.72 (s, 2H), 3.14 (d, J=27.9 Hz, 3H), 2.79 (d, J=107.5 Hz, 5H), 1.96 (s, 2H), 1.41 (s, 13H).

Step 2. N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-piperidine-4-carboxamide Tert-butyl 4-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl carbamoyl]piperidine-1-carboxylate (150 mg, 0.245 mmol) was partitioned between DCM (9 mL) and TFA (9.0 mL, 0.118 mol), the reaction mixture was stirred at rt for 2 h. Volatiles were evaporated and the dark red oil was dissolved in MeOH (10 ml) and loaded onto a SPE-SCX (5 g). Basic fractions were collected and evaporated to give the title compound (110 mg, 84%). m/z: 507 $[M+H]^+$. $^1$H NMR (400 MHz, DMSO-$d_6$) δ ppm 8.31 (s, 1H), 7.28 (q, J=8.9 Hz, 4H), 6.83 (s, 1H), 6.53 (d, J=9.1 Hz, 1H), 3.72 (s, 2H); 3.10 (t, J=6.6 Hz, 3H), 2.94 (d, J=29.7 Hz, 6H), 2.60 (dd, J=48.6, 9.9 Hz, 2H), 1.96 (s, 2H), 1.54 (d, J=30.1 Hz, 4H).

Step 3. [2-[4-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-1-piperidyl]-2-oxo-ethyl]acetate The compound was prepared according to general procedure 3 used for preparing examples 37-127. The crude was purified by flash chromatography (DCM/EtOAC from 0% to 20% of EtOAc) to obtain the title compound (102 mg, 73%). m/z: 607 $[M+H]^+$. $^1$H NMR (400 MHz, DMSO-$d_6$) δ ppm 8.31 (s, 1H), 7.42-7.11 (m, 4H), 6.83 (s, 1H), 6.51 (t, J=9.4 Hz, 1H), 4.77 (t, J=13.3 Hz, 2H), 4.30 (d, J=12.6 Hz, 1H), 3.73 (d, J=5.1 Hz, 3H), 3.21-2.99 (m, 4H), 2.94 (s, 3H), 2.78-2.59 (m, 2H), 1.98 (d, J=13.4 Hz, 3H), 1.83-1.31 (m, 4H).

Example 158 Step 4. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-(2-hydroxyacetyl)-N-methylpiperidine-4-carboxamide (CPD0073091)

[2-[4-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-1-piperidyl]-2-oxo-ethyl]acetate (102 mg, 0.151 mmol) was partitioned between 1,4-dioxane (0.9 mL) and water (0.4 mL) prior addition of lithium hydroxide hydrate (24 mg, 0.572 mmol). The reaction mixture was stirred at rt for 2 h. The reaction mixture was acidified to pH 3 with AcOH and then diluted with DCM (10 ml) and water (10 ml), phases were separated and the aqueous phase extracted with DCM (3×10 ml). The organic layers were combined, washed with a brine, dried over anhydrous $Na_2SO_4$, filtered and concentrated under reduced pressure. The crude was purified by reverse-phase chromatography (water/acetonitrile (with 0.1% AcOH) from water 100% to acetonitrile 100%) the title compound (10 mg, 11%). m/z: 565 $[M+H]^+$. $^1$H NMR (600 MHz, DMSO-$d_6$) δ ppm 8.30 (s, 1H), 7.17-7.49 (m, 4H), 6.82 (s, 1H), 6.24-6.59 (m, 1H), 4.48 (t, J=5.4 Hz, 1H), 4.28-4.40 (m, 1H), 3.99-4.18 (m, 2H), 3.66-3.76 (m, 3H), 3.10 (t, J=6.6 Hz, 2H), 3.01-3.08 (m, 2H), 2.93 (s, 3H), 2.67-2.79 (m, 1H), 1.92-2.02 (m, 2H), 1.36-1.83 (m, 4H).

Example 159-160 CPD0073976-CPD0073977

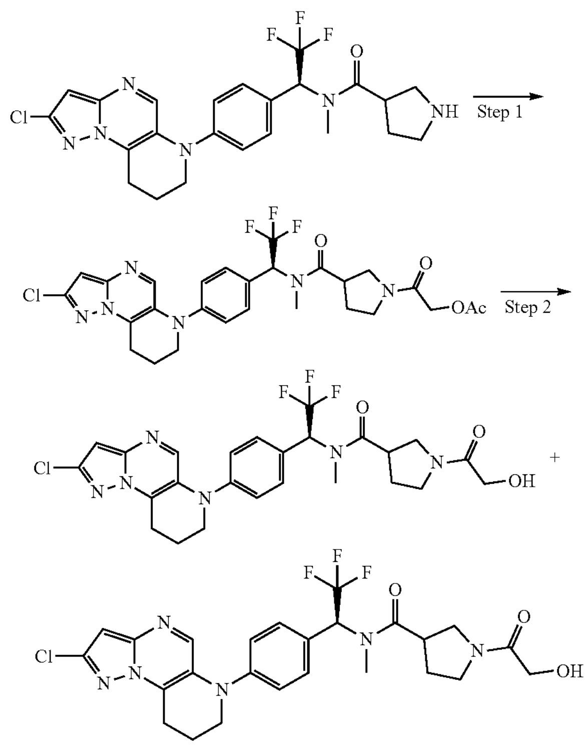

Step 1. [2-[3-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]pyrrolidin-1-yl]-2-oxo-ethyl]acetate The compound was prepared from intermediate 136 according to general procedure 3b for examples 37-127 to obtain the titled compound (213 mg, 69%). m/z: 593 $[M+H]^+$. $^1$H NMR (400 MHz, DMSO-$d_6$) δ ppm 8.32 (d, J=1.7 Hz, 1H), 7.33 (d, J=7.3 Hz, 2H), 7.27 (d, J=8.8 Hz, 2H), 6.83 (s, 1H), 6.51 (d, J=9.1 Hz, 1H), 4.77-4.61 (m, 2H), 3.79-3.37 (m, 7H), 3.11 (t, J=6.7 Hz, 2H), 2.94 (d, J=4.9 Hz, 3H), 2.71 (s, 1H), 2.37-2.11 (m, 1H), 2.08 (d, J=2.3 Hz, 3H), 1.98-1.78 (m, 2H).

Example 159 Step 2. (3 rel-R)—N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-(2-hydroxyacetyl)-N-methylpyrrolidine-3-carboxamide (CPD0073976)

To a solution of [2-[3-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]pyrrolidin-1-yl]-2-oxo-ethyl]acetate (203 mg, 0.335 mmol) in THF (2.8 mL) was added water (2.8 mL) and lithium hydroxide hydrate (23 mg, 0.503 mmol). The reaction mixture was stirred for 2 h at rt. The reaction mixture was quenched with sat. aq. $NH_4Cl$ until pH=3. The aqueous layer was extracted twice, then organic layer was dried over anhydrous $MgSO_4$ and concentrated under vacuum. The crude was purified by flash column chromatography (DCM/MeOH, from 0% to 5% of MeOH) to obtain a mixture of diastereomers. The mixture was purified by SFC preparative chromatography (Chiralpak IB 5 μm, 250×20 mm, $CO_2$/MeOH+0.5% IPAm 70/30) to afford the expected compound (20 mg, 11%). m/z: 551 $[M+H]^+$. $^1$H NMR (600 MHz, DMSO-$d_6$) δ ppm 8.31 (s, 1H), 7.47-7.15 (m, 4H), 6.82 (s, 1H), 6.50 (br d, J=9.2 Hz, 1H), 4.61-4.50 (m, 1H), 4.07-3.92 (m, 2H), 3.78-3.64 (m, 3H), 3.62-3.32 (m, 4H), 3.10 (s, 2H), 2.93 (s, 3H), 2.19-1.82 (m, 4H).

Example 160 (3rel-S)—N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-(2-hydroxyacetyl)-N-methylpyrrolidine-3-carboxamide (CPD0073977)

The product was obtained from the same purification as the previous compound (9 mg, 5%). m/z: 551 $[M+H]^+$. $^1$H NMR (600 MHz, DMSO-$d_6$) δ ppm 8.38-8.25 (m, 1H), 7.47-7.18 (m, 4H), 6.82 (d, J=0.9 Hz, 1H), 6.51 (br d, J=9.2 Hz, 1H), 4.64-4.49 (m, 1H), 4.13-3.92 (m, 2H), 3.82-3.32 (m, 7H), 3.18-3.02 (m, 2H), 2.99-2.63 (m, 3H), 2.30-1.76 (m, 4H).

Examples 161-162 CPD0073562/CPD0073563

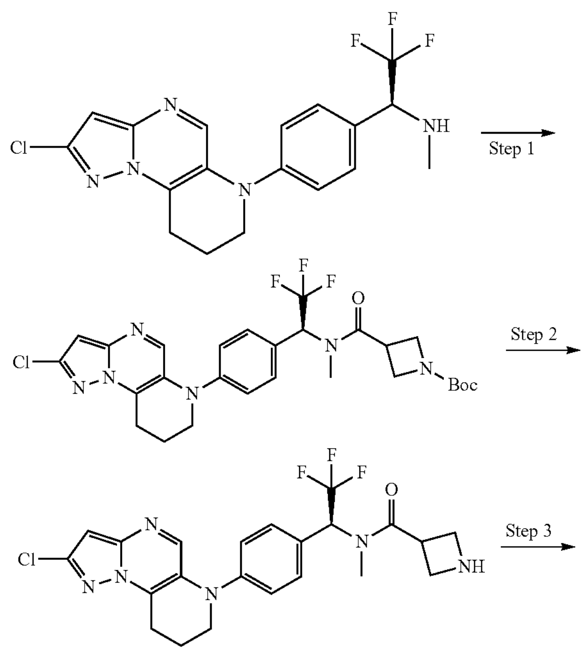

-continued

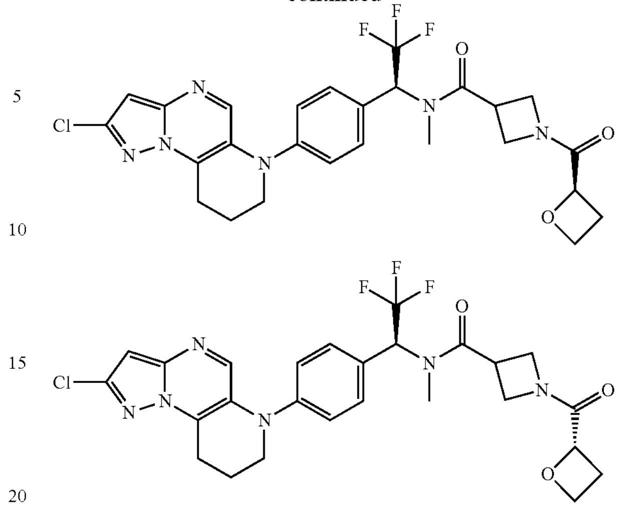

Step 1. tert-butyl 3-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]azetidine-1-carboxylate Prepared from intermediate 117 according to the general procedure 3 used for examples 37-127 The crude was purified by flash column chromatography (Heptane/EtOAc, from 0% to 100% of EtOAc) to obtain the titled compound as a yellow solid (266 mg, 83%). m/z: 579 $[M+H]^+$. $^1$H NMR (400 MHz, DMSO-$d_6$) δ ppm 8.31 (s, 1H), 7.34 (d, J=8.6 Hz, 2H), 7.26 (d, J=8.8 Hz, 2H), 6.82 (s, 1H), 6.48 (d, J=9.2 Hz, 1H), 4.06 (s, 2H), 3.92 (s, 2H), 3.88-3.80 (m, 1H), 3.72 (d, J=4.7 Hz, 2H), 3.10 (t, J=6.7 Hz, 2H), 2.73 (s, 3H), 1.95 (s, 2H), 1.38 (s, 9H).

Step 2. N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-azetidine-3-carboxamide Tert-butyl 3-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methylcarbamoyl]azetidine-1-carboxylate (181 mg, 0.306 mmol) was dissolved in dry DCM (1.5 mL). TFA (0.23 mL, 3.06 mmol) was added. The reaction mixture was stirred at rt for 2 h. The reaction mixture was quenched with aq. sat. $NaHCO_3$. DCM was added and the organic layers were washed 3 times with the saturated solution of $NaHCO_3$ then with brine, dried over anhydrous $MgSO_4$, filtered and concentrated in vacuo to afford the title compound (139 mg, 85%). m/z: 479 $[M+H]^+$. $^1$H NMR (400 MHz, DMSO-$d_6$) δ ppm 8.30 (s, 1H), 7.31 (d, J=8.7 Hz, 2H), 7.25 (d, J=8.8 Hz, 2H), 6.82 (s, 1H), 6.49 (q, J=9.5 Hz, 1H), 3.86 (p, J=8.1 Hz, 1H), 3.69 (ddd, J=14.8, 10.8, 6.4 Hz, 4H), 3.57 (t, J=8.0 Hz, 1H), 3.50 (t, J=7.9 Hz, 1H), 3.10 (t, J=6.7 Hz, 2H), 2.69 (s, 3H), 1.98-1.92 (m, 2H).

Example 161 Step 3. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1-[(2rel-R)-oxetane-2-carbonyl]azetidine-3-carboxamide (CPD0073562)

The compound was prepared according to the general procedure 3 used for preparing examples 37-127. The crude was purified by flash column chromatography (DCM/MeOH, from 0% to 15% of MeOH) to obtain a mixture of diastereomers. The mixture was purified by SFC preparative chromatography (Chiralpak IB 5 μm, 250×20 mm, $CO_2$/EtOH 80/20) to afford the expected compound as a white solid (24 mg, 10%). m/z: 563 $[M+H]^+$. $^1$H NMR (600 MHz, DMSO-$d_6$) δ ppm 8.30 (s, 1H), 7.20-7.42 (m, 4H), 6.82 (s, 1H), 5.74-6.60 (m, 1H), 5.08-5.21 (m, 1H), 4.44-4.60 (m, 2H), 4.32-4.41 (m, 1H), 4.09-4.28 (m, 2H), 3.88-4.07 (m, 2H), 3.68-3.75 (m, 2H), 3.09 (t, J=6.7 Hz, 2H), 2.76-2.84 (m, 1H), 2.74 (s, 3H), 2.62-2.69 (m, 1H), 1.91-1.99 (m, 2H).

Example 162 N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1-[(2rel-S)-oxetane-2-carbonyl]azetidine-3-carboxamide (CPD0073563)

The expected product was obtained during the same purification as the previous compound (23 mg, 10%). m/z: 563 $[M+H]^+$. $^1$H NMR (600 MHz, DMSO-$d_6$) δ ppm 8.30 (d, J=2.5 Hz, 1H), 7.19-7.43 (m, 4H), 6.82 (s, 1H), 5.78-6.57 (m, 1H), 5.14 (td, J=8.8, 7.1 Hz, 1H), 4.22-4.60 (m, 4H), 3.89-4.21 (m, 3H), 3.68-3.75 (m, 2H), 3.10 (t, J=6.7 Hz, 2H), 2.76-2.84 (m, 1H), 2.74 (s, 3H), 2.62-2.69 (m, 1H), 1.96 (br dd, J=4.5, 2.9 Hz, 2H).

Examples 163-164 CPD0073564/CPD0073565

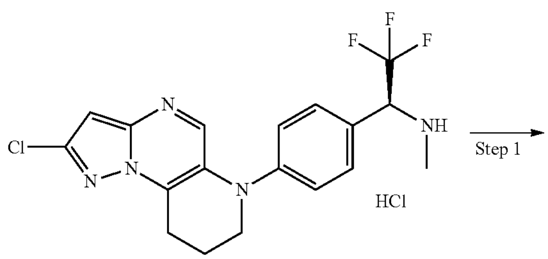

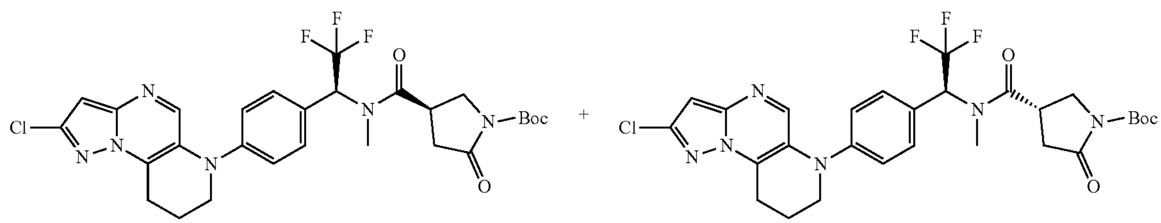

+

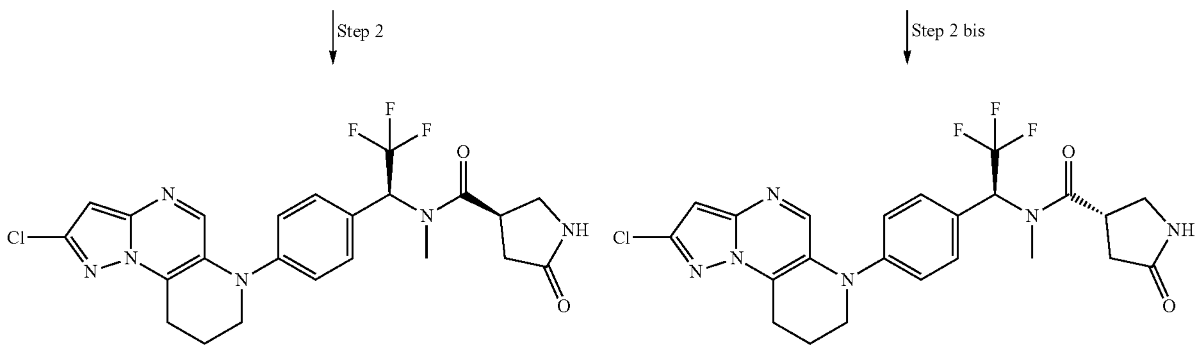

Step 1. tert-butyl (4REL-R)-4-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-2-oxo-pyrrolidine-1-carboxylate The compound was prepared from intermediate 117 and intermediate 181 according to the general procedure 3a used for preparing examples 37-127. The crude was purified by flash column chromatography (Heptane/EtOAc, from 40% to 70% of EtOAc) to obtain title compound as the first diastereomer to come out as a yellow oil (177 mg, 29%). m/z: 607 $[M+H]^+$.

tert-butyl (4rel-S)-4-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-2-oxo-pyrrolidine-1-carboxylate The second diastereomer to come out of the column corresponded to the title compound as a yellow oil (155 mg, 27%). m/z: 607 $[M+H]^+$.

Example 163 Step 2. (CPD0073564) (3rel-R)—N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-5-oxopyrrolidine-3-carboxamide To a solution of tert-butyl (4rel-R)-4-[[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-2-oxo-pyrrolidine-1-carboxylate (177 mg, 0.268 mmol) in dry DCM (1 mL) was added TFA (0.20 mL, 2.61 mmol). The reaction mixture was left stirring at rt for 1 h. The reaction mixture was quenched with a sat. aq. $NaHCO_3$ and diluted with EtOAc. The phases were separated and aqueous phase was extracted with EtOAc. The organic layers were combined, dried over anhydrous $Na_2SO_4$, filtered and concentrated under reduced pressure. The crude was purified by flash chromatography (DCM/MeOH, from 0% to 5% of MeOH) to obtain the title compound (72 mg, 53%). m/z: 507 $[M+H]^+$. $^1H$ NMR (600 MHz, DMSO-$d_6$) δ ppm 8.31 (s, 1H), 7.66 (s, 1H), 7.40-7.31 (m, 2H), 7.30-7.22 (m, 2H), 6.82 (s, 1H), 6.61-6.03 (m, 1H), 3.72 (br d, J=2.9 Hz, 3H), 3.53-3.32 (m, 2H), 3.10 (t, J=6.7 Hz, 2H), 2.92-2.67 (m, 3H), 2.53 (br d, J=9.8 Hz, 1H), 2.27 (dd, J=16.5, 6.7 Hz, 1H), 2.03-1.90 (m, 2H).

Example 164 (CPD0073565) Step 2 bis. (3rel-S)—N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-5-oxopyrrolidine-3-carboxamide To a solution of tert-butyl (4rel-S)-4-[[(1S)-1-[4-(4-chloro-2,3,7,10-tetrazatricyclo[7.4.0.0$^{2,6}$]trideca-1(9), 3,5,7-tetraen-10-yl)phenyl]-2,2,2-trifluoro-ethyl]-methyl-carbamoyl]-2-oxo-pyrrolidine-1-carboxylate (155 mg, 0.243 mmol) in dry DCM (1 mL) was added TFA (0.20 mL, 2.61 mmol). The reaction mixture was left stirring at rt for 1 h. The reaction mixture was quenched with a sat. aq. $NaHCO_3$ and diluted with EtOAc. The phases were separated and aqueous phase was extracted with EtOAc. The organic layers were combined, dried over anhydrous $Na_2SO_4$, filtered and concentrated under reduced pressure. The crude was purified by flash column chromatography (DCM/MeOH, from 0% to 5% of MeOH) to obtain the title compound (73 mg, 59%). m/z: 507 $[M+H]^+$. $^1H$ NMR (600 MHz, DMSO-$d_6$) δ ppm 8.31 (s, 1H), 7.66 (s, 1H), 7.42-7.31 (m, 2H), 7.30-7.23 (m, 2H), 6.82 (s, 1H), 6.57-6.05 (m, 1H), 3.82-3.65 (m, 3H), 3.61-3.49 (m, 1H), 3.27 (dd, J=9.5, 5.9 Hz, 1H), 3.10 (t, J=6.7 Hz, 2H), 2.94-2.68 (m, 3H), 2.45-2.29 (m, 2H), 2.03-1.86 (m, 2H).

Examples 165-166 CPD0077244/CPD0077245

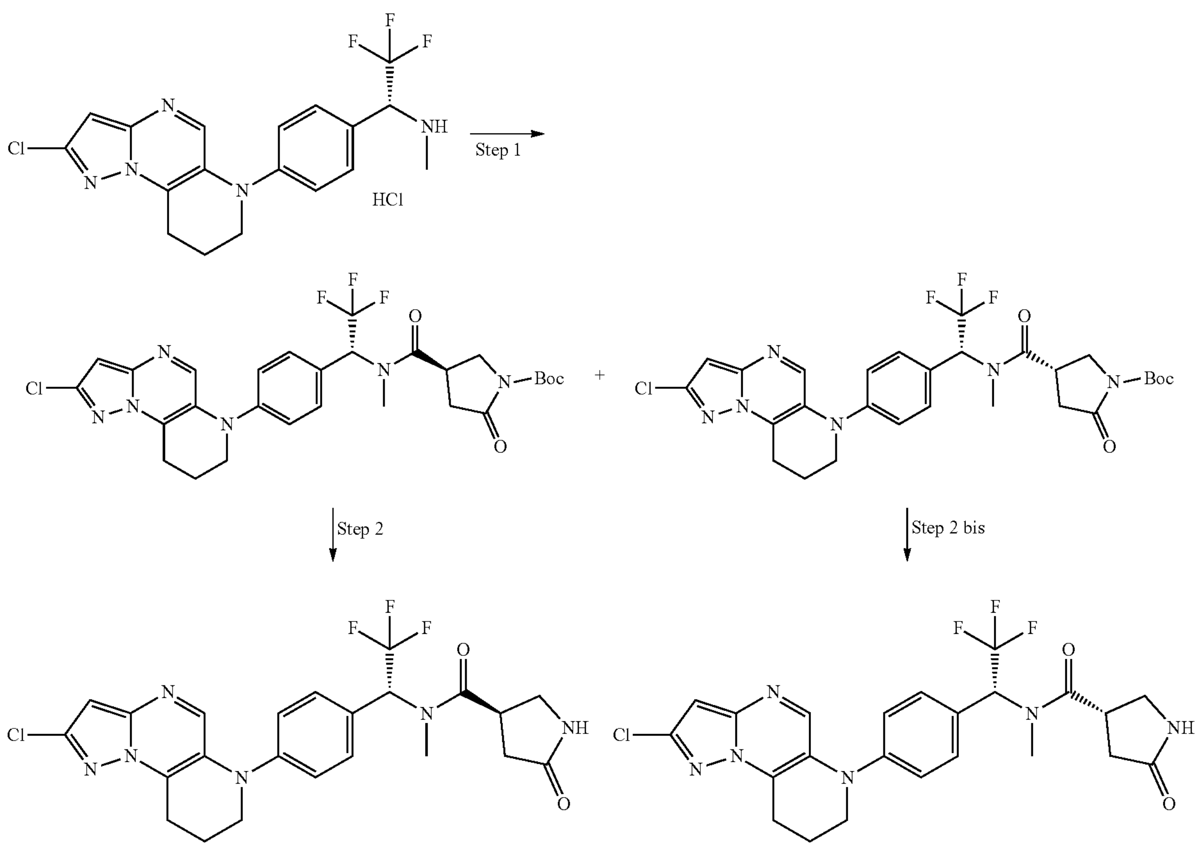

Step 1

To a solution of (1R)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-N-methyl-ethanamine (prepared as described for intermediates 115-125) (87%, 280 mg, 0.615 mmol) and 1-tert-butoxycarbonyl-5-oxo-pyrrolidine-3-carboxylic acid (70%, 202 mg, 0.615 mmol) in dry DCM (2.7 mL) TEA (1.7 mL, 12.3 mmol) was added, followed by $T_3P$ in Me-THF (50%, 3.8 mL, 6.15 mmol). The reaction mixture was stirred at rt for 1 h30. The reaction mixture was partitioned between sat. aq. $NH_4Cl$ and EtOAc, phases were separated and aqueous phase was extracted with EtOAc (3×15 mL). The organic layers were combined, dried over $Na_2SO_4$, filtered and concentrated under reduced pressure to obtain:

Tert-butyl (4rel-R)-4-[[(1R)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-2-oxo-pyrrolidine-1-carboxylate (102 mg; 24% yield). m/z: 607 $[M+H]^+$. $^1$H NMR (400 MHz, DMSO) δ ppm 8.30 (d, J=3.1 Hz, 1H), 7.43-7.22 (m, 4H), 6.82 (s, 1H), 6.48 (q, J=9.3 Hz, 1H), 3.95-3.62 (m, 5H), 3.10 (t, J=6.7 Hz, 2H), 2.89 (s, 3H), 2.85 (d, J=9.5 Hz, 2H), 1.96 (dd, J=11.6, 5.6 Hz, 2H), 1.45 (s, 9H). and Tert-butyl (4rel-S)-4-[[(1R)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-2-oxo-pyrrolidine-1-carboxylate (100 mg; 24% yield). m/z: 607 $[M+H]^+$. $^1$H NMR (400 MHz, DMSO) δ ppm 8.31 (s, 1H), 7.37-7.23 (m, 4H), 6.82 (s, 1H), 6.48 (q, J=9.4 Hz, 1H), 4.01-3.91 (m, 1H), 3.75-3.63 (m, 4H), 3.10 (t, J=6.7 Hz, 2H), 2.90 (s, 3H), 2.76-2.55 (m, 2H), 1.96 (d, J=5.4 Hz, 2H), 1.45 (s, 9H).

Step 2: Example 165 CPD0077244

To a solution of tert-butyl (4 rel-R)-4-[[(1R)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-methyl-carbamoyl]-2-oxo-pyrrolidine-1-carboxylate (87%, 102 mg, 0.146 mmol) in dry DCM (1 mL) was added 2,2,2-trifluoroacetic acid (0.15 mL, 1.96 mmol). The reaction mixture was stirred at rt for 3H. After that, the reaction was quenched with $NaHCO_3$ sat and diluted with EtOAc. Phases were separated and aqueous phase was extracted with EtOAc. The combined organic layers were dried over anhydrous $Na_2SO_4$, filtered and concentrated under reduced pressure. The crude was purified by flash column chromatography eluting with DCM/MeOH from 100/0 to 90/10 to obtain (3 rel-R)—N-[(1R)-1-[4-(4-chloro-2,3,7,10-tetrazatricyclo[7.4.0.02,6]trideca-1(9),3,5,7-tetraen-10-yl)phenyl]-2,2,2-trifluoro-ethyl]-N-methyl-5-oxo-pyrrolidine-3-carboxamide (45.4 mg, 61% Yield) as white solid. m/z: 507 $[M+H]^+$. $^1$H NMR (500 MHz, DMSO-$d_6$) δ ppm 1.93-1.99 (m, 2H) 2.24-2.38 (m, 2H) 2.88 (s, 3H) 3.10 (t, J=6.60 Hz, 2H) 3.32-3.39 (m, 1H) 3.45-3.50 (m, 1H) 3.70-3.78 (m, 3H) 6.50 (q, J=9.21 Hz, 1H) 6.82 (s, 1H) 7.24-7.40 (m, 4H) 7.63-7.69 (m, 1H) 8.31 (s, 1H).

Step 2-bis: Example 166 CPD0077245

Prepared as described for the example above to obtain (3 rel-S)—N-[(1R)-1-[4-(4-chloro-2,3,7,10-tetrazatricyclo [7.4.0.02,6]trideca-1(9),3,5,7-tetraen-10-yl)phenyl]-2,2,2-trifluoro-ethyl]-N-methyl-5-oxo-pyrrolidine-3-carboxamide (58.3 mg, 76% Yield) as white solid. m/z: 507 $[M+H]^+$. $^1$H NMR (500 MHz, DMSO-$d_6$) δ ppm 1.93-1.99 (m, 2H) 2.34-2.44 (m, 2H) 2.88 (s, 3H) 3.10 (t, J=6.72 Hz, 2H) 3.25-3.30 (m, 1H) 3.52-3.61 (m, 1H) 3.70-3.79 (m, 3H) 6.14-6.55 (m, 1H) 6.82 (s, 1H) 7.27 (s, 2H) 7.31-7.39 (m, 2H) 7.66 (s, 1H) 8.31 (s, 1H).

Example 167 CPD0072804

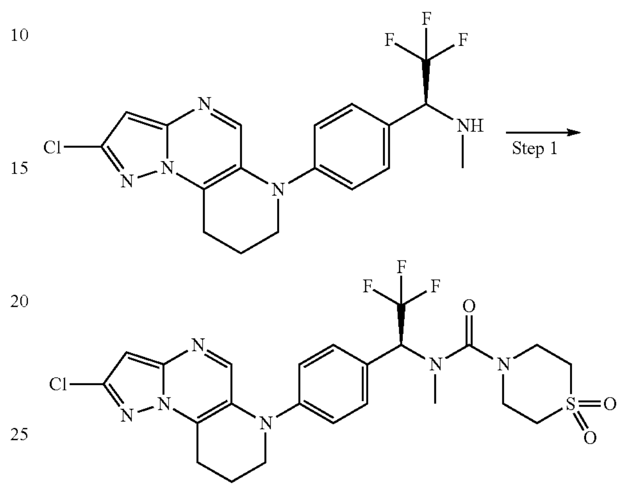

Step 1. N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1,1-dioxo-1λ$^6$-thiomorpholine-4-carboxamide (CPD0072804)

Intermediate 117 (40 mg, 0.0925 mmol) was suspended in dry DCM (0.5 mL) at rt. N-ethyl-N-isopropyl-propan-2-amine (81 μL, 0.463 mmol) was added, followed by triphosgene (9.3 mg, 0.0315 mmol). The reaction mixture was stirred at rt for 1 h. Thiomorpholine 1,1-dioxide (19 mg, 0.139 mmol) was added and the reaction mixture was stirred at rt for 1 h. The reaction mixture was diluted with water and extracted three times with EtOAc. Organic layers were combined, washed with brine, dried over anhydrous $Na_2SO_4$, filtered and concentrated. The residue was purified by flash column chromatography (Heptane/EtOAc, from 0% to 75% of EtOAc) and reverse phase column chromatography (water/acetonitrile with 0.1% AcOH from water 100% to acetonitrile 100%) to yield the title compound (25 mg, 48%). m/z: 557 $[M+H]^+$. $^1$H NMR (500 MHz, DMSO-$d_6$) δ ppm 8.31 (s, 1H), 7.43 (d, 2H, J=8.3 Hz), 7.27 (d, 2H, J=8.6 Hz), 6.82 (s, 1H), 5.98 (q, 1H, J=9.2 Hz), 3.7-3.8 (m, 2H), 3.5-3.7 (m, 4H), 3.2-3.3 (m, 2H), 3.0-3.2 (m, 4H), 2.77 (s, 3H), 1.9-2.0 (m, 2H).

Example 168 CPD0073084

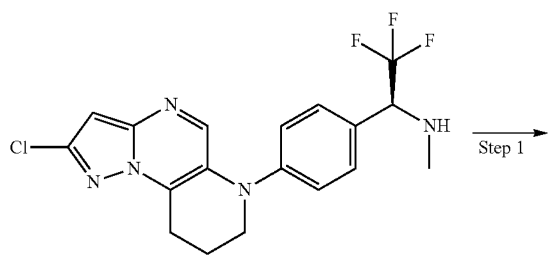

-continued

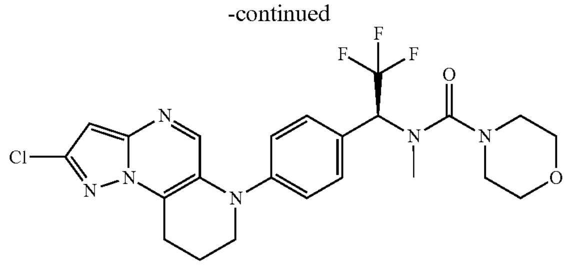

Step 1. N-[(1S)-1-(4-{4-chloro-2,3,7,10-tetraazatricyclo[7.4.0.0^{2,6}]trideca-1(9),3,5,7-tetraen-10-yl}phenyl)-2,2,2-trifluoroethyl]-N-methylmorpholine-4-carboxamide (CPD0073084)

Intermediate 117 (40 mg, 0.101 mmol) was dissolved in dry DCM (0.5 mL) at rt. N-ethyl-N-isopropyl-propan-2-amine (0.088 mL, 0.505 mmol) was added, followed by triphosgene (10 mg, 0.0344 mmol). The reaction mixture was stirred at rt for 1 h. Morpholine (0.018 mL, 0.152 mmol) was added and the reaction mixture was stirred at rt for 2 h. The reaction mixture was partitioned between a sat. aq. $NH_4Cl$ and EtOAc. The aqueous phase was isolated and extracted twice with EtOAc. Organic layers were combined, washed with brine, dried over anhydrous $Na_2SO_4$, filtered and concentrated. The residue was purified by reverse phase column chromatography (water/acetonitrile with 0.1% AcOH from water 100% to acetonitrile 100%) to afford the title compound (24 mg, 46%). m/z: 509 $[M+H]^+$. $^1H$ NMR (600 MHz, DMSO-$d_6$) δ ppm 8.30 (s, 1H), 7.41 (d, J=8.5 Hz, 2H), 7.26 (d, J=8.1 Hz, 2H), 6.81 (s, 1H), 6.01 (q, J=9.5 Hz, 1H), 3.71 (dd, J=6.8, 3.6 Hz, 2H), 3.63 (ddd, J=11.4, 6.5, 2.9 Hz, 2H), 3.56 (ddd, J=11.4, 6.7, 2.9 Hz, 2H), 3.26-3.29 (m, 2H), 3.08-3.14 (m, 4H), 2.71 (s, 3H), 1.93-1.99 (m, 2H).

Example 169 CPD0021755

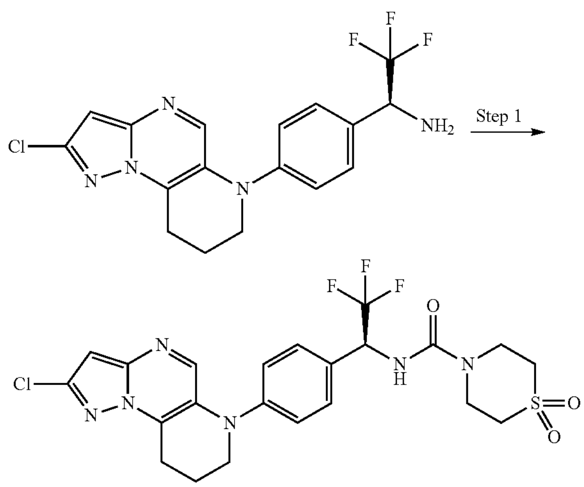

Step 1. N-[(1S)-1-(4{-4-chloro-2,3,7,10-tetraazatricyclo[7.4.0.0^{2,6}]trideca-1(9),3,5,7-tetraen-10-yl}phenyl)-2,2,2-trifluoroethyl]-1,1-dioxo-1λ^6-thiane-4-carboxamide (CPD0021755)

(1S)-1-(4-{4-chloro-2,3,7,10-tetraazatricyclo[7.4.0.0^{2,6}]trideca-1(9),3,5,7tetraen-10-yl}phenyl)-2,2,2-trifluoroethan-1-amine (93 mg, 0.222 mmol) (prepared following as for Intermediates 117-128) and 1,1-dioxo-1λ^6-thiane-4-carboxylic acid (59 mg, 0.333 mmol) were suspended in dry DCM (1.1 mL) at rt under $N_2$ atmosphere. TEA (0.25 mL, 1.78 mmol) was added, followed by T3P-50% in EtOAc (0.53 mL, 0.89 mmol). The reaction mixture was stirred at rt overnight. The reaction mixture was partitioned between water and EtOAc. The layers were separated and the aqueous phase was extracted twice with EtOAc. The organic layers were combined, washed with aqueous saturated solution of $NaHCO_3$, dried over anhydrous $Na_2SO_4$, filtered and concentrated. The crude was purified by flash column chromatography (Cyclophexane/EtOAc, from 0% to 60% of EtOAc) to obtain the title compound (85 mg, 68%). m/z: 542 $[M+H]^+$. $^1H$ NMR (600 MHz, DMSO-$d_6$) δ ppm 9.21 (d, J=9.5 Hz, 1H), 8.28 (s, 1H), 7.50 (d, J=8.6 Hz, 2H), 7.23 (d, J=8.6 Hz, 2H), 6.81 (s, 1H), 5.84-5.63 (m, 1H), 3.82-3.55 (m, 2H), 3.37-2.94 (m, 6H), 2.80-2.56 (m, 1H), 2.26-1.84 (m, 6H).

Scheme 15.

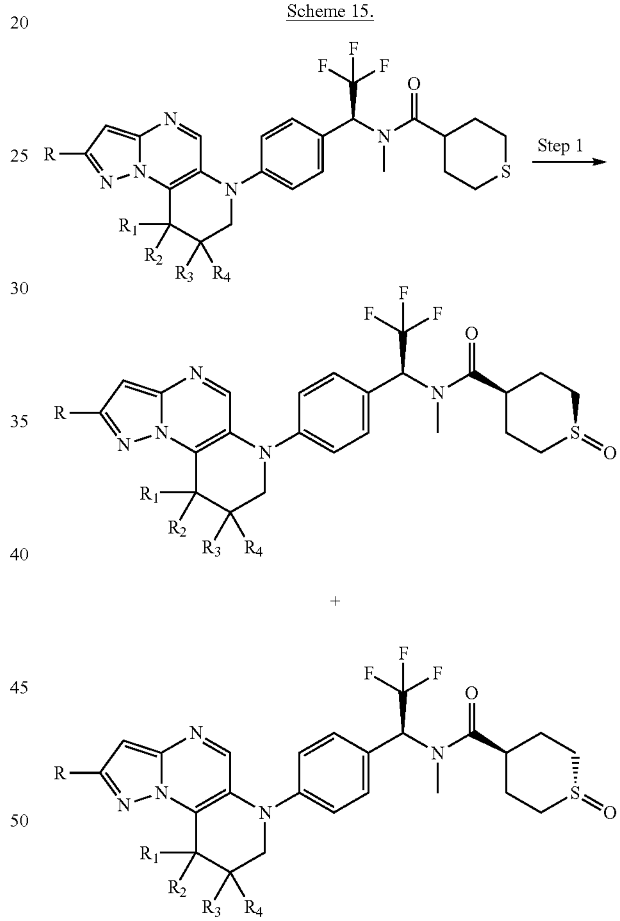

Step 1.

General Procedure:

Intermediates 144-153, 144-b or Example 47 (1 mmol) were dissolved in dry DCM (0.1 M) at 0° C. under $N_2$. A solution of m-CPBA 0.5 M in EtOAc (75% purity, 0.95 mmol) was added and the reaction mixture was stirred at 0° C. for 2 h. The reaction mixture was diluted with DCM and washed twice with sat. aq. $NaHCO_3$. The organic layer was separated, dried over anhydrous $Na_2SO_4$, filtered and concentrated under vacuum. The residue was purified by flash column chromatography (DCM/MeOH) to yield the 2 diastereomers. If the separation was not possible by normal phase chromatography, a) SFC separation conditions were performed using the method Chiralpak IB 5 μm, 250*20 mm, $CO_2$/EtOH 70/30

| Example 170 CPD0022136 | Procedure: 1 | Intermediate Example 47 | Yield 15% |
|---|---|---|---|
| 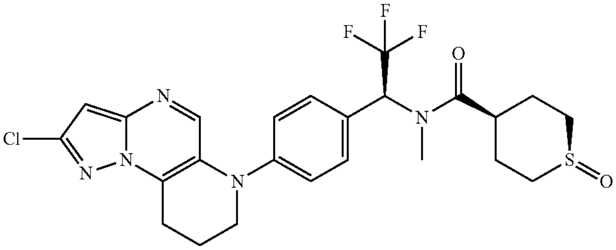 [SMILES: CN(C(=O)[C@H]1CC[S@@](=O)CC1)[C@@H](c1ccc(N2CCCc3c2cnc2cc(Cl)nn32)cc1)C(F)(F)F] | $^1$H NMR (400 MHz, DMSO-$d_6$) δ ppm 8.30 (s, 1H), 7.42-7.21 (m, 4H), 6.82 (s, 1H), 6.59-6.16 (m, 1H), 3.77-3.65 (m, 2H), 3.10 (t, J = 6.7 Hz, 2H), 3.08-2.99 (m, 1H), 2.95-2.64 (m, 7H), 2.36-2.18 (m, 2H), 2.01-1.91 (m, 2H), 1.78-1.57 (m, 2H). m/z: 540 [M + H]$^+$ | | |
| (1 rel-s,4 rel-s)-N-[(1S)-1-(4-{4-chloro-2,3,7,10-tetraazatricyclo[7.4.0.02,6]trideca-1(9),3,5,7-tetraen-10-yl}phenyl)-2,2,2-trifluoroethyl]-N-methyl-1-oxo-1λ$^4$-thiane-4-carboxamide | | | |

| Example 171 CPD0022137 | Procedure: 1 | Intermediate Example 47 | Yield 36% |
|---|---|---|---|
| 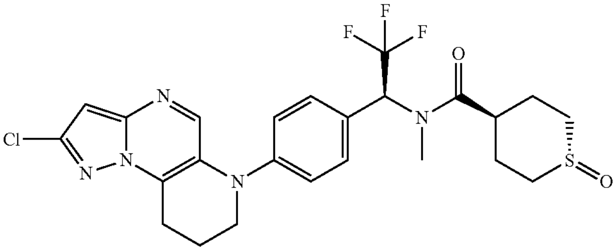 [SMILES: CN(C(=O)[C@H]1CC[S@](=O)CC1)[C@@H](c1ccc(N2CCCc3c2cnc2cc(Cl)nn32)cc1)C(F)(F)F] | $^1$H NMR (400 MHz, DMSO-d6) 0 ppm 8.30 (s, 1H), 7.41-7.20 (m, 4H), 6.82 (s, 1H), 6.58-6.16 (m, 1H), 3.77-3.66 (m, 2H), 3.29-3.19 (m, 2H), 3.14-3.02 (m, 3H), 2.92 (s, 3H), 2.76-2.64 (m, 2H), 2.17-2.01 (m, 2H), 2.01-1.90 (m, 2H), 1.78-1.63 (m, 2H). m/z: 540 [M + H]$^+$ | | |
| (1 rel-r,4 rel-r)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1-oxo-1λ$^4$-thiane-4-carboxamide | | | |

| Example 172 CPD0072778 | Procedure: 1a | Intermediate 148 | Yield 27% |
|---|---|---|---|
| 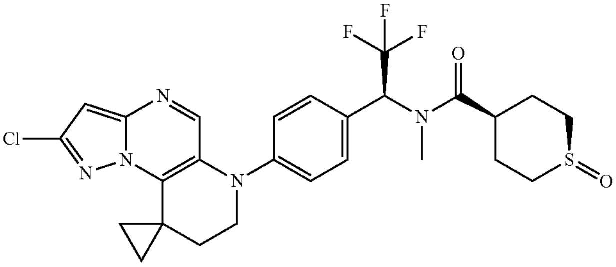 [SMILES: CN(C(=O)[C@H]1CC[S@@](=O)CC1)[C@@H](c1ccc(N2CCC3(CC3)c3c2cnc2cc(Cl)nn32)cc1)C(F)(F)F] | $^1$H NMR (600 MHz, DMSO-$d_6$) δ ppm 8.20 (s, 1H), 7.20-7.40 (m, 4H), 6.74 (s, 1H), 6.49 (q, J = 9.5 Hz, 1H), 3.73-3.79 (m, 2H), 3.33 (br d, J = 3.5 Hz, 1H), 3.22-3.29 (m, 2H), 3.06 (tt, J = 10.0, 3.4 Hz, 1H), 2.91 (s, 2H), 2.63-2.74 (m, 2H), 2.51-2.57 (m, 1H), 2.01-2.14 (m, 2H), 1.66-1.83 (m, 4H), 1.23 (s, 1H), 0.91-0.96 (m, 2H). m/z: 566 [M + H]$^+$ | | |
| (1 rel-s,4 rel-s)-N-[(1S)-1-(4-{4'-chloro-2',3',7',10'-tetraazaspiro[cyclopropane-1,13'-tricyclo[7.4.0.0$^{2,6}$]tridecane]-1'(9'),3',5',7'-tetraen-10'-yl}phenyl)-2,2,2-trifluoroethyl]-N-methyl-1-oxo-1λ$^4$-thiane-4-carboxamide | | | |

| Example 173 CPD0072779 | Procedure 1a | Intermediate 148 | Yield 8% |
|---|---|---|---|
| 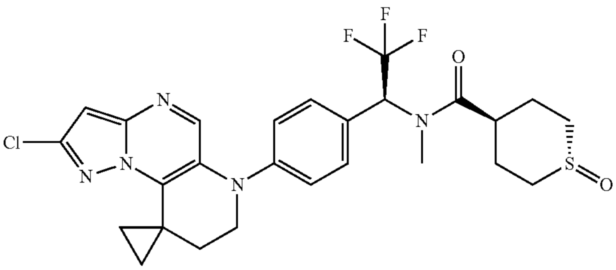 [SMILES: CN(C(=O)[C@H]1CC[S@](=O)CC1)[C@@H](c1ccc(N2CCC3(CC3)c3c2cnc2cc(Cl)nn32)cc1)C(F)(F)F] | $^1$H NMR (600 MHz, DMSO-$d_6$) δ ppm 8.21 (s, 1H), 7.24-7.39 (m, 4H), 6.75 (s, 1H), 6.53 (q, J = 9.3 Hz, 1H), 3.77 (dd, J = 6.1, 3.9 Hz, 2H), 2.99-3.10 (m, 1H), 2.86-2.94 (m, 4H), 2.65-2.79 (m, 3H), 2.52-2.59 (m, 2H), 2.20-2.38 (m, 2H), 1.80 (br d, J = 4.0 Hz, 2H), 1.67 (br t, J = 17.5 Hz, 2H), 0.90-0.98 (m, 2H). m/z: 566 [M + H]$^+$ | | |
| (1 rel-r,4 rel-r)-N-[(1S)-1-(4-{4'-chloro-2',3',7',10'-tetraazaspiro[cyclopropane-1,13'-tricyclo[7.4.0.02,6]tridecane]-1'(9'),3',5',7'-tetraen-10'-yl}phenyl)-2,2,2-trifluoroethyl]-N-methyl-1-oxo-1λ$^4$-thiane-4-carboxamide | | | |

-continued

| Example 174 CPD0072932 | Procedure 1a | Intermediate 144 | Yield: 30% |
|---|---|---|---|
| 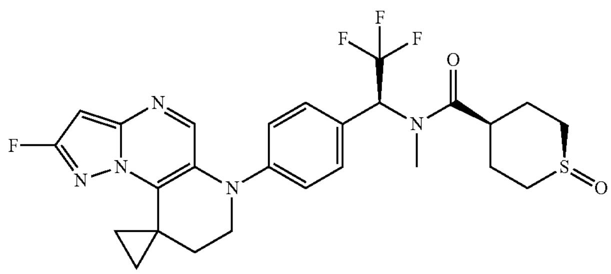 [SMILES: CN(C(=O)[C@H]1CC[S@@](=O)CC1)[C@@H](c1ccc(N2CCC3(CC3)c3c2cnc2cc(F)nn32)cc1)C(F)(F)F] | $^1$H NMR (500 MHz, DMSO-$d_6$) δ ppm 8.20 (s, 1H), 7.2-7.4 (m, 4H), 6.49 (q, 1H, J = 9.5 Hz), 6.37 (d, 1H, J = 5.1 Hz), 3.76 (br dd, 2H, J = 3.5, 5.3 Hz), 3.2-3.4 (m, 2H), 3.0-3.2 (m, 1H), 2.91 (s, 3H), 2.6-2.8 (m, 2H), 2.5-2.6 (m, 2H), 1.5-2.2 (m, 6H), 0.92 (d, 2H, J = 2.0 Hz). m/z: 550 [M + H]$^+$ | | |
| (1 rel-s,4 rel-s)-N-methyl-1-oxo-N-[(1S)-2,2,2-trifluoro-1-(4-{4'-fluoro-2',3',7',10'-tetraazaspiro[cyclopropane-1,13'-tricyclo[7.4.0.0$^{2,6}$]tridecane]-1'(9'),3',5',7'-tetraen-10'-yl}phenyl)ethyl]-1λ$^4$-thiane-4-carboxamide | | | |
| Example 175 CPD0072933 | Procedure 1a | Intermediate 144 | Yield 8% |
| 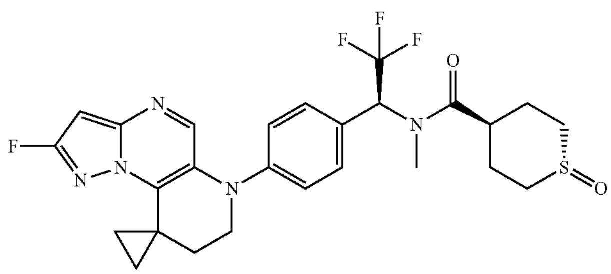 [SMILES: CN(C(=O)[C@H]1CC[S@](=O)CC1)[C@@H](c1ccc(N2CCC3(CC3)c3c2cnc2cc(F)nn32)cc1)C(F)(F)F] | $^1$H NMR (500 MHz, DMSO-$d_6$) δ ppm 8.20 (s, 1H), 7.16-7.40 (m, 4H), 6.52 (q, J = 9.4 Hz, 1H), 6.37 (d, J = 5.1 Hz, 1H), 3.70-3.82 (m, 2H), 2.97-3.10 (m, 1H), 2.91 (s, 3H), 2.65-2.90 (m, 4H), 2.52-2.56 (m, 2H), 2.19-2.34 (m, 2H), 1.73-1.83 (m, 2H), 1.58-1.72 (m, 2H), 0.92 (d, J = 2.2 Hz, 2H) m/z: 550 [M + H]$^+$ | | |
| (1 rel-r,4 rel-r)-N-methyl-1-oxo-N-[(1S)-2,2,2-trifluoro-1-(4-{4'-fluoro-2',3',7',10'-tetraazaspiro[cyclopropane-1,13'-tricyclo[7.4.0.02,6]tridecane]-1'(9'),3',5',7'-tetraen-10'-yl}phenyl)ethyl]-1λ$^4$-thiane-4-carboxamide | | | |
| Example 176 CPD0072776 | Procedure 1a | Intermediate 145 | Yield 37% |
| 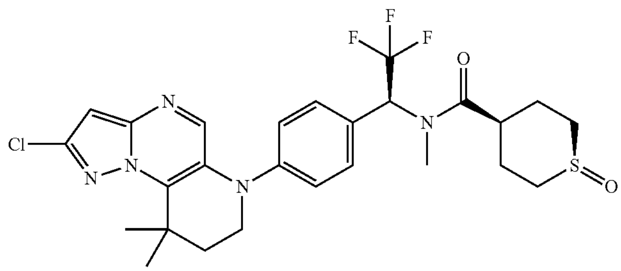 [SMILES: CN(C(=O)[C@H]1CC[S@@](=O)CC1)[C@@H](c1ccc(N2CCC(C)(C)c3c2cnc2cc(Cl)nn32)cc1)C(F)(F)F] | $^1$H NMR (400 MHz, DMSO-$d_6$) δ ppm 8.26 (s, 1H), 7.33-7.18 (m, 4H), 6.82 (s, 1H), 6.50 (d, J = 9.3 Hz, 1H), 4.34 (t, J = 5.1 Hz, 2H), 3.75-3.66 (m, 2H), 3.45 (qd, J = 7.0, 5.1 Hz, 3H), 3.12-2.98 (m, 1H), 2.92 (s, 3H), 2.70 (ddd, J = 15.1, 11.1, 8.3 Hz, 3H), 2.16-2.01 (m, 2H), 1.88-1.67 (m, 4H), 1.63 (s, 6H), 1.06 (t, J = 7.0 Hz, 4H). m/z: 568 [M + H]$^+$ | | |
| rel-s,4 rel-s)-N-[(1S)-1-(4-{4-chloro-13,13-dimethyl-2,3,7,10-tetraazatricyclo[7.4.0.0$^{2,6}$]trideca-1(9),3,5,7-tetraen-10-yl}phenyl)-2,2,2-trifluoroethyl]-N-methyl-1-oxo-1λ$^4$-thiane-4-carboxamide | | | |
| Example 177 CPD0072777 | Procedure 1a | Intermediate 145 | Yield 15% |
| 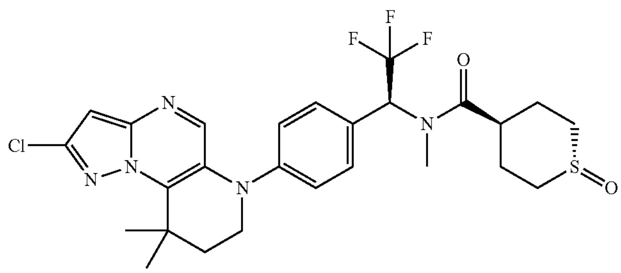 [SMILES: CN(C(=O)[C@H]1CC[S@](=O)CC1)[C@@H](c1ccc(N2CCC(C)(C)c3c2cnc2cc(Cl)nn32)cc1)C(F)(F)F] | $^1$H NMR (400 MHz, DMSO-$d_6$) δ ppm 8.26 (s, 1H), 1H), 7.38-7.16 (m, 4H), 6.82 (s, 1H), 6.53 (d, J = 9.5 Hz, 1H), 4.34 (t, J = 5.1 Hz, 1H), 3.73-3.62 (m, 2H), 3.45 (qd, J = 7.0, 5.1 Hz, 2H), 3.04 (s, 1H), 2.90 (d, J = 17.9 Hz, 5H), 2.72 (dd, J = 28.1, 14.5 Hz, 3H), 2.29 (d, J = 13.2 Hz, 2H), 1.85-1.66 (m, 4H), 1.64 (s, 7H), 1.06 (t, J = 7.0 Hz, 3H). m/z: 568 [M + H]$^+$ | | |
| (1 rel-r,4 rel-r)-N-[(1S)-1-(4-{4-chloro-13,13-dimethyl-2,3,7,10-tetraazatricyclo[7.4.0.0$^{2,6}$] trideca-1(9),3,5,7-tetraen-10-yl}phenyl)-2,2,2-trifluoroethyl]-N-methyl-1-oxo-1λ$^4$-thiane-4-carboxamide | | | |

-continued

| Example 178 CPD0072780 | Procedure 1a | Intermediate 146 | Yield 32% |
|---|---|---|---|
| 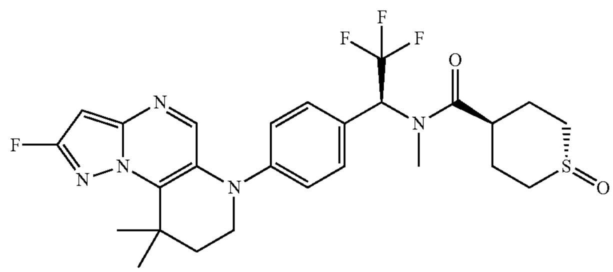 [SMILES: CN(C(=O)[C@H]1CC[S@](=O)CC1)[C@@H](c1ccc(N2CCC(C)(C)c3c2cnc2cc(F)nn32)cc1)C(F)(F)F] | $^1$H NMR (500 MHz, DMSO-$d_6$) δ ppm 8.25 (s, 1H), 7.14-7.41 (m, 4H), 6.52 (q, J = 9.2 Hz, 1H), 6.43 (d, J = 5.1 Hz, 1H), 3.70 (dt, J = 5.2, 2.4 Hz, 2H), 3.03 (br t, J = 11.4 Hz, 1H), 2.86-2.93 (m, 5H), 2.65-2.78 (m, 2H), 2.20-2.33 (m, 2H), 1.79 (dt, J = 5.4, 2.4 Hz, 2H), 1.63-1.73 (m, 2H), 1.61 (s, 6H) m/z: 552 [M + H]$^+$ | | |
| (1 rel-s,4 rel-s)-N-methyl-1-oxo-N-[(1S)-2,2,2-trifluoro-1-(4-{4-fluoro-13,13-dimethyl-2,3,7,10-tetraazatricyclo[7.4.0.0$^{2,6}$]trideca-1(9),3,5,7-tetraen-10-yl}phenyl)ethyl]-1λ$^4$-thiane-4-carboxamide | | | |
| Example 179 CPD0072781 | Procedure 1a | Intermediate 146 | Yield 9% |
| 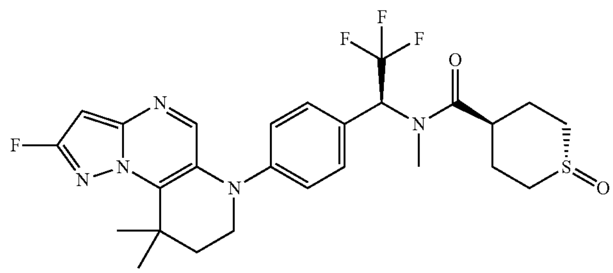 [SMILES: CN(C(=O)[C@H]1CC[S@](=O)CC1)[C@@H](c1ccc(N2CCC(C)(C)c3c2cnc2cc(F)nn32)cc1)C(F)(F)F] | $^1$H NMR (500 MHz, DMSO-$d_6$) δ ppm 8.25 (s, 1H), 7.21-7.31 (m, 3H), 7.17-7.42 (m, 1H), 6.42-6.52 (m, 2H), 3.69 (dt, J = 5.3, 2.4 Hz, 2H), 3.28 (br d, J = 3.2 Hz, 2H), 3.01-3.10 (m, 1H), 2.91 (s, 3H), 2.63-2.76 (m, 2H), 2.01-2.15 (m, 2H), 1.65-1.83 (m, 4H), 1.61 (s, 6H). m/z: 552 [M + H]$^+$ | | |
| (1 rel-r,4 rel-r)-N-methyl-1-oxo-N-[(1S)-2,2,2-trifluoro-1-(4-{4-fluoro-13,13-dimethyl-2,3,7,10-tetraazatricyclo[7.4.0.0$^{2,6}$]trideca-1(9),3,5,7-tetraen-10-yl}phenyl)ethyl]-1λ$^4$-thiane-4-carboxamide | | | |
| Example 180 CPD0073135 | Procedure 1a | Intermediate 149 | Yield 13% |
| 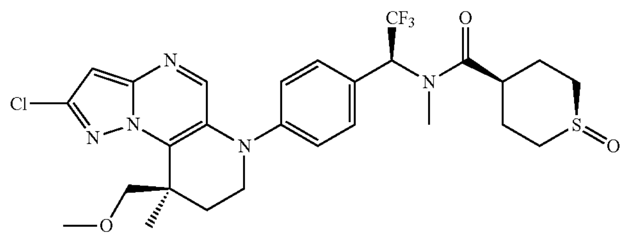 [SMILES: COC[C@]1(C)CCN(c2ccc([C@H](N(C)C(=O)[C@H]3CC[S@@](=O)CC3)C(F)(F)F)cc2)c2cnc3cc(Cl)nn3c21] | $^1$H NMR (600 MHz, DMSO-$d_6$, 300K) δ ppm 8.25 (s, 1H), 7.31 (d, J = 8.4 Hz, 2H), 7.20 (d, J = 8.7 Hz, 2H), 6.81 (s, 1H), 6.41-6.54 (m, 1H), 4.49 (d, J = 8.8 Hz, 1H), 3.76-3.89 (m, 1H), 3.61-3.69 (m, 1H), 3.55 (d, J = 8.8 Hz, 1H), 3.21-3.29 (m, 2H), 3.12 (s, 3H), 3.07 (s, 1H), 2.92 (s, 3H), 2.63-2.80 (m, 2H), 1.92-2.30 (m, 3H), 1.61-1.82 (m, 3H), 1.52 (s, 3H). m/z: 598 [M + H]$^+$ | | |
| (1 rel-s,4 rel-s)-N-[(1S)-1-[4-[(13 rel-R)-4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-N-methyl-1-oxo-1λ$^4$-thiane-4-carboxamide | | | |

-continued

| Example 181 CPD0073136 | Procedure 1a | Intermediate 149 | Yield 14% |
|---|---|---|---|
| 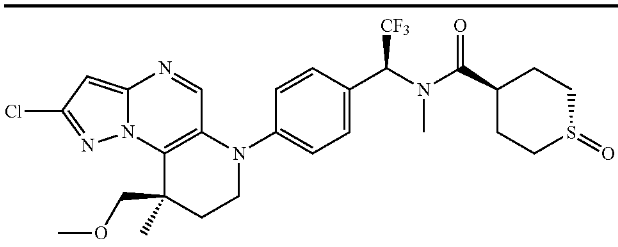 | $^1$H NMR (600 MHz, DMSO-$d_6$, 300K) δ ppm 8.25 (s, 1H), 7.31 (d, J = 8.4 Hz, 2H), 7.20 (d, J = 8.7 Hz, 2H), 6.81 (s, 1H), 6.41-6.54 (m, 1H), 4.49 (d, J = 8.8 Hz, 1H), 3.76-3.89 (m, 1H), 3.61-3.69 (m, 1H), 3.55 (d, J = 8.8 Hz, 1H), 3.21-3.29 (m, 2H), 3.12 (s, 3H), 3.07 (s, 1H), 2.92 (s, 3H), 2.63-2.80 (m, 2H), 1.92-2.30 (m, 3H), 1.61-1.82 (m, 3H), 1.52 (s, 3H). ). m/z: 598 [M + H]$^+$ | | |
| (1 rel-r,4 rel-r)-N-[(1S)-1-[4-[(13 rel-R)-4-chloro-13-(methoxymethyl)-13-methyl-2,3,7,10-tetrazatricyclo [7.4.0.02,6]trideca-1(9),3,5,7-tetraen-10-yl]phenyl]-2,2,2-trifluoro-ethyl]-N-methyl-1-oxo-1λ$^4$-thiane-4-carboxamide | | | |
| Example 182 CPD0073137 | Procedure 1a | Intermediate 149 | Yield 4% |
| 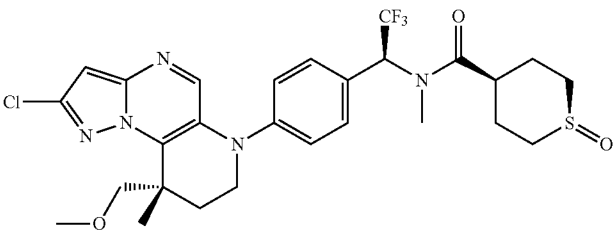 [SMILES: COC[C@@]1(C)CCN(c2ccc([C@H](N(C)C(=O)[C@H]3CC[S@@](=O)CC3)C(F)(F)F)cc2)c2cnc3cc(Cl)nn3c21] | $^1$H NMR (600 MHz, DMSO-d6, 300K) δ ppm 8.25 (s, 1H), 7.32 (d, J = 8.4 Hz, 2H), 7.20 (d, J = 8.8 Hz, 2H), 6.81 (s, 1H), 6.52 (br d, J = 9.1 Hz, 1H), 4.49 (d, J = 8.8 Hz, 1H), 3.75-3.87 (m, 1H), 3.58-3.70 (m, 1H), 3.54 (d, J = 8.8 Hz, 1H), 3.12 (s, 3H), 2.99-3.09 (m, 1H), 2.92 (s, 5 H), 2.65-2.81 (m, 2H), 2.14-2.34 (m, 3H), 1.60-1.78 (m, 3H), 1.52 (s, 3H). m/z: 598 [M + H]$^+$ | | |
| (1 rel-s,4 rel-s)-N-[(1S)-1-[4-[(13 rel-S)-4-chloro-13-(methoxymethyl)-13-methyl-2,3,7,10-tetrazatricyclo [7.4.0.02,6]trideca-1(9),3,5,7-tetraen-10-yl]phenyl]-2,2,2-trifluoro-ethyl]-N-methyl-1-oxo-1λ$^4$-thiane-4-carboxamide | | | |
| Example 183 CPD0073138 | Procedure 1a | Intermediate 149 | Yield 5% |
| 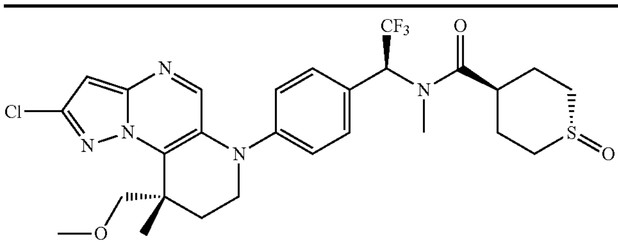 | $^1$H NMR (600 MHz, DMSO-d6, 300K) δ ppm 8.25 (s, 1H), 7.32 (d, J = 8.4 Hz, 2H), 7.20 (d, J = 8.8 Hz, 2H), 6.81 (s, 1H), 6.52 (br d, J = 9.1 Hz, 1H), 4.49 (d, J = 8.8 Hz, 1H), 3.75-3.87 (m, 1H), 3.58-3.70 (m, 1H), 3.54 (d, J = 8.8 Hz, 1H), 3.12 (s, 3H), 2.99-3.09 (m, 1H), 2.92 (s, 5 H), 2.65-2.81 (m, 2H), 2.14-2.34 (m, 3H), 1.60-1.78 (m, 3H), 1.52 (s, 3H). m/z: 598 [M + H]$^+$ | | |
| (1 rel-r,4 rel-r)-N-[(1S)-1-[4-[(13 rel-S)-4-chloro-13-(methoxymethyl)-13-methyl-2,3,7,10-tetrazatricyclo [7.4.0.02,6]trideca-1(9),3,5,7-tetraen-10-yl]phenyl]-2,2,2-trifluoro-ethyl]-N-methyl-1-oxo-1λ$^4$-thiane-4-carboxamide | | | |

Scheme 16.

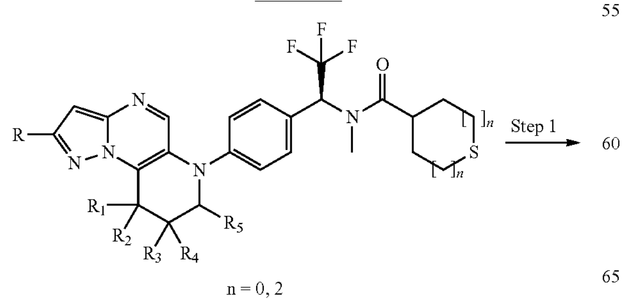

n = 0, 2

-continued

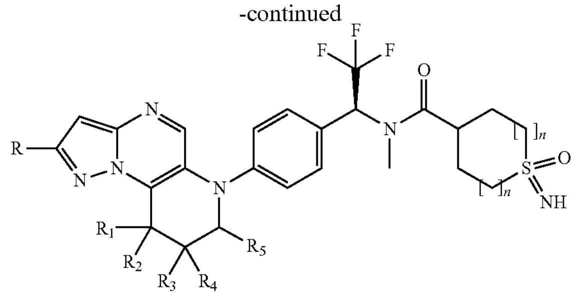

+

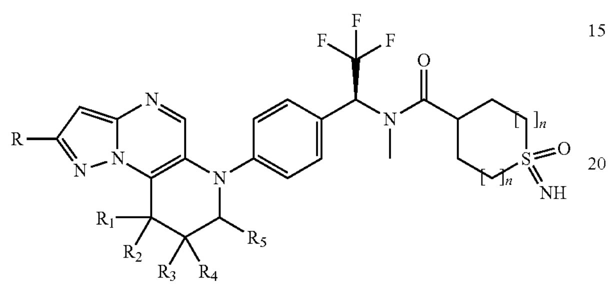

Step 1: General Procedure 1

Intermediates 144-153, 144-b or Example 47 (1 mmol) and ammonium carbamate (2 mmol) were suspended in dry methanol (0.5 M) at rt. Iodobenzene diacetate (2.5 mmol) was added and the reaction mixture was stirred at rt until complete consumption of starting material. The reaction mixture was concentrated under reduced pressure.

a) The residue was purified by flash column chromatography (DCM/MeOH) to yield the expected 2 diastereomers separated.

b) SFC chiral separation (Chiralpak IB 5 μm, 250*20 mm, $CO_2$/EtOH 80/20)

c) Kromasil C18 10 μm, 300×50 mm (acetonitrile/water 90/10+0.1% TFA)

| Example 184 CPD0072528 | Procedure 1a | Intermediate Example 47 | Yield 6% |
|---|---|---|---|
| 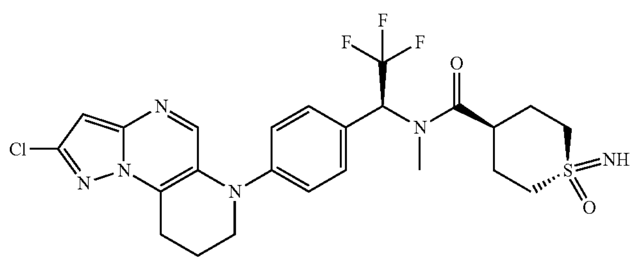 [SMILES: CN(C(=O)[C@H]1CC[S@@](=N)(=O)CC1)[C@@H](c1ccc(N2CCCc3c2cnc2cc(Cl)nn32)cc1)C(F)(F)F] | $^1$H NMR (600 MHz, DMSO-$d_6$) δ ppm 8.30 (s, 1H), 7.19-7.42 (m, 4H), 6.82 (s, 1H), 6.14-6.56 (m, 1H), 3.68-3.74 (m, 3H), 3.00-3.14 (m, 7H), 2.91 (s, 3H), 1.91-2.06 (m, 6H)m/z: 555 $[M + H]^+$ | | |
| (1 rel-s,4 rel-S)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-imino-N-methyl-1-oxo-1λ$^6$-thiane-4-carboxamide | | | |

| Example 185 CPD0072529 | Procedure 1a | Intermediate Example 47 | Yield 3% |
|---|---|---|---|
| 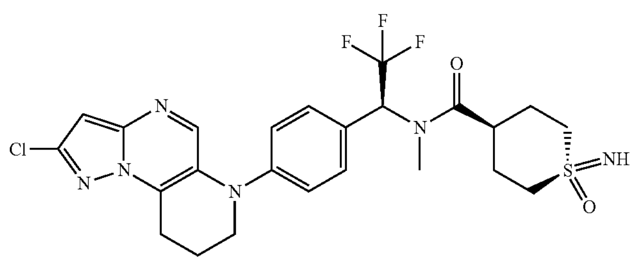 [SMILES: CN(C(=O)[C@H]1CC[S@](=N)(=O)CC1)[C@@H](c1ccc(N2CCCc3c2cnc2cc(Cl)nn32)cc1)C(F)(F)F] | $^1$H NMR (600 MHz, DMSO-$d_6$) δ ppm 8.30 (s, 1H), 7.21-7.41 (m, 4H), 6.82 (s, 1H), 6.16-6.54 (m, 1H), 3.68-3.74 (s, 3H), 3.47 (s, 1H), 2.98-3.22 (m, 7H), 2.91 (s, 2H), 1.80-2.22 (m, 6H). m/z: 555 $[M + H]^+$ | | |
| (1 rel-r,4 rel-r)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-1-imino-N-methyl-1-oxo-1λ$^6$-thiane-4-carboxamide | | | |

-continued

| Example 186 CPD0072772 | Procedure 1a | Intermediate 148 | Yield 14% |
|---|---|---|---|
| 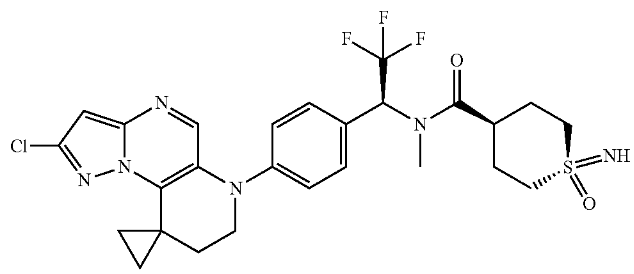<br>(1 rel-s,4 rel-s)-N-[(1S)-1-(4-{4'-chloro-2',3',7',10'-tetraazaspiro[cyclopropane-1,13'-tricyclo [7.4.0.0$^{2,6}$]tridecane]-1'(9'),3',5',7'-tetraen-10'-yl}phenyl)-2,2,2-trifluoroethyl]-1-imino-N-methyl-1-oxo-1λ$^6$-thiane-4-carboxamide | $^1$H NMR (600 MHz, DMSO-d$_6$) δ ppm 8.21 (s, 1H), 7.28-7.39 (m, 2H), 7.22-7.27 (m, 2H), 6.75 (s, 1H), 6.46-6.54 (m, 1H), 3.71-3.82 (m, 2H), 3.48 (s, 1H), 2.99-3.23 (m, 5H), 2.91 (s, 3H), 2.52-2.57 (m, 2H), 1.89-2.21 (m, 4H), 1.79 (q, J = 4.9 Hz, 2H), 0.93 (s, 2H) m/z: 581 [M + H]$^+$ | | |
| Example 187 CPD0072773 | Procedure 1a | Intermediate 148 | Yield 6% |
| 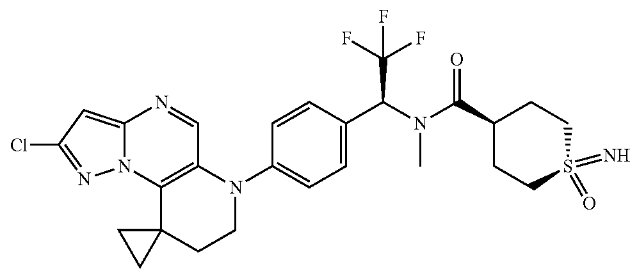<br>(1 rel-r,4 rel-r)-N-[(1S)-1-(4-{4'-chloro-2',3',7',10'-tetraazaspiro[cyclopropane-1,13'-tricyclo[7.4.0.0$^{2,6}$]tridecane]-1'(9'),3',5',7'-tetraen-10'-yl}phenyl)-2,2,2-trifluoroethyl]-1-imino-N-methyl-1-oxo-1λ$^6$-thiane-4-carboxamide | $^1$H NMR (500 MHz, DMSO-d$_6$) δ ppm 8.21 (s, 1H), 7.2-7.4 (m, 4H), 6.75 (s, 1H), 6.4-6.6 (m, 1H), 3.9-4.3 (m, 1H), 3.76 (br dd, 2H, J = 3.8, 5.7 Hz), 3.07 (br s, 5H), 2.91 (s, 3H), 2.55 (br s, 2H), 1.9-2.2 (m, 4H), 1.7-1.9 (m, 2H), 0.93 (d, 2H, J = 1.7 Hz) m/z: 581 [M + H]$^+$ | | |
| Example 188 CPD0072852 | Procedure 1a | Intermediate 144 | Yield 14% |
| 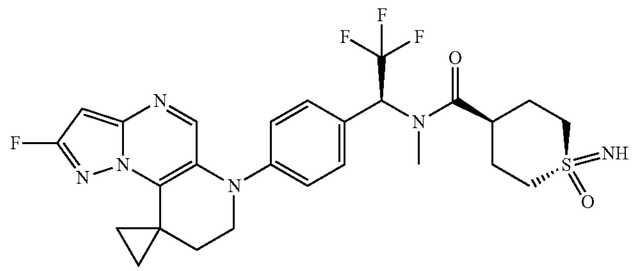<br>(1 rel-s,4 rel-s)-1-imino-N-methyl-1-oxo-N-[(1S)-2,2,2-trifluoro-1-(4-{4'-fluoro-2',3',7',10'-tetraazaspiro[cyclopropane-1,13'-tricyclo[7.4.0.0$^{2,6}$]tridecane]-1'(9'),3',5',7'-tetraen-10'-yl} phenyl)ethyl]-1λ$^6$-thiane-4-carboxamide | $^1$H NMR (500 MHz, DMSO-d$_6$) δ ppm 8.20 (s, 1H), 7.1-7.5 (m, 4H), 6.51 (q, 1H, J = 9.2 Hz), 6.37 (d, 1H, J = 5.1 Hz), 3.76 (br dd, 2H, J = 3.7, 5.6 Hz), 3.71 (s, 1H), 3.0-3.2 (m, 5H), 2.91 (s, 3H), 2.53 (br s, 2H), 1.9-2.1 (m, 4H), 1.78 (br d, 2H, J = 5.1 Hz), 0.92 (d, 2H, J = 2.0 Hz) m/z: 565 [M + H]$^+$ | | |
| Example 189 CPD0072853 | Procedure 1a | Intermediate 144 | Yield 25% |
| 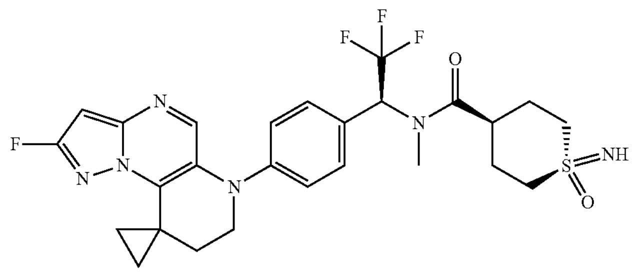<br>(1 rel-r,4 rel-r)-1-imino-N-methyl-1-oxo-N-[(1S)-2,2,2-trifluoro-1-(4-{4'-fluoro-2',3),7',10'-tetraazaspiro[cyclopropane-1,13'-tricyclo[7.4.0.0$^{2,6}$]tridecane]-1'(9'),3',5',7'-tetraen-10'-yl} phenyl)ethyl]-1λ$^6$-thiane-4-carboxamide | $^1$H NMR (500 MHz, DMSO-d$_6$) δ ppm 8.20 (s, 1H), 7.1-7.4 (m, 4H), 6.50 (q, 1H, J = 9.3 Hz), 6.37 (d, 1H, J = 5.1 Hz), 3.76 (br dd, 2H, J = 3 .8, 5.5 Hz), 3.48 (s, 1H), 2.9-3.3 (m, 5H), 2.91 (s, 3H), 2.53 (br s, 2H), 2.00 (br s, 4H), 1.7-1.8 (m, 2H), 0.93 (d, 2H, J = 2.0 Hz) m/z: 565 [M + H]$^+$ | | |

-continued

| Example 190 CPD0072784 | Procedure 1a | Intermediate 145 | Yield 40% |
|---|---|---|---|
| 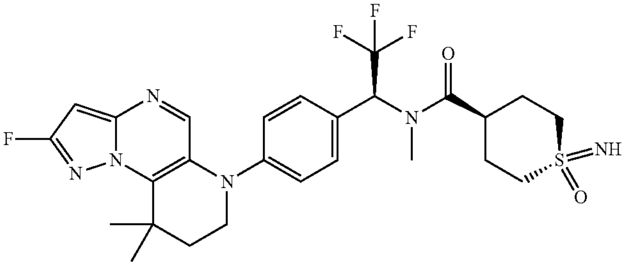 (1 rel-s,4 rel-s)-N-[(1S)-1-(4-{4-chloro-13,13-dimethyl-2,3,7,10-tetraazatricyclo[7.4.0.0$^{2,6}$]trideca-1(9),3,5,7-tetraen-10-yl}phenyl)-2,2,2-trifluoroethyl]-1-imino-N-methyl-1-oxo-1λ$^6$-thiane-4-carboxamide | $^1$H NMR (600 MHz, DMSO-d$_6$) δ ppm 8.25 (s, 1H), 7.1-7.5 (m, 4H), 6.7-6.9 (m, 1H), 6.51 (q, 1H, J = 9.4 Hz), 3.6-3.8 (m, 3H), 3.0-3.1 (m, 5H), 2.91 (s, 3H), 1.9-2.1 (m, 4H), 1.80 (td, 2H, J = 2.5, 5.3 Hz), 1.62 (s, 6H) m/z: 583 [M + H]$^+$ | | |
| Example 191 CPD0072785 | Procedure 1a | Intermediate 145 | Yield 20% |
| 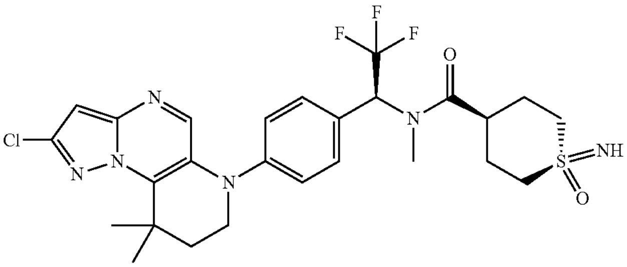 (1 rel-r,4 rel-r)-N-[(1S)-1-(4-{4-chloro-13,13-dimethyl-2,3,7,10-tetraazatricyclo[7.4.0.0$^{2,6}$]trideca-1(9),3,5,7-tetraen-10-yl}phenyl)-2,2,2-trifluoroethyl]-1-imino-N-methyl-1-oxo-1λ$^6$-thiane-4-carboxamide | $^1$H NMR (600 MHz, DMSO-d$_6$) δ ppm 8.25 (s, 1H), 7.28-7.39 (m, 2H), 7.21-7.28 (m, 2H), 6.81 (s, 1H), 6.50 (q, J = 9.2 Hz, 1H), 3.69 (dt, J = 5.4, 2.5 Hz, 2H), 3.48 (s, 1H), 3.07-3.16 (m, 3H), 3.00-3.06 (m, 2H), 2.91 (s, 3H), 1.90-2.19 (m, 4H), 1.80 (dt, J = 5.3, 2.5 Hz, 2H), 1.62 (s, 6H). m/z: 583 [M + H]$^+$ | | |
| Example 192 CPD0072782 | Procedure 1a | Intermediate 146 | Yield 19% |
| 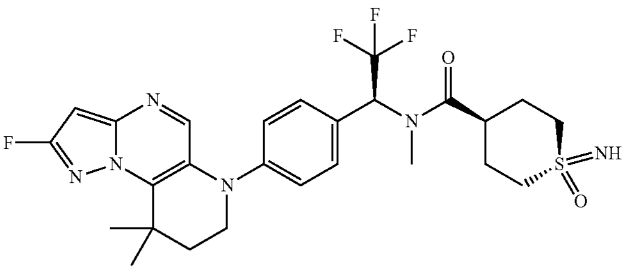 [SMILES: CN(C(=O)[C@H]1CC[S@@](=N)(=O)CC1)[C@@H](c1ccc(N2CCC(C)(C)c3c2cnc2cc(F)nn32)cc1)C(F)(F)F] (1 rel-s,4 rel-s)-1-imino-N-methyl-1-oxo-N-[(1S)-2,2,2-trifluoro-1-(4-{4'-fluoro-2',3',7',10'-tetraazaspiro[cyclopropane-1,13'-tricyclo[7.4.0.0$^{2,6}$]tridecane]-1'(9'),3',5',7'-tetraen-10'-yl}phenyl)ethyl]-1λ$^6$-thiane-4-carboxamide | $^1$H NMR (600 MHz, DMSO-d$_6$) δ ppm 8.25 (s, 1H), 7.27-7.39 (m, 2H), 7.23 (d, J = 8.8 Hz, 2H), 6.49 (q, J = 9.2 Hz, 1H), 6.43 (d, J = 5.1 Hz, 1H), 3.69 (dt, J = 5.3, 2.5 Hz, 2H), 3.48 (s, 1H), 2.99-3.21 (m, 5H), 2.91 (s, 3H), 1.86-2.12 (m, 4H), 1.79 (dt, J = 5.3, 2.5 Hz, 2H), 1.61 (s, 6H) m/z: 567 [M + H]$^+$ | | |
| Example 193 CPD0072783 | Procedure 1a | Intermediate 146 | Yield 7% |
| 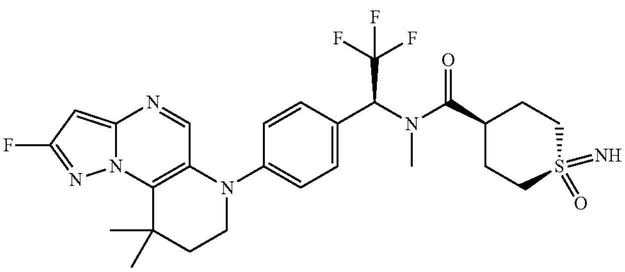 [SMILES: CN(C(=O)[C@H]1CC[S@](=N)(=O)CC1)[C@@H](c1ccc(N2CCC(C)(C)c3c2cnc2cc(F)nn32)cc1)C(F)(F)F] (1 rel-r,4 rel-r)-1-imino-N-methyl-1-oxo-N-[(1S)-2,2,2-trifluoro-1-(4-{4'-fluoro-2',3',7',10'-tetraazaspiro[cyclopropane-1,13'-tricyclo[7.4.0.0$^{2,6}$]tridecane]-1'(9'),3',5',7'-tetraen-10'-yl}phenyl)ethyl]-1λ$^6$-thiane-4-carboxamide | $^1$H NMR (600 MHz, DMSO-d$_6$) δ ppm 8.25 (s, 1H), 7.30 (d, J = 8.7 Hz, 2H), 7.23 (d, J = 8.7 Hz, 2H), 6.47-6.55 (m, 1H), 6.43 (d, J = 5.1 Hz, 1H), 3.64-3.78 (m, 3H), 2.98-3.17 (m, 5H), 2.91 (s, 3H), 1.92-2.06 (m, 4H), 1.79 (dt, J = 5.3, 2.5 Hz, 2H), 1.61 (s, 6H) m/z: 567 [M + H]$^+$ | | |

-continued

| Example 194 CPD0073192 | Procedure 1b | Intermediate 147 | Yield 7% |
|---|---|---|---|
| 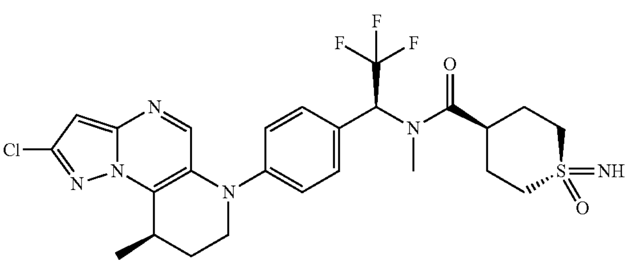 [SMILES: C[C@@H]1CCN(c2ccc([C@H](N(C)C(=O)[C@H]3CC[S@@](=N)(=O)CC3)C(F)(F)F)cc2)c2cnc3cc(Cl)nn3c21] | $^1$H NMR (600 MHz, DMSO-$d_6$) δ ppm 8.27 (s, 1H), 7.27-7.42 (m, 4H), 6.79 (s, 1H), 6.52 (q, J = 9.3 Hz, 1H), 3.66-3.75 (m, 3H), 3.49-3.55 (m, 1H), 2.99-3.14 (m, 5H), 2.91 (s, 3H), 1.96-2.08 (m, 5H), 1.76 (br d, J = 13.6 Hz, 1H), 1.44 (d, J = 6.9 Hz, 3H). m/z: 569 [M + H]$^+$ | | |
| (1 rel-s,4 rel-s)-N-[(1S)-1-{4-[(13 rel-R)-4-chloro-13-methyl-2,3,7,10-tetraazatricyclo[7.4.0.0$^{2,6}$] trideca-1(9),3,5,7-tetraen-10-yl]phenyl}-2,2,2-trifluoroethyl]-1-imino-N-methyl-1-oxo-1λ$^6$-thiane-4-carboxamide | | | |
| Example 195 CPD0073193 | Procedure 1b | Intermediate 147 | Yield 9% |
| 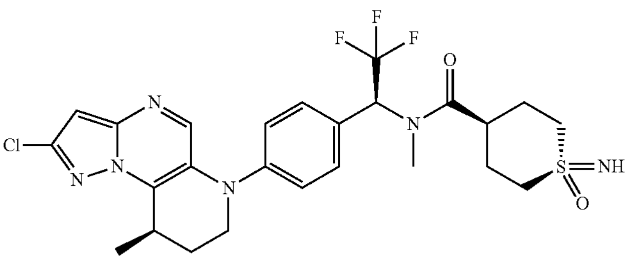 [SMILES: C[C@@H]1CCN(c2ccc([C@H](N(C)C(=O)[C@H]3CC[S@](=N)(=O)CC3)C(F)(F)F)cc2)c2cnc3cc(Cl)nn3c21] | $^1$H NMR (600 MHz, DMSO-$d_6$) δ ppm 8.27 (s, 1H), 7.2-7.5 (m, 4H), 6.79 (s, 1H), 6.51 (q, 1H, J = 9.2 Hz), 3.6-3.8 (m, 2H), 3.5-3.6 (m, 1H), 3.47 (s, 1H), 3.0-3.3 (m, 5H), 2.6-2.9 (m, 3H), 1.7-2.2 (m, 6H), 1.44 (d, 3H, J = 6.9 Hz) m/z: 569 [M + H]$^+$ | | |
| (1 rel-r,4 rel-r)-N-[(1S)-1-{4-[(13 rel-R)-4-chloro-13-methyl-2,3,7,10-tetraazatricyclo[7.4.0.0$^{2,6}$] trideca-1(9),3,5,7-tetraen-10-yl]phenyl}-2,2,2-trifluoroethyl]-1-imino-N-methyl-1-oxo-1λ$^6$-thiane-4-carboxamide | | | |
| Example 196 CPD0073194 | Procedure 1b | Intermediate 147 | Yield 6% |
| 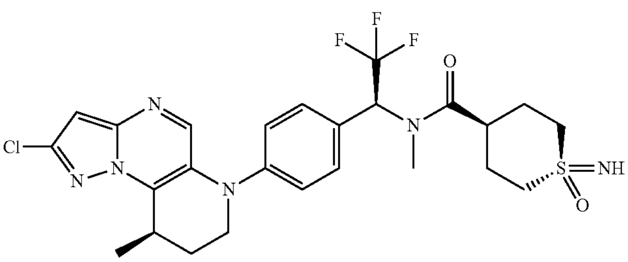 [SMILES: C[C@@H]1CCN(c2ccc([C@H](N(C)C(=O)[C@H]3CC[S@@](=N)(=O)CC3)C(F)(F)F)cc2)c2cnc3cc(Cl)nn3c21] | $^1$H NMR (600 MHz, DMSO-$d_6$) δ ppm 8.28 (s, 1H), 7.23-7.44 (m, 4H), 6.79 (s, 1H), 6.52 (q, J = 9.3 Hz, 1H), 3.64-3.80 (m, 3H), 3.52 (td, J = 6.5, 2.6 Hz, 1H), 2.99-3.17 (m, 5H), 2.92 (s, 3H), 1.70-2.19 (m, 6H), 1.44 (d, J = 6.9 Hz, 3H). m/z: 569 [M + H]$^+$ | | |
| (1 rel-s,4 rel-s)-N-[(1S)-1-{4-[(13 rel-S)-4-chloro-13-methyl-2,3,7,10-tetraazatricyclo[7.4.0.0$^{2,6}$]trideca-1(9),3,5,7-tetraen-10-yl]phenyl}-2,2,2-trifluoroethyl]-1-imino-N-methyl-1-oxo-1λ$^6$-thiane-4-carboxamide | | | |
| Example 197 CPD0073195 | Procedure 1b | Intermediate 147 | Yield 10% |
| 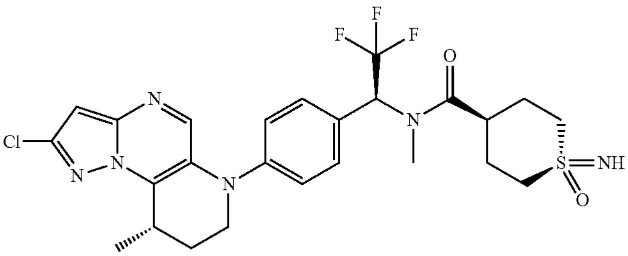 [SMILES: C[C@H]1CCN(c2ccc([C@H](N(C)C(=O)[C@H]3CC[S@](=N)(=O)CC3)C(F)(F)F)cc2)c2cnc3cc(Cl)nn3c21] | $^1$H NMR (600 MHz, DMSO-$d_6$) δ ppm 8.28 (s, 1H), 7.2-7.5 (m, 4H), 6.79 (s, 1H), 6.51 (q, 1H, J = 9.3 Hz), 3.6-3.8 (m, 2H), 3.52 (dt, 1H, J = 2.6, 6.5 Hz), 3.47 (s, 1H), 3.0-3.2 (m, 5H), 2.6-3.0 (m, 3H), 1.7-2.3 (m, 6H), 1.44 (d, 3H, J = 7.0 Hz). m/z: 569 [M + H]$^+$ | | |
| (1 rel-R,4 rel-R)-N-[(1S)-1-{4-[(13 rel-S)-4-chloro-13-methyl-2,3,7,10-tetraazatricyclo[7.4.0.0$^{2,6}$]trideca-1(9),3,5,7-tetraen-10-yl]phenyl}-2,2,2-trifluoroethyl]-1-imino-N-methyl-1-oxo-1λ$^6$-thiane-4-carboxamide | | | |

-continued

| Example 198 CPD0073131 | Procedure 1c | Intermediate 149 | Yield 9.5% |
|---|---|---|---|
| 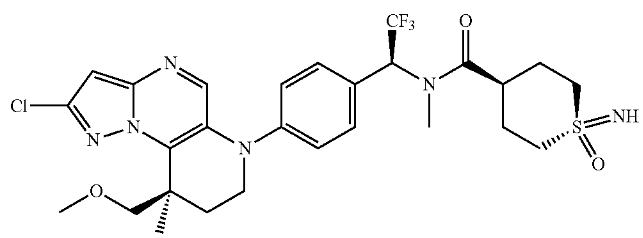 [SMILES: COC[C@]1(C)CCN(c2ccc([C@H](N(C)C(=O)[C@H]3CC[S@@](=N)(=O)CC3)C(F)(F)F)cc2)c2cnc3cc(Cl)nn3c21] | $^1$H NMR (DMSO-d$_6$, 600 MHz): δ ppm 8.25 (s, 1H), 7.32 (d, J = 8.5 Hz, 2H), 7.20 (d, J = 8.7 Hz, 2H), 6.81 (s, 1H), 6.50 (q, J = 9.2 Hz, 1H), 4.49 (d, J = 8.8 Hz, 1H), 3.81 (ddd, J = 13.3, 6.3, 3.0 Hz, 1H), 3.65 (ddd, J = 12.9, 10.2, 2.3 Hz, 1H), 3.55 (d, J = 8.8 Hz, 1H), 3.47 (s, 1H), 2.99-3.19 (m, 8H), 2.92 (s, 3H), 2.16-2.24 (m, 1H), 1.85-2.12 (m, 4H), 1.65 (ddd, J = 13.6, 6.2, 2.3 Hz, 1H), 1.52 (s, 3H). m/z: 612 [M + H]$^+$ | | |
| (1 rel-s,4 rel-s)-N-[(1S)-1-[4-[(13 rel-R)-4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-1-imino-N-methyl-1-oxo-1λ$^6$-thiane-4-carboxamide | | | |
| Example 199 CPD0073132 | Procedure 1c | Intermediate 149 | Yield 5% |
| 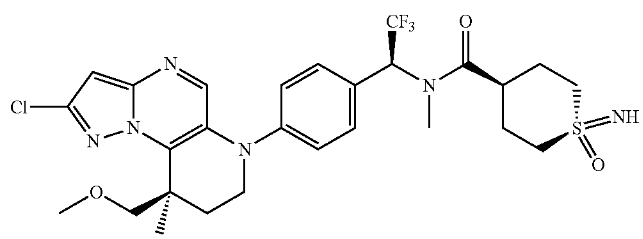 [SMILES: COC[C@]1(C)CCN(c2ccc([C@H](N(C)C(=O)[C@H]3CC[S@](=N)(=O)CC3)C(F)(F)F)cc2)c2cnc3cc(Cl)nn3c21] | $^1$H NMR (600 MHz, DMSO-d$_6$, 300K) δ ppm 8.25 (s, 1H), 7.32 (d, J = 8.4 Hz, 2H), 7.20 (d, J = 8.7 Hz, 2H), 6.81 (s, 1H), 6.51 (q, J = 9.3 Hz, 1H), 4.49 (d, J = 8,8 Hz, 1H), 3.81 (ddd, J = 13.0, 6.3, 3.2 Hz, 1H), 3.70 (s, 1H), 3.61-3.68 (m, 1H), 3.52-3.58 (m, 1H), 3.12 (s, 8 H), 2.92 (s, 3H), 2.16-2.28 (m, 1H), 2.02 (br d, J = 3.2 Hz, 4H), 1.60-1.70 (m, 1H), 1.52 (s, 3H) m/z : 612 [M + H]$^+$ | | |
| (1 rel-r,4 rel-r)-N-[(1S)-1-[4-[(13 rel-R)-4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-1-imino-N-methyl-1-oxo-1λ$^6$-thiane-4-carboxamide | | | |
| Example 200 CPD0073133 | Procedure 1c | Intermediate 149 | Yield 5.5% |
| 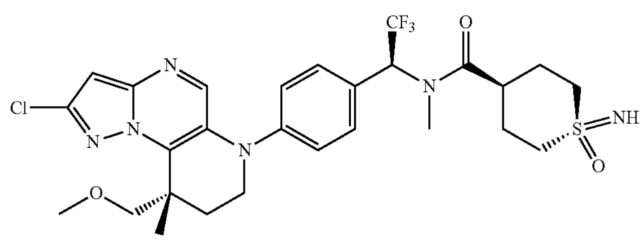 [SMILES: COC[C@@]1(C)CCN(c2ccc([C@H](N(C)C(=O)[C@H]3CC[S@@](=N)(=O)CC3)C(F)(F)F)cc2)c2cnc3cc(Cl)nn3c21] | $^1$H NMR (DMSO-d$_6$, 600 MHz): δ ppm 8.24 (s, 1H), 7.32 (d, J = 8.5 Hz, 2H), 7.20 (d, J = 8.8 Hz, 2H), 6.81 (s, 1H), 6.12-6.70 (m, 1H), 4.49 (d, J = 8.8 Hz, 1H), 3.78-3.87 (m, 1H), 3.70 (s, 1H), 3.61-3.67 (m, 1H), 3.54 (d, J = 8.8 Hz, 1H), 3.12 (s, 3H), 2.99-3.12 (m, 5H), 2.91 (s, 3H), 2.20 (ddd, J = 13.4, 10.3, 3.0 Hz, 1H), 1.94-2.07 (m, 4H), 1.65 (ddd, J = 13.6, 6.0, 2.1 Hz, 1H), 1.52 (s, 3H). m/z 612 [M + H]$^+$ | | |
| (1 rel-s,4 rel-s)-N-[(1S)-1-[4-[(13 rel-S)-4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-1-imino-N-methyl-1-oxo-1λ$^6$-thiane-4-carboxamide | | | |
| Example 201 CPD0073134 | Procedure 1c | Intermediate 149 | Yield 10% |
| 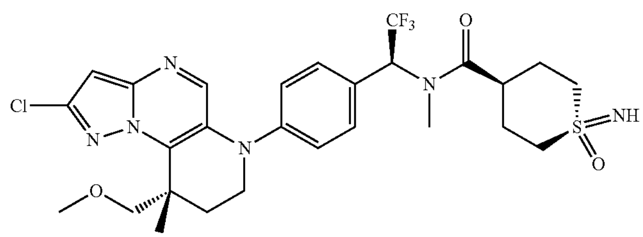 [SMILES: COC[C@@]1(C)CCN(c2ccc([C@H](N(C)C(=O)[C@H]3CC[S@](=N)(=O)CC3)C(F)(F)F)cc2)c2cnc3cc(Cl)nn3c21] | $^1$H NMR (DMSO-d$_6$, 600 MHz): δ ppm 8.24 (s, 1H), 7.31 (d, J = 8.5 Hz, 2H), 7.20 (d, J = 8.7 Hz, 2H), 6.81 (s, 1H), 6.13-6.60 (m, 1H), 4.49 (d, J = 8.8 Hz, 1H), 3,81 (ddd, J = 13.2, 6.1, 2.9 Hz, 1H), 3.64 (ddd, J = 12.9, 10.3, 2.1 Hz, 1H), 3.54 (d, J = 8.8 Hz, 1H), 3.47 (s, 1H), 3.00-3.24 (m, 8H), 2.91 (s, 3H), 2.20 (ddd, J = 13.3, 10.2, 2.8 Hz, 1H), 1.84-2.13 (m, 4H), 1.65 (ddd, J = 13.6, 6.0, 2.3 Hz, 1H), 1.52 (s, 3H). m/z 612 [M + H]$^+$ | | |
| (1 rel-r,4 rel-r)-N-[(1S)-1-[4-[(13 rel-S)-4-chloro-13-(methoxymethyl)-13-methyl-2,3,7,10-tetrazatricyclo[7.4.0.0$^{2,6}$]trideca-1(9),3,5,7-tetraen-10-yl]phenyl]-2,2,2-trifluoro-ethyl]-1-imino-N-methyl-1-oxo-1λ$^6$-thiane-4-carboxamide | | | |

-continued

| Example 202 CPD0073223 | Procedure 1c | Intermediate 153 | Yield 3% |
|---|---|---|---|
| 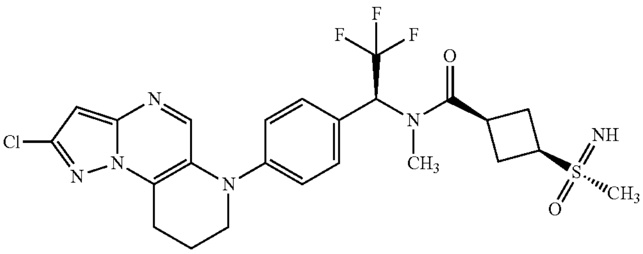 [SMILES: CN(C(=O)[C@H]1C[C@@H]([S@@](C)(=N)=O)C1)[C@@H](c1ccc(N2CCCc3c2cnc2cc(Cl)nn32)cc1)C(F)(F)F] (1R,3s)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-[(S)-imino(methyl)oxo-1λ$^6$-sulfanyl]-N-methylcyclobutane-1-carboxamide | $^1$H NMR (600 MHz, DMSO-d$_6$, 300K) δ ppm 8.30 (s, 1H), 7.17-7.43 (m, 4H), 6.82 (s, 1H), 6.45 (br d, J = 9.2 Hz, 1H), 3.78-3.87 (m, 1H), 3.68-3.75 (m, 2H), 3.54 (s, 1H), 3.43 (t, J = 8.8 Hz, 1 H), 3.10 (t, J = 6.7 Hz, 2H), 2.79 (s, 3H), 2.76 (s, 3H), 2.47 (d, J = 10.0 Hz, 4H), 1.91-2.00 (m, 2H). m/z 555 [M + H]$^+$ | | |
| Example 203 CPD0073224 | Procedure 1c | Intermediate 153 | Yield 3% |
| 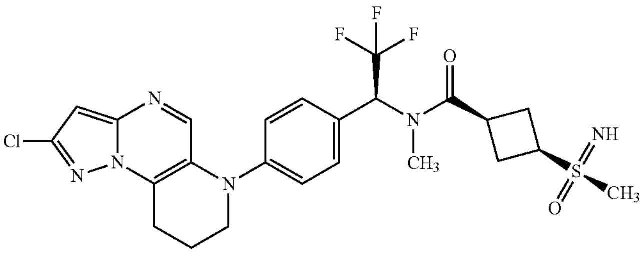 [SMILES: CN(C(=O)[C@H]1C[C@@H]([S@](C)(=N)=O)C1)[C@@H](c1ccc(N2CCCc3c2cnc2cc(Cl)nn32)cc1)C(F)(F)F] (1S,3s)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-[(S)-imino(methyl)oxo-1λ$^6$-sulfanyl]-N-methylcyclobutane-1-carboxamide | $^1$H NMR (600 MHz, DMSO-d$_6$, 300K) δ ppm 8.31 (s, 1H), 7.18-7.44 (m, 4H), 6.82 (s, 1H), 6.40-6.51 (m, 1H), 3.79-3.88 (m, 1H), 3.67-3.74 (m, 2H), 3.55 (s, 1H), 3.43 (quin, J = 9.0 Hz, 1H), 3.10 (t, J = 6.7 Hz, 2H), 2.78 (s, 3H), 2.76 (s, 3H), 2.33-2.48 (m, 4H), 1.91-2.00 (m, 2H). m/z 555 [M + H]$^+$ | | |
| Example 204 CPD0073225 | Procedure 1c | Intermediate 153 | Yield 8% |
| 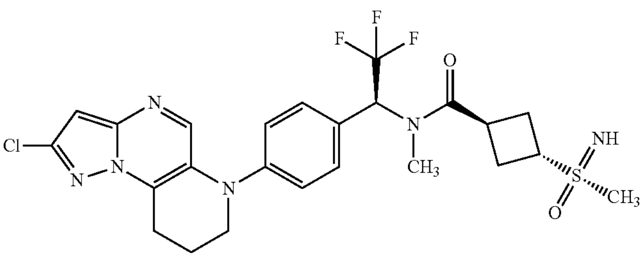 [SMILES: CN(C(=O)[C@H]1C[C@H]([S@@](C)(=N)=O)C1)[C@@H](c1ccc(N2CCCc3c2cnc2cc(Cl)nn32)cc1)C(F)(F)F] (1S,3r)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-[(S)-imino(methyl)oxo-1λ$^6$-sulfanyl]-N-methylcyclobutane-1-carboxamide | $^1$H NMR (600 MHz, DMSO-d$_6$, 300K) δ ppm 8.30 (s, 1H), 7.30-7.41 (m, 2H), 7.26 (d, J = 8.7 Hz, 2H), 6.82 (s, 1H), 6.50 (br d, J = 9.2 Hz, 1H), 3.74-3.82 (m, 1H), 3.66-3.74 (m, 3H), 3.46-3.56 (m, 1H), 3.10 (t, J = 6.7 Hz, 2H), 2.81 (s, 3H), 2.75 (s, 3H), 2.51-2.70 (m, 4H), 1.91-2.03 (m, 2H). m/z 555 [M + H]$^+$ | | |
| Example 205 CPD0073226 | Procedure 1c | Intermediate 153 | Yield 10% |
| 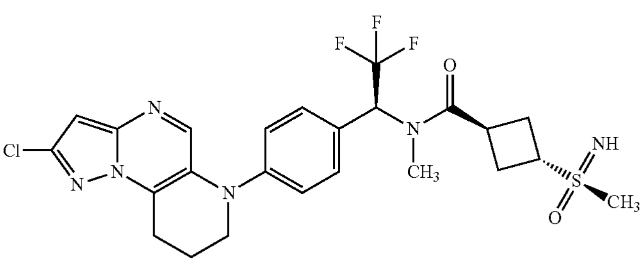 [SMILES: CN(C(=O)[C@H]1C[C@H]([S@](C)(=N)=O)C1)[C@@H](c1ccc(N2CCCc3c2cnc2cc(Cl)nn32)cc1)C(F)(F)F] (1R,3s)-N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-3-[(S)-imino(methyl)oxo-1λ$^6$-sulfany]l]-N-methylcyclobutane-1-carboxamide | $^1$H NMR (600 MHz, DMSO-d$_6$, 300K) δ ppm 8.31 (s, 1H), 7.33 (d, J = 8.5 Hz, 2H), 7.26 (d, J-8.8 Hz, 2H), 6.82 (s, 1H), 6.50 (q, J = 9.1 Hz, 1H), 3.74-3.83 (m, 1H), 3.70-3.73 (m, 2H), 3.69 (s, 1H), 3.48-3.56 (m, 1H), 3.10 (t, J = 6.7 Hz, 2H), 2.81 (s, 3H), 2.75 (s, 3H), 2.56-2.66 (m, 2H), 2.45-2.49 (m, 2H), 1.96 (br d, J = 5.1 Hz, 2H). m/z 555 [M + H]$^+$ | | |

-continued

| Example 206 CPD0073497 | Procedure 1a | Intermediate 150 | Yield 34% |
|---|---|---|---|
| 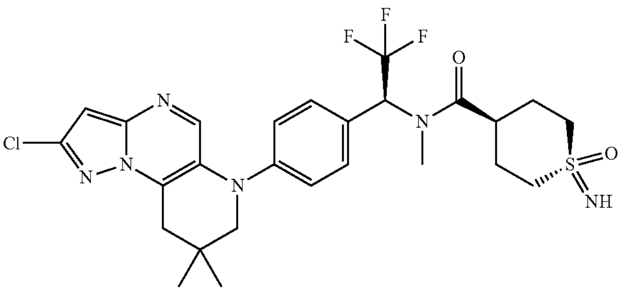 [SMILES: CN(C(=O)[C@H]1CC[S@](=N)(=O)CC1)[C@@H](c1ccc(N2CC(C)(C)Cc3c2cnc2cc(Cl)nn32)cc1)C(F)(F)F]<br>(1 rel r,4 rel r)-N-[(1S)-1-(4-{4-chloro-12,12-dimethyl-2,3,7,10-tetraazatricyclo[7.4.0.0$^{2,6}$]trideca-1(9),3,5,7-tetraen-10-yl}phenyl)-2,2,2-trifluoroethyl]-1-imino-N-methyl-1-oxo-1λ$^6$-thiane-4-carboxamide | $^1$H NMR (600 MHz, DMSO-d$_6$) δ ppm 8.40 (s, 1H), 7.27-7.43 (m, 4H), 6.80 (s, 1H), 6.52 (q, J = 9.4 Hz, 1H), 3.40-3.49 (m, 6H), 3.18-3.25 (m, 1H), 2.93 (d, J = 3.2 Hz, 5H), 2.00-2.18 (m, 4H), 1.03 (s, 6H). m/z: 583 [M + H]$^+$ | | |
| Example 207 CPD0073498 | Procedure 1a | Intermediate 150 | Yield 3% |
| 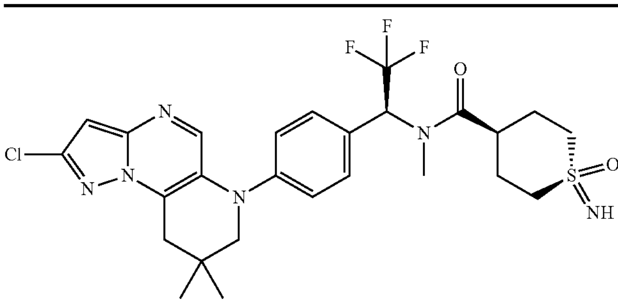<br>(1 rel s, 4 rel s)-N-[(1S)-1-(4-{4-chloro-12,12-dimethyl-2,3,7,10-tetraazatricyclo[7.4.0.0$^{2,6}$]trideca-1(9),3,5,7-tetraen-10-yl}phenyl)-2,2,2-trifluoroethyl]-1-imino-N-methyl-1-oxo-1λ$^6$-thiane-4-carboxamide | $^1$H NMR (600 MHz, DMSO-d$_6$) δ ppm 8.40 (s, 1H), 7.42-7.34 (m, 2H), 7.34-7.27 (m, 2H), 6.80 (s, 1H), 6.54-6.06 (m, 1H), 3.68-3.60 (m, 4H), 3.47 (s, 2H), 3.29-3.22 (m, 1H), 2.98-2.64 (m, 5H), 2.26-1.92 (m, 4H), 1.03 (s, 6H). m/z: 583 [M + H]$^+$. | | |
| Example 208 CPD0074553 | Procedure 1a | Intermediate 144-b | Yield 11% |
| 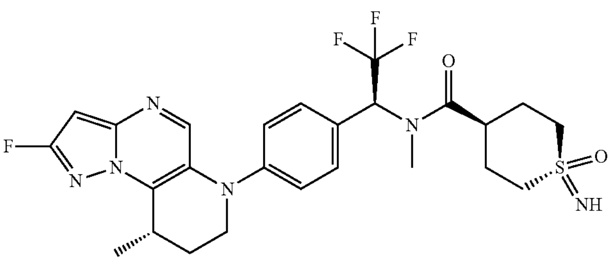 [SMILES: C[C@H]1CCN(c2ccc([C@H](N(C)C(=O)[C@H]3CC[S@](=N)(=O)CC3)C(F)(F)F)cc2)c2cnc3cc(F)nn3c21]<br>(1 rel s, 4 rel s)1-imino-N-methyl-1-oxo-N-[(1S)-2,2,2-trifluoro-1-[4-[(13 rel S)-4-fluoro-13-methyl-2,3,7,10-tetrazatricyclo[7.4.0.0$^{2,6}$]trideca-1(9),3,5,7-tetraen-10-yl]phenyl]ethyl]thiane-4-carboxamide | $^1$H NMR (DMSO-d6, 600 MHz): δ ppm 8.27 (s, 1H), 7.21-7.43 (m, 4H), 6.51 (q, J = 9.1 Hz, 1H), 6.40 (d, J = 5.1 Hz, 1H), 3.63-3.79 (m, 2H), 3.43-3.52 (m, 2H), 3.00-3.22 (m, 5H), 2.91 (s, 2H), 2.66 (s, 1H), 1.83-2.11 (m, 5H), 1.69-1.79 (m, 1H), 1.43 (d, J = 7.0 Hz, 3H). m/z: 553 [M + H]$^+$. | | |
| Example 209 CPD0074554 | Procedure 1a | Intermediate 144-b | Yield 8.5% |
| 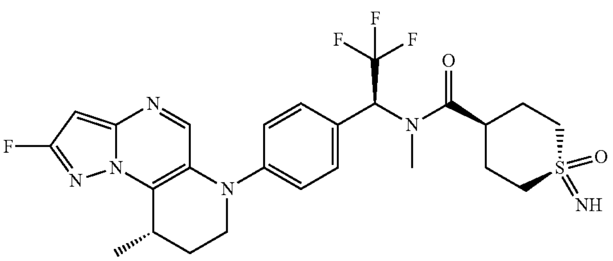 [SMILES: C[C@H]1CCN(c2ccc([C@H](N(C)C(=O)[C@H]3CC[S@@](=N)(=O)CC3)C(F)(F)F)cc2)c2cnc3cc(F)nn3c21]<br>(1 rel r, 4 rel r)1-imino-N-methyl-1-oxo-N-[(1S)-2,2,2-trifluoro-1-[4-[(13 rel S)-4-fluoro-13-methyl-2,3,7,10-tetrazatricyclo[7.4.0.0$^{2,6}$]trideca-1(9),3,5,7-tetraen-10-yl]phenyl]ethyl]thiane-4-carboxamide | $^1$H NMR (DMSO-d6, 600 MHz) δ ppm 8.27 (s, 1H), 7.18-7.48 (m, 4H), 6.52 (q, J = 9.3 Hz, 1H), 6.40 (d, J = 5.1 Hz, 1H), 3.65-3.77 (m, 3H), 3.42-3.51 (m, 1H), 2.98-3.19 (m, 5H), 2.91 (s, 3H), 1.85-2.20 (m, 5H), 1.69-1.79 (m, 1H), 1.43 (d, J = 7.0 Hz, 3H) ). m/z: 553 [M + H]$^+$. | | |

-continued

| Example 210 CPD0074555 | Procedure 1a-b | Intermediate 144-b | Yield 12% |
|---|---|---|---|
| 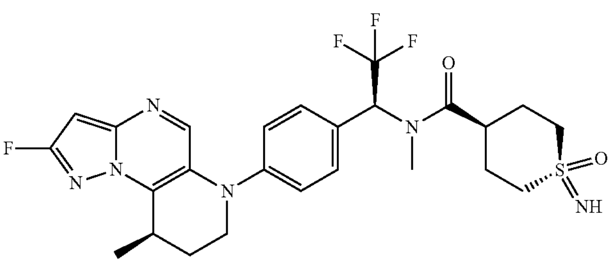 [SMILES: C[C@@H]1CCN(c2ccc([C@H](N(C)C(=O)[C@H]3CC[S@](=N)(=O)CC3)C(F)(F)F)cc2)c2cnc3cc(F)nn3c21] | $^1$H NMR (DMSO-d6, 600 MHz): δ ppm 8.27 (s, 1H), 7.20-7.42 (m, 4H), 6.51 (q, J = 9.3 Hz, 1H), 6.40 (d, J = 5.1 Hz, 1H), 3.62-3.80 (m, 2H), 3.36-3.53 (m, 2H), 2.99-3.22 (m, 5H), 2.92 (s, 2H), 2.66 (s, 1H), 1.91-2.12 (m, 5H), 1.69-1.79 (m, 1H), 1.43 (d, J = 6.9 Hz, 3H). m/z: 553 [M + H]+. | | |
| (1 rels, 4 rel s)1-imino-N-methyl-1-oxo-N-[(1S)-2,2,2-trifluoro-1-[4-[(13 rel R)-4-fluoro-13-methyl-2,3,7,10-tetrazatricyclo[7.4.0.0$^{2,6}$]trideca-1(9),3,5,7-tetraen-10-yl]phenyl]ethyl]thiane-4-carboxamide | | | |
| Example 211 CPD0074556 | Procedure 1a-b | Intermediate 144-b | Yield 7.5% |
| 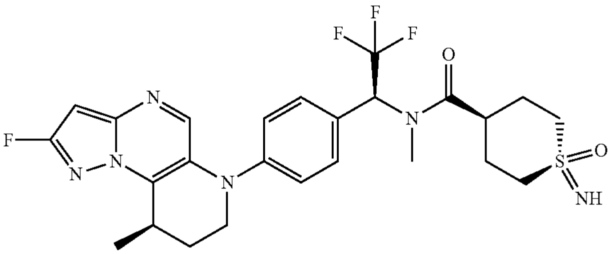 [SMILES: C[C@@H]1CCN(c2ccc([C@H](N(C)C(=O)[C@H]3CC[S@@](=N)(=O)CC3)C(F)(F)F)cc2)c2cnc3cc(F)nn3c21] | $^1$H NMR (DMSO-d6, 600 MHz): δ ppm 8.27 (s, 1H), 7.22-7.43 (m, 4H), 6.52 (q, J = 9.3 Hz, 1H), 6.40 (d, J = 5.1 Hz, 1H), 3.61-3.83 (m, 3H), 3.40-3.56 (m, 1H), 2.98-3.17 (m, 5H), 2.92 (s, 3H), 1.93-2.07 (m, 5H), 1.70-1.80 (m, 1H), 1.43 (d, J = 6.9 Hz, 3H). m/z: 553 [M + H]$^+$. | | |
| (1 rel r, 4 rel r)1-imino-N-methyl-1-oxo-N-[(1S)-2,2,2-trifluoro-1-[4-[(13 rel R)-4-fluoro-13-methyl-2,3,7,10-tetrazatricyclo[7.4.0.0$^{2,6}$]trideca-1(9),3,5,7-tetraen-10-yl]phenyl]ethyl]thiane-4-carboxamide | | | |
| Example 212 CPD0073761 | Procedure 1a | Intermediate 148-b | Yield 16% |
| 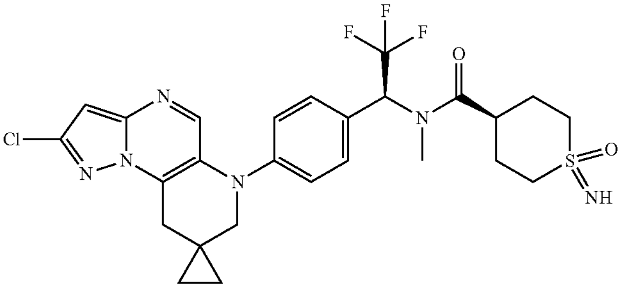 | $^1$H NMR (DMSO-$d_6$, 600 MHz): δ ppm: 8.35 (s, 1H), 7.28 (br s, 2H), 7.26 (s, 2H), 6.83 (s, 1H), 6.58-6.16 (m, 1H), 3.61-3.54 (m, 2H), 3.21-2.98 (m, 7H), 2.90 (s, 3H), 2.15-1.93 (m, 4H), 0.64-0.36 (m, 4H). m/z: 580 [M + H]$^+$.<br>Mixture of diastereoisomers | | |
| N-[(1S)-1-[4-(4-chlorospiro[2,3,7,10-tetrazatricyclo[7.4.0.0$^{2,6}$]trideca-1(9),3,5,7-tetraene-12,1'-cyclopropane]-10-yl)phenyl]-2,2,2-trifluoro-ethyl]-1-imino-N-methyl-1-oxo-thiane-4-carboxamide | | | |
| Example 213 CPD0074564 | Procedure 1b | Intermediate 151 | Yield 22% |
| 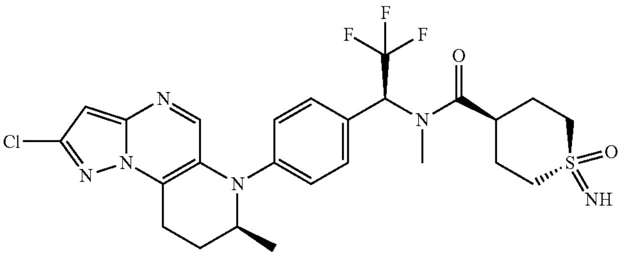 [SMILES: C[C@H]1CCc2c(cnc3cc(Cl)nn23)N1c1ccc([C@H](N(C)C(=O)[C@H]2CC[S@](=N)(=O)CC2)C(F)(F)F)cc1] | $^1$H NMR (DMSO-$d_6$, 600 MHz): δ ppm: 8.22 (s, 1H), 7.32 (m, 2H),<br>7.26 (m, 2H), 6.80 (s, 1H), 6,51 (q, J = 9.3 Hz, 1H), 4.06 (qq, J = 6.8, 3.4 Hz, 1H), 3.48 (s, 1H), 3.09 (m, 7H), 2.91 (s, 3H), 2.01 (m, 6H), 1.23 (d, J = 6.7 Hz, 3H). m/z: 569 [M + H]$^+$. | | |
| (1 rel r 4 rel r) N-[(1S)-1-[4-[(11-rel S)-4-chloro-11-methyl-2,3,7,10-tetrazatricyclo[7.4.0.0$^{2,6}$]trideca-1(9),3,5,7-tetraen-10-yl]phenyl]-2,2,2-trifluoro-ethyl]-1-imino-N-methyl-1-oxo-thiane-4-carboxamide | | | |

-continued

| Example 214 CPD0074565 | Procedure 1b | Intermediate 151 | Yield 9.3% |
|---|---|---|---|
| 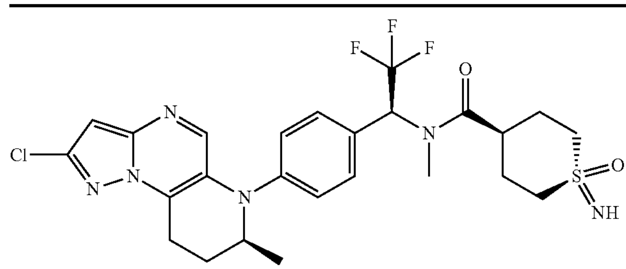 | $^1$H NMR (DMSO-$d_6$, 600 MHz): δ ppm: 8.22 (s, 1H), 7.32 (m, 2H), 7.27 (m, 2H), 6.80 (s, 1H), 6,52 (q, J = 9.1 Hz, 1H), 4.07 (ddt, J = 10.2, 6.8, 3.4, 3.4 Hz, 1H), 3.70 (s, 1H), 3.09 (m, 7 H), 2.92 (s, 3H), 1.95 (m, 6 H), 1.23 (d, J = 6.7 Hz, 3H). m/z: 569 [M + H]$^+$. | | |
| (1 rel s 4 rel s) N-[(1S)-1-[4-[(11-rel S)-4-chloro-11-methyl-2,3,7,10-tetrazatricyclo[7.4.0.0$^{2,6}$]trideca-1(9),3,5,7-tetraen-10-yl]]phenyl]-2,2,2-trifluoro-ethyl]-1-imino-N-methyl-1-oxo-thiane-4-carboxamide | | | |
| Example 215 CPD0074552 | Procedure 1b | Intermediate 152 | Yield: 11 |
| 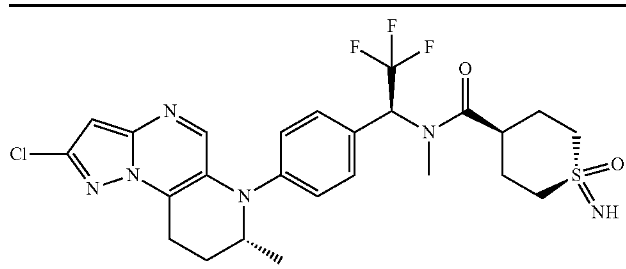 | $^1$H NMR (DMSO-$d_6$, 600 MHz): δ ppm: 8.21 (s, 1H), 7.1-7.5 (m, 4H), 6.80 (s, 1H), 6.52 (q, 1H, J = 9.2 Hz), 4.0-4.2 (m, 1H), 3.7-3.8 (m, 1H), 3.0-3.2 (m, 7H), 2.6-2.9 (m, 3H), 1.7-2.2 (m, 6H), 1.23 (d, 3H, J = 6.7 Hz). m/z: 569 [M + H]$^+$. | | |
| (1 rel s 4 rel s) N-[(1S)-1-[4-[(11-rel R)-4-chloro-11-methyl-2,3,7,10-tetrazatricyclo[7.4.0.0$^{2,6}$]trideca-1(9),3,5,7-tetraen-10-yl]phenyl]-2,2,2-trifluoro-ethyl]-1-imino-N-methyl-1-oxo-thiane-4-carboxamide | | | |
| Example 216 CPD0074551 | Procedure 1b | Intermediate 152 | Yield: 36% |
| 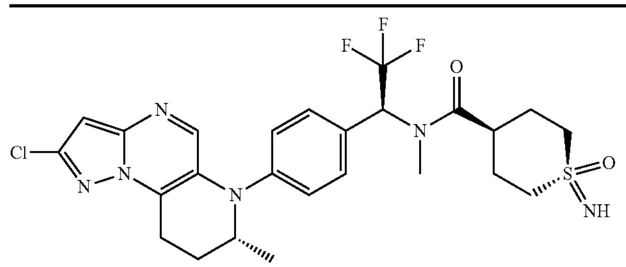 | $^1$H NMR (DMSO-$d_6$, 600 MHz): δ ppm: 8.21 (s, 1H), 7.1-7.5 (m, 4H), 6.80 (s, 1H), 6.51 (q, 1H, J-9.5 Hz), 4.0-4.2 (m, 1H), 3.48 (s, 1H), 2.9-3.3 (m, 7H), 2.6-2.9 (m, 3H), 1.7-2.2 (m, 6H), 1.24 (d, 3H, J = 6.8 Hz). m/z: 569 [M + H]$^+$. | | |
| (1 rel r 4 rel r) N-[(1S)-1-[4-[(11-rel R)-4-chloro-11-methyl-2,3,7,10-tetrazatricyclo[7.4.0.0$^{2,6}$]trideca-1(9),3,5,7-tetraen-10-yl]phenyl]-2,2,2-trifluoro-ethyl]-1-imino-N-methyl-1-oxo-thiane-4-carboxamide | | | |

Examples 217-218 CPD0072530/CPD0072531

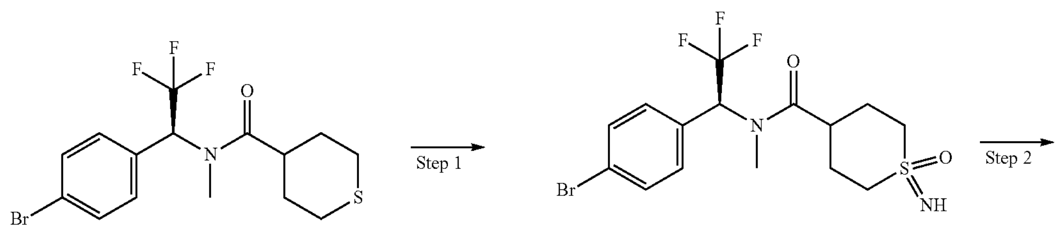

-continued

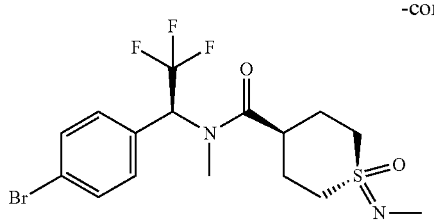

+

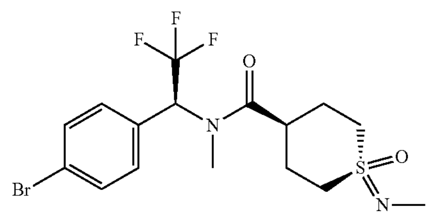

Step 3

Step 3 bis

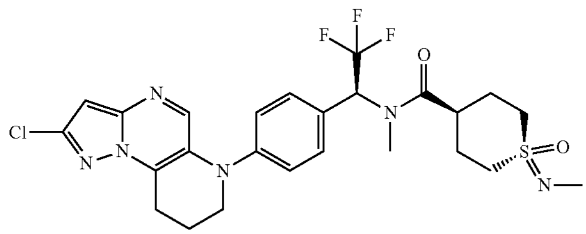

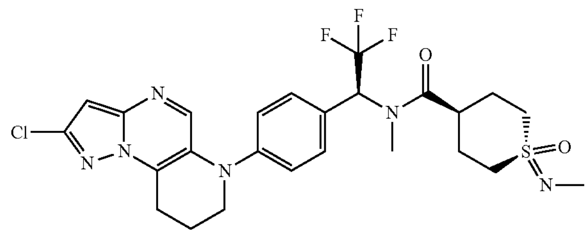

Step 1. N-[(1S)-1-(4-bromophenyl)-2,2,2-trifluoro-ethyl]-1-imino-N-methyl-1-oxo-thiane-4-carboxamide N-[(1S)-1-(4-bromophenyl)-2,2,2-trifluoro-ethyl]-N-methyl-tetrahydrothiopyran-4-carboxamide (963 mg, 2.41 mmol) was dissolved in dry methanol (4.8 mL) at rt. Ammonium carbamate (395 mg, 4.81 mmol) was added, followed by iodobenzene diacetate (2.04 g, 6.01 mmol). The reaction mixture was stirred at rt for 1 h. Volatiles were removed under reduced pressure and the residue was partitioned between water and EtOAc. The aqueous layer was isolated and extracted twice with EtOAc. Organic layers were combined, washed with brine, dried over anhydrous $Na_2SO_4$, filtered and concentrated. The residue was purified by flash column chromatography (DCM/MeOH, from 0% to 10% of MeOH) and reverse phase column chromatography (acetonitrile[+0.1% AcOH]:$H_2O$[+0.1% AcOH] 0:100 to 100:0) to give the title (378 mg, 36%) as a mixture of 2 diastereomers in proportion 6/4. m/z: 427 $[M+H]^+$. $^1H$ NMR (400 MHz, DMSO-$d_6$) δ ppm 7.77-7.63 (m, 2H), 7.44-7.27 (m, 2H), 6.65-6.19 (m, 1H), 3.86-3.46 (m, 1H), 3.21-2.97 (m, 5H), 2.92-2.59 (m, 3H), 2.13-1.91 (m, 4H).

Step 2. (1 rel-S,4rel-S)—N-[(1S)-1-(4-bromophenyl)-2,2,2-trifluoro-ethyl]-N-methyl-1-methylimino-1-oxo-thiane-4-carboxamide N-[(1S)-1-(4-bromophenyl)-2,2,2-trifluoro-ethyl]-1-imino-N-methyl-1-oxo-thiane-4-carboxamide (368 mg, 0.861 mmol) and paraformaldehyde (59 mg, 1.89 mmol) were suspended in formic acid (2.4 mL, 64.6 mmol) and the reaction mixture was stirred at 90° C. overnight. The reaction mixture was concentrated and the residue was partitioned between sat. aq. $NaHCO_3$ and EtOAc. The aqueous phase was isolated and extracted twice with EtOAc. Organic layers were combined, washed with brine, dried over anhydrous $Na_2SO_4$, filtered and concentrated. The crude residue was purified by flash column chromatography (DCM/MeOH, from 0% to 10% of MeOH) to give the title product (107 mg, 35%) as a white solid (first diastereomer to come out of the column, major diastereomer). m/z: 441 $[M+H]^+$. $^1H$ NMR (600 MHz, DMSO-$d_6$) δ ppm 7.77-7.58 (m, 2H), 7.41-7.18 (m, 2H), 6.62-6.20 (m, 1H), 3.31-3.24 (m, 2H), 3.20-2.96 (m, 3H), 2.88 (s, 3H), 2.62-2.58 (m, 3H), 2.02-1.85 (m, 4H).

(1 rel-R,4rel-R)—N-[(1S)-1-(4-bromophenyl)-2,2,2-trifluoro-ethyl]-N-methyl-1-methylimino-1-oxo-thiane-4-carboxamide The compound was obtained from the same purification as above (107 mg, 26%). m/z: 441 $[M+H]^+$. $^1H$ NMR (600 MHz, DMSO-$d_6$) δ ppm 7.81-7.57 (m, 2H), 7.47-7.23 (m, 2H), 6.63-6.22 (m, 1H), 3.25-3.09 (m, 3H), 3.09-2.94 (m, 2H), 2.88 (s, 3H), 2.66-2.61 (m, 3H), 2.12-1.88 (m, 4H).

Example 217 (CPD0072528) Step 3. (1 rel-S,4rel-S)—N-(1S)-1-(4-{4-chloro-2,3,7,10-tetraazatricyclo[$7.4.0.0^{2,6}$]trideca-1(9),3,5,7-tetraen-10-yl}phenyl)-2,2,2-trifluoroethyl]-N-methyl-1-(methylimino)-1-oxo-1$\lambda^6$-thiane-4-carboxamide 4-chloro-2,3,7,10-tetrazatricyclo[$7.4.0.0^{2,6}$]trideca-1(9),3,5,7-tetraene (47 mg, 0.222 mmol), (1 rel-S,4rel-S)—N-[(1S)-1-(4-bromophenyl)-2,2,2-trifluoro-ethyl]-N-methyl-1-methylimino-1-oxo-thiane-4-carboxamide (99 mg, 0.222 mmol) were suspended and cesium carbonate (362 mg, 1.11 mmol) in dry Toluene (1.1 mL) at rt under $N_2$ atmosphere. The reaction mixture was bubbled with $N_2$ for 5 min. [1-(2-diphenylphosphanyl-1-naphthyl)-2-naphthyl]-diphenyl-phosphane (8.3 mg, 0.0133 mmol) was added and the reaction mixture was bubbled with $N_2$. Diacetoxypalladium (2.5 mg, 0.0111 mmol) was added and the reaction mixture was bubbled with $N_2$ for 5 min. The vial was capped and the reaction mixture was stirred at 100° C. for 2 h. The reaction mixture was partitioned between water and EtOAc. The aqueous layer was isolated and extracted twice with EtOAc. Organic layers were combined, washed with brine, dried over anhydrous $Na_2SO_4$, filtered and concentrated under reduced pressure. The residue was purified by flash column chromatography (DCM/MeOH, from 0% to 10% of MeOH). The residue was purified by reverse phase column chromatography (MeCN:H2O 0:100 to 100:0) to afford the title compound (66 mg, 52%) as a yellow solid. m/z: 569 $[M+H]^+$. $^1H$ NMR (500 MHz, DMSO-$d_6$) δ ppm 8.31 (s, 1H), 7.2-7.5 (m, 4H), 6.82 (s, 1H), 6.52 (q, 1H, J=9.3 Hz), 3.71 (br dd, 2H, J=3.9, 6.4 Hz), 3.10 (s, 7H), 2.92 (s, 3H), 2.65 (s, 3H), 1.8-2.2 (m, 6H).

Example 218 (CPD0072529) Step 3 bis. (1 rel-R, 4rel-R)—N-[(1S)-1-(4-{4-chloro-2,3,7,10-tetraazatricyclo[7.4.0.0$^{2,6}$]trideca-1(9),3,5,7-tetraen-10-yl}phenyl)-2,2,2-trifluoroethyl]-N-methyl-1-(methylimino)-1-oxo-16-thiane-4-carboxamide 4-chloro-2,3,7,10-tetrazatricyclo[7.4.0.0$^{2,6}$]trideca-1(9), 3,5,7-tetraene (70 mg, 0.330 mmol), (1rel-R,4rel-R)—N-[(1S)-1-(4-bromophenyl)-2,2,2-trifluoro-ethyl]-N-methyl-1-methylimino-1-oxo-thiane-4-carboxamide (150 mg, 0.330 mmol) and cesium carbonate (537 mg, 1.65 mmol) were suspended in dry toluene (1.65 mL) at rt under $N_2$ atmosphere. The reaction mixture was bubbled with $N_2$ for 5 min. [1-(2-diphenylphosphanyl-1-naphthyl)-2-naphthyl]-diphenyl-phosphane (12 mg, 0.0198 mmol) was added and the reaction mixture was bubbled with $N_2$. diacetoxypalladium (3.7 mg, 0.016 mmol) was added and the reaction mixture was bubbled with $N_2$ for 5 min. The vial was capped and the reaction mixture was stirred at 100° C. for 2 h. The reaction mixture was partitioned between water and EtOAc. The aqueous layer was isolated and extracted twice with EtOAc. Organic layers were combined, washed with brine, dried over anhydrous $Na_2SO_4$, filtered and concentrated. The residue was purified by flash column chromatography (DCM/MeOH, from 0% to 10% of MeOH). The residue was purified by reverse phase column chromatography (acetonitrile/$H_2O$ from 0:100 to 100:0) to afford the title compound as a yellow solid (90 mg, 48%). m/z: 569 $[M+H]^+$. $^1H$ NMR (500 MHz, DMSO-$d_6$) δ ppm 8.30 (s, 1H), 7.1-7.4 (m, 4H), 6.82 (s, 1H), 6.4-6.6 (m, 1H), 3.6-3.8 (m, 2H), 3.31 (s, 7H), 2.92 (s, 3H), 2.60 (s, 3H), 1.8-2.2 (m, 6H).

Examples 219-264

General Procedure 1

A solution of bromo-aryl derivatives (1 mmol), amino-naphthyridine intermediates (0.95 mmol) and cesium carbonate (2 mmol) in dry 1,4-dioxane (2 M), was degassed with nitrogen for 5 min prior addition of Pd Xphos G2 (0.2 mmol) at rt. The reaction mixture was then heated at 100° C. upon completion. After that, the reaction mixture was partitioned between EtOAc and a sat. aq. $NH_4Cl$. Phases were separated and the aqueous phase extracted with EtOAc (3 times). The organic layers were combined, dried over anhydrous $Na_2SO_4$, filtered and concentrated under reduced pressure. The crude was:

a) purified by flash column chromatography (Heptane/EtOAc, 0 to 100% of EtOAc)
b) subjected to chiral separation using Chiralpak IC 5 μm, 250×20 mm eluting with a mobile phase 70/30 ($CO_2$/ETOH+0.5% IPAM)

General Procedure 2

A solution of intermediate 94 (1 mmol), halogen-naphthyridine intermediates (1.1 mmol) and cesium carbonate (2 mmol) in dry 1,4-dioxane (2 M) was degassed with nitrogen for 5 min prior to addition of Pd Xphos G2 (0.02 mmol) at rt. The reaction mixture was then heated at 100° C. for 1 h. The reaction mixture was diluted with EtOAc and saturated $NH_4Cl$ solution was added. The aqueous phase was extracted with EtOAc. The organic layers were combined, dried over $Na_2SO_4$, filtered and concentrated under reduced pressure.

General Procedure 3

To a solution of intermediates 188-191, 194, 195 (1 mmol) in dry DCM (0.1 M) was added TFA (1 mmol). The reaction mixture was stirred at rt upon completion (2-4 h). Once the reaction was complete it was quenched with a sat. aq. $NaHCO_3$ and diluted with EtOAc. The phases were separated and aqueous phase was extracted with EtOAc (3 times), the organic phases were combined, dried over $Na_2SO_4$ concentrated and:

a) purified by flash chromatography.
b) Chiral separation on a AD 250×4.6 5 μm Column with 20% MEOH+0.5% IPAM General Procedure 4

Intermediates 167-170 (110 mg, 0.201 mmol) were dissolved in DCM (4 mL). A 0.5 M solution of m-CPBA in EtOAc (75%, 0.069 mL, 0.190 mmol) was added at 0° C. The reaction mixture was stirred for 2 h. The reaction mixture was quenched with a sat. aq. $NaHCO_3$. The aqueous phase was extracted twice with EtOAc. The organic layers were washed with a sat. aq. solution of $NaHCO_3$, dried over anhydrous $Na_2SO_4$, filtered and concentrated under reduced pressure. The crude was purified by chiral separation using Chiralpak IB (250×320 mm) 5 μm with a mobile phase 75/25 ($CO_2$/EtOH) to afford the title compounds General Procedure 5

Intermediates 167-170 (1.33 g, 2.33 mmol) and ammonium carbamate (2 mmol) were suspended in methanol (1 M) at rt. Iodobenzene diacetate (2 mmol) was added and the reaction mixture was stirred at rt for 30 min. The reaction mixture was partitioned between a sat. aq. $NaHCO_3$ and EtOAc. The aqueous layer was isolated and extracted twice with EtOAc. Organic phases were combined, washed with a sat. aq. $NaHCO_3$, dried over anhydrous $Na_2SO_4$, filtered and concentrated in vacuo. The crude was purified by flash column chromatography (DCM/MeOH, from 0% to 5% of MeOH), then by reverse phase column chromatography (MeCN/$H_2O$ 0/100 to 100/0) to afford the expected compounds.

General Procedure 6

To a solution of intermediate 187 (1 mmol) in dry DCM (0.2 M) at rt under nitrogen atmosphere, was added TEA (20 mmol) and T3P-50% in EtOAc (10 mmol), followed by the corresponding carboxylic acid (1.5 mmol). The reaction mixture was stirred at rt upon completion. The reaction mixture was quenched with sat. aq. $NaHCO_3$. The reaction mixture was diluted in DCM, the phases were separated, and the aqueous phase extracted with DCM (2 times), dried over anhydrous $Na_2SO_4$ and concentrated under reduced pressure. The crude was flash chromatography on silica gel using a gradient of MeOH in DCM.

| Example 219 CPD0019079 | Procedure 1a | Intermediates 86 and 157 | Yield: 90% |
|---|---|---|---|
| 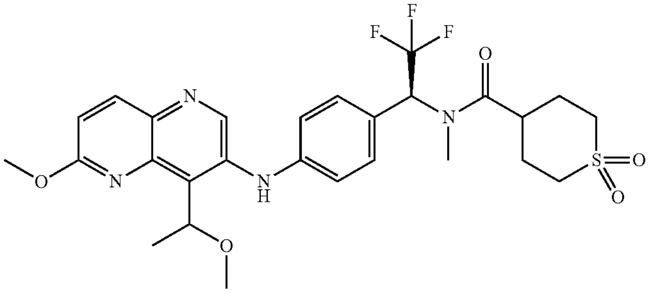 [SMILES: COc1ccc2ncc(Nc3ccc([C@H](N(C)C(=O)C4CCS(=O)(=O)CC4)C(F)(F)F)cc3)c(C(C)OC)c2n1] | $^1$H NMR (400 MHz, DMSO-$d_6$) δ ppm 8.79 (d, J = 1.7 Hz, 1H), 8.17 (d, J = 8.9 Hz, 1H), 8.05 (s, 1H), 7.28 (q, J = 8.5 Hz, 4H), 7.08 (d, J = 8.9 Hz, 1H), 6.60-6.44 (m, 1H), 5.85 (q, J = 6.7 Hz, 1H), 4.02 (s, 3H), 3.31 (s, 3H), 3.28-3.07 (m, 5H), 2.94 (d, J = 2.2 Hz, 3H), 2.19-1.95 (m, 4H), 1.51 (d, J = 6.7 Hz, 3H). m/z: 581 $[M + H]^+$. | | |

N-methyl-1,1-dioxo-N-[(1S)-2,2,2-trifluoro-1-(4-{[6-methoxy-4-(1-methoxyethyl)-1,5-naphthyridin-3-yl]amino}phenyl)ethyl]-1λ$^6$-thiane-4-carboxamide

| Example 220 CPD0019170 | Procedure 1b | Intermediates 86 and 157 | Yield: 25% |
|---|---|---|---|
| 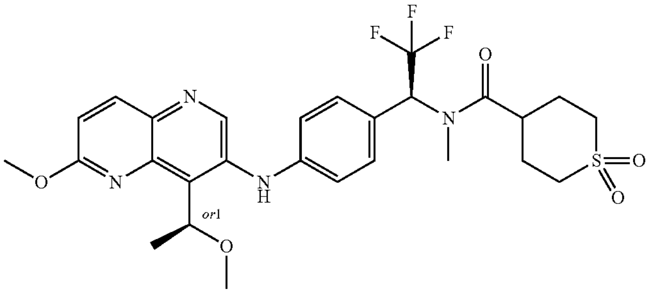 [SMILES: COc1ccc2ncc(Nc3ccc([C@H](N(C)C(=O)C4CCS(=O)(=O)CC4)C(F)(F)F)cc3)c([C@H](C)OC)c2n1] | $^1$H NMR (600 MHz, DMSO-$d_6$) δ ppm 8.76-8.78 (m, 1H), 8.16 (d, J = 8.95 Hz, 1H), 8.02-8.06 (m, 1H), 7.21-7.39 (m, 4H), 7.07 (d, J = 8.95 Hz, 1H), 6,48 (q, J = 9.19 Hz, 1H), 5.85 (q, J = 6.60 Hz, 1H), 4.01 (s, 3H), 3.30-3.30 (m, 3H), 3.09-3.25 (m, 5H), 2.67-2.95 (m, 3H), 1.96-2.15 (m, 4H), 1.50 (d, J = 6.75 Hz, 3H). m/z: 581 $[M + H]^+$. | | |

N-methyl-1,1-dioxo-N-[(1S)-2,2,2-trifluoro-1-[4-({6-methoxy-4-[(1 rel S)-1-methoxyethyl]-1,5-naphthyridin-3-yl}amino)phenyl]ethyl]-1λ$^6$-thiane-4-carboxamide

| Example 221 CPD0019171 | Procedure 1b | Intermediates 86 and 157 | Yield: 25% |
|---|---|---|---|
| 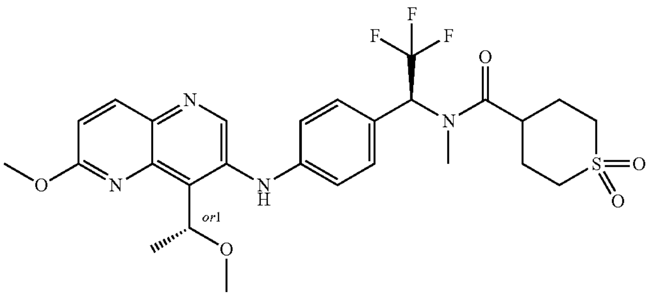 [SMILES: COc1ccc2ncc(Nc3ccc([C@H](N(C)C(=O)C4CCS(=O)(=O)CC4)C(F)(F)F)cc3)c([C@@H](C)OC)c2n1] | $^1$H NMR (600 MHz, DMSO-$d_6$) δ ppm 8.78 (s, 1H), 8.16 (d, J = 8.80 Hz, 1H), 8.02-8.06 (m, 1H), 7.20-7.38 (m, 4H), 7.07 (d, J = 8.95 Hz, 1H), 6.49 (q, J = 9.24 Hz, 1H), 5.84 (q, J = 6.65 Hz, 1H), 4.01 (s, 3H), 3.30-3.31 (m, 3H), 3.09-3.28 (m, 5H), 2.93 (s, 2H), 1.97-2.14 (m, 4H), 1.50 (d, J = 6.60 Hz, 3H), 1.17 (d, J = 6.60 Hz, 1H). m/z: 581 $[M + H]^+$. | | |

N-methyl-1,1-dioxo-N-[(1S)-2,2,2-trifluoro-1-[4-({6-methoxy-4-[(1 rel R)-1-methoxyethyl]-1,5-naphthyridin-3-yl}amino)phenyl]ethyl]-1λ$^6$-thiane-4-carboxamide

| Example 222 CPD0019007 | Procedure 1a | Intermediates 87 and 157 | Yield: 28% |
|---|---|---|---|
| 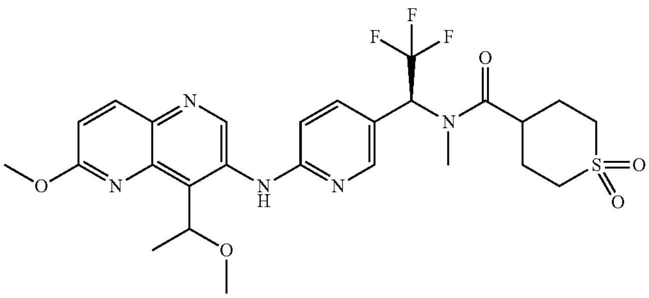 [SMILES: COc1ccc2ncc(Nc3ccc([C@H](N(C)C(=O)C4CCS(=O)(=O)CC4)C(F)(F)F)cn3)c(C(C)OC)c2n1] | $^1$H NMR (DMSO-$d_6$, 600 MHz) δ ppm 9.47 (s, 1H), 8.88 (s, 1H), 8.20 (d, J = 9.0 Hz, 1H), 8.17 (s, 1H), 7.69 (dd, J = 8.6, 2.3 Hz, 1H), 7.12 (d, J = 8.9 Hz, 1H), 7.08-7.14 (m, 1H), 6.48-6.55 (m, 1H), 5.88 (q, J = 6.6 Hz, 1H), 4.02 (s, 3H), 3.31 (s, 3H), 3.08-3.27 (m, 5H), 2.97 (s, 3H), 1.95-2.18 (m, 4H), 1.51 (d, J = 6.7 Hz, 3H). m/z $[M + H]^+$ 582. | | |

-continued

N-[(1S)-2,2,2-trifluoro-1-(6-{[6-methoxy-4-(1-methoxyethyl)-1,5-naphthyridin-3-yl]amino}pyridin-3-yl)ethyl]-1λ$^6$-thiane-4-carboxamide

| Example 223 CPD0018621 | Procedure 1b | Intermediates 87 and 157 | Yield: 40% |
|---|---|---|---|

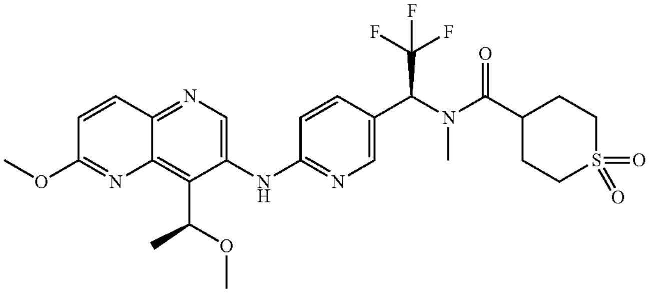 [SMILES: COc1ccc2ncc(Nc3ccc([C@H](N(C)C(=O)C4CCS(=O)(=O)CC4)C(F)(F)F)cn3)c([C@H](C)OC)c2n1]

$^1$H NMR (400 MHz, DMSO-$d_6$) δ ppm 9.49 (s, 1H), 8.89 (s, 1H), 8.30-8.14 (m, 2H), 7.70 (d, J = 10.7 Hz, 1H), 7.14 (dd, J = 8.9, 5.0 Hz, 2H), 6.51 (t, J = 9.3 Hz, 1H), 5.89 (q, J = 6.6 Hz, 1H), 4.03 (s, 3H), 3.31 (s, 3H), 3.30-3.06 (m, 5H), 2.98 (s, 3H), 2.18-1.93 (m, 4H), 1.52 (d, J = 6.7 Hz, 3H). m/z $[M + H]^+$ 582.

N-methyl-1,1-dioxo-N-[(1S)-2,2,2-trifluoro-1-[6-({6-methoxy-4-[(1 rel R)-1-methoxyethyl]-1,5-naphthyridin-3-yl}amino)pyridin-3-yl]ethyl]-1λ$^6$-thiane-4-carboxamide

| Example 224 CPD0019006 | Procedure 1b | Intermediates 87 and 157 | Yield: 39% |
|---|---|---|---|

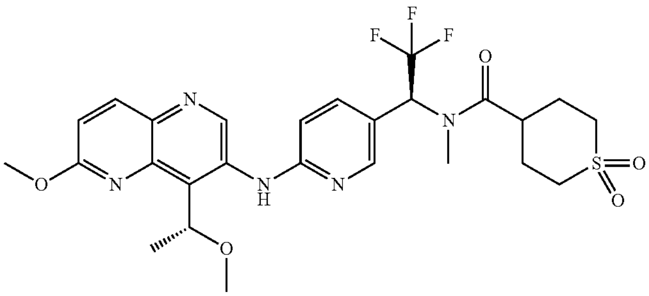 [SMILES: COc1ccc2ncc(Nc3ccc([C@H](N(C)C(=O)C4CCS(=O)(=O)CC4)C(F)(F)F)cn3)c([C@@H](C)OC)c2n1]

$^1$H NMR (600 MHz, DMSO-$d_6$) δ ppm 9.46-9.49 (m, 1H), 8.88 (s, 1H), 8.16-8.21 (m, 2H), 7.69 (dd, J = 2.27, 8.73 Hz, 1H), 7.11-7.16 (m, 2H), 6.51 (q, J = 9.24 Hz, 1H), 5.88 (q, J = 6.70 Hz, 1H), 4.02 (s, 3H), 3.31-3.31 (m, 3H), 3.07-3.27 (m, 5H), 2.97 (s, 3H), 1.96-2.13 (m, 4H), 1.51 (d, J = 6.75 Hz, 3H). m/z $[M + H]^+$ 582.

N-methyl-1,1-dioxo-N-[(1S)-2,2,2-trifluoro-1-[6-({6-methoxy-4-[(1 rel S)-1-methoxyethyl]-1,5-naphthyridin-3-yl}amino)pyridin-3-yl]ethyl]-1λ$^6$-thiane-4-carboxamide

| Example 225 CPD0018619 | Procedure 2 | Intermediates 161 and 94 | Yield: 39% |
|---|---|---|---|

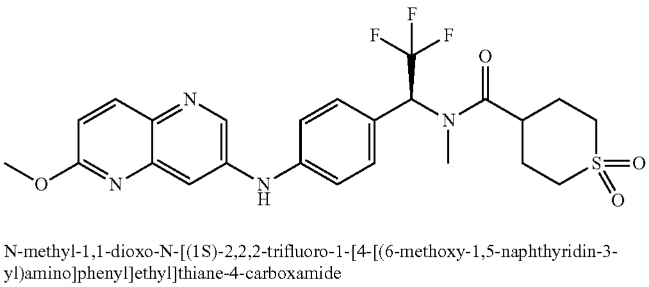

$^1$H NMR (600 MHz, DMSO-$d_6$) δ ppm 9.07 (s, 1H) 8.59 (d, J = 2.64 Hz, 1H) 8.10 (d, J = 8.95 Hz, 1H) 7.64 (d, J = 2.49 Hz, 1H) 7.35 (d, J = 5.58 Hz, 4H) 6.97 (d, J = 8.95 Hz, 1H) 6.45-6.54 (m, 1H) 3.96 (s, 3H) 3.03-3.25 (m, 4H) 2.94 (s, 3H) 1.84-2.24 (m, 4H). m/z: 523 $[M + H]^+$ N-methyl-1,1-dioxo-N-[(1S)-2,2,2-trifluoro-1-[4-[(6-methoxy-1,5-naphthyridin-3-yl)amino]phenyl]ethyl]thiane-4-carboxamide

| Example 226 CPD0018620 | Procedure 1a | Intermediates 163 and 87 | Yield: 42% |
|---|---|---|---|

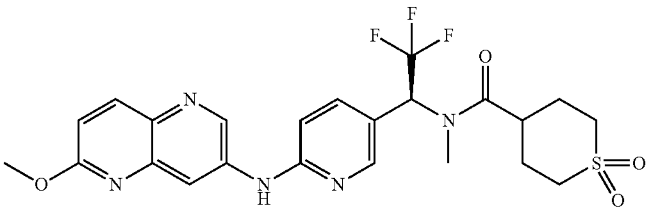

$^1$H NMR (DMSO-d6, 600 MHz): δ ppm 9.95 (s, 1H), 8.92 (d, J = 2.3 Hz, 1H), 8.78 (d, J = 2.5 Hz, 1H), 8.33 (d, J = 2.2 Hz, 1H), 8.13 (d, J = 8.8 Hz, 1H), 7.71 (dd, J = 8.7, 2.3 Hz, 1H), 7.07 (d, J = 8.7 Hz, 1H), 7.02 (d, J = 8.8 Hz, 1H), 6.53 (q, J = 9.2 Hz, 1H), 4.00 (s, 3H), 3.06-3.29 (m, 5H), 2.97 (s, 3H), 1.93-2.26 (m, 4H). m/z: 524 $[M + H]^+$.

-continued

N-methyl-1,1-dioxo-N-[(1S)-2,2,2-trifluoro-1-{6-[(6-methoxy-1,5-naphthyridin-3-yl)amino]pyridin-3-yl}ethyl]-1λ$^6$-thiane-4-carboxamide

| Example 227 CPD0021585 | Procedure 1a | Intermediates 165 and 86 | Yield: 70% |
|---|---|---|---|
| 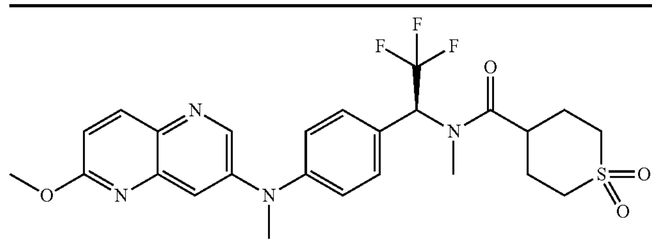 | $^1$H NMR (600 MHz, DMSO-$d_6$) δ ppm 8.50 (d, J = 2.8 Hz, 1H), 8.12 (d, J = 9.0 Hz, 1H), 7.53 (d, J = 2.6 Hz, 1H), 7.46-7.21 (m, 4H), 7.02 (d, J = 8.8 Hz, 1H), 6.54 (q, J = 9.1 Hz, 1H), 3.97 (s, 3H), 3.44 (s, 3H), 3.13 (br s, 5H), 2.94 (s, 3H), 2.15-1.94 (m, 4H). m/z: 537 [M + H]$^+$. | | |

N-methyl-1,1-dioxo-N-[(1S)-2,2,2-trifluoro-1-{4-[(6-methoxy-1,5-naphthyridin-3-yl)(methyl)amino]phenyl}ethyl]-1λ$^6$-thiane-4-carboxamide

| Example 228 CPD0019496 | Procedure 1a | Intermediates 166 and 86 | Yield: 20% |
|---|---|---|---|
| 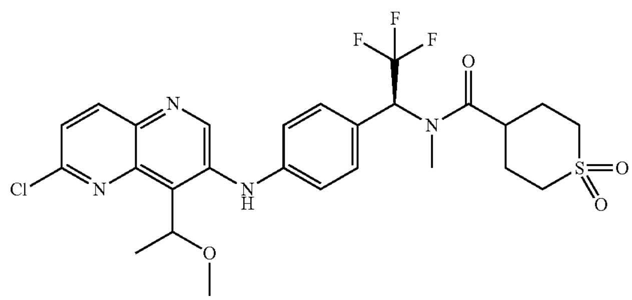 [SMILES: CO[C@H](C)c1c(Nc2ccc([C@H](N(C)C(=O)C3CCS(=O)(=O)CC3)C(F)(F)F)cc2)cnc2ccc(Cl)nc12] | $^1$H NMR (600 MHz, DMSO-$d_6$) δ ppm 8.99 (s, 1H) 8.34 (d, J = 8.51 Hz, 1H) 8.21 (m, J = 0.60 Hz, 1H) 0.00 (d, J = 8.66 Hz, 1H) 7.26-7.43 (m, 4H) 6.47-6.55 (m, 1H) 5.61-5.84 (m, 1H) 3.31 (br s, 3H) 3.07-3.28 (m, 5H) 2.93 (s, 3H) 1.84-2.20 (m, 4H) 1.50 (d, J = 6.60 Hz, 3H). m/z: 585 [M + H]$^+$ | | |

N-[(1S)-1-(4-{[6-chloro-4-(1-methoxyethyl)-1,5-naphthyridin-3-yl]amino}phenyl)-2,2,2-trifluoroethyl]-N-methyl-1,1-dioxo-1λ$^6$-thiane-4-carboxamide

| Example 229 CPD0019498 | Procedure 1b | Intermediates 166 and 86 | Yield: 3.1% |
|---|---|---|---|
| 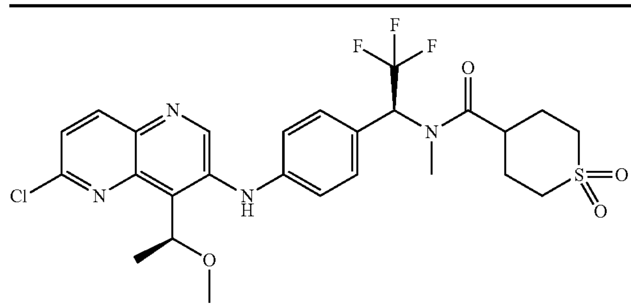 | $^1$H NMR (600 MHz, DMSO-$d_6$) δ ppm 8.98 (s, 1H), 8.34 (d, J = 8.66 Hz, 1H), 8.20-8.25 (m, 1H), 7.63 (d, J = 8.66 Hz, 1H), 7.26-7.42 (m, 4H), 6.50 (q, J = 9.44 Hz, 1H), 5.75 (q, J = 6.70 Hz, 1H), 3.31-3.33 (m, 3H), 3.09-3.28 (m, 6H), 2.93 (s, 2H), 1.98-2.13 (m, 4H), 1.50 (d, J = 6.75 Hz, 3H). m/z: 585 [M + H]$^+$ | | |

N-[(1S)-1-(4-{[6-chloro-4-[(1 rel S)-1-methoxyethyl]-1,5-naphthyridin-3-yl}amino)phenyl]-2,2,2-trifluoroethyl]-N-methyl-1,1-dioxo-1λ$^6$-thiane-4-carboxamide

| Example 230 CPD0019497 | Procedure 1b | Intermediates 166 and 86 | Yield: 3.6% |
|---|---|---|---|
| 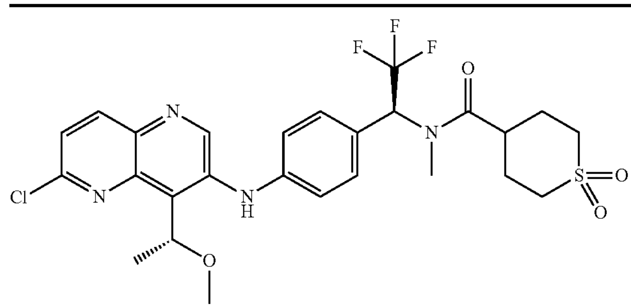 | $^1$H NMR (600 MHz, DMSO-$d_6$) δ ppm 8.98 (s, 1H), 8.34 (d, J = 8.66 Hz, 1H), 8.19-8.24 (m, 1H), 7.63 (d, J = 8.66 Hz, 1H), 7.25-7.41 (m, 4H), 6.51 (q, J = 9.24 Hz, 1H), 5.75 (q, J = 6.65 Hz, 1H), 3.30-3.32 (m, 3H), 3.09-3.28 (m, 5H), 2.49 (s, 3H), 1.97-2.14 (m, 4H), 1.50 (d, J = 6.75 Hz, 3H). m/z: 585 [M + H]$^+$ | | |

-continued

N-[(1S)-1-[4-({6-chloro-4-[(1 rel R)-1-methoxyethyl]-1,5-naphthyridin-3-yl}amino)phenyl]-2,2,2-trifluoroethyl]-N-methyl-1,1-dioxo-1λ6-thiane-4-carboxamide

| Example 231 CPD0019499 | Procedure 1a | Intermediates: 166 and 87 | Yield: 21% |
|---|---|---|---|
| 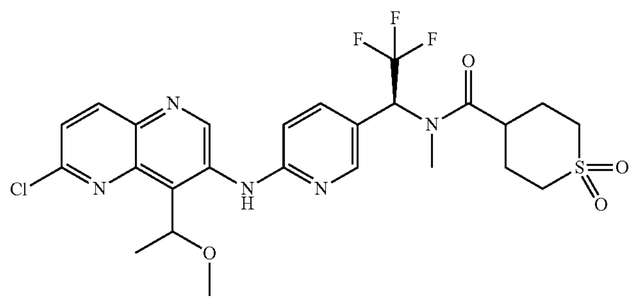 [SMILES: COC(C)c1c(Nc2ccc([C@H](N(C)C(=O)C3CCS(=O)(=O)CC3)C(F)(F)F)cn2)cnc2ccc(Cl)nc12] | $^1$H NMR (600 MHz, DMSO-$d_6$) δ ppm 9.70 (s, 1H), 9.01 (s, 1H), 8.39 (d, J = 8.7 Hz, 1H), 8.18 (br s, 1H), 7.69 (d, J = 8.7 Hz, 2H), 7.20 (d, J = 8.8 Hz, 1H), 6.52 (br s, 1H), 5.79 (q, J = 6.8 Hz, 1H), 3.31 (s, 4H), 3.23-3.01 (m, 4H), 2.97 (s, 3H), 2.24-1.88 (m, 4H), 1.50 (d, J = 6.7 Hz, 3H). m/z 586 [M + H]$^+$. | | |

N-[(1S)-1-(6-{[6-chloro-4-(1-methoxyethyl)-1,5-naphthyridin-3-yl]amino}pyridin-3-yl)-2,2,2-trifluoroethyl]-N-methyl-1,1-dioxo-1λ6-thiane-4-carboxamide

| Example 232 CPD0019500 | Procedure 1b | Intermediates: 166 and 87 | Yield: 5% |
|---|---|---|---|
| 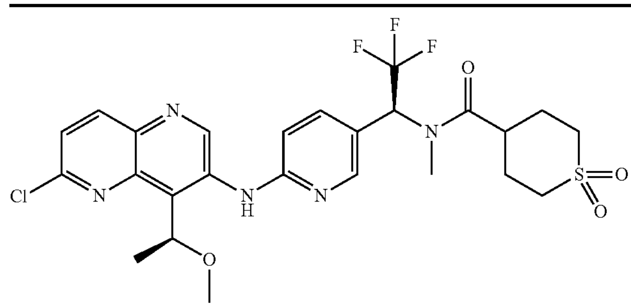 | $^1$H NMR (600 MHz, DMSO-$d_6$) δ ppm 9.71 (s, 1H), 9.01 (s, 1H), 8.39 (d, J = 8.66 Hz, 1H), 8.18 (d, J = 2.20 Hz 1H), 7.72 (dd, J = 2.13, 8.73 Hz, 1H), 7.69 (d, J = 8.66 Hz, 1H), 7.20 (d, J = 8.66 Hz, 1H), 6.53 (q, J = 9.15 Hz 1H), 5.79 (q, J = 6.75 Hz, 1H), 3.31-3.32 (m, 3H), 3.08-3.26 (m, 5H), 2.97, (s, 3H), 1.96-2.14 (m, 4H), 1.50 (d, J = 6.75 Hz, 3H). m/z: 586 [M + H]$^+$. | | |

N-[(1S)-1-[6-({6-chloro-4-[(1 rel S)-1-methoxyethyl]-1,5-naphthyridin-3-yl}amino)pyridin-3-yl]-2,2,2-trifluoroethyl]-N-methyl-1,1-dioxo-1λ6-thiane-4-carboxamide

| Example 233 CPD0019501 | Procedure 1b | Intermediates: 166 and 87 | Yield 4.7% |
|---|---|---|---|
| 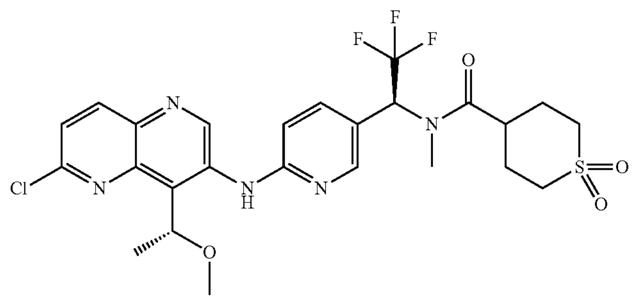 | $^1$H NMR (600 MHz, DMSO-$d_6$) δ ppm 9.70 (s, 1H), 9.00 (s, 1H), 8.39 (d, J = 8.66 Hz, 1H), 8.18 (d, J = 2.20 Hz, 1H), 7.72 (dd, J = 2.27, 8.58 Hz, 1H), 7.69 (d, J = 8.66 Hz, 1H), 7.20 (d, J = 8.80 Hz, 1H), 6.16-6.57 (m, 1H), 5.79 (q, J = 6.75 Hz, 1H), 3.31 (s, 3H), 3.08-3.26 (m, 5H), 2.97 (s, 3H), 2.27 (s, 1H), 1.96-2.15 (m, 4H), 1.50 (d, J = 6.75 Hz, 3H), m/z: 586 [M + H]$^+$. | | |

N-[(1S)-1-[6-({6-chloro-4-[(1 rel S)-1-methoxyethyl]-1,5-naphthyridin-3-yl}amino)pyridin-3-yl]-2,2,2-trifluoroethyl]-N-methyl-1,1-dioxo-1λ6-thiane-4-carboxamide

| Example 234 CPD0019078 | Procedure 1a | Intermediates 86 | Yield 99% |
|---|---|---|---|
| 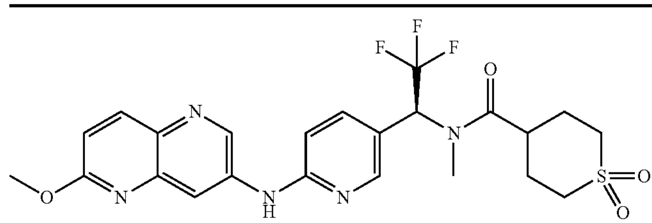 | $^1$H NMR (600 MHz, DMSO-$d_6$) δ ppm 8.70-8.87 (m, 1H) 8.04 (d, J = 8.66 Hz, 1H) 7.72 (d, J = 8.80 Hz, 1H) 7.35-7.43 (m, 1H) 7.26-7.34 (m, 4H) 7.17 (dd, J = 8.66, 2.35 Hz, 1H) 6.71-6.80 (m, 1H) 6.41-6.55 (m, 1H) 3.93 (s, 3H) 3.07-3.29 (m, 5 H) 2.93 (s, 3H) 1.89-2.25 (m, 4H). m/z: 522 [M + H]$^+$. | | |

-continued

N-methyl-1,1-dioxo-N-[(1S)-2,2,2-trifluoro-1-{4-[(2-methoxyquinolin-7-yl)amino]phenyl}ethyl]-1λ$^6$-thiane-4-carboxamide

| Example 235 CPD0074039 | Procedure 1b | Intermediates 155 and 174 | Yield 13% |
|---|---|---|---|

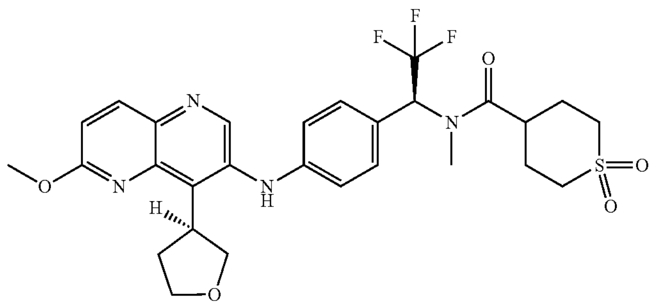 [SMILES: COc1ccc2ncc(Nc3ccc([C@H](N(C)C(=O)C4CCS(=O)(=O)CC4)C(F)(F)F)cc3)c([C@@H]3CCOC3)c2n1]

$^1$H NMR (600 MHz, DMSO) δ 8.63 (s, 1H),8.30 (s, 1H) 8.19 (d, J = 9.0 Hz, 1H), 7.21 (d, J = 8.4 Hz, 2H), 7.17 (d, J = 9.0 Hz, 1H), 6.97-6.89 (m, 2H), 6.43 (q, J = 9.3 Hz, 1H), 4.32 (dd, J = 8.6, 7.6 Hz, 1H), 4.18-4.08 (m, 2H), 4.01 (s, 3H), 3.93 (dd, J = 8.4, 7.5 Hz, 1H), 3.86 (q, J = 7.7 Hz, 1H), 3.28-3.13 (m, 3H), 3.13-3.07 (m, 2H), 2.91 (s, 3H), 2.72 (dq, J = 11.4, 8.5 Hz, 1H), 2.19-2.12 (m, 1H), 2.12-1.95 (m, 4H). m/z: 593 [M + H]$^+$.

N-methyl-1,1-dioxo-N-[(1S)-2,2,2-trifluoro-1-[4-[6-methoxy-4-[(3 rel-R)-tetrahydrofuran-3-yl]-1,5-naphthyridin-3-yl]amino]phenyl]ethyl]thiane-4-carboxamide

| Example 236 CPD0074040 | Procedure 1b | Intermediates 155 and 174 | Yield 11% |
|---|---|---|---|

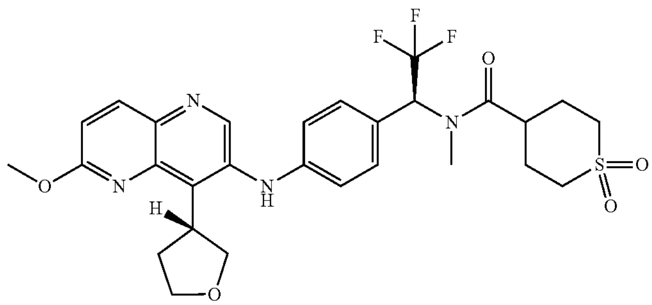 [SMILES: COc1ccc2ncc(Nc3ccc([C@H](N(C)C(=O)C4CCS(=O)(=O)CC4)C(F)(F)F)cc3)c([C@H]3CCOC3)c2n1]

$^1$H NMR (DMSO-d$_6$, 600 MHz): δ ppm 8.63 (s, 1H), 8.29 (s, 1H), 8.19 (d, J = 9.0 Hz, 1H), 7.21 (d, J = 8.5 Hz, 2H), 7.14 (d, J = 8.9 Hz, 1H), 6.90-6.95 (m, 2H), 6.05-6.50 (m, 1H), 4.29-4.34 (m, 1H), 4.10-4.17 (m, 2H), 4.01 (s, 3H), 3.92 (t, J = 7.9 Hz, 1H), 3.86 (q, J = 7.6 Hz, 1H), 3.06-3.28 (m 5H), 2.91 (s, 3H), 2.69-2.79 (m, 1H), 1.97-2.20 (m, 5H). m/z: 593 [M + H]$^+$.

N-methyl-1,1-dioxo-N-[(1S)-2,2,2-trifluoro-1-[4-[6-methoxy-4-[(3 rel-S)-tetrahydrofuran-3-yl]-1,5-naphthyridin-3-yl]amino]phenyl]ethyl]thiane-4-carboxamide

| Example 237 CPD0074043 | Procedure 2 | Intermediates: 94 and 176 | Yield 7% |
|---|---|---|---|

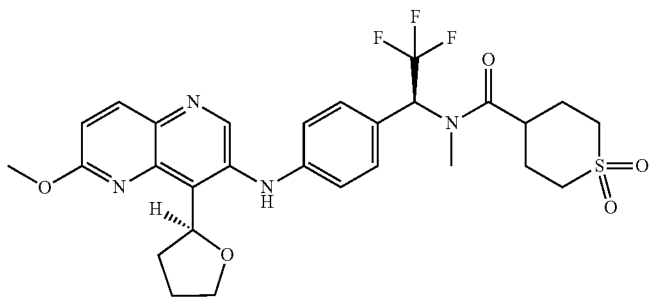 [SMILES: COc1ccc2ncc(Nc3ccc([C@H](N(C)C(=O)C4CCS(=O)(=O)CC4)C(F)(F)F)cc3)c([C@@H]3CCCO3)c2n1]

$^1$H NMR (DMSO-d$_6$, 500 MHz) δ ppm 8.74 (s, 1H), 7.9-8.5 (m, 2H), 7.1-7.5 (m, 4H), 7.09 (d, 1H, J = 8.8 Hz), 6.46 (q, 1H, J = 9.2 Hz),6.00 (dd, 1H, J = 6.7, 9.7 Hz), 4.2-4.3 (m, 1H), 4.00 (s, 3H), 3.8-3.9 (m, 1H), 3.0-3.3 (m, 5H), 2.7-3.0 (m, 3H), 2.3-2.4 (m, 1H), 1.8-2.2 (m, 7H). m/z: 593 [M + H]$^+$.

N-methyl-1,1-dioxo-N-[(1S)-2,2,2-trifluoro-1-[4-[6-methoxy-4-[(2 rel-R)-tetrahydrofuran-2-yl]-1,5-naphthyridin-3-yl]amino]phenyl]ethyl]thiane-4-carboxamide -continued

| Example 238 CPD0074044 | Procedure 2 | Intermediates: 94 and 176 | Yield: 9% |
|---|---|---|---|
| 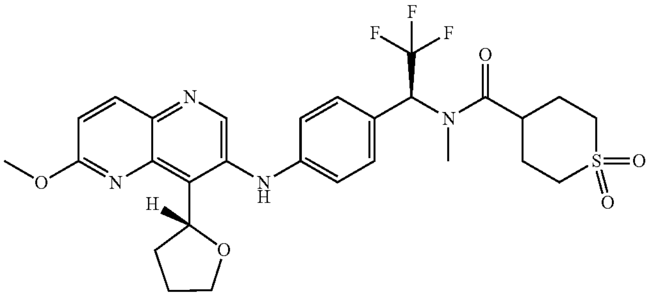 [SMILES: COc1ccc2ncc(Nc3ccc([C@H](N(C)C(=O)C4CCS(=O)(=O)CC4)C(F)(F)F)cc3)c([C@H]3CCCO3)c2n1] | $^1H$ NMR (DMSO-$d_6$, 500 MHz) δ 8.74 (s, 1H), 7.9-8.5 (m, 2H), 7.1-7.5 (m, 4H), 7.09 (d, 1H, J = 8.8 Hz), 6.46 (q, 1H, J = 9.2 Hz), 6.00 (dd, 1H, J = 6.7, 9.7 Hz), 4.2-4.3 (m, 1H), 4.00 (s, 3H), 3.8-3.9 (m, 1H), 3.0-3.3 (m, 5H), 2.7-3.0 (m, 3H), 2.3-2.4 (m, 1H), 1.8-2.2 (m, 7H), m/z: 593 [M + H]$^+$. | | |
| N-methyl-1,1-dioxo-N-[(1S)-2,2,2-trifluoro-1-[4-[6-methoxy-4-[(2 rel-S)-tetrahydrofuran-2-yl]-1,5-naphthyridin-3-yl]amino]phenyl]ethyl]thiane-4-carboxamide | | | |

| Example 239 CPD0076413 | Procedure 2 | Intermediates: 94 and 179 | Yield: 11% |
|---|---|---|---|
| 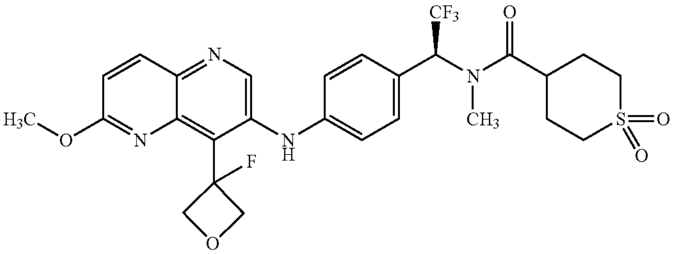 [SMILES: COc1ccc2ncc(Nc3ccc([C@H](N(C)C(=O)C4CCS(=O)(=O)CC4)C(F)(F)F)cc3)c(C3(F)COC3)c2n1] | $^1H$ NMR (600 MHz, DMSO-$d_6$) δ ppm 8.73 (s, 1H), 8.27-8.20 (m, 2H), 7.24 (d, J = 8.5 Hz, 2H), 7.19-7.16 (m, 1H), 7.13-7.09 (m, 2H), 6.52-6.10 (m, 1H), 5.24-5.04 (m, 4H), 3.96 (s, 3H),3.28-3.00 (m, 5H), 2.96-2.64 (m, 3H), 2.21-1.93 (m, 4H). m/z: 597 [M + H]$^+$. | | |
| N-methyl-1,1-dioxo-N-[(1S)-2,2,2-trifluoro-1-[4-[4-(3-fluorooxetan-3-yl)-6-methoxy-1,5-naphthyridin-3-yl]amino]phenyl]ethyl]thiane-4-carboxamide | | | |

| Example 240 CPD0076414 | Procedure 2 | Intermediates: 94 and 178 | Yield: 10% |
|---|---|---|---|
| 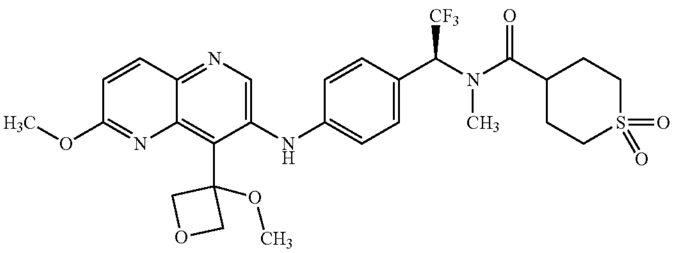 [SMILES: COc1ccc2ncc(Nc3ccc([C@H](N(C)C(=O)C4CCS(=O)(=O)CC4)C(F)(F)F)cc3)c(C3(OC)COC3)c2n1] | $^1H$ NMR (500 MHz, DMSO-$d_6$) δ ppm 1.96-2.13 (m, 4H) 2.93 (s, 3H) 3.08-3.29 (m, 8H) 3.97 (s, 3H) 4.96 (d, J = 8.31 Hz, 2H) 5.03 (br d, J = 6.85 Hz, 2H) 6.08-6.50 (m, 1H) 7.12-7.17 (m, 3H) 7.21-7.31 (m, 2H) 7.53-7.59 (m, 1H) 8.23 (d, J = 8.80 Hz, 1H) 8.71 (s, 1H). m/z: 609 [M + H]$^+$. | | |
| N-methyl-1,1-dioxo-N-[(1S)-2,2,2-trifluoro-1-[4-[6-methoxy-4-(3-methoxyoxetan-3-yl)-1,5-naphthyridin-3-yl]amino]phenyl]ethyl]thiane-4-carboxamide | | | |

| Example 241 CPD0077097 | Procedure 2 | Intermediates: 94 and 185 | Yield: 13% |
|---|---|---|---|
| 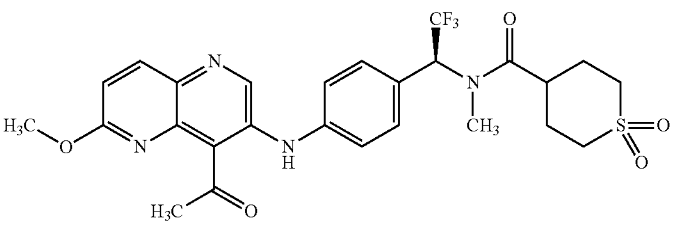 [SMILES: COc1ccc2ncc(Nc3ccc([C@H](N(C)C(=O)C4CCS(=O)(=O)CC4)C(F)(F)F)cc3)c(C(C)=O)c2n1] | $^1H$ NMR (400 MHz, DMSO) δ ppm 8.95 (s, 1H), 8.79 (s, 1H), 8.21 (d, J = 9.0 Hz, 1H), 7.38-7.19 (m, 4H), 7.10 (d, J = 9.0 Hz, 1H), 6.58-6.12 (m, 1H), 3.98 (s, 3H), 3.26-3.07 (m, 5H), 2.92 (s, 3H), 2.77 (s, 3H), 2.18-1.92 (m, 4H). m/z: 565 [M + H]$^+$. | | |
| N-[(1S)-1-[4-[(4-acetyl-6-methoxy-1,5-naphthyridin-3-yl)amino]phenyl]-2,2,2-trifluoro-ethyl]-N-methyl-1,1-dioxo-thiane-4-carboxamide | | | |

-continued

| Example 242 CPD0074550 | Procedure 3b | Intermediate 188 | Yield: 5% |
|---|---|---|---|
| 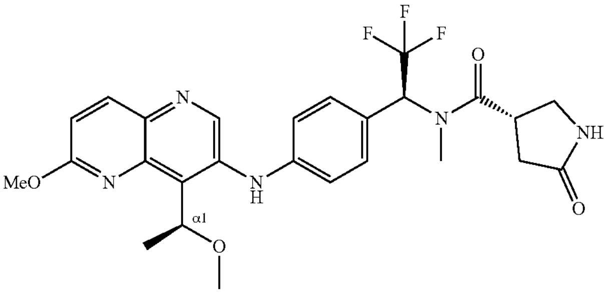 [SMILES: COc1ccc2ncc(Nc3ccc([C@H](N(C)C(=O)[C@@H]4CNC(=O)C4)C(F)(F)F)cc3)c([C@H](C)OC)c2n1] | $^1H$ NMR (DMSO-$d_6$, 600 MHz): δ ppm 8.78 (s, 1H), 8.16 (d, J = 8.8 Hz, 1H), 8.04 (s, 1H), 7.66 (s, 1H), 7.22-7.36 (m, 4H), 7.07 (d, J = 8.8 Hz, 1H), 6.09-6.56 (m, 1H), 5.84 (q, J = 6.7 Hz, 1H), 4.01 (s, 3H), 3.70-3.87 (m, 1H), 3.58 (t, J = 9.2 Hz, 1H), 3.29 (s, 3H), 3.29 (br s, 1H), 2.88 (s, 3H), 2.31-2.44 (m, 2H), 1.50 (d, J = 6.7 Hz, 3H). m/z: 532 $[M + H]^+$. | | |

(3 rel S)-N-methyl-5-oxo-N-[(1S)-2,2,2-trifluoro-1-[4-[6-methoxy-4-[(1 rel S)-1-methoxyethyl]-1,5-naphthyridin-3-yl]amino]phenyl]ethyl]pyrrolidine-3-carboxamide

| Example 243 CPD0074562 | Procedure 3b | Intermediates 188 | Yield: 11% |
|---|---|---|---|
| 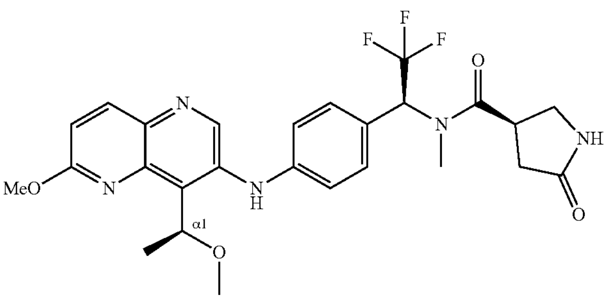 [SMILES: COc1ccc2ncc(Nc3ccc([C@H](N(C)C(=O)[C@H]4CNC(=O)C4)C(F)(F)F)cc3)c([C@H](C)OC)c2n1] | $^1H$ NMR (DMSO-$d_6$, 600 MHz) δ 8.6-8.9 (m, 1H), 8.16 (d, 1H, J = 8.8 Hz), 7.9-8.1 (m, 1H), 7.66 (s, 1H), 7.1-7.4 (m, 4H), 7.07 (d, 1H, J = 9.0 Hz), 6.48 (q, 1H, J = 9.2 Hz), 5.84 (q, 1H, J = 6.7 Hz), 4.01 (s, 3H), 3.7-3.8 (m, 1H), 3.2-3.5 (m, 5H), 2.7-3.0 (m, 3H), 2.50 (td, 1H, J = 1.8, 3.6 Hz), 2.28 (dd, 1H, J = 6.8, 16.5 Hz), 1.50 (d, 3H, J = 6.7 Hz). m/z: 532 $[M + H]^+$. | | |

(3 rel R)-N-methyl-5-oxo-N-[(1S)-2,2,2-trifluoro-1-[4-[6-methoxy-4-[(1 rel S)-1-methoxyethyl]-1,5-naphthyridin-3-yl]amino]phenyl]ethyl]pyrrolidine-3-carboxamide

| Example 244 CPD0075580 | Procedure 3a | Intermediate 191 | Yield: 48% |
|---|---|---|---|
| 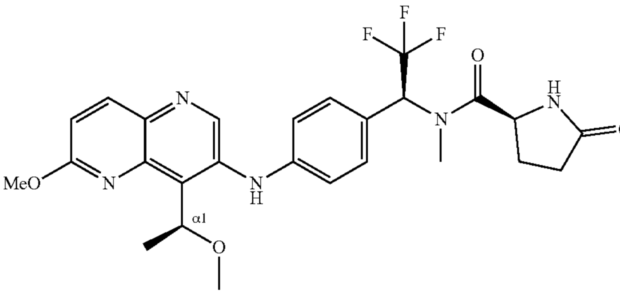 | $^1H$ NMR (DMSO-d6, 500 MHz): δ ppm 8.78 (s, 1H), 8.16 (d, J = 8.8 Hz, 1H), 8.05 (s, 1H), 7.80 (s, 1H), 7.29-7.40 (m, 2H), 7.23-7.29 (m, 2H), 7.08 (d, J = 9.0 Hz, 1H), 6.47 (q, J = 9.3 Hz, 1H), 5.77-5.95 (m, 1H), 4.58-4.74 (m, 1H), 4.01 (s, 3H), 3.30 (s, 3H), 2.91 (s, 3H), 2.39-2.48 (m, 1H), 2.09-2.23 (m, 2H), 1.79-1.92 (m, 1H), 1.51 (d, J = 6.6 Hz, 3H). m/z: 532 $[M + H]^+$. | | |

(2 rel S)-N-methyl-5-oxo-N-[(1S)-2,2,2-trifluoro-1-[4-[6-methoxy-4-[(1 rel S)-1-methoxyethyl]-1,5-naphthyridin-3-yl]amino]phenyl]ethyl]pyrrolidine-2-carboxamide

| Example 245 CPD0075581 | Procedure 3a | Intermediate 190 | Yield: 56% |
|---|---|---|---|
| 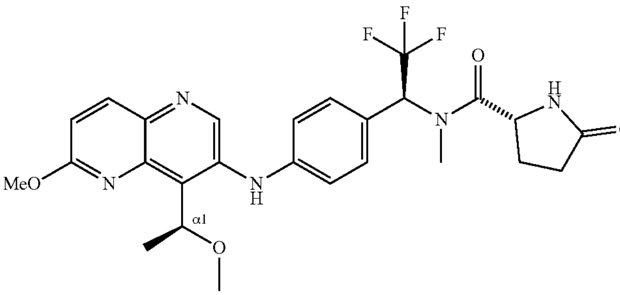 | $^1H$ NMR (DMSO-$d_6$, 600 MHz): δ ppm 8.78 (s, 1H), 8.16 (d, J = 9.0 Hz, 1H), 8.05 (s, 1H), 7.92 (s, 1H), 7.23-7.41 (m, 4H), 7.07 (d, J = 8.8 Hz, 1H), 6.10-6.48 (m, 1H), 5.84 (q, J = 6.7 Hz, 1H), 4.66 (dd, J = 8.9, 3.8 Hz, 1H), 4.01 (s, 3H), 3.30 (s, 3H), 2.87 (s, 3H), 2.34-2.40 (m, 1H), 2.08-2.26 (m, 2H), 1.80-1.89 (m, 1H), 1.50 (d, J = 6.7 Hz, 3H). m/z: 532 $[M + H]^+$. | | |

-continued (2 rel R)-N-methyl-5-oxo-N-[(1S)-2,2,2-trifluoro-1-[4-[6-methoxy-4-[(1 rel S)-1-methoxyethyl]-1,5-naphthyridin-3-yl]amino]phenyl]ethyl]pyrrolidine-2-carboxamide

| | Procedure | Intermediate | Yield: |
|---|---|---|---|
| Example 246 CPD0072935 | 4 | 167 | 36% |
| 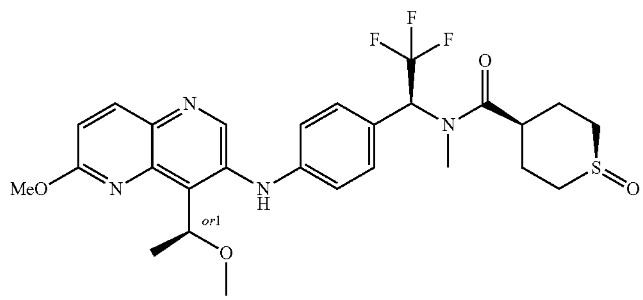 [SMILES: COc1ccc2ncc(Nc3ccc([C@H](N(C)C(=O)[C@H]4CC[S@@](=O)CC4)C(F)(F)F)cc3)c([C@H](C)OC)c2n1] | $^1H$ NMR (600 MHz, DMSO-$d_6$) δ ppm 8.77 (s, 1H), 8.16 (d, 1H, J = 8.9 Hz), 8.0-8.1 (m, 1H), 7.2-7.4 (m, 4H), 7.07 (d, 1H, J = 9.0 Hz), 6.48 (q, 1H, J = 9,2 Hz), 5.84 (q, 1H, J = 6.7 Hz), 4.01 (s, 3H), 3.30 (d, 5H, J = 1.6 Hz), 3.0-3.1 (m, 1H), 2.92 (s, 3H), 2.6-2.8 (m, 2H), 1.9-2.2 (m, 2H), 1.6-1.9 (m, 2H), 1.50 (d, 3H, J = 6.7 Hz). m/z: 565[M + H]$^+$. | | |

(1 rel-s,4 rel-s)-N-methyl-1-oxo-N-[(1S)-2,2,2-trifluoro-1-[4-({6-methoxy-4-[(1 rel-S)-1-methoxyethyl]-1,5-naphthyridin-3-yl}amino)phenyl]ethyl]-1A4-thiane-4-carboxamide

| | Procedure | Intermediate | Yield: |
|---|---|---|---|
| Example 247 CPD0072936 | 4 | 167 | 15% |
| 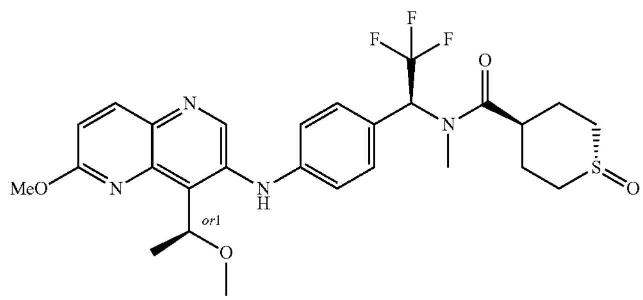 [SMILES: COc1ccc2ncc(Nc3ccc([C@H](N(C)C(=O)[C@H]4CC[S@](=O)CC4)C(F)(F)F)cc3)c([C@H](C)OC)c2n1] | $^1H$ NMR (600 MHz, DMSO-$d_6$) δ ppm 8.78 (s, 1H), 8.16 (d, 1H, J = 8.9 Hz), 7.9-8.1 (m, 1H), 7.2-7.4 (m, 4H), 7.07 (d, 1H, J = 9.0 Hz), 6.51 (br d, 1H, J = 9.5 Hz), 6.1-6.3 (m, 1H), 5.85 (q, 1H, J = 6.7 Hz), 4.01 (s, 3H), 3.30 (s, 3H), 3.0-3.1 (m, 1H), 2.8-3.0 (m, 4H), 2.6-2.8 (m, 2H), 2.2-2.3 (m, 2H), 1.6-1.8 (m, 2H), 1.51 (d, 3H, J = 6.7 Hz). m/z: 565 [M + H]$^+$. | | |

(1 rel-r,4 rel-r)-N-methyl-1-oxo-N-[(1S)-2,2,2-trifluoro-1-[4-({6-methoxy-4-[(1 rel-S)-1-methoxyethyl]-1,5-naphthyridin-3-yl}amino)phenyl]ethyl]-1X4-thiane-4-carboxamide

| | Procedure | Intermediate | Yield: |
|---|---|---|---|
| Example 248 CPD0073129 | 5 | 167 | 36% |
| 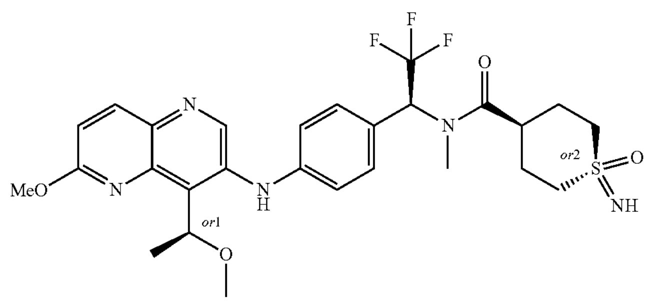 [SMILES: COc1ccc2ncc(Nc3ccc([C@H](N(C)C(=O)[C@H]4CC[S@](=N)(=O)CC4)C(F)(F)F)cc3)c([C@H](C)OC)c2n1] | $^1H$ NMR (600 MHz, DMSO-$d_6$): δ ppm 8.77 (s, 1H), 8.15-8.17 (m, J = 8.8 Hz, 1H), 8.02-8.06 (m, 1H), 7.22-7.41 (m, 4H), 7.06-7.09 (m, J = 8.9 Hz, 1H), 6.14-6.55 (m, 1H), 5.84 (q, J = 6.7 Hz, 1H), 4.01 (s, 3H), 3.68-3.73 (m, 1H), 3.29-3.30 (m, 3H), 2.99-3.16 (m, 5H), 2.66-2.96 (m, 3H), 1.87-2.14 (m, 4H), 1.50 (d, J = 6.7 Hz, 3H). m/z: 580 [M + H]$^+$. | | |

(1 rel-s,4 rel-s)-1-imino-N-methyl-1-oxo-N-[(1S)-2,2,2-trifluoro-1-[4-({6-methoxy-4-[(1 rel-S)-1-methoxyethyl]-1,5-naphthyridin-3-yl}amino)phenyl]ethyl]-1λ$^6$-thiane-4-carboxamide -continued

| Example 249 CPD0073130 | Procedure 5 | Intermediate 167 | Yield: 9% |
|---|---|---|---|
| 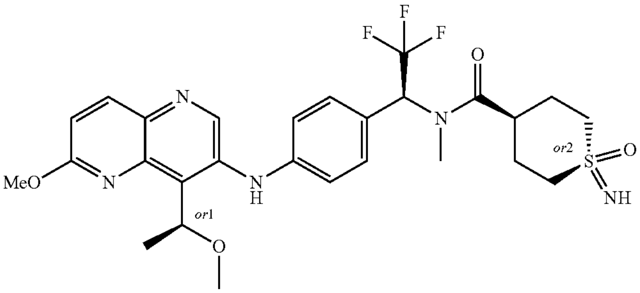 [SMILES: COc1ccc2ncc(Nc3ccc([C@H](N(C)C(=O)[C@H]4CC[S@@](=N)(=O)CC4)C(F)(F)F)cc3)c([C@H](C)OC)c2n1] | $^1$H NMR (500 MHz, DMSO-$d_6$): δ ppm 8.78 (s, 1H), 8.16 (d, J = 8.8 Hz, 1H), 8.02-8.06 (m, 1H), 7.17-7.39 (m, 4H), 7.07 (d, J = 9.0 Hz, 1H), 6.49 (q, J = 9.2 Hz, 1H), 5.85 (q, J = 6.6 Hz, 1H), 4.01 (s, 3H), 3.48 (s, 1H), 3.29-3.30 (m, 3H), 3.01-3.21 (m, 5H), 2.92 (s, 3H), 1.93-2.11 (m, 4H), 1.50 (d, J = 6.8 Hz, 3H). m/z: 580 [M + H]$^+$. | | |
| (1 rel-r,4 rel-r)-1-imino-N-methyl-1-oxo-N-[(1S)-2,2,2-trifluoro-1-[4-{{6-methoxy-4-[(1 rel-S)-1-methoxyethyl]-1,5-naphthyridin-3-yl}amino)phenyllethyl]-1λ$^6$-thiane-4-carboxamide | | | |

| Example 250 CPD0077187 | Procedure 5 | Intermediate 169 | Yield: 21% |
|---|---|---|---|
| 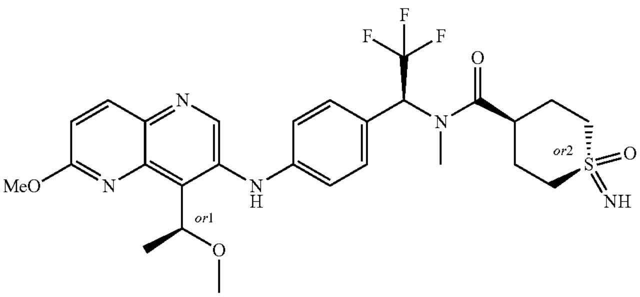 [SMILES: COc1ccc2ncc(Nc3ccc([C@H](N(C)C(=O)[C@H]4CC[S@@](=N)(=O)CC4)C(F)(F)F)cc3)c([C@H](C)OC)c2n1] | $^1$H NMR (DMSO-$d_6$, 600 MHz): δ ppm 8.77-8.78 (m, 1H), 8.16 (d, J = 8.8 Hz, 1H), 8.04 (s, 1H), 7.17-7.39 (m, 4H), 7.07, (d, J = 8.9 Hz, 1H), 6.11-6.60 (m, 1H), 5.84 (q, J = 6.7 Hz, 1H), 4.01 (s, 3H), 3.70 (s, 1H), 3.30 (s, 3H), 2.96-3.20 (m, 5H), 2.89-2.96 (m, 3H), 1.85-2.14 (m, 4H), 1.50 (d, J = 6.7 Hz, 3H). m/z: 580 [M + H]$^+$. | | |
| (1 rel-s,4 rel-s)-1-imino-N-methyl-1-oxo-N-[(1R)-2,2,2-trifluoro-1-[4-({6-methoxy-4-[(1 rel-S)-1-methoxyethyl]-1,5-naphthyridin-3-y|}amino)phenyl]ethyl]-1λ$^6$-thiane-4-carboxamide | | | |

| Example 251 CPD0077186 | Procedure 5 | Intermediate 169 | Yield: 36% |
|---|---|---|---|
| 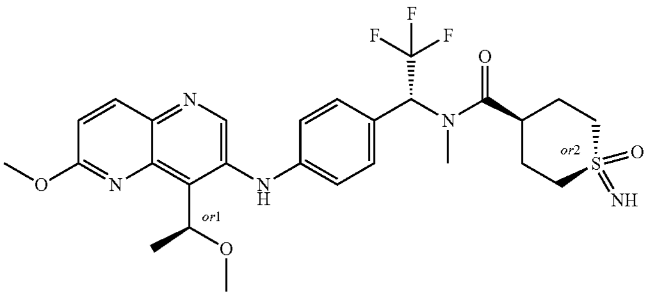 [SMILES: COc1ccc2ncc(Nc3ccc([C@@H](N(C)C(=O)[C@H]4CC[S@@](=N)(=O)CC4)C(F)(F)F)cc3)c([C@H](C)OC)c2n1] | $^1$H NMR (DMSO-$d_6$, 600 MHz): δ ppm 8.78 (s, 1H), 8.16 (d, J = 8.9 Hz, 1H), 8.04 (s, 1H), 7.21-7.36 (m, 4H), 7.07 (d, J = 9.0 Hz, 1H), 6.14-6.53 (m, 1H), 5.84 (d, J = 6.7 Hz, 1H), 4.00-4.02 (m, 3H), 3.48 (s, 1H), 3.30 (s, 3H), 2.97-3.24 (m, 5H), 2.89-2.95 (m, 3H), 1.91-2.16 (m, 4H), 1.50 (d, J = 6.7 Hz, 3H). m/z: 580 [M + H]$^+$. | | |
| (1 rel-r,4 rel-s)-1-imino-N-methyl-1-oxo-N-[(1R)-2,2,2-trifluoro-1-[4-({6-methoxy-4-[(1 rel-S)-1-methoxyethyl]-1,5-naphthyridin-3-yl}amino)phenyl]ethyl]-1λ$^6$-thiane-4-carboxamide | | | |

| Example 252 CPD0077189 | Procedure 5 | Intermediate 170 | Yield: 26% |
|---|---|---|---|
| 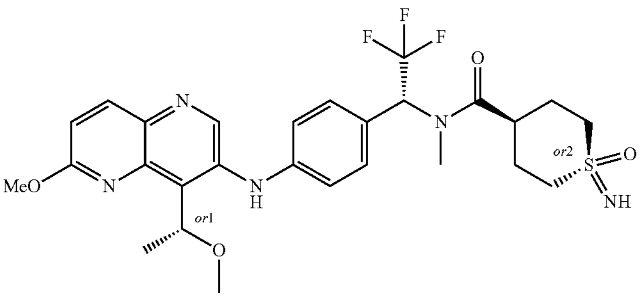 [SMILES: COc1ccc2ncc(Nc3ccc([C@@H](N(C)C(=O)[C@H]4CC[S@](=N)(=O)CC4)C(F)(F)F)cc3)c([C@@H](C)OC)c2n1] | $^1$H NMR (DMSO-$d_6$, 600 MHz): δ ppm 8.71-8.85 (m, 1H), 8.16 (d, J = 8.9 Hz, 1H), 8.04 (s, 1H), 7.19-7.40 (m, 4H), 7.07 (d, J = 8.9 Hz, 1H), 6.50 (br q, J = 9.4 Hz, 1H), 5.84 (q, J = 6.7 Hz, 1H), 4.01 (s, 3H), 3.67-3.78 (m, 1H), 3.30 (s, 3H), 2.97-3.19 (m, 5H), 2.92 (s, 3H), 1.92-2.16 (m, 4H), 1.50 (d, J = 6.7 Hz, 3H). m/z: 580 [M + H]$^+$. | | |

-continued (1 rel-s,4 rel-s)-1-imino-N-methyl-1-oxo-N-[(1R)-2,2,2-trifluoro-1-[4-({6-methoxy-4-[(1 rel-R)-1-methoxyethyl]-1,5-naphthyridin-3-yl}amino)phenyl]ethyl]-1λ$^6$-thiane-4-carboxamide

| | | Intermediate | Yield: |
|---|---|---|---|
| Example 253 CPD0077188 | Procedure 5 | 170 | 27% |

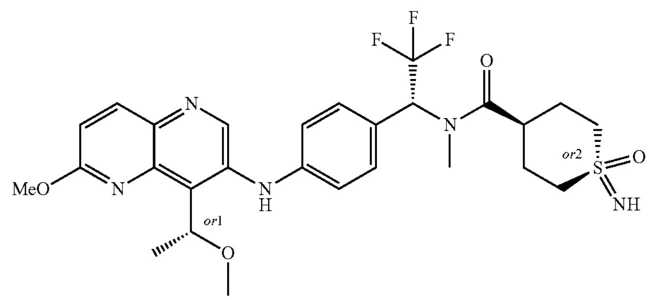 [SMILES: COc1ccc2ncc(Nc3ccc([C@@H](N(C)C(=O)[C@H]4CC[S@@](=N)(=O)CC4)C(F)(F)F)cc3)c([C@@H](C)OC)c2n1]

$^1$H NMR (DMSO-d6, 600 MHz): δ ppm 8.77 (s, 1H), 8.16 (d, J = 9.0 Hz, 1H), 8.04 (s, 1H), 7.18-7.38 (m, 4H), 7.07 (d, J = 8.9 Hz, 1H), 6.49 (q, J = 9.4 Hz, 1H), 5.84 (q, J = 6.7 Hz, 1H), 4.01 (s, 3H), 3.48 (br d, J = 1.8 Hz, 1H), 3.30 (s, 3H), 3.00-3.24 (m, 5H), 2.92 (s, 3H), 1.91-2.19 (m, 4H), 1.50 (d, J = 6.7 Hz, 3H). m/z: 580 [M + H]$^+$.

(1 rel-r,4 rel-r)-1-imino-N-methyl-1-oxo-N-[(1R)-2,2,2-trifluoro-1-[4-({6-methoxy-4-[(1 rel-R)-1-methoxyethyl]-1,5-naphthyridin-3-yl}amino)phenyl]ethyl]-1λ$^6$-thiane-4-carboxamide

| | | Intermediate | Yield: |
|---|---|---|---|
| Example 254 CPD0075763 | Procedure 5 | 168 | 26% |

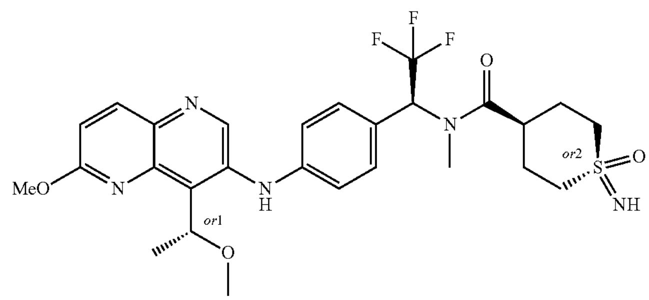 [SMILES: COc1ccc2ncc(Nc3ccc([C@H](N(C)C(=O)[C@H]4CC[S@](=N)(=O)CC4)C(F)(F)F)cc3)c([C@@H](C)OC)c2n1]

$^1$H NMR (DMSO-$d_6$, 500 MHz) δ ppm 8.78 (s, 1H), 8.16 (d, 1H, J = 9.0 Hz), 8.0-8.1 (m, 1H) 7.2-7.4 (m, 4H), 7.08 (d, 1H, J = 8.8 Hz), 6.4-6.6 (m, 1H) 5.85 (q, 1H, J = 6.7 Hz), 4.01 (s, 3H), 3.7-3.8 (m, 1H), 3.2-3.4 (m, 3H), 3.0-3.21 (m, 5H), 2.93 (s, 3H), 1.8-2.1 (m, 4H), 1.51 (d, 3H, J = 6.8 Hz). m/z: 580 [M + H]$^+$.

(1 rel-s,4 rel-s)-1-imino-N-methyl-1-oxo-N-[(1S)-2,2,2-trifluoro-1-[4-({6-methoxy-4-[(1 rel-R)-1-methoxyethyl]-1,5-naphthyridin-3-yl}amino)phenyl]ethyl]-1λ$^6$-thiane-4-carboxamide

| | | Intermediate | Yield: |
|---|---|---|---|
| Example 255 CPD0075764 | Procedure 5 | 168 | 32% |

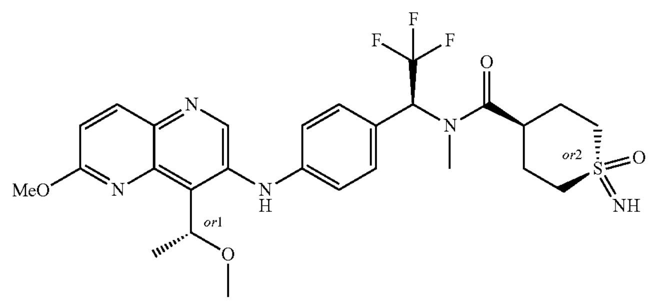 [SMILES: COc1ccc2ncc(Nc3ccc([C@H](N(C)C(=O)[C@H]4CC[S@@](=N)(=O)CC4)C(F)(F)F)cc3)c([C@@H](C)OC)c2n1]

$^1$H NMR (DMSO-$d_6$, 500 MHz) δ ppm 8.78 (s, 1H), 8.16 (d, 1H, J = 9.0 Hz), 8.0-8.1 (m, 1H), 7.2-7.4 (m, 4H), 7.08 (d, 1H, J = 9.0 Hz), 6.49 (q, 1H, J = 9.4 Hz), 5.85 (q, 1H, J = 6.6 Hz), 4.01 (s, 3H); 3.48 (s, 1H), 3.3-3.4 (m, 3H), 3.0-3.2 (m, 5H), 2.93 (s, 3H), 1.8-2.2 (m, 4H), 1.51 (d, 3H, J = 6.8 Hz). m/z: 580 [M + H]$^+$.

(1 rel-r,4 rel-r)-1-imino-N-methyl-1-oxo-N-[(1S)-2,2,2-trifluoro-1-[4-({6-methoxy-4-[(1 rel-R)-1-methoxyethyl]-1,5-naphthyridin-3-yl}amino)phenyl]ethyl]-1λ$^6$-thiane-4-carboxamide -continued

| Example 256 CPD0074559 | Procedure 6 | Intermediate 187 | Yield: 59% |
|---|---|---|---|
| 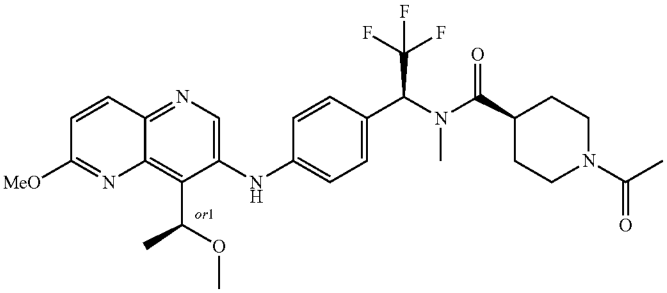 | $^1$H NMR (DMSO-$d_6$, 500 MHz): δ ppm 8.78 (s, 1H), 8.16 (d, J = 9.0 Hz, 1H), 8.04 (s, 1H), 7.22-7.37 (m, 4H), 7.07 (d, J = 8.8 Hz, 1H), 6.50 (q, J = 9.3 Hz, 1H), 5.85 (q, J = 6.8 Hz, 1H), 4.38 (br d, J = 12.2 Hz, 1H), 4.01 (s, 3H), 3.80-3.88 (m, 1H), 3.30 (s, 3H), 2.99-3.20 (m, 2H), 2.94 (s, 2H), 2.56-2.71 (m, 2H), 2.00 (s, 3H), 1.34-1.77 (m, 7H). m/z: 574 [M + H]$^+$. | | |

1-acetyl-N-methyl-N-[(1S)-2,2,2-trifluoro-1-[4-[6-methoxy-4-[(1 rel S)-1-methoxyethyl]-1,5-naphthyridin-3-yl]amino]phenyl]ethyl]piperidine-4-carboxamide

| Example 257 CPD0084142 | Procedure 3a-b | Intermediate 194 | Yield: 29.6% |
|---|---|---|---|
| 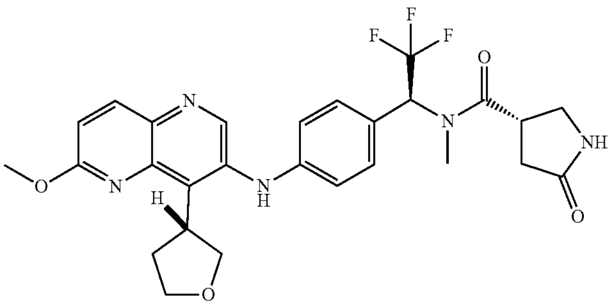 [SMILES: COc1ccc2ncc(Nc3ccc([C@H](N(C)C(=O)[C@@H]4CNC(=O)C4)C(F)(F)F)cc3)c([C@H]3CCOC3)c2n1] | $^1$H NMR (DMSO-$d_6$, 500 MHz): δ ppm: 8.63 (s, 1H), 8.30 (s, 1H), 8.19 (d, J = 8.9 Hz, 1H), 7.65 (s, 1H), 7.20-7.29 (m, 2H), 7.14 (d, J = 9.0 Hz, 1H), 6.86-6.98 (m, 2H), 6.01-6.55 (m, 1H), 4.32 (t, J = 8.1 Hz, 1H), 4.08-4.19 (m, 2H), 4.01 (s, 3H), 3.92 (t, J = 7.9 Hz, 1H), 3.86 (q, J = 7.6 Hz, 1H), 3.69-3.78 (m, 1H), 3.56 (t, J = 9.2 Hz, 1H), 3.27 (dd, J = 9.5, 5.7 Hz, 1H), 2.87 (s, 3H), 2.67-2.80 (m, 1H), 2.32-2.44- (m, 2H), 2.11-2.22 (m, 1H) m/z: 544.4 [M + H]$^+$. | | |

(3 rel S)-N-methyl-5-oxo-N-[(1S)-2,2,2-trifluoro-1-[4-[6-methoxy-4-[(3 rel S)-tetrahydrofuran-3-yl]-1,5-naphthyridin-3-yl]amino]phenyl]ethyl]pyrrolidine-3-carboxamide

| Example 258 CPD0084143 | Procedure 3a-b | Intermediate 194 | Yield: 28.7% |
|---|---|---|---|
| 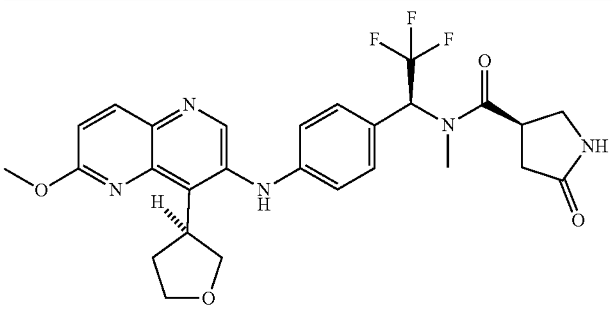 [SMILES: COc1ccc2ncc(Nc3ccc([C@H](N(C)C(=O)[C@H]4CNC(=O)C4)C(F)(F)F)cc3)c([C@@H]3CCOC3)c2n1] | 2.25-2.35 (m, 1H) 2.49-2.49 (m, 1H) 2.68-2.76 (m, 1H) 2.87 (s, 3H) 3.31-3.38 (m, 1H) 3.42-3.50 (m, 1H) 3.70-3.76 (m, 1H) 3.86 (q, J = 7.73 Hz, 1H) 3.91-3.95 (m, 1H) 4.00-4.02 (m, 3H) 4.08-4.17 (m, 2H) 4.29-4.34 (m, 1H) 6.43 (q, J = 9.44 Hz, 1H) 6.90-6.95 (m, 2H) 7.14 (d, J = 8.95 Hz, 1H) 7.22 (m, J = 8.51 Hz, 2H) 7.62-7.68 (m, 1H) 8.19 (d, J = 8.95 Hz, 1H) 8.28-8.32 (m, 1H) 8.63 (s, 1H). m/z: 544.4 [M + H]$^+$. | | |

(3 rel R)-N-methyl-5-oxo-N-[(1S)-2,2,2-trifluoro-1-[4-[[6-methoxy-4-[(3 rel R)-tetrahydrofuran-3-yl]-1,5-naphthyridin-3-yl]amino]phenyl]ethyl]pyrrolidine-3-carboxamide

| Example 259 CPD0084144 | Procedure 3a-b | Intermediate 195 | Yield: 29.1% |
|---|---|---|---|
| 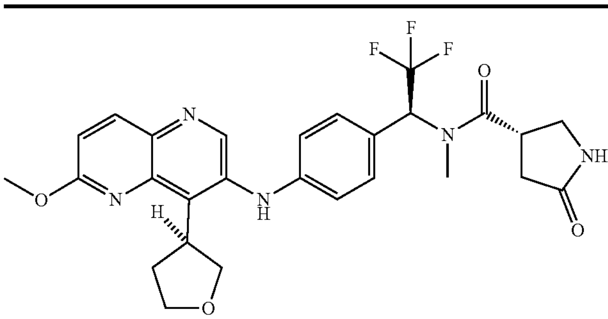 | $^1$H NMR (DMSO-$d_6$, 500 MHz) δ ppm 2.12-2.18 (m, 1H) 2.33-2.43 (m, 2H) 2.69-2.76 (m, 1H) 2.87 (s, 3H) 3.27 (dd, J = 9.54, 5.87 Hz, 1H) 3.53-3.59 (m, 1H) 3.71-3.77 (m, 1H) 3.86 (q, J = 7.73 Hz, 1H) 3.93 (t, J = 8.00 Hz, 1H) 4.01 (s, 3H) 4.08-4.16 (m, 2H) 4.32 (t, J = 8.07 Hz, 1H) 6.40-6.46 (m, 1H) 6.90-6.94 (m, 2H) 7.14 (d, J = 8.95 Hz, 1H) 7.22 (m, J = 8.51 Hz, 2H) 7.65 (s, 1H) 8.19 (d, J = 8.95 Hz, 1H) 8.29-8.31 (m, 1H) 8.63 (s, 1H). m/z: 544.4 [M + H]$^+$. | | |

-continued (3 rel S)-N-methyl-5-oxo-N-[(1S)-2,2,2-trifluoro-1-[4-[6-methoxy-4-[(3 rel R)-tetrahydrofuran-3-yl]-1,5-naphthyridin-3-yl]amino]phenyl]ethyl]pyrrolidine-3-carboxamide

| | Procedure | Intermediate | Yield: |
|---|---|---|---|
| Example 260 CPD0082477 | 3a-b | 195 | 29.5% |

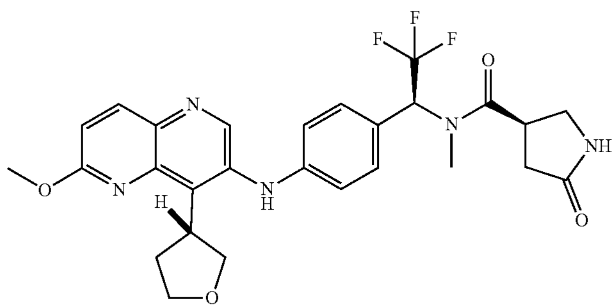 [SMILES: COc1ccc2ncc(Nc3ccc([C@H](N(C)C(=O)[C@H]4CNC(=O)C4)C(F)(F)F)cc3)c([C@H]3CCOC3)c2n1]

$^1$H NMR (DMSO-$d_6$, 500 MHz): δ ppm 2.13-2.19 (m, 1H) 2.25-2.36 (m, 1H) 2.52-2.53 (m, 1H) 2.68-2.76 (m, 1H) 2.87 (s, 3H) 3.31-3.34 (m, 1H) 3.42-3.50 (m, 1H) 3.73 (tt, J = 9.15, 6.40 Hz, 1H) 3.84-4.04 (m, 5 H) 4.08-4.17 (m, 2H) 4.31 (t, J = 8.07 Hz, 1H) 6.43 (q, J = 9.29 Hz, 1H) 6.90- 7.01 (m, 2H) 7.14 (d, J = 8.95 Hz, 1H) 7.22 (m, J = 8.51 Hz, 2H) 7.61-7.69 (m, 1H) 8.19 (d, J = 8.95 Hz, 1H) 8.28-8.32 (m, 1H) 8.63 (s, 1H). m/z: 544.4 $[M + H]^+$.

(3 rel R)-N-methyl-5-oxo-N-[(1S)-2,2,2-trifluoro-1-[4-[6-methoxy-4-[(3 rel S)-tetrahydrofuran-3-yl]-1,5-naphthyridin-3-yl]amino]phenyl]ethyl]pyrrolidine-3-carboxamide

| | | Intermediates | Yield: |
|---|---|---|---|
| Example 261 CPD0074048 | Procedure 1 | 201 and 86 | 16.4% |

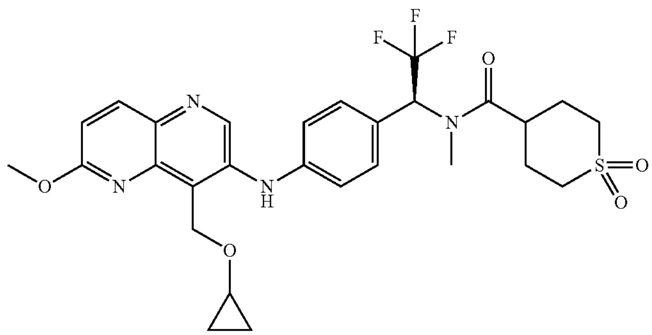 [SMILES: COc1ccc2ncc(Nc3ccc([C@H](N(C)C(=O)C4CCS(=O)(=O)CC4)C(F)(F)F)cc3)c(COC3CC3)c2n1]

$^1$H NMR (DMSO-$d_6$, 500 MHz): δ ppm 8.75 (s, 1H), 8.0-8.3 (m, 2H), 6.9-7.5 (m, 5H), 6.47 (q, 1H, J = 9.4 Hz), 5.13 (s, 2H), 4.04 (s, 3H), 3.40 (tt, 1H, J = 2.9, 6.0 Hz), 3.0-3.3 (m, 5H), 2.6-3.0 (m, 3H), 1.8-2.3 (m, 4H), 0.3-0.6 (m, 4H). m/z: 593.4 $[M + H]^+$.

N-[(1S)-1-[4-[4-(cyclopropoxymethyl)-6-methoxy-1,5-naphthyridin-3-yl]amino]phenyl]-2,2,2-trifluoro-ethyl]-N-methyl-1,1-dioxo-thiane-4-carboxamide

| | | Intermediates | Yield: |
|---|---|---|---|
| Example 262 CPD0074046 | Procedure 2 | 203 and 94 | 34% |

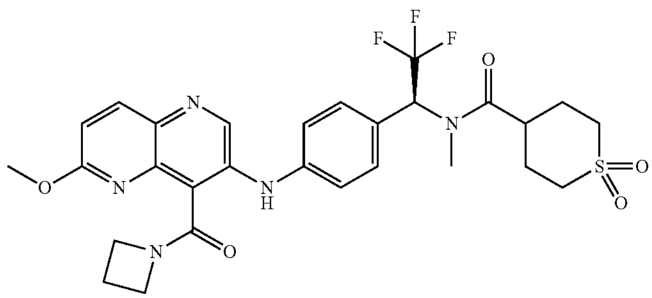 [SMILES: COc1ccc2ncc(Nc3ccc([C@H](N(C)C(=O)C4CCS(=O)(=O)CC4)C(F)(F)F)cc3)c(C(=O)N3CCC3)c2n1]

$^1$H NMR (DMSO-$d_6$, 500 MHz): δ ppm 8.75 (s, 1H), 8.32 (s, 1H), 8.18 (d, J = 9.1 Hz, 1H), 7.27 (d, J = 8.7 Hz, 2H), 7.16-7.23 (m, 2H), 7.09 (d, J = 9.1 Hz, 1H), 6.48 (q, J = 9.2 Hz, 1H), 4.04 (br t, J = 6.5 Hz, 2H), 4.01 (s, 3H), 3.84 (br s, 2H), 3.07-3.29 (m, 5H), 2.93 (s, 2H), 2.68 (s, 1H), 2.18-2.28 (m, 2H), 1.93-2.13 (m, 4H) m/z: 606.3 $[M + H]^+$.

N-[(1S)-1-[4-[4-(azetidine-1-carbonyl)-6-methoxy-1,5-naphthyridin-3-yl]amino]phenyl]-2,2,2-trifluoro-ethyl]-N-methyl-1,1-dioxo-thiane-4-carboxamide -continued

| Example 263 CPD0084918 | Procedure 6 | Intermediate 187 | Yield: 16.7% |
|---|---|---|---|
| 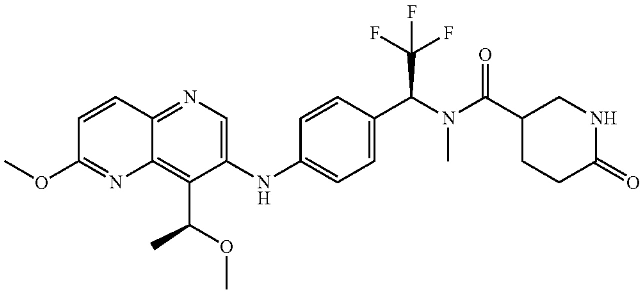 [SMILES: COc1ccc2ncc(Nc3ccc([C@H](N(C)C(=O)C4CCC(=O)NC4)C(F)(F)F)cc3)c([C@H](C)OC)c2n1] | $^1$H NMR (DMSO-d, 500 MHz): δ ppm 8.78 (s, 1H), 8.16 (d, 1H, J = 9.0 Hz), 8.0-8.1 (m, 1H), 7.48 (br d, 1H, J = 3.9 Hz), 7.2-7.4 (m, 4H), 7.07 (d, 1H, J = 8.8 Hz), 6.49 (quin, 1H, J = 9.2 Hz), 5.85 (q, 1H, J = 6.6 Hz), 4.01 (s, 3H), 3.1-3.5 (m, 6H), 2.95 (s, 3H), 2.1-2.3 (m, 2H), 1.6-2.0 (m, 2H), 1.51 (d, 3H, J = 6.8 Hz) m/z: 546 [M + H]$^+$. | | |
| N-methyl-6-oxo-N-[(1S)-2,2,2-trifluoro-1-[4-[6-methoxy-4-[(1 rel S)-1-methoxyethyl]-1,5-naphthyridin-3-yl]amino]phenyl]ethyl]piperidine-3-carboxamide | | | |

Example 264 1-(2-aminoacetyl)-N-[(1S)-1-[4-(4-chloro-2,3,7,10-tetrazatricyclo[7.4.0.0$^{2,6}$]trideca-1(9),3,5,7-tetraen-10-yl)phenyl]-2,2,2-trifluoro-ethyl]-N-methyl-pyrrolidine-3-carboxamide (CPD008491)

Intermediate 192 (95%, 400 mg, 0.771 mmol) and N-[(9H-fluoren-9-ylmethoxy) carbonyl]glycine (344 mg, 1.16 mmol) were dissolved in DCM-Anhydrous (8 mL) prior addition of pyridine (0.25 mL, 3.08 mmol) and phosphoryl trichloride (0.11 mL, 1.21 mmol). The reaction mixture was left stirring at rt for 2 hours. After that, DCM (20 mL) and piperidine (2.0 mL, 20.2 mmol) were added and the reaction mixture was left at rt for 20 minutes. The reaction mixture was well evaporated and the crude was purified by reverse-phase chromatography using a gradient of water/acetonitrile from water 100% (with 0.1% AcOH) to acetonitrile 100% (with 0.1% AcOH). Relevant fractions were combined and concentrated to afford title compound (124.2 mg, 29% Yield). m/z [M+H]+=550.4. $^1$H NMR (DMSO-d6, 500 MHz) δ 8.31 (d, 1H, J=0.7 Hz), 7.2-7.5 (m, 4H), 6.82 (s, 1H), 6.4-6.6 (m, 1H), 3.3-3.9 (m, 7H), 3.2-3.3 (m, 2H), 3.10 (t, 2H, J=6.7 Hz), 2.7-3.0 (m, 3H), 1.8-2.3 (m, 4H), 1.62 (br d, 2H, J=9.8 Hz).

Examples 265-266 CPD0075882/CPD0075883

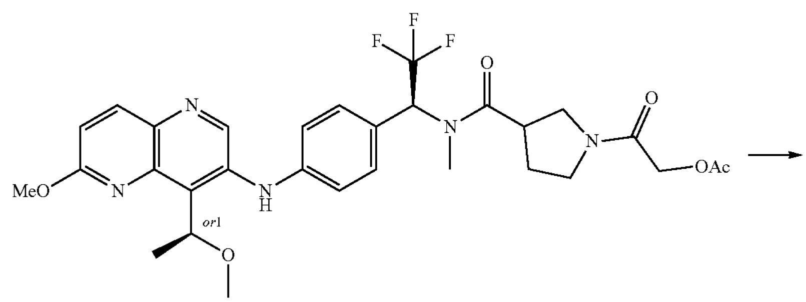

-continued

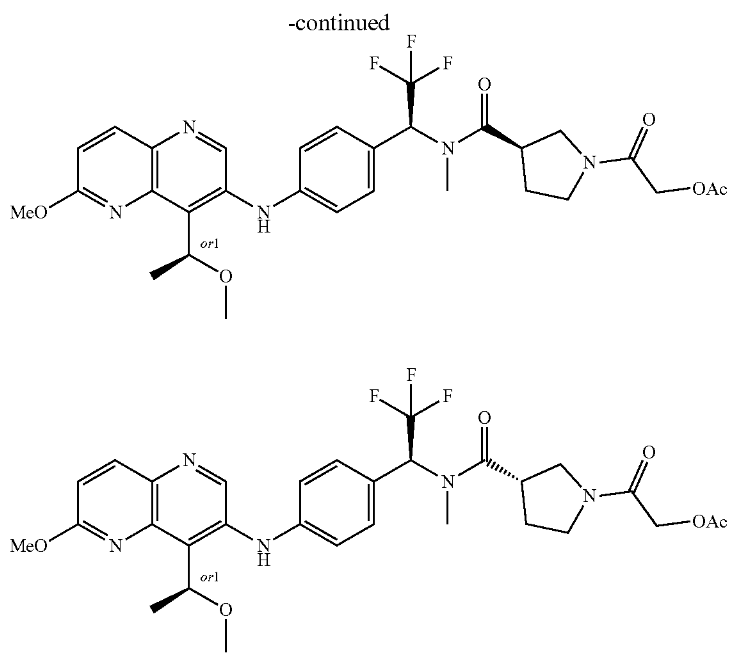

To a solution of intermediate 193 in THF (6 mL) and water (6 mL) was added lithium hydroxide hydrate (32 mg, 0.754 mmol). The reaction mixture was stirred at rt for 30 min. A sat. aq. $NaHCO_3$ and DCM were added to the reaction mixture. The aqueous layer was extracted twice with DCM. The organic layers were combined, dried over magnesium sulfate, filtered and dried under reduced pressure and the crude separated by chiral chromatography using a Chiralcel OD-H (100 mm×4.6) 5 μm column with 70/30 Heptane/EtOH as Eluent.

Example 265 CPD0075882 (3 rel S)-1-(2-hydroxyacetyl)-N-methyl-N-[(1S)-2,2,2-trifluoro-1-[4-[[6-methoxy-4-[(1_rel S)-1-methoxyethyl]-1,5-naphthyridin-3-yl]amino]phenyl]ethyl]pyrrolidine-3-carboxamide Yield: 25% $^1$H NMR (DMSO-d6, 600 MHz): δ ppm 8.78 (d, J=1.9 Hz, 1H), 8.15-8.17 (m, J=8.9 Hz, 1H), 8.04 (s, 1H), 7.20-7.39 (m, 4H), 7.06-7.09 (m, J=8.9 Hz, 1H), 6.45-6.53 (m, 1H), 5.84 (q, J=6.7 Hz, 1H), 4.48-4.56 (m, 1H), 4.01 (s, 3H), 3.96-4.05 (m, 2H), 3.33-3.66 (m, 5H), 3.30 (s, 3H), 2.94 (d, J=2.3 Hz, 2H), 1.85 (br d, J=7.6 Hz, 3H), 1.50 (d, J=6.6 Hz, 3H). m/z: 574 [M+H]+.

Example 266 CPD0075883 (3 rel R)-1-(2-hydroxyacetyl)-N-methyl-N-[(1S)-2,2,2-trifluoro-1-[4-[[6-methoxy-4-[(1 rel S-1-methoxyethyl]-1,5-naphthyridin-3-yl]amino]phenyl]ethyl]pyrrolidine-3-carboxamide Yield: 35%, $^1$H NMR (DMSO-d6, 600 MHz): δ ppm 8.78 (d, J=1.9 Hz, 1H), 8.15-8.17 (m, J=8.9 Hz, 1H), 8.04 (s, 1H), 7.20-7.39 (m, 4H), 7.06-7.09 (m, J=8.9 Hz, 1H), 6.45-6.53 (m, 1H), 5.84 (q, J=6.7 Hz, 1H), 4.48-4.56 (m, 1H), 4.01 (s, 3H), 3.96-4.05 (m, 2H), 3.33-3.66 (m, 5H), 3.30 (s, 3H), 2.94 (d, J=2.3 Hz, 2H), 1.85 (br d, J=7.6 Hz, 3H), 1.50 (d, J=6.6 Hz, 3H). m/z: 574 [M+H]+.

Examples 267-268 CPD0084255/CPD0084256

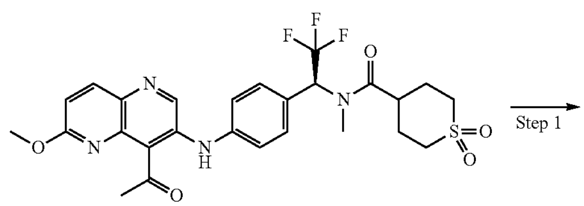

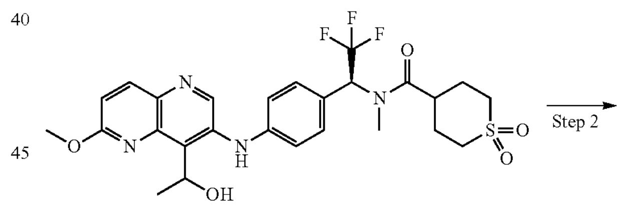

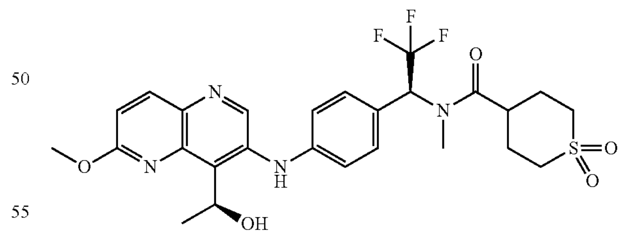

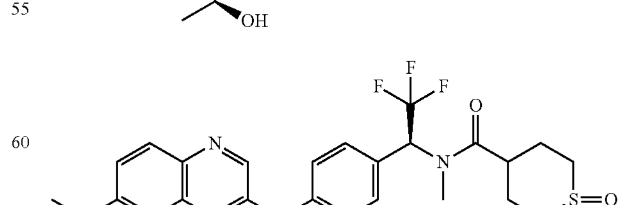

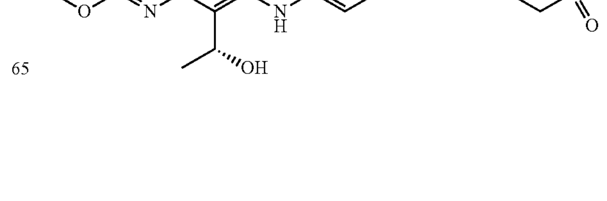

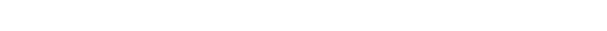

Step 1: N-methyl-1,1-dioxo-N-[(1S)-2,2,2-trifluoro-1-[4-[[4-(1-hydroxyethyl)-6-methoxy-1,5-naphthyridin-3-yl]amino]phenyl]ethyl]thiane-4-carboxamide Example 241 (85%, 500 mg, 0.75 mmol) was suspended in dry THF (7.5 mL) at −78° C. under $N_2$ atmosphere. A solution of 1 M lithium tri{sec}-butylboranuide in THF (0.75 mL, 0.75 mmol) was added dropwise and the reaction mixture was stirred at −78° C. under $N_2$ atmosphere for 1 h. The reaction mixture was allowed to warm to rt and sat. aq. $NH_4Cl$ (5 mL) was added. The triphasic mixture was diluted with water (5 mL) and the resulting biphasic mixture was vigorously stirred at rt for 10 minutes. The aqueous layer was isolated and extracted twice with EtOAc (10 mL). Organic layers were combined, washed with brine, dried over anhydrous $Na_2SO_4$, filtered and concentrated. The residue was purified by flash column chromatography (eluent MeOH:DCM 0:100 to 5:95) to give expected product as mixture of diastereomers which was separated by SFC80 Chiralpak AD-H 5 μm, 250×20 mm Mobile phase: CO2/(MeOH+0.5% IPAm) 80/20.

Example 267 CPD0084255

N-methyl-1,1-dioxo-N-[(1S)-2,2,2-trifluoro-1-[4-[[4-[(1 rel S)-1-hydroxyethyl]-6-methoxy-1,5-naphthyridin-3-yl]amino]phenyl]ethyl]thiane-4-carboxamide $^1$H NMR (600 MHz, DMSO-d6) δ ppm 1.46 (d, J=6.6 Hz, 3H) 2.02-2.07 (m, 4H) 2.92 (s, 3H) 3.11-3.27 (m, 5H) 4.00 (s, 3H) 6.09 (m, 1H) 6.25 (br s, 1H) 6.47 (q, J=9.3 Hz, 1H) 7.07 (d, J=9.0 Hz, 1H) 7.18 (d, J=8.7 Hz, 2H) 7.27 (d, J=8.5 Hz, 2H) 8.15 (d, J=8.8 Hz, 1H) 8.64 (s, 1H) 8.76 (s, 1H). m/z; 567.4 [M+H]+

Example 268 CPD0084256

N-methyl-1,1-dioxo-N-[(1S)-2,2,2-trifluoro-1-[4-[[4-[(1 rel R)-1-hydroxyethyl]-6-methoxy-1,5-naphthyridin-3-yl]amino]phenyl]ethyl]thiane-4-carboxamide $^1$H NMR (600 MHz, DMSO-$d_6$) δ ppm 1.46 (d, J=6.60 Hz, 3H) 1.91-2.19 (m, 4H) 2.93 (s, 3H) 3.07-3.28 (m, 5H) 4.00 (s, 3H) 6.04-6.21 (m, 1H) 6.25 (br s, 1H) 6.48 (q, J=9.29 Hz, 1H) 7.07 (d, J=8.95 Hz, 1H) 7.18 (d, J=8.66 Hz, 2H) 7.27 (d, J=8.51 Hz, 2H) 8.15 (d, J=8.80 Hz, 1H) 8.64 (s, 1H) 8.77 (s, 1H). m/z; 567.4 [M+H]+

Examples 269-270 CPD0084307/CPD0084308

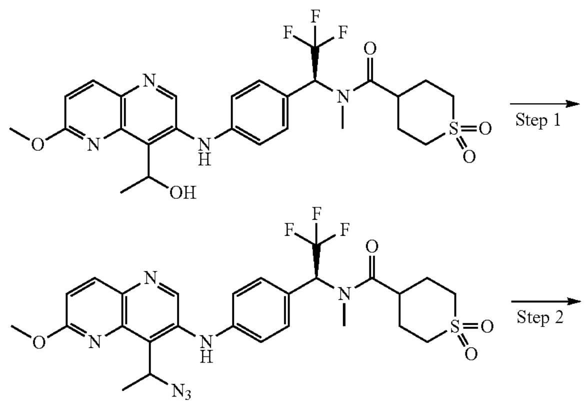

-continued

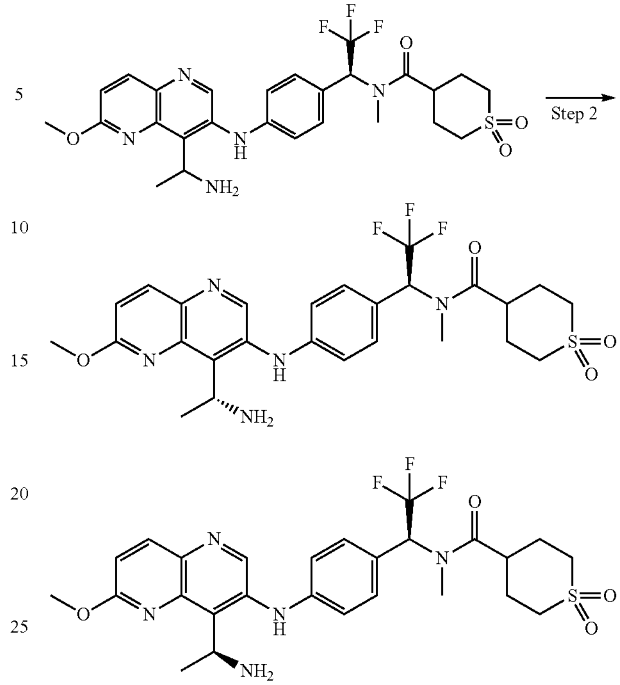

Step 1: N-methyl-1,1-dioxo-N-[(1S)-2,2,2-trifluoro-1-[4-[[4-(1-hydroxyethyl)-6-methoxy-1,5-naphthyridin-3-yl]amino]phenyl]ethyl]thiane-4-carboxamide N-methyl-1,1-dioxo-N-[(1S)-2,2,2-trifluoro-1-[4-[[4-(1-hydroxyethyl)-6-methoxy-1,5-naphthyridin-3-yl]amino]phenyl]ethyl]thiane-4-carboxamide (534 mg, 0.924 mmol) was suspended in dry THF (9.2 mL) at rt under $N_2$ atmosphere. [azido (phenoxy)phosphoryl]oxybenzene (0.41 mL, 1.85 mmol) was added and the yellow suspension was stirred at rt for 15 minutes. 2,3,4,6,7,8,9,10-octahydropyrimido[1,2-a]azepine (0.28 mL, 1.85 mmol) was added and the reaction mixture turned red. The red solution was stirred at rt for 4 hours. A sat. aq. $NaHCO_3$ was added, followed by water and EtOAc. The aqueous phase was isolated and extracted with EtOAc. Organic layers were combined, washed with brine, dried over anhydrous $Na_2SO_4$, filtered and concentrated. The residue was purified by flash column chromatography (EtOAc:heptane 0:100 to 80:20) to give the title compound (313 mg, 56.7% Yield). m/z 592.5 [M+H]+. $^1$H NMR (400 MHz, DMSO-$d_6$) δ ppm 8.68 (s, 1H), 8.32-8.25 (m, 1H), 8.22 (d, J=9.0 Hz, 1H), 7.34-7.21 (m, 2H), 7.17 (d, J=9.0 Hz, 1H), 7.06-6.98 (m, 2H), 6.51-6.09 (m, 1H), 5.75-5.67 (m, 1H), 4.07 (s, 3H), 3.30-3.06 (m, 5H), 2.94-2.63 (m, 3H), 2.17-1.93 (m, 4H), 1.81 (d, J=7.0 Hz, 3H).

Step 2:

N-[(1S)-1-[4-[[4-(1-azidoethyl)-6-methoxy-1,5-naphthyridin-3-yl]amino]phenyl]-2,2,2-trifluoro-ethyl]-N-methyl-1,1-dioxo-thiane-4-carboxamide (99%, 310 mg, 0.519 mmol) was dissolved in a mixture of THF (3 mL) and Water (0.3 mL) at rt. Triphenylphosphine (143 mg, 0.545 mmol) was added and the yellow solution was stirred at rt for 4 hours and at 80° C. for 3 hours and 60° C. overnight.

Volatiles were removed under reduced pressure and the residue was partitioned between DCM and sat. aq. $NaHCO_3$. The aqueous phase was isolated and extracted twice with DCM. The organic layers were combined, washed with brine, dried over anhydrous $Na_2SO_4$, filtered and concentrated. The residue was purified by flash column chromatography (DCM:(DCM/MeOH 95/5) 100:0 to 0:100) to give expected product (210 mg, 70.8% Yield) as a yellow solid. A chiral separation was carried out onto Chiralcel AS-V 20 μm, 300×76.5 mm (Mobile phase: acetonitrile+0.5% isopropylamine)

Example 269 CPD0084307

N-[(1S)-1-[4-[[4-[(1 rel S)-1-aminoethyl]-6-methoxy-1,5-naphthyridin-3-yl]amino]phenyl]-2,2,2-trifluoro-ethyl]-N-methyl-1,1-dioxo-thiane-4-carboxamide (90.9 mg, 30.714% Yield), as a yellow solid. m/z 566.3 [M+H]+. $^1H$ NMR (DMSO-d6, 600 MHz): δ ppm 9.38-10.52 (m, 1H), 8.73 (s, 1H), 8.16 (d, J=8.9 Hz, 1H), 7.24-7.36 (m, 2H), 7.09-7.15 (m, 2H), 7.07 (d, J=9.0 Hz, 1H), 6.46 (q, J=9.4 Hz, 1H), 5.35 (br q, J=8.2 Hz, 1H), 4.02 (s, 3H), 3.08-3.28 (m, 5H), 3.30 (br s, 2H), 2.92 (s, 2H), 2.67 (s, 1H), 1.93-2.23 (m, 4H), 1.45 (br d, J=4.4 Hz, 3H)

Example 270 CPD0084308

N-[(1S)-1-[4-[[4-[(1 rel R)-1-aminoethyl]-6-methoxy-1,5-naphthyridin-3-yl]amino]phenyl]-2,2,2-trifluoro-ethyl]-N-methyl-1,1-dioxo-thiane-4-carboxamide (80.6 mg, 27.5% Yield), as a yellow solid. m/z [M+H]+=566.3. $^1H$ NMR (DMSO-d6, 600 MHz): δ ppm 9.47-10.66 (m, 1H), 8.73 (s, 1H), 8.15 (d, J=8.9 Hz, 1H), 7.23-7.36 (m, 2H), 7.09-7.15 (m, 2H), 7.06 (d, J=9.0 Hz, 1H), 6.08-6.59 (m, 1H), 5.29-5.45 (m, 1H), 4.01 (s, 3H), 3.08-3.28 (m, 5H), 3.30 (br s, 2H), 2.66-2.94 (m, 3H), 1.96-2.22 (m, 4H), 1.43 (br d, J=6.2 Hz, 3H)

Example 271 EX00S72449

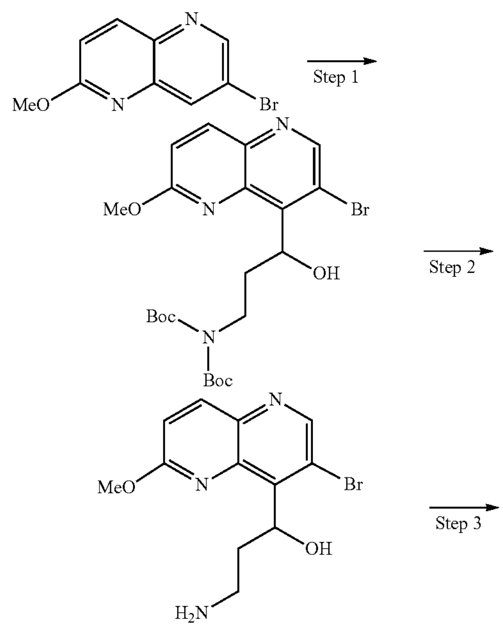

-continued

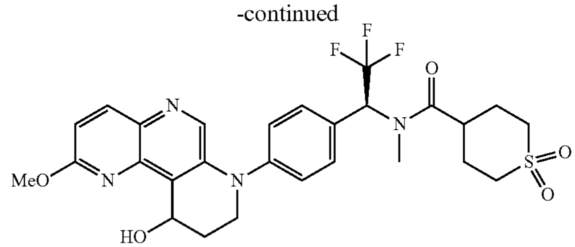

Step 1: Tert-butyl N-[3-(3-bromo-6-methoxy-1,5-naphthyridin-4-yl)-3-hydroxy-propyl]-N-tert-butoxy-carbonyl-carbamate To a stirred solution of 7-bromo-2-methoxy-1,5-naphthyridine (2.00 g, 8.37 mmol) in dry THF (42 mL) was added dropwise at 0° C., 1 M lithium chloro-(2,2,6,6-tetramethyl-1-piperidyl) magnesium chloride in THF/Toluene (21 mL, 20.9 mmol). After 30 min, tert-butyl N-[(tert-butoxy) carbonyl]-N-(3-oxopropyl)carbamate (96%, 5.4 mL, 15.1 mmol) was added at 0° C., and the reaction mixture was kept at rt for 4 h. The mixture was poured in EtOAc and quenched with a sat $NH_4Cl$. Then the organic layer was washed with brine and dried over anhydrous MgSO4 and concentrated under reduced pressure. The residue was purified by flash column chromatography (EtOAc/Heptane (from 0% of EtOAc to 100% of EtOAc) to afford the expected product (1.47 g, 32%). m/z: 512 $[M+H]^+$. $^1H$ NMR (400 MHz, DMSO-d6) δ 8.86 (s, 1H), 8.31 (d, J=9.1 Hz, 1H), 7.35 (d, J=9.0 Hz, 1H), 6.92 (s, 1H), 6.67 (s, 1H), 4.08 (s, 3H), 3.19-3.05 (m, 2H), 2.33 (s, 1H), 1.99 (s, 1H), 1.35 (s, 9H), 1.30 (s, 9H).

Step 2: 3-amino-1-(3-bromo-6-methoxy-1,5-naphthyridin-4-yl) propan-1-ol

Tert-butyl N-[3-(3-bromo-6-methoxy-1,5-naphthyridin-4-yl)-3-hydroxy-propyl]-N-tert-butoxycarbonyl-carbamate (80%, 46 mg, 0.0718 mmol) was dissolved in DCM (0.4 mL) and then TFA (0.082 mL, 1.08 mmol) was added. The reaction mixture was stirred at rt for 3 h. Then volatiles were removed under reduced pressure and the residue purified by reverse flash column chromatography (MeCN/H2O from 0% of MeCN to 100% of MeCN) to obtain the expected product (59 mg, 53%) as white solid. m/z: 312 $[M+H]^+$. $^1H$ NMR (400 MHz, DMSO-d6) 8.90 (s, 1H), 8.36 (d, J=9.1 Hz, 1H), 7.70 (s, 2H), 7.38 (d, J=9.1 Hz, 1H), 5.98 (d, J=7.3 Hz, 1H), 5.70 (s, 1H), 4.07 (s, 3H), 3.09 (s, 1H), 2.94 (s, 1H), 2.43 (d, J=4.3 Hz, 1H), 2.16-2.02 (m, 1H).

Step 3: Example 271 N-methyl-1,1-dioxo-N-[(1S)-2,2,2-trifluoro-1-[4-(10-hydroxy-2-methoxy-9,10-dihydro-8H-pyrido[2,3-f][1,7]naphthyridin-7-yl) phenyl]ethyl]thiane-4-carboxamide

[2-(2-aminophenyl)phenyl]-chloro-palladium; dicyclohexyl-[3-(2,4,6-triisopropylphenyl)phenyl]phosphane (467 mg, 0.594 mmol), cesium carbonate (1.55 g, 4.75 mmol) and 3-amino-1-(3-bromo-6-methoxy-1,5-naphthyridin-4-yl) propan-1-ol (97%, 382 mg, 1.19 mmol) were suspended in dry 1,4-dioxane (24 mL). The reaction mixture was stirred at 100° C. for 1 h. Intermediate 86 (275 mg, 0.642 mmol) was added and the reaction stirred at 100° C. overnight. The reaction was partitioned between EtOAc and sat. aq. $NH_4Cl$. The aqueous layer was extracted twice with EtOAc (15 mL).

The organic layers were combined, dried over anhydrous $MgSO_4$ and concentrated under vacuum. The crude was purified by flash column chromatography (Heptane/EtOAc (from 0% to 100% of EtOAc) to afford the title compound (45 mg, 15%). m/z: 579 $[M+H]^+$. $^1H$ NMR (DMSO-d6, 600 MHz): δ ppm 8.28 (d, J=1.2 Hz, 1H), 8.05 (d, J=8.8 Hz, 1H), 7.42-7.50 (m, 4H), 6.94 (d, J=8.8 Hz, 1H), 6.57 (br d, J=9.5 Hz, 1H), 5.57 (br s, 1H), 5.20-5.22 (m, 1H), 4.02-4.05 (m, 3H), 3.79-3.84 (m, 1H), 3.70 (br s, 1H), 3.08-3.26 (m, 5H), 2.95 (d, J=2.8 Hz, 3H), 1.92-2.13 (m, 6H).

Example 272 CPD0072532 N-methyl-1,1-dioxo-N-[(1S)-2,2,2-trifluoro-1-[4-(2-methoxy-9,10-dihydro-8H-pyrido[2,3-f][1,7]naphthyridin-7-yl)phenyl]ethyl]thiane-4-carboxamide

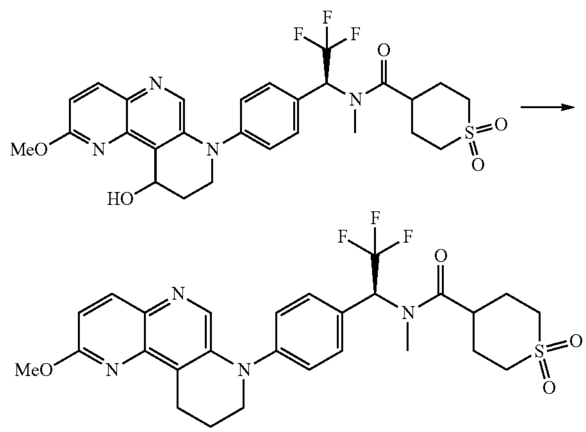

N-methyl-1,1-dioxo-N-[(1S)-2,2,2-trifluoro-1-[4-(10-hydroxy-2-methoxy-9,10-dihydro-8H-pyrido[2,3-f][1,7]naphthyridin-7-yl)phenyl]ethyl]thiane-4-carboxamide (84%, 50 mg, 0.0726 mmol) in dry DCE (0.36 mL), then triethylsilane (99%, 0.11 mL, 0.690 mmol) and TFA (0.066 mL, 0.859 mmol) were successively added. The reaction mixture was stirred for 1 h at rt. The reaction mixture was partitioned between DCM. The organic layer was washed twice with aqueous sat. aq. $NaHCO_3$, brine, dried over $MgSO_4$ and concentrated under reduced pressure. The residue was purified by flash column chromatography (Heptane/EtOAc (from 0% to 100% of EtOAc) to afford title compound (24 mg, 54%). m/z: 563 $[M+H]^+$. $^1H$ NMR (DMSO-d6, 600 MHz) δ ppm 8.29 (s, 1H), 8.05 (d, 1H, J=8.8 Hz), 7.38 (s, 4H), 6.96 (d, 1H, J=8.8 Hz), 6.54 (q, 1H, J=9.4 Hz), 4.01 (s, 3H), 3.7-3.8 (m, 2H), 3.18 (br t, 7H, J=6.5 Hz), 2.94 (s, 3H), 1.9-2.2 (m, 6H).

Example 273 CPD0072532

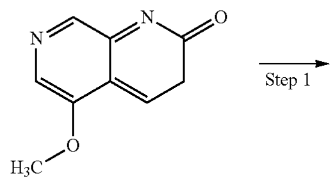

-continued

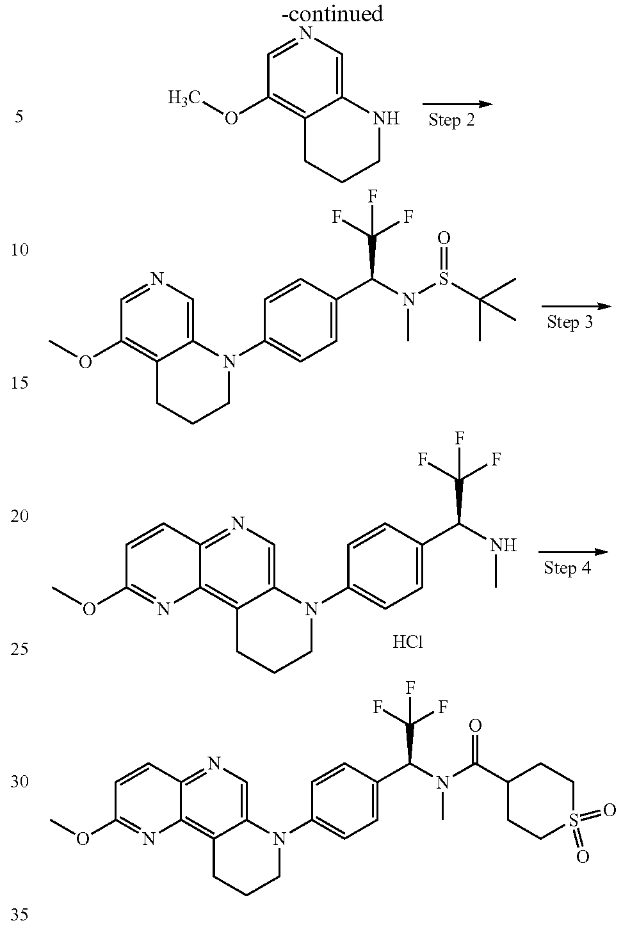

Step 1: 5-methoxy-1,2,3,4-tetrahydro-1,7-naphthyridine

To a solution of 5-methoxy-3,4-dihydro-1,7-naphthyridin-2 (1H)-one (1.06 g, 5.97 mmol) in dry THF (30 mL) was added 2 M lithium aluminium hydride (6.0 mL, 11.9 mmol) at 0° C. The reaction mixture was stirred at rt for 1 h. The reaction mixture was titrated with $H_2O$ (4 mL), NaOH 4N (4 mL) and $H_2O$ (24 mL). The mixture was left stirring for 30 min at rt and then filtered. The filtrate was concentrated under reduced pressure. The crude was purified by flash column chromatography (DCM/MeOH, 0% to 5% of MeOH) to afford the title compound. m/z: 165 $[M+H]^+$. $^1H$ NMR (400 MHz, DMSO-d6) δ ppm 7.48 (d, J=14.9 Hz, 2H), 5.87 (s, 1H), 3.78 (s, 3H), 3.12 (dq, J=5.8, 2.5 Hz, 2H), 2.50 (d, J=2.2 Hz, 2H), 1.75 (dt, J=11.9, 6.4 Hz, 2H).

Step 2: N,2-dimethyl-N-[(1S)-2,2,2-trifluoro-1-[4-(5-methoxy-3,4-dihydro-2H-1,7-naphthyridin-1-yl)phenyl]ethyl]propane-2-sulfinamide A solution of N-[(1S)-1-(4-bromophenyl)-2,2,2-trifluoro-ethyl]-N,2-dimethyl-propane-2-sulfinamide (227 mg, 0.61 mmol), 5-methoxy-1,2,3,4-tetrahydro-1,7-naphthyridine (100%, 100 mg, 0.61 mmol) and cesium carbonate (397 mg, 1.22 mmol) was degassed with $N_2$ for 5 min prior addition of [2-(2-aminophenyl)phenyl]-chloro-palladium dicyclohexyl-[3-(2,4,6-triisopropylphenyl)phenyl]phosphane (24 mg, 0.030 mmol). The reaction mixture was stirred at 100° C. overnight. [2-(2-aminophenyl)phenyl]-chloro-palladium dicyclohexyl-[3-(2,4,6-triisopropylphenyl)phenyl]phosphane (24 mg, 0.0305 mmol) was added and the reaction mixture was stirred at 100° C. for 6 h. The reaction mixture was partitioned between EtOAc and sat. aq. $NH_4Cl$ and the aqueous phase was extracted with EtOAc. The organic layers were combined, dried over $Na_2SO_4$, filtered and concentrated under reduced pressure. The crude was purified by flash column chromatography (Heptane/EtOAc/MeOH, from 0% to 100% of EtOAc and up to 10% of MeOH). N,2-dimethyl-N-[(1S)-2,2,2-trifluoro-1-[4-(5-methoxy-3,4-dihydro-2H-1,7-naphthyridin-1-yl)phenyl]ethyl]propane-2-sulfinamide (67 mg, 23% Yield) was obtained as a yellow oil. m/z: 165 $[M+H]^+$. $^1H$ NMR (400 MHz, DMSO-$d_6$) δ 7.71 (d, J=26.5 Hz, 2H), 7.43 (d, J=8.5 Hz, 2H), 7.30 (d, J=8.6 Hz, 2H), 5.52 (q, J=9.2 Hz, 1H), 3.87 (s, 3H), 3.61-3.54 (m, 2H), 2.65 (t, J=6.6 Hz, 2H), 2.43 (s, 3H), 1.90 (dt, J=12.2, 6.7 Hz, 2H), 1.14 (s, 9H).

Step 3: (1S)-2,2,2-trifluoro-1-[4-(5-methoxy-3,4-dihydro-2H-1,7-naphthyridin-1-yl)phenyl]-N-methyl-ethanamine hydrochloride To a solution of N,2-dimethyl-N-[(1S)-2,2,2-trifluoro-1-[4-(5-methoxy-3,4-dihydro-2H-1,7-naphthyridin-1-yl)phenyl]ethyl]propane-2-sulfinamide (95%, 67 mg, 0.140 mmol) in ethyl acetate (1.4 mL) was added 4 M hydrogen chloride (0.14 mL, 0.559 mmol). The reaction mixture was stirred at rt for 30 min. The reaction mixture was concentrated under reduced pressure to obtain title compound product (64, 113% Yield). m/z: 165 $[M+H]^+$. $^1H$ NMR (400 MHz, DMSO-d6) δ7.96 (s, 1H), 7.70 (s, 1H), 7.67 (d, J=3.1 Hz, 2H), 7.51 (d, J=8.4 Hz, 2H), 3.98 (s, 3H), 3.70-3.64 (m, 4H), 2.81 (t, J=6.5 Hz, 2H), 2.47 (s, 3H), 1.99 (t, J=5.4 Hz, 2H).

Example 273 CPD0021939 Step 4: N-methyl-1,1-dioxo-N-[(1S)-2,2,2-trifluoro-1-[4-(5-methoxy-3,4-dihydro-2H-1,7-naphthyridin-1-yl)phenyl]ethyl]thiane-4-carboxamide To a solution of (1S)-2,2,2-trifluoro-1-[4-(5-methoxy-3,4-dihydro-2H-1,7-naphthyridin-1-yl)phenyl]-N-methyl-ethanamine hydrochloride (64 mg, 0.165 mmol) and tetrahydro-2H-thiopyran-4-carboxylic acid 1,1-dioxide (97%, 45 mg, 0.248 mmol) in dry DCM (0.33 mL) was added TEA (0.46 mL, 3.30 mmol) followed by $T_3P$ (0.98 mL, 1.65 mmol). The reaction mixture was stirred at rt overnight. The reaction mixture was partitioned between $NaHCO_3$sat and DCM, phases were separated and aqueous phase was extracted with DCM. The combined organic layer was washed with brine, dried over $Na_2SO_4$, filtered and concentrated under reduced pressure. The crude was purified by flash column chromatography (DCM/MeOH from 0% to 15% of MeOH) a second purification by flash reverse column chromatography ($H_2O$/MeCN from 0% to 100% of MeCN). m/z: 512 $[M+H]^+$. $^1H$ NMR (DMSO-d6, 600 MHz) δ ppm 7.75 (s, 1H), 7.69 (s, 1H), 7.2-7.5 (m, 4H), 6.5-6.6 (m, 1H), 3.87 (s, 3H), 3.5-3.6 (m, 2H), 3.1-3.4 (m, 5H), 2.93 (s, 3H), 2.65 (br t, 2H, J=6.6 Hz), 1.91 (s, 6H).

Examples 274-291

Procedure 1

A solution of Intermediates 219 or 219-b (1 mmol), Br-aryl derivatives (1.1 mmol) and cesium carbonate (2 mmol) in dry 1,4-dioxane (0.05 M) was degassed with nitrogen for 5 min prior addition of Pd XPhos G2 (0.2 mmol) at rt. The reaction mixture was then heated at 100° C. until LCMS showed the reaction to be complete. The reaction mixture was diluted with EtOAc and saturated $NH_4Cl$ solution was added. The aqueous phase was extracted with EtOAc. The organic layers were combined, dried over anhydrous $Na_2SO_4$, filtered and concentrated under reduced pressure.

a) The crude was purified by flash column chromatography (Heptane/EtOAc or DCM/MeOH)

b) The crude was purified by reverse phase column chromatography ($H_2O$/MeCN+0.1% AcOH from 0% to 100% of MeCN)

c) The crude was purified by Chiral SFC

General Procedure 2

To a stirred solution of Intermediates (1 mmol) in DCM (0.1 M), TFA (20 mmol) was added and the reaction mixture was stirred at rt upon completion.

The reaction mixture was diluted with DCM and quenched by addition of sat. aq. $NaHCO_3$. The biphasic mixture was vigorously stirred at rt. Layers were separated and the aqueous phase was extracted with DCM. Organic layers were combined, dried over anhydrous $Na_2SO_4$, filtered and concentrated. The residue was purified by flash column chromatography (EtOAc:heptane 0:100 to 100:0)

General Procedure 3

Intermediate 228 (1 mmol) was dissolved in DCM (0.2 M), carboxylic acid (1.2 mmol) and TEA (20 mmol) in DCM (0.6 mL) at rt $T_3P$-50% in EtOAc (10 mmol) was added and the reaction mixture was stirred at rt overnight. The reaction mixture was carefully quenched by addition of sat. aq. $NaHCO_3$. After gas evolution ceased, the biphasic mixture was partitioned between water and EtOAc. The aqueous layer was isolated and extracted twice with EtOAc. Organic layers were combined, washed with brine, dried over anhydrous $Na_2SO_4$, filtered and concentrated. The residue was purified by flash column chromatography (EtOAc:Heptane or DCM/MeOH).

Procedure 4

Intermediate 223 (1 mmol) was dissolved in dry MeOH (1 M) at rt. Sulfuric acid (0.05 mmol) was added and the reaction mixture was stirred at 50° C. for 2 hours and 35° C. for 18 hours. The reaction mixture was partitioned between EtOAc and sat. aq. $NaHCO_3$. The aqueous phase was isolated and extracted twice with EtOAc. Organic layers were combined, washed with brine, dried over anhydrous $Na_2SO_4$, filtered and concentrated. The residue was purified by flash column chromatography (EtOAc:Heptane 50:50 to 100:0)

Procedure 5

Intermediate 234 (1 mmol) was dissolved in MeOH (0.5 M) at rt, ammonia carbamic acid (2 mmol) was added, followed by [acetoxy (phenyl)-I^{3}nyl]acetate (2.5 mmol), and the suspension was stirred at rt upon completion. Volatiles were removed under reduced pressure and the residue was purified by flash column chromatography (MeOH:DCM 0:100 to 10:90) first and then separated by chiral SFC.

Procedure 6

Intermediate 237 (1 mmol) was dissolved in methanol (0.2 M), then $K_2CO_3$ (3 mmol) was added and the mixture was stirred at 0° C. for 1 h. After that the reaction was quenched with a sat. aq. $NH_4Cl$ at 0° C. DCM was added and the phases were separated. The organic layer was washed with sat. aq. $NH_4Cl$, then dried over anhydrous $MgSO_4$ and concentrate under reduce pressure to give a residue which was purified by preparative chiral SFC

| Example 274 CPD0018617 | Procedure 1a-b | Intermediates 212; 86 | Yield: 18% |
|---|---|---|---|

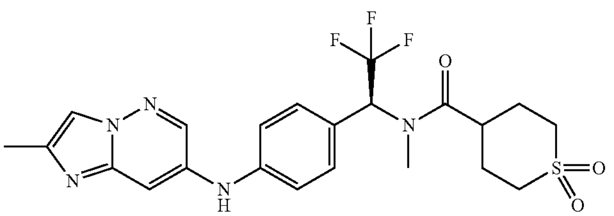 [SMILES: Cc1cn2ncc(Nc3ccc([C@H](N(C)C(=O)C4CCS(=O)(=O)CC4)C(F)(F)F)cc3)cc2n1]

N-methyl-1,1-dioxo-N-[(1S)-2,2,2-trifluoro-1-[4-({2-methylimidazo[1,2-b]pyridazin-7-yl}amino)phenyl]ethyl]-1$\lambda^6$-thiane-4-carboxamide $^1$H NMR (DMSO-$d_6$, 500 MHz) δ ppm 11.67-12.30 (m, 1H), 8.91 (s, 1H), 8.24 (d, J = 2.6 Hz, 1H), 7.76 (s, 1H), 7.35-7.37 (m, 1H), 7.30-7.33 (m, 2H), 7.22-7.28 (m, 2H), 6.42-6.53 (m, 1H), 3.08-3.24 (m, 4H), 2.92 (s, 3H), 2.29 (s, 3H), 1.96-2.12 (m, 4H). m/z: 496 $[M + H]^+$.

| Example 275 CPD0018618 | Procedure 1b | Intermediate 212; 87 | Yield: 12% |
|---|---|---|---|

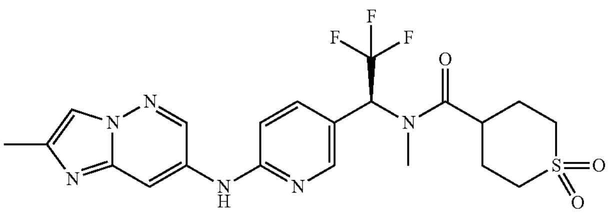 [SMILES: Cc1cn2ncc(Nc3ccc([C@H](N(C)C(=O)C4CCS(=O)(=O)CC4)C(F)(F)F)cn3)cc2n1]

N-methyl-1,1-dioxo-N-[(1S)-2,2,2-trifluoro-1-[6-({2-methylimidazo[1,2-b]pyridazin-7-yl}amino)pyridin-3-yl]ethyl]-1$\lambda^6$-thiane-4-carboxamide $^1$H NMR (DMSO-$d_6$, 500 MHz) δ ppm 9.84 (s, 1H), 8.55 (d, J = 2.3 Hz, 1H), 8.45 (d, J = 2.5 Hz, 1H), 8.28 (d, J = 2.2 Hz, 1H), 7.80 (s, 1H), 7.73-7.67 (m, 1H), 7.00 (d, J = 8.8 Hz, 1H), 6.58-6.47 (m, 1H), 3.30-3.06 (m, 5H), 2.96 (s, 3H), 2.32 (s, 3H), 2.06 (dq, J = 26.8, 13.9, 12.6 Hz, 4H). m/z: 497 $[M + H]^+$.

| Example 276 CPD0072526 | Procedure 1a | Intermediate 219-b; 86 | Yield: 44.9% |
|---|---|---|---|

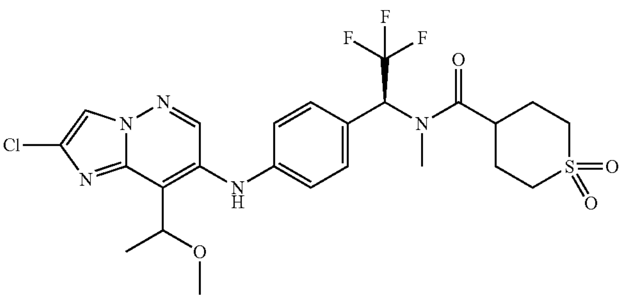

N-[(1S)-1-[4-[2-chloro-8-(1-methoxyethyl)imidazo[1,2-b]pyridazin-7-yl]amino]phenyl]-2,2,2-trifluoro-ethyl]-N-methyl-1,1-dioxo-thiane-4-carboxamide $^1$H NMR (DMSO-$d_6$, 500 MHz) δ ppm 8.48 (d, 1H, J = 1.0 Hz), 8.29 (s, 1H), 7.9-8.1 (m, 1H), 7.0-7.5 (m, 4H), 6.47 (q, 1H, J = 9.5 Hz), 5.08 (q, 1H, J = 6.6 Hz), 3.0-3.6 (m, 8H), 2.92 (s, 3H), 1.9-2.2 (m, 4H), 1.54 (d, 3H, J = 6.6 Hz). m/z: 574.2 $[M + H]^+$.

| Example 277 CPD0072849 | Procedure 1a | Intermediate 219-b; 86 | Yield: 10.8% |
|---|---|---|---|

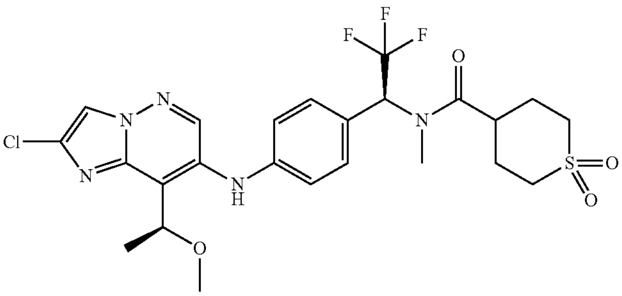 [SMILES: CO[C@@H](C)c1c(Nc2ccc([C@H](N(C)C(=O)C3CCS(=O)(=O)CC3)C(F)(F)F)cc2)cnn2cc(Cl)nc12]

N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-1,1-dioxo-thiane-4-carboxamide $^1$H NMR (DMSO-$d_6$, 500 MHz) δ ppm 8.47-8.48 (m, 1H), 8.28 (s, 1H), 8.00-8.05 (m, 1H), 7.09-7.38 (m, 4H), 6.47 (q, J = 9.2 Hz, 1H), 5.08 (q, J = 6.6 Hz, 1H), 3.09-3.27 (m, 8H), 2.92 (s, 3H), 1.97-2.13 (m, 4H), 1.54 (d, J = 6.6 Hz, 3H). m/z: 574.2 $[M + H]^+$.

-continued

| Example 278 CPD0072850 | Procedure 1a-c | Intermediate 219-b; 86 | Yield: 11.3% |
|---|---|---|---|
| 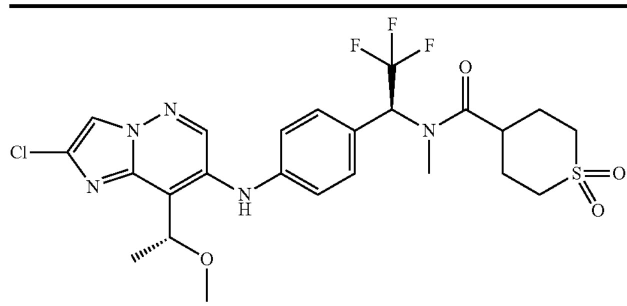 | $^1H$ NMR (DMSO-$d_6$, 500 MHz) δ ppm 8.47 (s, 1H), 8.28 (s, 1H), 8.00-8.04 (m, 1H), 7.12-7.36 (m, 4H), 6.47 (q, J = 9.2 Hz, 1H), 5.08 (q, J = 6.6 Hz, 1H), 3.06-3.28 (m, 8H), 2.92 (s, 3H), 1.94-2.17 (m, 4H), 1.54 (d, J = 6.6 Hz, 3H). m/z: 574.2 $[M + H]^+$. | | |

N-[(1S)-1-[4-[2-chloro-8-[(1R)-1-methoxyethyl]imidazo[1,2-b]pyridazin-7-yl]amino]phenyl]-2,2,2-trifluoro-ethyl]-N-methyl-1,1-dioxo-thiane-4-carboxamide

| Example 279 CPD0082468 | Procedure 2 | Intermediate 230 | Yield: 77.4% |
|---|---|---|---|
| 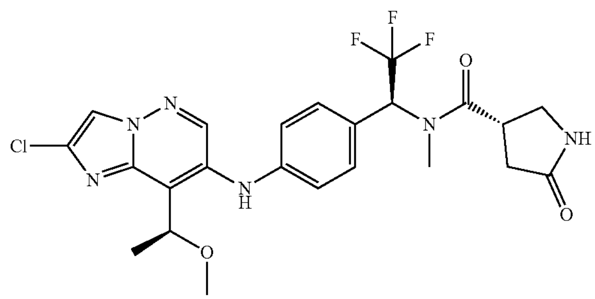 [SMILES: CO[C@@H](C)c1c(Nc2ccc([C@H](N(C)C(=O)[C@@H]3CNC(=O)C3)C(F)(F)F)cc2)cnn2cc(Cl)nc12] | $^1H$ NMR (DMSO-$d_6$, 600 MHz) δ ppm 8.48 (s, 1H), 8.28 (s, 1H), 8.01 (s, 1H), 7.66 (s, 1H), 7.28 (d, J = 8.4 Hz, 2H), 7.16 (d, J = 8.5 Hz, 2H), 6.59-6.02 (m, 1H), 5.08 (d, J = 6.6 Hz, 1H), 4.04-3.69 (m, 1H), 3.52-3.32 (m, 2H), 3.22 (s, 3H), 2.95-2.66 (m, 3H), 2.55-2.50 (m, 1H), 2.27 (dd, J = 16.6, 6.7 Hz, 1H), 1.53 (d, J = 6.6 Hz, 3H). m/z: 525 $[M + H]^+$. | | |

(3 rel R)-N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-5-oxo-pyrrolidine-3-carboxamide

| Example 280 CPD0082467 | Procedure 2 | Intermediate 229 | Yield: 72.9% |
|---|---|---|---|
| 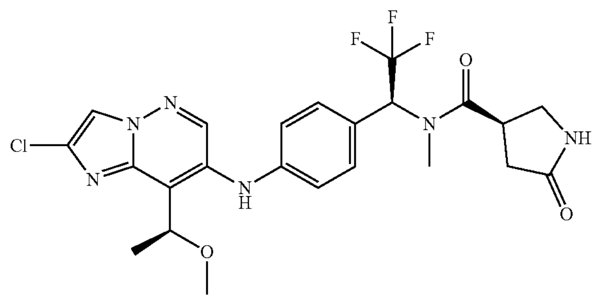 [SMILES: CO[C@@H](C)c1c(Nc2ccc([C@H](N(C)C(=O)[C@H]3CNC(=O)C3)C(F)(F)F)cc2)cnn2cc(Cl)nc12] | $^1H$ NMR (DMSO-$d_6$, 500 MHz) δ ppm 1.53 (d, J = 6.60 Hz,3H) 2.31-2.45 (m, 2H) 2.87 (s, 3H) 3.22 (s, 3H) 3.27 (dd, J = 9.46, 5.65 Hz, 1H) 3.57 (t, J = 9.17 Hz, 1H) 3.67-4.11 (m, 1H) 5.08 (q, J = 6.60 Hz, 1H) 6.47 (q, J = 9.29 Hz, 1H) 7.16 (d, J = 8.51 Hz, 2H) 7.28 (d, J = 8.36 Hz, 2H) 7.66 (s, 1H) 8.02 (s, 1H) 8.28 (s, 1H) 8.48 (s, 1H). m/z: 525 $[M + H]^+$. | | |

(3 rel S)-N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-5-oxo-pyrrolidine-3-carboxamide

| Example 281 CPD0084936 | Procedure 3 | Intermediate 228 | Yield: 75.1% |
|---|---|---|---|
| 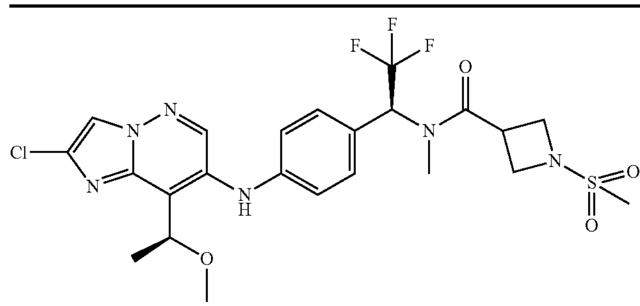 | $^1H$ NMR (DMSO-$d_6$, 500 MHz) δ ppm 8.4-8.5 (m, 1H), 8.2-8.3 (m, 1H), 7.9-8.1 (m, 1H), 7.2-7.4 (m, 2H), 7.0-7.2 (m, 2H), 6.45 (q, 1H, J = 9.3 Hz), 4.9-5.2 (m, 1H), 3.8-4.3 (m, 5H), 3.2-3.2 (m, 3H), 3.0-3.0 (m, 3H), 2.7-2.8 (m, 3H), 1.54 (d, 3H, J = 6.8 Hz). m/z: 575.3 $[M + H]^+$. | | |

-continued

N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-1-methylsulfonyl-azetidine-3-carboxamide

| Example 282 CPD0084934 | Procedure 3 | Intermediate 228 | Yield: 85% |
|---|---|---|---|
| 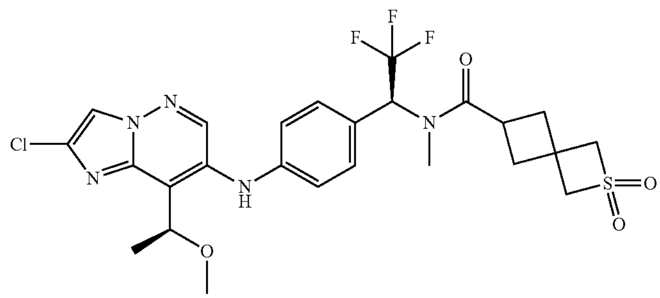 [SMILES: CO[C@@H](C)c1c(Nc2ccc([C@H](N(C)C(=O)C3CC4(C3)CS(=O)(=O)C4)C(F)(F)F)cc2)cnn2cc(Cl)nc12] | $^1$H NMR (DMSO-$d_6$, 500 MHz): δ ppm 8.47-8.48 (m, 1H), 8.28-8.29 (m, 1H), 7.99-8.03 (m, 1H), 7.24-7.31 (m, 2H), 7.13-7.19 (m, 2H), 6.43 (q, J = 9.3 Hz, 1H), 5.08 (q, J = 6.7 Hz, 1H), 4.10-4.31 (m, 4H), 3.48 (quin, J = 8.5 Hz, 1H), 3.22 (s, 3H), 2.75 (s, 2H), 2.64-2.68 (m, 1H), 2.51-2.58 (m, 2H), 2.44-2.49 (m, 2H), 1.49-1.55 (m, 3H). m/z: 586 [M + H]$^+$. | | |

N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-2,2-dioxo-1λ$^6$-thiaspiro[3.3]heptane-6-carboxamide

| Example 283 CPD0084141 | Procedure 6 | Intermediate 223 | Yield: 81% |
|---|---|---|---|
| 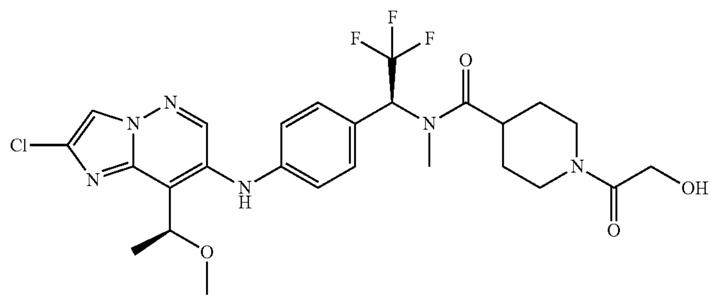 [SMILES: CO[C@@H](C)c1c(Nc2ccc([C@H](N(C)C(=O)C3CCN(C(=O)CO)CC3)C(F)(F)F)cc2)cnn2cc(Cl)nc12] | $^1$H NMR (DMSO-$d_6$, 600 MHz) δ ppm 8.48 (s, 1H), 8.28 (s, 1H), 8.01 (s, 1H), 7.0-7.4 (m, 4H), 6.48 (q, 1H, J = 9.1 Hz), 5.08 (q, 1H, J = 6.7 Hz), 4.49 (s, 1H), 4.3-4.4 (m, 1H), 3.9-4.2 (m, 2H), 3.5-3.8 (m, 1H), 3.22 (s, 3H), 3.03 (ddd, 2H, J-3.4, 7.6, 11.1 Hz), 2.92 (s, 3H), 2.6-2.8 (m, 1H), 1.2-1.9 (m, 7H). m/z: 583 [M + H]$^+$. | | |

N-[(1S)-1-[4-[2-chloro-8-[(1S)-1-methoxyethyl]imidazo[1,2-b]pyridazin-7-yl]amino]phenyl]-2,2,2-trifluoro-ethyl]-1-(2-hydroxyacetyl)-N-methyl-piperidine-4-carboxamide

| Example 284 CPD0084933 | Procedure 3 | Intermediate 228 | Yield: 53.5% |
|---|---|---|---|
| 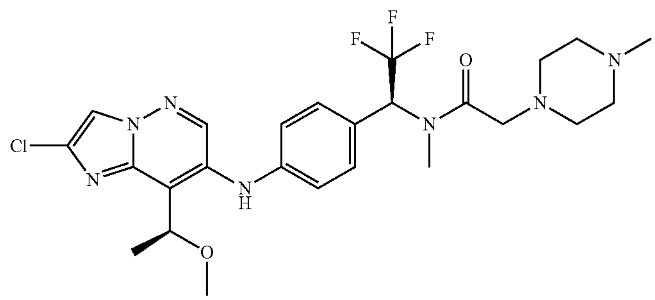 [SMILES: CO[C@@H](C)c1c(Nc2ccc([C@H](N(C)C(=O)CN3CCN(C)CC3)C(F)(F)F)cc2)cnn2cc(Cl)nc12] | $^1$H NMR (DMSO-$d_6$, 600 MHz) δ ppm 8.4-8.5 (m, 1H), 8.2-8.3 (m, 1H), 7.9-8.1 (m, 1H), 7.0-7.5 (m, 4H), 6.2-6.5 (m, 1H), 5.08 (d, 1H, J = 6.7 Hz), 3.0-3.6 (m, 7H), 2.6-3.0 (m, 3H), 2.2-2.5 (m, 6H), 2.0-2.2 (m, 3H), 1.54 (d, 3H, J = 6.7 Hz). m/z: 554 [M + H]$^+$. | | |

N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-2-(4-methylpiperazin-1-yl)acetamide -continued

| Example 285 CPD0084935 | Procedure 3 | Intermediate 228 | Yield: 24% |
|---|---|---|---|

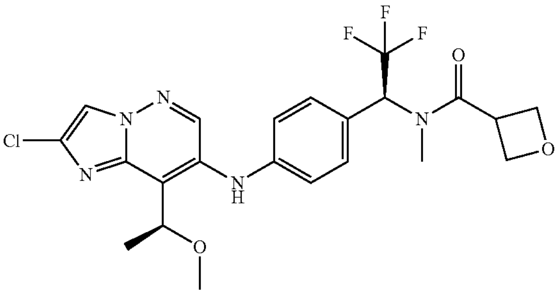 [SMILES: CO[C@@H](C)c1c(Nc2ccc([C@H](N(C)C(=O)C3COC3)C(F)(F)F)cc2)cnn2cc(Cl)nc12]

$^1H$ NMR (DMSO-$d_6$, 500 MHz) δ ppm 1.53 (d, J = 6.60 Hz, 3H) 2.64 (s, 3H) 3.22 (s, 3H) 4.23-4.35 (m, 1H) 4.60-4.81 (m, 4H) 5.04-5.12 (m, 1H) 6.43-6.50 (m, 1H) 7.16 (d, J = 8.80 Hz, 2H) 7.28 (d, J = 8.51 Hz, 2H) 8.01 (s, 1H) 8.28 (s, 1H) 8.47 (s, 1H). m/z: 498 $[M + H]^+$.

N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-oxetane-3-carboxamide

| Example 286 CPD0082473 | Procedure 5 | Intermediate 234 | Yield: 27% |
|---|---|---|---|

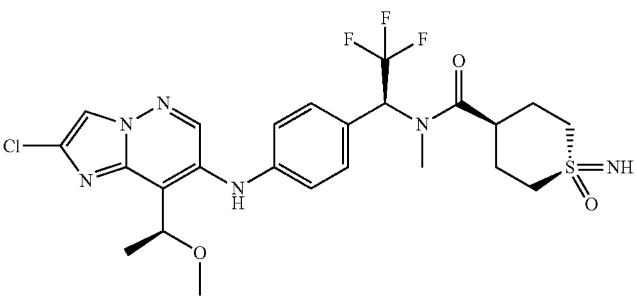 [SMILES: CO[C@@H](C)c1c(Nc2ccc([C@H](N(C)C(=O)[C@H]3CC[S@](=N)(=O)CC3)C(F)(F)F)cc2)cnn2cc(Cl)nc12]

$^1H$ NMR (DMSO-$d_6$, 500 MHz): δ ppm 8.47 (s, 1H), 8.29 (s, 1H), 7.99-8.07 (m, 1H), 7.02-7.43 (m, 4H), 6.00-6.53 (m, 1H), 5.03-5.15 (m, 1H), 3.63-3.80 (m, 5H), 3.25-3.32 (m, 1H), 3.20-3.24 (m, 3H), 2.65-2.94 (m, 3H), 1.94-2.28 (m, 4H), 1.54 (d, J = 6.6 Hz, 3H). m/z: 573 $[M + H]^+$.

(1 rel-r,4 rel-r) N-[(1S)-1-[4-[2-chloro-8-[(1S)-1-methoxyethyl]imidazo[1,2-b]pyridazin-7-yl]amino]phenyl]-2,2,2-trifluoro-ethyl]-1-imino-N-methyl-1-oxo-thiane-4-carboxamide

| Example 287 CPD0082474 | Procedure 5 | Intermediate 234 | Yield: 14% |
|---|---|---|---|

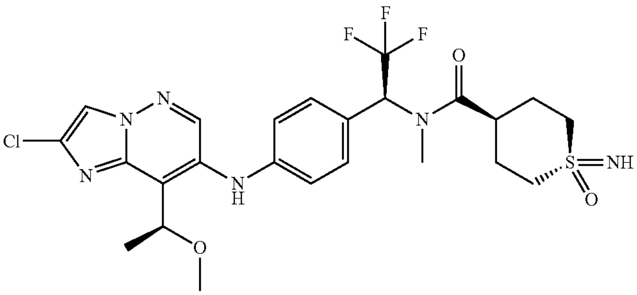 [SMILES: CO[C@@H](C)c1c(Nc2ccc([C@H](N(C)C(=O)[C@H]3CC[S@@](=N)(=O)CC3)C(F)(F)F)cc2)cnn2cc(Cl)nc12]

$^1H$ NMR (DMSO-$d_6$, 500 MHz): δ (ppm) 8.46-8.48 (m, 1H), 8.29 (s, 1H), 8.01-8.06 (m, 1H), 7.13-7.39 (m, 4H), 6.09-6.53 (m, 1H), 5.02-5.15 (m, 1H), 3.42-3.62 (m, 5H), 3.18-3.28 (m, 4H), 2.67-2.95 (m, 3H), 1.99-2.22 (m, 4H), 1.49-1.58 (m, 3H). m/z: 573 $[M + H]^+$.

(1 rel-s,4 rel-s) N-[(1S)-1-[4-[2-chloro-8-[(1S)-1-methoxyethyl]imidazo[1,2-b]pyridazin-7-yl]amino]phenyl]-2,2,2-trifluoro-ethyl]-1-imino-N-methyl-1-oxo-thiane-4-carboxamide

| Example 288 CPD0082472 | Procedure 1b-c | Intermediate 228 and 224 | Yield 31% |
|---|---|---|---|

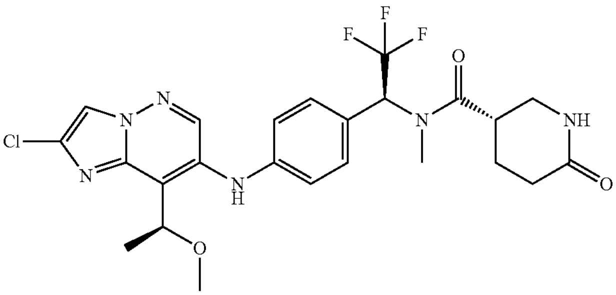 [SMILES: CO[C@@H](C)c1c(Nc2ccc([C@H](N(C)C(=O)[C@H]3CCC(=O)NC3)C(F)(F)F)cc2)cnn2cc(Cl)nc12]

$^1H$ NMR (500 MHz, DMSO-$d_6$) δ ppm 1.54 (d, J = 6.60 Hz, 3H) 1.74-1.96 (m, 2H) 2.14-2.31 (m, 2H) 2.94 (s, 3H) 3.15-3.21 (m, 1H) 3.22 (s, 3H) 3.24-3.29 (m, 2H) 5.09 (d, J = 6.85 Hz, 1H) 6.21-6.54 (m, 1H) 7.17 (d, J = 8.80 Hz, 2H) 7.23-7.41 (m, 2H) 7.49 (br s, 1H) 8.02 (s, 1H) 8.29 (s, 1H) 8.48 (s, 1H). m/z :539 $[M + H]^+$.

-continued

| (3 rel R)-N-[(1 S)-1-[4-[2-chloro-8-[(1S)-1-methoxyethyl]imidazo[1,2-b]pyridazin-7-yl]amino]phenyl]-2,2,2-trifluoro-ethyl]-N-methyl-6-oxo-piperidine-3-carboxamide | | | |
|---|---|---|---|
| Example 289 CPD0082471 | Procedure<br>1b-c | Intermediate<br>228 and 224 | Yield:<br>34% |
| 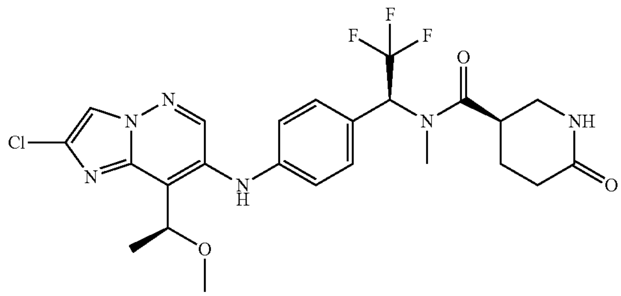 [SMILES: CO[C@@H](C)c1c(Nc2ccc([C@H](N(C)C(=O)[C@@H]3CCC(=O)NC3)C(F)(F)F)cc2)cnn2cc(Cl)nc12] | $^1$H NMR (500 MHz, DMSO-$d_6$) δ ppm 1.54 (d, J = 6.60 Hz, 3H) 1.71-2.03 (m, 2H) 2.14-2.33 (m, 2H) 2.35-2.46 (m, 1H) 2.94 (s, 3H) 3.12-3.22 (m, 2H) 3.22 (s, 3H) 5.01-5.17 (m, 1H) 6.20-6.59 (m, 1H) 7.16 (d, J = 8.80 Hz, 2H) 7.28 (d, J = 8.56 Hz, 2H) 7.48 (br d, J = 2.69 Hz, 1H) 8.01 (s, 1H) 8.28 (s, 1H) 8.48 (s, 1H). m/z: 539 [M + H]$^+$. | | |
| (3 rel S)-N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-6-oxo-piperidine-3-carboxamide | | | |
| Example 290 CPD0082469 | Procedure 2 | Intermediate<br>231 | Yield:<br>69% |
| 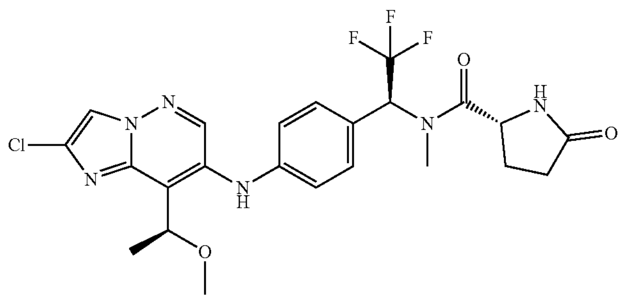 [SMILES: CO[C@@H](C)c1c(Nc2ccc([C@H](N(C)C(=O)[C@H]3CCC(=O)N3)C(F)(F)F)cc2)cnn2cc(Cl)nc12] | $^1$H NMR (DMSO-$d_6$, 500 MHz) δ ppm 1.54 (d, J = 6.85 Hz, 4H) 1.73-1.95 (m, 1H) 2.08-2.23 (m, 2H) 2.90 (s, 3H) 3.22 (s, 3H) 4.66 (dd, J = 9.29, 4.16 Hz, 1H) 4.96-5.14 (m, 1H) 6.45 (q, J = 9.21 Hz, 1H) 7.17 (d, J = 8.80 Hz, 2H) 7.29 (d, J = 8.31 Hz, 2H) 7.80 (s, 1H) 8.02 (s, 1H) 8.29 (s, 1H) 8.48 (s, 1H). m/z: 525 [M + H]$^+$. | | |
| (2R)-N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-5-oxo-pyrrolidine-2-carboxamide | | | |
| Example 291 CPD0082470 | Procedure | Intermediate<br>232 | Yield:<br>93% |
| 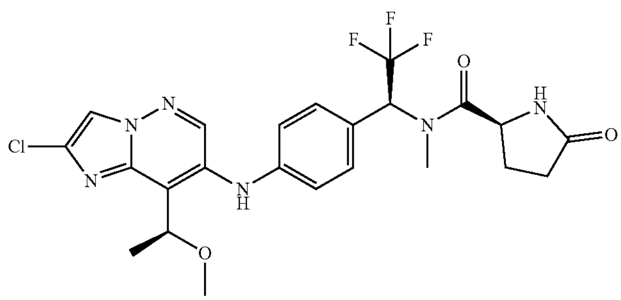 [SMILES: CO[C@@H](C)c1c(Nc2ccc([C@H](N(C)C(=O)[C@@H]3CCC(=O)N3)C(F)(F)F)cc2)cnn2cc(Cl)nc12] | $^1$H NMR (DMSO-$d_6$, 500 MHz) δ ppm 1.54 (d, J = 6.85 Hz, 3H) 1.70-1.90 (m, 1H) 2.05-2.26 (m, 2H) 2.32-2.42 (m, 1H) 2.86 (s, 3H) 3.22 (s, 3H) 4.65 (dd, J = 8.80, 3.91 Hz, 1H) 5.08 (q, J = 6.60 Hz, 1H) 6.42 (q, J = 9.37 Hz, 1H) 7.11-7.23 (m, 2H) 7.27 (d, J = 8.56 Hz, 2H) 7.92 (s, 1H) 8.02 (s, 1H) 8.29 (s, 1H) 8.49 (s, 1H). m/z: 525 [M + H]$^+$ | | |
| (2S)-N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-5-oxo-pyrrolidine-2-carboxamide | | | |

-continued

| Example 292 CPD0084508 | Procedure 1b | Intermediate 219-b | Yield: 20% |
|---|---|---|---|

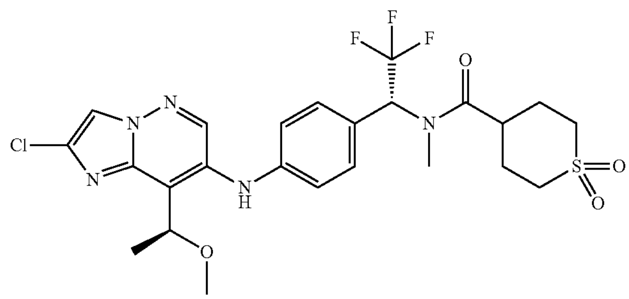 [SMILES: CO[C@@H](C)c1c(Nc2ccc([C@@H](N(C)C(=O)C3CCS(=O)(=O)CC3)C(F)(F)F)cc2)cnn2cc(Cl)nc12]

$^1$H NMR (600 MHz, DMSO-$d_6$) δ ppm 8.47 (s, 1H), 8.28 (s, 1H), 8.01 (s, 1H), 7.27 (d, J = 8.5 Hz, 2H), 7.16 (d, J = 8.5 Hz, 2H), 6.47 (q, J = 9.2 Hz, 1H), 5.08 (d, J = 6.7 Hz, 1H), 3.22 (s, 8H), 2.92 (s, 3H), 2.20-1.92 (m, 4H), 1.53 (d, J = 6.6 Hz, 3H) m/z: 575 $[M + H]^+$.

N-[(1S)-1-[4-[2-chloro-8-[(1S)-1-methoxyethyl]imidazo[1,2-b]pyridazin-7-yl]amino]phenyl]-2,2,2-trifluoro-ethyl]-N-methyl-1,1-dioxo-thiane-4-carboxamide

| Example 293 CPD0084509 | Procedure 1b-c | Intermediate 219-b and | Yield: 35% |
|---|---|---|---|

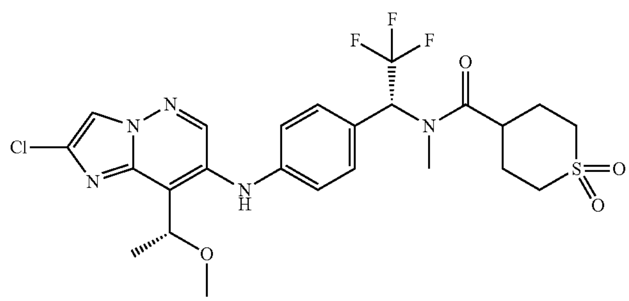 [SMILES: CO[C@H](C)c1c(Nc2ccc([C@@H](N(C)C(=O)C3CCS(=O)(=O)CC3)C(F)(F)F)cc2)cnn2cc(Cl)nc12]

$^1$H NMR (500 MHz, DMSO-$d_6$) δ ppm 8.53-8.46 (m, 1H), 8.29 (s, 1H), 8.01 (s, 1H), 7.39-7.24 (m, 2H), 7.16 (d, J = 8.8 Hz, 2H), 6.47 (br d, J = 9.5 Hz, 1H), 5.09 (d, J = 6.8 Hz, 1H), 3.29-3.24 (m, 1H), 3.23-3.21 (m, 3H), 3.21-3.05 (m, 4H), 2.92 (s, 3H), 2.18-1.89 (m, 4H), 1.54 (d, J = 6.6 Hz, 3H). m/z: 575 [M + H]+.

N-[(1S)-1-[4-[2-chloro-8-[(1R)-1-methoxyethyl]imidazo[1,2-b]pyridazin-7-yl]amino]phenyl]-2,2,2-trifluoro-ethyl]-N-methyl-1,1-dioxo-thiane-4-carboxamide

| Example 294 CPD0084139 | Procedure 6 | Intermediate 237 | Yield: 22% |
|---|---|---|---|

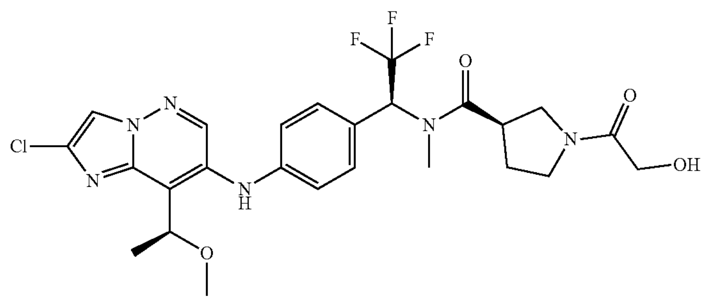 [SMILES: CO[C@@H](C)c1c(Nc2ccc([C@H](N(C)C(=O)[C@@H]3CCN(C(=O)CO)C3)C(F)(F)F)cc2)cnn2cc(Cl)nc12]

$^1$H NMR (500 MHz, DMSO-$d_6$) δ ppm 8.48 (m, 1H), 8.29 (d, J = 1.0 Hz, 1H), 8.02 (s, 1 (H), 7.27 (m, 4H), 6.48 (d, J = 9.5 Hz, 1H), 5.09 (d, J = 6.6 Hz, 1H), 4.54 (q, J = 5.6 Hz, 1H), 4.00 (m, 2H), 3.50 (m, 5 H), 3.22 (s, 3H), 2.93 (s, 3H), 2.07 (s, 2H), 1.54 (d, J = 6.6 Hz, 3H) m/z: 569 $[M + H]^+$.

(3 rel S)-N-[(1S)-1-[4-[2-chloro-8-[(1S)-1-methoxyethyl]imidazo[1,2-b]pyridazin-7-yl]amino]phenyl]-2,2,2-trifluoro-ethyl]-1-(2-hydroxyacetyl)-N-methyl-pyrrolidine-3-carboxamide -continued

| Example 295 CPD0084130 | Procedure 6 | Intermediate 237 | Yield: 16% |
|---|---|---|---|
| 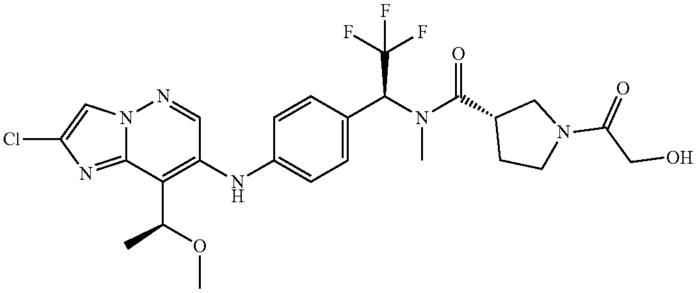 [SMILES: CO[C@@H](C)c1c(Nc2ccc([C@H](N(C)C(=O)[C@H]3CCN(C(=O)CO)C3)C(F)(F)F)cc2)cnn2cc(Cl)nc12] | $^1H$ NMR (500 MHz, DMSO-$d_6$) δ ppm 8.48 (s, 1H), 8.29 (s, 1H), 8.02 (s, 1H), 7.29 (m, 4H), 6.34 (m, 1H), 5.09 (q, J = 6.8 Hz, 1H), 4.55 (t, J = 5.6 Hz, 1H), 4.00 (m, 2H), 3.61 (m, 5H), 3.22 (s, 3H), 2,93 (s, 3H), 2.01 (m, 2H), 1.54 (d, J = 6.6 Hz, 3H). m/z: 569 $[M + H]^+$. | | |
| (3 rel R)-N-[(1S)-1-[4-[2-chloro-8-[(1S)-1-methoxyethyl]imidazo[1,2-b]pyridazin-7-yl]amino]phenyl]-2,2,2-trifluoro-ethyl]-1-(2-hydroxyacetyl)-N-methyl-pyrrolidine-3-carboxamide | | | |

Example 296—Biological Assays

MALT-1 Inhibition Assay

MALT-1 paracaspase activity was measured using the fluorogenic substrate Ac-LRSR-Rh110-DP (purchased from Biosantan GmbH). Proteolytic cleavage of the peptide—rhodamine conjugate results in an increase of rhodamine fluorescence which is inhibited by test compounds. Test compounds were diluted in DMSO in a series of 10 semi-log step doses, 15 nL of each compound dose were dispensed in 384 well polypropylene plates (HiBase non-binding, Greiner Bio-One cat #784900). All other assay components were diluted to appropriate working concentrations in assay buffer composed of: 200 mM Tris-HCl (pH 7.5; Sigma-Aldrich cat #T2663-1L), 0.1 mM EGTA (Sigma-Aldrich cat #E3889-10G), 0.05% CHAPS-Sigma-Aldrich cat #C9426-1G), 1 mM TCEP (Sigma-Aldrich cat #646547-10×1 mL), 0.8 M sodium citrate (Sigma-Aldrich cat #S1804-500G). Recombinant human MALT-1 (amino acids 340-824, accession NP_006776.1) was added to compound doses and equilibrated for 40 minutes at rt. The reaction was initiated by addition of substrate. Final concentrations of MALT-1 and substrate were 3 nM and 10 μM respectively. Reactions were incubated in the dark for 60 minutes at 25° C. Fluorescence was measured in a PHERAstar FSX plate reader (BMG LABTECH) with optical setup for excitation at 485 nM and emission at 520 nM, focal height of 11.8 mm, 20 flashes, gain 300. Percent inhibition values were calculated from relative fluorescence units at different doses and fitted to a 4-parameter logistic curve to determine IC50 values (see Table 1).

Effector Memory T Cells IL-2 Release Assay

Test compound-mediated inhibition of NFκB signalling in T cells was assessed by quantification of the IL-2 secretion by human effector memory T cells (TEM) upon treatment and stimulation. Human TEM cells were isolated from buffy coats of healthy donors obtained from the French blood bank. First, peripheral blood mononuclear cells (PBMC) were purified from buffy coats diluted 1:1 with DPBS (Gibco, cat #14190-094) by Pancoll (PAN BIOTECH, cat #P04-60500) density gradient centrifugation at 400×g for 20 minutes. TEM cells were further enriched by negative immuno-magnetic cell sorting using a human CD4+ Effector Memory T Cell Isolation Kit (Miltenyi, cat #130-094-125) according to the manufacturer's instructions. Aliquots of 3×10E6 purified TEM cells were kept frozen in Cryo-SFM medium (PromoCell, cat #C-29912) in gas phase nitrogen until used. Cell purity was verified by flow cytometry analysis of 200 000 PFA-fixed cells previously labelled with monoclonal antibodies anti-CD4-PerCP-Cy5.5 (BD Pharmigen, cat #332772), anti-CD8-V500 (BD Biosciences, cat #561617), anti-CD14-Pacific Blue (Biolegend, cat #325616), anti-CD45 RA-FITC (Biolegend, cat #304106) and anti-CCR7-APC (in CD4+ Effector Memory T Cell Isolation Kit, Miltenyi, cat #130-094-125).

TEM cells were resuspended in complete RPMI medium composed of: RPMI 1640 (Gibco, cat #31870-025), 10% heat inactivated fetal bovine serum (Sigma, cat #F7524), 2 mM GlutaMAX (Gibco, cat #35050-038), 1 mM sodium pyruvate 100× (Gibco, cat #11360-039), 1% MEM non-essential amino acids solution (Gibco, cat #11140-035) and 100 U/mL penicillin, 100 μg/mL streptomycin (Sigma-Aldrich, cat #11074440001). 5,000 cells per well were plated onto flat clear bottom 384 well plates (Corning, cat #3770). 5,000 Dynabeads Human T-Activator CD3/CD28 (Gibco, cat #11132D) were added to each well for cell stimulation. Finally, 10 doses of test compound, originally prepared in DMSO by serial semi-log step dilution, were also added to cells in triplicate wells. Final DMSO concentration in wells was 0.1% in a total volume of 100 μL complete medium. Plates were incubated for 24 h at 37° C. in 5% $CO_2$ atmosphere. After incubation, cell suspensions were centrifuged at 400×g and culture supernatants were recovered and stored at −80° C. Cell viability was assessed by flow cytometry after staining the cells with Fixable Viability Dye eFluor 780 (Invitrogen, cat #65-086514). IL-2 levels were determined in cell supernatants using an HTRF human IL-2 detection kit (Cisbio, cat #62HIL02PEH). IL-2 data at the different compound doses were fitted to a 4-parameter logistic curve to determine IC50 values, corresponding to the compound concentration leading to 50% reduction of the maximal IL-2 levels observed in each experiment. Viability data were analysed similarly to exclude cytotoxicity as a cause of IL-2 decrease (see Table 1).

TABLE 1

IC50 biochemical data for representative compounds of the disclosure.

| Compound Reference | Structure | MALT-1 IC50 [nM] | CD4TC IL2 IC50 [nm] |
|---|---|---|---|
| CPD0084141 | 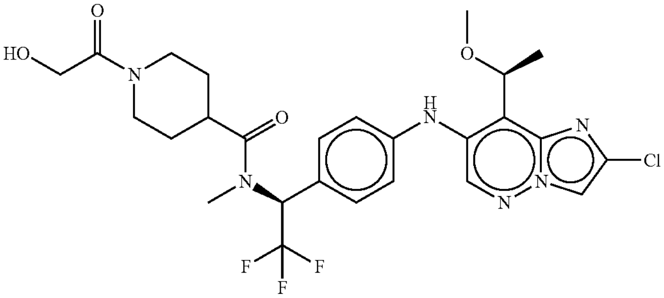<br>CO[C@@H](C)c1c(Nc2ccc(cc2)[C@H](N(C)C(=O)<br>C3CCN(CC3)C(=O)CO)C(F)(F)F)cnn4cc(Cl)nc14 | 43 | |
| CPD0084140 | 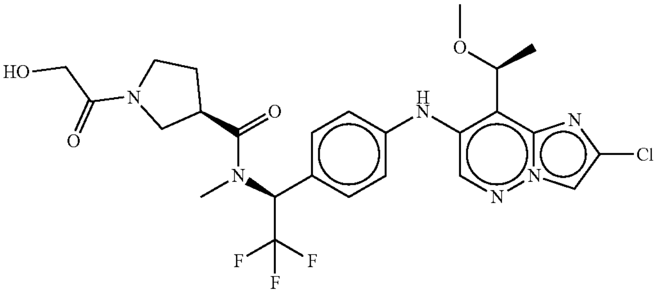<br>CO[C@@H](C)c1c(Nc2ccc(cc2)[C@H](N(C)C(=O)<br>[C@@H]3CCN(C3)C(=O)CO)C(F)(F)F)cnn4cc(Cl)nc<br>14 | 45 | |
| CPD0075581 | 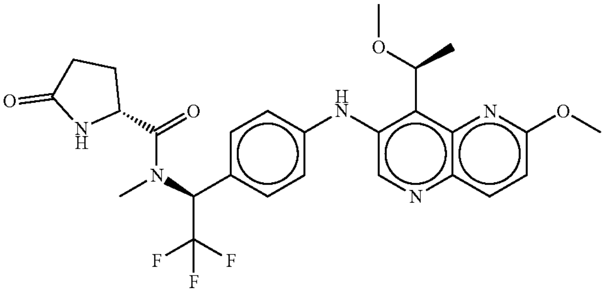<br>CO[C@@H](C)c1c(Nc2ccc(cc2)[C@H](N(C)C(=O)<br>[C@H]3CCC(=O)N3)C(F)(F)F)cnc4ccc(OC)nc14 | 37 | 29 |
| CPD0075580 | 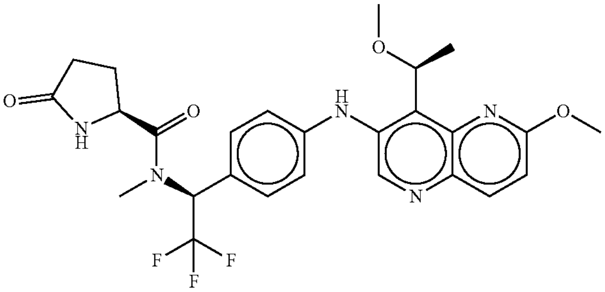<br>CO[C@@H](C)c1c(Nc2ccc(cc2)[C@H](N(C)C(=O)<br>[C@@H]3CCC(=O)N3)C(F)(F)F)cnc4ccc(OC)nc14 | 47 | 35 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073565 | 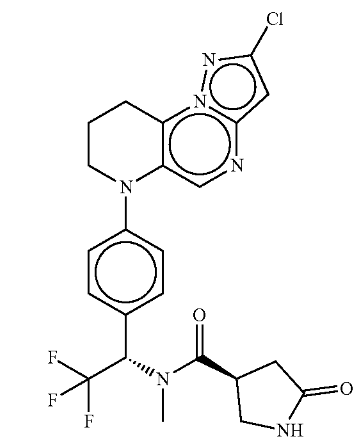 CN([C@@H](c1ccc(cc1)N2CCCc3c2cnc4cc(Cl)nn34)C(F)(F)F)C(=O)[C@@H]5CNC(=O)C5 | 43 | 101 |
| CPD0073130 | 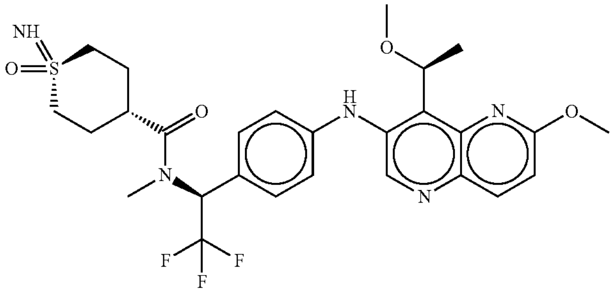 CO[C@@H](C)c1c(Nc2ccc(cc2)[C@H](N(C)C(=O)[C@@H]3CC[S@@](=N)(=O)CC3)C(F)(F)F)cnc4ccc | 61 | 24 |
| CPD0072783 | 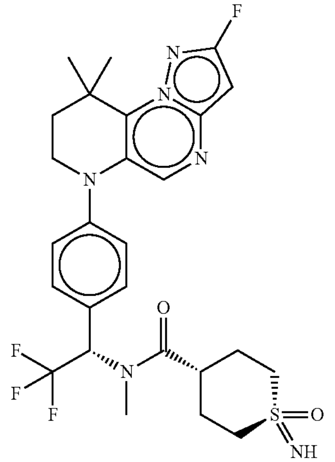 CN([C@@H](c1ccc(cc1)N2CCC(C)(C)c3c2cnc4cc F)nn34)C(F)(F)F)C(=O)[C@@H]5CC[S@@](=N)(=O)CC5 | 63 | 114 |

TABLE 1-continued

IC50 biochemical data for representative compounds of the disclosure.

| Compound Reference | Structure | MALT-1 IC50 [nM] | CD4TC IL2 IC50 [nm] |
|---|---|---|---|
| CPD0075882 | 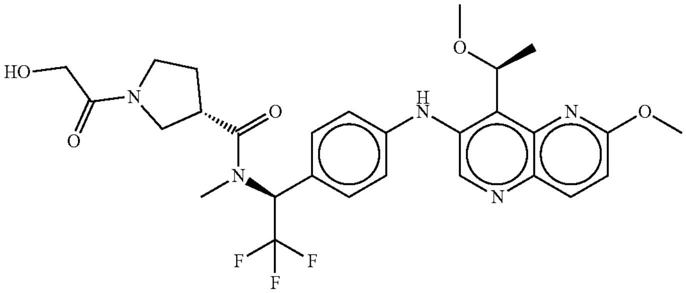 CO[C@@H](C)c1c(Nc2ccc(cc2)[C@H](N(C)C(=O)[C@H]3CCN(C3)C(=O)CO)C(F)(F)F)cnc4ccc(OC)nc14 | 64 | 40 |
| CPD0073129 | 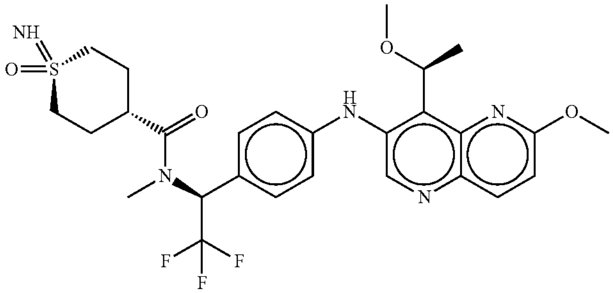 CO[C@@H](C)c1c(Nc2ccc(cc2)[C@H](N(C)C(=O)[C@@H]3CC[S@](=N)(=O)CC3)C(F)(F)F)cnc4ccc(OC)nc14 | 64 | 36 |
| CPD0075883 | 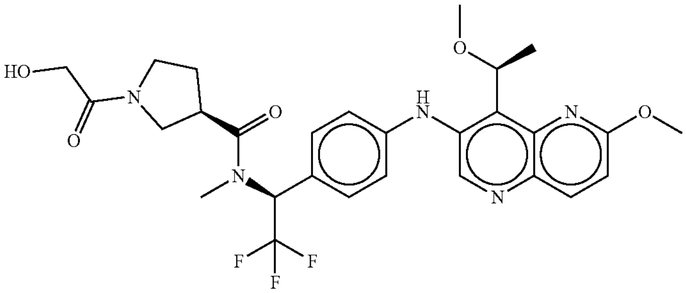 CO[C@@H](C)c1c(Nc2ccc(cc2)[C@H](N(C)C(=O)[C@@H]3CCN(C3)C(=O)CO)C(F)(F)F)cnc4ccc(OC)nc14 | 52 | 47 |
| CPD0072936 | 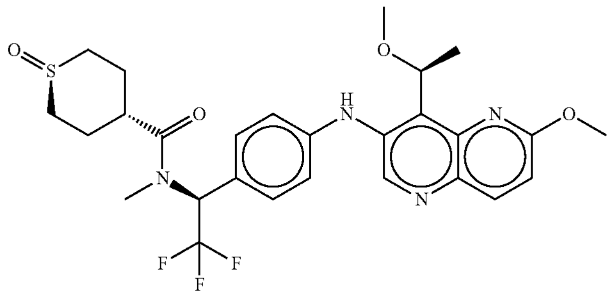 CO[C@@H](C)c1c(Nc2ccc(cc2)[C@H](N(C)C(=O)[C@@H]3CC[S@@](=O)CC3)C(F)(F)F)cnc4ccc(OC)nc14 | 68 | 17 |

TABLE 1-continued

IC50 biochemical data for representative compounds of the disclosure.

| Compound Reference | Structure | MALT-1 IC50 [nM] | CD4TC IL2 IC50 [nm] |
|---|---|---|---|
| CPD0082482 | 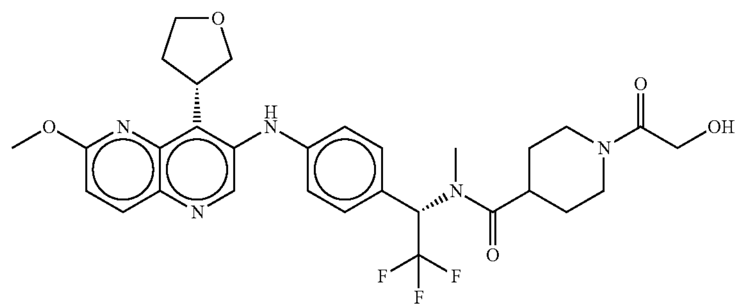<br>COc1ccc2ncc(Nc3ccc(cc3)[C@H](N(C)C(=O)<br>C4CCN(CC4)C(=O)CO)C(F)(F)F)c([C@@H]<br>5CCOC5)c2n1 | 72 | |
| CPD0082481 | 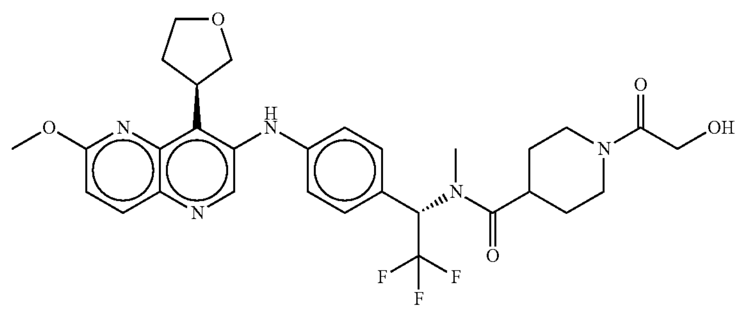<br>COc1ccc2ncc(Nc3ccc(cc3)[C@H](N(C)C(=O)<br>C4CCN(CC4)C(=O)CO)C(F)(F)F)c([C@H]<br>5CCOC5)c2n1 | 73 | |
| CPD0072935 | 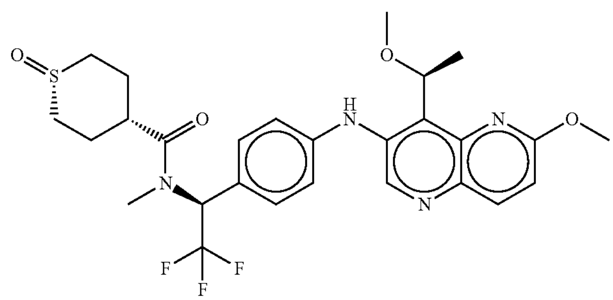<br>CO[C@@H](C)c1c(Nc2ccc(cc2)[C@H](N(C)C(=O)<br>[C@@H]3CC[S@](=O)CC3)C(F)(F)F)cnc4ccc<br>(OC)nc14 | 75 | 34 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0019481 | 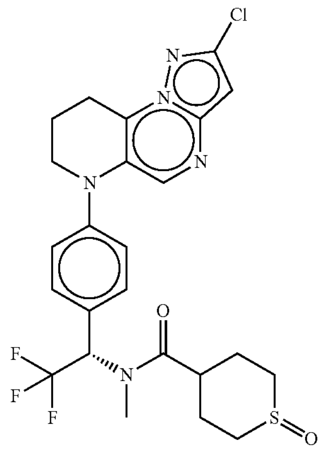 CN([C@@H](c1ccc(cc1)N2CCCc3c2cnc4cc(Cl)nn34)C(F)(F)F)C(=O)C5CCS(=O)CC5 | 76 | 86 |
| CPD0084139 | 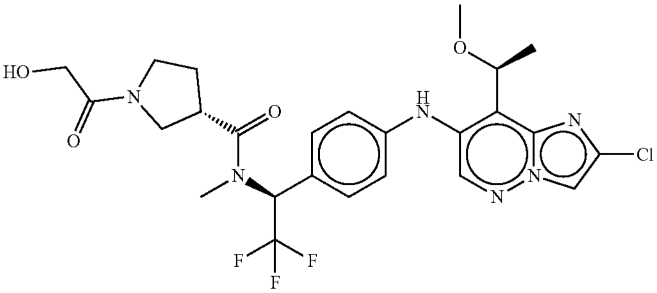 CO[C@@H](C)c1c(Nc2ccc(cc2)[C@H](N(C)C(=O)[C@H]3CCN(C3)C(=O)CO)C(F)(F)F)cnn4cc(Cl)nc14 | 52 | |
| CPD0073133 | 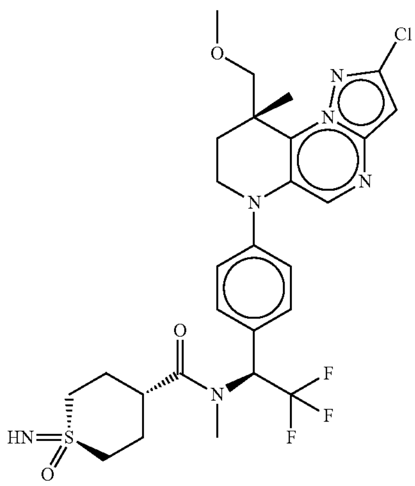 COC[C@@]1(C)CCN(c2ccc(cc2)[C@H](N(C)C(=O)[C@@H]3CC[S@](=N)(=O)CC3)C(F)(F)F)c4cnc5cc(Cl)nn5c14 | 81 | 64 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0074040 | 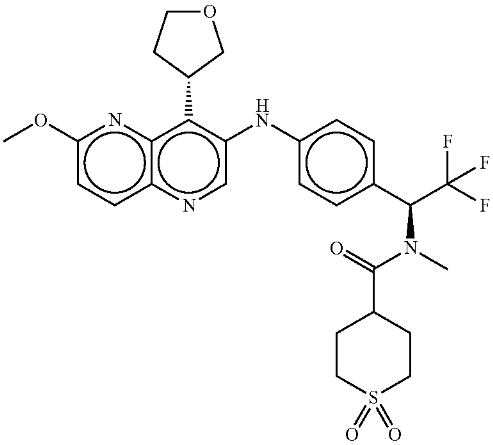 COc1ccc2ncc(Nc3ccc(cc3)[C@H](N(C)C(=O)C4CCS(=O)(=O)CC4)C(F)(F)F)c([C@@H]5CCOC5)c2n1 | 83 | 33 |
| CPD0072853 | 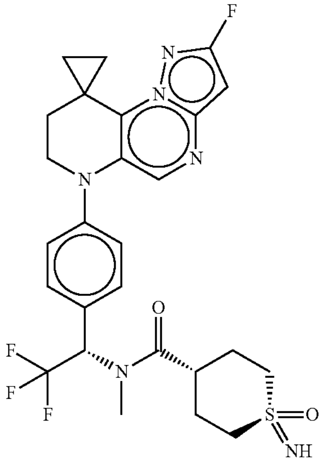 CN([C@@H](c1ccc(cc1)N2CCC3(CC3)c4c2cnc5cc(F)nn45)C(F)(F)F)C(=O)[C@@H]6CC[S@@](=N)(=O)CC6 | 23 | 62 |

TABLE 1-continued
IC50 biochemical data for representative compounds of the disclosure.
| Compound Reference | Structure | MALT-1 IC50 [nM] | CD4TC IL2 IC50 [nm] |
| --- | --- | --- | --- |
| CPD0073134 | 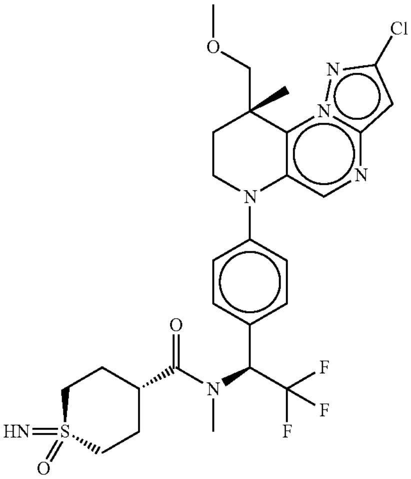<br>COC[C@@]1(C)CCN(c2ccc(cc2)[C@H](N(C)C(=O)[C@@H]3CC[S@@](=N)(=O)CC3)C(F)(F)F)c4cnc5cc(Cl)nn5c14 | 85 | 57 |
| CPD0072850 | 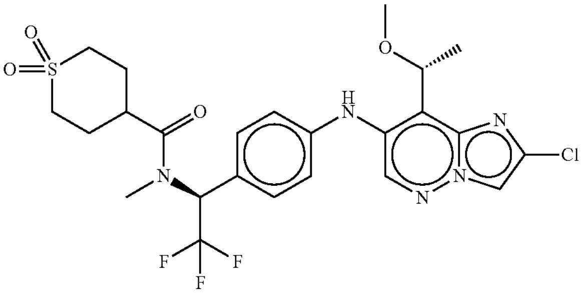<br>CO[C@H](C)c1c(Nc2ccc(cc2)[C@H](N(C)C(=O)C3CCS(=O)(=O)CC3)C(F)(F)F)cnn4cc(Cl)nc14 | 43 | 114 |
| CPD0073976 | 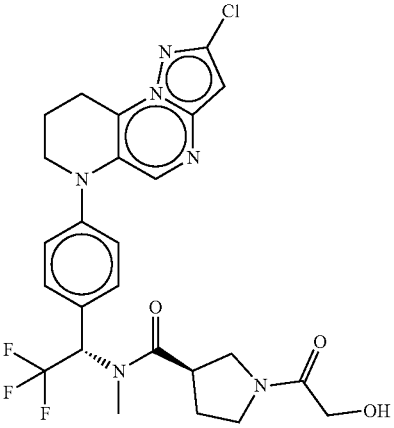<br>CN([C@@H](c1ccc(cc1)N2CCCc3c2cnc4cc(Cl)nn34)C(F)(F)F)C(=O)[C@@H]5CCN(C5)C(=O)CO | 57 | 149 |

TABLE 1-continued

IC50 biochemical data for representative compounds of the disclosure.

| Compound Reference | Structure | MALT-1 IC50 [nM] | CD4TC IL2 IC50 [nm] |
|---|---|---|---|
| CPD0019499 | 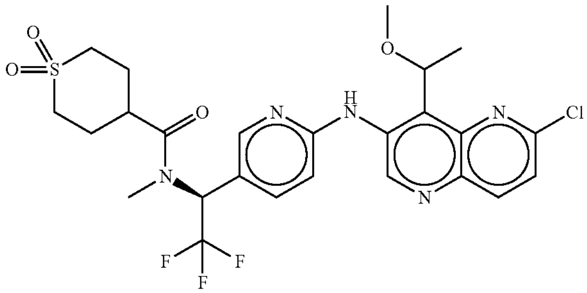 COC(C)c1c(Nc2ccc(cn2)[C@H](N(C)C(=O)C3CCS(=O)(=O)CC3)C(F)(F)F)cnc4ccc(Cl)nc14 | 80 | 190 |
| CPD0084143 | 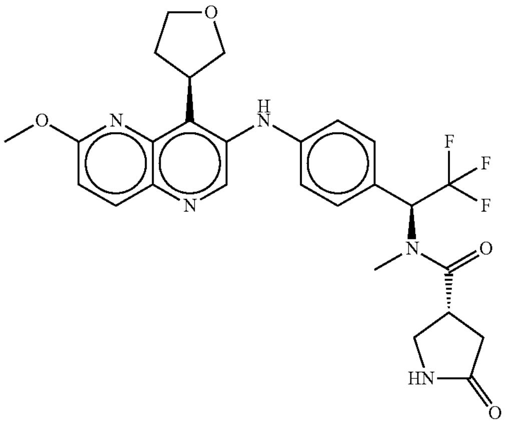 COc1ccc2ncc(Nc3ccc(cc3)[C@H](N(C)C(=O)[C@H]4CNC(=O)C4)C(F)(F)F)c([C@H]5CCOC5)c2n1 | 72 | |
| CPD0082480 | 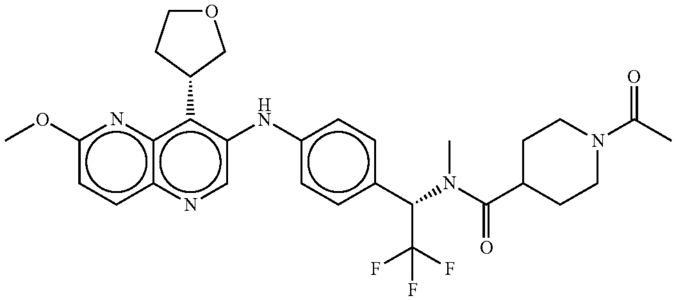 COc1ccc2ncc(Nc3ccc(cc3)[C@H](N(C)C(=O)C4CCN(CC4)C(=O)C)C(F)(F)F)c([C@@H]5CCOC5)c2n1 | 77 | |
| CPD0072526 | 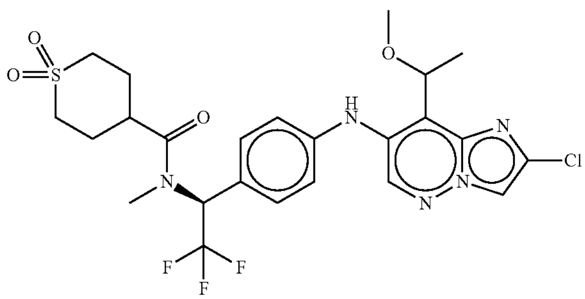 COC(C)c1c(Nc2ccc(cc2)[C@H](N(C)C(=O)C3CCS(=O)(=O)CC3)C(F)(F)F)cnn4cc(Cl)nc14 | 47 | 71 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0075564 | 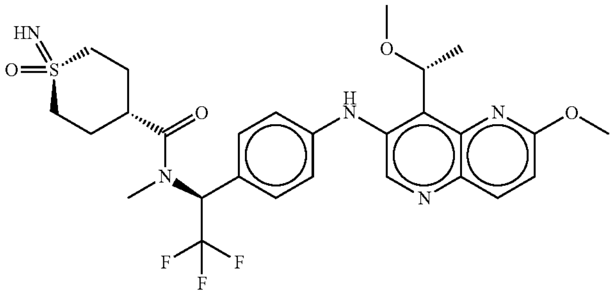 CO[C@H](C)c1c(Nc2ccc(cc2)[C@H](N(C)C(=O)[C@@H]3CC[S@](=N)(=O)CC3)C(F)(F)F)cnc4ccc(OC)nc14 | 89 | 175 |
| CPD0075577 | 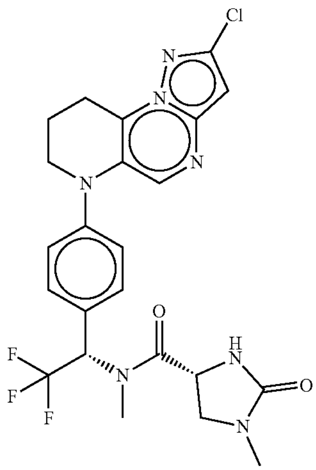 CN([C@@H](c1ccc(cc1)N2CCCc3c2cnc4cc(Cl)nn34)C(F)(F)F)C(=O)[C@H]5CN(C)C(=O)N5 | 42 | |
| CPD0074039 | 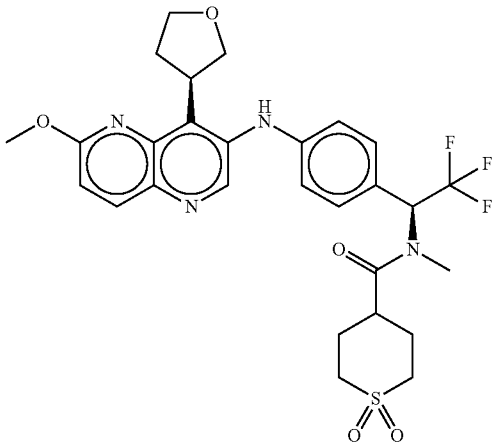 COc1ccc2ncc(Nc3ccc(cc3)[C@H](N(C)C(=O)C4CCS(=O)(=O)CC4)C(F)(F)F)c([C@H]5CCOC5)c2n1 | 138 | 34 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073567 | 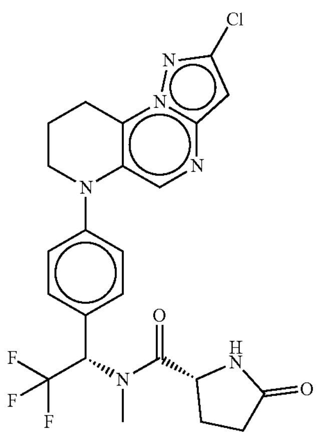 CN([C@@H](c1ccc(cc1)N2CCCc3c2cnc4cc(Cl)nn34)C(F)(F)F)C(=O)[C@H]5CCC(=O)N5 | 35 | 119 |
| CPD0073977 | 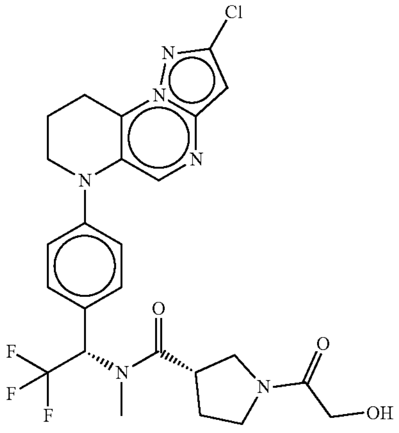 CN([C@@H](c1ccc(cc1)N2CCCc3c2cnc4cc(Cl)nn34)C(F)(F)F)C(=O)[C@H]5CCN(C5)C(=O)CO | 39 | 115 |
| CPD0074559 | 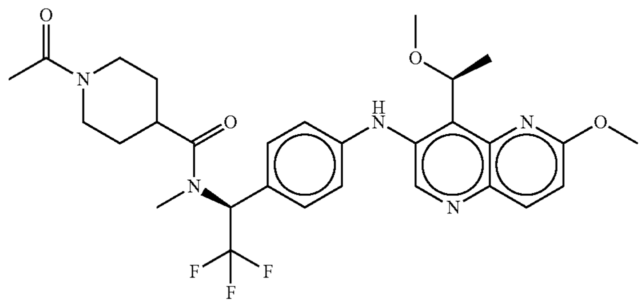 CO[C@@H](C)c1c(Nc2ccc(cc2)[C@H](N(C)C(=O)C3CCN(CC3)C(=O)C)C(F)(F)F)cnc4ccc(OC)nc14 | 153 | 27 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073563 | 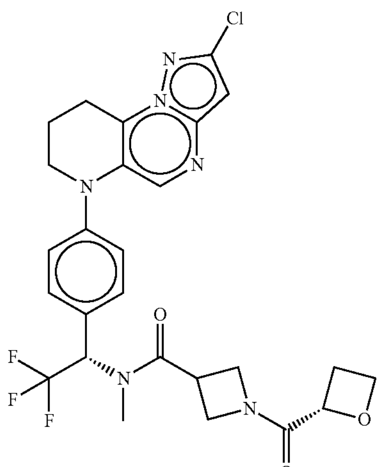 CN([C@@H](c1ccc(cc1)N2CCCc3c2cnc4cc(Cl)nn34)C(F)(F)F)C(=O)C5CN(C5)C(=O)[C@@H]6CCO6 | 62 | 269 |
| CPD0072852 | 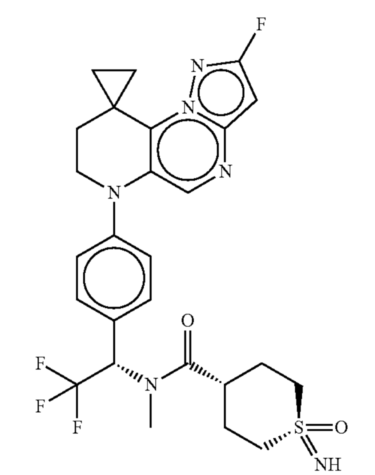 CN([C@@H](c1ccc(cc1)N2CCC3(CC3)c4c2cnc5cc(F)nn45)C(F)(F)F)C(=O)[C@@H]6CC[S@](=N)(=O)CC6 | 28 | 65 |
| CPD0077186 | 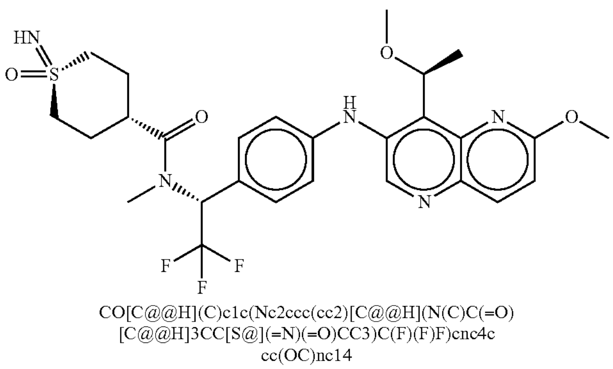 CO[C@@H](C)c1c(Nc2ccc(cc2)[C@@H](N(C)C(=O)[C@@H]3CC[S@](=N)(=O)CC3)C(F)(F)F)cnc4ccc(OC)nc14 | 126 | 158 |

TABLE 1-continued

| IC50 biochemical data for representative compounds of the disclosure. | | | |
|---|---|---|---|
| Compound Reference | Structure | MALT-1 IC50 [nM] | CD4TC IL2 IC50 [nm] |
| CPD0075563 | 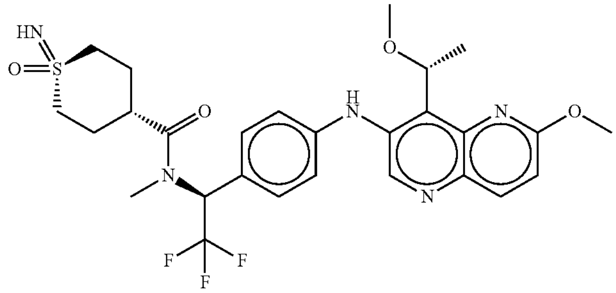 CO[C@H](C)c1c(Nc2ccc(cc2)[C@H](N(C)C(=O)[C@@H]3CC[S@@](=N)(=O)CC3)C(F)(F)F)cnc4ccc(OC)nc14 | 102 | 257 |
| CPD0074562 | 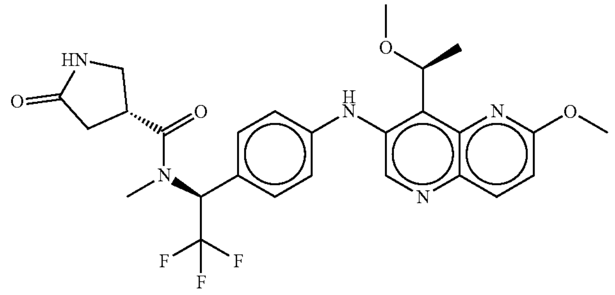 CO[C@@H](C)c1c(Nc2ccc(cc2)[C@H](N(C)C(=O)[C@H]3CNC(=O)C3)C(F)(F)F)cnc4ccc(OC)nc14 | 79 | 68 |
| CPD0082467 | 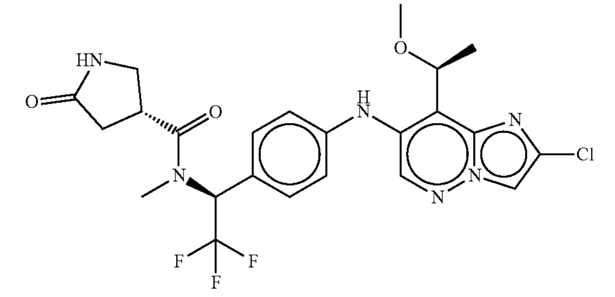 CO[C@@H](C)c1c(Nc2ccc(cc2)[C@H](N(C)C(=O)[C@H]3CNC(=O)C3)C(F)(F)F)cnn4cc(Cl)nc14 | 42 | |
| CPD0082468 | 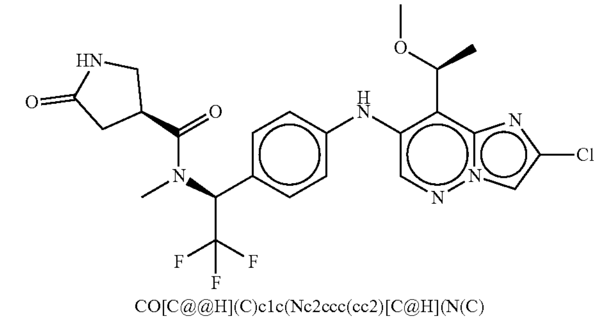 CO[C@@H](C)c1c(Nc2ccc(cc2)[C@H](N(C)C(=O)[C@@H]3CNC(=O)C3)C(F)(F)F)cnn4cc(Cl)nc14 | 37 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0082477 | 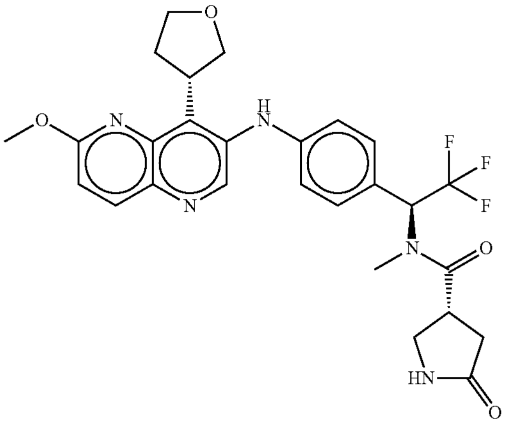 COc1ccc2ncc(Nc3ccc(cc3)[C@H](N(C)C(=O)[C@H]4CNC(=O)C4)C(F)(F)F)c([C@@H]5CCOC5)c2n1 | 41 | |
| CPD0077187 | 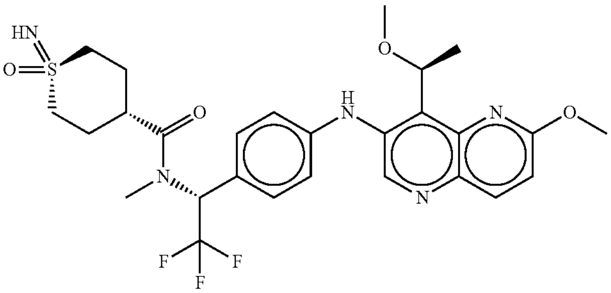 CO[C@@H](C)c1c(Nc2ccc(cc2)[C@@H](N(C)C(=O c4ccc(OC | 117 | 209 |
| CPD0073226 | 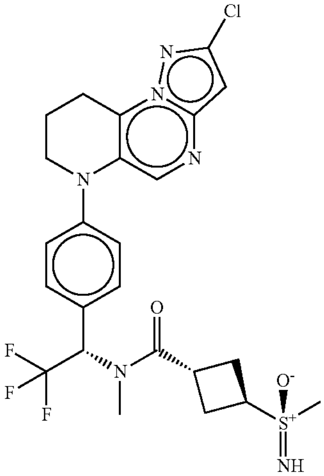 CN([C@@H](c1ccc(cc1)N2CCCc3c2cnc4cc(Cl)nn34)C(F)(F)F)C(=O)[C@@H]5C[C@H](C5)[S@@+](=N)(C)[O-] | 60 | 105 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073920 | 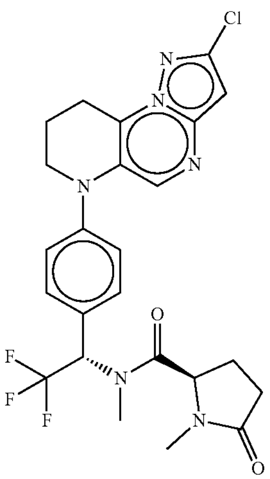 CN([C@@H](c1ccc(cc1)N2CCCc3c2cnc4cc(Cl)nn34)C(F)(F)F)C(=O)[C@H]5CCC(=O)N5C | 60 | 94 |
| CPD0074556 | 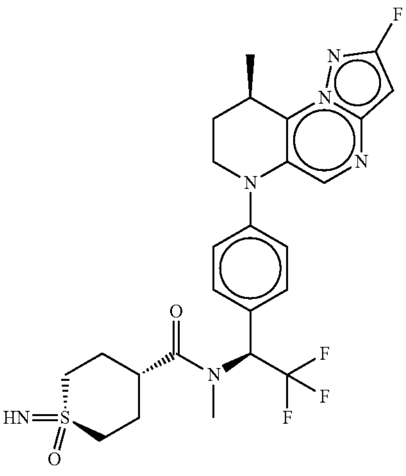 C[C@@H]1CCN(c2ccc(cc2)[C@H](N(C)C(=O)[C@@H]3CC[S@](=N)(=O)CC3)C(F)(F)F)c4cnc5cc(F)nn5c14 | 62 | 168 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0022137 | 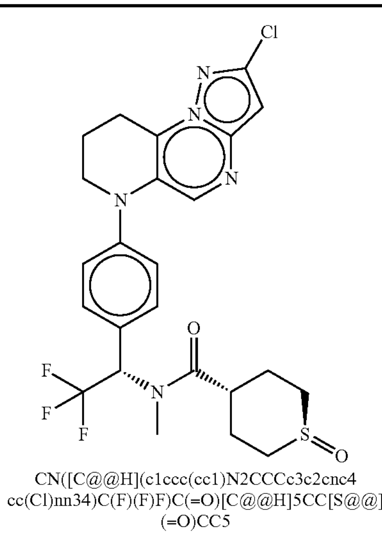 CN([C@@H](c1ccc(cc1)N2CCCc3c2cnc4cc(Cl)nn34)C(F)(F)F)C(=O)[C@@H]5CC[S@@](=O)CC5 | 73 | 127 |
| CPD0084933 | 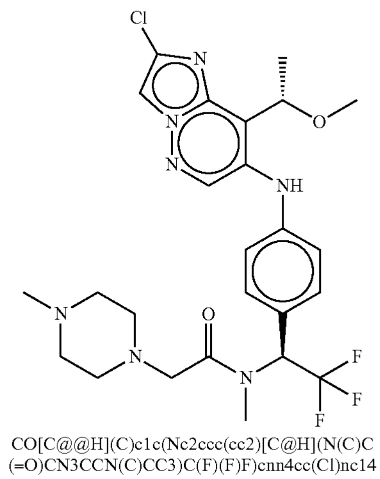 CO[C@@H](C)c1c(Nc2ccc(cc2)[C@H](N(C)C(=O)CN3CCN(C)CC3)C(F)(F)F)cnn4cc(Cl)nc14 | 137 | |
| CPD0073564 | 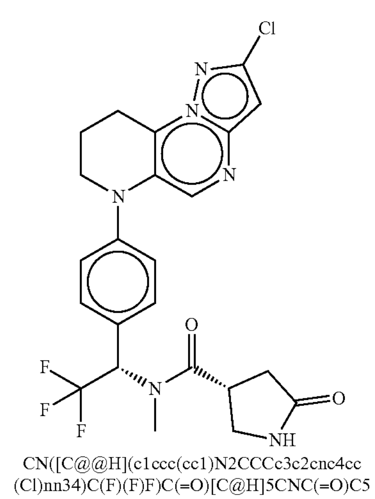 CN([C@@H](c1ccc(cc1)N2CCCc3c2cnc4cc(Cl)nn34)C(F)(F)F)C(=O)[C@H]5CNC(=O)C5 | 53 | 250 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0084142 | 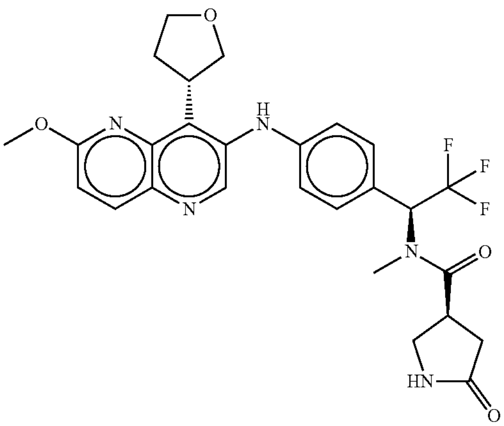 COc1ccc2ncc(Nc3ccc(cc3)[C@H](N(C)C(=O)[C@@ 2n1 | 41 | |
| CPD0073225 | 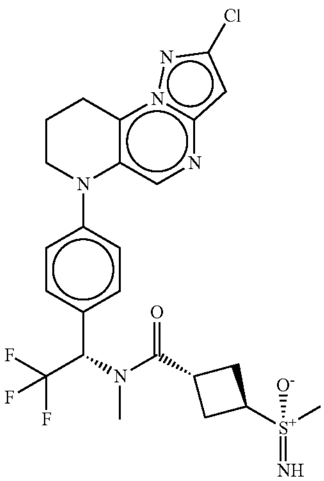 CN([C@@H](c1ccc(cc1)N2CCCc3c2cnc4cc(Cl) nn34)C(F)(F)F)C(=O)[C@@H]5C[C@H](C5)[S@+] (=N)(C)[O-] | 53 | 122 |
| CPD0073569 | 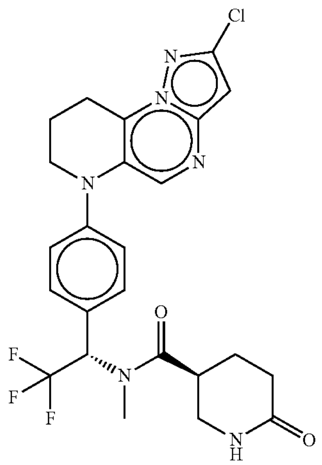 CN([C@@H](c1ccc(cc1)N2CCCc3c2cnc4 cc(Cl)nn34)C(F)(F)F)C(=O)[C@H]5CCC(=O)NC5 | 47 | 140 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0082479 | 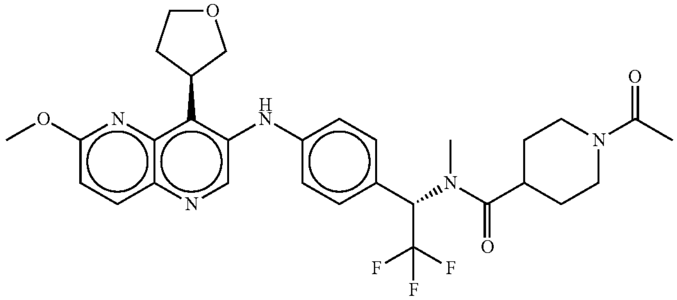 COc1ccc2ncc(Nc3ccc(cc3)[C@H](N(C)C(=O)C4CCN(CC4)C(=O)C)C(F)(F)F)c([C@H]5CCOC5)c2 | 111 | |
| CPD0074555 | 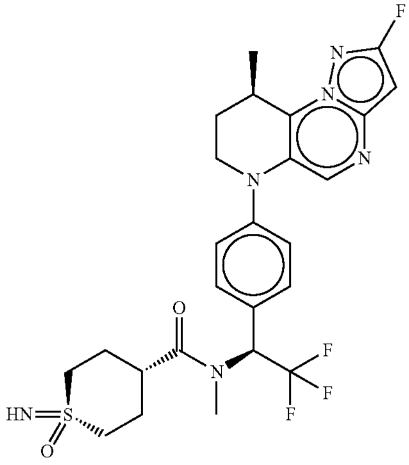 C[C@@H]1CCN(c2ccc(cc2)[C@H](N(C)C(=O)[C@@H]3CC[S@@](=N)(=O)CC3)C(F)(F)F)c4cnc5cc(F)nn5c14 | 35 | 101 |
| CPD0072531 | 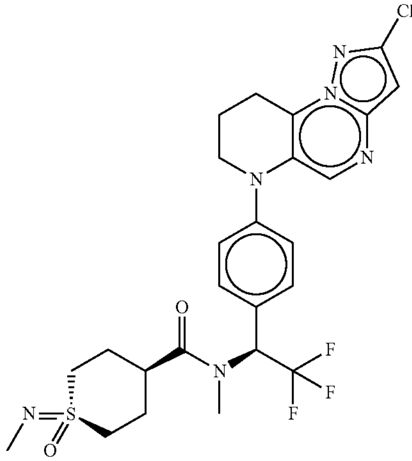 CN=[S@@]1(=O)CC[C@H](CC1)C(=O)N(C)[C@@H](c2ccc(cc2)N3CCCc4c3cnc5cc(Cl)nn45)C(F)(F)F | 38 | 141 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0074550 | 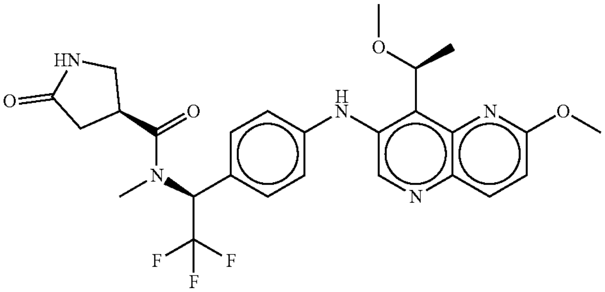 CO[C@@H](C)c1c(Nc2ccc(cc2)[C@H](N(C)C(=O)[C@@H]3CNC(=O)C3)C(F)(F)F)cnc4ccc(OC)nc14 | 81 | 41 |
| CPD0084256 | 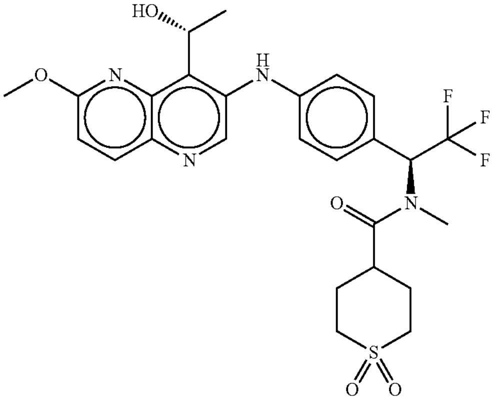 COc1ccc2ncc(Nc3ccc(cc3)[C@H](N(C)C(=O)C4CC | 38 | |
| CPD0084144 | 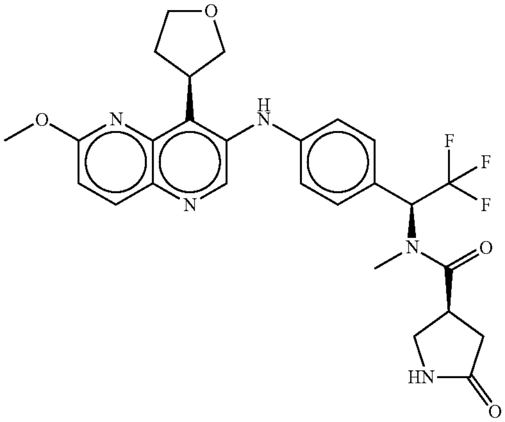 COc1ccc2ncc(Nc3ccc(cc3)[C@H](N(C)C(=O)[C@@H]4CNC(=O)C4)C(F)(F)F)c([C@H]5CCOC5)c2n1 | 76 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072782 | 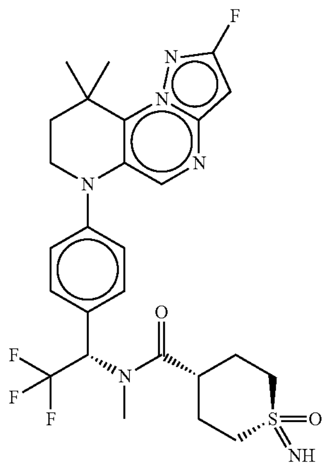<br>CN([C@@H](c1ccc(cc1)N2CCC(C)(C)c3c2cnc4cc(F)nn34)C(F)(F)F)C(=O)[C@@H]5CC[S@](=N)(=O)CC5 | 53 | 95 |
| CPD0021812 | 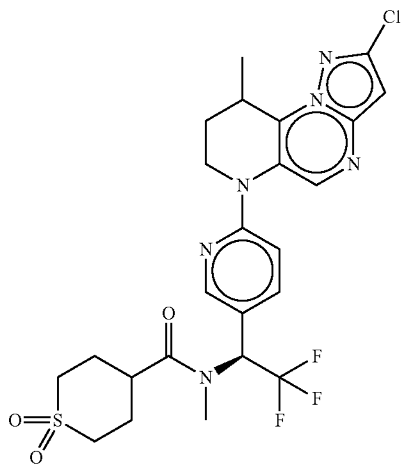<br>CC1CCN(c2ccc(cn2)[C@H](N(C)C(=O)C3CCS(=O)(=O)CC3)C(F)(F)F)c4cnc5cc(Cl)nn5c14 | 108 | 213 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073919 | 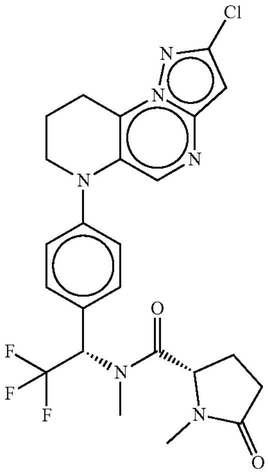 CN([C@@H](c1ccc(cc1)N2CCCc3c2cnc4cc(Cl)nn34)C(F)(F)F)C(=O)[C@@H]5CCC(=O)N5C | 61 | 112 |
| CPD0021939 | 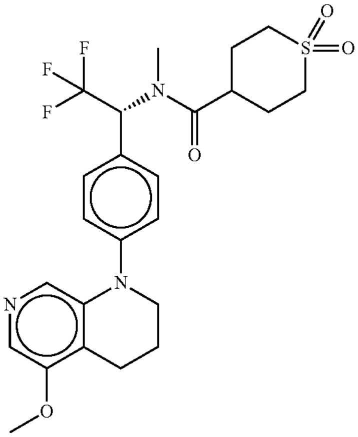 COc1cncc2N(CCCc12)c3ccc(cc3)[C@@H]N(C)C(=O)C4CCS(=O)(=O)CC4)C(F)(F)F | 271 | 894 |
| CPD0019344 | 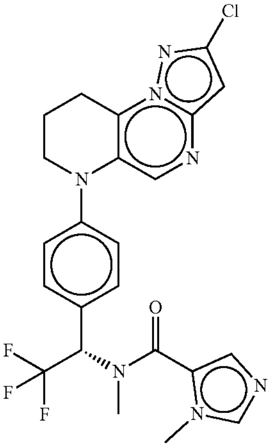 CN([C@@H](c1ccc(cc1)N2CCCc3c2cnc4cc(Cl)nn34)C(F)(F)F)C(=O)c5cncn5C | 213 | 295 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0082471 | 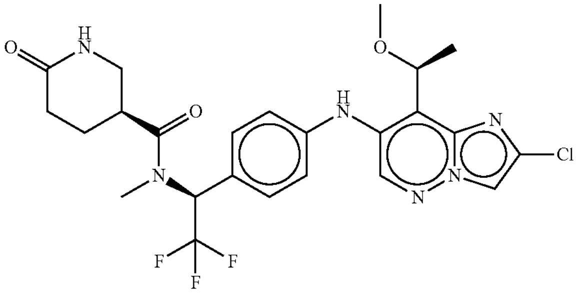 CO[C@@H](C)c1c(Nc2ccc(cc2)[C@H](N(C)C(=O)[C@H]3CCC(=O)NC3)C(F)(F)F)cnn4cc(Cl)nc14 | 37 | |
| CPD0073556 | 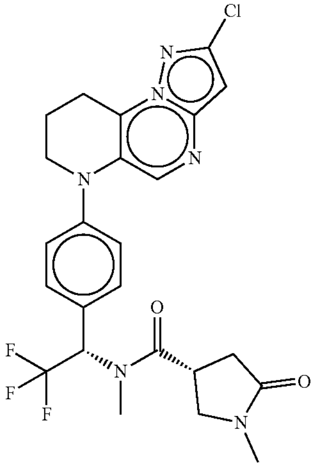 CN([C@@H](c1ccc(cc1)N2CCCc3c2cnc4cc(Cl)nn34)C(F)(F)F)C(=O)[C@H]5CN(C)C(=O)C5 | 79 | 200 |
| CPD0073192 | 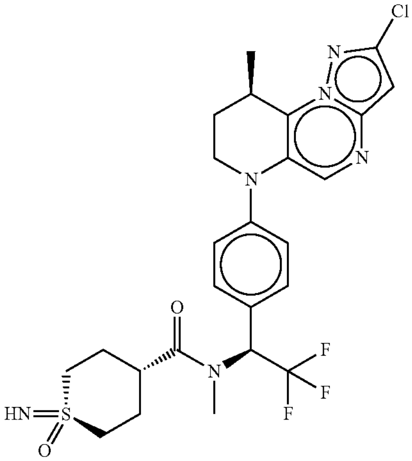 C[C@@H]1CCN(c2ccc(cc2)[C@H](N(C)C(=O)[C@@H]3CC[S@](=N)(=O)CC3)C(F)(F)F)c4cnc5cc(Cl)nn5c14 | 25 | 80 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072530 | 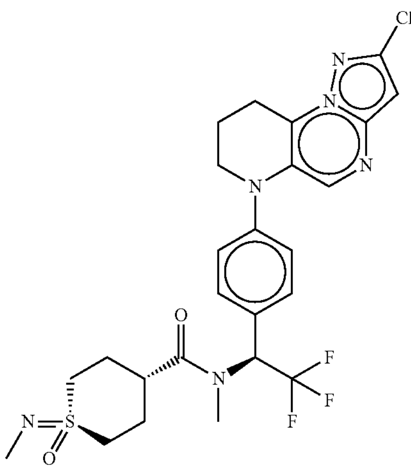 CN=[S@@]1(=O)cc[C@@H](CC1)C(=O)N(C)[C@@H](c2ccc(cc2)N3CCCc4c3cnc5cc(Cl)nn45)C(F)(F)F | 59 | 127 |
| CPD0074043 | 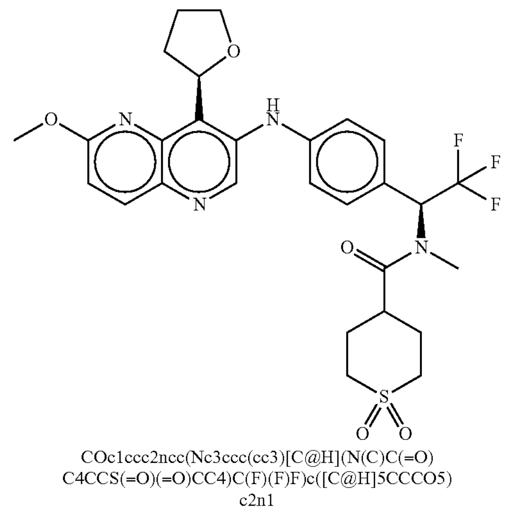 COc1ccc2ncc(Nc3ccc(cc3)[C@H](N(C)C(=O)C4CCS(=O)(=O)CC4)C(F)(F)F)c([C@H]5CCCO5)c2n1 | 107 | 80 |
| CPD0075878 | 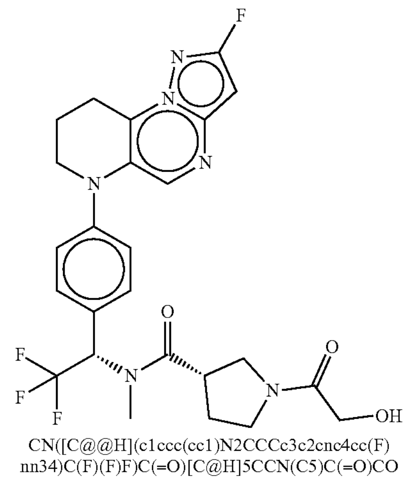 CN([C@@H](c1ccc(cc1)N2CCCc3c2cnc4cc(F)nn34)C(F)(F)F)C(=O)[C@H]5CCN(C5)C(=O)CO | 111 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0074050 | 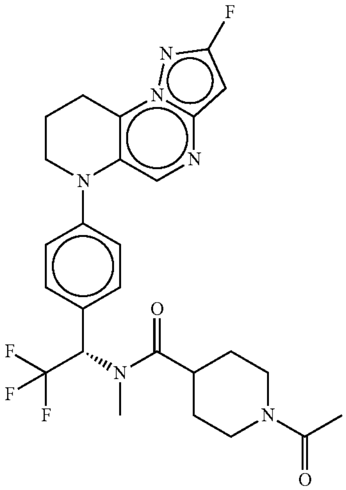 CN([C@@H](c1ccc(cc1)N2CCCc3c2cnc 4cc(F)nn34)C(F)(F)F)C(=O)C5CCN(CC5)C(=O)C | 85 | |
| CPD0022136 | 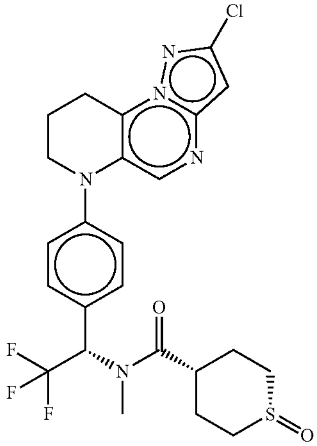 CN([C@@H](c1ccc(cc1)N2CCCc3c2cnc4cc(Cl)nn3 | 45 | 106 |
| CPD0082472 | 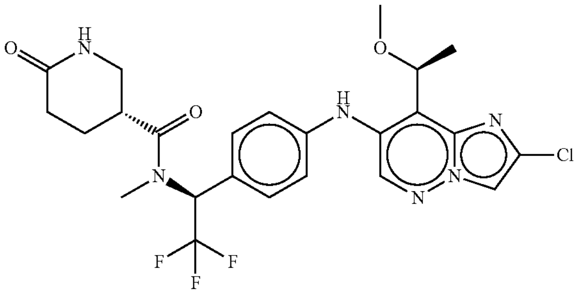 CO[C@@H](C)c1c( Nc2ccc(cc2)[C@H](N(C) C(=O)[C@@H]3CCC(=O)NC3)C(F)(F)F)cnn4cc(Cl) nc14 | 41 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0075874 | 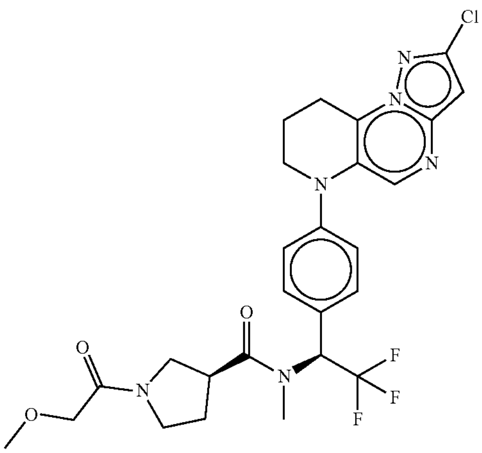<br>COCC(=O)N1CC[C@@H](C1)C(=O)N(C)<br>[C@@H](c2ccc(cc2)N3CCCc4c3cnc5cc(Cl)nn45)C<br>(F)(F)F | 95 | 230 |
| CPD0073131 | 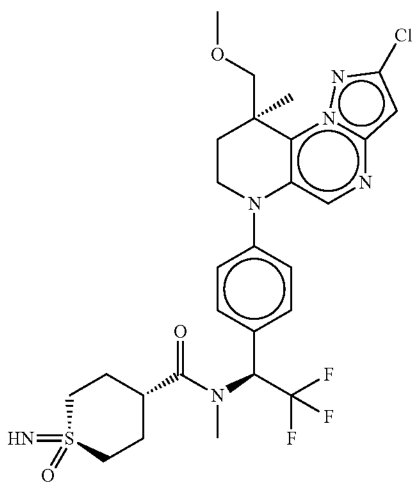<br>COC[C@]1(C)CCN(c2ccc(cc2)[C@H](N(C)C(=O)<br>[C@@H]3CC[S@](=N)(=O)CC3)C(F)(F)F)c4cnc5cc<br>(Cl)nn5c14 | 67 | 97 |

TABLE 1-continued
| Compound Reference | Structure | MALT-1 IC50 [nM] | CD4TC IL2 IC50 [nm] |
|---|---|---|---|
| CPD0072775 | 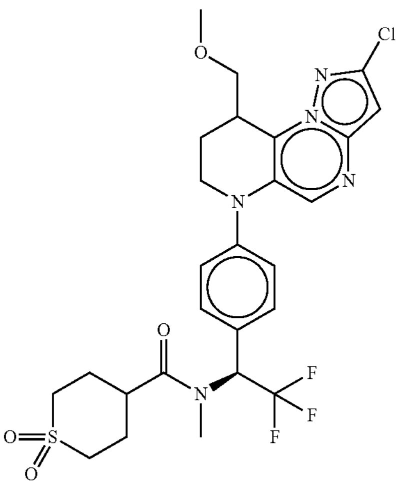 COCC1CCN(c2ccc(cc2)[C@H](N(C)C(=O)C3CCS(=O)(=O)CC3)C(F)(F)F)c4cnc5cc(Cl)nn5c14 | 94 | 143 |
| CPD0075574 | 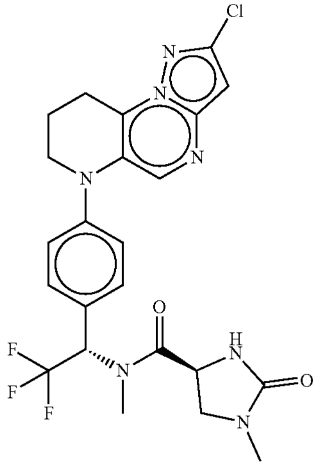 CN([C@@H](c1ccc(cc1)N2CCCc3c2cnc4cc(Cl)nn34)C(F)(F)F)C(=O)[C@@H]5CN(C)C(=O)N5 | 80 | |
| CPD0073142 | 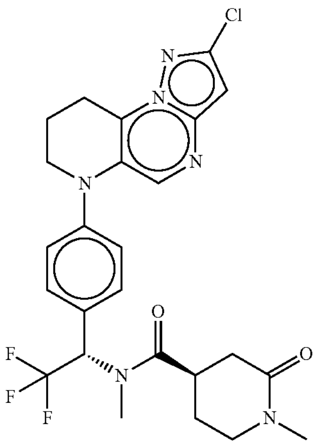 CN([C@@H](c1ccc(cc1)N2CCCc3c2cnc4cc(Cl)nn34)C(F)(F)F)C(=O)[C@@H]5CCN(C)C(=O)C5 | 68 | 122 |
IC50 biochemical data for representative compounds of the disclosure.

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0074553 | 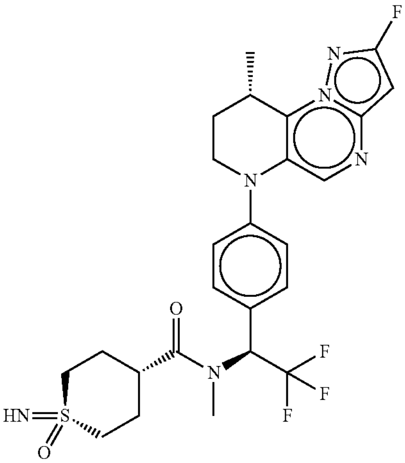 C[C@H]1CCN(c2ccc(cc2)[C@H](N(C)C(=O)[C@@H]3CC[S@@](=N)(=O)CC3)C(F)(F)F)c4cnc5cc(F)nn5c14 | 39 | 162 |
| CPD0074554 | 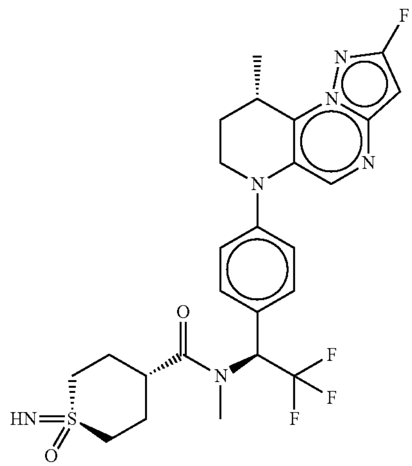 C[C@H]1CCN(c2ccc(cc2)[C@H](N(C)C(=O)[C@@H]3CC[S@](=N)(=O)CC3)C(F)(F)F)c4cnc5cc(F)nn5c14 | 44 | 170 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072813 | 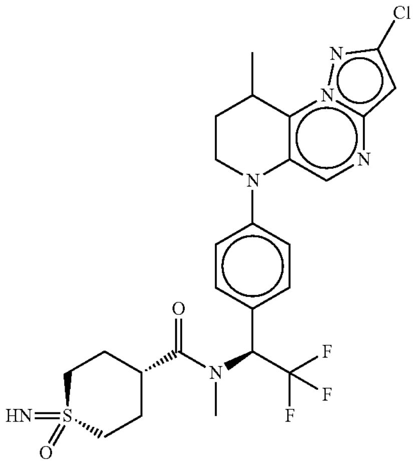 CC1CCN(c2ccc(cc2)[C@H](N(C)C(=O)[C@@H]3CC[S@@](=N)(=O)CC3)C(F)(F)F)c4cnc5cc(Cl)nn5c14 | 27 | 61 |
| CPD0073566 | 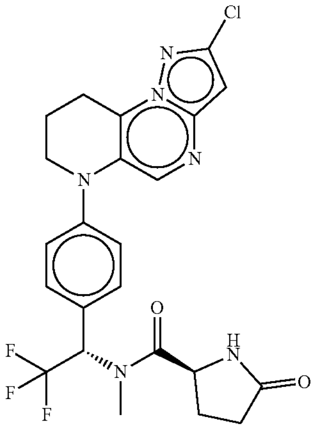 CN([C@@H](c1ccc(cc1)N2CCCc3c2cnc4cc(Cl)nn34)C(F)(F)F)C(=O)[C@@H]5CCC(=O)N5 | 76 | 241 |
| CPD0074051 | 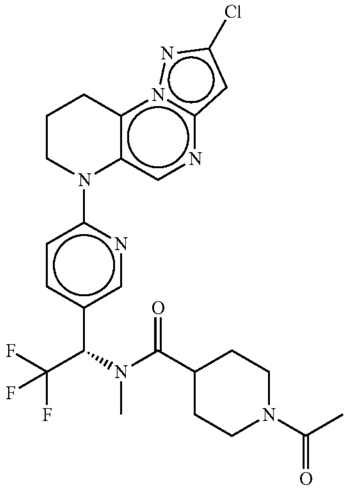 CN([C@@H](c1ccc(nc1)N2CCCc3c2cnc4cc(Cl)nn34)C(F)(F)F)C(=O)C5CCN(CC5)C(=O)C | 154 | |

TABLE 1-continued
IC50 biochemical data for representative compounds of the disclosure.
| Compound Reference | Structure | MALT-1 IC50 [nM] | CD4TC IL2 IC50 [nm] |
| --- | --- | --- | --- |
| CPD0073196 | 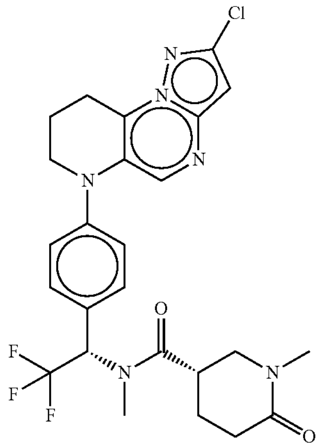<br>CN([C@@H](c1ccc(cc1)N2CCCc3c2cnc4cc(Cl)nn34)C(F)(F)F)C(=O)[C@H]5CCC(=O)N(C)C5 | 80 | 122 |
| CPD0073188 | 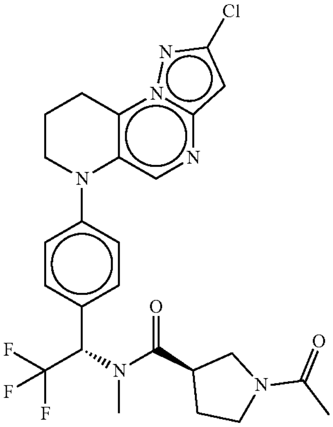<br>CN([C@@H](c1ccc(cc1)N2CCCc3c2cnc4cc(Cl)nn34)C(F)(F)F)C(=O)[C@@H]5CCN(C5)C(=O)C | 113 | 235 |
| CPD0019576 | 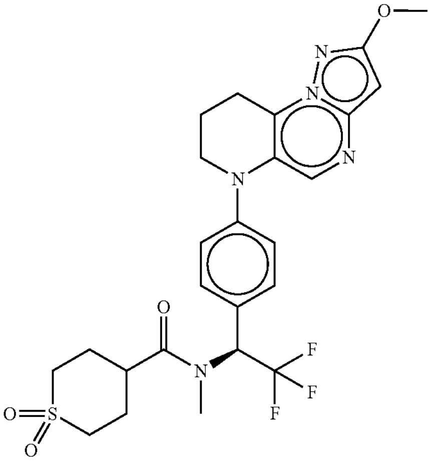<br>COc1cc2ncc3N(CCCc3n2n1)c4ccc(cc4)[C@H](N(C)C(=O)C5CCS(=O)(=O)CC5)C(F)(F)F | 313 | 1249 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0084936 | 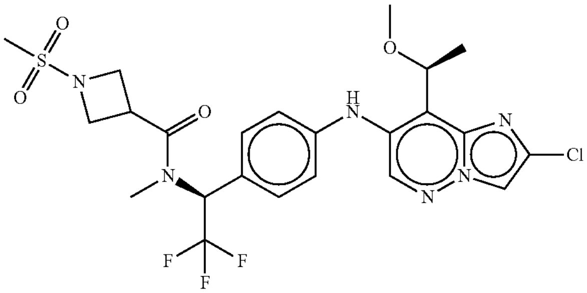 CO[C@@H](C)c1c(Nc2ccc(cc2)[C@H](N(C)C(=O)C3CN(C3)S(=O)(=O)C)C(F)(F)F)cnn4cc(Cl)nc14 | 65 | |
| CPD0073091 | 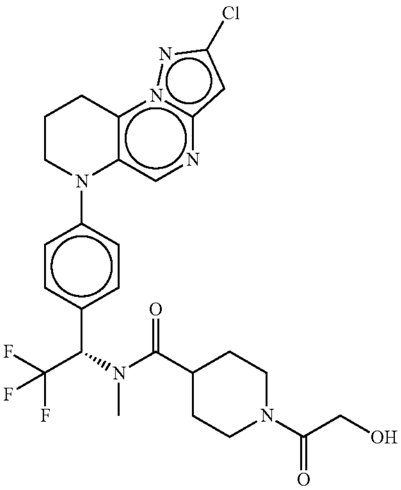 CN([C@@H](c1ccc(cc1)N2CCCc3c2cnc4cc(Cl)nn34)C(F)(F)F)C(=O)C5CCN(CC5)C(=O)CO | 59 | 101 |
| CPD0019342 | 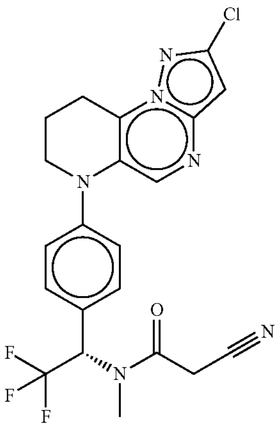 CN([C@@H](c1ccc(cc1)N2CCCc3c2cnc4cc(Cl)nn34)C(F)(F)F)C(=O)CC#N | 170 | 96 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072532 | 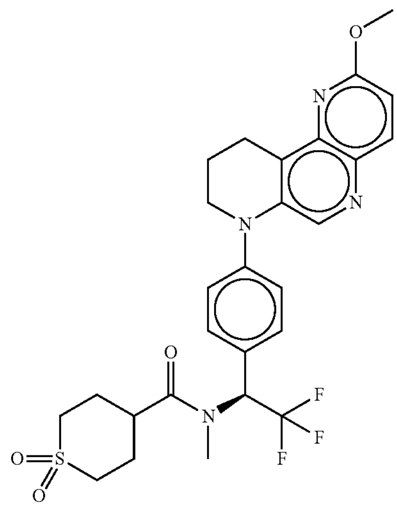 COc1ccc2ncc3N(CCCc3c2n1)c4ccc(cc4)[C@H](N(C)C(=O)C5CCS(=O)(=O)CC5)C(F)(F)F | 217 | 548 |
| CPD0073193 | 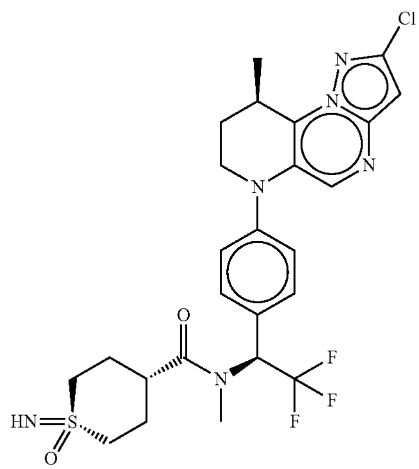 C[C@@H]1CCN(c2ccc(cc2)[C@H](N(C)C(=O)[C@@H]3CC[S@@](=N)(=O)CC3)C(F)(F)F)c4cnc5c | 22 | 68 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0076414 | 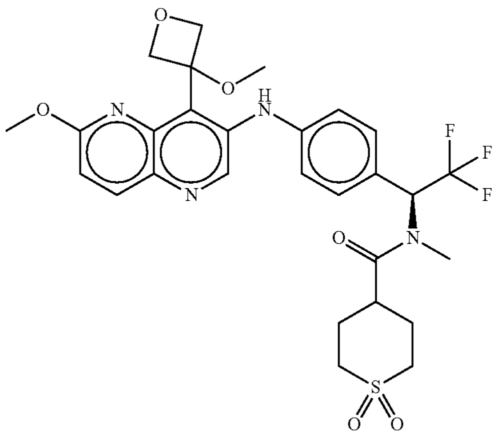 COc1ccc2ncc(Nc3ccc(cc3)[C@H](N(C)C(=O)C4CCS(=O)(=O)CC4)C(F)(F)F)c(c2n1)C5(COC5)OC | 124 | 267 |
| CPD0075879 | 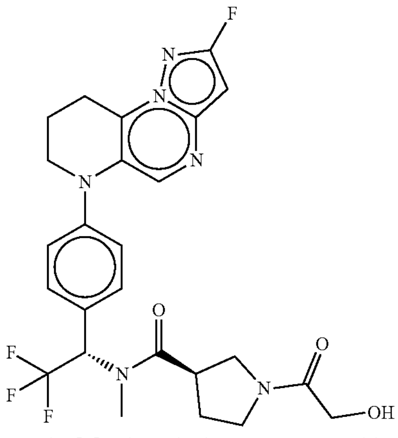 CN([C@@H](c1ccc(cc1)N2CCCc3c2cnc4cc(F)nn34)C(F)(F)F)C(=O)[C@@H]5CCN(C5)C(=O)CO | 154 | |
| CPD0073055 | 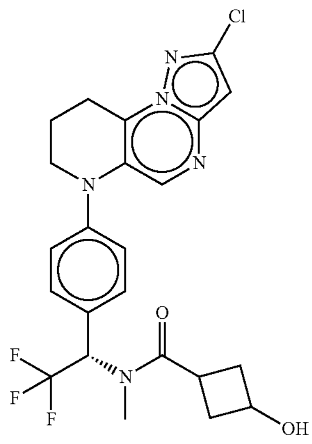 CN([C@@H](c1ccc(cc1)N2CCCc3c2cnc4cc(Cl)nn34)C(F)(F)F)C(=O)C5CC(O)C5 | 46 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0084934 | 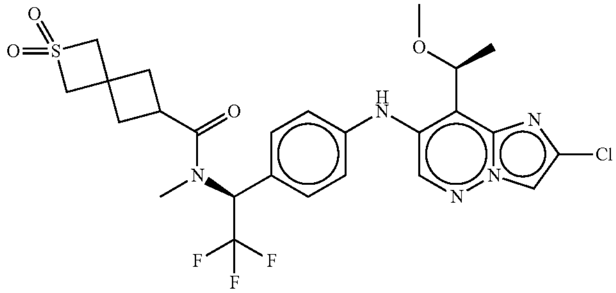 CO[C@@H](C)c1c(Nc2ccc(cc2)[C@H](N(C)C(=O)C3CC4(C3)CS(=O)(=O)C4)C(F)(F)F)cnn5cc(Cl)nc15 | 54 | |
| CPD0072784 | 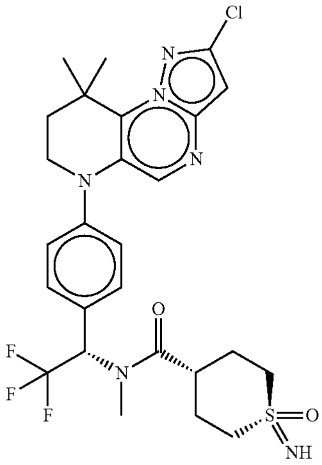 CN([C@@H](c1ccc(cc1)N2CCC(C)(C)c3c2cnc4cc(Cl)nn34)C(F)(F)F)C(=O)[C@@H]5CC[S@](=N)(=O)CC5 | 74 | 56 |
| CPD0074567 | 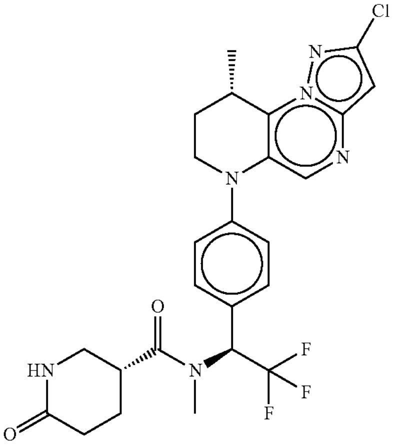 C[C@H]1CCN(c2ccc(cc2)[C@H](N(C)C(=O)[C@@H]3CCC(=O)NC3)C(F)(F)F)c4cnc5cc(Cl)nn5c14 | 31 | 87 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0074552 | 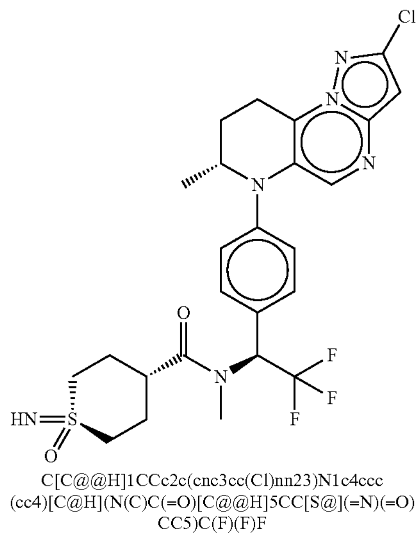 C[C@@H]1CCc2c(cnc3cc(Cl)nn23)N1c4ccc(cc4)[C@H](N(C)C(=O)[C@@H]5CC[S@](=N)(=O)CC5)C(F)(F)F | 78 | |
| CPD0019170 | 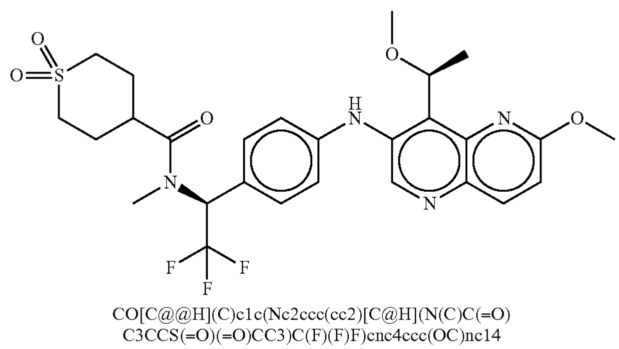 CO[C@@H](C)c1c(Nc2ccc(cc2)[C@H](N(C)C(=O)C3CCS(=O)(=O)CC3)C(F)(F)F)cnc4ccc(OC)nc14 | 65 | 20 |
| CPD0019349 | 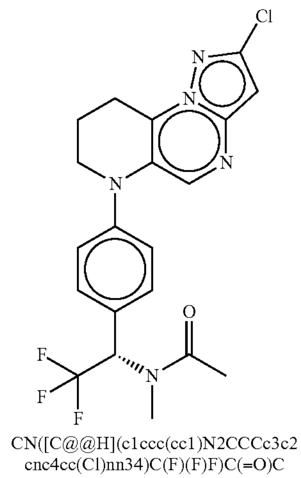 CN([C@@H](c1ccc(cc1)N2CCCc3c2cnc4cc(Cl)nn34)C(F)(F)F)C(=O)C | 230 | 83 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073141 | 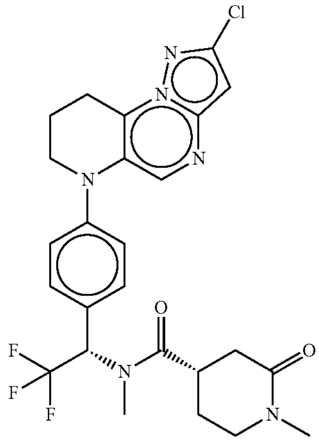<br>CN([C@@H](c1ccc(cc1)N2CCCc3c2cnc 4cc(Cl)nn34)C(F)(F)F)C(=O)[C@H]5CCN(C)C(=O) C5 | 67 | 197 |
| CPD0021562 | 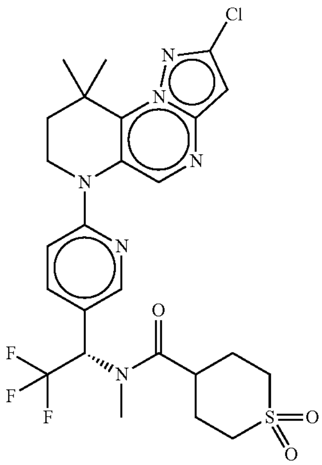<br>CN([C@@H](c1ccc(nc1)N2CCC(C)(C)c3c2cnc4 cc(Cl)nn34)C(F)(F)F)C(=O)C5CCS(=O)(=O)CC5 | 80 | 103 |
| CPD0019006 | 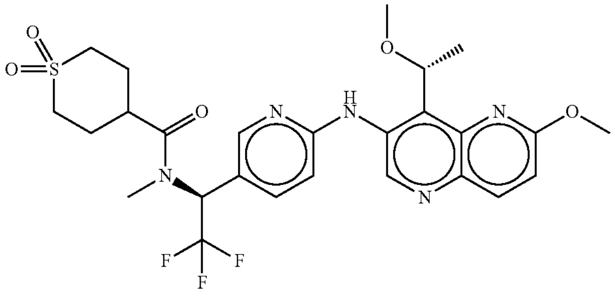<br>CO[C@H](C)c1c(Nc2ccc(cn2)[C@H](N(C) C(=O)C3CCS(=O)(=O)CC3)C(F)(F)F)cnc4ccc(OC) nc14 | 139 | 180 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0019498 | 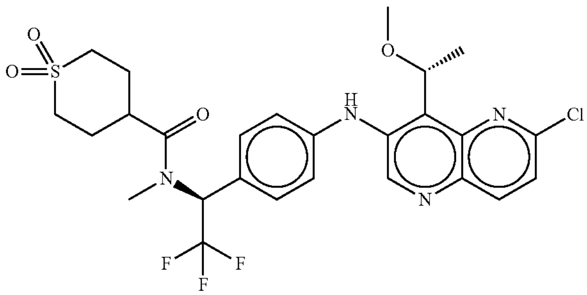 CO[C@H](C)c1c(Nc2ccc(cc2)[C@H](N(C)C(=O)C3CCS(=O)(=O)CC3)C(F)(F)F)cnc4ccc(Cl)nc14 | 146 | 122 |
| CPD0073197 | 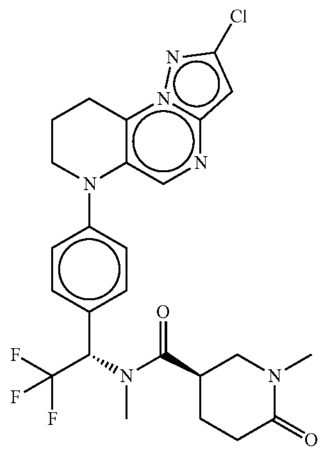 CN([C@@H](c1ccc(cc1)N2CCCc3c2cnc4cc(Cl)nn34)C(F)(F)F)C(=O)[C@@H]5CCC(=O)N(C)C5 | 103 | 207 |
| CPD0073132 | 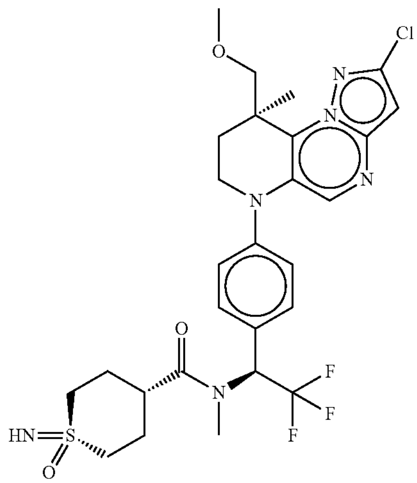 COC[C@]1(C)CCN(c2ccc(cc2)[C@H](N(C)C(=O)[C@@H]3CC[S@@](=N)(=O)CC3)C(F)(F)F)c4cnc5c | 101 | 150 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0082469 | 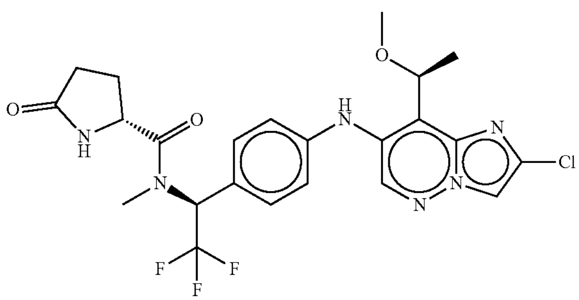 CO[C@@H](C)c1c(Nc2ccc(cc2)[C@H](N(C)C(=O)[C@H]3CCC(=O)N3)C(F)(F)F)cnn4cc(Cl)nc14 | 45 | |
| CPD0075875 | 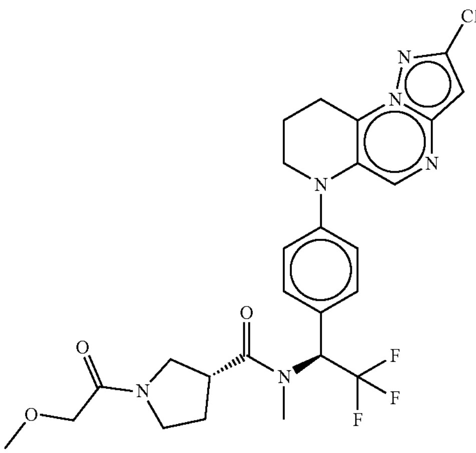 COCC(=O)N1CC[C@H](C1)C(=O)N(C)[C@@H](c2ccc(cc2)N3CCCc4c3cnc5cc(Cl)nn45)C(F)(F)F | 85 | 116 |
| CPD0074551 | 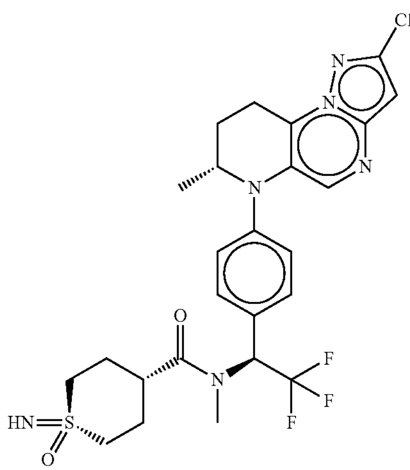 C[C@@H]1CCc2c(cnc3cc(Cl)nn23)N1c4ccc(cc4)[C@H](N(C)C(=O)[C@@H]5cc[S@@](=N)(=O)CC5 | 57 | |

TABLE 1-continued

| IC50 biochemical data for representative compounds of the disclosure. | | | |
|---|---|---|---|
| Compound Reference | Structure | MALT-1 IC50 [nM] | CD4TC IL2 IC50 [nm] |
| CPD0019007 | 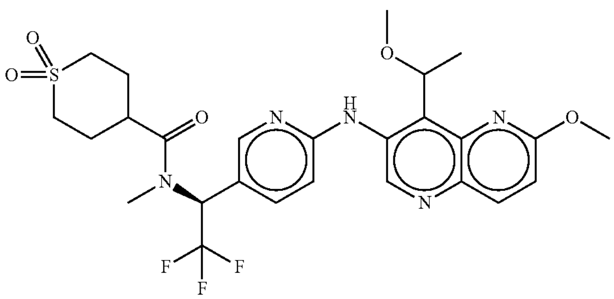 COC(C)c1c(Nc2ccc(cn2)[C@H](N(C)C(=O)C3CCS(=O)(=O)CC3)C(F)(F)F)cnc4ccc(OC)nc14 | 242 | 115 |
| CPD0084508 | 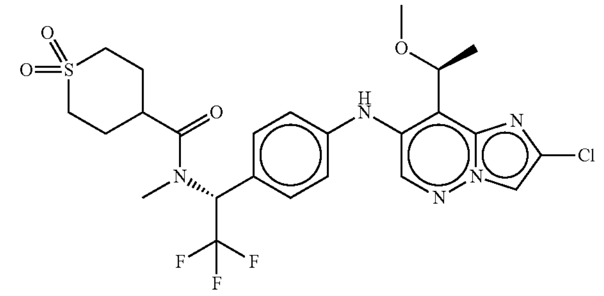 CO[C@@H](C)c1c(Nc2ccc(cc2)[C@@H](N(C)C(=O)C3CCS(=O)(=O)CC3)C(F)(F)F)cnn4cc(Cl)nc14 | 182 | |
| CPD0082470 | 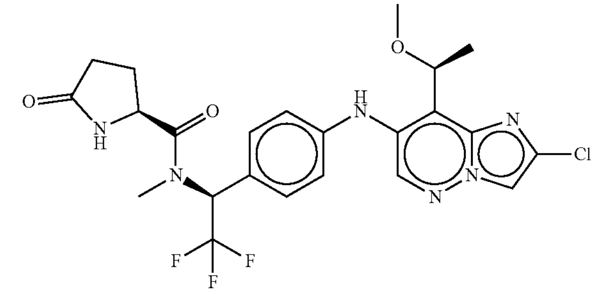 CO[C@@H](C)c1c(Nc2ccc(cc2)[C@H](N(C)C(=O)[C@@H]3CCC(=O)N3)C(F)(F)F)cnn4cc(Cl)nc14 | 45 | |
| CPD0073189 | 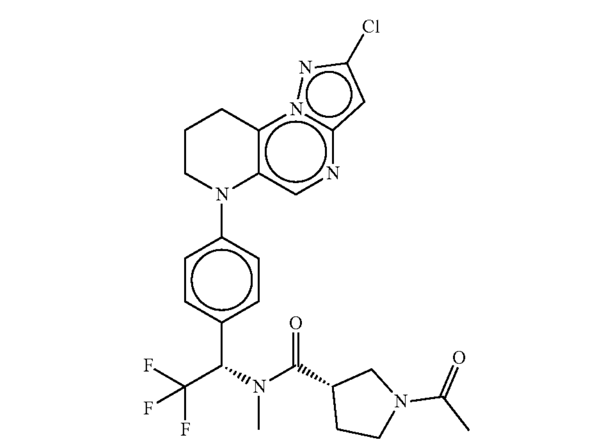 CN([C@@H](c1ccc(cc1)N2CCCc3c2cnc4cc(Cl)nn34)C(F)(F)F)C(=O)[C@H]5CCN(C5)C(=O)C | 76 | 160 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0077189 | 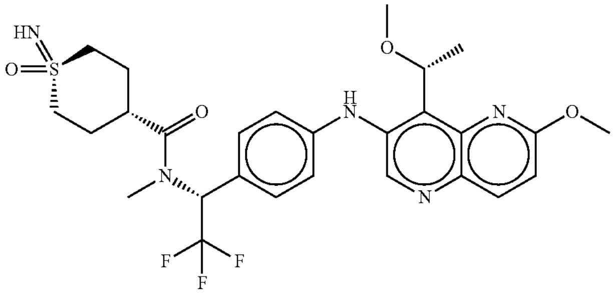 CO[C@H](C)c1c(Nc2ccc(cc2)[C@@H](N(C)C(=O)[C@@H]3CC[S@@](=N)(=O)CC3)C(F)(F)F)cnc4ccc(OC)nc14 | 274 | |
| CPD0021660 | 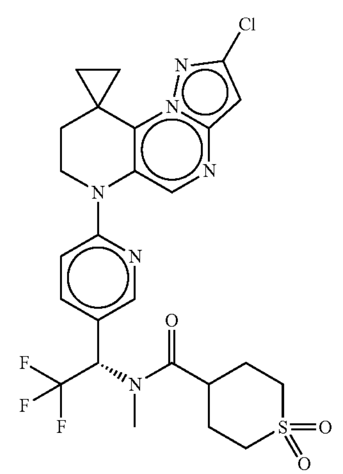 CN([C@@H](c1ccc(nc1)N2CCC3(CC3)c4c2cnc5cc(Cl)nn45)C(F)(F)F)C(=O)C6CCS(=O)(=O)CC6 | 87 | 112 |
| CPD0021585 | 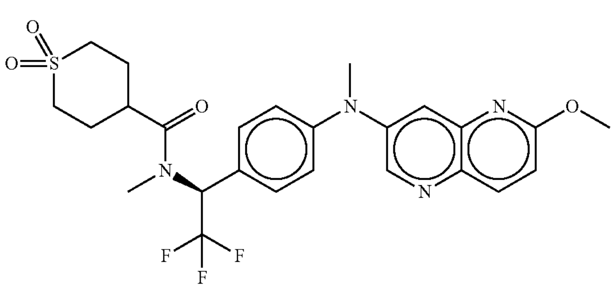 COc1ccc2ncc(cc2n1)N(C)c3ccc(cc3)[C@H](N(C)C(=O)C4CCS(=O)(=O)CC4)C(F)(F)F | 863 | 1679 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073497 | 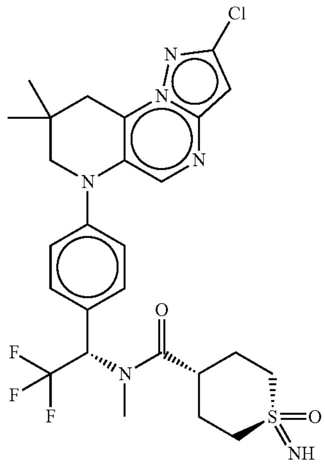 CN([C@@H](c1ccc(cc1)N2CC(C)(C)Cc3c2cnc4cc(Cl)nn34)C(F)(F)F)C(=O)[C@@H]5CC[S@@](=N)(=O)CC5 | 52 | 183 |
| CPD0077188 | 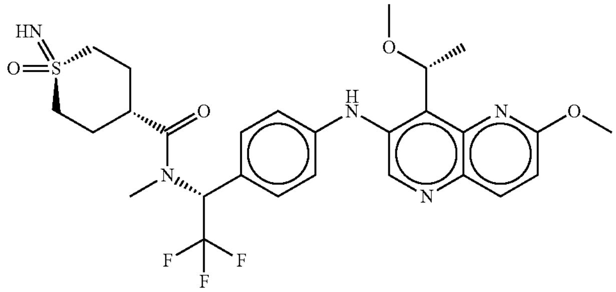 CO[C@H](C)c1c(Nc2ccc(cc2)[C@@H](N(C)C(=O)[C@@H]3CC[S@](=N)(=O)CC3)C(F)(F)F)cnc4ccc(OC)nc14 | 255 | |
| CPD0073572 | 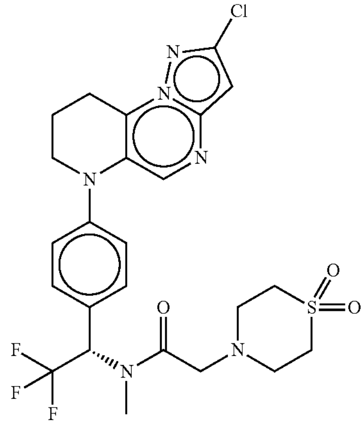 CN([C@@H](c1ccc(cc1)N2CCCc3c2cnc4cc(Cl)nn34)C(F)(F)F)C(=O)CN5CCS(=O)(=O)CC5 | 163 | 253 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0021746 | 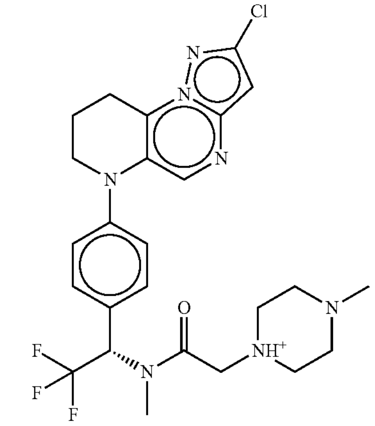 CN([C@@H](c1ccc(cc1)N2CCCc3c2cnc4cc(Cl)nn34)C(F)(F)F)C(=O) C[NH+]5CCN(C)CC5 | 522 | 466 |
| CPD0077245 | 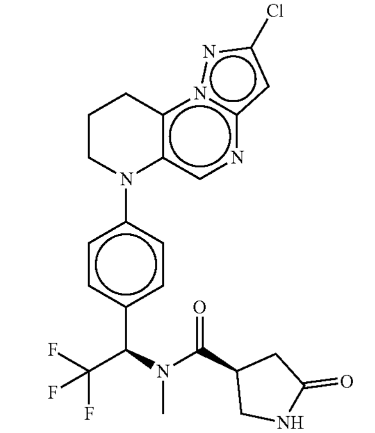 CN([C@H](c1ccc(cc1)N2CCCc3c2cnc4cc(Cl)nn34)C(F)(F)F)C(=O)[C@@H]5CNC(=O)C5 | 355 | |
| CPD0019347 | 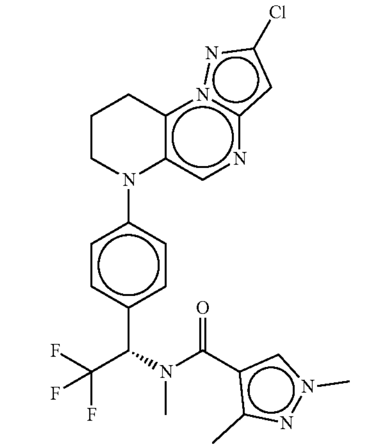 CN([C@@H](c1ccc(cc1)N2CCCc3c2cnc4cc(Cl)nn34)C(F)(F)F)C(=O)c5cn(C)nc5C | 244 | 132 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0075869 | 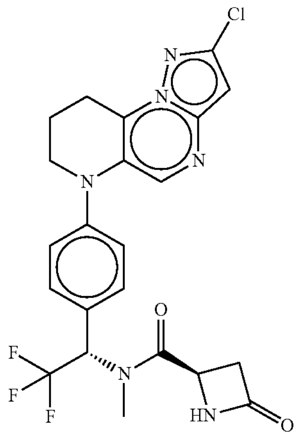 CN([C@@H](c1ccc(cc1)N2CCCc3c2cnc4cc(Cl)nn34)C(F)(F)F)C(=O)[C@H]5CC(=O)N5 | 75 | |
| CPD0072812 | 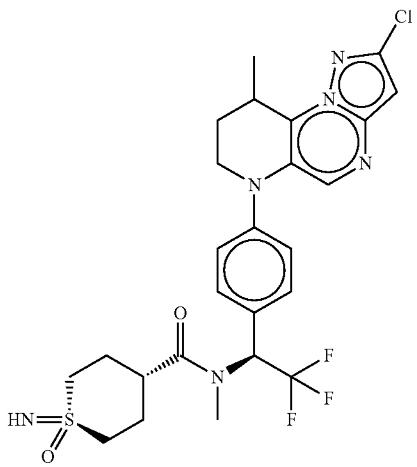 CC1CCN(c2ccc(cc2)[C@H](N(C)C(=O)[C@@H]3CC[S@](=N)(=O)CC3)C(F)(F)F)c4cnc5cc(Cl)nn5c14 | 31 | 79 |
| CPD0072528 | 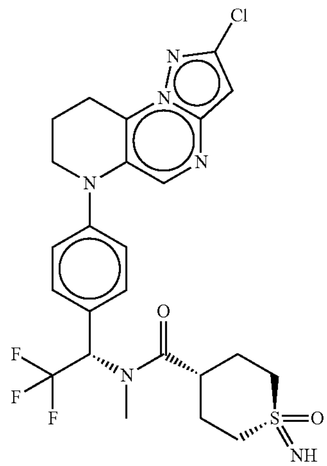 CN([C@@H](c1ccc(cc1)N2CCCc3c2cnc4cc(Cl)nn34)C(F)(F)F)C(=O)[C@@H]5CC[S@](=N)(=O)CC5 | 32 | 108 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0074549 | 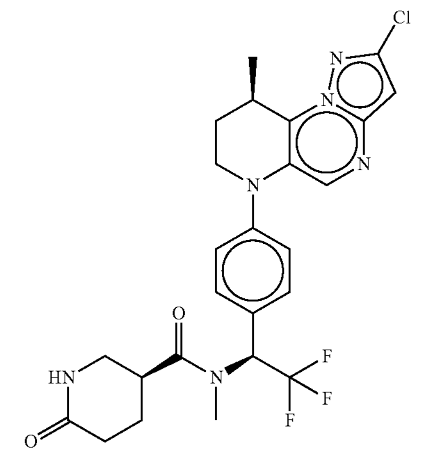 C[C@@H]1CCN(c2ccc(cc2)[C@H](N(C)C(=O)[C@H]3CCC(=O)NC3)C(F)(F)F)c4cnc5cc(Cl)nn5c14 | 37 | 142 |
| CPD0073761 | 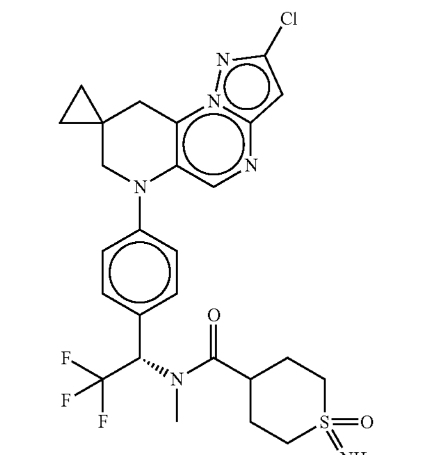 CN([C@@H](c1ccc(cc1)N2CC3(CC3)Cc4c2cnc5cc(Cl)nn45)C(F)(F)F)C(=O)C6CCS(=N)(=O)CC6 | 78 | 317 |
| CPD0084509 | 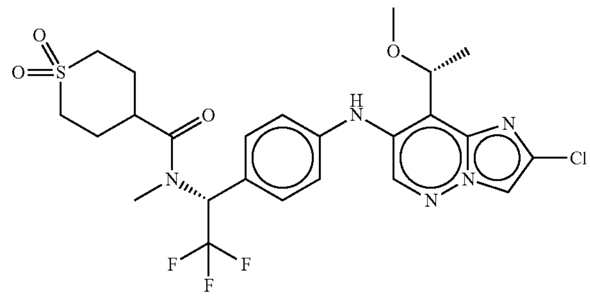 CO[C@H](C)c1c(Nc2ccc(cc2)[C@@H](N(C)C(=O)C3CCS(=O)(=O)CC3)C(F)(F)F)cnn4cc(Cl)nc14 | 253 | |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073194 | 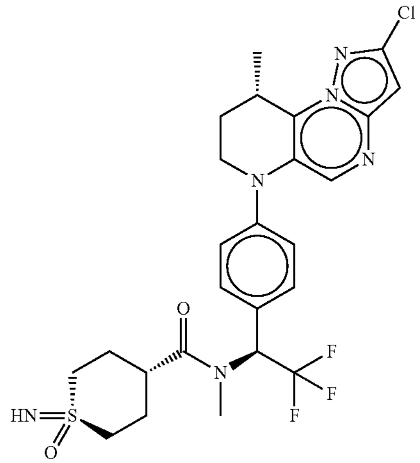 C[C@H]1CCN(c2ccc(cc2)[C@H](N(C)C(=O)[C@@H nn5c14 | 20 | 51 |
| CPD0074044 | 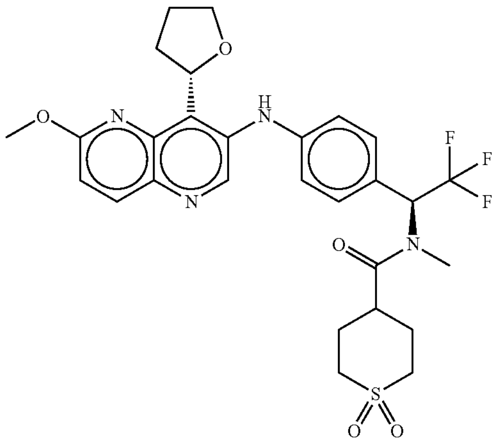 COc1ccc2ncc(Nc3ccc(cc3)[C@H](N(C)C(=O) C4CC S(=O)(=O)CC4)C(F)(F)F)c([C@@H]5CCCO5)c2n1 | 218 | |
| CPD0073089 | 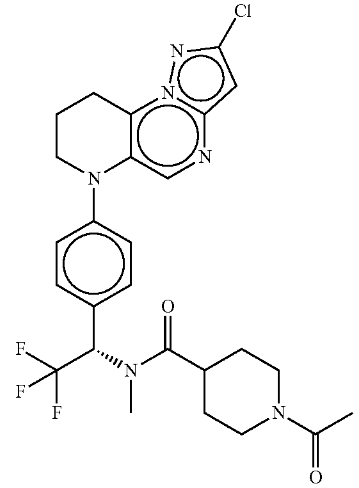 CN([C@@H](c1ccc(cc1)N2CCCc3c2cnc4cc (Cl)nn34)C(F)(F)F)C(=O)C5CCN(CC5)C(=O)C | 46 | 79 |

TABLE 1-continued

IC50 biochemical data for representative compounds of the disclosure.

| Compound Reference | Structure | MALT-1 IC50 [nM] | CD4TC IL2 IC50 [nm] |
|---|---|---|---|
| CPD0018621 | 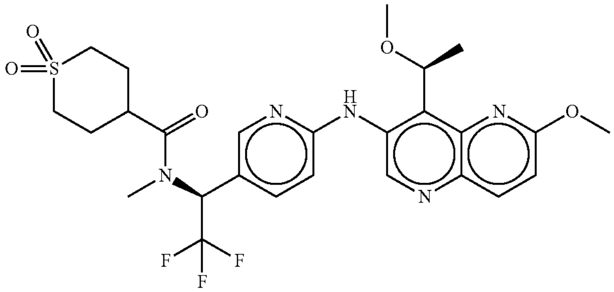 CO[C@@H](C)c1c(Nc2ccc(cn2)[C@H](N(C)C(=O)C3CCS(=O)(=O)CC3)C(F)(F)F)cnc4ccc(OC)nc14 | 567 | 571 |
| CPD0019497 | 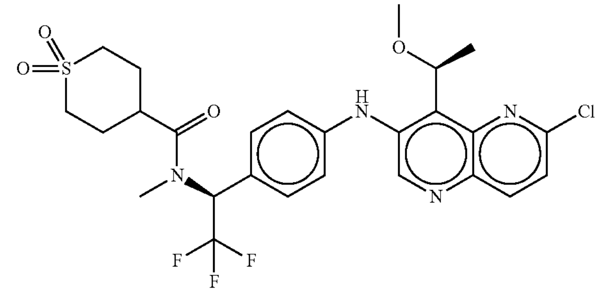 CO[C@@H](C)c1c(Nc2ccc(cc2)[C@H](N(C)C(=O)C3CCS(=O)(=O)CC3)C(F)(F)F)cnc4ccc(Cl)nc14 | 57 | 23 |
| CPD0073498 | 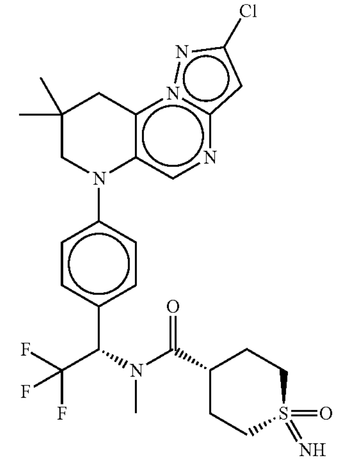 CN([C@@H](c1ccc(cc1)N2CC(C)(C)Cc3c2cnc4cc(Cl)nn34)C(F)(F)F)C(=O)[C@@H]5CC[S@](=N)(=O) | 53 | 163 |
| CPD0084918 | 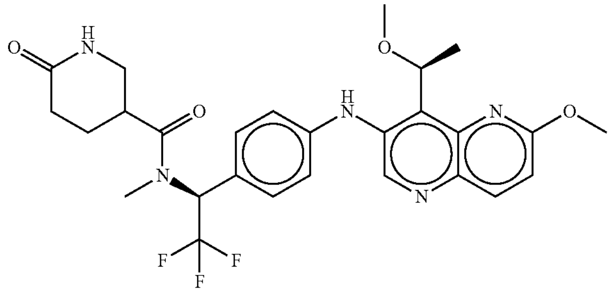 CO[C@@H](C)c1c(Nc2ccc(cc2)[C@H](N(C)C(=O)C3CCC(=O)NC3)C(F)(F)F)cnc4ccc(OC)nc14 | | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073568 | 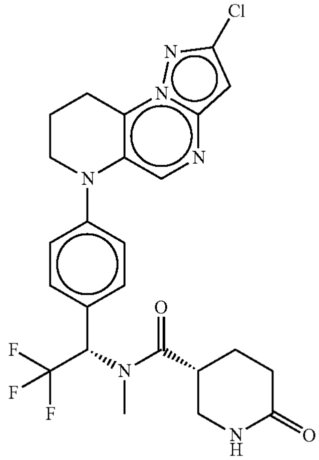 CN([C@@H](c1ccc(cc1)N2CCCc3c2cnc4cc(Cl)nn34)C(F)(F)F)C(=O)[C@@H]5CCC(=O)NC5 | 38 | 131 |
| CPD0072449 | 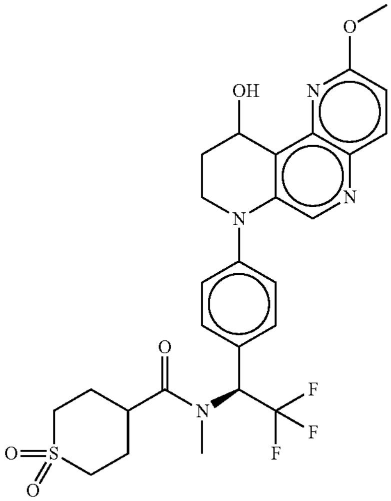 COc1ccc2ncc3N(CCC(O)c3c2n1)c4ccc(cc4)[C@H](N(C)C(=O)C5CCS(=O)(=O)CC5)C(F)(F)F | 432 | 940 |
| CPD0019079 | 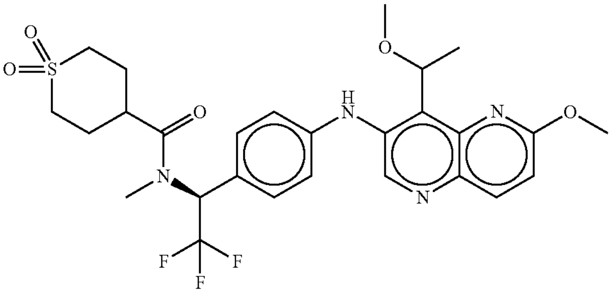 COC(C)c1c(Nc2ccc(cc2)[C@H](N(C)C(=O)C3CCS(=O)(=O)CC3)C(F)(F)F)cnc4ccc(OC)nc14 | 147 | 102 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073557 | 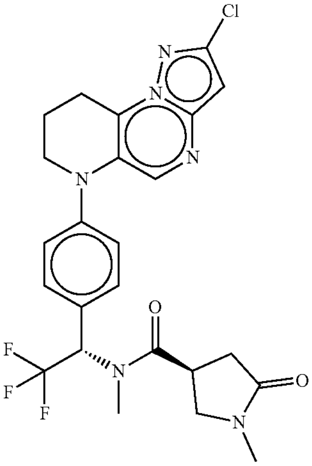 CN([C@@H](c1ccc(cc1)N2CCCc3c2cnc4cc(Cl)n n34)C(F)(F)F)C(=O)[C@@H]5CN(C)C(=O)C5 | 121 | 282 |
| CPD0072529 | 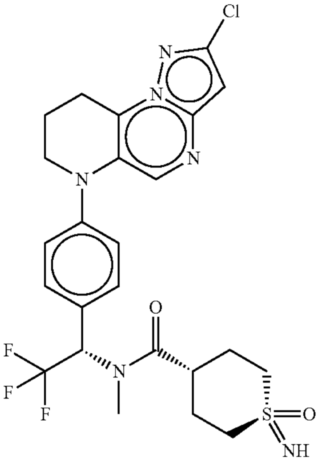 CN([C@@H](c1ccc(cc1)N2CCCc3c2cnc4cc(Cl) nn34)C(F)(F)F)C(=O)[C@@H]5CC[@@](=N)(=O) CC5 | 26 | 94 |
| CPD0021810 | 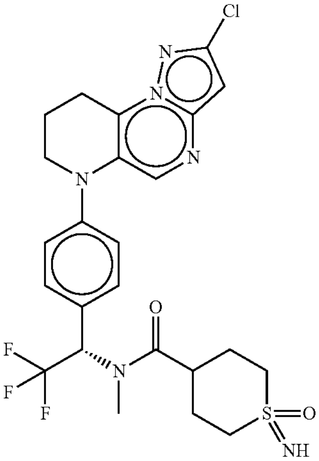 CN([C@@H](c1ccc(cc1)N2CCCc3c2cnc4cc (Cl)nn34)C(F)(F)F)C(=O)C5CCS(=N)(=O)CC5 | 63 | 194 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0072785 | 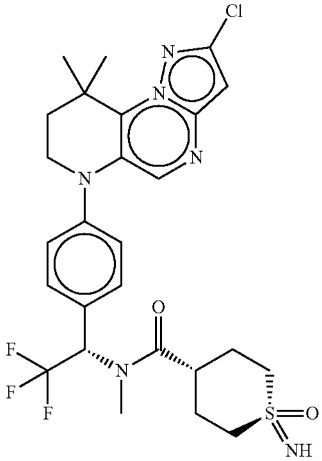<br>CN([C@@H](c1ccc(cc1)N2CCC(C)(C)c3c2cnc4cc(C<br>(=O) CC5 | 76 | 51 |
| CPD0075880 | 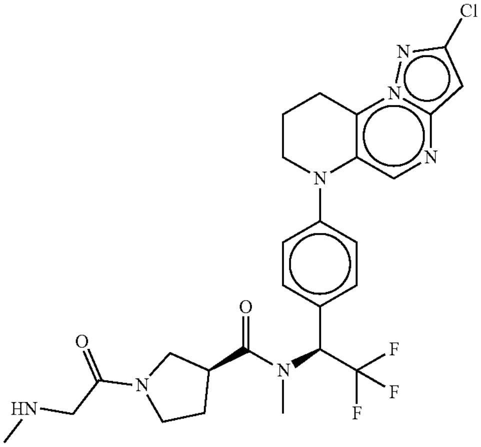<br>CNCC(=O)N1CC[C@@H](C1)C(=O)N(C)[C@@H]<br>(c2ccc(cc2)N3CCCc4c3cnc5cc(Cl)nn45)C(F)(F)F | 99 | 363 |
| CPD0074048 | 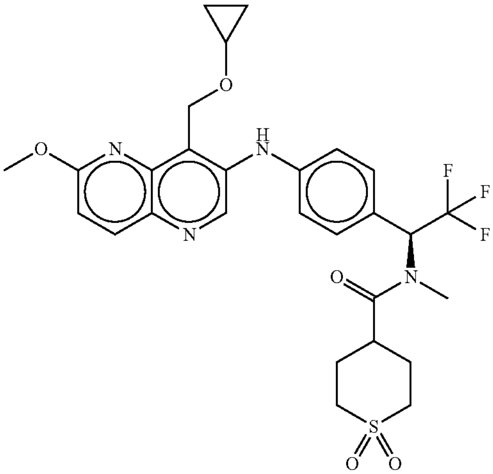<br>COc1ccc2ncc(Nc3ccc(cc3)[C@H](N(C)C(=O)<br>C4CCS(=O)(=O)CC4)C(F)(F)F)c(COC5CC5)c2n1 | 163 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0074548 | 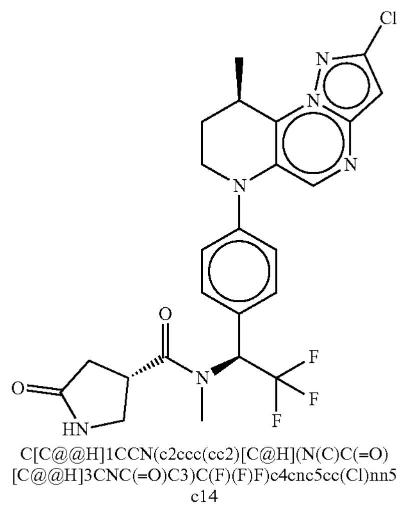<br>C[C@@H]1CCN(c2ccc(cc2)[C@H](N(C)C(=O)[C@@H]3CNC(=O)C3)C(F)(F)F)c4cnc5cc(Cl)nn5c14 | 46 | |
| CPD0019346 | 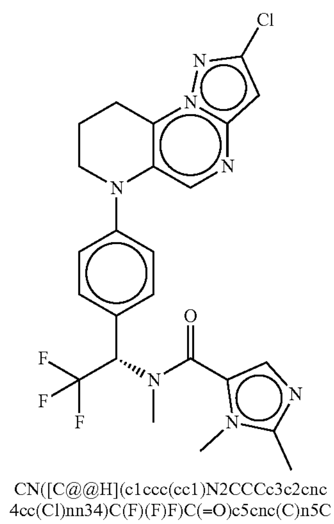<br>CN([C@@H](c1ccc(cc1)N2CCCc3c2cnc4cc(Cl)nn34)C(F)(F)F)C(=O)c5cnc(C)n5C | 535 | 720 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073224 | 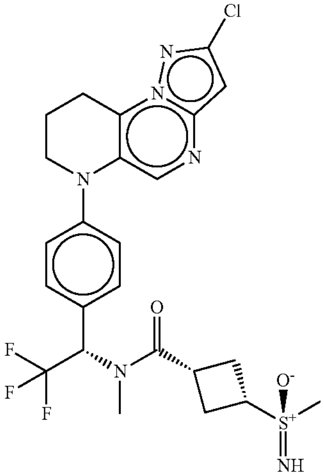 CN([C@@H](c1ccc(cc1)N2CCCc3c2cnc4cc(Cl)nn34)C(F)(F)F)C(=O)[C@@H]5C[C@@H](C5)[S@@+](=N)(C)[O-] | 56 | 181 |
| CPD0077244 | 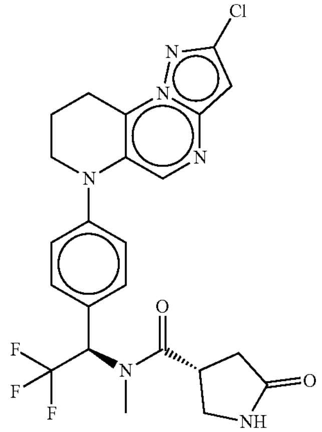 CN([C@H](c1ccc(cc1)N2CCCc3c2cnc4cc(Cl)nn34)C(F)(F)F)C(=O)[C@H]5CNC(=O)C5 | 581 | |
| CPD0084307 | 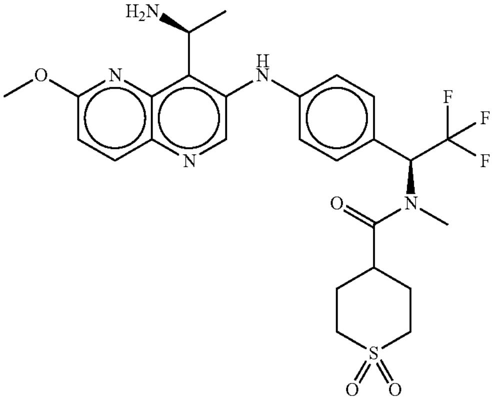 COc1ccc2ncc(Nc3ccc(cc3)[C@H](N(C)C(=O)C4CCS(=O)(=O)CC4)C(F)(F)F)c([C@H](C)N)c2n1 | 124 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0075576 | 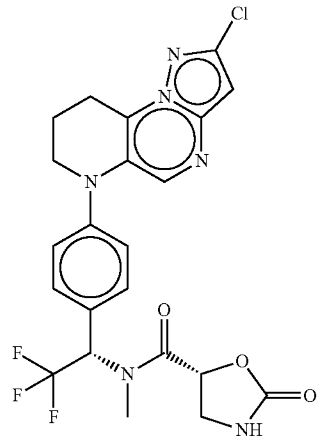 CN([C@@H](c1ccc(cc1)N2CCCc3c2cnc4cc(Cl)nn34)C(F)(F)F)C(=O)[C@H]5CNC(=O)O5 | 46 | 57 |
| CPD0074569 | 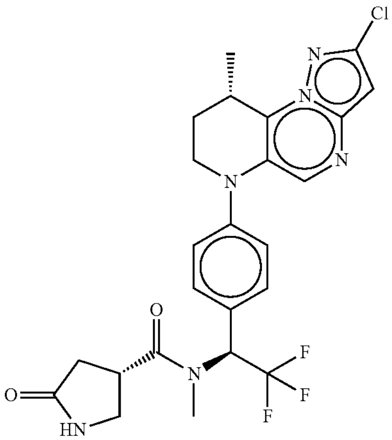 C[C@H]1CCN(c2ccc(cc2)[C@H](N(C)C(=O)[C@@H]3CNC(=O)C3)C(F)(F)F)c4cnc5cc(Cl)nn5c14 | 30 | |
| CPD0072849 | 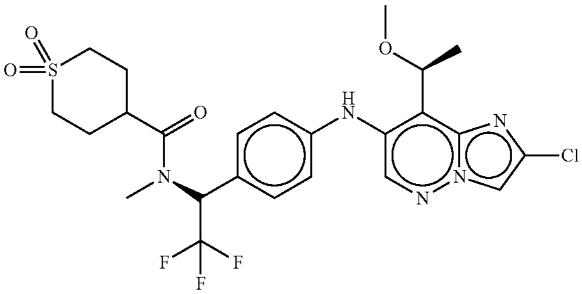 CO[C@@H](C)c1c(Nc2ccc(cc2)[C@H](N(C)C(=O)C3CCS(=O)(=O)CC3)C(F)(F)F)cnn4cc(Cl)nc14 | 37 | 55 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0075881 | 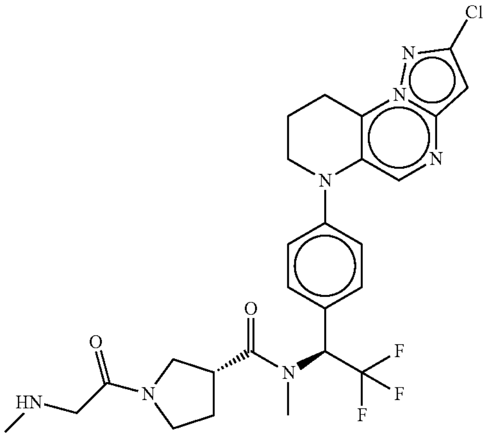 CNCC(=O)N1CC[C@H](C1)C(=O)N(C)[C@@H](c2ccc(cc2)N3CCCc4c3cnc5cc(Cl)nn45)C(F)(F)F | 68 | 210 |
| CPD0073571 | 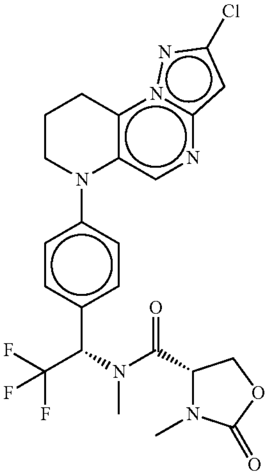 CN([C@@H](c1ccc(cc1)N2CCCc3c2cnc4cc(Cl)nn34)C(F)(F)F)C(=O)[C@@H]5COC(=O)N5C | 52 | 153 |
| CPD0073056 | 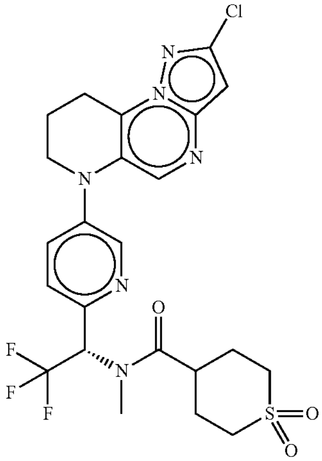 CN([C@@H](c1ccc(cn1)N2CCCc3c2cnc4cc(Cl)nn34)C(F)(F)F)C(=O)C5CCS(=O)(=O)CC5 | 197 | 780 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0075870 | 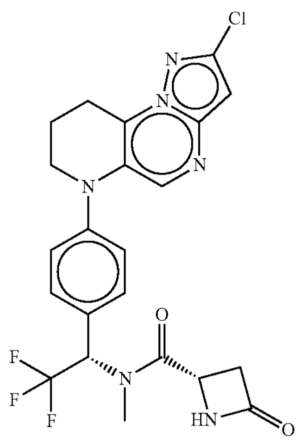 CN([C@@H](c1ccc(cc1)N2CCCc3c2cnc4cc(Cl)nn34)C(F)(F)F)C(=O)[C@@H]5CC(=O)N5 | 63 | 120 |
| CPD0073223 | 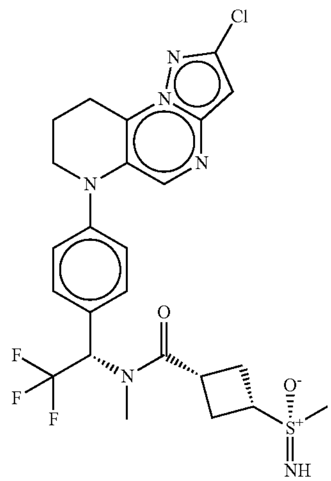 CN([C@@H](c1ccc(cc1)N2CCCc3c2cnc4cc(Cl)nn34)C(F)(F)F)C(=O)[C@@H]5C[C@@H](C5)[S@+](=N)(C)[O-] | 57 | 172 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0075573 | 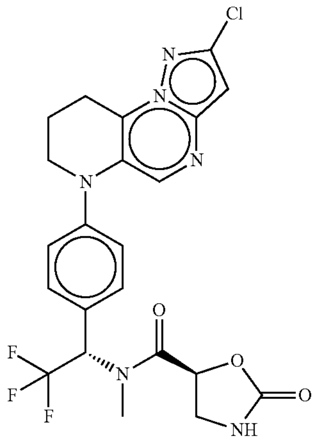 CN([C@@H] (c1ccc(c c1)N2CCCc3c2cnc4cc(Cl)nn34)C(F)(F)F)C(=O)[C @@H]5CNC(=O)O5 | 197 | |
| CPD0075876 | 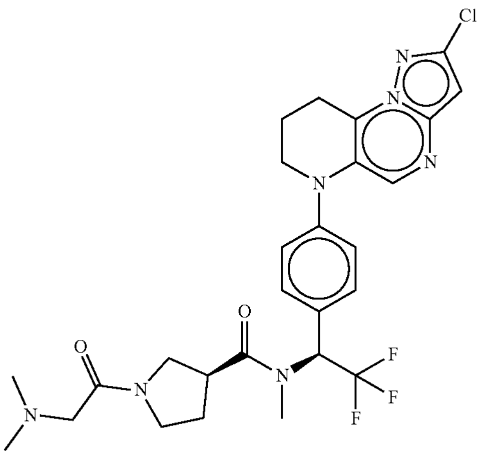 CN(C)CC(=O)N1CC[C@@H](C1)C(=O)N(C)[C@@ H](c2ccc(cc2)N3CCCc4c3cnc5cc(Cl)nn45)C(F)(F)F | 138 | 207 |
| CPD0019171 | 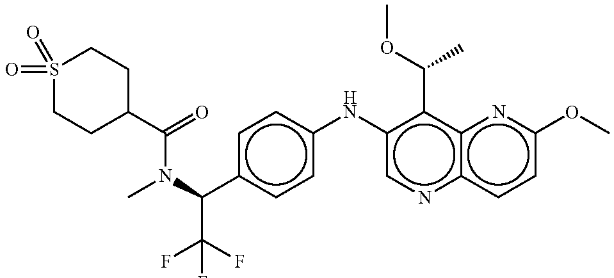 CO[C@H](C)c1c(Nc2ccc(cc2)[C@H](N(C)C(=O)C3 CCS(=O)(=O)CC3)C(F)(F)F)cnc4ccc(OC)nc14 | 196 | 110 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073562 | 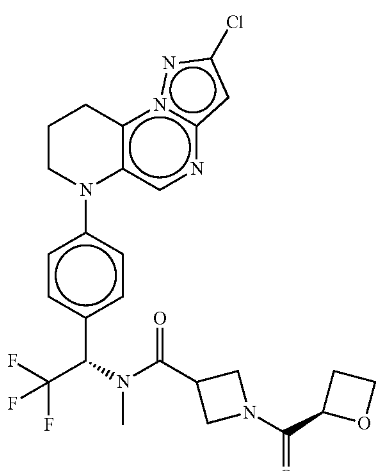 CN([C@@H](c1ccc(cc1)N2CCCc3c2cnc4cc(Cl)nn3 4)C(F)(F)F)C(=O)C5CN(C5)C(=O)[C@H]6CCO6 | 80 | 352 |
| CPD0019341 | 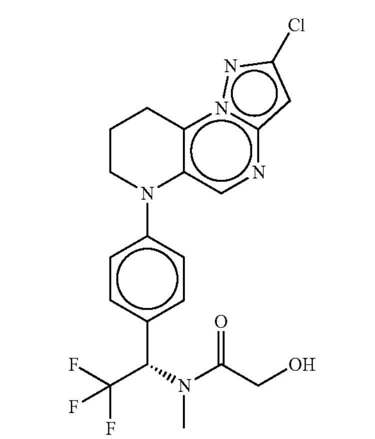 CN([C@@H](c1ccc(cc1)N2CCCc3c2cnc4cc(Cl)nn3 4)C(F)(F)F)C(=O)CO | 200 | 104 |
| CPD0019212 | 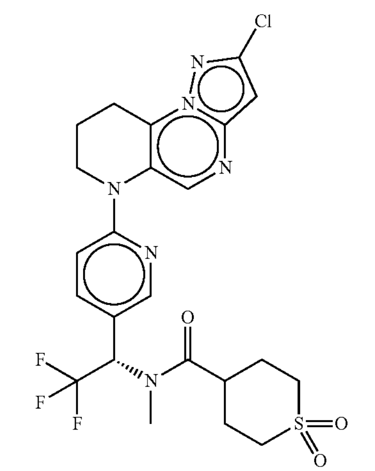 CN([C@@H](c1ccc(nc1)N2CCCc3c2cnc4cc(Cl)nn3 4)C(F)(F)F)C(=O)C5CCS(=O)(=O)CC5 | 313 | 452 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0074560 | 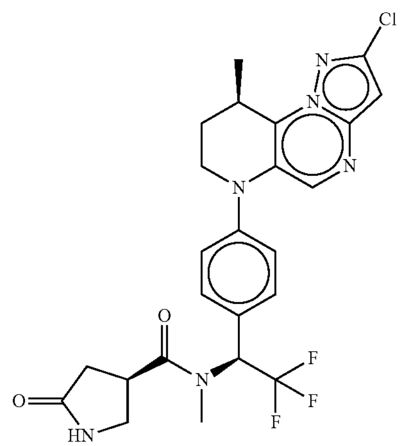 C[C@@H]1CCN(c2ccc(cc2)[C@H](N(C)C(=O)[C@H]3CNC(=O)C3)C(F)(F)F)c4cnc5cc(Cl)nn5c14 | 43 | |
| CPD0073195 | 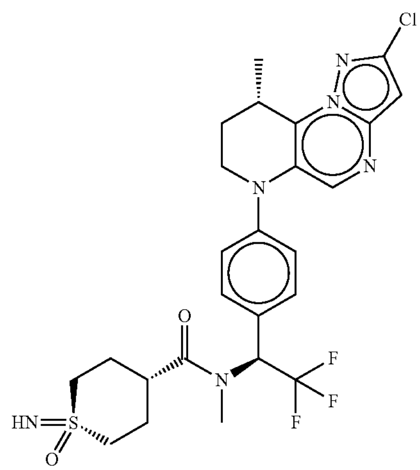 C[C@H]1CCN(c2ccc(cc2)[C@H](N(C)C(=O)[C@@H]3CC[S@@](=N)(=O)CC3)C(F)(F)F)c4cnc5cc(Cl)nn5c14 | 22 | 51 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0074565 | 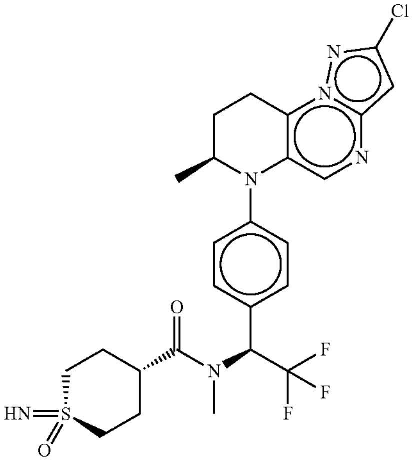 C[C@H]1CCc2c(cnc3cc(Cl)nn23)N1c4ccc(cc4)[C@H](N(C)C(=O)[C@@H]5CC[S@](=N)(=O)CC5C(F)(F)F | 377 | |
| CPD0082473 | 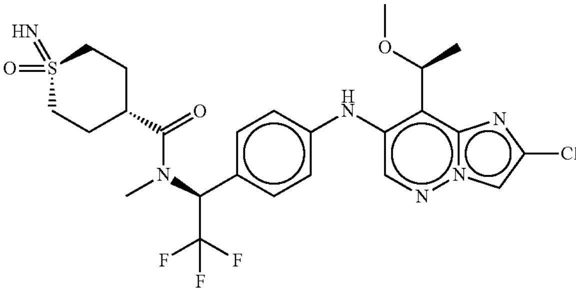 CO[C@@H](C)c1c(Nc2ccc(cc2)[C@H](N(C)C(=O)[C@@H]3CC[S@@](=N)(=O)CC3)C(F)(F)F)cnn4cc(Cl)nc14 | 52 | |
| CPD0074564 | 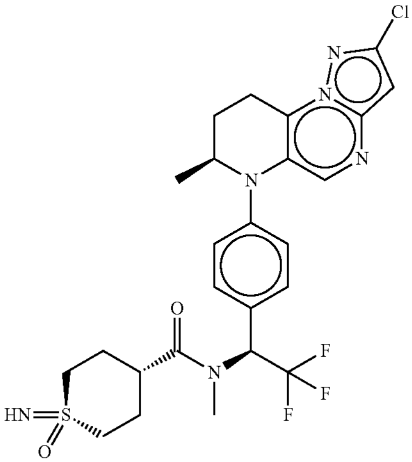 C[C@H]1CCc2c(cnc3cc(Cl)nn23)N1c4ccc(cc4)[C@H](N(C)C(=O)[C@@H]5CC[S@@](=N)(=O)CC5)C(F)(F)F | 248 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072773 | 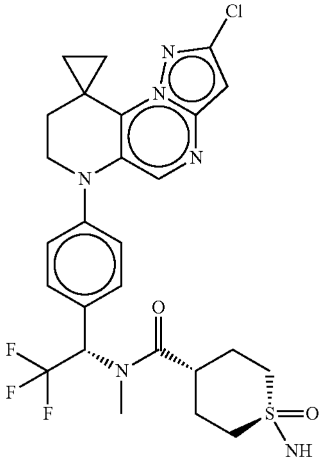<br>CN([C@@H](c1ccc(cc1)N2CCC3(CC3)c4c2cnc5cc(Cl)nn45)C(F)(F)F)C(=O)[C@@H]6CC[S@@](=N)(=O)CC6 | 52 | 54 |
| CPD0072781 | 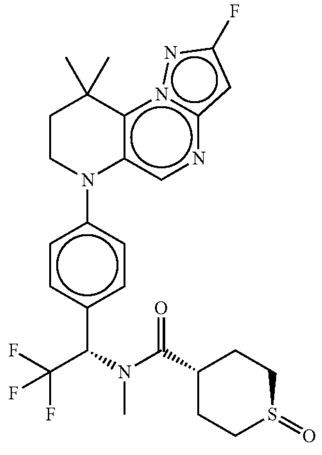<br>CN([C@@H](c1ccc(cc1)N2CCC(C)(C)c3c2cnc4cc(F)nn34)C(F)(F)F)C(=O)[C@@H]5CC[S@@](=O)CC5 | 60 | 75 |
| CPD0019496 | 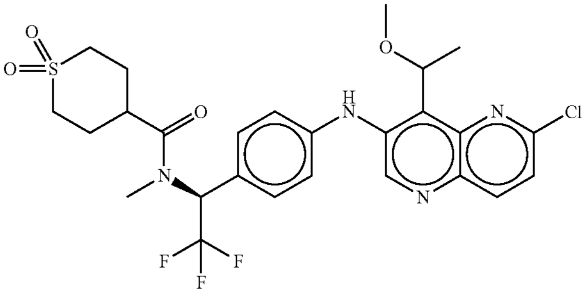<br>COC(C)c1c(Nc2ccc(cc2)[C@H](N(C)C(=O)C3CCS(=O)(=O)CC3)C(F)(F)F)cnc4ccc(Cl)nc14 | 112 | 22 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0019348 | 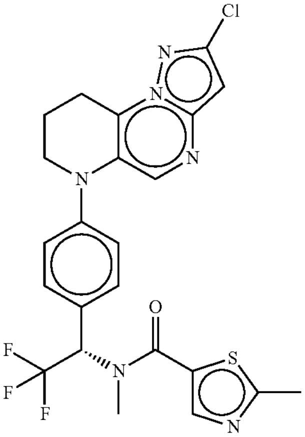 CN([C@@H](c1ccc(cc1)N2CCCc3c2cnc4cc(Cl)nn34)C(F)(F)F)C(=O)c5cnc(C)s5 | 193 | 157 |
| CPD0073973 | 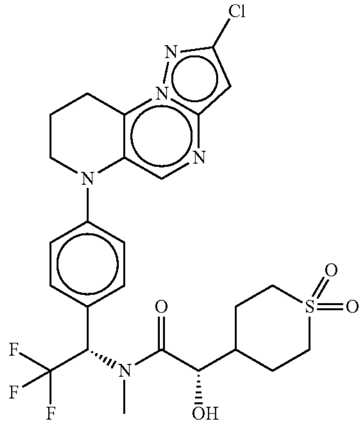 CN([C@@H](c1ccc(cc1)N2CCCc3c2cnc4cc(Cl)nn34)C(F)(F)F)C(=O)[C@@H](O)C5CCS(=O)(=O)CC5 | 57 | 149 |
| CPD0019183 | 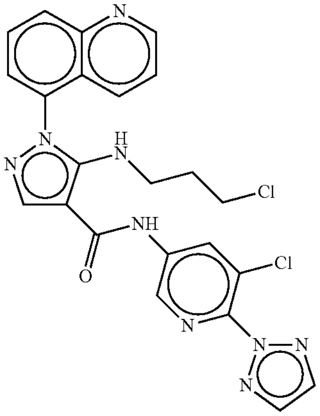 ClCCCNc1c(cnn1c2cccc3ncccc23)C(=O)Nc4cnc(c(Cl)c4)n5nccn5 | 464 | 10000 |

TABLE 1-continued
IC50 biochemical data for representative compounds of the disclosure.
| Compound Reference | Structure | MALT-1 IC50 [nM] | CD4TC IL2 IC50 [nm] |
| --- | --- | --- | --- |
| CPD0019501 | 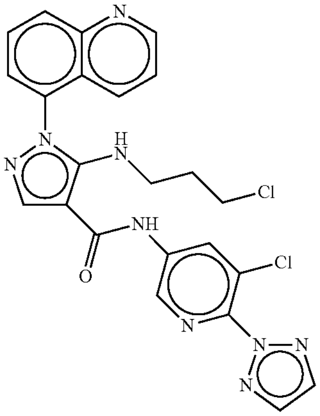 CO[C@H](C)c1c(Nc2ccc(cn2)[C@H](N(C)C(=O)C3CCS(=O)(=O)CC3)C(F)(F)F)cnc4ccc(Cl)nc14 | 348 | 380 |
| CPD0021665 | 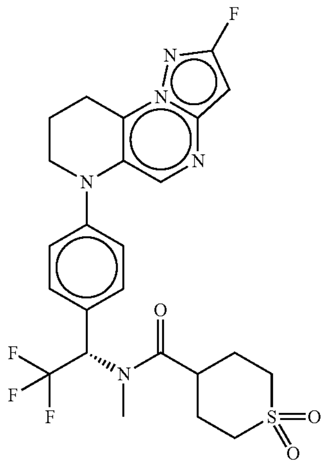 CN([C@@H](c1ccc(nc1)N2CCCc3c2cnc4cc(F)nn34)C(F)(F)F)C(=O)C5CCS(=O)(=O)CC5 | 638 | 2100 |
| CPD0082474 | 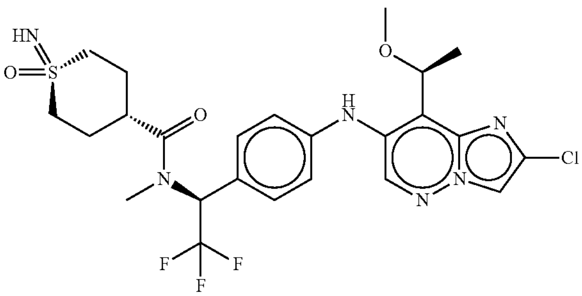 CO[C@@H](C)c1c(Nc2ccc(cc2)[C@H](N(C)C(=O)[C@@H]3CC[S@](=N)(=O)CC3)C(F)(F)F)cnn4cc(Cl)nc14 | 50 | |

TABLE 1-continued
| Compound Reference | Structure | MALT-1 IC50 [nM] | CD4TC IL2 IC50 [nm] |
|---|---|---|---|
| IC50 biochemical data for representative compounds of the disclosure. | | | |
| CPD0072772 | 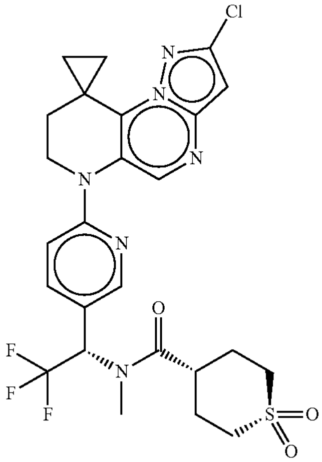 CN([C@@H](c1ccc(cc1)N2CCC3(CC3)c4c2cnc5cc(Cl)nn45)C(F)(F)F)C(=O)[C@@H]6CC[S@](=N)(=O)CC6 | 27 | 27 |
| CPD0019354 | 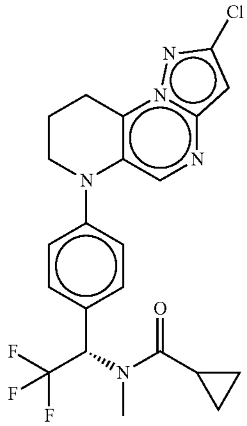 CN([C@@H](c1ccc(cc1)N2CCCc3c2cnc4cc(Cl)nn34)C(F)(F)F)C(=O)C5CC5 | 164 | 83 |
| CPD0075877 | 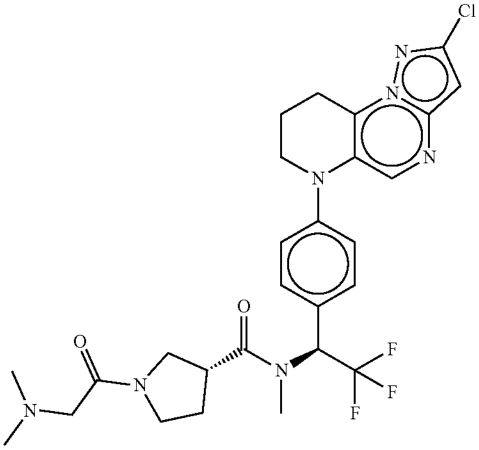 CN(C)CC(=O)N1CC[C@H](C1)C(=O)N(C)[C@@H](c2ccc(cc2)N3CCCc4c3cnc5cc(Cl)nn45)C(F)(F)F | 115 | 172 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0075579 | 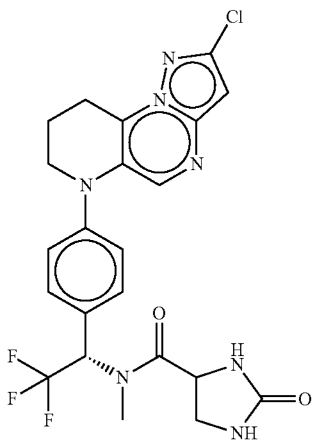<br>CN([C@@H](c1ccc(cc1)N2CCCc3c2cnc4cc(Cl)nn34)C(F)(F)F)C(=O)[C@H]5CNC(=O)N5 | 44 | |
| CPD0075578 | 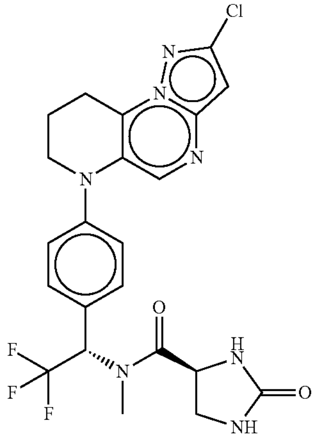<br>CN([C@@H](c1ccc(cc1)N2CCCc3c2cnc4cc(Cl)nn34)C(F)(F)F)C(=O)[C@@H]5CNC(=O)N5 | 51 | |
| CPD0074568 | 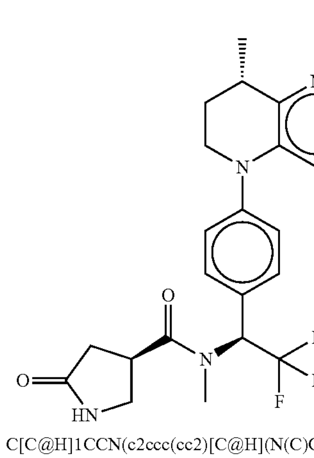<br>C[C@H]1CCN(c2ccc(cc2)[C@H](N(C)C(=O)[C@H]3CNC(=O)C3)C(F)(F)F)c4cnc5cc(Cl)nn5c14 | 33 | |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0074566 | 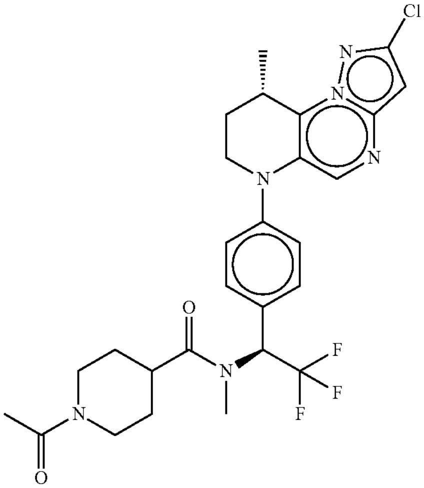 C[C@H]1CCN(c2ccc(cc2)[C@H](N(C)C(=O)C3CCN(CC3)C(=O)C)C(F)(F)F)c4cnc5cc(Cl)nn5c14 | 54 | 58 |
| CPD0074561 | 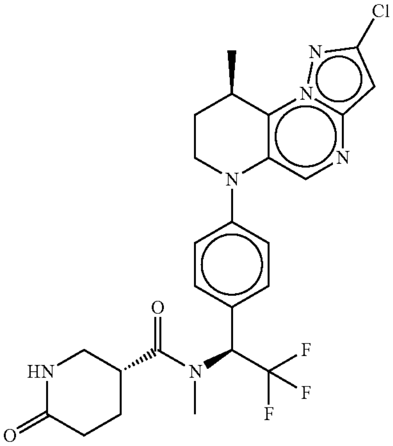 C[C@@H]1CCN(c2ccc(cc2)[C@H](N(C)C(=O)[C@@H]3CCC(=O)NC3)C(F)(F)F)c4cnc5cc(Cl)nn5c14 | 29 | 92 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0074558 | 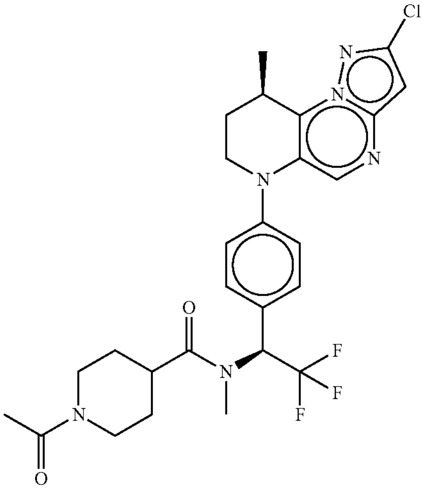<br>C[C@@H]1CCN(c2ccc(cc2)[C@H](N(C)C(=O)C3C CN(CC3)C(=O)C)C(F)(F)F)c4cnc5cc(Cl)nn5c14 | 74 | 67 |
| CPD0074538 | 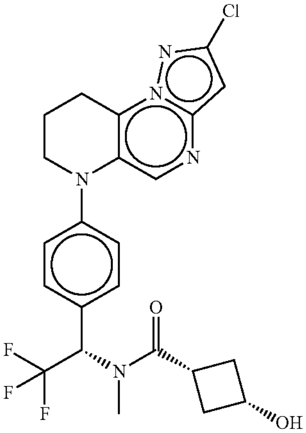<br>CN([C@@H](c1ccc(cc1)N2CCCc3c2cnc4cc(Cl)nn3 4)C(F)(F)F)C(=O)[C@@H]5C[C@H](O)C5 | 57 | |
| CPD0074046 | 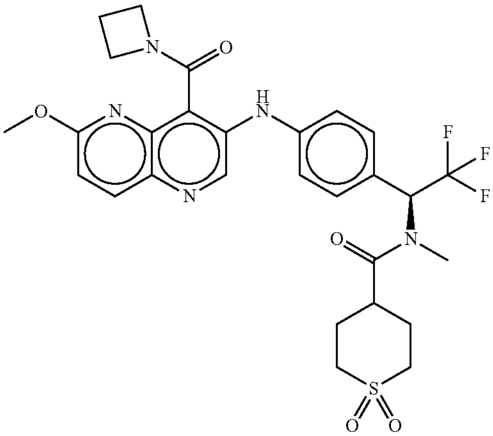<br>COc1ccc2ncc(Nc3ccc(cc3)[C@H](N(C)C(=O)C4CC S(=O)(=O)CC4)C(F)(F)F)c(C(=O)N5CCC5)c2n1 | 494 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073979 | 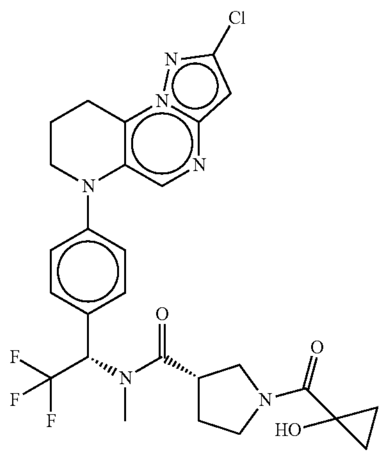 CN([C@@H](c1ccc(cc1)N2CCCc3c2cnc4cc(Cl)nn3 4)C(F)(F)F)C(=O)[C@H]5CCN(C5)C(=O)C6(O)CC6 | 75 | |
| CPD0073978 | 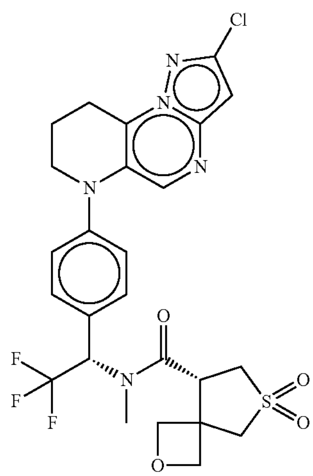 CN([C@@H](c1ccc(cc1)N2CCCc3c2cnc4cc(Cl)nn3 4)C(F)(F)F)C(=O)[C@@H]5CCN(C5)C(=O)C6(O)C C6 | 54 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073975 | 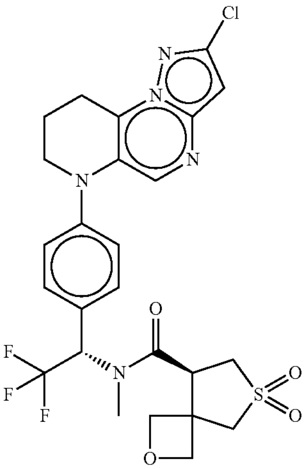 CN([C@@H](c1ccc(cc1)N2CCCc3c2cnc4cc(Cl)nn34)C(F)(F)F)C(=O)[C@H]5CS(=O)(=O)CC56COC6 | 112 | 341 |
| CPD0073974 | 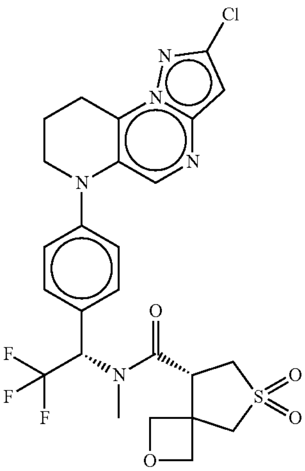 CN([C@@H](c1ccc(cc1)N2CCCc3c2cnc4cc(Cl)nn34)C(F)(F)F)C(=O)[C@@H]5CS(=O)(=O)CC56COC6 | 155 | 340 |
| CPD0073972 | 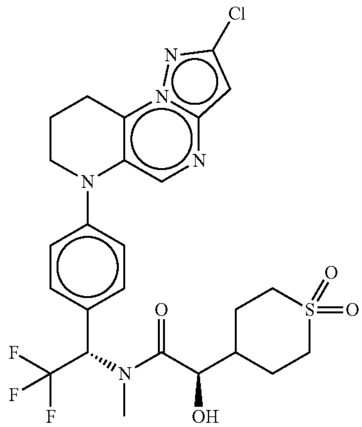 CN([C@@H](c1ccc(cc1)N2CCCc3c2cnc4cc(Cl)nn34)C(F)(F)F)C(=O)[C@H](O)C5CCS(=O)(=O)CC5 | 109 | |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073969 | 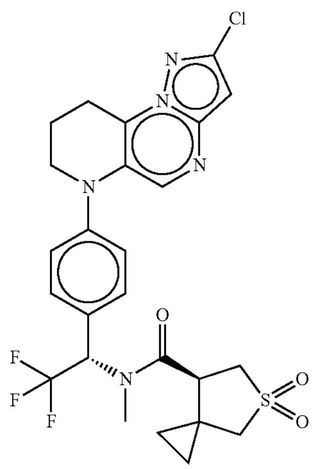 CN([C@@H](c1ccc(cc1)N2CCCc3c2cnc4cc(Cl)nn34)C(F)(F)F)C(=O)[C@H]5CS(=O)(=O)CC56CC6 | 101 | 252 |
| CPD0073968 | 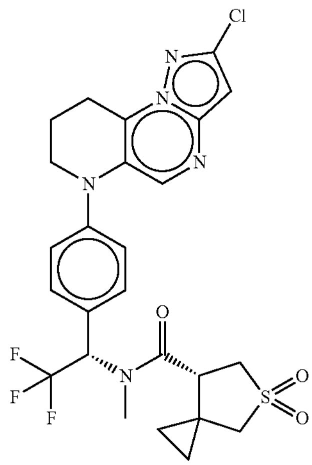 CN([C@@H](c1ccc(cc1)N2CCCc3c2cnc4cc(Cl)nn34)C(F)(F)F)C(=O)[C@@H]5CS(=O)(=O)CC56CC6 | 100 | 199 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073763 | 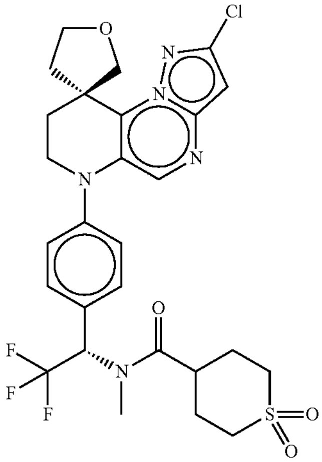 CN([C@@H](c1ccc(cc1)N2CC[C@]3(CCOC3)c4c2cnc5cc(Cl)nn45)C(F)(F)F)C(=O)C6CCS(=O)(=O)CC6 | 57 | 109 |
| CPD0073762 | 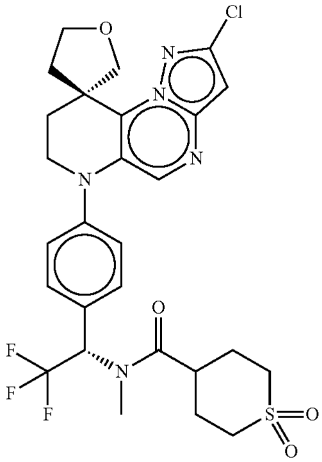 CN([C@@H](c1ccc(cc1)N2CC[C@@]3(CCOC3)c4c2cnc5cc(Cl)nn45)C(F)(F)F)C(=O)C6CCS(=O)(=O)CC6 | 53 | 104 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073570 | 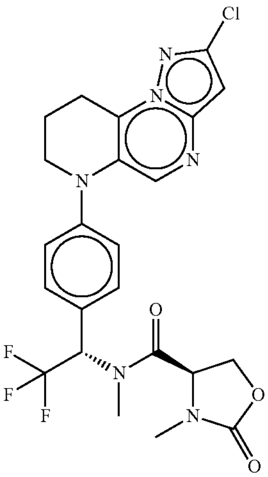 CN([C@@H](c1ccc(cc1)N2CCCc3c2cnc4cc(Cl)nn3 4)C(F)(F)F)C(=O)[C@H]5COC(=O)N5C | 62 | 216 |
| CPD0073560 | 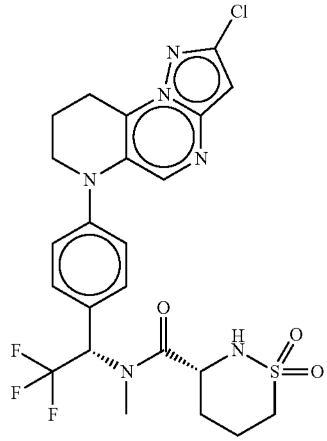 CN([C@@H](c1ccc(cc1)N2CCCc3c2cnc4cc(Cl)nn3 4)C(F)(F)F)C(=O)[C@H]5CCCS(=O)(=O)N5 | 92 | 157 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073553 | 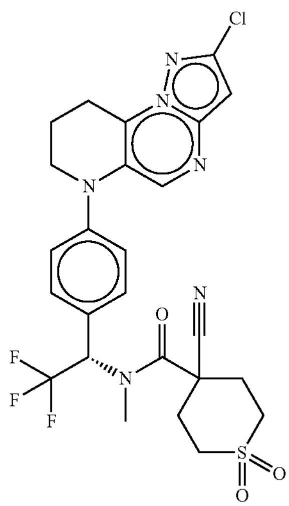 CN([C@@H](c1ccc(cc1)N2CCCc3c2cnc4cc(Cl)nn34)C(F)(F)F)C(=O)C5(CCS(=O)(=O)CC5)C#N | 50 | 77 |
| CPD0073535 | 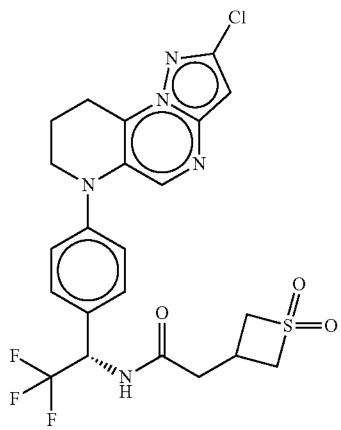 FC(F)(F)[C@@H](NC(=O)CC1CS(=O)(=O)C1)c2ccc(cc2)N3CCCc4c3cnc5cc(Cl)nn45 | 403 | 2073 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073502 | 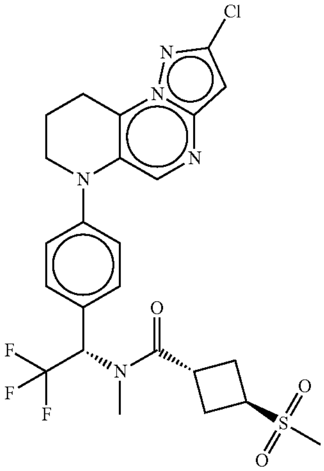 CN([C@@H](c1ccc(cc1)N2CCCc3c2cnc4cc(Cl)nn34)C(F)(F)F)C(=O)[C@@H]5C[C@H](C5)S(=O)(=O)C | 61 | 104 |
| CPD0073501 | 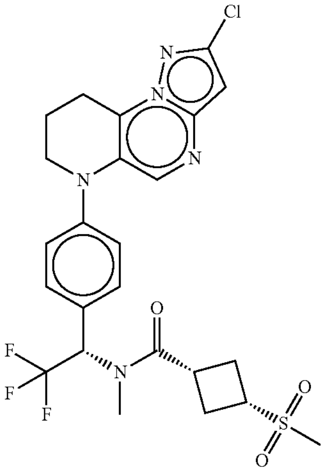 CN([C@@H](c1ccc(cc1)N2CCCc3c2cnc4cc(Cl)nn34)C(F)(F)F)C(=O)[C@@H]5C[C@@H](C5)S(=O)(=O)C | 66 | 140 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073243 | 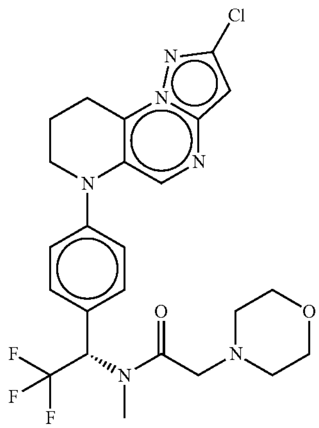 CN([C@@H](c1ccc(cc1)N2CCCc3c2cnc4cc(Cl)nn3 4)C(F)(F)F)C(=O)CN5CCOCC5 | 273 | 315 |
| CPD0073238 | 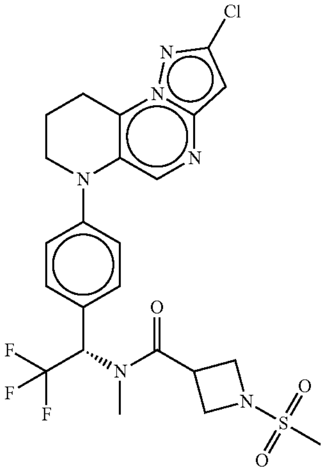 CN([C@@H](c1ccc(cc1)N2CCCc3c2cnc4cc(Cl)nn3 4)C(F)(F)F)C(=O)C5CN(C5)S(=O)(=O)C | 87 | 174 |
| CPD0073191 | 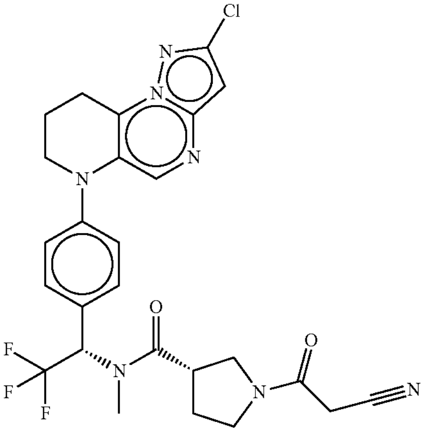 CN([C@@H](c1ccc(cc1)N2CCCc3c2cnc4cc(Cl)nn3 4)C(F)(F)F)C(=O)[C@H]5CCN(C5)C(=O)CC#N | 96 | 148 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073190 | 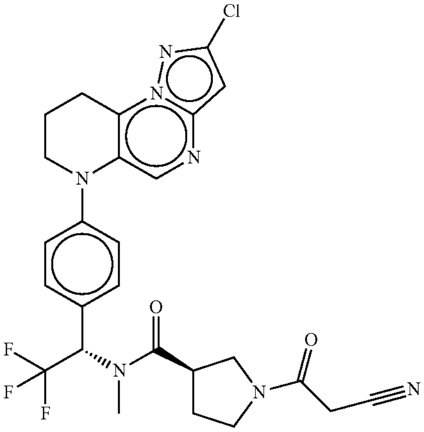 CN([C@@H](c1ccc(cc1)N2CCCc3c2cnc4cc(Cl)nn3 4)C(F)(F)F)C(=O)[C@@H]5CCN(C5)C(=O)CC#N | 114 | 239 |
| CPD0073144 | 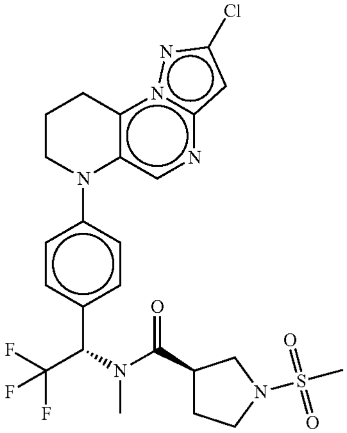 CN([C@@H](c1ccc(cc1)N2CCCc3c2cnc4cc(Cl)nn3 4)C(F)(F)F)C(=O)[C@@H]5CCN(C5)S(=O)(=O)C | 66 | 116 |
| CPD0073143 | 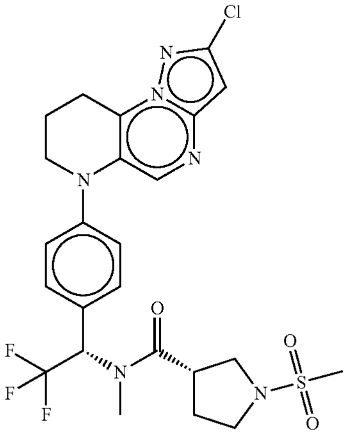 CN([C@@H](c1ccc(cc1)N2CCCc3c2cnc4cc(Cl)nn3 4)C(F)(F)F)C(=O)[C@H]5CCN(C5)S(=O)(=O)C | 68 | 107 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073140 | 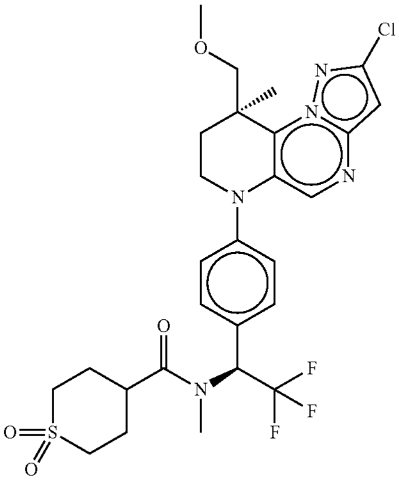 COC[C@]1(C)CCN(c2ccc(cc2)[C@H](N(C)C(=O)C3CCS(=O)(=O)CC3)C(F)(F)F)c4cnc5cc(Cl)nn5c14 | 92 | 192 |
| CPD0073139 | 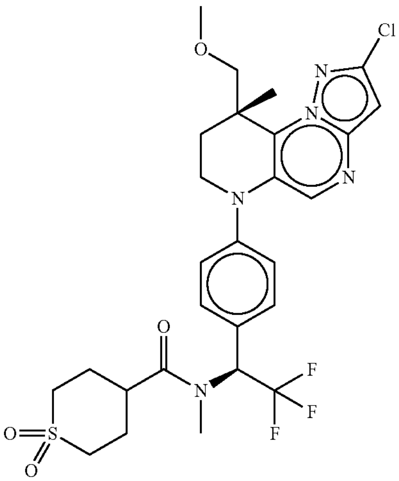 COC[C@@]1(C)CCN(c2ccc(cc2)[C@H](N(C)C(=O)C3CCS(=O)(=O)CC3)C(F)(F)F)c4cnc5cc(Cl)nn5c14 | 112 | 65 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073138 | 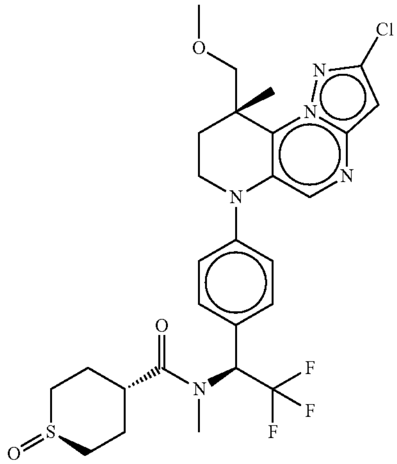 COC[C@@]1(C)CCN(c2ccc(cc2)[C@H](N(C)C(=O)[C@@H]3CC[S@@](=O)CC3)C(F)(F)F)c4cnc5cc(Cl)nn5c14 | 79 | 55 |
| CPD0073137 | 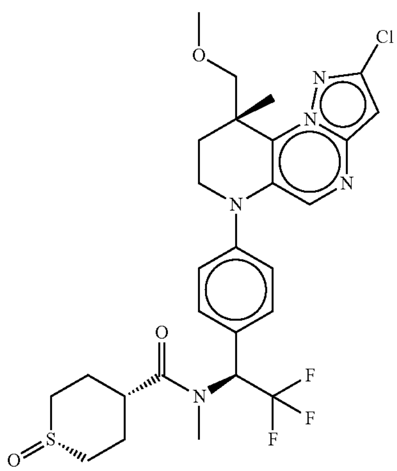 COC[C@@]1(C)CCN(c2ccc(cc2)[C@H](N(C)C(=O)[C@@H]3CC[S@](=O)CC3)C(F)(F)F)c4cnc5cc(Cl)nn5c14 | 90 | 45 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073136 | 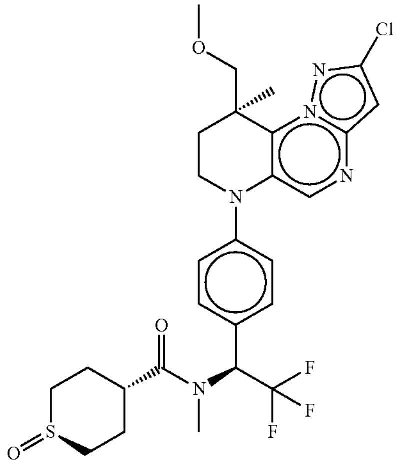 COC[C@]1(C)CCN(c2ccc(cc2)[C@H](N(C)C(=O)[C@@H]3CC[S@@](=O)CC3)C(F)(F)F)c4cnc5cc(Cl)nn5c14 | 138 | 63 |
| CPD0073135 | 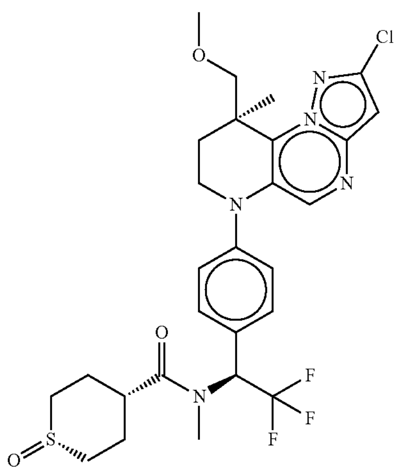 COC[C@]1(C)CCN(c2ccc(cc2)[C@H](N(C)C(=O)[C@@H]3CC[S@](=O)CC3)C(F)(F)F)c4cnc5cc(Cl)nn5c14 | 106 | 130 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073088 | 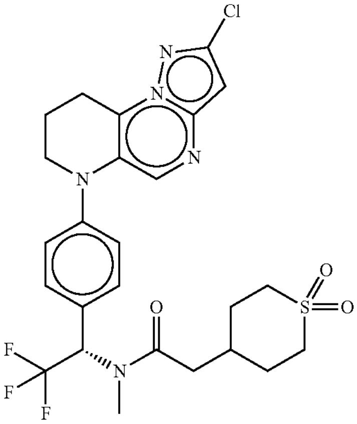 CN([C@@H](c1ccc(cc1)N2CCCc3c2cnc4cc(Cl)nn34)C(F)(F)F)C(=O)CC5CCS(=O)(=O)CC5 | 91 | 142 |
| CPD0073087 | 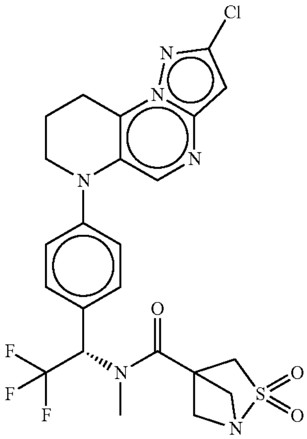 CN([C@@H](c1ccc(cc1)N2CCCc3c2cnc4cc(Cl)nn34)C(F)(F)F)C(=O)C56CN(C5)S(=O)(=O)C6 | 78 | 103 |
| CPD0073085 | 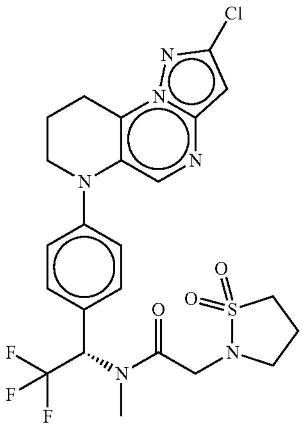 CN([C@@H](c1ccc(cc1)N2CCCc3c2cnc4cc(Cl)nn34)C(F)(F)F)C(=O)CN5CCCS5(=O)=O | 154 | 286 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073084 | 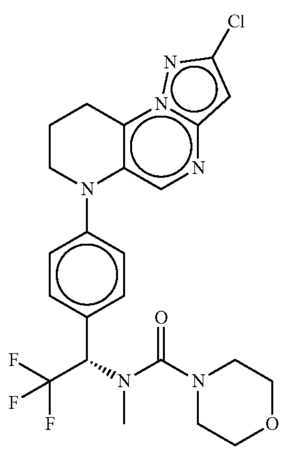 CN([C@@H](c1ccc(cc1)N2CCCc3c2cnc4cc(Cl)nn34)C(F)(F)F)C(=O)N5CCOCC5 | 168 | 255 |
| CPD0073083 | 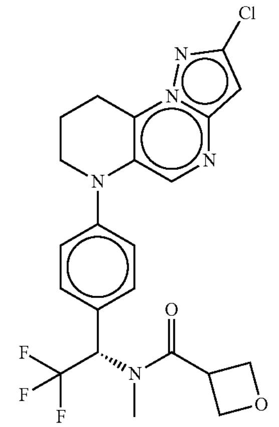 CN([C@@H](c1ccc(cc1)N2CCCc3c2cnc4cc(Cl)nn34)C(F)(F)F)C(=O)C5COC5 | 90 | 146 |
| CPD0073041 | 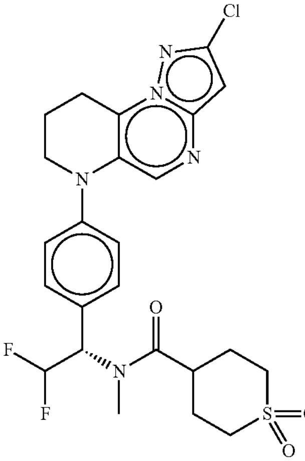 CN([C@H](C(F)F)c1ccc(cc1)N2CCCc3c2cnc4cc(Cl)nn34)C(=O)C5CCS(=O)(=O)CC5 | 432 | 5784 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073040 | 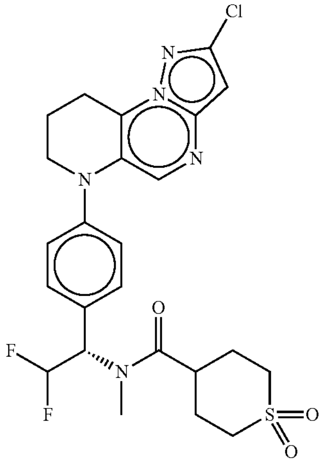 COc1cc(ccc1N2CCCc3c2cnc4cc(Cl)nn34)[C@H](N(C)C(=O)C5CCS(=O)(=O)CC5)C(F)(F)F | 368 | 642 |
| CPD0072938 | 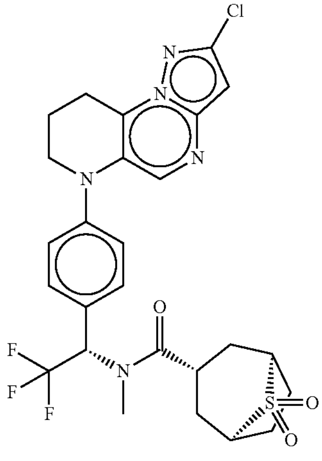 CN([C@@H](c1ccc(cc1)N2CCCc3c2cnc4cc(Cl)nn34)C(F)(F)F)C(=O)[C@@H]5C[C@H]6Cc[C@@H](C5)S6(=O)=O | 90 | 92 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072937 | 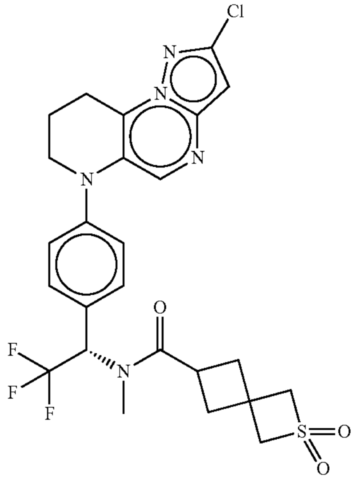 CN([C@@H](c1ccc(cc1)N2CCCc3c2cnc4cc(Cl)nn3 4)C(F)(F)F)C(=O)C5CC6(C5)CS(=O)(=O)C6 | 75 | 93 |
| CPD0072934 | 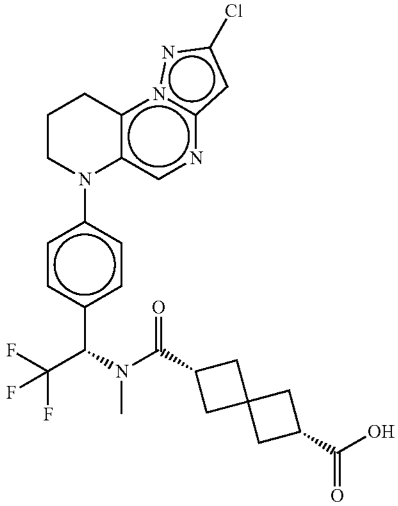 CN([C@@H](c1ccc(cc1)N2CCCc3c2cnc4cc(Cl)nn3 4)C(F)(F)F)C(=O)[C@@H]5C[C@@H](C5)C(=O)O | 72 | 422 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072933 | 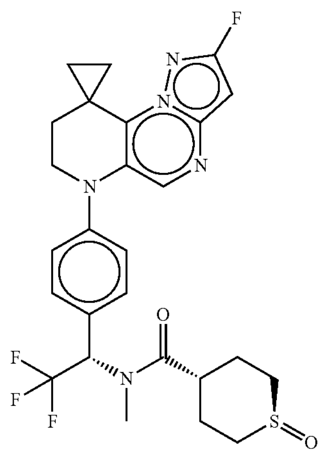 CN([C@@H](c1ccc(cc1)N2CCC3(CC3)c4c2cnc5cc(F)nn45)C(F)(F)F)C(=O)[C@@H]6cc[S@@](=O)CC6 | 33 | 58 |
| CPD0072932 | 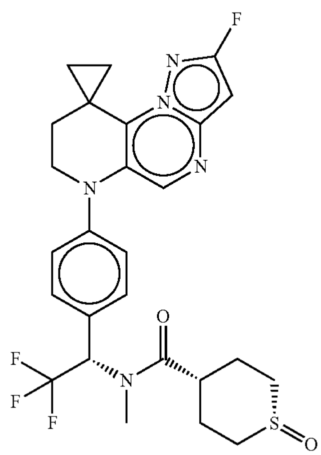 CN([C@@H](c1ccc(cc1)N2CCC3(CC3)c4c2cnc5cc(F)nn45)C(F)(F)F)C(=O)[C@@H]6CC[S@](=O)CC6 | 49 | 56 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072808 | 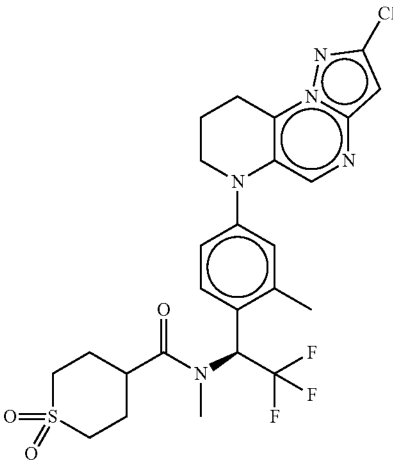 CN([C@@H](c1ccc(cc1C)N2CCCc3c2cnc4cc(Cl)nn34)C(F)(F)F)C(=O)C5CCS(=O)(=O)CC5 | 127 | 237 |
| CPD0072806 | 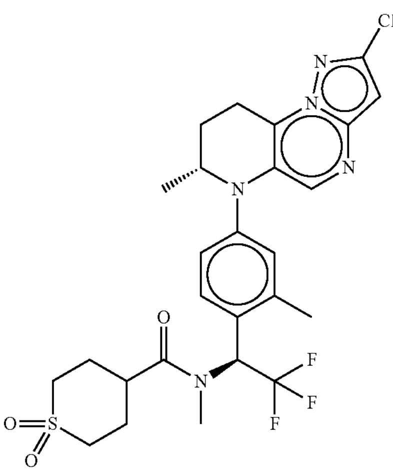 C[C@@H]1CCc2c(cnc3cc(Cl)nn23)N1c4ccc(cc4)[C@H](N(C)C(=O)C5CCS(=O)(=O)CC5)C(F)(F)F | 69 | 206 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072805 | 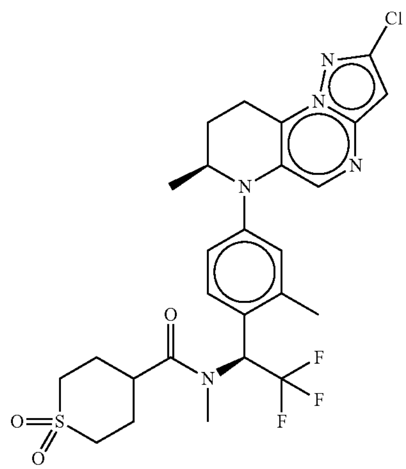 C[C@H]1CCc2c(cnc3cc(Cl)nn23)N1c4ccc(cc4)[C@H](N(C)C(=O)C5CCS(=O)(=O)CC5)C(F)(F)F | 172 | 1023 |
| CPD0072804 | 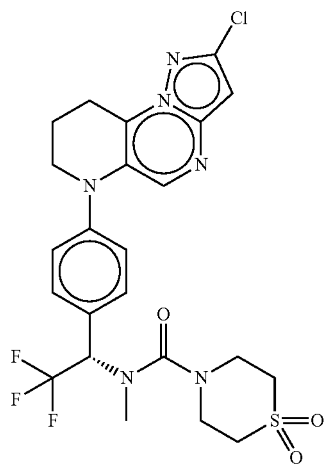 CN([C@@H](c1ccc(cc1)N2CCCc3c2cnc4cc(Cl)nn34)C(F)(F)F)C(=O)N5CCS(=O)(=O)CC5 | 159 | 307 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072803 | 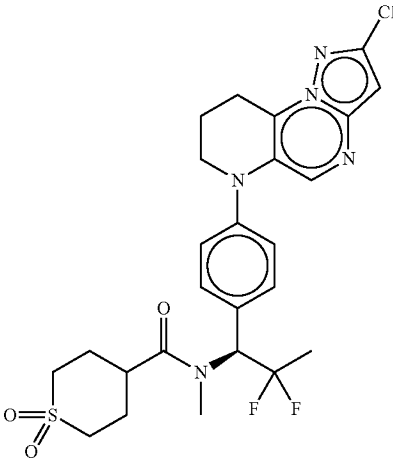 CN([C@@H](c1ccc(cc1)N2CCCc3c2cnc4cc(Cl)nn34)C(C)(F)F)C(=O)C5CCS(=O)(=O)CC5 | 322 | 1889 |
| CPD0072801 | 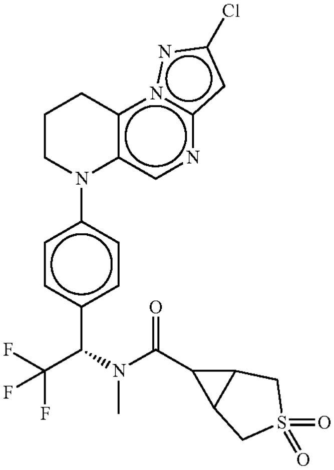 CN([C@@H](c1ccc(cc1)N2CCCc3c2cnc4cc(Cl)nn34)C(F)(F)F)C(=O)C5C6CS(=O)(=O)CC56 | 95 | 147 |
| CPD0072800 | 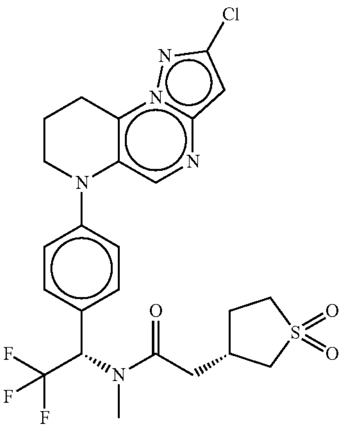 CN([C@@H](c1ccc(cc1)N2CCCc3c2cnc4cc(Cl)nn34)C(F)(F)F)C(=O)C[C@@H]5CCS(=O)(=O)C5 | 92 | 187 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072799 | 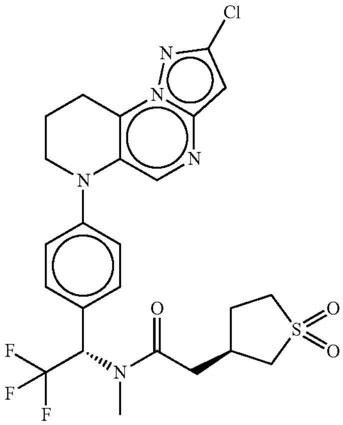 CN([C@@H](c1ccc(cc1)N2CCCc3c2cnc4cc(Cl)nn34)C(F)(F)F)C(=O)C[C@H]5CCS(=O)(=O)C5 | 88 | 178 |
| CPD0072798 | 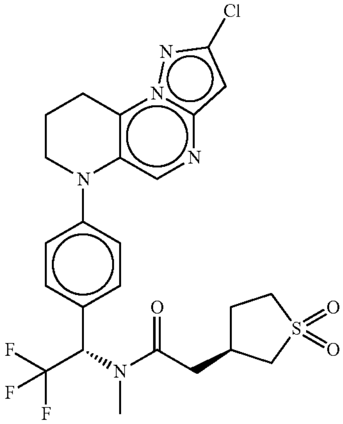 CN([C@@H](c1ccc(cc1)N2CCCc3c2cnc4cc(Cl)nn34)C(F)(F)F)C(=O)CC5CS(=O)(=O)C5 | 142 | 200 |
| CPD0072779 | 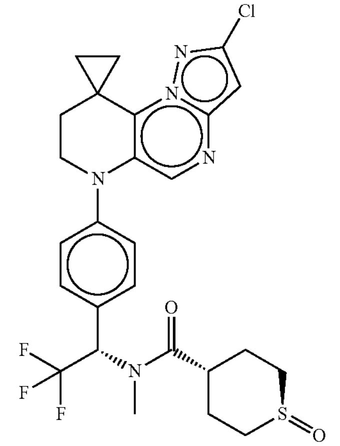 CN([C@@H](c1ccc(cc1)N2CCC3(CC3)c4c2cnc5cc(Cl)nn45)C(F)(F)F)C(=O)[C@@H]6CC[S@@](=O)CC6 | 57 | 33 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0072778 | 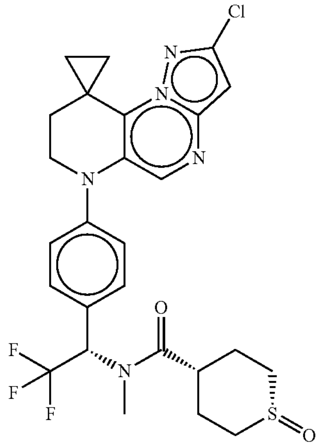 CN([C@@H](c1ccc(cc1)N2CCC3(CC3)c4c2cnc5cc(Cl)nn45)C(F)(F)F)C(=O)[C@@H]6CC[S@](=O)CC6 | 58 | 42 |
| CPD0072777 | 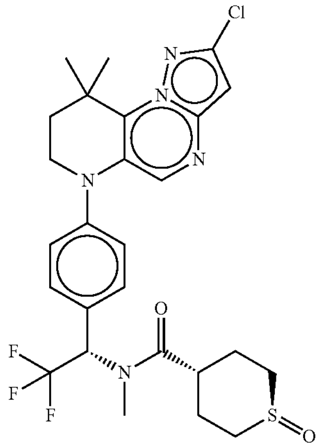 CN([C@@H](c1ccc(cc1)N2CCC(C)(C)c3c2cnc4cc(Cl)nn34)C(F)(F)F)C(=O)[C@@H]5CC[S@@](=O)CC5 | 62 | 36 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072776 | 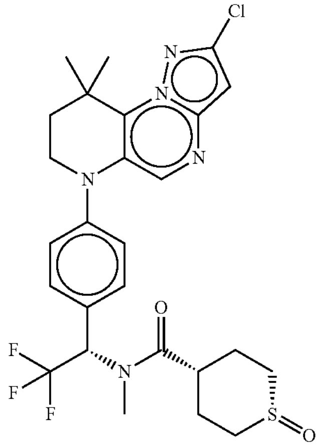 CN([C@@H](c1ccc(cc1)N2CCC(C)(C)c3c2cnc4cc(Cl)nn34)C(F)(F)F)C(=O)[C@@H]5CC[S@](=O)CC5 | 73 | 35 |
| CPD0072441 | 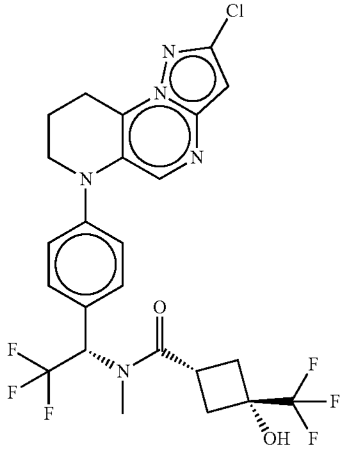 CN([C@@H](c1ccc(cc1)N2CCCc3c2cnc4cc(Cl)nn34)C(F)(F)F)C(=O)[C@@H]5C[C@](O)(C5)C(F)(F)F | 113 | 222 |
| CPD0072439 | 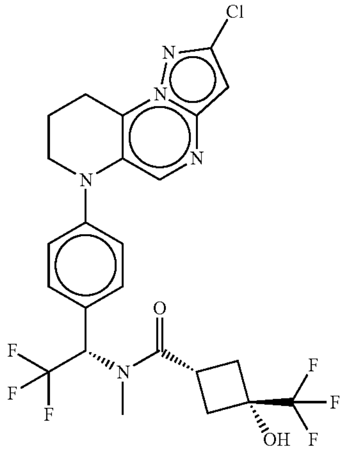 CN([C@@H](c1ccc(cc1)N2CCCc3c2cnc4cc(Cl)nn34)C(F)(F)F)C(=O)[C@@H]5C[C@H](C5)C(=O)O | 35 | 557 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0072437 | 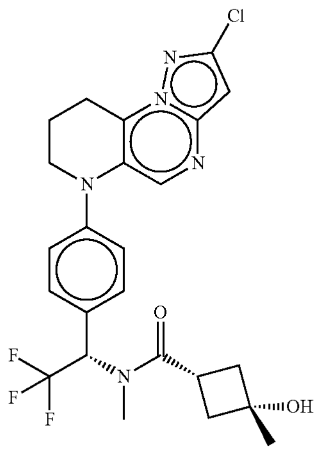 CN([C@@H](c1ccc(cc1)N2CCCc3c2cnc4cc(Cl)nn34)C(F)(F)F)C(=O)[C@@H]5C[C@](C)(O)C5 | 123 | 178 |
| CPD0022148 | 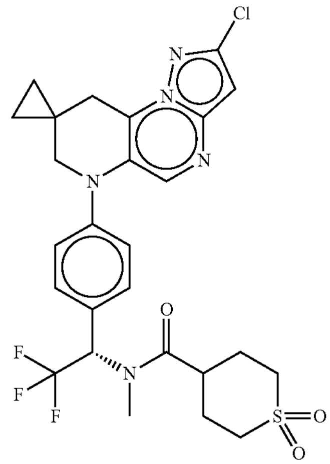 CN([C@@H](c1ccc(cc1)N2CC3(CC3)Cc4c2cnc5cc(Cl)nn45)C(F)(F)F)C(=O)C6CCS(=O)(=O)CC6 | 121 | 116 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0021811 | 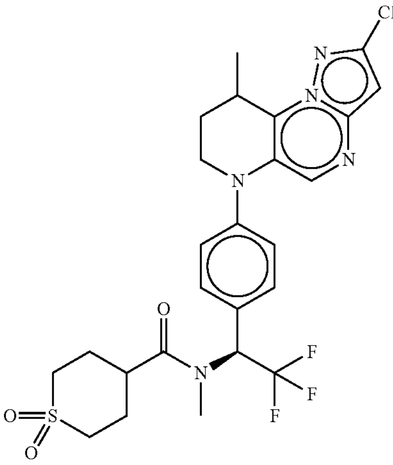 CC1CCN(c2ccc(cc2)[C@H](N(C)C(=O)C3CCS(=O)(=O)CC3)C(F)(F)F)c4cnc5cc(Cl)nn5c14 | 68 | 82 |
| CPD0021574 | 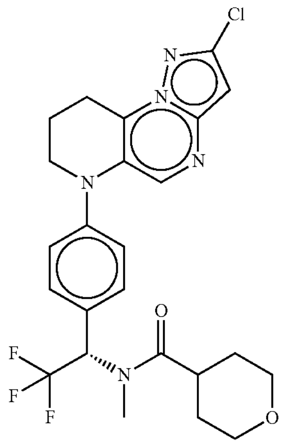 CN([C@@H](c1ccc(cc1)N2CCCc3c2cnc4cc(Cl)nn3 4)C(F)(F)F)C(=O)C5CCOCC5 | 123 | 121 |
| CPD0021565 | 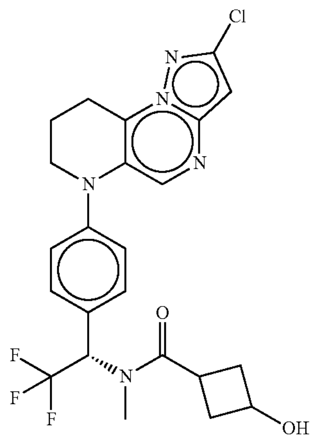 CN([C@@H](c1ccc(cc1)N2CCCc3c2cnc4cc(Cl)nn3 4)C(F)(F)F)C(=O)C5CC(O)C5 | 84 | 86 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0019590 | 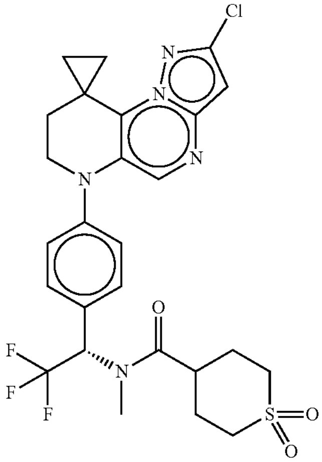 CN([C@@H](c1ccc(cc1)N2CCC3(CC3)c4c2cnc5cc(Cl)nn45)C(F)(F)F)C(=O)C6CCS(=O)(=O)CC6 | 64 | 37 |
| CPD0019589 | 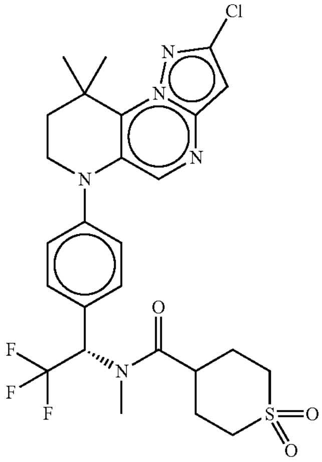 CN([C@@H](c1ccc(cc1)N2CCC(C)(C)c3c2cnc4cc(Cl)nn34)C(F)(F)F)C(=O)C5CCS(=O)(=O)CC5 | 38 | 32 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0019494 | 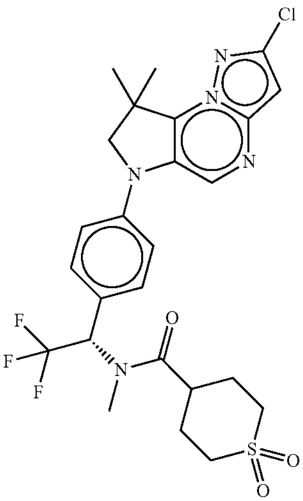 CN([C@@H](c1ccc(cc1)N2CC(C)(C)c3c2cnc4cc(Cl)nn34)C(F)(F)F)C(=O)C5CCS(=O)(=O)CC5 | 25 | 59 |
| CPD0019351 | 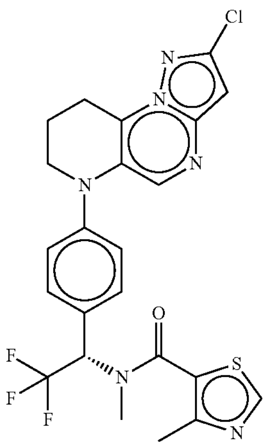 CN([C@@H](c1ccc(cc1)N2CCCc3c2cnc4cc(Cl)nn34)C(F)(F)F)C(=O)c5scnc5C | 278 | 152 |
| CPD0019350 | 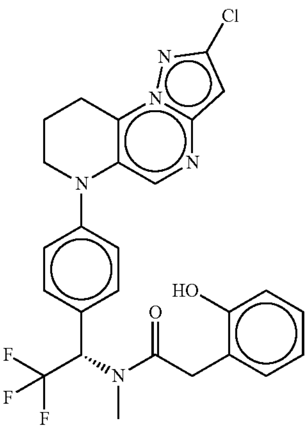 CN([C@@H](c1ccc(cc1)N2CCCc3c2cnc4cc(Cl)nn34)C(F)(F)F)C(=O)Cc5ccccc5O | 70 | 103 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0019184 | 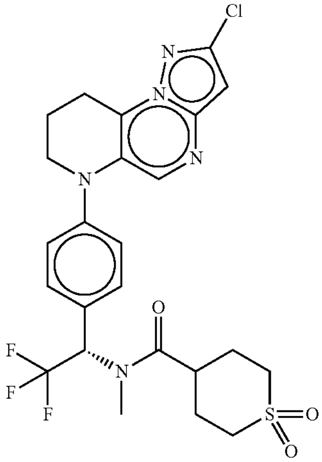 CN([C@@H](c1ccc(cc1)N2CCCc3c2cnc4cc(Cl)nn34)C(F)(F)F)C(=O)C5CCS(=O)(=O)CC5 | 59 | 68 |
| CPD0019078 | 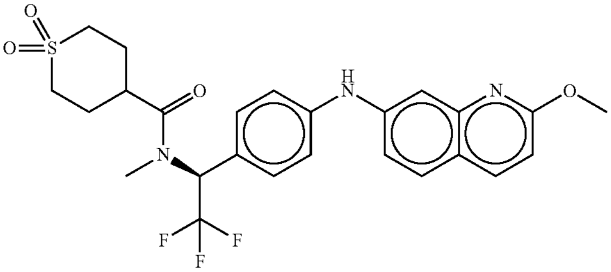 COc1ccc2ccc(Nc3ccc(cc3)[C@H](N(C)C(=O)C4CCS(=O)(=O)CC4)C(F)(F)F)cc2n1 | 182 | 108 |
| CPD0073922 | 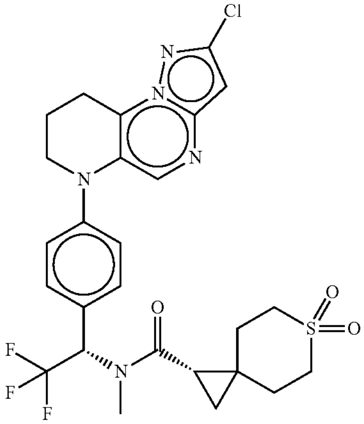 CN([C@@H](c1ccc(cc1)N2CCCc3c2cnc4cc(Cl)nn34)C(F)(F)F)C(=O)[C@H]5CC56CCS(=O)(=O)CC6 | 173 | 994 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073921 | 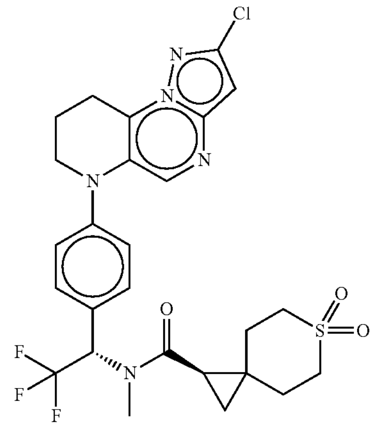 CN([C@@H](c1ccc(cc1)N2CCCc3c2cnc4cc(Cl)nn34)C(F)(F)F)C(=O)[C@@H]5CC56CCS(=O)(=O)CC6 | 109 | 186 |
| CPD0073918 | 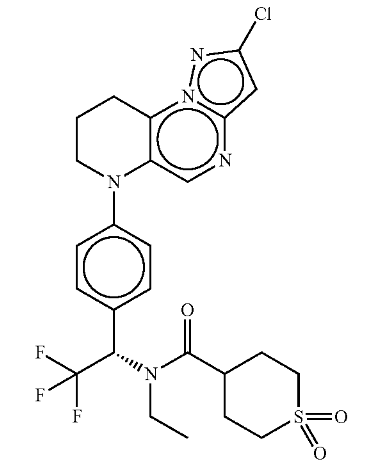 CCN([C@@H](c1ccc(cc1)N2CCCc3c2cnc4cc(Cl)nn34)C(F)(F)F)C(=O)C5CCS(=O)(=O)CC5 | 106 | 145 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073691 | 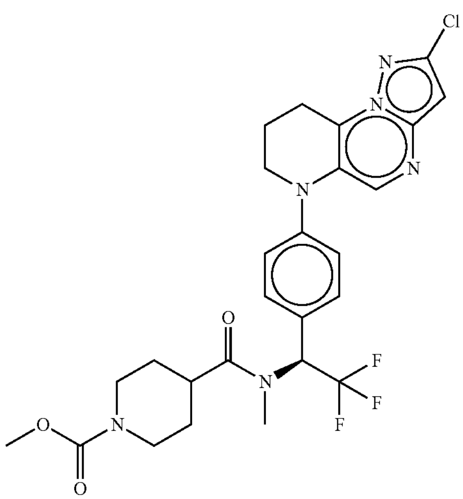 COC(=O)N1CCC(CC1)C(=O)N(C)[C@@H](c2ccc(c c2)N3CCCc4c3cnc5cc(Cl)nn45)C(F)(F)F | 101 | 149 |
| CPD0073504 | 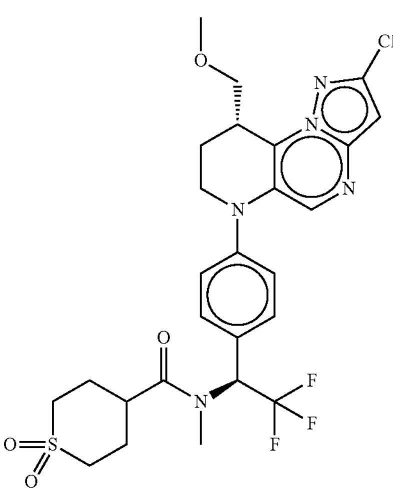 COC[C@H]1CCN(c2ccc(cc2)[C@H](N(C)C(=O)C3 CCS(=O)(=O)CC3)C(F)(F)F)c4cnc5cc(Cl)nn5c14 | 88 | 88 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0073503 | 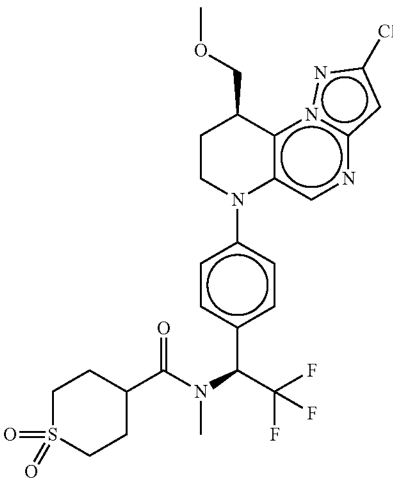<br>COC[C@@H]1CCN(c2ccc(cc2)[C@H](N(C)C(=O)C3CCS(=O)(=O)CC3)C(F)(F)F)c4cnc5cc(Cl)nn5c14 | 115 | 209 |
| CPD0073500 | 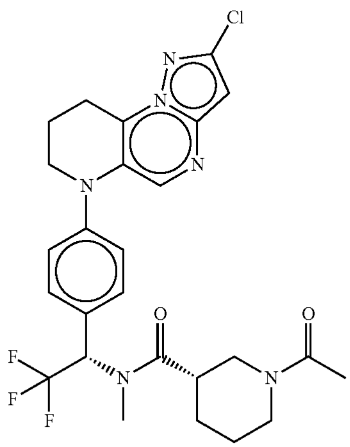<br>CN([C@@H](c1ccc(cc1)N2CCCc3c2cnc4cc(Cl)nn34)C(F)(F)F)C(=O)[C@H]5CCCN(C5)C(=O)C | 167 | 267 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0073499 | 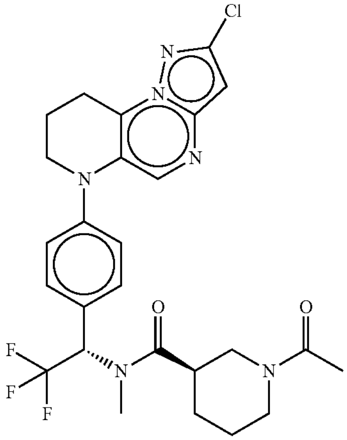 CN([C@@H](c1ccc(cc1)N2CCCc3c2cnc4cc(Cl)nn34)C(F)(F)F)C(=O)[C@@H]5CCCN(C5)C(=O)C | 127 | 175 |
| CPD0073237 | 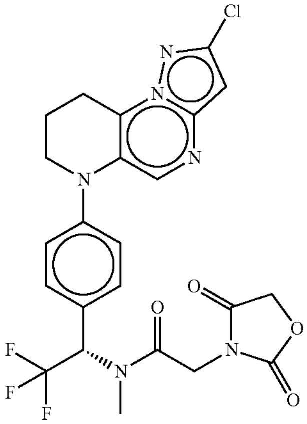 CN([C@@H](c1ccc(cc1)N2CCCc3c2cnc4cc(Cl)nn34)C(F)(F)F)C(=O)CN5C(=O)COC5=O | 174 | 513 |
| CPD0072780 | 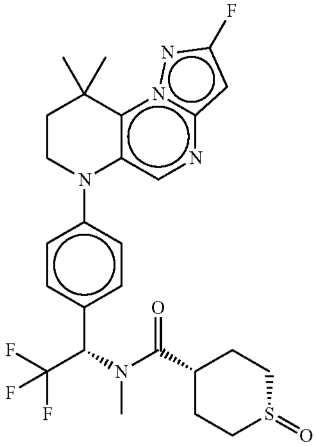 CN([C@@H](c1ccc(cc1)N2CCC(C)(C)c3c2cnc4cc(F)nn34)C(F)(F)F)C(=O)[C@@H]5CC[S@](=O)CC5 | 75 | 107 |

TABLE 1-continued
IC50 biochemical data for representative compounds of the disclosure.
| Compound Reference | Structure | MALT-1 IC50 [nM] | CD4TC IL2 IC50 [nm] |
| --- | --- | --- | --- |
| CPD0072461 | 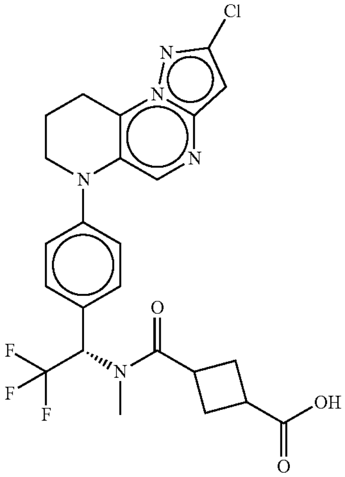<br>CN([C@@H](c1ccc(cc1)N2CCCc3c2cnc4cc(Cl)nn3<br>4)C(F)(F)F)C(=O)C5CC(C5)C(=O)O | 63 | 732 |
| CPD0072442 | 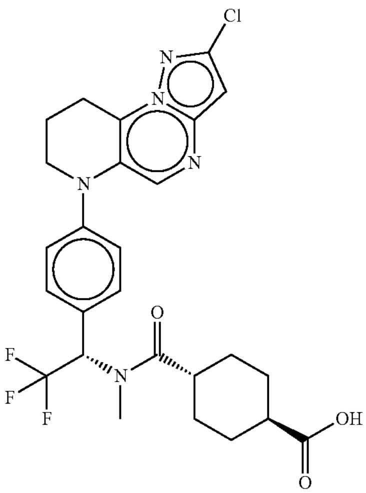<br>CN([C@@H](c1ccc(cc1)N2CCCc3c2cnc4cc(Cl)nn3<br>4)C(F)(F)F)C(=O)[C@@H]5CC[C@H](CC5)C(=O)<br>O | 43 | 300 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0022149 | 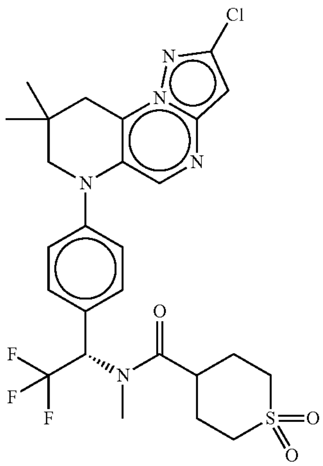 CN([C@@H](c1ccc(cc1)N2CC(C)(C)Cc3c2cnc4cc(Cl)nn34)C(F)(F)F)C(=O)C5CCS(=O)(=O)CC5 | 71 | 93 |
| CPD0022134 | 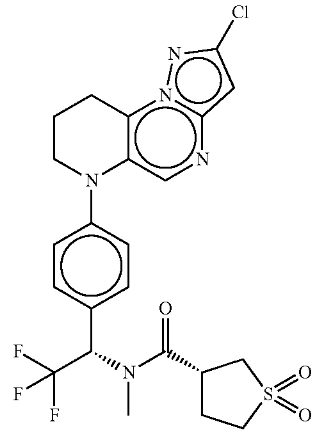 CN([C@@H](c1ccc(cc1)N2CCCc3c2cnc4cc(Cl)nn34)C(F)(F)F)C(=O)[C@H]5CCS(=O)(=O)C5 | 134 | 175 |
| CPD0021934 | 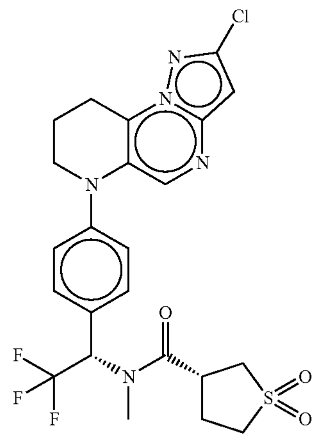 CN([C@@H](c1ccc(cc1)N2CCCc3c2cnc4cc(Cl)nn34)C(F)(F)F)C(=O)CC5CCCS5(=O)=O | 369 | 588 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0021874 | 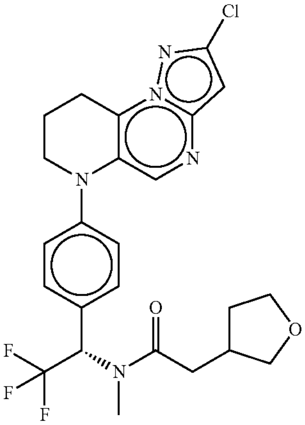 CN([C@@H](c1ccc(cc1)N2CCCc3c2cnc4cc(Cl)nn3 4)C(F)(F)F)C(=O)CC5CCOC5 | 256 | 209 |
| CPD0021849 | 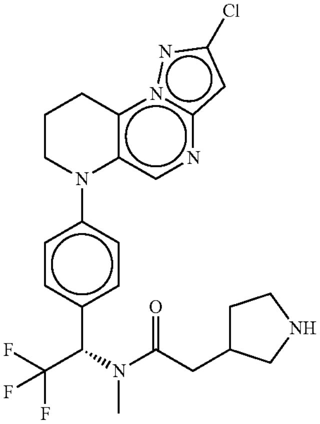 CN([C@@H](c1ccc(cc1)N2CCCc3c2cnc4cc(Cl)nn3 4)C(F)(F)F)C(=O)CC5CCNC5 | 203 | 558 |
| CPD0021815 | 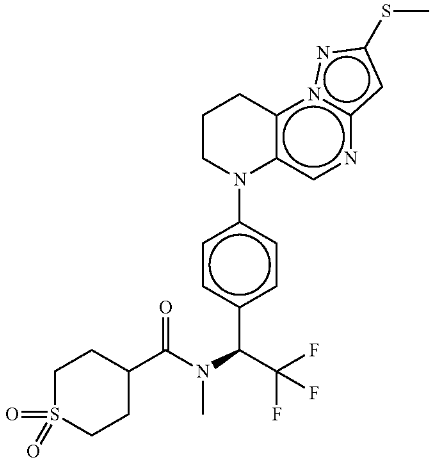 CSc1cc2ncc3N(CCCc3n2n1)c4ccc(cc4)[C@H](N(C) C(=O)C5CCS(=O)(=O)CC5)C(F)(F)F | 332 | 228 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0021809 | 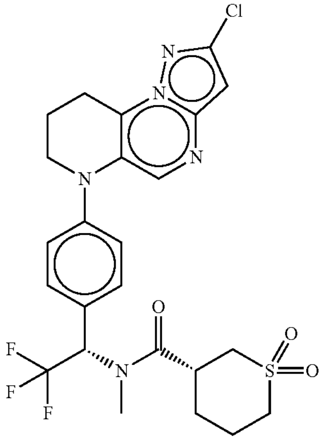<br>CN([C@@H](c1ccc(cc1)N2CCCc3c2cnc4cc(Cl)nn34)C(F)(F)F)C(=O)[C@H]5CCCS(=O)(=O)C5 | 154 | 143 |
| CPD0021755 | 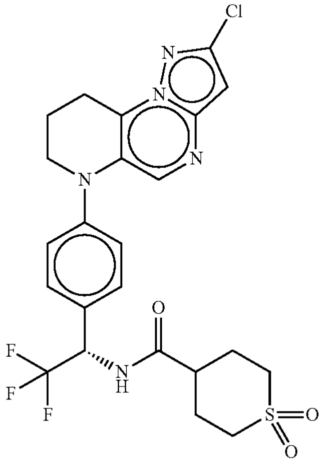<br>FC(F)(F)[C@@H](NC(=O)C1CCS(=O)(=O)CC1)c2ccc(cc2)N3CCCc4c3cnc5cc(Cl)nn45 | 433 | 845 |
| CPD0021751 | 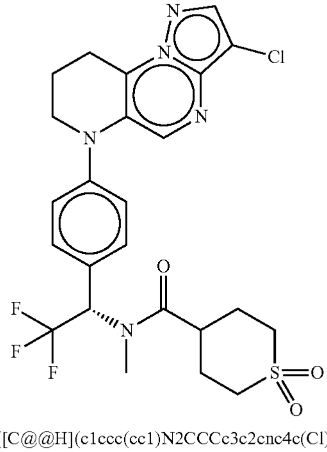<br>CN([C@@H](c1ccc(cc1)N2CCCc3c2cnc4c(Cl)cnn34)C(F)(F)F)C(=O)C5CCS(=O)(=O)CC5 | 2115 | 3275 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0021750 | 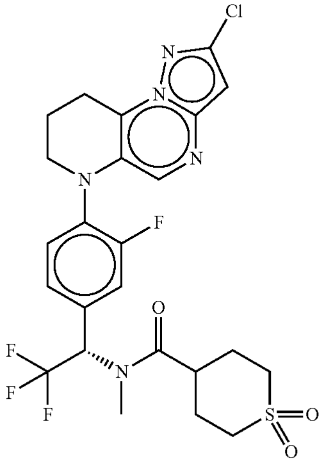 CN([C@@H](c1ccc(N2CCCc3c2cnc4cc(Cl)nn34)c(F)c1)C(F)(F)F)C(=O)C5CCS(=O)(=O)CC5 | 76 | 111 |
| CPD0021745 | 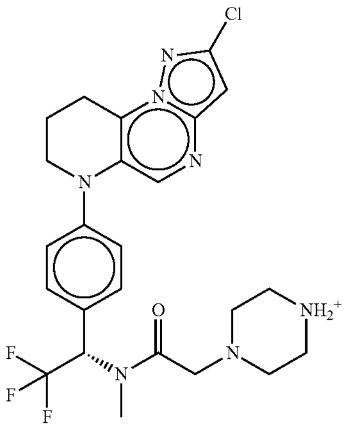 CN([C@@H](c1ccc(cc1)N2CCCc3c2cnc4cc(Cl)nn34)C(F)(F)F)C(=O)CN5CC[NH2+]CC5 | 368 | 748 |
| CPD0021733 | 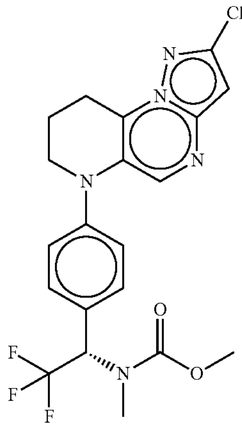 COC(=O)N(C)[C@@H](c1ccc(cc1)N2CCCc3c2cnc4cc(Cl)nn34)C(F)(F)F | 339 | 412 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0021661 | 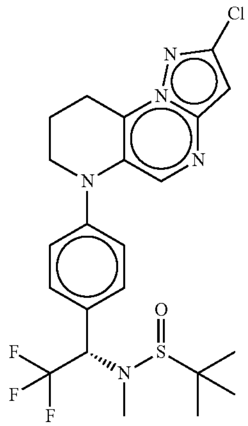 CN([C@@H](c1ccc(cc1)N2CCCc3c2cnc4cc(Cl)nn34)C(F)(F)F)[S@](=O)C(C)(C)C | 302 | 1469 |
| CPD0021581 | 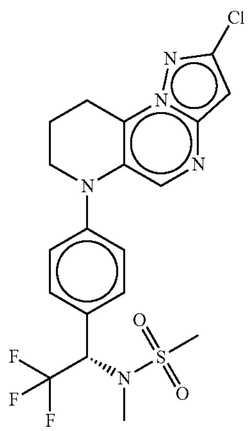 CN([C@@H](c1ccc(cc1)N2CCCc3c2cnc4cc(Cl)nn34)C(F)(F)F)S(=O)(=O)C | 370 | 538 |
| CPD0021576 | 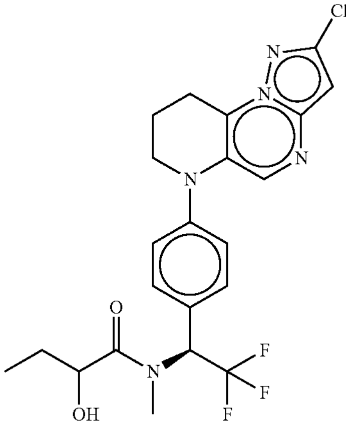 CCC(O)C(=O)N(C)[C@@H](c1ccc(cc1)N2CCCc3c2cnc4cc(Cl)nn34)C(F)(F)F | 146 | 333 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0021575 | 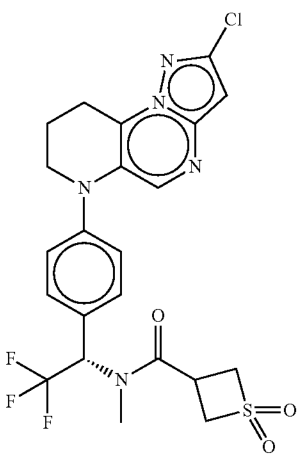 CN([C@@H](c1ccc(cc1)N2CCCc3c2cnc4cc(Cl)nn34)C(F)(F)F)C(=O)C5CS(=O)(=O)C5 | 123 | 128 |
| CPD0021573 | 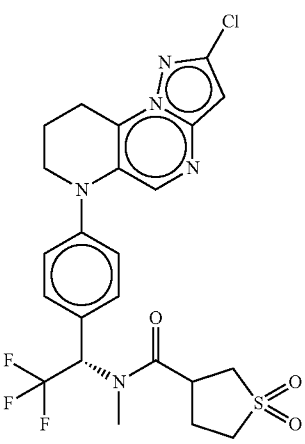 CN([C@@H](c1ccc(cc1)N2CCCc3c2cnc4cc(Cl)nn34)C(F)(F)F)C(=O)C5CCS(=O)(=O)C5 | 131 | 85 |
| CPD0021572 | 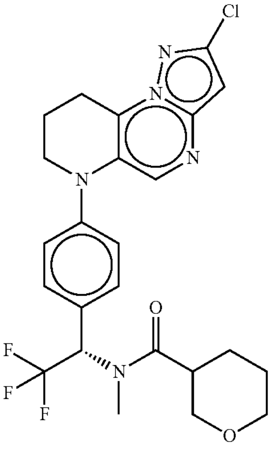 CN([C@@H](c1ccc(cc1)N2CCCc3c2cnc4cc(Cl)nn34)C(F)(F)F)C(=O)C5CCCOC5 | 166 | 193 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0021571 | 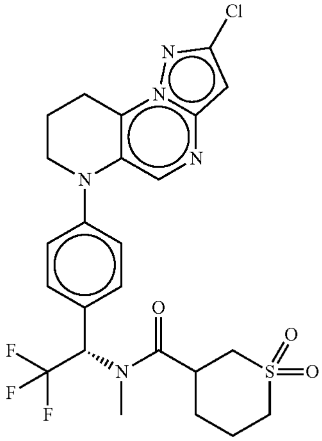 CN([C@@H](c1ccc(cc1)N2CCCc3c2cnc4cc(Cl)nn34)C(F)(F)F)C(=O)C5CCCS(=O)(=O)C5 | 247 | 332 |
| CPD0021570 | 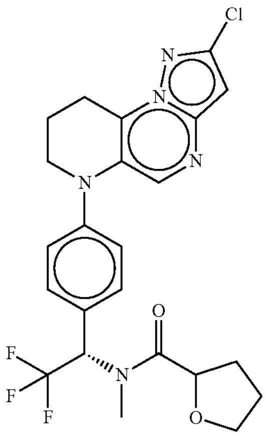 CN([C@@H](c1ccc(cc1)N2CCCc3c2cnc4cc(Cl)nn34)C(F)(F)F)C(=O)C5CCCO5 | 147 | 142 |
| CPD0021568 | 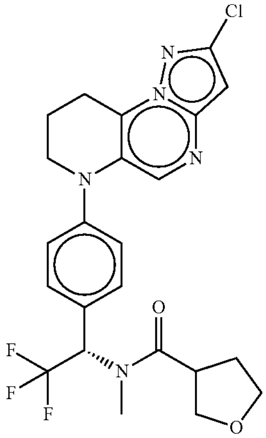 CN([C@@H](c1ccc(cc1)N2CCCc3c2cnc4cc(Cl)nn34)C(F)(F)F)C(=O)C5CCOC5 | 169 | 143 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0019482 | 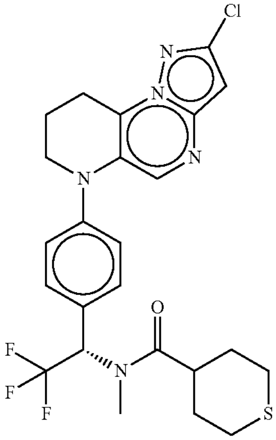 CN([C@@H](c1ccc(cc1)N2CCCc3c2cnc4cc(Cl)nn34)C(F)(F)F)C(=O)C5CCSCC5 | 91 | 146 |
| CPD0019340 | 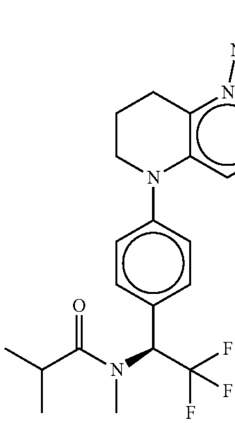 CC(C)C(=O)N(C)[C@@H](c1ccc(cc1)N2CCCc3c2cnc4cc(Cl)nn34)C(F)(F)F | 130 | 139 |
| CPD0018617 | 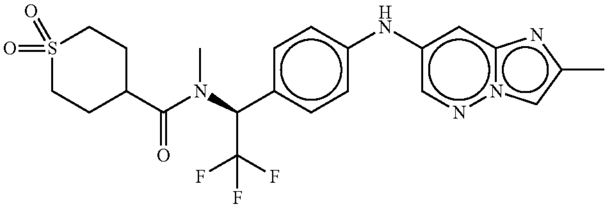 CN([C@@H](c1ccc(Nc2cnn3cc(C)nc3c2)cc1)C(F)(F)F)C(=O)C4CCS(=O)(=O)CC4 | 598 | 386 |

TABLE 1-continued
| IC50 biochemical data for representative compounds of the disclosure. | | | |
|---|---|---|---|
| Compound Reference | Structure | MALT-1 IC50 [nM] | CD4TC IL2 IC50 [nm] |
| CPD0022135 | 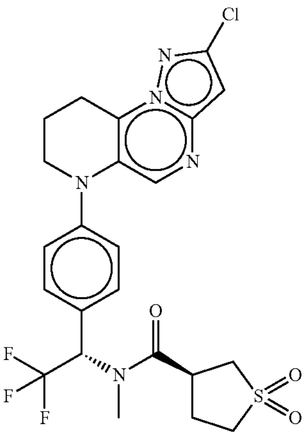 CN([C@@H](c1ccc(cc1)N2CCCc3c2cnc4cc(Cl)nn3 4)C(F)(F)F)C(=O)[C@@H]5CCS(=O)(=O)C5 | 84 | 95 |
| CPD0021664 | 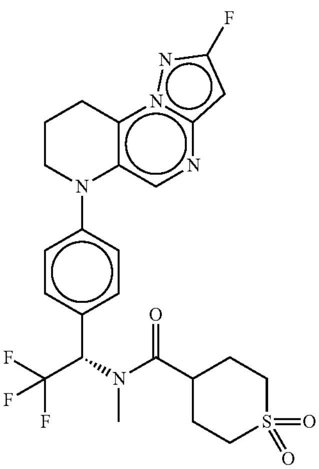 CN([C@@H](c1ccc(cc1)N2CCCc3c2cnc4cc(F)nn3 4)C(F)(F)F)C(=O)C5CCS(=O)(=O)CC5 | 83 | 195 |
| CPD0021569 | 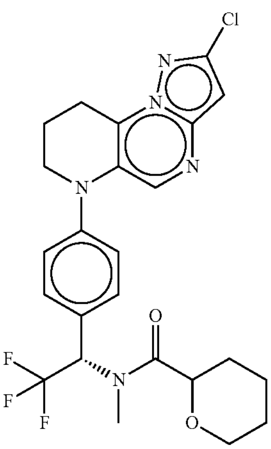 CN([C@@H](c1ccc(cc1)N2CCCc3c2cnc4cc(Cl)nn3 4)C(F)(F)F)C(=O)C5CCCCO5 | 211 | 325 |

TABLE 1-continued
IC50 biochemical data for representative compounds of the disclosure.
| Compound Reference | Structure | MALT-1 IC50 [nM] | CD4TC IL2 IC50 [nm] |
|---|---|---|---|
| CPD0021561 | 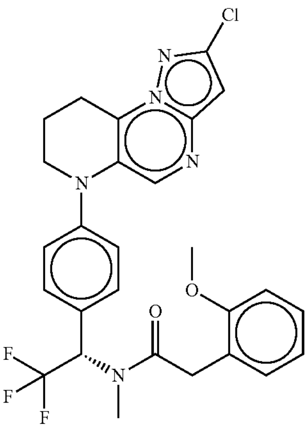 COc1ccccc1CC(=O)N(C)[C@@H](c2ccc(cc2)N3CCCc4c3cnc5cc(Cl)nn45)C(F)(F)F | 63 | 900 |
| CPD0019352 | 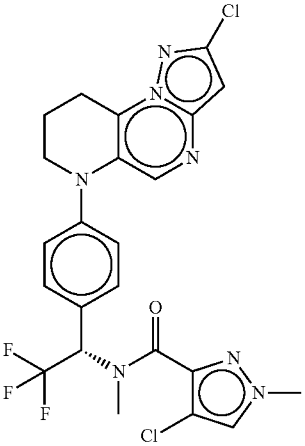 CN([C@@H](c1ccc(cc1)N2CCCc3c2cnc4cc(Cl)nn34)C(F)(F)F)C(=O)c5nn(C)cc5Cl | 196 | 417 |
| CPD0018619 | 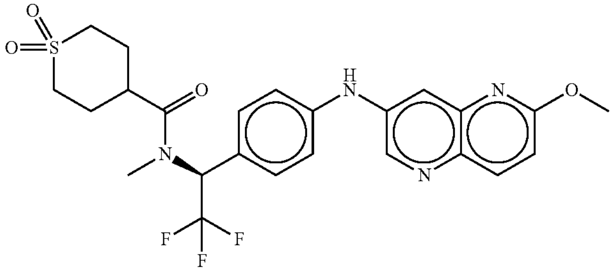 COc1ccc2ncc(Nc3ccc(cc3)[C@H](N(C)C(=O)C4CCS(=O)(=O)CC4)C(F)(F)F)cc2n1 | 361 | 190 |

TABLE 1-continued

| IC50 biochemical data for representative compounds of the disclosure. | | | |
|---|---|---|---|
| Compound Reference | Structure | MALT-1 IC50 [nM] | CD4TC IL2 IC50 [nm] |
| CPD0076413 | 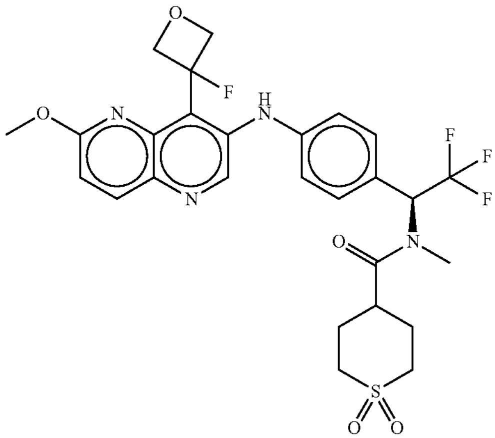 COc1ccc2ncc(Nc3ccc(cc3)[C@H](N(C)C(=O)C4CCS(=O)(=O)CC4)C(F)(F)F)c(c2n1)C5(F)COC5 | 109 | |
| CPD0019353 | 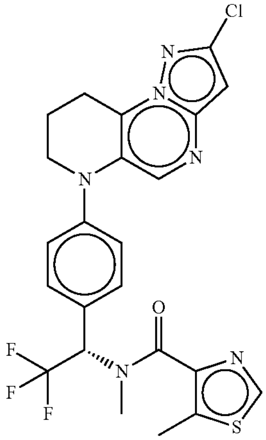 CN([C@@H](c1ccc(cc1)N2CCCc3c2cnc4cc(Cl)nn34)C(F)(F)F)C(=O)c5ncsc5C | 582 | 271 |

Alternative expressions of the inventive concept are set out in each of the following numbered clauses:

1. A method of treating or preventing an autoimmune disorder, inflammatory disease, cancer and/or oncologic disease in a subject in need thereof, the method comprising administering to the subject an effective amount of the compound of formula (I):

(I)

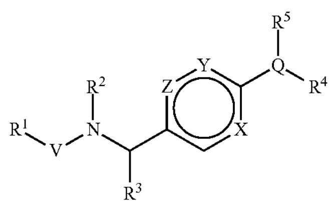

wherein

Q is N or $CR^a$, where $R^a$ is selected from hydrogen, OH, alkyl, alkoxy;

X, Y and Z are each selected independently from N or $CR^b$, where $R^b$ is selected from hydrogen, alkoxy, alkyl, halo alkyl, halogen;

V is selected from the group consisting of: CO, SO and $SO_2$;

$R^1$ is selected from the group consisting of: alkyl, alkenyl, alkynyl, hydroxyalkyl, alkoxy, cycloalkyl, a 4-7 membered saturated or unsaturated heterocyclic ring having heteroatoms selected from N, S and O optionally substituted with hydroxyl, nitrile, oxo, amino, aminoalkyl and/or dioxo, sulfonyl, sulfoxide, sulfoximine, alkyl sulfonyl, alkyl sulfoxide, cycloalkyl sulfonyl, cycloalkyl sulfoxide, sulfamoyl, alkyl sulfamoyl, cycloalkyl sulfamoyl; or one of the following structures:

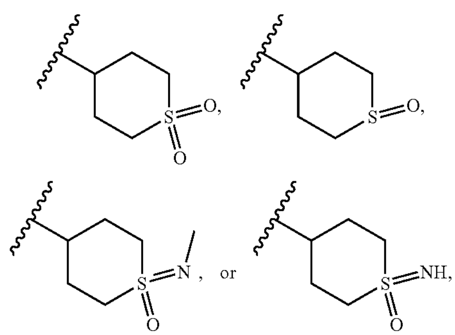
or any one of the following structures: structures:
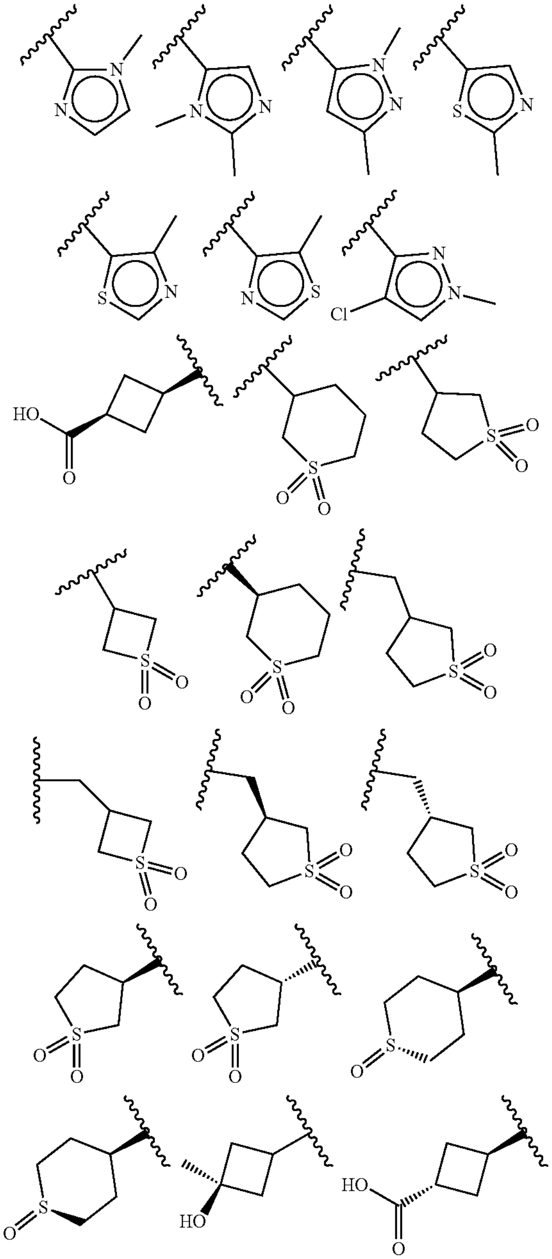
-continued
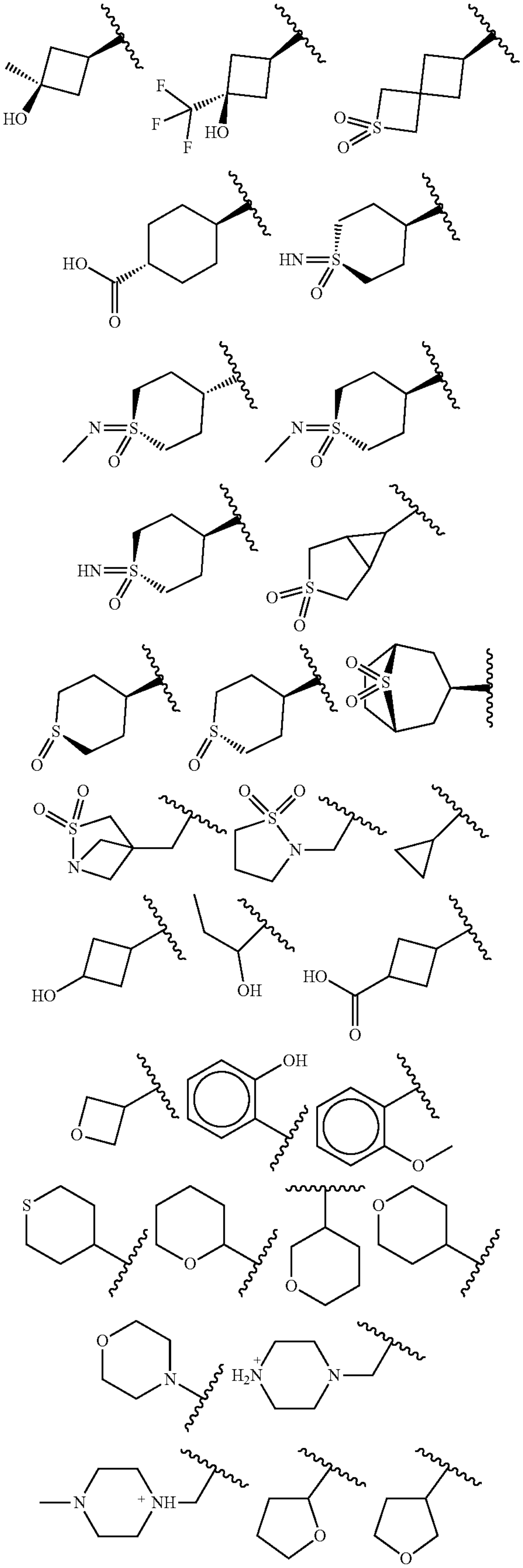

-continued
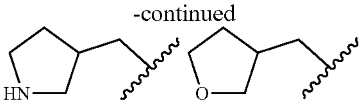
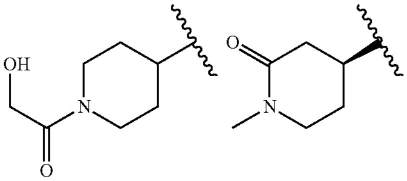
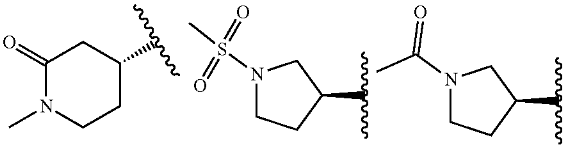
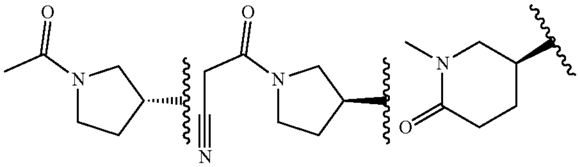
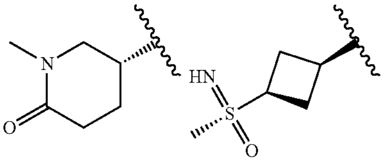
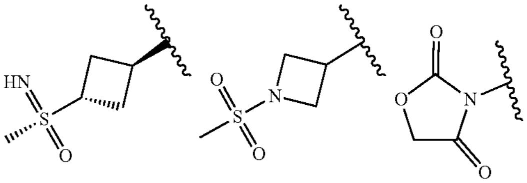
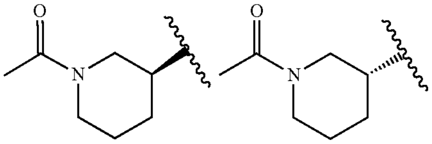
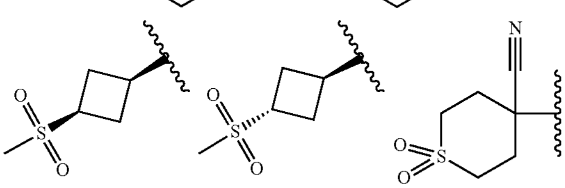
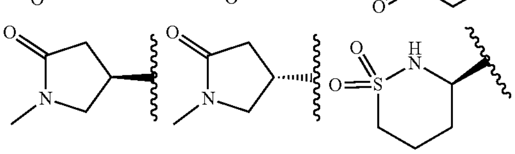
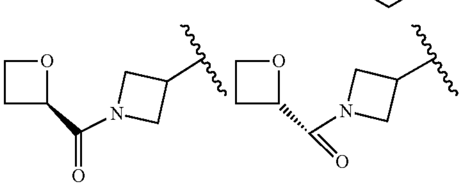
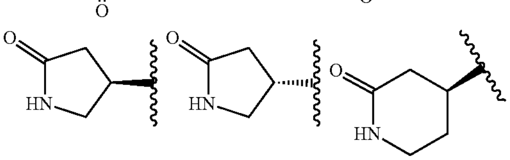
-continued
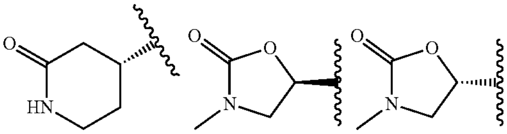
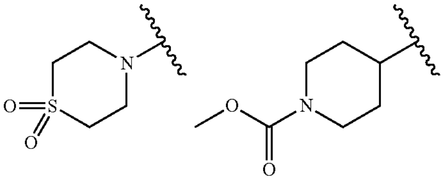
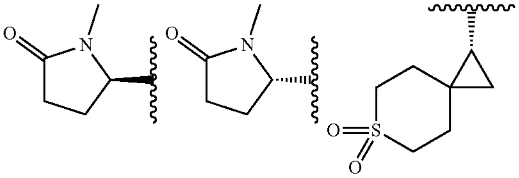
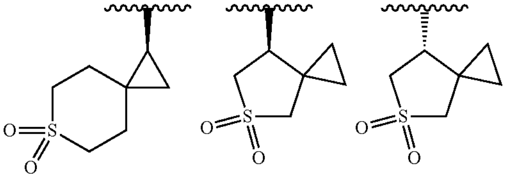
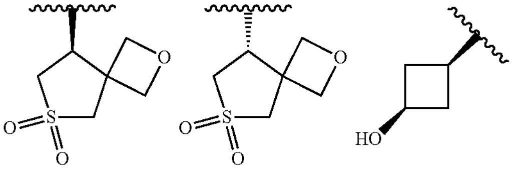
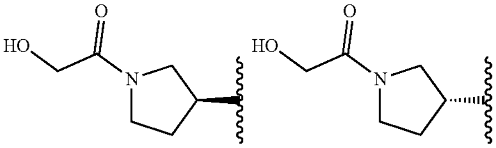
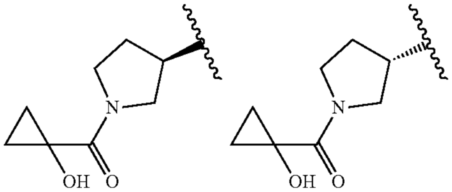
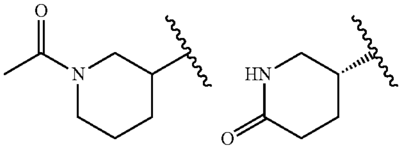
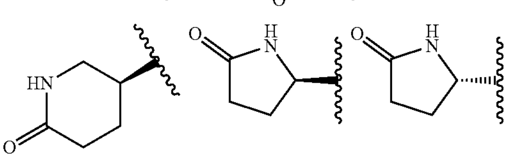
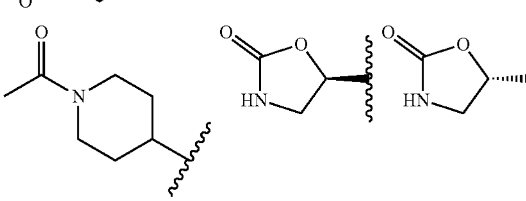

-continued

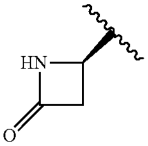 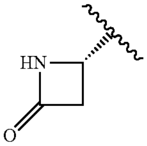 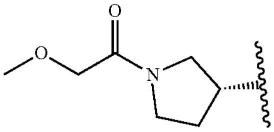

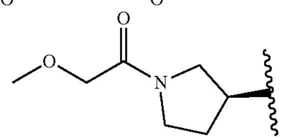 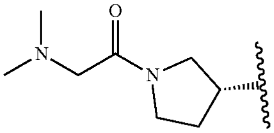

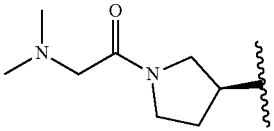 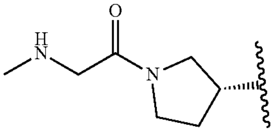

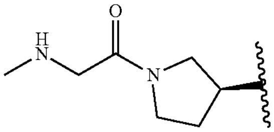 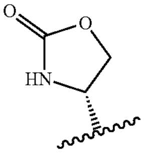 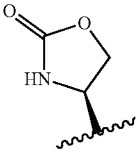

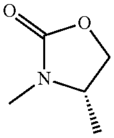 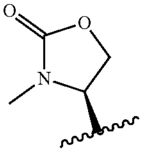 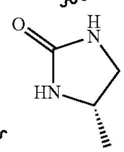 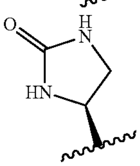

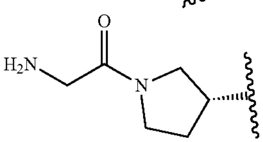 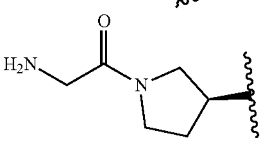

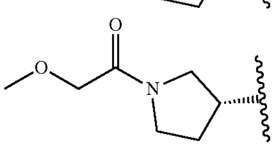 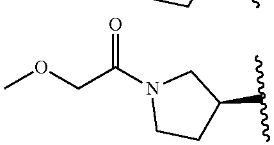

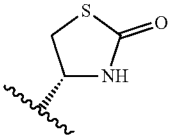 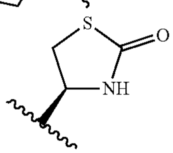 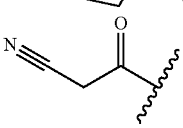

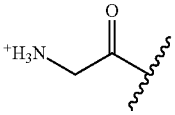 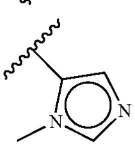 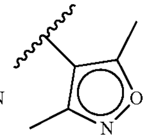

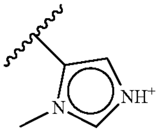 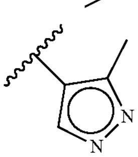 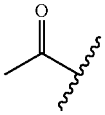 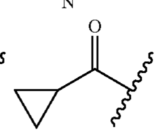

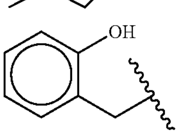 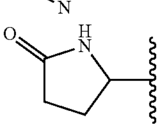 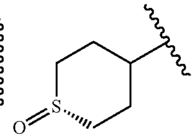

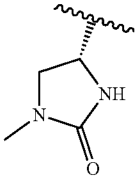 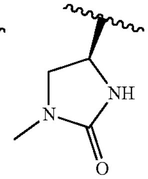 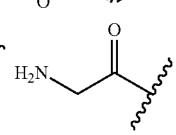

-continued

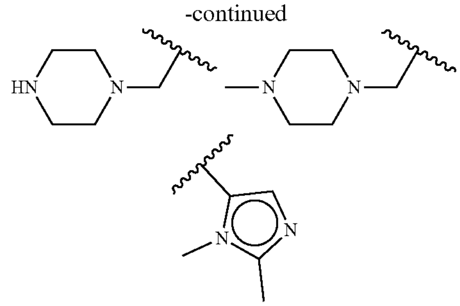

where each of the afore-mentioned hydrocarbon groups may be further substituted by one or more residues independently selected from halogen, hydroxyl, nitrile or C1-4-alkoxy groups;

$R^2$ is selected from the group consisting of: hydrogen, C1-3 alkyl, C1-3 alkoxyl, or C1-3 haloalkyl; or $R^1$ and $R^2$ together form a 4-7 membered ring; particularly a 5-6 membered heterocyclic ring having a further heteroatom selected from N, or O, which is optionally substituted with oxo, amino, aminoalkyl, sulfoxide, sulfoxide imine, sulfonyl, alkyl sulfoxide, sulfoximine, alkyl sulfonyl, cycloalkyl sulfoxide, cycloalkyl sulfonyl, sulfamoyl, alkyl sulfamoyl, cycloalkyl sulfamoyl;

$R^3$ is selected from the group consisting of: hydrogen, C1-3 alkyl, C1-3 alkoxyl, or C1-3 haloalkyl; or $R^4$ and $R^5$ are each independently selected from the group consisting of: hydrogen, C1-3 alkyl, pyridinyl, phenyl, pyrazidinyl or pyrimidinyl, optionally wherein the pyridinyl, phenyl, pyrazidinyl or pyrimidinyl is fused with a pyrrolyl, phenyl, pyrimidinyl, pyrazidinyl, imidazolyl, triazolyl, pyrazolyl, pyridinyl, quinolinyl, isoquinolinyl, quinazolinyl, which may be optionally substituted with C1-3 alkyl, C1-3 alkoxy, cyano, amine, difluoromethyl or halogen; or $R^4$ and $R^5$ together with the Q to which they attach form a non-aromatic heterocyclic 4-8 membered ring containing at least one heteroatom, particularly nitrogen, and optionally an additional heteroatom such as nitrogen or oxygen; and wherein the ring is fused with phenyl, pyridinyl, pyrazidinyl, pyrimidinyl which may be optionally substituted with halogen, nitrile, methyl, methoxy, difluoromethyl, aminyl, or trifluoromethyl, pyrazidinyl or pyrimidinyl, wherein the phenyl, pyridinyl, pyrazidinyl or pyrimidinyl is optionally fused with a further heterocyclic 5- or 6-membered, which is optionally substituted with 1 to 3 groups selected from the group consisting of: C1-3 alkyl, C1-3 alkoxyl, C1-3 haloalkyl, pyrrolyl, imidazolyl, triazolyl, nitro, cyano, hydroxyl or halogen; or $R^4$ and $R^5$ together with the Q to which they attach form one of the following structures:

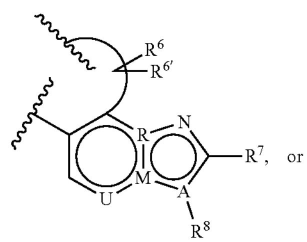

or

-continued

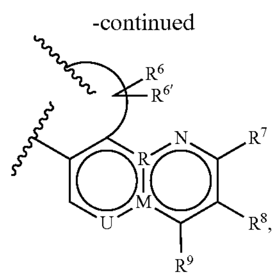

M, R and A are selected independently from the group consisting of: N, S or C, preferably M and R are selected independently from the group consisting of: N, S or C and A is C;

U is selected from the group consisting of: N, or $CR^c$, wherein $R^c$ is selected from hydrogen, halogen or alkyl;

$R^6$ and $R^{6'}$ are independently selected from the group consisting of: hydrogen, halogen C1-3 alkyl, C1-3 alkoxyl, C1-3 alkyl alkoxy, hydroxyl, alkyl hydroxyl, amino alkyl, C1-3 alkyl amino alkyl, tertiary aminyl, cyclic aminyl, spirocyclic aminyl, C1-2 alkyl-4-6 saturated heterocyclic aminyl, C0-2 alkyl oxetane, C0-2 alkyl oxolane, C0-2 alkyl azetidinyl or C0-2 alkyl pyrrolidinyl, C1-3 carboxyl, C1-3 haloalkyl, methylacetyl (OAc) or ethanoate;

alternatively, $R^{6'}$ and $R^6$ together form a C3-5 membered saturated ring or C4-5 membered saturated heterocycle ring containing oxygen;

$R^7$ is selected from the group consisting of: C1-3 alkyl, C1-3 alkoxyl, C1-3 haloalkyl, nitro, cyano, SMe, SOMe, $SO_2Me$, pyrrolyl, imidazolyl, triazolyl, or halogen; and $R^8$ and $R^9$ are each independently selected from the group consisting of: hydrogen, C1-3 alkyl, C1-3 alkoxyl, hydroxyl, C1-3 hydroxyalkyl or halogen.

2. The method of clause 1, wherein:
(i) one of X, Y and Z is CF and the rest are CH;
(ii) X is CF;
(iii) one of X, Y and Z is N;
(iv) one of X or Y is N and the rest are CH; or
(v) X, Y and Z are CH.

3. The method of clause 1 or clause 2, wherein:
(i) V is CO;
(ii) $R^2$ is methyl; and/or
(iii) M and R are selected independently from the group consisting of: N or C, and A is selected independently from the group consisting of: N, S or C.

4. The method of any preceding clause, wherein $R^4$ and $R^5$ together with the Q to which they attach form a non-aromatic heterocyclic 4-8 membered ring containing at least one nitrogen, and optionally an additional heteroatom such as nitrogen or oxygen; and wherein the ring is fused with phenyl, pyridinyl, pyrazidinyl, pyrimidinyl which may be optionally substituted with halogen (e.g. fluorine, bromine or chlorine), nitrile, methyl, methoxy, difluoromethyl, aminyl, or trifluoromethyl, pyrazidinyl or pyrimidinyl, wherein the phenyl, pyridinyl, pyrazidinyl or pyrimidinyl is optionally fused with a further heterocyclic 5- or 6-membered ring (e.g. pyrrolyl, imidazolyl, triazolyl, pyrazolyl or pyridinyl), which is optionally substituted with 1 or 2 groups selected from the group consisting of: C1-3 alkyl, C1-3 alkoxyl, C1-3 haloalkyl, pyrrolyl, imidazolyl, triazolyl, nitro, cyano, hydroxyl or halogen.

5. The method of any preceding clause, wherein $R^4$ and $R^5$ together with the Q to which they attach form one of the following structures, wherein n=1-3:

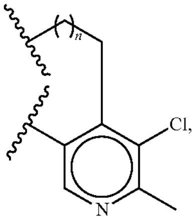
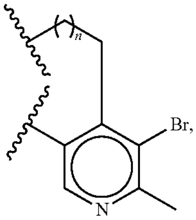
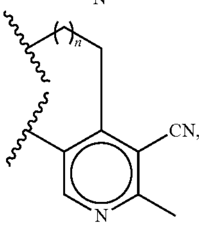
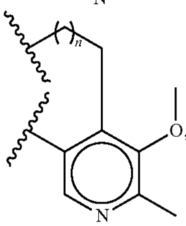
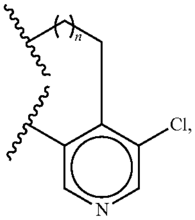
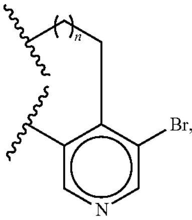
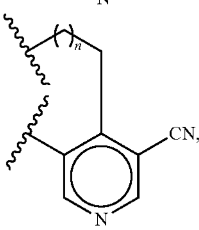
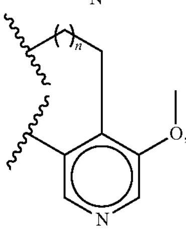
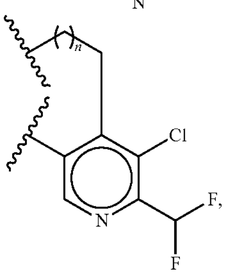
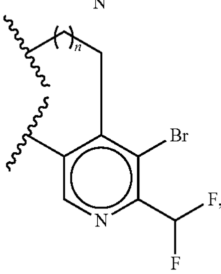
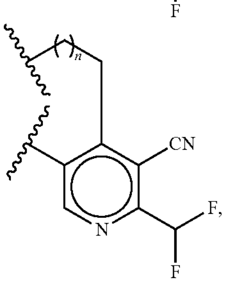
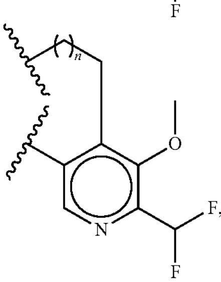
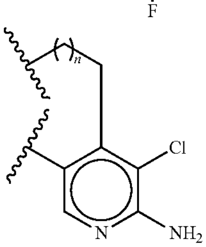
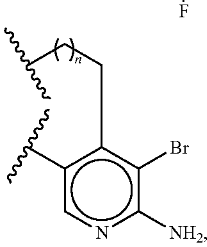

-continued

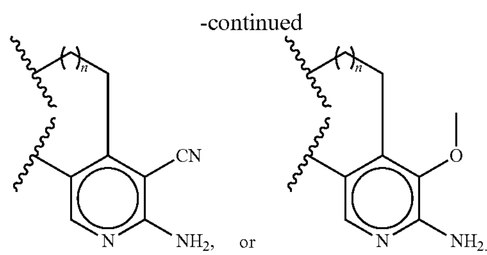

or

6. The method of any preceding clause, wherein $R^6$ and/or $R^{6'}$ are independently selected from the group consisting of: hydrogen, fluorine, methyl, ethyl, methoxy, ethoxy, hydroxyl, $CH_2OH$, $CH_2NHMe$ and $CH_2N(Me)_2$, preferably $R^6$ and $R^{6'}$ together are gem dimethyl or cyclopropyl, oxetane or furane and are more preferably installed in the benzylic position.
7. The method of any of clauses 1 to 5, wherein:
   (i) $R^6$ and $R^{6'}$ together form a C3-5 saturated ring (e.g. cyclopropyl) or C4-5 saturated heterocycle ring containing O (e.g. oxetane or furan);
   (ii) at least one of $R^6$ and $R^{6'}$ is methyl or methoxy;
   (iii) at least one of $R^6$ and $R^{6'}$ is hydrogen; or
   (iv) both $R^6$ and $R^{6'}$ are methyl or both $R^6$ and $R^{6'}$ are hydrogen.
8. The method of any preceding clause, wherein U is selected from N or $CR^c$, preferably U is N.
9. The method of any preceding clause, wherein, R and M are each independently selected from N or C, preferably one of R and M is N and the other is C.
10. The method of any preceding clause, wherein A is selected from S or C, preferably where A is S, and M and R are C.
11 The method of any preceding clause, wherein $R^7$ is selected from the group consisting of: chlorine, fluorine, methyl or methoxy.
12. The method of any preceding clause, wherein $R^7$ is methyl, fluorine or chlorine; preferably wherein $R^7$ is fluorine or chlorine.
13. A method of treating or preventing an autoimmune disorder, inflammatory disease, cancer and/or oncologic disease in a subject in need thereof, the method comprising administering to the subject an effective amount of a compound according to Table 1, or a pharmaceutically acceptable salt, solvate, prodrug, or pharmaceutically active metabolite thereof, or combinations thereof.
14. The method of any preceding clause, wherein the disorders or diseases are selected from the group consisting of: rheumatoid arthritis, multiple sclerosis, psoriasis, Sjogren's syndrome and systemic lupus erythematosus or vasculitic conditions, cancers of hematopoietic origin or solid tumors, including chronic myelogenous leukemia, myeloid leukemia, non-Hodgkin lymphoma or other B cell lymphomas.
15. A method of treating or preventing an autoimmune disorder, inflammatory disease, cancer and/or oncologic disease in a subject in need thereof, the method comprising administering to the subject an effective amount of a compound according to:
   any of Examples 1 to 295;
   any compound disclosed in Table 1;
   any compound defined in the present disclosure.
16. A method of treating or preventing an autoimmune disorder, inflammatory disease, cancer and/or oncologic disease in a subject in need thereof, the method comprising administering to the subject an effective amount of a compound as defined in any of the appended claims; particularly as defined in any of Claims 1 to 28 appended hereto.
17. A pharmaceutical composition comprising a compound of formula (I) as defined in any of clauses 1 to 16, in Table 1, or as otherwise defined in accordance with the present disclosure.
18. A compound of formula (I) as defined in any of clauses 1 to 16, in Table 1, or as otherwise defined in accordance with the present disclosure.
19. A compound as defined in clause 18, or a pharmaceutical composition comprising a compound as defined in clause 18, or a pharmaceutically acceptable salt, solvate, prodrug, or pharmaceutically active metabolite thereof, or combinations thereof, for use in the treatment of an autoimmune disorder, inflammatory disease, cancer and/or oncologic disease as disclosed herein.

The skilled person will appreciate that many modifications may be made to the above examples, the aspects and the embodiments disclosed herein without departing from the scope of the present invention as defined in the accompanying claims and/or the above clauses.

The invention claimed is:

1. A compound selected from the group consisting of:

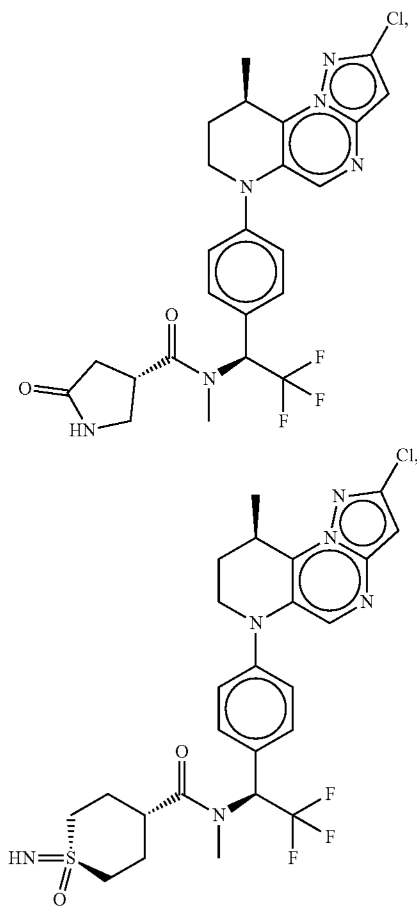

-continued
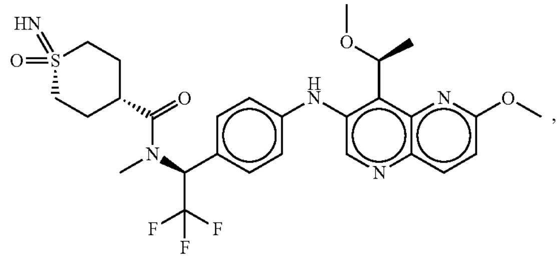
,
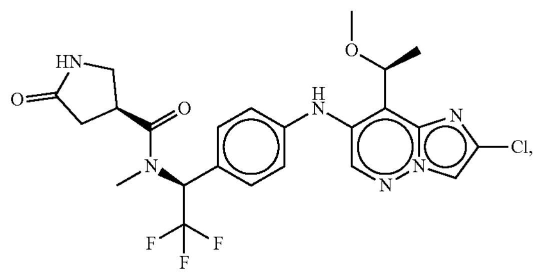
,
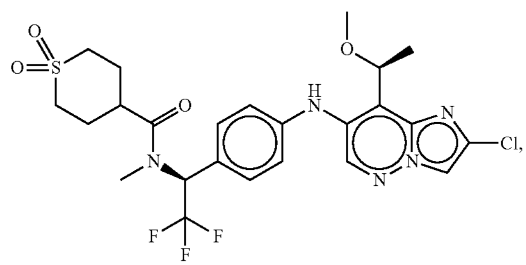
,
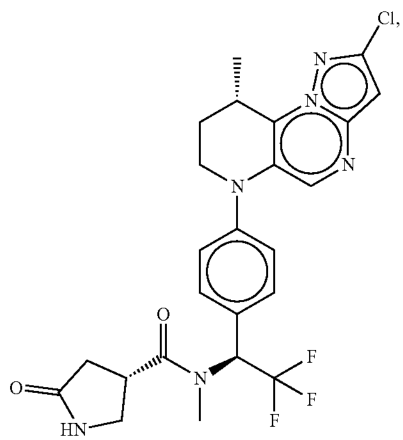
,
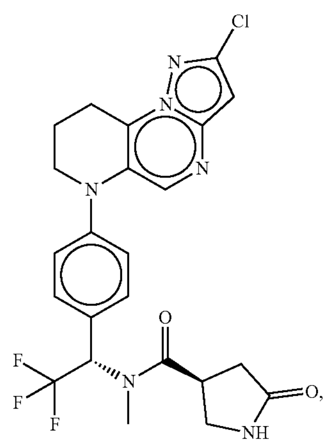
,
-continued
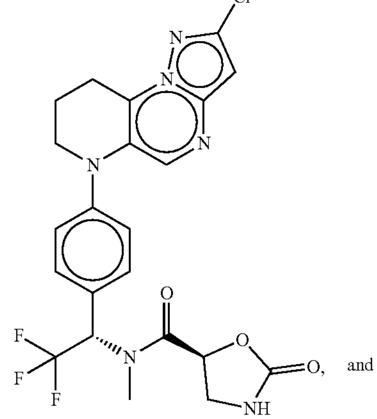
, and
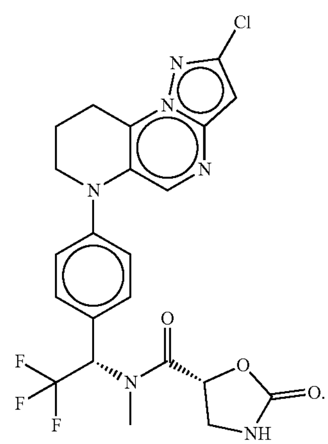
.
2. The compound according to claim 1, wherein the compound has the following structure:
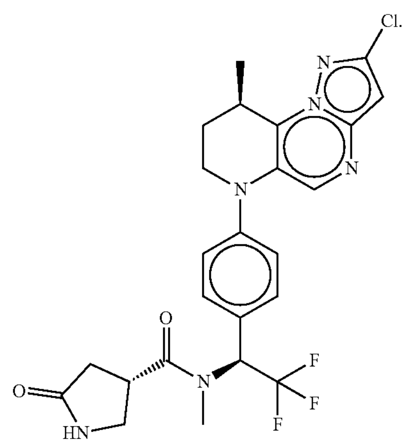
.
3. The compound according to claim 1, wherein the compound has the following structure:

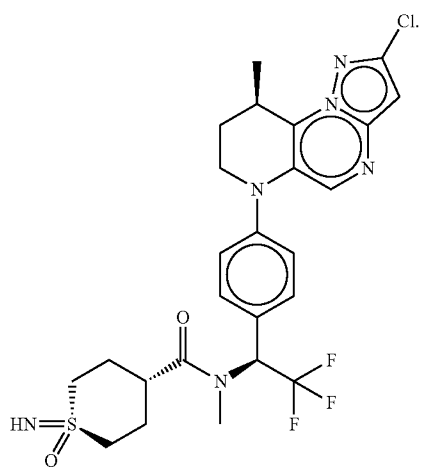

4. The compound according to claim 1, wherein the compound has the following structure:

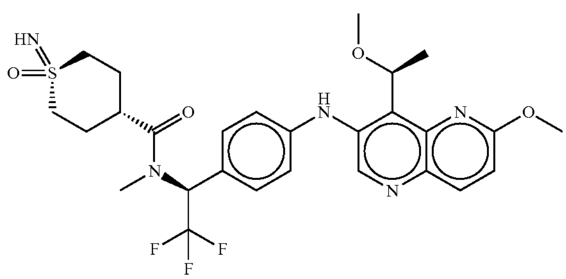

5. The compound according to claim 1, wherein the compound has the following structure:

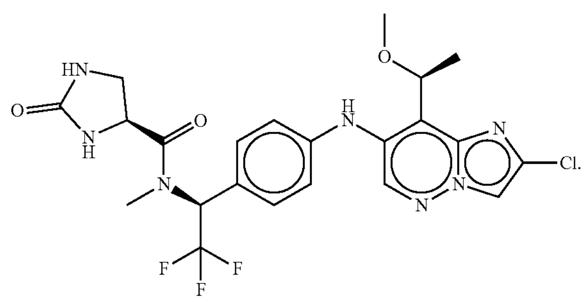

6. The compound according to claim 1, wherein the compound has the following structure:

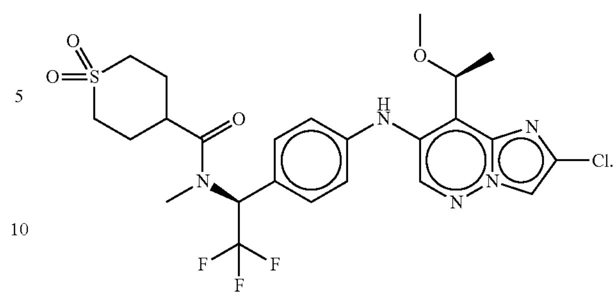

7. The compound according to claim 1, wherein the compound has the following structure:

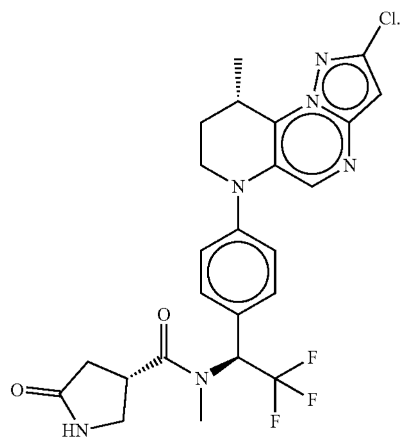

8. The compound according to claim 1, wherein the compound has the following structure:

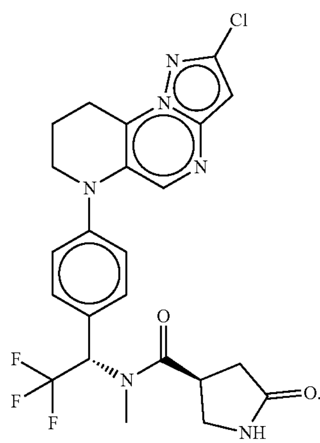

9. A compound having the following structure:
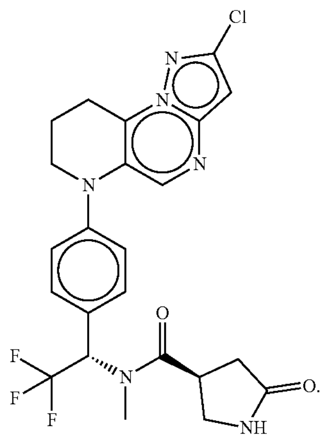
10. A compound having the following structure:
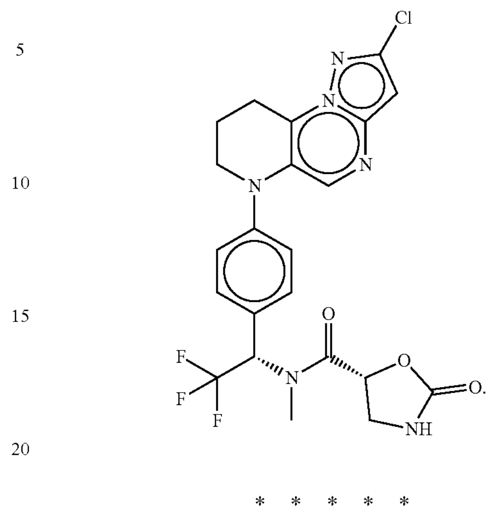
* * * * *